US012673954B2

(12) United States Patent
Fink et al.

(10) Patent No.: US 12,673,954 B2
(45) Date of Patent: Jul. 7, 2026

(54) BENZOFURAN COMPOUNDS AS STING AGONISTS

(71) Applicant: BRISTOL-MYERS SQUIBB COMPANY, Princeton, NJ (US)

(72) Inventors: Brian E. Fink, Yardley, PA (US); Emily Charlotte Cherney, Newtown, PA (US); Liping Zhang, East Windsor, NJ (US); Julian C. Lo, Burlingame, CA (US); Gretchen M. Schroeder, Bayou Vista, TX (US); Tram N. Huynh, Frankford, DE (US); Donna D. Wei, Belle Mead, NJ (US); Vijay T. Ahuja, Princeton, NJ (US); Claude A. Quesnelle, Denver, CO (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 399 days.

(21) Appl. No.: 18/264,298

(22) PCT Filed: Feb. 3, 2022

(86) PCT No.: PCT/US2022/015010

§ 371 (c)(1),
(2) Date: Aug. 4, 2023

(87) PCT Pub. No.: WO2022/169921

PCT Pub. Date: Aug. 11, 2022

(65) Prior Publication Data

US 2024/0109899 A1 Apr. 4, 2024

Related U.S. Application Data

(60) Provisional application No. 63/145,541, filed on Feb. 4, 2021.

(51) Int. Cl.

| | |
|---|---|
| ***C07D 487/04*** | (2006.01) |
| ***C07D 471/04*** | (2006.01) |
| ***C07D 519/00*** | (2006.01) |

(52) U.S. Cl.
CPC ......... *C07D 487/04* (2013.01); *C07D 471/04* (2013.01); *C07D 519/00* (2013.01)

(58) Field of Classification Search
CPC ... C07D 487/04; C07D 471/04; C07D 519/00
See application file for complete search history.

(56) References Cited

FOREIGN PATENT DOCUMENTS

| | | | | |
|---|---|---|---|---|
| GB | 2572526 A | | 10/2019 | |
| GB | 2574862 A | | 12/2019 | |
| WO | WO-9509159 A1 | * | 4/1995 | ........... C07D 401/06 |
| WO | 2018234805 A1 | | 12/2018 | |
| WO | WO-2018234808 A1 | * | 12/2018 | .......... C07F 9/65128 |

OTHER PUBLICATIONS

Lee et al. Studies on Benzofuran-7-carboxamides as Poly(ADP-ribose) Polymerase-1 (PARP-1) Inhibitors, Korea Research Institute of Chemical Technology, Sep. 2011, pp. 1147-1153. (Year: 2011).*
WO-9509159-A1 (Year: 1995) part 1.*
WO-9509159-A1 (Year: 1995) part 2.*
Chemical Abstracts Service Database Registry, Apr. 19, 2016, retrieved from STN, Database accession No. 1893159-27-7, 1893007-10-7.
Chemical Abstracts Service Database Registry, Aug. 25, 2017, retrieved from STN, Database accession No. 2120032-19-9, 2119999-30-1.

(Continued)

*Primary Examiner* — Sarah Pihonak
*Assistant Examiner* — Mikhail O'donnel Robinson
(74) *Attorney, Agent, or Firm* — Roy Issac

(57) ABSTRACT

The present invention is directed to compounds of formula (I) and (II), wherein all substituents are defined herein, as well as pharmaceutically acceptable compositions comprising compounds of the invention and methods of using said compositions in the treatment of various disorders.

(I)

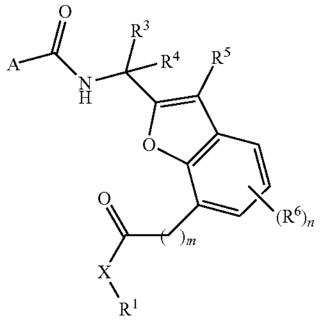

(II)

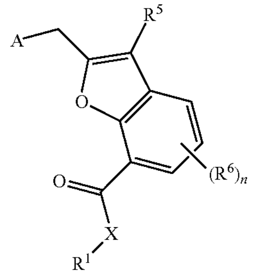

12 Claims, No Drawings

(56) References Cited

OTHER PUBLICATIONS

Chemical Abstracts Service Database Registry, Aug. 28, 2017, retrieved from STN, Database accession No. 2121519-00-2, 2121518-82-7, 2121518-69-0.
Lee, S., et al. "Studies on Benzofuran-7-carboxamides as Poly(ADP-ribose) Polymerase-1 (PARP-1) Inhibitors" Bull. Korean Chem. Soc. vol. 33(4), pp. 1147-1153 (2012).

* cited by examiner

BENZOFURAN COMPOUNDS AS STING AGONISTS

CROSS REFERENCE TO RELATED APPLICATIONS

This application is a 35 U.S.C. § 371 national stage application of International Application No. PCT/US2022/015010, filed Feb. 3, 2022, which claims the benefit of U.S. Provisional Application No. 63/145,541, filed Feb. 4, 2021, the entire content of which is hereby incorporated herein by reference.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (STimulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al. 2013).

Activation of STING results in up-regulation of IRF3 and NF-κB pathways leading to induction of Interferon-β and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

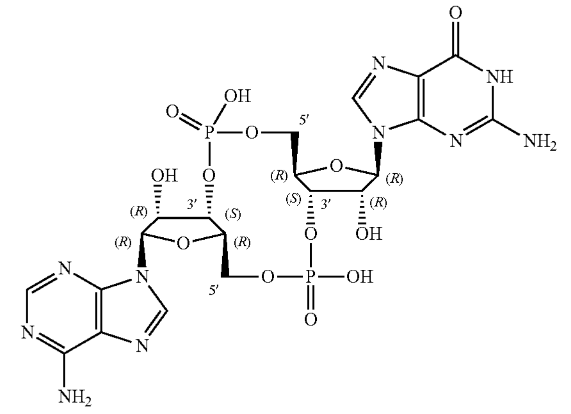

3'3'-cGAMP

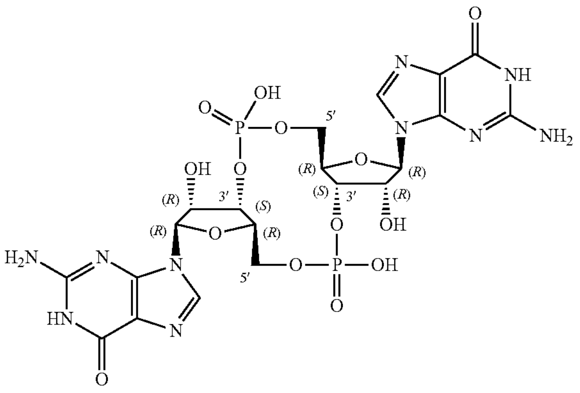

c-di-GMP

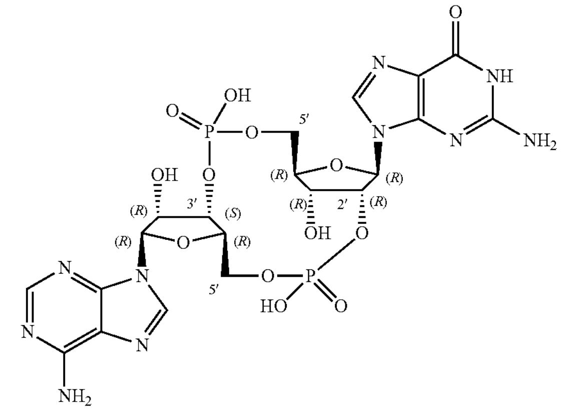

2'3'-cGAMP

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al. 2015a). For reviews on the role of STING in infection, inflammation, and/or cancer, see Ahn et al. 2015; Corrales et al. 2015b and 2016; and Barber 2015.

The present invention, therefore, provides novel compounds which may be useful for the treatment of cancer.

DESCRIPTION OF THE INVENTION

One aspect of the invention is a compound of formula I

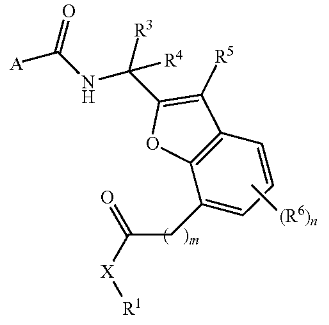

wherein

A is a 5-12 membered heterocyclic group substituted with 0-4 $R^2$ groups,

X is O, S or NH, $R^1$ is hydrogen, $CD_3$, $CF_3$, OH, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$; with the proviso that $R^1$ is OH only when X is NH;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;

$R^{1b}$ is halogen or $C_{1-4}$ alkyl,

R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^3$ and $R^4$ are independently hydrogen or $C_{1-3}$ alkyl, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl m is 0 or 1, n is 0, 1, 2 or 3, or a pharmaceutically acceptable salt thereof.

A second aspect of the invention is a compound of formula II

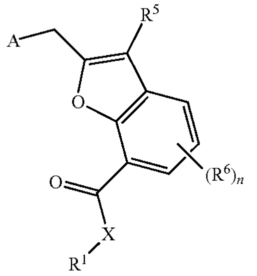

wherein

A is a 5-12 membered heterocyclic group substituted with 0-4 $R^2$ groups,

X is O, S or NH, $R^1$ is hydrogen, $CD_3$, $CF_3$, OH, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$, with the proviso that $R^1$ is OH only when X is NH;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;

$R^{1b}$ is halogen or $C_{1-4}$ alkyl,

R' is hydrogen, OH, $C_{1-3}$ alkoxy or $C_{1-3}$ alkyl;

$R^2$ is, independently at each occurrence, hydrogen, halogen, CN, OH, carbonyl, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In a third aspect of the invention, within the first aspect is a compound of the formula

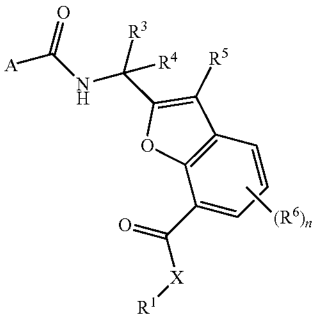

wherein

A is a 5-12 membered heterocyclic group substituted with 0-4 $R^2$ groups,

X is O, S or NH, $R^1$ is hydrogen, $CD_3$, $CF_3$, OH, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$, with the proviso that $R^1$ is OH only when X is NH;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;

$R^{1b}$ is halogen or $C_{1-4}$ alkyl,

R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^3$ and $R^4$ are independently hydrogen or $C_{1-3}$ alkyl, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In a 4th aspect of the invention, there is disclosed a compound of the formula

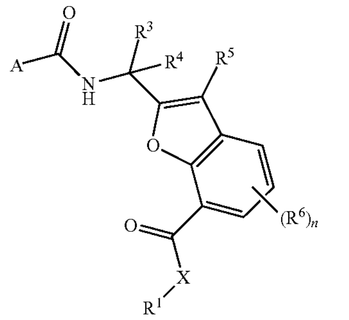

wherein

A is a 5-12 membered heterocyclic group substituted with 0-4 $R^2$ groups,

X is O, $R^1$ is hydrogen, $CD_3$, $CF_3$, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;

$R^{1b}$ is halogen or $C_{1-4}$ alkyl,

R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^3$ and $R^4$ are independently hydrogen or $C_{1-3}$ alkyl, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In a 5th aspect of the invention, there is disclosed a compound of the formula

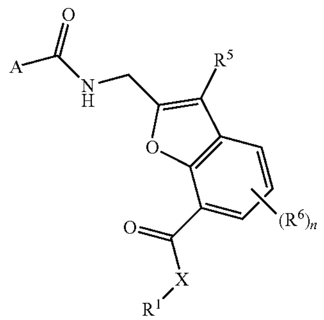

wherein

A is a 5-12 membered heterocyclic group substituted with 0-4 $R^2$ groups,

X is O, $R^1$ is hydrogen, $CD_3$, $CF_3$, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;

$R^{1b}$ is halogen or $C_{1-4}$ alkyl,

R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In a 6th aspect of the invention, there is disclosed a compound of the formula

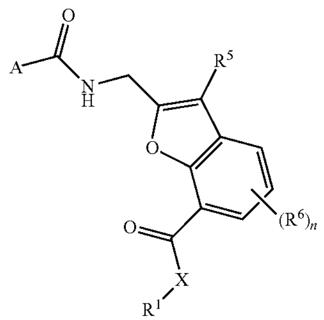

wherein

A is a 6-10 membered heterocyclic group substituted with 0-4 $R^2$ groups,

X is O,

- $R^1$ is hydrogen, $CD_3$, $CF_3$, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$;
- $R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;
- $R^{1b}$ is halogen or $C_{1-4}$ alkyl,
- R' is hydrogen, OH, $C_{1-3}$ alkoxy or $C_{1-3}$ alkyl;
- $R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$,
- $R^{2a}$ is halogen,
- $R^5$ is hydrogen, halogen, $CF_3$, $C_{1-6}$ alkyl, $C_{1-6}$ alkoxy or $C_{1-6}$ alkenyl,
- $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl
- n is 0, 1, 2 or 3, or a pharmaceutically acceptable salt thereof.

In a $7^{th}$ aspect of the invention, there is disclosed a compound of the formula

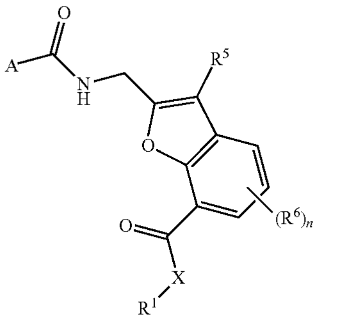

wherein

- A is a pyrazinyl group, a pyrimidinyl group, a pyridinyl group, a pyrazole-pyrimidinyl group, an imidazo-pyridazinyl group, a thiazolo-pyrdinyl group, imidazo-pyridinyl group or a naphthyridinyl group, each of said groups substituted with 0-4 $R^2$ groups,
- X is O,
- $R^1$ is hydrogen, $CD_3$, $CF_3$, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$;
- $R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;
- $R^{1b}$ is halogen or $C_{1-4}$ alkyl,
- R' is hydrogen, OH, $C_{1-3}$ alkoxy or $C_{1-3}$ alkyl;
- $R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$,
- $R^{2a}$ is halogen,
- $R^5$ is hydrogen, halogen, $CF_3$, $C_{1-6}$ alkyl, $C_{1-6}$ alkoxy or $C_{1-6}$ alkenyl,

- $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl
- n is 0, 1, 2 or 3, or a pharmaceutically acceptable salt thereof.

In another aspect of the invention within the second aspect, there is disclosed a compound of the formula

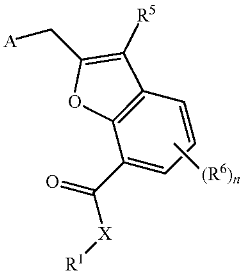

wherein A is

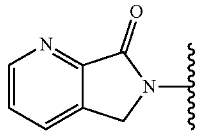, 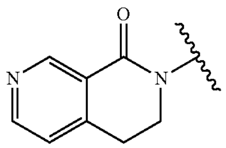,

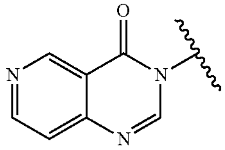, 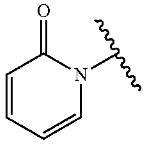,

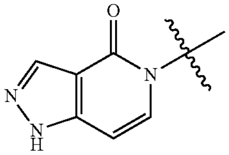, 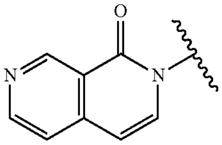,

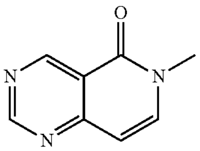, 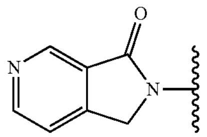, or

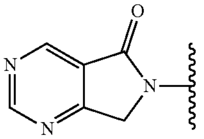

substituted with 0-4 $R^2$ groups,

- X is O, S or NH,
- $R^1$ is hydrogen, $CD_3$, $CF_3$, OH, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$, with the proviso that $R^1$ is OH only when X is NH;
- $R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$;
- $R^{1b}$ is halogen or $C_{1-4}$ alkyl,
- R' is hydrogen, OH, $C_{1-3}$ alkoxy or $C_{1-3}$ alkyl;
- $R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In another aspect of the invention within the second aspect, there is disclosed a compound of the formula

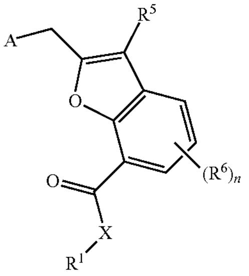

wherein A is

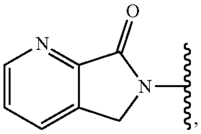,
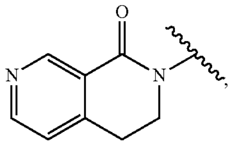,
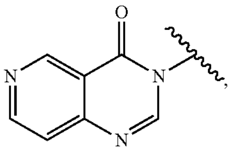,
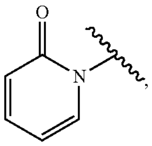,
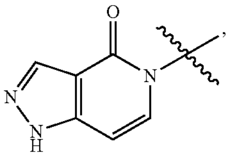,
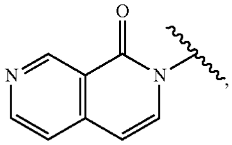,
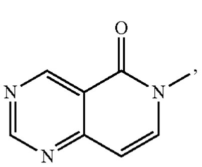,
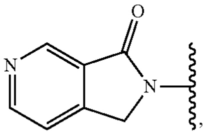, or
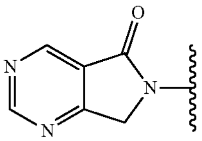

substituted with 0-4 $R^2$ groups,

X is O, $R^1$ is hydrogen, $CD_3$, $CF_3$, $C_{1-6}$ alkyl, $C_{1-6}$ alkoxy, $C_{3-6}$ cycloalkyl or halo $C_{1-3}$ alkyl, all of said alkyl groups substituted with 0-4 $R^{1a}$;

$R^{1a}$ is halogen;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen or $R^{1a}$ is halogen, $R^5$ is hydrogen, halogen, $CF_3$, $C_{1-6}$ alkyl, $C_{1-6}$ alkoxy or $C_{1-6}$ alkenyl;

$R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

In another aspect, there is provided a compound selected from the exemplified examples within the scope of the first or second aspects, or a pharmaceutically acceptable salt, tautomer or stereoisomer thereof.

In another aspect, there is provided a compound selected from any subset list of compounds within the scope of any of the above aspects.

In another aspect of the invention, there is provided a compound which is

Tert-butyl 3-((5-chloro-2-((pyrazolo[1,5-a]pyrimidine-3-carboxamido)methyl)benzofuran-7-carbonyl)oxy)azetidine-1-carboxylate, (247)

Acetoxymethyl 5-chloro-2-((13yrazole[1,5-a]pyrimidine-3-carboxamido)methyl)benzofuran-7-carboxylate, (259)

((Ethoxycarbonyl)oxy)methyl 5-chloro-2-((pyrazolo[1,5-a]pyrimidine-3-carboxamido)methyl)benzofuran-7-carboxylate, (260), 1-((Ethoxycarbonyl)oxy)ethyl 5-chloro-2-((pyrazolo[1,5-a]pyrimidine-3-carboxamido)methyl)benzofuran-7-carboxylate, (261)

1-Ethoxy-2,2-difluoroethyl 5-fluoro-2-((pyrazolo[1,5-a]pyrimidine-3-carboxamido)methyl)benzofuran-7-carboxylate, (323,324)

S-(2-(Trimethylsilyl)ethyl) 3-chloro-5-fluoro-2-((pyrazolo[1,5-a]pyrimidine-3-carboxamido)methyl)benzofuran-7-carbothioate, (392)

S-(2-(Trimethylsilyl)ethyl) (S)-5-fluoro-2-(1-(pyrazolo[1,5-a]pyrimidine-3-carboxamido)ethyl)benzofuran-7-carbothioate (398)

S-(2-(Trimethylsilyl)ethyl) (S)-5-chloro-2-(1-(pyrazolo[1,5-a]pyrimidine-3-carboxamido)ethyl)benzofuran-7-carbothioate (400)

N-((5-Chloro-7-(1H-tetrazol-5-yl)benzofuran-2-yl)methyl) pyrazolo[1,5-a]pyrimidine-3-carboxamide (409), N-((5-Chloro-7-(1H-tetrazol-5-yl)benzofuran-2-yl)methyl)-1,6-naphthyridine-8-carboxamide (410), N-((5-chloro-7,9-dioxo-8,9-dihydro-7H-benzofuro[7,6-e][1,3]oxazin-2-yl)methyl)pyrazolo[1,5-a]pyrimidine-3-carboxamide, or 1-methyl-2-((pyrazolo[1,5-a]pyrimidine-3-carboxamido)methyl)-1H-benzo[d]imidazole-4-carboxylic acid, or a pharmaceutically acceptable salt thereof.

In another aspect of the invention, there is provided a compound which is

N-((5-chloro-7,9-dioxo-8,9-dihydro-7H-benzofuro[7,6-e][1,3]oxazin-2-yl)methyl)pyrazolo[1,5-a]pyrimidine-3-carboxamide, N-((5-Chloro-7-(1H-tetrazol-5-yl)benzofuran-2-yl)methyl) pyrazolo[1,5-a]pyrimidine-3-carboxamide, N-((5-Chloro-7-(1H-tetrazol-5-yl)benzofuran-2-yl)methyl)-1,6-naphthyridine-8-carboxamide, 1-methyl-2-((pyrazolo[1,5-a]pyrimidine-3-carboxamido)methyl)-1H-benzo[d]imidazole-4-carboxylic acid, or a pharmaceutically acceptable salt thereof.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The compounds of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the compounds of Formula (I) or (II), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the compounds of Formulae (I) and (II) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the compounds of the present invention can be used for cytokine induction immunotherapy of immunosuppressed individuals.

In this example, a compound of Formula (I) or (II) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a compound of Formula (I) or (II) or a pharmaceutically acceptable salt or prodrug thereof.

In another embodiment, the compounds of the present invention can be used for cytokine induction immunotherapy in combination with chemotherapy. In this example, a compound of Formula (I) or (II) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound (s) of the present invention, and cytotoxicity, provided by the chemotherapeutic agent(s), might be less toxic to the patient, cause fewer side effects in the patient and/or exhibit greater anti-tumor efficacy than would the chemotherapeutic agent (s) when used as monotherapy.

The present invention thus discloses a method for treating cancer, said method comprising administering to a patient in need thereof: a chemotherapeutic agent; and a compound of Formula (I) or (II) or a pharmaceutically acceptable salt or prodrug thereof.

Another object of the present invention is a compound of Formula (I) or (II) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a compound of Formula (I) or (II) or a pharmaceutically acceptable salt or prodrug thereof.

Another object of the present invention is the compound of Formula (I) or (II) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day.

Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol  is used in formulas and tables to show the bond that is the point of attachment of the moiety or substituent to the core/nucleus of the structure.

Additionally, for purposes of clarity, where a substituent has a dash (–) that is not between two letters or symbols; this is used to indicate a point of attachment for a substituent. For example, —$CONH_2$ is attached through the carbon atom.

Additionally, for purposes of clarity, when there is no substituent shown at the end of a solid line, this indicates that there is a methyl ($CH_3$) group connected to the bond.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "haloalkyl" which includes the term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least one saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —0-phenyl, and —O— heteroaryl. Preferred examples of EWG include, but are not limited to, $CF_3$, $CF_2CF_3$, CN, halogen, $SO_2$($C_{1-4}$ alkyl), CONH($C_{1-4}$ alkyl), CON($C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^{1}H$ (hydrogen), $^{2}H$ (deuterium) and $^{3}H$ (tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy,* 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988);
e) Kakeya, N. et al., *Chem. Pharm. Bull.,* 32:692 (1984); and
f) Rautio, J (Editor). *Prodrugs and Targeted Delivery* (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabo-*

*lism. Chemistry, Biochemistry and Enzymology*, VCHA and Wiley-VCH, Zurich, Switzerland (2003); Wermuth, C. G., ed., *The Practice of Medicinal Chemistry*, 3rd edition, Academic Press, San Diego, CA (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by synthetic routes that include processes analogous to those well-known in the chemical arts, particularly in light of the description provided herein. For illustrative purposes, Schemes 1-23 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Compound 4 can be prepared from starting material 1 as shown in Scheme 1. First, benzylic bromination of 1 to give bromide intermediate 2 can be performed with a radical brominating reagent such as NBS in the presence of a radical initiator such as AIBN typically using heat or light to initiate the transformation. Benzyl bromide 2 can be displaced by 2-aminomethyl benzofuran 3 in the presence of a base such as TEA in a variety of solvents including THF. Once displacement has occurred, heating the reaction mixture can lead to intramolecular lactamization yielding lactam 4. The temperature required to cause lactamization could vary depending on the nature of the ester and substitution pattern of the pyridine ring.

Scheme 1

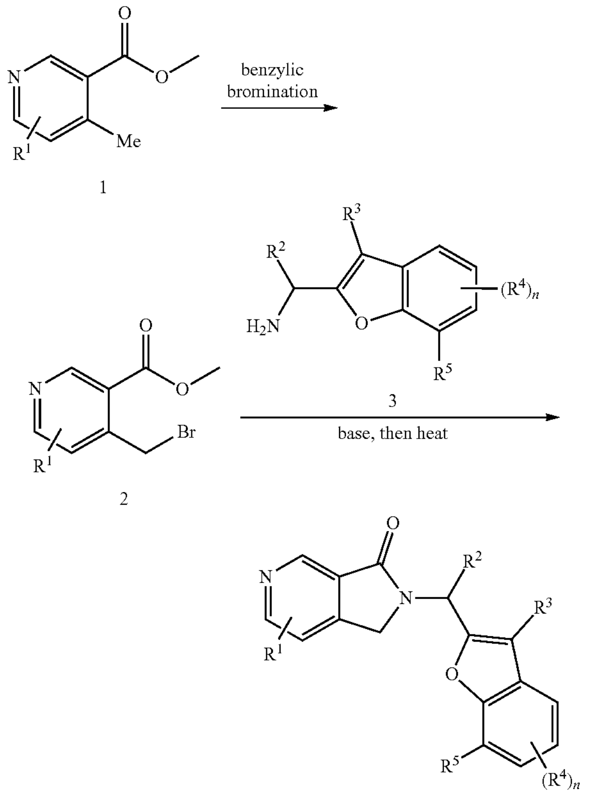

1, 2, 3, 4

Lactam 7 can be prepared in an analogous manner as demonstrated in Scheme 2. Picolinic esters 5 are again brominated in the benzylic position and then subsequently treated with 2-aminomethyl benzofuran 3 followed by heat to give the desired compounds 7.

Scheme 2

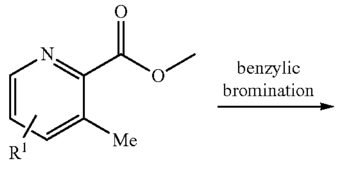

5

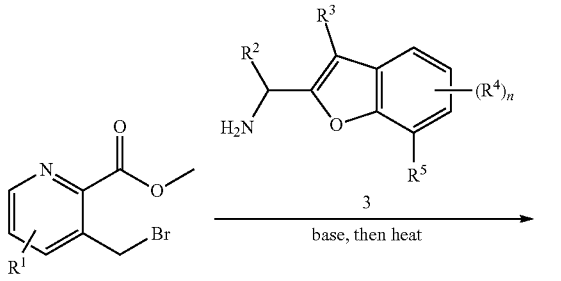

6

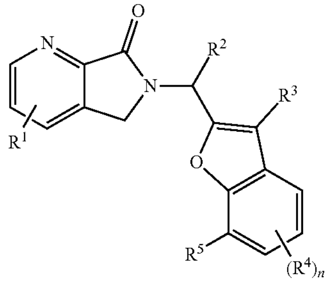

7

Alternatively, compound 4 can be made from pyridine aldehyde 8 and 2-aminomethyl benzofuran 3 under reductive amination conditions (Scheme 3). In the presence of a reducing agent such as sodium triacetoxyborohydride and often in the presence of an acid such as acetic acid, aldehyde 8 can be coupled to amine 3. Subsequent, in situ intramolecular lactamization can occur to yield 4. Likewise, pyrimidine aldehyde 9 gives lactam 10 under analogous conditions.

Scheme 3

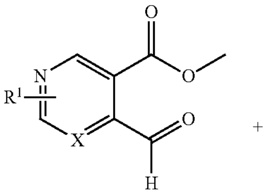

X = CH 8
N 9

-continued

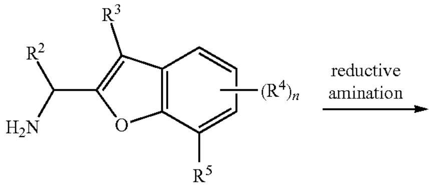

3

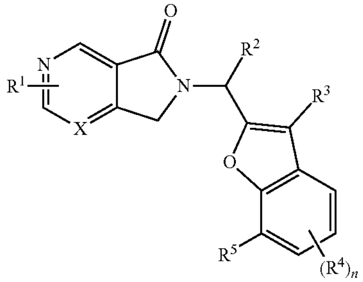

X = CH 4
N 10

Six-membered ring lactam 12 can be prepared from lactone 11 as shown in Scheme 4. Heating lactone 11 with 2-aminomethyl benzofuran 3 either as a solution or neat, conventionally or in a microwave reactor, with or without a base (such as pyridine), generates lactam 12.

Scheme 4

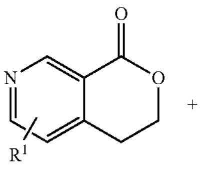

11

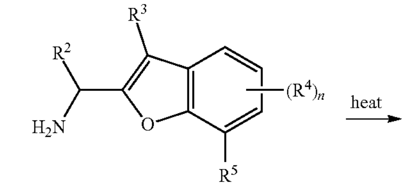

3

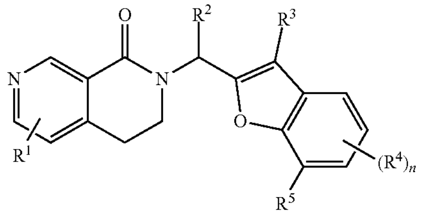

12

Pyridopyrimidinone 15 can be synthesized as outlined in Scheme 5. Nicotinic acid 13 can be heated conventionally or in a microwave reactor in the presence of DMF-DMA to give amidine intermediate 14. The amidine can then be treated with 2-aminomethylbenzofuran 3 with heating in the presence of an acid, such as acetic acid, to give the desired pyridopyrimidinone 15.

Scheme 5

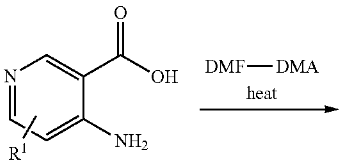

13

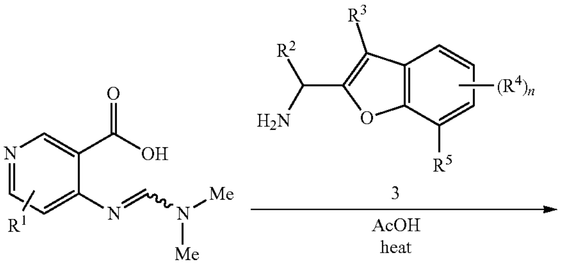

14

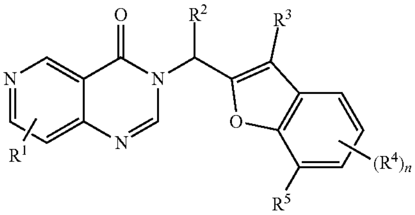

15

Following a similar protocol, naphthyridinone 18 can be synthesized as shown in Scheme 6. Nicotinic acid 16 can be heated with DMF-DMA to provide enamine 17. Once again, heating with 2-aminomethyl benzofuran 3 in the presence of an acid such as acetic acid gives naphthyridinone 18.

Scheme 6

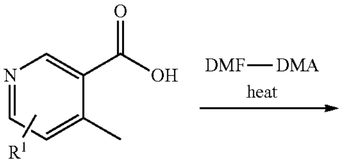

16

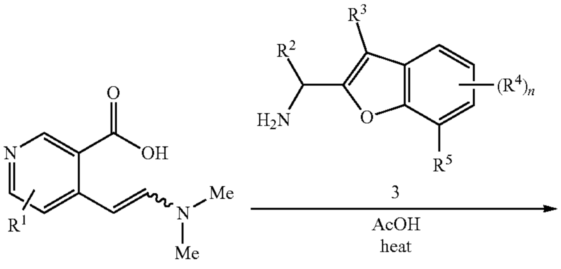

17

-continued

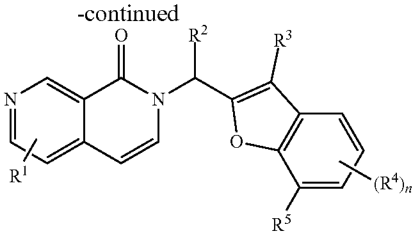

18

Alternatively, compounds of type 18 can be synthesized from pre-formed naphthyridinones as outlined in Scheme 7. Naphthyridinone 20 can be synthesized from 4-methylnicotinonitrile 19 by heating either conventionally or in a microwave reactor with DMF-DMA, followed by removal of excess DMF-DMA, and further heating in acid (such as acetic acid and/or sulfuric acid). The resulting naphthyridinone 20 can then be alkylated with benzylic bromide 21 in the presence of a base such as sodium hydride in a solvent such as DMF to give 18.

Scheme 7

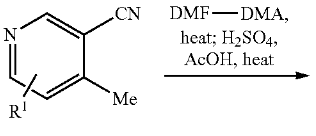

19

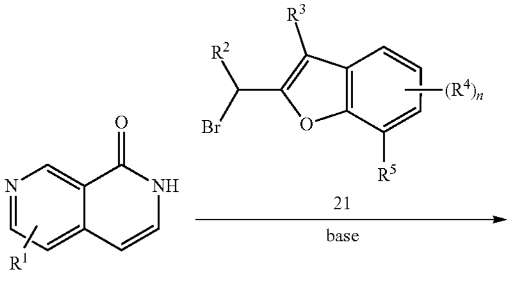

20

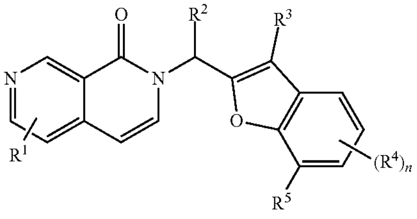

18

In cases where the amide is not embedded in a ring, as is the case in Scheme 8, standard amide coupling protocols can be employed to join a variety of acids with 2-aminomethyl benzofuran 3. Indeed, various substituted pyridine-, pyrimidine-, and pyrazine-acids (22-24) can be coupled to 3 using a variety of coupling reagents such as BOP or HATU in the presence of a base such as Hunig's base to give the corresponding amides 25-27. These conditions can also be employed with a variety of other heteroaromatic acids to give, for example, pyrimidinone 29 (Scheme 9), naphthyridine 31 (Scheme 10), imidazopyridine 33 (Scheme 11), pyrazolopyridine 35 (Scheme 12), imidazopyridazine 37 (Scheme 13), and pyrazolopyrimidine 39 (Scheme 14).

Scheme 8
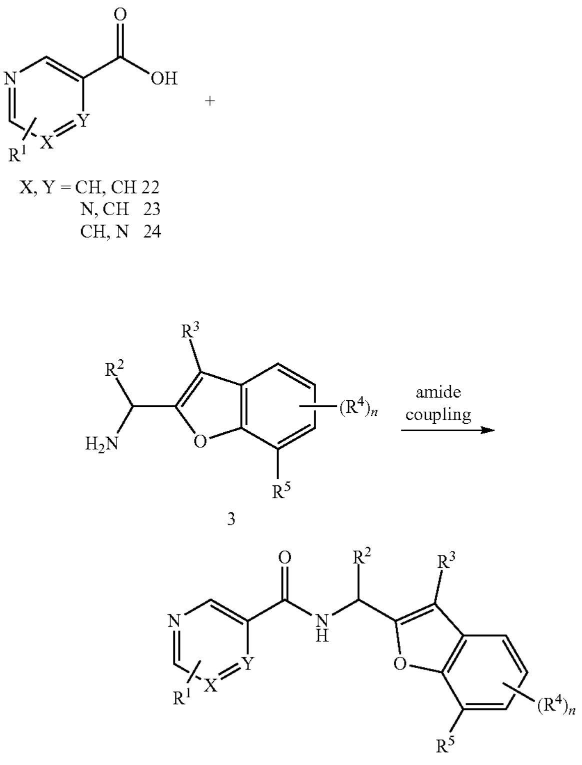
X, Y = CH, CH 22
N, CH 23
CH, N 24
3
X, Y = CH, CH 25
N, CH 26
CH, N 27
Scheme 9
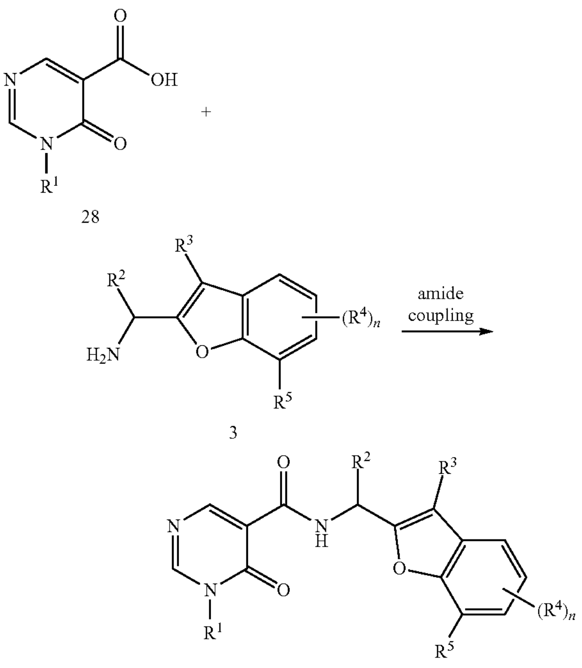
28
3
29
Scheme 10
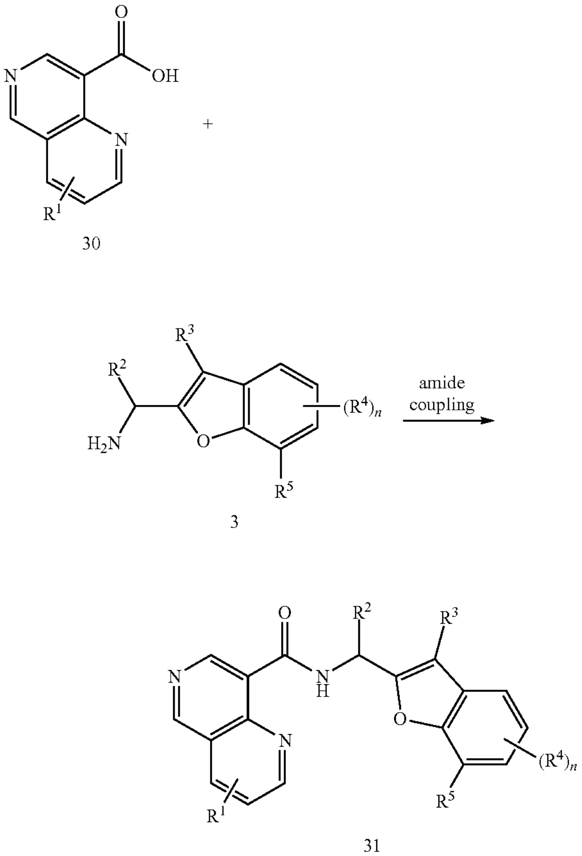
30
3
31
Scheme 11
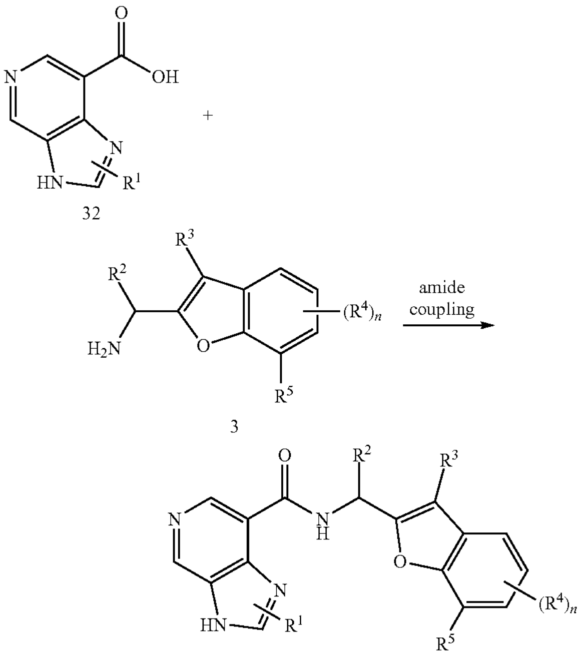
32
3
33

Scheme 12

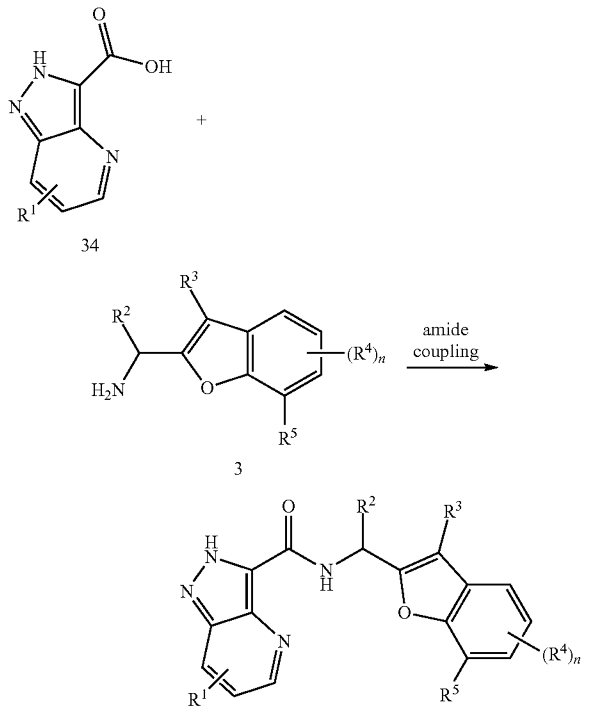

34 3 35

Scheme 13

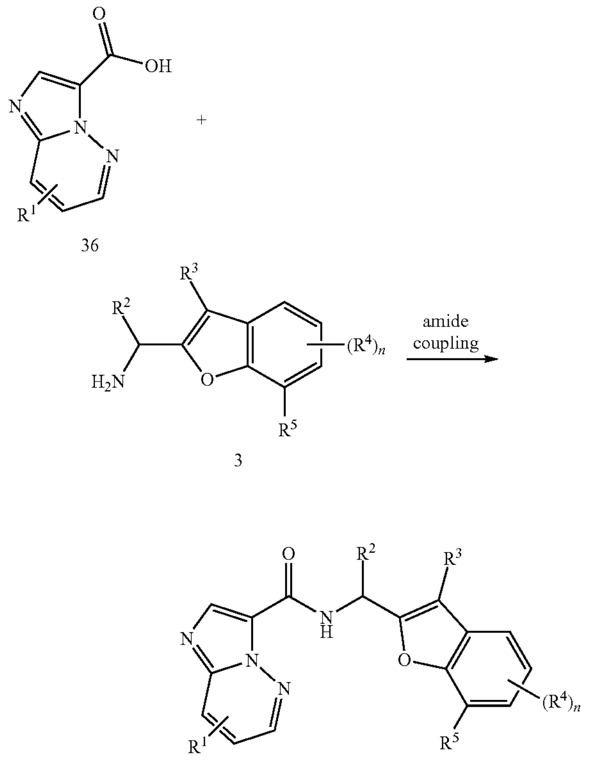

36 3 37

Scheme 14

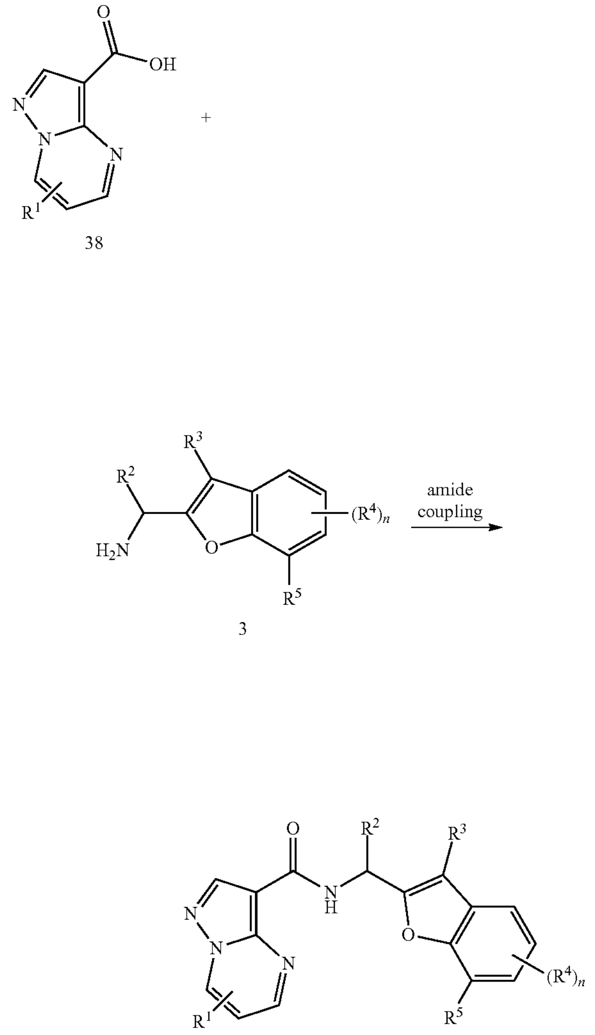

38 3 39

Benzofuran esters 40 (Scheme 15) can be derivatized by first hydrolyzing them under basic conditions in the presence of water to give acid 41. The acid can be converted to various alternative esters (42) upon activation with a coupling reagent such as BOP or PyBOP, typically in the presence of a base such as Hunig's base, followed by addition of the appropriate alcohol. Thioesterification of acid 41 could be affected by multiple synthetic routes. Conversion of acid 41 to an acid chloride followed by treatment with the sodium salt of the desired thiol gives thioester 43. Alternatively, acid 41 could be coupled to (trimethylsilyl)ethane-1-thiol in the presence of BOP and Hunig's base. This 2-(trimethylsilyl)ethyl thioester intermediate could be converted to thioester 43 by treating with TBAF in the presence of an alkyl halide. Additionally, hydroxamic acids and esters (44) can be synthesized from acid 41 using standard amide coupling conditions such as BOP and Hunig's base.

Scheme 15

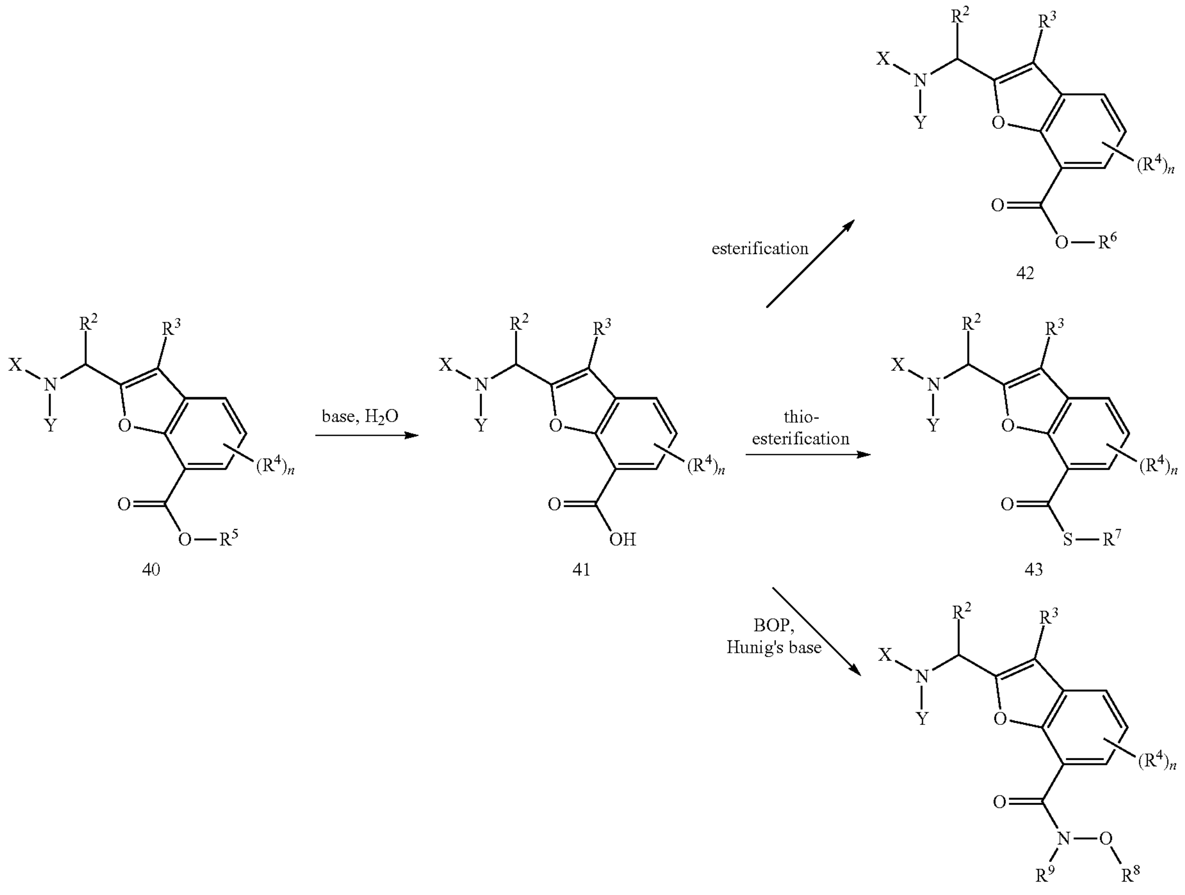

40 41 42 43 44

Benzofuran carboxylic esters 52 can also be prepared as shown in Scheme 16. Substituted 2-bromo phenol 45 can be converted to aldehyde 46 by treating with paraformaldehyde in the presence of magnesium dichloride and triethylamine. Treatment of 46 with an alpha-halo acetate such as ethyl bromoacetate in the presence of a base such as potassium carbonate at elevated temperatures can lead to benzofuran-2-carboxylic acids that can be readily re-esterified upon treatment with, for example, TMS-diazomethane to give methyl ester 47. Reduction of the ester using a reducing agent such as LAH in an ethereal solvent like THE or ether gives alcohol 48. Mitsunobu displacement with phthalimide can give phthalimide protected 2-aminomethyl benzofuran 49. Deprotection of the phthalimide under basic conditions with a nucleophile such as hydrazine can give primary amine 50. Amine 50 can then be coupled as described previously to give 7-bromobenzofuran-amide 51. Finally, the bromide could be converted to 52 by treating with carbon monoxide, a suitable palladium catalyst, and the necessary alcohol.

Scheme 16

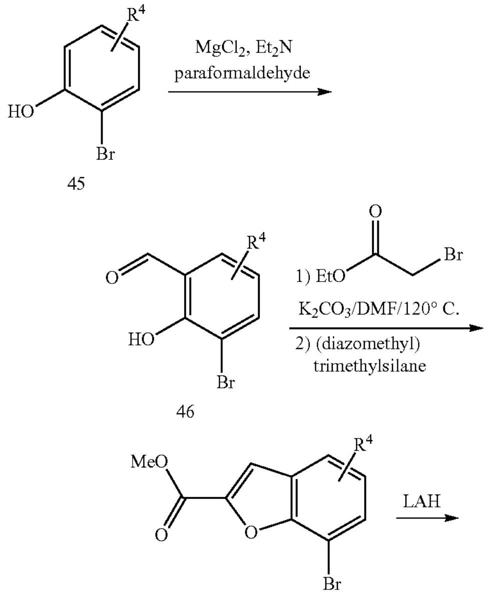

45 46 47

-continued

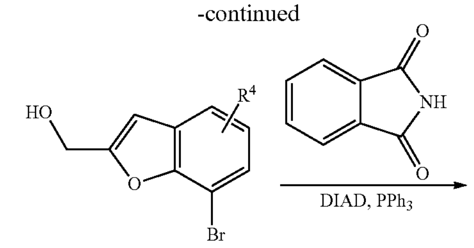

48

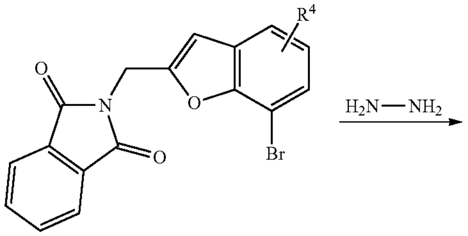

49

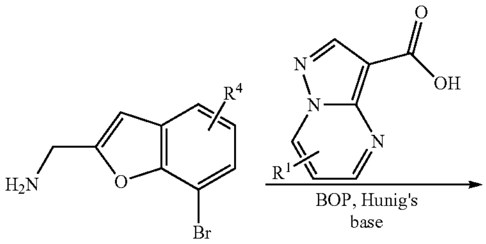

50

-continued

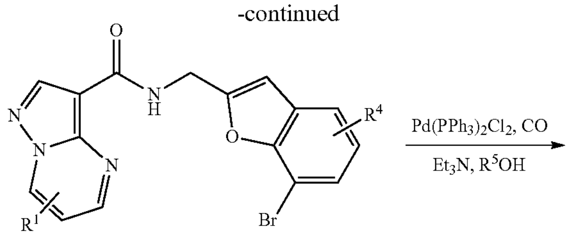

51

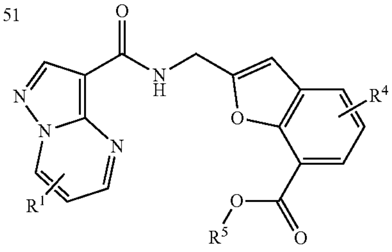

52

Synthetic strategies to access variously substituted benzofurans 3 are shown in Schemes 17-22. C5-Substituted benzofurans 56 can be prepared starting from phenol 53 (Scheme 17). Electrophilic iodination of phenol 53 using either commercial or in situ generated electrophilic iodine sources such as NIS or sodium iodide/chloramine T respectively gives iodide 54. Sonogashira coupling of N-Boc propargyl amine at elevated temperatures followed by cyclization gives benzofuran 55. Benzofuran 55 can be deprotected using standard Boc deprotection conditions such as TFA in DCM to provide C5-substituted benzofuran 56. Alternatively, when $R^4$ is an aryl halide, it can be removed via hydrogenation with an appropriate palladium catalyst such as palladium on carbon or Pearlman's catalyst in the presence of hydrogen to give Boc-protected amine 57. The Boc group can be deprotected as described previously with TFA to give 58.

Scheme 17

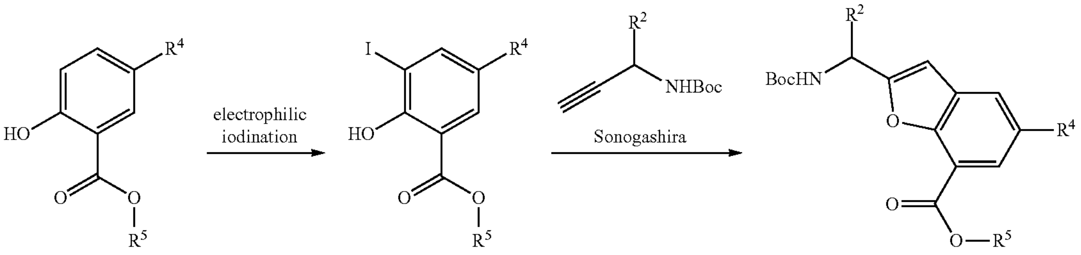

53 54 55

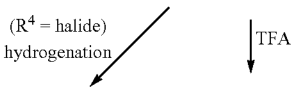

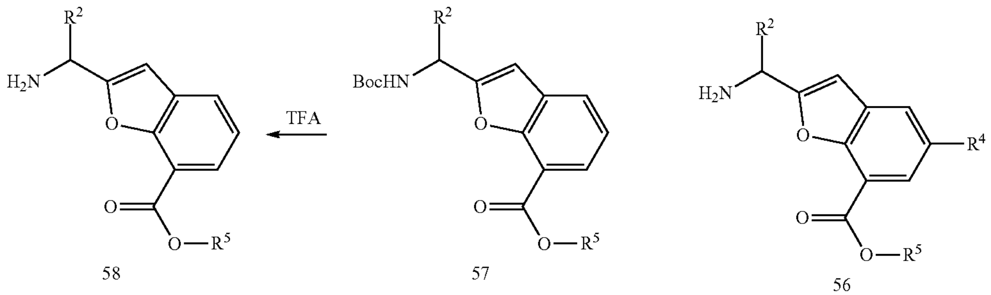

58 57 56

C6-substituted benzofurans 63 can be synthesized as shown in Schemes 18 and 19. Phenol 59 can undergo electrophilic iodination as described previously to give iodide 60. Sonogashira coupling can furnish the benzofuran 61. When X is a halide such as bromide, the bromide can be removed by palladium-catalyzed hydrogenation to give Boc-protected amine 62. The BOC protecting group can be removed under standard conditions, such as treatment with TFA in DCM, to give C6-substituted benzofuran 63. When X=H, compound 61 can be treated with TFA directly to give C6-substituted benzofuran 63.

Scheme 18

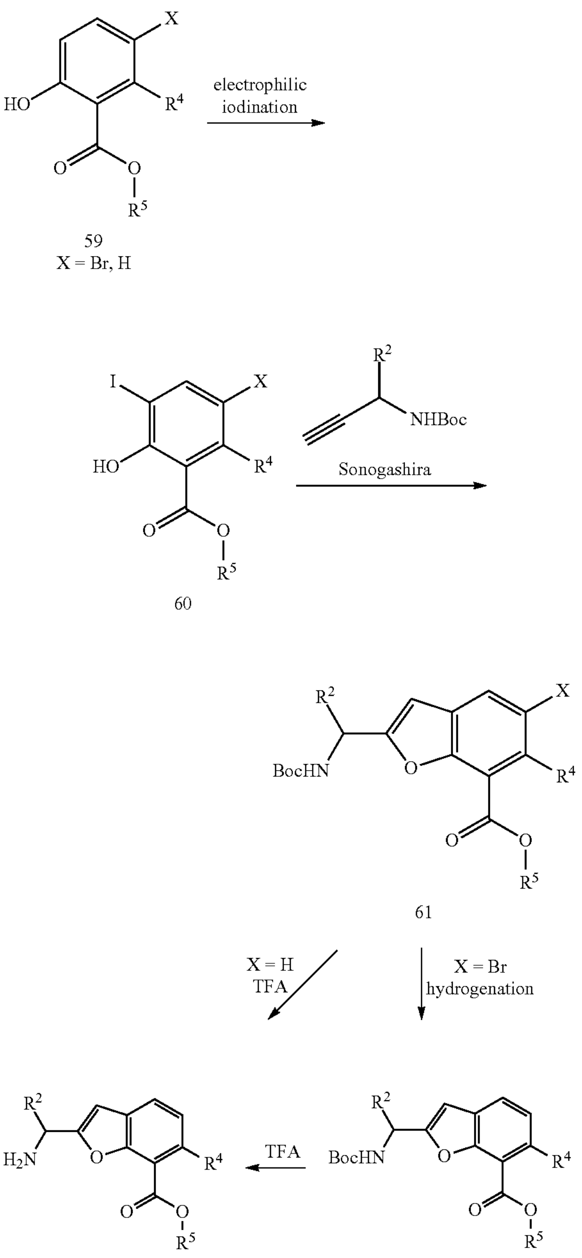

Alternatively, C6-substituted benzofurans can be synthesized as shown in Scheme 19. Phenol 64 can be alkylated with propargyl bromide in the presence of a base such as potassium carbonate to give ether 65. Heating 65 at elevated temperatures either conventionally or in a microwave provides 2-methyl benzofuran 66. Benzylic bromination with a radical brominating reagent such as NBS and an initiator like AIBN gives benzyl bromide 67. Conversion of the bromide to primary amine 63 can be achieved via a variety of synthetic sequences including displacement with sodium azide followed by Staudinger reduction. One skilled in the art would be familiar with other routes to achieve this transformation.

Scheme 19

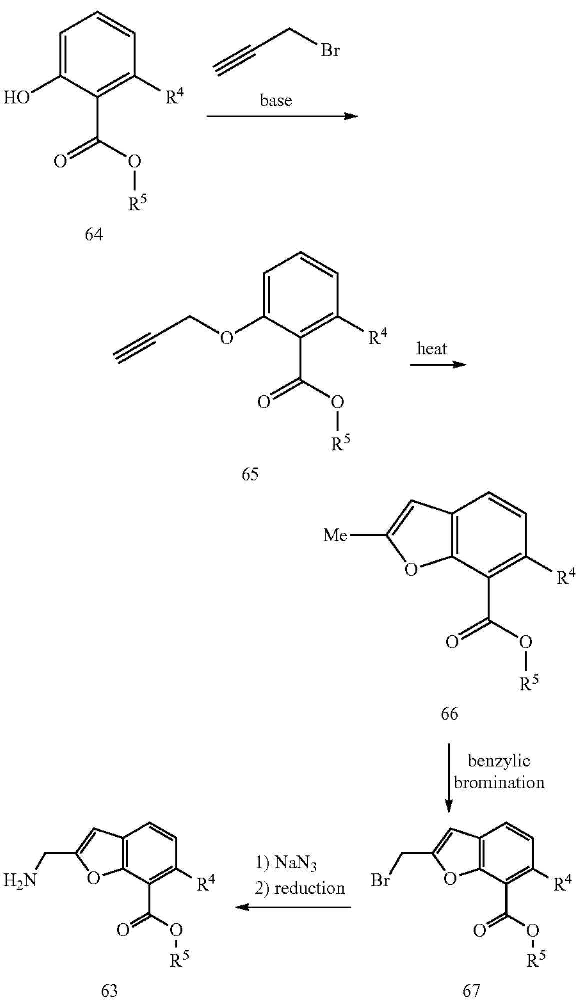

C3-Substituted benzofurans can be synthesized as shown in Scheme 20. Boc-protected benzofuran 68 can undergo iridium catalyzed borylation at C3 in the presence of bis-pinocolatodiboron and an appropriate ligand such as 4,4'-di-tert-butyl-2,2'-bipyridine to give 69. From this intermediate, the boronic ester can be converted to a variety of substituents. Halides 70 and 71 can be prepared upon treatment of the boronic ester 69 with the appropriate cupric halide. A variety of carbon-linked alkyl or aryl groups can be prepared from 69 via transition metal catalyzed cross coupling, for example, Suzuki coupling to give C3-substituted benzofuran 72. Other groups at $R^3$ could be installed from the boronic ester intermediate 69 by methods familiar to one skilled in the art.

Scheme 20

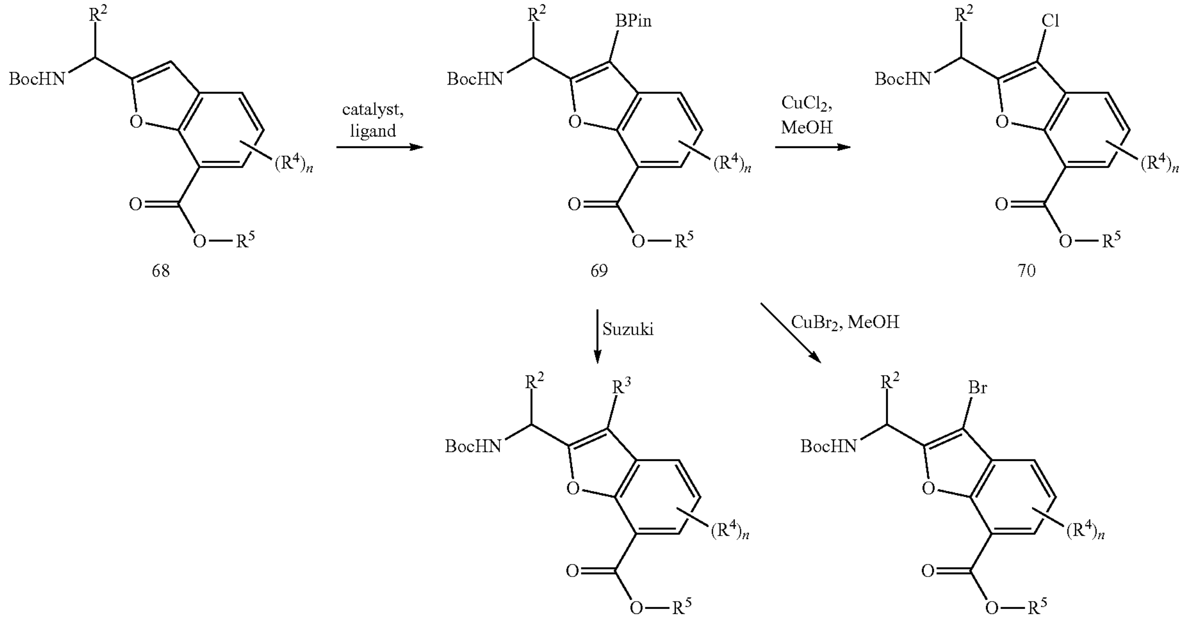

68 69 70 72 71

Benzofuran 79 can be synthesized as outlined in Scheme 21. Phenyl acetic acid 73 can be esterified to give 74 under a variety of conditions including but not limited to trans-esterification with an alcohol in the presence of acid or treatment with TMS-diazomethane. Deprotection of the methoxy group with, for example, $BBr_3$ gives phenol 75. Ester hydrolysis and electrophilic iodination (as outlined in the above schemes) provides 76. Benzofuran formation was again achieved by implementing a Sonogashira coupling with N-Boc progargyl amine to give acid 77. Esterification with the appropriate alcohol followed by deprotection of the Boc-amine gives 2-aminomethyl benzofuran 78. This amine could be coupled to pyrazolopyrimidine acid 38 using standard amide coupling conditions such as BOP and Hunig's base to give benzofuran 79.

Scheme 21

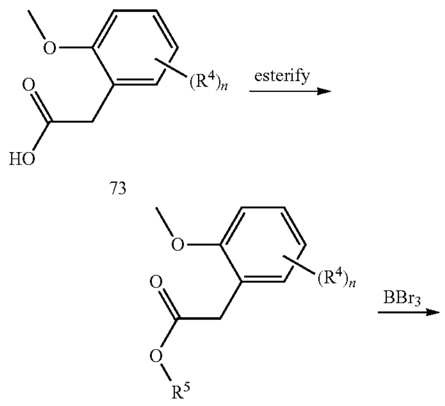

73 74

-continued

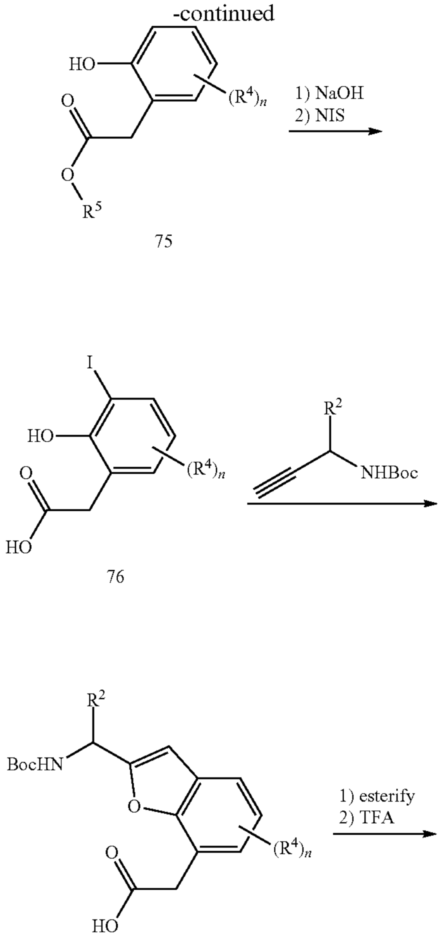

75 76 77

-continued

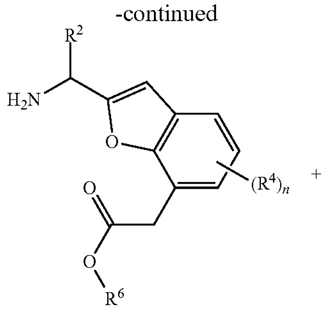

78

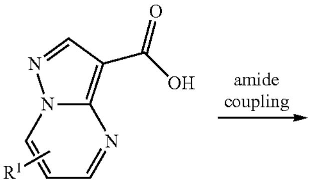

38

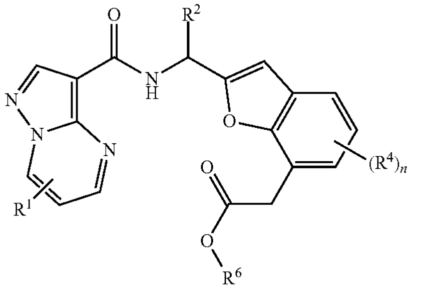

79

Bromobenzofuran intermediate 21 can be made via the route outlined in Scheme 22. Starting from phenol 80, iodination can be performed as before to give 81. Sonogashira coupling with a protected propargyl alcohol such as TBS-protected propargyl alcohol gives benzofuran 82. Deprotection of the TBS group under a variety of standard conditions such as TBAF gives free alcohol 83. Conversion of the alcohol to the bromide or other suitable halide with, for example, $PBr_3$ gives bromide 21.

Scheme 22

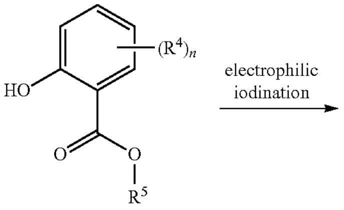

80

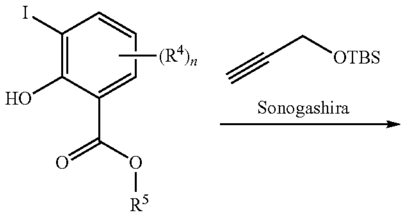

81

-continued

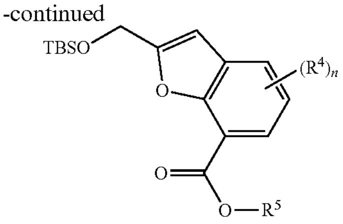

82

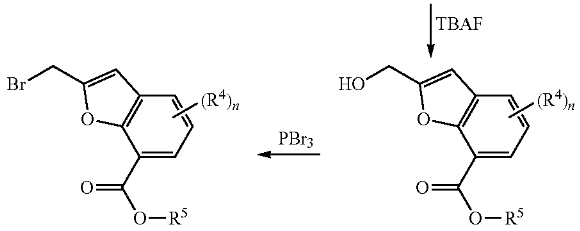

21 83

Acid 32 can be synthesized from diaminopyridine 84 as shown in Scheme 23. Treatment of the diamine with an orthoformate or orthoformate equivalent with or without the presence of an acid can generate imidazole 85. Next, palladium catalyzed carbonylation in the presence of an alcohol can first provide an ester. Subsequent hydrolysis under basic conditions gives acid 32.

Scheme 23

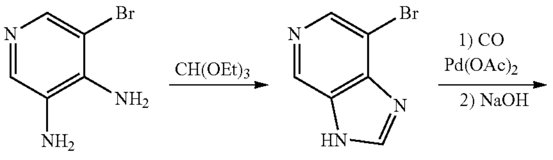

84 85

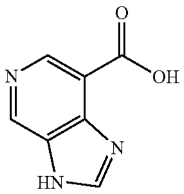

32

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked RediSep© $R_f$ silica gel columns or prepacked RediSep© $R_f$ Gold C18 columns on a CombiFlash $R_f$ machine.

Preparative Reverse Phase (RP) HPLC was performed using a Shimadzu HPLC system with linear gradient elution using $H_2O$/MeCN mixtures buffered with 0.1% trifluoroacetic acid or 10 mM $NH_4OAc$ and detection at 220 nm on one of the following columns:

Method A: XBridge C18 19×200 mm (flow rate=20 mL/min); $H_2O$/MeCN/TFA

Method B: XBridge C18 19×200 mm (flow rate=20 mL/min); $H_2O$/MeCN/$NH_4OAc$

Method C: C18 Phenomenex Luna S5 ODS 30×100 mm (flow rate=30 mL/min); $H_2O$/MeCN/TFA In cases where racemic compounds were initially prepared, enantiomers were separated on a Waters 100 prep HPLC system using the columns and conditions detailed below (detection at 220 nm):

Method D: Column: Chiral AD 30×250 mm; Mobile Phase: 85% $CO_2$/15% IPA with 0.1% DEA; Flow Rate: 100 mL/min.

Method E: Column: Chiral AD 30×250 mm; Mobile Phase: 90% $CO_2$/10% 1:1 MeOH-MeCN; Flow Rate: 100 mL/min.

Method F: Column: Chiral AD 25×3 cm; Mobile Phase: 80% $CO_2$/20% 1:1 IPA-MeCN with 0.1% DEA; Flow Rate: 100 mL/min.

Method G: Column: Chiral IC 25×3 cm; Mobile Phase: 50% $CO_2$/50% MeOH with 0.1% DEA; Flow Rate: 60-85 mL/min.

Method H: Column: Chiral AD 30×250 mm; Mobile Phase: 65% $CO_2$/35% MeOH with 0.1% DEA; Flow Rate: 100 mL/min.

Method I: Column: Chiral AD-H 50×250 mm; Mobile Phase: 54% $CO_2$/46% MeOH; Flow Rate: 320 mL/min.

Method J: Column: Chiral AD 25×3 cm; Mobile Phase: 80% $CO_2$/20% MeOH with 0.1% DEA; Flow Rate: 100 mL/min.

Method K: Column: Chiral AD, 30×250 mm; Mobile Phase: 65% $CO_2$/35% 1:1 IPA-MeCN; Flow Rate: 100 mL/min.

Method L: Column: Chiral AD-H 30×250 mm; Mobile Phase: 6000 $CO_2$/40% MeOH; Flow Rate: 100-200 mL/min.

Method M: Column: Chiral OJ, 30×250 mm; Mobile Phase: 700% $CO_2$/30% IPA with 0.10% DEA; Flow Rate: 100 mL/min.

All final products were characterized by $^1$H NMR, RP HPLC and electrospray ionization (ESI) or atmospheric pressure ionization (API) mass spectrometry (MS). $^1$H NMR spectra were obtained on a 500 MHz or a 400 MHz Bruker instrument. Field strengths are expressed in units of 6 (parts per million, ppm) relative to the solvent peaks, and peak multiplicities are designated as follows: s, singlet; d, doublet; dd, doublet of doublets; t, triplet; q, quartet; sxt, sextet; br, broad; m, multiplet.

Abbreviations

Abbreviations used in the synthetic methods, schemes, and examples generally follow conventions used in the art.

| | |
|---|---|
| Ac | Acetyl |
| AcOH | Acetic acid |
| AIBN | Azobisisobutyronitrile |
| aq | Aqueous |
| Boc | t-Butoxycarbonyl |
| $Boc_2O$ | Di-t-butyl dicarbonate |
| BOP | (Benzotriazol-1-yloxy)tris(dimethylamino)phosphonium hexafluorophosphate |
| Br | Bromide |
| Conc | Concentrated |
| DCE | 1,2-Dichloroethane |
| DCM | Dichloromethane |

-continued

| | |
|---|---|
| DEA | Diethylamine |
| DEAD | Diethyl azodicarboxylate |
| DIAD | Diisopropyl azodicarboxylate |
| DIPEA | N,N-Diisopropylethylamine |
| DMAP | 4-N,N-dimethylaminopyridine |
| DME | 1,2-Dimethoxyethane |
| DMF | N,N-Dimethylformamide |
| DMF-DMA | N,N-Dimethylformamide dimethyl acetate |
| DMSO | Dimethyl sulfoxide |
| dppp | 1,3-Bis(diphenylphosphanyl)propane |
| eq | Equivalents |
| EtOAc | Ethyl acetate |
| EtOH | Ethanol |
| $Et_2O$ | Diethyl ether |
| $Et_3N$ | Triethylamine |
| h | Hour(s) |
| HATU | 1-[Bis(dimethylamino)methylene]-1H-1,2,3-triazolo[4,5-b]pyridinium 3-oxide hexafluorophosphate |
| HPLC | High performance liquid chromatography |
| i-PrOH or IPA | Isopropanol |
| LAH | Lithium aluminum hydride |
| LiOH | Lithium hydroxide |
| m or min | Minute(s) |
| Me | Methyl |
| MeCN | Acetonitrile |
| MeOH | Methanol |
| NaOH | Sodium hydroxide |
| $Na(OAc)_3BH$ | Sodium triacetoxyborohydride |
| NBS | N-Bromosuccinimide |
| $NH_4OAc$ | Ammonium acetate |
| NIS | N-Iodosuccinimide |
| NMP | N-methylpyrrolidinone |
| NMR | Nuclear magnetic resonance |
| Pd/C | Palladium on carbon |
| $POCl_3$ | Phosphorus(III) oxychloride |
| PSI | Pounds per square inch |
| RT or rt | Room temperature |
| Sat | Saturated |
| SFC | Supercritical fluid chromatography |
| t-Bu | Tertiary butyl |
| t-BuOH | Tertiary butanol |
| TBAF | Tetra-n-butylammonium fluoride |
| TEA | Triethylamine |
| TFA | Trifluoroacetic acid |
| THF | Tetrahydrofuran |
| TMS | Trimethylsilyl |

Example 1

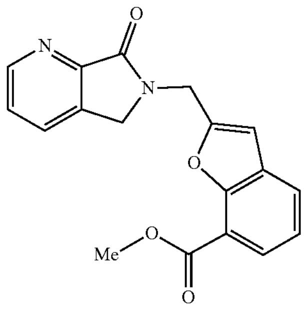 [SMILES: COC(=O)c1cccc2cc(CN3Cc4cccnc4C3=O)oc12]

Methyl 2-((7-oxo-5,7-dihydro-6H-pyrrolo[3,4-b]pyridin-6-yl)methyl)benzofuran-7-carboxylate

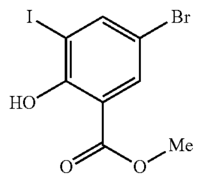 [SMILES: COC(=O)c1cc(Br)cc(I)c1O]

A) Methyl 5-bromo-2-hydroxy-3-iodobenzoate

Methyl 5-bromo-2-hydroxybenzoate (10 g, 43.3 mmol) was dissolved in dry DMF (43 ml). Sodium iodide (7.79 g, 51.9 mmol) was added followed by chloramine-T (12.8 g, 51.9 mmol) (reaction immediately turned dark) and the reaction was stirred at room temperature. The reaction was monitored by LCMS. After 6 hours, the reaction was diluted with water and extracted with ether and then EtOAc. Combined organics were dried with magnesium sulfate, filtered, and concentrated in vacuo. The resulting pale yellow solid was recrystallized from EtOH (30 mL) to give methyl 5-bromo-2-hydroxy-3-iodobenzoate (9.26 g, 25.9 mmol, 59.9% yield). $^1$H NMR (400 MHz, Chloroform-d) δ 11.57 (s, 1H), 8.05 (d, J=2.4 Hz, 1H), 7.98 (d, J=2.4 Hz, 1H), 3.99 (s, 3H); MS (ESI+) m/z=356.9 $(M+H)^+$.

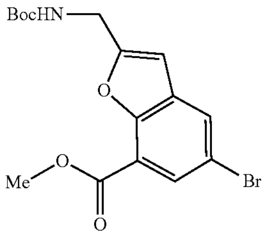 [SMILES: COC(=O)c1cc(Br)cc2cc(CNC(=O)OC(C)(C)C)oc12]

B) Methyl 5-bromo-2-(((tert-butoxycarbonyl)amino)methyl) benzofuran-7-carboxylate Methyl 5-bromo-2-hydroxy-3-iodobenzoate (9.26 g, 25.9 mmol) was dissolved in triethylamine (130 ml) in a 350 mL sealed tube. tert-Butyl prop-2-yn-1-ylcarbamate (3.62 g, 23.4 mmol) was added followed by cuprous iodide (0.247 g, 1.30 mmol) and bis(triphenylphosphine)palladium(II)dichloride (1.82 g, 2.59 mmol). The reaction was degassed with dry nitrogen for 10 minutes before sealing and heating to 85° C. for 2 hours. The reaction was then cooled, filtered, and concentrated in vacuo. The resulting crude residue was purified via ISCO (120 g column, 0-60% EtOAc in hexanes) to give methyl 5-bromo-2-(((tert-butoxycarbonyl)amino)methyl)benzofuran-7-carboxylate (7.52 g, 19.6 mmol, 75% yield). $^1$H NMR (400 MHz, Chloroform-d) δ 8.02 (d, J=2.0 Hz, 1H), 7.84 (d, J=2.0 Hz, 1H), 6.63 (s, 1H), 5.11 (br s, 1H), 4.51 (br d, J=5.9 Hz, 2H), 4.00 (s, 3H), 1.47 (s, 9H); MS (ESI+) m/z=328.1 $(M-tBu+H)^+$.

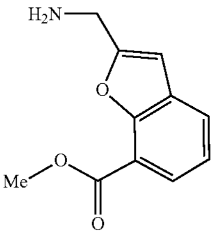 [SMILES: COC(=O)c1cccc2cc(CN)oc12]

C) Methyl 2-(aminomethyl)benzofuran-7-carboxylate

Methyl 5-bromo-2-(((tert-butoxycarbonyl)amino)methyl) benzofuran-7-carboxylate (7.52 g, 19.6 mmol) was taken up in MeOH (78 ml) in a Parr vessel, flushed with nitrogen, and 5% palladium hydroxide on carbon (0.825 g, 0.587 mmol) was added. The reaction was then placed in a Parr apparatus and placed under 45 PSI of hydrogen gas. After 30 minutes, the reaction was filtered over pressed celite and concentrated in vacuo to give crude methyl 2-(((tert-butoxycarbonyl) amino)methyl) benzofuran-7-carboxylate (4.44 g). (NOTE: partial Boc deprotection occurred in this step)

Crude methyl 2-(((tert-butoxycarbonyl)amino)methyl) benzofuran-7-carboxylate (4.44 g, 14.5 mmol) was taken up in DCM (21.8 ml) and cooled to 0° C. over an ice bath. TFA (7.27 ml) was added and the reaction stirred at room temperature. After 3 hours, the reaction was then concentrated in vacuo and azeotroped several times with toluene to remove excess TFA. The crude product was taken up in water, basified with saturated aqueous bicarbonate solution, and extracted with EtOAc followed by 30% iPrOH in chloroform. The combined organics were dried over sodium sulfate, filtered, and concentrated in vacuo to give a solid. This brown solid was found to be methyl 2-(aminomethyl) benzofuran-7-carboxylate (4.16 g, 11.0 mmol, 76% yield). $^1$H NMR (400 MHz, Methanol-$d_4$) δ 8.00 (dd, J=7.7, 1.1 Hz, 1H), 7.92 (dd, J=7.8, 1.2 Hz, 1H), 7.40 (t, J=7.8 Hz, 1H), 7.08 (s, 1H), 4.41 (s, 2H), 4.00 (s, 3H); MS (ESI+) m/z=411.2 $(2M+H)^+$.

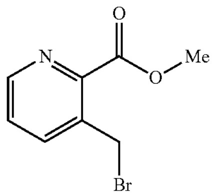 [SMILES: COC(=O)c1ncccc1CBr]

D) Methyl 3-(bromomethyl)picolinate

Methyl 3-methylpicolinate (500 mg, 3.31 mmol) was taken up in $CCl_4$ (13.2 ml). NBS (765 mg, 4.30 mmol) was added followed by AIBN (54.3 mg, 0.331 mmol). The reaction was sealed and heated to 90° C. for 2 hours and then stirred at room temperature overnight. After stirring overnight at room temperature, a precipitate forms, the reaction was filtered, concentrated in vacuo and purified directly via ISCO (24 g column, 0-50% EtOAc in hexanes) to give methyl 3-(bromomethyl)picolinate (454 mg, 1.97 mmol, 59.7% yield) as a clear oil that solidifies upon standing. $^1$H NMR (400 MHz, Chloroform-d) δ 8.67 (dd, J=4.6, 1.5 Hz, 1H), 7.90 (dd, J=7.9, 1.5 Hz, 1H), 7.48 (dd, J=7.9, 4.6 Hz, 1H), 4.95 (s, 2H), 4.04 (s, 3H); MS (ESI+) m/z=232.0 $(M+H)^+$.

E) Methyl 2-((7-oxo-5,7-dihydro-6H-pyrrolo[3,4-b]pyridin-6-yl)methyl)benzofuran-7-carboxylate Methyl 2-(aminomethyl)benzofuran-7-carboxylate (252 mg, 1.23 mmol) was taken up in ethanol (2.73 mL) and TEA (228 μl, 1.64 mmol) was added followed by dropwise addition of a solution of ethyl 3-(bromomethyl)picolinate (200 mg, 0.819 mmol) in 1 mL of ethanol. Once the addition was complete, the reaction was sealed and heated to 100° C. for 1 hour. The reaction was concentrated in vacuo. The crude reaction mixture was taken up in DMF, filtered, and purified via HPLC (Method B) to give the title compound (23.7 mg, 0.074 mmol, 8.97% yield). $^1H$ NMR (500 MHz, DMSO-$d_6$) δ 8.73 (d, J=4.3 Hz, 1H), 8.08 (d, J=7.6 Hz, 1H), 7.89 (d, J=7.6 Hz, 1H), 7.82 (d, J=7.6 Hz, 1H), 7.58 (dd, J=7.8, 4.7 Hz, 1H), 7.35 (t, J=7.6 Hz, 1H), 6.99 (s, 1H), 5.00 (s, 2H), 4.61 (s, 2H), 3.86 (s, 3H); MS (ESI+) m/z=323.3 $(M+H)^+$.

Example 2

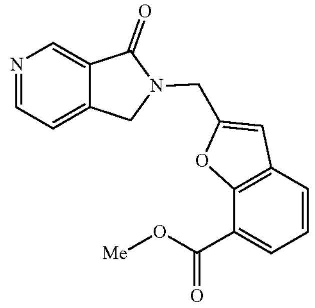 [SMILES: COC(=O)c1cccc2cc(CN3Cc4ccncc4C3=O)oc12]

Methyl 2-((3-oxo-1,3-dihydro-2H-pyrrolo[3,4-c]pyridin-2-yl)methyl)benzofuran-7-carboxylate Methyl 4-methylnicotinate (500 mg, 3.31 mmol) was taken up in $CCl_4$ (15.1 ml). NBS (765 mg, 4.30 mmol) was added followed by AIBN (54.3 mg, 0.331 mmol). The reaction was sealed and heated to 90° C. After 1 hour, the reaction was cooled, filtered, and concentrated in vacuo to give crude methyl 4-(bromomethyl)nicotinate. Material was used directly without further purification.

Methyl 3-(aminomethyl)benzofuran-7-carboxylate (489 mg, 2.38 mmol, Step C of Example 1) was taken up in THE (9.94 mL) and TEA (554 μl, 3.97 mmol) was added. Freshly prepared, crude methyl 4-(bromomethyl)nicotinate was taken up in THE (2 mL) and added dropwise to the benzofuran solution at room temperature and then allowed to stir at room temperature. After 1 hour the reaction was heated to 60° C. for 16 hours. After 16 hours, the reaction was filtered, concentrated in vacuo and purified via ISCO (12 g column, 0-100% EtOAc) to give methyl 2-((3-oxo-1,3-dihydro-2H-pyrrolo[3,4-c]pyridin-2-yl)methyl)benzofuran-7-carboxylate (111 mg, 0.344 mmol, 17.3% yield). $^1H$ NMR (500 MHz, DMSO-$d_6$) δ 8.96 (br s, 1H), 8.77 (br d, J=3.7 Hz, 1H), 7.88 (d, J=7.6 Hz, 1H), 7.83 (d, J=7.3 Hz, 1H), 7.71 (br d, J=4.9 Hz, 1H), 7.36 (t, J=7.6 Hz, 1H), 6.99 (s, 1H), 4.98 (s, 2H), 4.68 (s, 2H), 3.87 (s, 3H); MS (ESI+) m/z=323.2 $(M+H)^+$.

Example 3

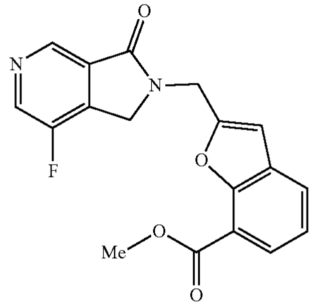 [SMILES: COC(=O)c1cccc2cc(CN3Cc4c(F)cncc4C3=O)oc12]

Methyl 2-((7-fluoro-3-oxo-1,3-dihydro-2H-pyrrolo[3,4-c]pyridin-2-yl)methyl)benzofuran-7-carboxylate

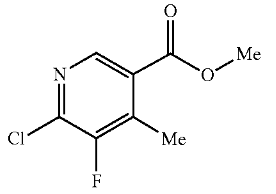 [SMILES: COC(=O)c1cnc(Cl)c(F)c1C]

A) Methyl 6-chloro-5-fluoro-4-methylnicotinate

To a round bottom flask charged with a magnetic stir bar and 2,6-dichloro-5-fluoro-4-methylnicotinic acid (3.66 g, 16.3 mmol) (Reference: *J. Med. Chem.* 1991, 35, 518-525) was added MeOH (163 ml) and Hunig's Base (5.71 ml, 32.7 mmol). To this solution was carefully added palladium on carbon (0.174 g, 1.63 mmol). The resulting reaction mixture was purged with nitrogen and placed under an atmosphere of hydrogen (1 atm) using a balloon. The reaction was allowed to stir at ambient temperature for 48 h. The reaction was then filtered through a bed of celite. The filtrate was concentrated in vacuo to a volume of ~20 ml and diluted with ether. A precipitate formed which was filtered off using a Buchner funnel. The filtrate was concentrated in vacuo to give a mixture of 6-chloro-5-fluoro-4-methylnicotinic acid and a small amount of 5-fluoro-4-methylnicotinic acid which was used directly without further purification (2.5 g total yield).

Crude 6-chloro-5-fluoro-4-methylnicotinic acid (2.5 g, 13.2 mmol) was taken up in DMF (13.2 ml) and $K_2CO_3$ (4.56 g, 33.0 mmol) was added. Methyl iodide (1.24 ml, 19.8 mmol) was then added in one portion at room temperature and the reaction was stirred at room temperature overnight. The reaction was diluted with water and then extracted with EtOAc. The combined organic extracts were dried with sodium sulfate, filtered, and concentrated in vacuo. The crude residue was purified via ISCO (40 g column, 0-50% EtOAc in hexanes) to give methyl 6-chloro-5-fluoro-4-methylnicotinate (1.33 g, 6.5 mmol). $^1H$ NMR (400 MHz, Chloroform-d) δ 8.22 (s, 1H), 3.99 (s, 3H), 2.29 (d, J=2.0 Hz, 3H); MS (ESI+) m/z=204.1 $(M+H)^+$.

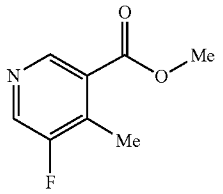 [SMILES: COC(=O)c1cncc(F)c1C]

B) Methyl 5-fluoro-4-methylnicotinate

To a round bottom flask charged with a magnetic stir bar and methyl 6-chloro-5-fluoro-4-methylnicotinate (1.33 g, 6.53 mmol) was added MeOH (65.3 ml) and Hunig's Base (2.28 ml, 13.1 mmol). To this solution was carefully added palladium on carbon (0.070 g, 0.653 mmol). The resulting reaction mixture was purged with nitrogen and placed under an atmosphere of hydrogen gas (1 atm) using a balloon. The reaction was allowed to stir at ambient temperature. After stirring vigorously for 16 hours, the reaction was filtered through a bed of celite and the celite was washed with methanol. The filtrate was concentrated in vacuo to a volume of −25 ml and diluted with EtOAc and extracted with water. The combined organic extracts were dried over sodium sulfate, filtered, and concentrated in vacuo to give methyl 5-fluoro-4-methylnicotinate (930 mg, 5.50 mmol, 84% yield). $^1$H NMR (400 MHz, Chloroform-d) δ 8.89 (s, 1H), 8.50 (d, J=0.9 Hz, 1H), 3.95 (s, 3H), 2.56 (d, J=2.0 Hz, 3H); MS (ESI+) m/z=170.1 $(M+H)^+$.

C) Methyl 2-((7-fluoro-3-oxo-1,3-dihydro-2H-pyrrolo[3,4-c]pyridin-2-yl)methyl)benzofuran-7-carboxylate Methyl 5-fluoro-4-methylnicotinate (50 mg, 0.296 mmol) was taken up in $CCl_4$ (2.96 mL). NBS (63.1 mg, 0.355 mmol) was added followed by AIBN (4.85 mg, 0.030 mmol). The reaction was sealed and heated to 90° C. overnight. After 16 hours, the reaction was cooled, filtered, and concentrated in vacuo to give crude methyl 4-(bromomethyl)-5-fluoronicotinate which was used immediately without further purification.

Methyl 3-(aminomethyl)benzofuran-7-carboxylate (60.4 mg, 0.294 mmol, Step C of Example 1) was taken up in THE (2.94 mL) and TEA (123 μl, 0.883 mmol) was added. The freshly prepared, crude methyl 4-(bromomethyl)-5-fluoronicotinate was taken up in THE (2 mL) and added dropwise to the benzofuran solution at room temperature. The reaction was stirred at room temperature for 30 minutes and then heated to 65° C. After 5 hours, the reaction was concentrated in vacuo, taken up in DMF, filtered, and purified via HPLC (Method B) to give methyl 2-((7-fluoro-3-oxo-1,3-dihydro-2H-pyrrolo[3,4-c]pyridin-2-yl)methyl)benzofuran-7-carboxylate (14.6 mg, 0.041 mmol, 14% yield). $^1$H NMR (500 MHz, DMSO-$d_6$) δ 8.84 (s, 1H), 8.77 (s, 1H), 7.89 (d, J=7.6 Hz, 1H), 7.83 (d, J=7.3 Hz, 1H), 7.36 (t, J=7.6 Hz, 1H), 7.02 (s, 1H), 4.98 (s, 2H), 4.82 (s, 2H), 3.88 (s, 3H); MS (ESI+) m/z=341.1 $(M+H)^+$.

Example 4

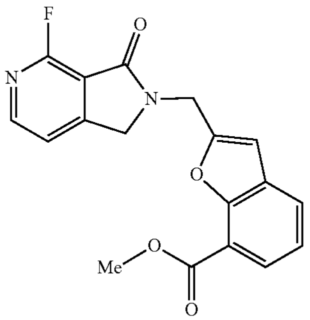 [SMILES: COC(=O)c1cccc2cc(CN3Cc4ccnc(F)c4C3=O)oc12]

Methyl 2-((4-fluoro-3-oxo-1,3-dihydro-2H-pyrrolo[3,4-c]pyridin-2-yl)methyl)benzofuran-7-carboxylate

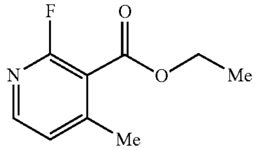 [SMILES: CCOC(=O)c1c(C)ccnc1F]

A) Ethyl 2-fluoro-4-methylnicotinate

Ethyl 2-fluoro-4-iodonicotinate (1.0 g, 3.39 mmol) (Org. Lett. (2005) 7, 1943-1946) was taken up in toluene (7.53 ml), ethanol (0.94 ml), and water (0.941 ml). 2,4,6-Trimethyl-1,3,5,2,4,6-trioxatriborinane (0.57 ml, 4.07 mmol) was added followed by $K_2CO_3$ (0.70 g, 5.08 mmol). The reaction was bubbled with dry nitrogen gas prior to the addition of $Pd(Ph_3P)_4$ (0.98 g, 0.85 mmol) and bubbling continued another 2 minutes before the reaction was sealed and heated to 100° C. overnight. The reaction was concentrated in vacuo and purified directly via ISCO (24 g column, 0-50% EtOAc) to give ethyl 2-fluoro-4-methylnicotinate (288 mg, 1.57 mmol, 46.4% yield). $^1$H NMR (400 MHz, Chloroform-d) δ 8.13 (d, J=5.1 Hz, 1H), 7.10-7.01 (m, 1H), 4.43 (q, J=7.2 Hz, 2H), 2.48 (s, 3H), 1.41 (t, J=7.2 Hz, 3H); MS (ESI+) m/z=184.1 $(M+H)^+$.

B) Methyl 2-((4-fluoro-3-oxo-1,3-dihydro-2H-pyrrolo[3,4-c]pyridin-2-yl)methyl)benzofuran-7-carboxylate Ethyl 2-fluoro-4-methylnicotinate (50 mg, 0.273 mmol) was taken up in $CCl_4$ (2.73 mL). NBS (58.3 mg, 0.328 mmol) was added followed by AIBN (4.48 mg, 0.027 mmol). Reaction was sealed and heated to 90° C. overnight. After heating for 16 hours, the reaction was cooled, filtered, and concentrated to give crude methyl 4-(bromomethyl)-2-fluoronicotinate which was used immediately without further purification.

Methyl 3-(aminomethyl)benzofuran-7-carboxylate (60.4 mg, 0.294 mmol, Step C of Example 1) was taken up in THE (2.94 mL) and TEA (123 μl, 0.883 mmol) was added. Crude methyl 4-(bromomethyl)-2-fluoronicotinate was taken up in THE (2 mL) and added dropwise to the benzofuran solution at room temperature. The reaction was then allowed to stir at room temperature for 30 minutes and then heated to 65° C. After stirring for 8 hours, the reaction was concentrated in vacuo, taken up in DMF, filtered, and purified via HPLC (Method B) to give methyl 2-((4-fluoro-3-oxo-1,3-dihydro-2H-pyrrolo[3,4-c]pyridin-2-yl)methyl)benzofuran-7-carboxylate (15.1 mg, 0.044 mmol, 15.1% yield). $^1$H NMR (500 MHz, DMSO-$d_6$) δ 8.40 (d, J=5.2 Hz, 1H), 7.88 (d, J=7.6 Hz, 1H), 7.83 (d, J=7.0 Hz, 1H), 7.65 (br d, J=2.7 Hz, 1H), 7.36 (t, J=7.6 Hz, 1H), 6.99 (s, 1H), 4.94 (s, 2H), 4.72 (s, 2H), 3.87 (s, 3H); MS (ESI+) m/z=340.9 $(M+H)^+$.

Example 5

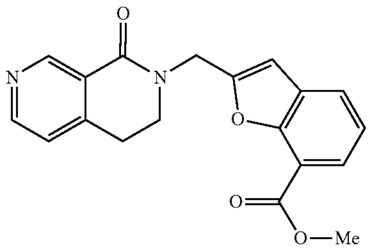 [SMILES: COC(=O)c1cccc2cc(CN3CCc4ccncc4C3=O)oc12]

Methyl 2-((1-oxo-3,4-dihydro-2,7-naphthyridin-2(1H)-yl)methyl)benzofuran-7-carboxylate 3,4-Dihydro-1H-pyrano[3,4-c]pyridin-1-one (30 mg, 0.201 mmol) (WO 2005063768) and methyl 2-(aminomethyl)benzofuran-7-carboxylate (124 mg, 0.603 mmol, Step C of Example 1) were added to a small pressure relief vial and heated neat at 100° C. After 30 minutes, the reaction was heated at 120° C. After 2 hours, the reaction was cooled. The reaction was diluted with 2 mL DMF, filtered, and purified via HPLC (Method A) to give methyl 2-((1-oxo-3,4-dihydro-2,7-naphthyridin-2(1H)-yl)methyl)benzofuran-7-carboxylate (17.3 mg, 0.051 mmol, 25.3% yield). $^1$H NMR (500 MHz, DMSO-$d_6$) δ 9.01 (br s, 1H), 8.67 (br d, J=4.9 Hz, 1H), 7.87 (d, J=7.9 Hz, 1H), 7.82 (d, J=7.3 Hz, 1H), 7.47 (d, J=4.9 Hz, 1H), 7.35 (t, J=7.6 Hz, 1H), 6.98 (s, 1H), 4.95 (s, 2H), 3.87 (s, 3H), 3.78 (t, J=6.6 Hz, 2H), 3.13 (br t, J=6.6 Hz, 2H); MS (ESI+) m/z=337.0 $(M+H)^+$.

Example 6

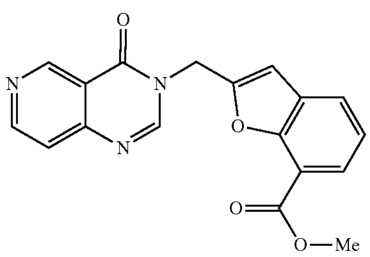 [SMILES: COC(=O)c1cccc2cc(Cn3cnc4ccncc4c3=O)oc12]

Methyl 2-((4-oxopyrido[4,3-d]pyrimidin-3(4H)-yl)methyl)benzofuran-7-carboxylate

4-Aminonicotinic acid (25 mg, 0.18 mmol) was taken up in DMF (180 μl) and 1,1-dimethoxy-N,N-dimethylmethanamine (54 mg, 0.45 mmol) was added in a 2 mL microwave vial. The reaction mixture was heated at 100° C. for 15 minutes in a microwave reactor.

The reaction was then concentrated in vacuo, taken up in 0.6 mL of acetic acid and methyl 2-(aminomethyl)benzofuran-7-carboxylate (37 mg, 0.18 mmol, Step C of Example 1) was added. The reaction was once again sealed and heated at 100° C. in a microwave reactor for 15 minutes. The solvent was evaporated and the crude product was taken up in DMF, filtered, and purified via HPLC (Method B) to give methyl 2-((4-oxopyrido[4,3-d]pyrimidin-3(4H)-yl)methyl)benzofuran-7-carboxylate (20.4 mg, 0.061 mmol, 33.6% yield). $^1$H NMR (500 MHz, DMSO-$d_6$) δ 9.33 (s, 1H), 8.87 (d, J=5.6 Hz, 1H), 8.80 (s, 1H), 7.88 (d, J=7.7 Hz, 1H), 7.83 (d, J=7.5 Hz, 1H), 7.65 (d, J=5.6 Hz, 1H), 7.36 (t, J=7.7 Hz, 1H), 7.02 (s, 1H), 5.47 (s, 2H), 3.86 (s, 3H); MS (ESI+) m/z=335.9 $(M+H)^+$.

Example 7

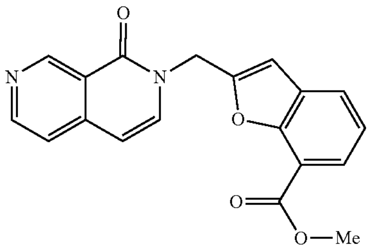 [SMILES: COC(=O)c1cccc2cc(Cn3ccc4ccncc4c3=O)oc12]

Methyl 2-((1-oxo-2,7-naphthyridin-2(1H)-yl)methyl)benzofuran-7-carboxylate

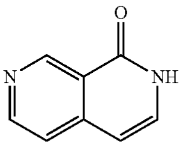 [SMILES: O=c1[nH]ccc2ccncc12]

A) 2,7-Naphthyridin-1(2H)-one

4-Methylnicotinonitrile (250 mg, 2.12 mmol) was taken up DMF (1.4 mL). 1,1-Dimethoxy-N,N-dimethylmethanamine (277 mg, 2.33 mmol) was added and the reaction was heated in a microwave reactor at 100° C. for 15 minutes. The reaction was then concentrated in vacuo. The residue was taken up in $H_2SO_4$ (0.7 mL) and acetic acid (0.7 mL) and the reaction was once again heated to 100° C. for 15 minutes in the microwave (conversion was incomplete by LCMS). The reaction was heated again at 100° C. for 15 minutes in the microwave. The reaction was carefully diluted with water and quenched with ammonium hydroxide. The aqueous mixture was then extracted with chloroform/isopropanol (7:3) three times. The combined organics were dried over sodium sulfate, filtered, and concentrated in vacuo. The crude residue was taken up in DCM/MeOH and purified via ISCO (24 g column, 0-15% MeOH in DCM) to give 2,7-naphthyridin-1(2H)-one (28 mg, 0.19 mmol, 9.1% yield) as a white solid. $^1$H NMR (400 MHz, Methanol-$d_4$) δ

9.40 (s, 1H), 8.66 (d, J=5.6 Hz, 1H), 7.60 (dd, J=5.6, 0.7 Hz, 1H), 7.43 (d, J=7.1 Hz, 1H), 6.65 (d, J=7.2 Hz, 1H); MS (ESI+) m/z=147.0 $(M+H)^+$.

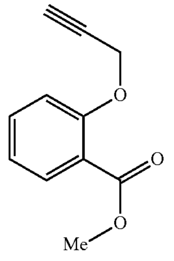

B) Methyl 2-(prop-2-yn-1-yloxy)benzoate

Methyl 2-hydroxybenzoate (3 g, 19.7 mmol) was taken up in DMF (19.7 ml). Cesium carbonate (7.71 g, 23.7 mmol) was added at room temperature. After 15 minutes, 3-bromoprop-1-yne (3.81 g, 25.6 mmol, 80% solution in xylenes) was added and the reaction was stirred at room temperature for 2.5 hours. The reaction was then diluted with water and extracted with EtOAc. The combined organics were washed with half saturated brine twice, dried over sodium sulfate, filtered, and concentrated in vacuo. The crude residue was purified via ISCO (40 g column, 0-50% EtOAc in hexanes) to give methyl 2-(prop-2-yn-1-yloxy)benzoate (3.55 g, 17.7 mmol, 90% yield). $^1$H NMR (400 MHz, Chloroform-d) δ 7.82 (dd, J=7.7, 1.8 Hz, 1H), 7.51-7.45 (m, 1H), 7.14 (d, J=8.3 Hz, 1H), 7.05 (td, J=7.5, 0.9 Hz, 1H), 4.80 (d, J=2.3 Hz, 2H), 3.89 (s, 3H), 2.53 (t, J=2.4 Hz, 1H); MS (ESI+) m/z=191.2 $(M+H)^+$.

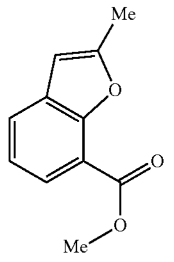 [SMILES: COC(=O)c1cccc2cc(C)oc12]

C) Methyl 2-methylbenzofuran-7-carboxylate

Methyl 2-(prop-2-yn-1-yloxy)benzoate (0.5 g, 2.63 mmol) was taken up in N,N-diethyl aniline (2.63 ml) in a pressure relief vial and cesium fluoride (0.52 g, 3.42 mmol) was added. The reaction was sealed and heated to 200° C. for 3 hours. The reaction was cooled and the solids were decanted away. The resulting liquid was purified directly via silica gel column chromatography (40 g column, 0-20% EtOAc in hexanes) to give methyl 2-methylbenzofuran-7-carboxylate (164 mg, 0.86 mmol, 32.8% yield). $^1$H NMR (400 MHz, Chloroform-d) δ 7.86 (d, J=7.7 Hz, 1H), 7.67 (d, J=7.7 Hz, 1H), 7.24 (t, J=7.7 Hz, 1H), 6.44 (s, 1H), 4.01 (s, 3H), 2.55 (s, 3H); MS (ESI+) m/z=190.8 $(M+H)^+$.

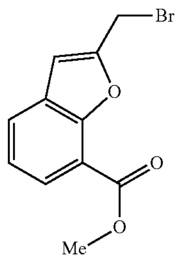 [SMILES: COC(=O)c1cccc2cc(CBr)oc12]

D) Methyl 2-(bromomethyl)benzofuran-7-carboxylate

Methyl 2-methylbenzofuran-7-carboxylate (164 mg, 0.86 mmol) was taken up in $CCl_4$ (8.6 mL) and NBS (161 mg, 0.91 mmol) and AIBN (35.4 mg, 0.22 mmol) were added. The reaction was sealed in a pressure relief vial and heated to 90° C. for 4 hours. The reaction concentrated in vacuo and purified via ISCO (12 g column, 0-30% EtOAc in hexanes) to give methyl 2-(bromomethyl)benzofuran-7-carboxylate (185 mg, 0.69 mmol, 80% yield). $^1$H NMR (400 MHz, CHLOROFORM-d) δ 7.99 (dd, J=7.7, 1.2 Hz, 1H), 7.75 (dd, J=7.7, 1.2 Hz, 1H), 7.31 (t, J=7.7 Hz, 1H), 6.83 (s, 1H), 4.66 (s, 2H), 4.03 (s, 3H).

E) Methyl 2-((1-oxo-2,7-naphthyridin-2(1H)-yl) methyl)benzofuran-7-carboxylate 2,7-Naphthyridin-1(2H)-one (15 mg, 0.103 mmol) was taken up in DMF (1.0 mL) and cooled to 0° C. Sodium hydride (6.2 mg, 0.15 mmol) was added and after 30 minutes, methyl 2-(bromomethyl)benzofuran-7-carboxylate (38.7 mg, 0.14 mmol) was added. The reaction was allowed to warm to room temperature. After 30 minutes, the reaction was quenched with a few drops of saturated aqueous ammonium chloride solution, filtered, and purified directly via HPLC (Method B) to give methyl 2-((1-oxo-2,7-naphthyridin-2(1H)-yl)methyl)benzofuran-7-carboxylate (24.2 mg, 0.072 mmol, 70.5% yield). $^1$H NMR (500 MHz, DMSO-$d_6$) δ 9.37 (s, 1H), 8.73 (d, J=5.4 Hz, 1H), 7.94-7.78 (m, 3H), 7.60 (d, J=5.4 Hz, 1H), 7.35 (t, J=7.7 Hz, 1H), 6.91 (s, 1H), 6.72 (d, J=7.4 Hz, 1H), 5.44 (s, 2H), 3.88 (s, 3H); MS (ESI+) m/z=335.0 $(M+H)^+$.

Example 8

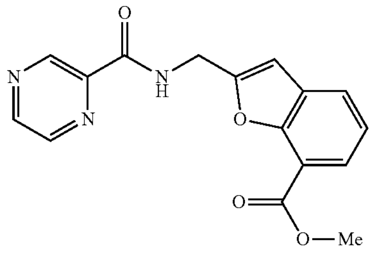 [SMILES: COC(=O)c1cccc2cc(CNC(=O)c3cnccn3)oc12]

Methyl 2-((pyrazine-2-carboxamido)methyl)benzofuran-7-carboxylate

Pyrazine-2-carboxylic acid (11 mg, 0.088 mmol) was dissolved in DMF (365 μl) and then DIPEA (51 μl, 0.292 mmol) and methyl 2-(aminomethyl)benzofuran-7-carboxylate (15 mg, 0.073 mmol, Step C of Example 1) were added. BOP (48.5 mg, 0.11 mmol) was added and the reaction was stirred at room temperature for 1 hour. The reaction was diluted with 1.5 mL DMF, filtered, and purified directly via HPLC (Method B) to give methyl 2-((pyrazine-2-carboxamido)methyl)benzofuran-7-carboxylate (14.7 mg, 0.047 mmol, 64.6% yield). $^1$H NMR (500 MHz, DMSO-$d_6$) δ 9.53-9.36 (m, 1H), 9.22 (s, 1H), 8.88 (d, J=2.3 Hz, 1H), 8.75 (s, 1H), 7.85 (d, J=7.7 Hz, 1H), 7.81 (d, J=7.6 Hz, 1H), 7.33 (t, J=7.7 Hz, 1H), 6.84 (s, 1H), 4.74 (d, J=6.1 Hz, 2H), 3.90 (s, 3H); MS (ESI+) m/z=312.0 (M+H)$^+$.

Examples 9-13

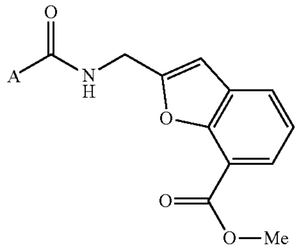

Example 9 to 13 were prepared according to the procedures described in the synthesis of Example 8 from methyl 2-(aminomethyl)benzofuran-7-carboxylate (Step C of Example 1) and the necessary, commercially available carboxylic acid.

| Ex. No. | A | Name | $^1$H NMR | LC/MS (M + H)$^+$ |
|---|---|---|---|---|
| 9 | 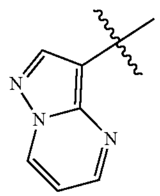 [SMILES: *c1cnn2cccnc12] | Methyl 2-((pyrazolo[1,5-a]pyrimidine-3-carboxamido) methyl) benzofuran-7-carboxylate | $^1$H NMR (500 MHz, DMSO-$d_6$) δ 9.32 (br d, J = 6.7 Hz, 1H), 8.83 (br d, J = 3.1 Hz, 1H), 8.63 (s, 1H), 8.52 (br t, J = 5.6 Hz, 1H), 7.86 (d, J = 7.6 Hz, 1H), 7.81 (d, J = 7.3 Hz, 1H), 7.34 (t, J = 7.6 Hz, 1H), 7.29 (dd, J = 6.9, 4.1 Hz, 1H), 6.86 (s, 1H), 4.81 (br d, J = 5.8 Hz, 2H), 3.89 (s, 3H) | 350.9 |
| 10 | 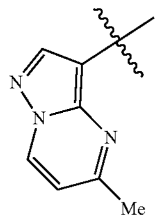 [SMILES: *c1cnn2ccc(C)nc12] | Methyl 2-((5-methylpyrazolo[1,5-a]pyrimidine-3-carboxamido)methyl) benzofuran-7-carboxylate | $^1$H NMR (500 MHz, DMSO-$d_6$) δ 9.07 (br d, J = 7.0 Hz, 1H), 8.57-8.49 (m, 2H), 7.88-7.79 (m, 2H), 7.34 (t, J = 7.7 Hz, 1H), 7.14 (d, J = 7.2 Hz, 1H), 3.90 (s, 3H), 2.66 (s, 3H) | 365.1 |
| 11 | 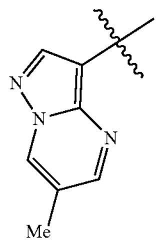 [SMILES: *c1cnn2cc(C)cnc12] | Methyl 2-((6-methylpyrazolo[1,5-a]pyrimidine-3-carboxamido) methyl) benzofuran-7-carboxylate | $^1$H NMR (500 MHz, DMSO-$d_6$) δ 9.09 (br s, 1H), 8.72 (s, 1H), 8.53 (s, 1H), 8.44 (br s, 1H), 7.85 (d, J = 7.7 Hz, 1H), 7.81 (d, J = 7.6 Hz, 1H), 7.34 (t, J = 7.7 Hz, 1H), 6.86 (s, 1H), 4.81 (d, J = 5.9 Hz, 2H), 3.90 (s, 3H), 2.40 (s, 3H) | 365.1 |

-continued

| Ex. No. | A | Name | $^1H$ NMR | LC/MS (M + H)$^+$ |
|---|---|---|---|---|
| 12 | 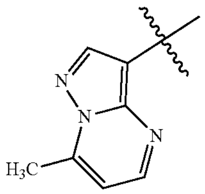 [SMILES: *c1cnn2c(C)ccnc12] | Methyl 2-((7-methylpyrazolo[1,5-a]pyrimidine-3-carboxamido) methyl) benzofuran-7-carboxylate | $^1H$ NMR (500 MHz, DMSO-$d_6$) δ 8.70 (br d, J = 4.3 Hz, 1H), 8.63 (s, 1H), 8.57 (br s, 1H), 7.86 (br d, J = 7.7 Hz, 1H), 7.81 (br d, J = 7.7 Hz, 1H), 7.34 (t, J = 7.7 Hz, 1H), 7.21 (br d, J = 3.8 Hz, 1H), 6.86 (s, 1H), 4.82 (br d, J = 5.7 Hz, 2H), 3.93-3.88 (s, 3H), 2.81 (s, 3H) | 365.2 |
| 13 | 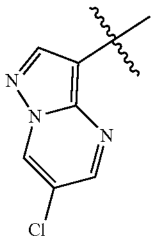 [SMILES: *c1cnn2cc(Cl)cnc12] | Methyl 2-((6-chloropyrazolo[1,5-a]pyrimidine-3-carboxamido) methyl) benzofuran-7-carboxylate | $^1H$ NMR (500 MHz, DMSO-$d_6$) δ 9.77-9.74 (m, 1H), 8.91-8.88 (m, 1H), 8.67 (s, 1H), 8.45 (br t, J = 5.8 Hz, 1H), 7.87 (d, J = 7.6 Hz, 1H), 7.82 (d, J = 7.6 Hz, 1H), 7.35 (t, J = 7.6 Hz, 1H), 6.87 (s, 1H), 4.80 (d, J = 5.8 Hz, 2H), 3.90 (s, 3H) | 385.1 |

Example 14

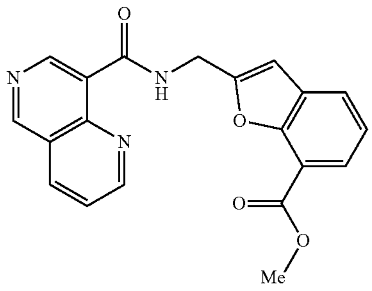 [SMILES: COC(=O)c1cccc2cc(CNC(=O)c3cncc4cccnc34)oc12]

Methyl 2-((1,6-naphthyridine-8-carboxamido) methyl)benzofuran-7-carboxylate

A mixture of 1,6-naphthyridine-8-carboxylic acid, HCl (10 mg, 0.047 mmol), methyl 2-(aminomethyl)benzofuran-7-carboxylate, TFA (15.16 mg, 0.047 mmol, Step C of Example 1), HATU (18.05 mg, 0.047 mmol) and Hunig's Base (0.033 mL, 0.190 mmol) in DMF (0.5 mL) was stirred at rt for 3 h. The reaction was quenched with 1:1 DMF/AcOH and purified by preparative LC/MS (Method B) to give the title compound (2.3 mg, 5.95 μmol, 12.53% yield). $^1H$ NMR (500 MHz, DMSO-$d_6$) δ 10.90 (br s, 1H), 9.63-9.59 (m, 1H), 9.39 (s, 1H), 9.30 (br d, J=2.8 Hz, 1H), 8.79 (d, J=6.9 Hz, 1H), 7.91-7.85 (m, 2H), 7.83 (d, J=7.7 Hz, 1H), 7.36 (t, J=7.7 Hz, 1H), 6.97 (s, 1H), 4.93 (d, J=5.7 Hz, 2H), 3.19 (br s, 3H); MS (ESI+) m/z=362.0 (M+H)$^+$.

Example 15

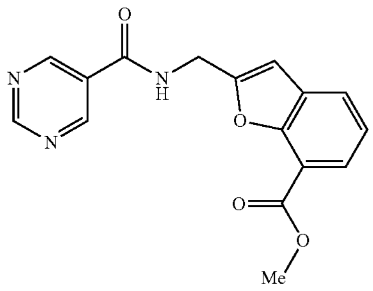 [SMILES: COC(=O)c1cccc2cc(CNC(=O)c3cncnc3)oc12]

Methyl 2-((pyrimidine-5-carboxamido)methyl)benzofuran-7-carboxylate

A mixture of methyl 2-(aminomethyl)benzofuran-7-carboxylate, TFA salt (10 mg, 0.031 mmol, Step C of Example 1), pyrimidine-5-carboxylic acid (7.77 mg, 0.063 mmol), HATU (23.82 mg, 0.063 mmol) and Hunig's base (0.022 mL, 0.125 mmol) in DMF (1 mL) was stirred at room temperature for 14 hours. The reaction mixture was quenched with 1:1 DMF/AcOH and purified by preparative HPLC (Method B). The appropriate fractions were combined and dried via centrifugal evaporation to afford the title compound (7.2 mg, 73.8% yield). $^1H$ NMR (500 MHz, DMSO-$d_6$) δ 9.59 (br t, J=5.3 Hz, 1H), 9.32 (s, 1H), 9.20 (s, 2H), 7.92-7.79 (m, 2H), 7.36 (t, J=7.6 Hz, 1H), 6.94 (s, 1H), 4.72 (d, J=5.5 Hz, 2H), 3.65 (br s, 3H); MS (ESI+) m/z=312.0 (M+H)$^+$.

Example 16

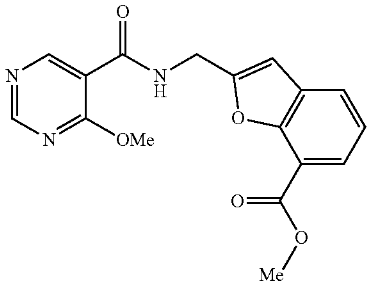 [SMILES: COC(=O)c1cccc2cc(CNC(=O)c3cncnc3OC)oc12]

Methyl 2-((4-methoxypyrimidine-5-carboxamido) methyl)benzofuran-7-carboxylate

A mixture of methyl 2-(aminomethyl)benzofuran-7-carboxylate, TFA (10 mg, 0.031 mmol, Step C of Example 1), 4-methoxypyrimidine-5-carboxylic acid (9.7 mg, 0.063 mmol), HATU (23.8 mg, 0.063 mmol) and Hunig's base (0.022 mL, 0.125 mmol) in DMF (1 mL) was stirred at room temperature for 1 hour. The reaction mixture was quenched with 1:1 DMF/AcOH and purified by preparative HPLC (Method B). The appropriate fractions were combined and dried via centrifugal evaporation to afford the title compound (7.8 mg, 71.0% yield). $^1$H NMR (500 MHz, DMSO-$d_6$) δ 8.99 (br t, J=5.5 Hz, 1H), 8.90 (s, 1H), 8.85 (s, 1H), 7.89 (d, J=7.3 Hz, 1H), 7.83 (d, J=7.6 Hz, 1H), 7.36 (t, J=7.8 Hz, 1H), 6.88 (s, 1H), 4.70 (d, J=5.8 Hz, 2H), 4.06 (s, 3H), 3.91 (s, 3H); MS (ESI+) m/z=341.9 $(M+H)^+$.

Example 17

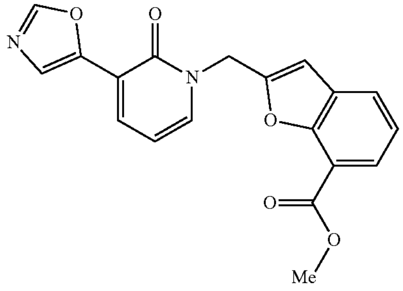 [SMILES: COC(=O)c1cccc2cc(Cn3cccc(-c4cnco4)c3=O)oc12]

Methyl 2-((3-(oxazol-5-yl)-2-oxopyridin-1(2H)-yl) methyl)benzofuran-7-carboxylate

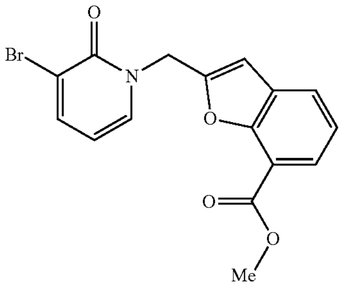 [SMILES: COC(=O)c1cccc2cc(Cn3cccc(Br)c3=O)oc12]

A) Methyl 2-((3-bromo-2-oxopyridin-1(2H)-yl) methyl)benzofuran-7-carboxylate

A mixture of 3-bromopyridin-2(1H)-one (14 mg, 0.080 mmol), methyl 2-(bromomethyl)benzofuran-7-carboxylate (23.8 mg, 0.089 mmol, Step D of Example 7) and $K_2CO_3$ (33.4 mg, 0.241 mmol) in DMF (400 μl) was stirred at room temperature for 4 hours. The mixture was loaded on a 24 g silica gel column and eluted with 0-30% EtOAc in hexanes to afford the product. (27.8 mg, 95% yield). MS (ESI+) m/z=364.0 $(M+H)^+$.

B. Methyl 2-((3-(oxazol-5-yl)-2-oxopyridin-1(2H)-yl)methyl)benzofuran-7-carboxylate A mixture of methyl 2-((3-bromo-2-oxopyridin-1(2H)-yl) methyl)benzofuran-7-carboxylate (10 mg, 0.028 mmol), 5-(4,4,5,5-tetramethyl-1,3,2-dioxaborolan-2-yl)oxazole (5.4 mg, 0.028 mmol) and cesium carbonate (18.0 mg, 0.055 mmol) in DMF (270 μl) and water (5.4 μl) was degassed. $Pd(Ph_3P)_4$ (3.2 mg, 2.76 μmol) was added and the reaction was heated to 100° C. for 2.5 hours. The reaction mixture was quenched with 1:1 DMF/AcOH and purified by preparative HPLC (Method B). The appropriate fractions were combined and dried via centrifugal evaporation to afford the title compound (4.4 mg, 45.5% yield). $^1$H NMR (500 MHz, DMSO-$d_6$) δ 8.45 (s, 1H), 7.97 (br dd, J=14.2, 6.9 Hz, 1H), 7.90 (d, J=7.6 Hz, 1H), 7.85 (d, J=7.6 Hz, 1H), 7.75 (s, 1H), 7.37 (t, J=7.6 Hz, 1H), 6.90-6.88 (m, 1H), 6.91 (s, 1H), 6.57 (t, J=6.9 Hz, 1H), 5.50 (s, 2H), 3.90 (s, 3H); MS (ESI+) m/z=351.0 $(M+H)^+$.

Example 18

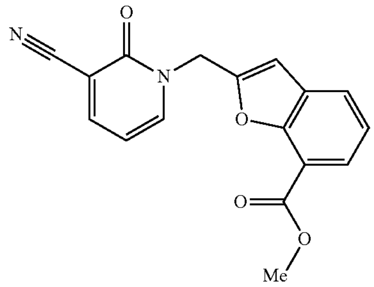 [SMILES: COC(=O)c1cccc2cc(Cn3cccc(C#N)c3=O)oc12]

Methyl 2-((3-cyano-2-oxopyridin-1(2H)-yl)methyl) benzofuran-7-carboxylate

A mixture of methyl 2-((3-bromo-2-oxopyridin-1(2H)-yl) methyl)benzofuran-7-carboxylate (10 mg, 0.028 mmol, Step A of Example 17) and zinc cyanide (3.9 mg, 0.033 mmol) in DMF (550 μl) was degassed. $Pd(Ph_3P)_4$ (3.2 mg, 2.76 μmol) was added and the reaction was heated to 100° C. for 18 hours. The reaction mixture was quenched with 1:1 DMF/AcOH and purified by preparative HPLC (Method B). The appropriate fractions were combined and dried via centrifugal evaporation to afford the title compound (5 mg, 58.7% yield). $^1$H NMR (500 MHz, DMSO-$d_6$) δ 8.26-8.22 (m, 1H), 8.20 (dd, J=7.0, 1.8 Hz, 1H), 7.90 (d, J=7.3 Hz, 1H), 7.85 (d, J=7.6 Hz, 1H), 7.38 (t, J=7.8 Hz, 1H), 6.95 (s, 1H), 6.53 (t, J=7.0 Hz, 1H), 5.41 (s, 2H), 3.89 (s, 3H); MS (ESI+) m/z=309.4 $(M+H)^+$.

Example 19

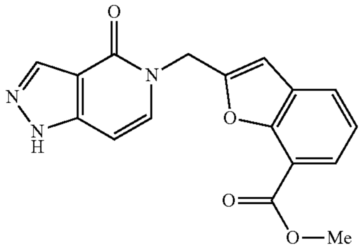 [SMILES: COC(=O)c1cccc2cc(Cn3ccc4[nH]ncc4c3=O)oc12]

Methyl 2-({4-oxo-1H,4H,5H-pyrazolo[4,3-c]pyridin-5-yl}methyl)-1-benzofuran-7-carboxylate

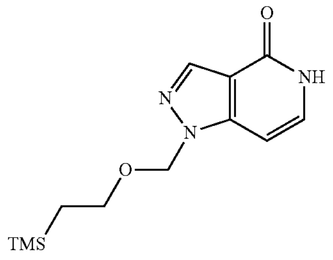 [SMILES: C[Si](C)(C)CCOCn1ncc2c(=O)[nH]ccc21]

A) 1-((2-(Trimethylsilyl)ethoxy)methyl)-1,5-dihydro-4H-pyrazolo[4,3-c]pyridin-4-one To a suspension of 1,5-dihydro-4H-pyrazolo[4,3-c]pyridin-4-one (80 mg, 0.592 mmol) and cesium carbonate (212 mg, 0.651 mmol) in DMF (1.48 mL), was added 2-(trimethylsilyl)ethoxymethyl chloride (1.03 mL, 5.92 mmol) dropwise. The reaction mixture was stirred at room temperature for 3 hours under nitrogen and then poured into water and extracted with a EtOAc three times. The organic phase was washed with saturated aqueous NaCl solution, dried over $Na_2SO_4$, filtered and concentrated to dryness. The residue was purified by silica gel chromatography (40 g column) eluting with 0-10% MeOH/DCM to give the product (61 mg, 38.8% yield). MS (ESI+) m/z=266.1 $(M+H)^+$.

B) Methyl 2-((3-(oxazol-5-yl)-2-oxopyridin-1(2H)-yl)methyl)benzofuran-7-carboxylate A mixture of 1-((2-(trimethylsilyl)ethoxy)methyl)-1,5-dihydro-4H-pyrazolo[4,3-c]pyridin-4-one (20 mg, 0.075 mmol), methyl 2-(bromomethyl)benzofuran-7-carboxylate (42.6 mg, 0.158 mmol, Step D of Example 7) and $K_2CO_3$ (31.2 mg, 0.226 mmol) in DMF (377 μl) was stirred at room temperature for 24 hours. The mixture was diluted with water (5 mL) and extracted with EtOAc three times. The organic layer was separated, concentrated and the residue was taken up in DCM (377 μl). 4M HCl in dioxane (94 μl, 0.377 mmol) was added and the reaction was stirred at room temperature for 18 hours. The solvent was evaporated and the residue was purified by preparative HPLC (Method A).

The appropriate fractions were combined and dried via centrifugal evaporation to afford the title compound as a TFA salt (7.9 mg, 23.59% yield). $^1H$ NMR (500 MHz, DMSO-$d_6$) δ 8.08 (br s, 1H), 8.04-8.03 (m, 1H), 7.86 (br d, J=7.7 Hz, 1H), 7.82 (br d, J=7.7 Hz, 1H), 7.60 (br s, 1H), 7.35 (t, J=7.7 Hz, 1H), 6.80 (s, 1H), 6.62 (d, J=7.4 Hz, 1H), 5.38 (br s, 2H), 3.90 (s, 3H); MS (ESI+) m/z=324.2 $(M+H)^+$.

Example 20

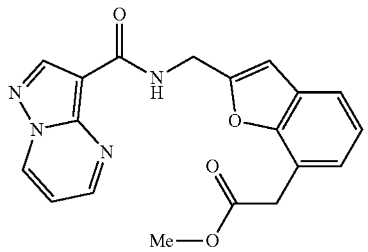 [SMILES: COC(=O)Cc1cccc2cc(CNC(=O)c3cnn4cccnc34)oc12]

Methyl 2-(2-((pyrazolo[1,5-a]pyrimidine-3-carboxamido)methyl)benzofuran-7-yl)acetate To a solution of methyl 2-(5-bromo-2-((pyrazolo[1,5-a]pyrimidine-3-carboxamido)methyl)benzofuran-7-yl)acetate (40 mg, 0.090 mmol, Example 80) in DME (1 mL) was added sodium carbonate (0.135 mL, 0.271 mmol), methylboronic acid (16.21 mg, 0.271 mmol), and tetrakis(triphenylphosphine)palladium(0) (10.4 mg, 9.02 μmol). The reaction mixture was degassed by bubbling Ar through it and heated at 80° C. for 18 h. The reaction mixture was concentrated and purified with prep HPLC (Method B) to give the desired des-bromo byproduct (1.7 mg, 17% yield). $^1H$ NMR (500 MHz, DMSO-$d_6$) δ 9.29 (br d, J=7.0 Hz, 1H), 8.82 (br d, J=3.1 Hz, 1H), 8.62 (s, 1H), 8.48 (br t, J=5.5 Hz, 1H), 7.49 (br d, J=7.0 Hz, 1H), 7.28 (dd, J=6.9, 4.1 Hz, 1H), 7.21-7.11 (m, 2H), 6.77 (s, 1H), 4.75 (br d, J=5.8 Hz, 2H), 3.92 (s, 2H), 3.58 (s, 3H); MS (ESI+) m/z=365.2 $(M+H)^+$.

Example 21

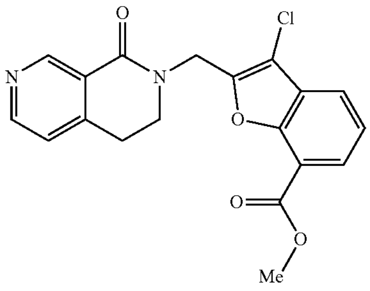 [SMILES: COC(=O)c1cccc2c(Cl)c(CN3CCc4ccncc4C3=O)oc12]

Methyl 3-chloro-2-((1-oxo-3,4-dihydro-2,7-naphthyridin-2(1H)-yl)methyl)benzofuran-7-carboxylate

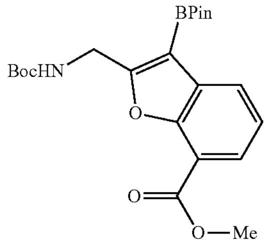

A) Methyl-2-(aminomethyl)-5-methyl-3-(4,4,5,5-tetramethyl-1,3,2-dioxaborolan-2-yl)benzofuran-7-carboxylate A vial was charged with methyl 2-(((tert-butoxycarbonyl) amino)methyl) benzofuran-7-carboxylate (0.5 g, 1.638 mmol, Step B of Example 1), 4,4'-di-tert-butyl-2,2'-bipyridine (0.044 g, 0.164 mmol), bis(pinacolato)diboron (0.474 g, 1.876 mmol) and (1,5-cyclooctadiene)(methoxy)iridium (I) dimer (0.065 g, 0.098 mmol) in hexane (15 ml). The reaction mixture was purged with nitrogen and heated to 80° C. for 16 hours. The reaction mixture was filtered and concentrated in vacuo. The crude product mixture was purified by a silica gel ISCO 40 g column eluting with 0-20% ethyl acetate in hexanes over a 15 minute gradient. The appropriate fractions were isolated and concentrated in vacuo to afford the product (0.373 g, 53% yield) as a solid. $^1$H NMR (400 MHz, Chloroform-d) δ 8.09 (dd, J=7.8, 1.2 Hz, 1H), 7.97-7.85 (m, 1H), 7.34-7.25 (m, 1H), 4.73 (br d, J=4.6 Hz, 2H), 4.02-3.95 (m, 3H), 1.47 (s, 9H), 1.41-1.35 (m, 12H); MS (ESI+) m/z=376.1 $(M-55+H)^+$.

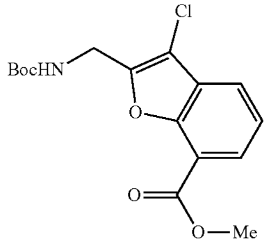 [SMILES: COC(=O)c1cccc2c(Cl)c(CNC(=O)OC(C)(C)C)oc12]

B) Methyl 2-(((tert-butoxycarbonyl)amino)methyl)-3-chlorobenzofuran-7-carboxylate A vial was charged with a mixture of methyl 2-(((tert-butoxycarbonyl) amino)methyl)-3-(4,4,5,5-tetramethyl-1,3,2-dioxaborolan-2-yl)benzofuran-7-carboxylate (113 mg, 0.262 mmol), copper(II) chloride (70.5 mg, 0.524 mmol) and MeOH (3 mL). The reaction mixture was heated to 50° C. for 16 hours. The solution was filtered through celite and concentrated in vacuo. The crude product mixture was purified by a silica gel ISCO 12 g column eluting with 0-100% ethyl acetate in hexanes over a 15 minute gradient. The appropriate fractions were isolated and concentrated in vacuo to afford the product (0.040 g, 45% yield) as a solid. 1H NMR (400 MHz, Chloroform-d) δ 7.99 (dd, J=7.7, 1.2 Hz, 1H), 7.74 (dd, J=7.8, 1.3 Hz, 1H), 7.36 (t, J=7.7 Hz, 1H), 4.67-4.50 (m, 2H), 4.06-3.96 (m, 3H), 1.48 (s, 9H); MS (ESI+) m/z=376.1 $(M-55+H)^+$.

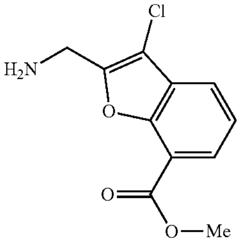 [SMILES: COC(=O)c1cccc2c(Cl)c(CN)oc12]

C) Methyl 2-(aminomethyl)-3-chlorobenzofuran-7-carboxylate, TFA

To a solution of the above intermediate (0.04 g, 0.118 mmol) in $CH_2Cl_2$ (2 mL) was added TFA (0.5 mL). The reaction mixture was stirred at room temperature for 2 hours. The reaction mixture was concentrated in vacuo to afford the product methyl 2-(aminomethyl)-3-chlorobenzofuran-7-carboxylate as a TFA salt (41 mg, 89% yield). $^1$H NMR (400 MHz, CHLOROFORM-d) δ 8.11-7.97 (m, 1H), 7.86 (br d, J=7.8 Hz, 1H), 7.55-7.40 (m, 1H), 4.44 (s, 2H), 4.04-3.91 (m, 3H); MS (ESI+) m/z=223.0 $(M-16)^+$.

D) Methyl 3-chloro-2-((1-oxo-3,4-dihydro-2,7-naphthyridin-2(1H)-yl)methyl)benzofuran-7-carboxylate A mixture of 3,4-dihydro-1H-pyrano[3,4-c]pyridin-1-one, HCl (20 mg, 0.108 mmol) (WO2005063768), methyl 2-(aminomethyl)-3-chlorobenzofuran-7-carboxylate, TFA salt (38.1 mg, 0.108 mmol) and pyridine (216 μl) was heated at 110° C. for 2 hours. The reaction was diluted with MeOH. The crude material was purified via preparative HPLC (Method C) to yield the title compound (5.78 mg, 14% yield). $^1$H NMR (400 MHz, Methanol-$d_4$) δ 9.05 (s, 1H), 8.59 (d, J=5.1 Hz, 1H), 8.00 (dd, J=7.6, 1.2 Hz, 1H), 7.86-7.79 (m, 1H), 7.49-7.42 (m, 1H), 7.42-7.37 (m, 1H), 5.09 (s, 2H), 3.98-3.91 (m, 3H), 3.90-3.84 (m, 2H), 3.23-3.12 (m, 2H); MS (ESI+) m/z=371.1 $(M+H)^+$.

Example 22

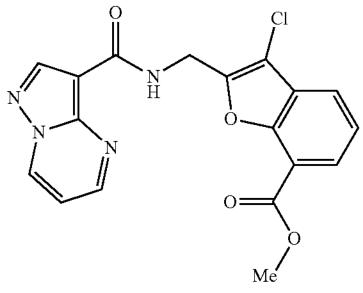 [SMILES: COC(=O)c1cccc2c(Cl)c(CNC(=O)c3cnn4cccnc34)oc12]

Methyl 3-chloro-2-((pyrazolo[1,5-a]pyrimidine-3-carboxamido)methyl)benzofuran-7-carboxylate To a suspension of pyrazolo[1,5-a]pyrimidine-3-carboxylic acid (15 mg, 0.092 mmol) and BOP (48.8 mg, 0.110 mmol) in DMF (2 mL) was added methyl 2-(aminomethyl)-3-chlorobenzofuran-7-carboxylate, TFA salt (32.5 mg, 0.092 mmol, Step C of Example 21) and DIPEA (0.064 mL, 0.368 mmol). The reaction was stirred at room temperature for 2 hours. The reaction was quenched with water, and a precipitate resulted. The precipitate was collected via filtration, and then dissolved in 2 mL of DMF for purification. The crude material was purified via preparative HPLC (Method B) to afford the product (19.6 mg, 54.6% yield). $^{1}$H NMR (500 MHz, DMSO-$d_6$) δ 9.30-9.27 (m, 1H), 8.84 (d, J=2.7 Hz, 1H), 8.61 (s, 1H), 8.54 (br t, J=5.6 Hz, 1H), 7.93 (d, J=7.3 Hz, 1H), 7.85 (d, J=7.6 Hz, 1H), 7.49 (t, J=7.6 Hz, 1H), 7.28 (dd, J=6.7, 4.3 Hz, 1H), 4.87 (d, J=5.8 Hz, 2H), 3.86 (s, 3H); MS (ESI+) m/z=385.3 (M+H)$^+$.

Example 23 and Example 24

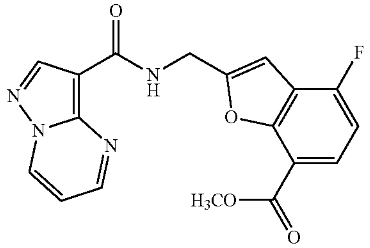

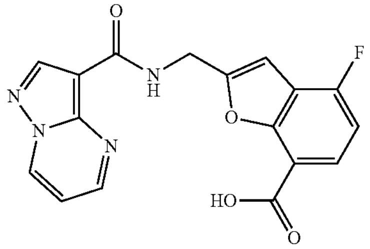

Methyl 4-fluoro-2-((pyrazolo[1,5-a]pyrimidine-3-carboxamido)methyl)-benzofuran-7-carboxylate and 4-Fluoro-2-((pyrazolo[1,5-a]pyrimidine-3-carboxamido)methyl)benzofuran-7-carboxylic acid To a solution of 2,2,2-trifluoroethyl 4-fluoro-2-((pyrazolo[1,5-a]pyrimidine-3-carboxamido)methyl)benzofuran-7-carboxylate (137 mg, 0.314 mmol, Example 222) in THE (4 mL) and MeOH (4 mL) was added a 3M aqueous sodium hydroxide solution (0.314 mL, 0.942 mmol). The reaction mixture was stirred at rt for 1 h and then neutralized with 4 N HCl in 1,4-dioxane to pH ~2. The mixture was concentrated in vacuo. The residue was dissolved in MeOH and purified by prep HPLC (Method B) to give methyl 4-fluoro-2-((pyrazolo[1,5-a]pyrimidine-3-carboxamido)methyl)-benzofuran-7-carboxylate, Example 23 (47 mg, 40% yield) and 4-fluoro-2-((pyrazolo[1,5-a]pyrimidine-3-carboxamido)methyl)benzofuran-7-carboxylic acid, Example 24 (40 mg, 41% yield).

Example 23: $^{1}$H NMR (500 MHz, DMSO-$d_6$) δ 9.28 (br d, J=6.9 Hz, 1H), 8.84 (br d, J=3.4 Hz, 1H), 8.62 (s, 1H), 8.50 (br s, 1H), 7.89 (dd, J=8.3, 5.5 Hz, 1H), 7.28 (dd, J=6.8, 4.3 Hz, 1H), 7.20 (t, J=8.9 Hz, 1H), 6.95 (s, 1H), 4.84 (br d, J=5.8 Hz, 2H), 3.90 (s, 3H); MS (ESI+) m/z=369.0 (M+H)$^+$.

Example 24: $^{1}$H NMR (500 MHz, DMSO-$d_6$) δ 9.23 (br d, J=6.5 Hz, 1H), 8.81 (br d, J=2.9 Hz, 1H), 8.60 (s, 1H), 8.54-8.47 (m, 1H), 7.85 (br dd, J=8.1, 5.8 Hz, 1H), 7.26 (br s, 1H), 7.15 (br t, J=8.8 Hz, 1H), 6.92 (s, 1H), 4.81 (br d, J=5.7 Hz, 2H); MS (ESI+) m/z=355.0 (M+H)$^+$.

Example 25

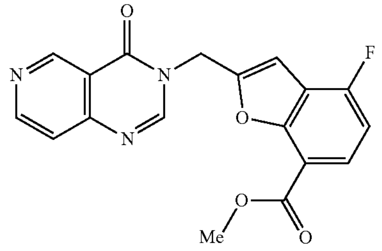 [SMILES: COC(=O)c1ccc(F)c2cc(Cn3cnc4ccncc4c3=O)oc12]

Methyl 4-fluoro-2-((4-oxo-3,4-dihydropyrido[4,3-d]pyrimidine-3-carboxamido)methyl)benzofuran-7-carboxylate To a solution of 2,2,2-trifluoroethyl 4-fluoro-2-((4-oxopyrido[4,3-d]pyrimidin-3(4H)-yl)methyl)benzofuran-7-carboxylate (20 mg, 0.047 mmol, Example 226) in MeOH (1 mL) and THE (1 mL) was added 3 M aqueous sodium hydroxide solution (0.047 mL, 0.142 mmol). The reaction mixture was stirred at room temperature for 2 hours, and acidified to pH 2-3 with 1 N aqueous HCl solution. The reaction mixture was concentrated in vacuo and purified by prep HPLC (Method C) to give the desired acid (10 mg). MS (ESI+) m/z=340.0 (M+H)$^+$.

To a solution of the above benzofuran-7-carboxylic acid (10 mg, 0.029 mmol) in DCM (1 mL) and MeOH (0.2 mL) at room temperature was added (diazomethyl)trimethylsilane, 2 M in diethyl ether (0.029 mL, 0.059 mmol) dropwise. The reaction mixture was stirred for 1 h, and concentrated in vacuo. The residue was purified with prep HPLC, Method B, to give the desired product (2.8 mg, 27%). $^{1}$H NMR (500 MHz, DMSO-$d_6$) δ 9.33 (s, 1H), 8.87 (d, J=5.5 Hz, 1H), 8.77 (s, 1H), 7.90 (dd, J=8.5, 5.2 Hz, 1H), 7.65 (d, J=5.8 Hz, 1H), 7.22 (t, J=8.9 Hz, 1H), 7.17 (s, 1H), 5.48 (s, 2H), 3.85 (s, 3H); MS (ESI+) m/z=354.0 (M+H)$^+$.

Example 26 and Example 27

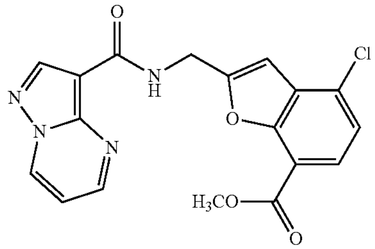

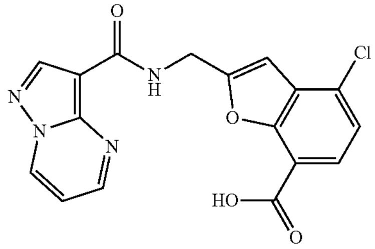

Methyl 4-chloro-2-((pyrazolo[1,5-a]pyrimidine-3-carboxamido)methyl)benzofuran-7-carboxylate To the solution of N-((7-bromo-4-chlorobenzofuran-2-yl)methyl)pyrazolo[1,5-a]pyrimidine-3-carboxamide (21 mg, 0.052 mmol, Step F of Example 227) in DMSO (4 mL) was added methanol (33.2 mg, 1.035 mmol), palladium(II) acetate (1.2 mg, 5.18 μmol), 1,3-bis(diphenylphosphanyl)propane, dppp (2.1 mg, 5.18 μmol), and triethylamine (0.072 mL, 0.518 mmol). The reaction mixture was degassed by bubbling Ar through and heated at 80° C. under a CO atmosphere for 4 hours. The reaction mixture was concentrated in vacuo. The residue was purified by prep HPLC (Method A) to give both Example 26 (7.9 mg, 39% yield) and Example 27 (3.1 mg, 16% yield).

Example 26: $^1$H NMR (500 MHz, DMSO-$d_6$) δ 9.30 (br d, J=7.0 Hz, 1H), 8.84 (br d, J=2.7 Hz, 1H), 8.64 (s, 1H), 8.59 (s, 1H), 7.84 (d, J=8.2 Hz, 1H), 7.46 (d, J=8.2 Hz, 1H), 7.29 (dd, J=7.0, 4.3 Hz, 1H), 6.89 (s, 1H), 4.83 (br d, J=5.8 Hz, 2H), 3.90 (s, 3H); MS (ESI+) m/z=385.0 $(M+H)^+$.

Example 27: $^1$H NMR (500 MHz, DMSO-$d_6$) δ 9.25 (br s, 1H), 8.82 (br s, 1H), 8.61 (s, 1H), 8.52 (br s, 1H), 7.77 (br d, J=8.2 Hz, 1H), 7.39 (br d, J=8.2 Hz, 1H), 7.30-7.23 (m, 1H), 6.85 (s, 1H), 4.82 (br d, J=5.6 Hz, 2H); MS (ESI+) m/z=371.0 $(M+H)^+$.

Example 28

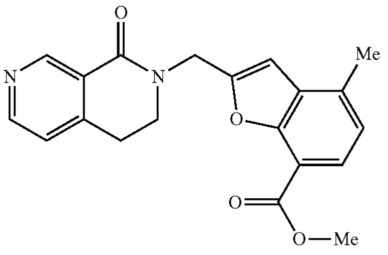 [SMILES: COC(=O)c1ccc(C)c2cc(CN3CCc4ccncc4C3=O)oc12]

Methyl 4-methyl-2-((1-oxo-3,4-dihydro-2,7-naphthyridin-2(1H)-yl)methyl)benzofuran-7-carboxylate

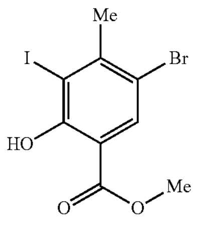 [SMILES: COC(=O)c1cc(Br)c(C)c(I)c1O]

A) Methyl 5-bromo-2-hydroxy-3-iodo-4-methylbenzoate

To a solution of methyl 5-bromo-2-hydroxy-4-methylbenzoate (1.2 g, 4.90 mmol) in N,N-dimethylformamide (10 mL) was added sodium iodide (0.88 g, 5.88 mmol), followed by slow addition of chloramine T trihydrate (1.52 g, 5.39 mmol). The resulting mixture was stirred at room temperature for 2 hours. The reaction mixture was diluted with ethyl acetate and 1 N aqueous HCl solution. The organic layer was separated and then washed with brine and $Na_2S_2O_3$ solution. The combined organics were dried over $MgSO_4$ and filtered. The filtrate was concentrated in vacuo to give a light yellow solid.

The solid was mixed with MeOH and the resulting white solid was filtered to give crude methyl 5-bromo-2-hydroxy-3-iodo-4-methylbenzoate (1.4 g, 77% yield). $^1$H NMR (499 MHz, Chloroform-d) δ 11.67 (s, 1H), 8.05 (s, 1H), 3.99 (s, 3H), 2.75 (s, 3H); MS (ESI+) m/z=370.8 $(M+H)^+$.

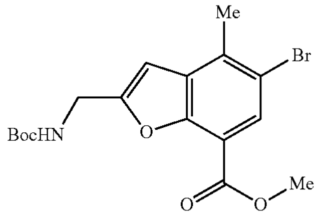 [SMILES: COC(=O)c1cc(Br)c(C)c2cc(CNC(=O)OC(C)(C)C)oc12]

B) Methyl 5-bromo-2-(((tert-butoxycarbonyl)amino)methyl)-4-methylbenzofuran-7-carboxylate The reaction mixture of methyl 5-bromo-2-hydroxy-3-iodo-4-methylbenzoate (1.6 g, 4.31 mmol), tert-butyl prop-2-yn-1-ylcarbamate (0.77 g, 4.96 mmol), TEA (12.0 mL, 86 mmol), copper(I) iodide (0.082 g, 0.43 mmol) in DMF (10 mL) was purged with nitrogen stream for 5 mins, then bis(triphenylphosphine)palladium(II) chloride (0.30 g, 0.43 mmol) was added. The resulting mixture was heated at 80° C. for 3 hours. The reaction mixture was diluted with ethyl acetate and saturated aqueous $NaHCO_3$ solution. The organic layer was separated, washed with brine, dried over $MgSO_4$, filtered, and concentrated in vacuo. The crude product was dissolved in DCM and then purified by silica gel column chromatography (80 gram column, eluted with 0-30% EtOAc in hexanes) to give methyl 5-bromo-2-(((tert-butoxycarbonyl)amino)methyl)-4-methylbenzofuran-7-carboxylate (0.55 g, 32%). $^1$H NMR (400 MHz, Chloroform-d) δ 8.08 (s, 1H), 6.68 (s, 1H), 4.51 (d, J=6.1 Hz, 2H), 3.99 (s, 3H), 2.57 (s, 3H), 1.48 (s, 9H); MS (ESI+) m/z=344.0 $(M-54)^+$.

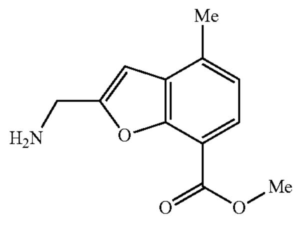 [SMILES: COC(=O)c1ccc(C)c2cc(CN)oc12]

C) Methyl 2-(aminomethyl)-4-methylbenzofuran-7-carboxylate

The reaction mixture of methyl 5-bromo-2-(((tert-butoxycarbonyl) amino)methyl)-4-methylbenzofuran-7-carboxylate (0.55 g, 1.38 mmol) and palladium hydroxide on carbon (0.14 g, 0.21 mmol) in MeOH (15 mL) was evacuated and filled with hydrogen (balloon). The reaction was stirred under hydrogen atmosphere at room temperature overnight. The reaction mixture was filtered and concentrated in vacuo. To the residue was added DCM (6 mL) and TFA (1.5 mL, 19.5 mmol). The reaction mixture was stirred at room temperature for 3 hours. The reaction mixture was concentrated in vacuo and the residue was mixed with saturated aqueous $NaHCO_3$ solution and ethyl acetate. The organic layer was separated, washed with brine, dried over $MgSO_4$, filtered, and concentrated in vacuo to give methyl 2-(aminomethyl)-4-methylbenzofuran-7-carboxylate (0.21 g, 69% yield). $^1H$ NMR (400 MHz, Chloroform-d) δ 7.81 (d, J=7.8 Hz, 1H), 7.06 (dd, J=7.8, 0.7 Hz, 1H), 6.61 (s, 1H), 4.07 (d, J=0.8 Hz, 2H), 3.99 (s, 3H), 2.53 (s, 3H); MS (ESI+) m/z=439.2 $(M+H)^+$.

D) Methyl 4-methyl-2-((1-oxo-3,4-dihydro-2,7-naphthyridin-2(1H)-yl)methyl)benzofuran-7-carboxylate 3,4-Dihydro-1H-pyrano[3,4-c]pyridin-1-one (25 mg, 0.17 mmol) (WO 2005063768) and methyl 2-(aminomethyl)-4-methylbenzofuran-7-carboxylate (73.5 mg, 0.33 mmol) were added to a pressure relief vial and heated neat at 120° C. After heating for 4 hours, the reaction was cooled, taken up in 2 mL DMF, filtered and purified via HPLC (Method B) to give methyl 4-methyl-2-((1-oxo-3,4-dihydro-2,7-naphthyridin-2(1H)-yl)methyl)benzofuran-7-carboxylate (17.2 mg, 0.049 mmol, 29.3% yield). $^1H$ NMR (500 MHz, DMSO-$d_6$) δ 8.99 (s, 1H), 8.64 (br d, J=4.6 Hz, 1H), 7.75 (d, J=7.6 Hz, 1H), 7.40 (d, J=4.6 Hz, 1H), 7.17 (d, J=7.9 Hz, 1H), 7.04 (s, 1H), 4.95 (s, 2H), 3.87 (s, 3H), 3.78 (t, J=6.4 Hz, 2H), 3.12 (br t, J=6.4 Hz, 2H), 2.53 (s, 3H); MS (ESI+) m/z=351.1 $(M+H)^+$.

Example 29

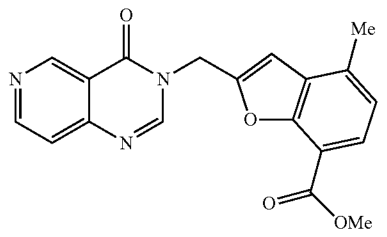 [SMILES: COC(=O)c1ccc(C)c2cc(Cn3cnc4ccncc4c3=O)oc12]

Methyl 4-methyl-2-((4-oxopyrido[4,3-d]pyrimidin-3(4H)-yl)methyl)benzofuran-7-carboxylate 4-Aminonicotinic acid (28.4 mg, 0.205 mmol) and N,N-dimethylformamide dimethyl acetal (0.092 mL, 0.684 mmol) were taken up in DMF (0.3 mL) in a 0.2-0.5 mL of microwave vial. The vial was sealed and heated to 100° C. for 15 min in a microwave reactor. After, 15 minutes, the reaction was removed from the reactor, cooled, and concentrated in vacuo. To the residue was added 1 mL of acetic acid and methyl 2-(aminomethyl)-4-methylbenzofuran-7-carboxylate (30 mg, 0.137 mmol, Step C in Example 28). The vial was re-sealed and heated at 120° C. in a microwave for another 15 minutes. The reaction mixture was cooled and concentrated in vacuo. The residue was diluted with water and extracted with EtOAc. The organics were separated, dried over sodium sulfate, filtered, and concentrated in vacuo. The residue was dissolved in MeOH, filtered, and purified via HPLC (method B) to give the title compound (3 mg, 6.0% yield). $^1H$ NMR (500 MHz, DMSO-$d_6$) δ 9.35 (s, 1H), 8.89 (d, J=5.5 Hz, 1H), 8.80 (s, 1H), 7.76 (d, J=7.9 Hz, 1H), 7.67 (d, J=5.8 Hz, 1H), 7.18 (d, J=7.9 Hz, 1H), 7.09 (s, 1H), 5.48 (s, 2H), 3.86 (s, 3H), 2.50 (s, 3H); MS (ESI+) m/z=350.2 $(M+H)^+$.

Example 30

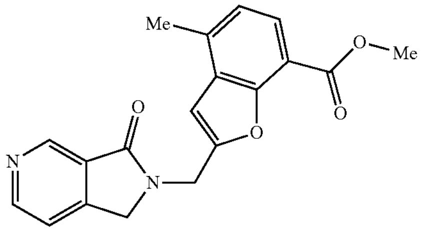 [SMILES: COC(=O)c1ccc(C)c2cc(CN3Cc4ccncc4C3=O)oc12]

Methyl 4-methyl-2-((3-oxo-1,3-dihydro-2H-pyrrolo[3,4-c]pyridin-2-yl)methyl)benzofuran-7-carboxylate To a solution of methyl 2-(aminomethyl)-4-methylbenzofuran-7-carboxylate (51.5 mg, 0.235 mmol, Step C of Example 28) in THE (1 mL) was added TEA (0.182 mL, 1.304 mmol). Subsequently, a solution of crude methyl 2-(bromomethyl)nicotinate (150 mg, 0.130 mmol, prepared as in Example 2) in THE (1 mL) was added. The reaction mixture was stirred at room temperature for 0.6 hours, then heated at 70° C. for 2 hours. After 2 hours, the reaction was cooled and concentrated in vacuo. The residue was taken up in DMSO, filtered, and purified via HPLC (method B) to give the title compound (2.6 mg, 4.4%). $^1H$ NMR (500 MHz, DMSO-$d_6$) δ 9.00 (s, 1H), 8.80 (d, J=4.9 Hz, 1H), 7.82-7.71 (m, 2H), 7.30-7.00 (m, 2H), 4.99 (s, 2H), 4.73 (s, 2H), 3.86 (s, 3H), 2.56 (s, 3H); MS (ESI+) m/z=337.1 $(M+H)^+$.

Example 31

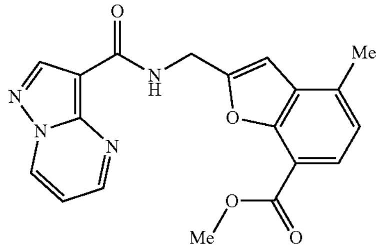 [SMILES: COC(=O)c1ccc(C)c2cc(CNC(=O)c3cnn4cccnc34)oc12]

Methyl 4-methyl-2-((pyrazolo[1,5-a]pyrimidine-3-carboxamido)methyl)benzofuran-7-carboxylate To a solution of 4-methyl-2-((pyrazolo[1,5-a]pyrimidine-3-carboxamido)methyl)benzofuran-7-carboxylic acid (25 mg, 0.071 mmol, Example 127) in DCM (1 mL) and MeOH (0.2 mL) at room temperature was added (diazomethyl)trimethylsilane, 2 M in diethyl ether (0.071 mL, 0.143 mmol) dropwise. The reaction mixture was stirred for 4 hours. The reaction mixture was concentrated and the residue was purified with prep HPLC, Method B, to give the desired product (4.6 mg, 18% yield). $^1H$ NMR (500 MHz, DMSO-$d_6$) δ 9.27 (br d, J=7.0 Hz, 1H), 8.85 (br d, J=3.1 Hz, 1H), 8.65 (s, 1H), 8.60 (br t, J=5.5 Hz, 1H), 7.75 (d, J=7.9 Hz, 1H), 7.30 (dd, J=6.9, 4.1 Hz, 1H), 7.18 (br d, J=7.6 Hz, 1H), 6.92 (s, 1H), 4.82 (br d, J=5.8 Hz, 2H), 3.88 (s, 3H), 2.51 (s, 3H); MS (ESI+) m/z=365.0 $(M+H)^+$.

Example 32

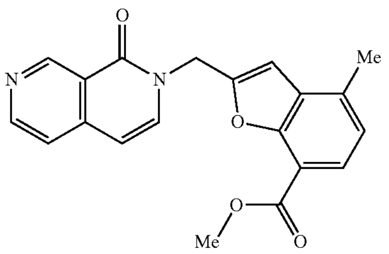 [SMILES: COC(=O)c1ccc(C)c2cc(Cn3ccc4ccncc4c3=O)oc12]

Methyl 4-methyl-2-((1-oxo-1,2-dihydro-2,7-naphthyridine-2-carboxamido)methyl)benzofuran-7-carboxylate To a solution of 4-methyl-2-((1-oxo-2,7-naphthyridin-2(1H)-yl)methyl)benzofuran-7-carboxylic acid (30 mg, 0.090 mmol, Step B of Example 232) in DCM (1 mL) and MeOH (0.2 mL) at room temperature was added (diazomethyl)trimethylsilane, 2 M in diethyl ether (0.090 mL, 0.179 mmol) dropwise. The reaction mixture was stirred for 2 h. The reaction mixture was purified with prep HPLC (Method A) to afford the product (5.4 mg, 17% yield). $^1$H NMR (500 MHz, DMSO-$d_6$) δ 7.88 (d, J=7.3 Hz, 1H), 7.75 (d, J=7.9 Hz, 1H), 7.65 (br s, 1H), 7.27 (br s, 1H), 7.17 (br d, J=7.6 Hz, 1H), 7.07 (br s, 1H), 6.98 (s, 1H), 6.76 (d, J=7.3 Hz, 1H), 5.44 (s, 2H), 3.86 (s, 3H), 2.50 (s, 3H); MS (ESI+) m/z=349.0 $(M+H)^+$.

Example 33

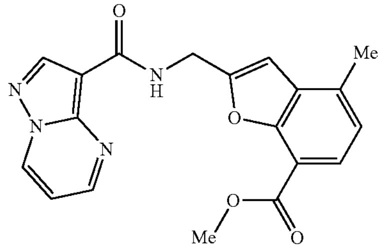 [SMILES: COC(=O)c1ccc(C)c2cc(CNC(=O)c3cnn4cccnc34)oc12]

Methyl 4-methoxy-2-((pyrazolo[1,5-a]pyrimidine-3-carboxamido)methyl)benzofuran-7-carboxylate

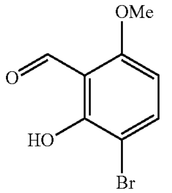 [SMILES: COc1ccc(Br)c(O)c1C=O]

A) 3-Bromo-2-hydroxy-6-methoxybenzaldehyde

A mixture of paraformaldehyde (3.64 g, 121 mmol), magnesium chloride (7.69 g, 81 mmol) and triethylamine (11.3 mL, 81 mmol) was stirred at rt for 10 minutes. Then, 2-bromo-5-methoxyphenol (8.2 g, 40.4 mmol) was added. The reaction mixture was stirred at 85° C. for 4 hours and then concentrated in vacuo. The residue was dissolved in hydrochloric acid (10% aqueous solution, 50 mL) and stirred at room temperature for 30 minutes. Ethyl acetate (200 mL) was added and the layers were separated. The organic layer was dried over sodium sulfate and concentrated in vacuo. The residue was purified through ISCO, 330 column, eluting with 0-20% EtOAc in hexane to give the desired product as a light yellow solid (4.34 g, 47%). $^1$H NMR (400 MHz, Methanol-$d_4$) δ 9.81 (br s, 1H), 7.62-7.49 (m, 2H), 3.81 (s, 3H); MS (ESI+) m/z=230.8 $(M+H)^+$.

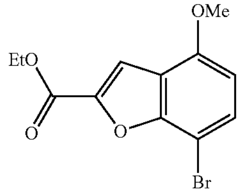 [SMILES: CCOC(=O)c1cc2c(OC)ccc(Br)c2o1]

B) Ethyl 7-bromo-4-methoxybenzofuran-2-carboxylate

To a solution of 3-bromo-2-hydroxy-6-methoxybenzaldehyde (1.0 g, 4.33 mmol) in DMF (5 mL) was added ethyl 2-bromoacetate (2.17 g, 13.0 mmol) and cesium carbonate (4.9 g, 15.1 mmol). The reaction mixture was stirred at 120° C. for 8 h. After cooling to rt, the reaction was acidified with 1 N aqueous HCl solution to pH 2-3 and then extracted with EtOAc, three times. The combined organic extracts were dried over sodium sulfate, filtered, concentrated, and purified with ISCO, 120 g column, eluting with 0-30% EtOAc in hexanes to give the product as a light yellow solid. (0.52 g, 40%). $^1$H NMR (400 MHz, Chloroform-d) δ 7.68 (s, 1H), 7.52 (d, J=8.5 Hz, 1H), 6.62 (d, J=8.6 Hz, 1H), 4.46 (q, J=7.1 Hz, 2H), 3.96 (s, 3H), 1.45 (t, J=7.1 Hz, 3H); MS (ESI+) m/z=298.9 $(M+H)^+$.

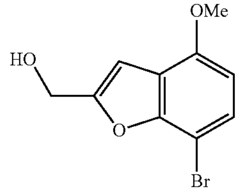 [SMILES: COc1ccc(Br)c2oc(CO)cc12]

C) (7-Bromo-4-methoxybenzofuran-2-yl)methanol

To a stirred solution of ethyl 7-bromo-4-methoxybenzofuran-2-carboxylate (520 mg, 1.74 mmol) in THE (20 mL) at −30° C. under N2 was added lithium aluminum hydride (1.74 mL, 1.74 mmol) dropwise via syringe over 5 min. The reaction mixture was stirred at this temperature for 2 hours. The reaction was quenched with Fieser Method (at −30° C. add 0.5 ml of water, add 0.5 ml of 15% NaOH, add 0.5 ml of water, and stirred at room temperature for 30 min). Some anhydrous magnesium sulfate was added and the mixture was stirred for 15 min and then filtered over celite. The filtrate was concentrated to give the desired product as a white solid (440 mg, 98%). $^1$H NMR (400 MHz, CHLOROFORM-d) δ 7.35 (d, J=8.5 Hz, 1H), 6.83 (s, 1H), 6.58 (d, J=8.5 Hz, 1H), 4.80 (s, 2H), 3.93 (s, 3H), 2.23 (br s, 1H).

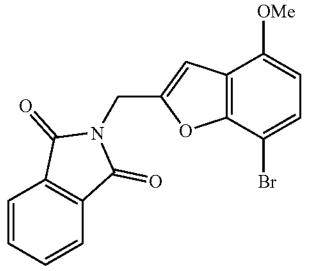 [SMILES: COc1ccc(Br)c2oc(CN3C(=O)c4ccccc4C3=O)cc12]

D) 2-((7-Bromo-4-methoxybenzofuran-2-yl)methyl) isoindoline-1,3-dione

To a stirred solution of (7-bromo-4-methoxybenzofuran-2-yl)methanol (0.5 g, 1.95 mmol) and phthalimide (0.286 g, 1.95 mmol) in THE (20 mL) under N2 was added triphenylphosphine (0.612 g, 2.33 mmol) and DIAD (0.454 mL, 2.33 mmol). After stirring at rt for 18 h, the reaction was concentrated in vacuo. The residue was purified by flash chromatography, with a 80 g ISCO column, eluting with 0-30% EtOAc in hexanes to give the desired product as a white solid (0.54 g, 72%). $^1$H NMR (400 MHz, CHLOROFORM-d) δ 7.92 (dd, J=5.5, 3.0 Hz, 2H), 7.77 (dd, J=5.5, 3.0 Hz, 2H), 7.32 (d, J=8.6 Hz, 1H), 6.84 (s, 1H), 6.55 (d, J=8.5 Hz, 1H), 5.06 (d, J=0.9 Hz, 2H), 3.90 (s, 3H).

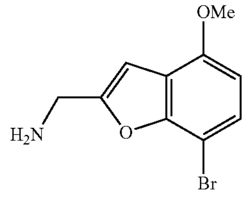 [SMILES: COc1ccc(Br)c2oc(CN)cc12]

E) 2-((7-Bromo-4-methoxybenzofuran-2-yl)methyl) isoindoline-1,3-dione

To a stirred suspension of 2-((7-bromo-4-methoxybenzofuran-2-yl)methyl)isoindoline-1,3-dione (0.47 g, 1.22 mmol) in ethanol (20 mL) was added hydrazine (0.873 mL, 9.74 mmol). The reaction was heated at 50° C. with stirring. After 15 min the reaction mixture reached a homogeneous solution. After 10 more min, a white solid formed gradually. After stirring at 50° C. for 45 min, the reaction mixture was cooled to rt. $Et_2O$ (50 mL) was added and the mixture was stirred for 10 min. The solid was removed by filtration and washed with $Et_2O$. The filtrate was concentrated to give an oil. To the oil was added 50 ml of ether. Some more solid formed. The solid was removed by filtration and washed with ether. The filtrate was concentrated to give the desired product as an oil (0.30 g, 96%). $^1$H NMR (400 MHz, Chloroform-d) δ 7.29 (d, J=8.5 Hz, 1H), 6.67 (s, 1H), 6.54 (d, J=8.5 Hz, 1H), 3.98 (d, J=0.7 Hz, 2H), 3.90 (s, 3H), 1.74 (br s, 2H); MS (ESI+) m/z=238.9 $(M-NH_2)^+$.

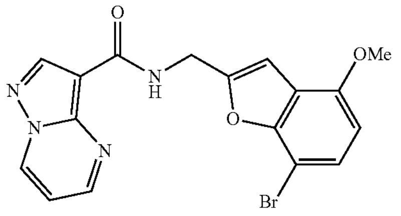 [SMILES: COc1ccc(Br)c2oc(CNC(=O)c3cnn4cccnc34)cc12]

F) N-((7-Bromo-4-methoxybenzofuran-2-yl)methyl) pyrazolo[1,5-a]pyrimidine-3-carboxamide To a solution of (7-bromo-4-methoxybenzofuran-2-yl) methanamine (120 mg, 0.469 mmol) in DMF (2 mL) was added pyrazolo[1,5-a]pyrimidine-3-carboxylic acid (76 mg, 0.469 mmol), ((1H-benzo[d][1,2,3]triazol-1-yl)oxy)tris(dimethylamino)phosphonium hexafluorophosphate(V) (311 mg, 0.703 mmol), and DIPEA (182 mg, 1.41 mmol). The reaction mixture was stirred at room temperature for 2 hours. The reaction mixture was diluted with water and the solid formed was collected by filtration, washed with water and ether, and dried under vacuum to provide the product (152 mg, 81%). MS (ESI+) m/z=401.1 $(M+H)^+$.

G) Methyl 4-methoxy-2-((pyrazolo[1,5-a]pyrimidine-3-carboxamido)methyl)benzofuran-7-carboxylate To a suspension of N-((7-bromo-4-methoxybenzofuran-2-yl)methyl)pyrazolo[1,5-a]pyrimidine-3-carboxamide (152 mg, 0.379 mmol) in DMF (1.5 mL) and MeOH (0.5 mL) was added triethylamine (383 mg, 3.79 mmol), diacetoxypalladium (8.5 mg, 0.038 mmol), and 1,3-bis(diphenylphosphanyl)propane (15.6 mg, 0.038 mmol). The reaction mixture was degassed by bubbling argon through and heated under CO at 100° C. for 20 h. The reaction mixture was concentrated in vacuo. The residue was washed with MeOH. The solid formed was collected by filtration as the desired product (130 mg, 90% yield). $^1$H NMR (500 MHz, DMSO-$d_6$) δ 9.19 (br d, J=7.0 Hz, 1H), 8.80 (br d, J=4.1 Hz, 1H), 8.60 (s, 1H), 8.50 (br s, 1H), 7.83 (d, J=8.2 Hz, 1H), 7.25 (dd, J=6.2, 4.8 Hz, 1H), 6.90 (d, J=8.4 Hz, 1H), 6.79 (s, 1H), 4.77 (d, J=5.8 Hz, 2H), 3.94 (s, 3H), 3.84 (s, 3H); MS (ESI+) m/z=381.1 $(M+H)^+$.

Example 34

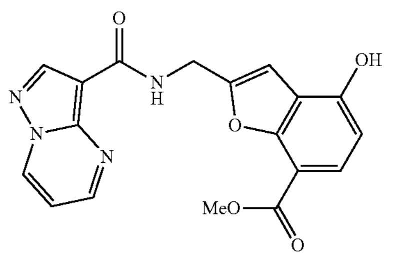 [SMILES: COC(=O)c1ccc(O)c2cc(CNC(=O)c3cnn4cccnc34)oc12]

Methyl 4-hydroxy-2-((pyrazolo[1,5-a]pyrimidine-3-carboxamido)methyl)benzofuran-7-carboxylate To a solution of methyl 4-methoxy-2-((pyrazolo[1,5-a] pyrimidine-3-carboxamido)methyl)benzofuran-7-carboxylate (40 mg, 0.105 mmol, Example 33) in DCM (2 mL) at 0° C. was added tribromoborane (0.020 mL, 0.210 mmol). The reaction mixture was stirred at 0° C. for 4 h and then diluted with DCM. The organic layer was washed with sat. NaCl, dried over sodium sulfate and concentrated in vacuo. The residue was purified by prep HPLC (Method B) to give the product as a white solid (4.6 mg, 12% yield). $^1$H NMR (500 MHz, DMSO-$d_6$) δ 9.32-9.25 (m, 1H), 8.83 (dd, J=4.0, 1.4 Hz, 1H), 8.62 (s, 1H), 8.43 (br t, J=5.7 Hz, 1H), 7.69 (d, J=8.4 Hz, 1H), 7.27 (dd, J=7.0, 4.2 Hz, 1H), 6.85 (s, 1H), 6.66 (d, J=8.5 Hz, 1H), 4.77 (d, J=5.8 Hz, 2H), 3.83 (s, 3H); MS (ESI+) m/z=367.1 (M+H)$^+$.

Example 35

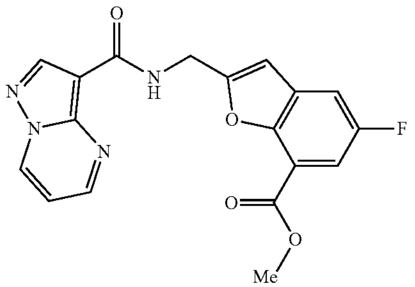 [SMILES: COC(=O)c1cc(F)cc2cc(CNC(=O)c3cnn4cccnc34)oc12]

Methyl 5-fluoro-2-((pyrazolo[1,5-a]pyrimidine-3 carboxamido)methyl)benzofuran-7-carboxylate

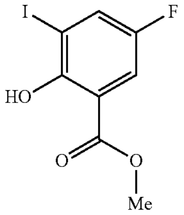 [SMILES: COC(=O)c1cc(F)cc(I)c1O]

A) Methyl 5-fluoro-2-hydroxy-3-iodobenzoate

To a solution of methyl 5-fluoro-2-hydroxybenzoate (2.0 g, 11.8 mmol) in N,N-dimethylformamide (20 mL) was added sodium iodide (2.11 g, 14.1 mmol), followed by addition of chloramine T trihydrate (3.64 g, 12.9 mmol) slowly. The resulting mixture was stirred at room temperature for 20 hours. The reaction mixture was diluted with ethyl acetate and 1 N aqueous HCl solution. The organic layer was separated and washed with brine, $Na_2S_2O_3$ solution and dried over $MgSO_4$. The filtrate was concentrated in vacuo to give a light yellow oil. To the residue was added MeOH. This slurry was allowed to stand at room temperature for 30 minutes before being sonicated. A white solid precipitated out and the solid was filtered to give the desired product. The filtrate also contained the product. The filtrate was concentrated in vacuo, dissolved in DCM, and then purified by flash chromatography (ISCO 80 g column, 0-15% ethyl acetate in hexanes) to give the title compound. Both isolates were combined to give methyl 5-fluoro-2-hydroxy-3-iodobenzoate (2.5 g, 72% yield) as a white solid.

$^1$H NMR (400 MHz, Chloroform-d) δ 11.40 (s, 1H), 7.73 (dd, J=7.3, 3.1 Hz, 1H), 7.59 (dd, J=8.4, 3.1 Hz, 1H), 4.01 (s, 3H); MS (ESI+) m/z=297 (M+H)$^+$.

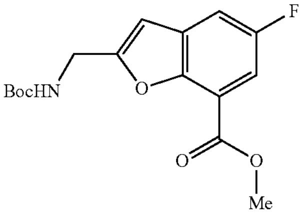 [SMILES: COC(=O)c1cc(F)cc2cc(CNC(=O)OC(C)(C)C)oc12]

B) Methyl 2-(((tert-butoxycarbonyl)amino)methyl)-5-fluorobenzofuran-7-carboxylate A mixture of methyl 5-fluoro-2-hydroxy-3-iodobenzoate (2.5 g, 8.44 mmol, Step A of Example 64), tert-butyl prop-2-yn-1-ylcarbamate (1.51 g, 9.71 mmol), TEA (14.1 mL, 101 mmol), and copper(I) iodide (0.161 g, 0.844 mmol) in DMF (10 mL) was purged with a stream of nitrogen for 5 min, then bis(triphenylphosphine) palladium(II) chloride (0.296 g, 0.422 mmol) was added. The resulting mixture was heated at 80° C. for 2 hours. The reaction mixture was cooled to rt and diluted with ethyl acetate and saturated aqueous $NaHCO_3$ solution. The organic layer was separated, washed with brine, and dried over $MgSO_4$. The filtrate was concentrated in vacuo. The residue was dissolved in DCM and purified by flash chromatography (ISCO 80 g column, 0-30% ethyl acetate in hexanes) to give the title compound (2.5 g, 92% yield) as a light brown oily solid. $^1$H NMR (400 MHz, Chloroform-d) δ 7.64 (dd, J=9.5, 2.7 Hz, 1H), 7.41 (dd, J=7.8, 2.6 Hz, 1H), 6.67 (s, 1H), 5.10 (br s, 1H), 4.52 (br d, J=5.9 Hz, 2H), 4.02 (s, 3H), 1.49 (s, 9H); MS (ESI+) m/z=268.1 [M+H−55]$^+$.

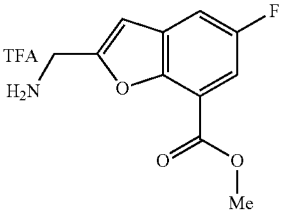 [SMILES: COC(=O)c1cc(F)cc2cc(CN)oc12]

C) Methyl 2-(aminomethyl)-5-fluorobenzofuran-7-carboxylate TFA salt

To a solution of methyl 2-(((tert-butoxycarbonyl)amino) methyl)-5-fluorobenzofuran-7-carboxylate (0.5 g, 1.55 mmol) in $CH_2Cl_2$ (8 mL) was added TFA (0.95 mL, 12.4 mmol). The reaction mixture was stirred at room temperature for 18 hours. The reaction mixture was concentrated in vacuo to give the title compound (0.45 g, 86% yield) as a light brown oily solid. $^1$H NMR (499 MHz, Methanol-$d_4$) δ 7.74 (dd, J=9.5, 2.7 Hz, 1H), 7.68 (dd, J=7.9, 2.7 Hz, 1H), 7.10 (s, 1H), 4.42 (s, 2H), 4.03 (s, 3H); MS (ESI+): m/z=207.2 [M−16+H]$^+$.

D) Methyl 5-fluoro-2-((pyrazolo[1,5-a]pyrimidine-3-carboxamido)methyl)benzofuran-7-carboxylate To a suspension of pyrazolo[1,5-a]pyrimidine-3-carboxylic acid (12.6 mg, 0.077 mmol) and BOP (26 mg, 0.059 mmol) in DMF (2 mL) was added methyl 2-(aminomethyl)-5-fluorobenzofuran-7-carboxylate, TFA salt (20 mg, 0.059 mmol) and DIPEA (0.041 mL, 0.24 mmol). The reaction mixture turned into a clear solution and was stirred at room temperature for 1 h. The reaction mixture was concentrated in vacuo and the residue was dissolved in DMF, filtered and purified by preparative HPLC (Method B). Fractions containing the desired product were combined and dried via centrifugal evaporation to give the title compound (20 mg, 87% yield). $^1$H NMR (500 MHz, DMSO-$d_6$) δ 9.31 (br d, J=7.0 Hz, 1H), 8.84 (br d, J=2.7 Hz, 1H), 8.63 (s, 1H), 8.55 (br t, J=5.8 Hz, 1H), 7.73 (dd, J=8.2, 2.4 Hz, 1H), 7.56 (dd, J=9.8, 2.4 Hz, 1H), 7.29 (dd, J=7.0, 4.3 Hz, 1H), 6.87 (s, 1H), 4.81 (br d, J=5.8 Hz, 2H), 3.91 (s, 3H); MS (ESI+) m/z=369.09 (M+H)$^+$.

Example 36

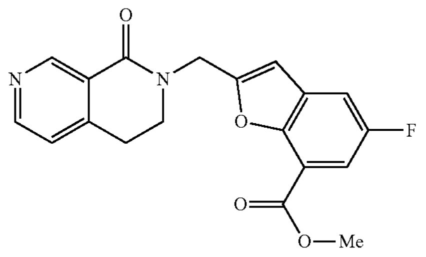 [SMILES: COC(=O)c1cc(F)cc2cc(CN3CCc4ccncc4C3=O)oc12]

Methyl 5-fluoro-2-((1-oxo-3,4-dihydro-2,7-naphthyridin-2(1H)-yl)methyl)benzofuran-7-carboxylate 3,4-Dihydro-1H-pyrano[3,4-c]pyridin-1-one (20 mg, 0.134 mmol) (WO 2005063768) and methyl 2-(aminomethyl)-5-fluorobenzofuran-7-carboxylate (44.9 mg, 0.201 mmol, Step C of Example 35) were added to a pressure relief vial and heated neat at 100° C. After 30 minutes, the reaction was heated to 120° C. After 4 hours, the reaction was cooled, taken up in DMF, filtered, and purified via HPLC (Method B) to give methyl 5-fluoro-2-((1-oxo-3,4-dihydro-2,7-naphthyridin-2(1H)-yl)methyl)benzofuran-7-carboxylate (16.3 mg, 0.045 mmol, 33.6% yield). $^1$H NMR (500 MHz, DMSO-$d_6$) δ 8.96 (s, 1H), 8.63 (d, J=5.0 Hz, 1H), 7.74 (dd, J=8.2, 2.6 Hz, 1H), 7.57 (dd, J=9.6, 2.6 Hz, 1H), 7.38 (d, J=5.0 Hz, 1H), 6.98 (s, 1H), 4.93 (s, 2H), 3.88 (s, 3H), 3.75 (t, J=6.6 Hz, 2H), 3.09 (t, J=6.5 Hz, 2H); MS (ESI+) m/z=355.0 (M+H)$^+$.

Example 37

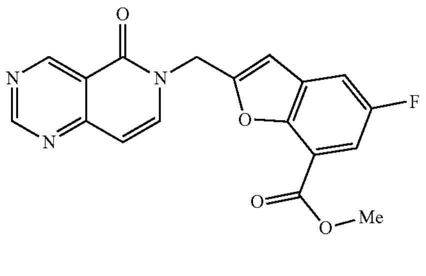 [SMILES: COC(=O)c1cc(F)cc2cc(Cn3ccc4ncncc4c3=O)oc12]

Methyl 5-fluoro-2-((5-oxopyrido[4,3-d]pyrimidin-6(5H)-yl)methyl)benzofuran-7-carboxylate A mixture of ethyl 4-methylpyrimidine-5-carboxylate (37.5 mg, 0.225 mmol), and 1,1-dimethoxy-N,N-dimethylmethanamine (0.12 mL, 0.91 mmol) in DMF (0.5 mL) in a microwave tube was heated in a microwave reactor at 160° C. for 40 min. The reaction mixture was concentrated in vacuo. To the residue was added 1 mL of acetic acid and methyl 2-(aminomethyl)-5-fluorobenzofuran-7-carboxylate TFA salt (38 mg, 0.113 mmol, Step C of Example 35) and the mixture was again heated in a microwave at 110° C. for 25 min. The reaction mixture was concentrated in vacuo. The residue was dissolved in DMF, filtered and purified by preparative HPLC (Method B). Fractions containing the desired product were combined and dried via centrifugal evaporation to give the title compound (37 mg, 67%). $^1$H NMR (500 MHz, DMSO-$d_6$) δ 9.50 (s, 1H), 9.37 (s, 1H), 8.16 (d, J=7.6 Hz, 1H), 7.73 (dd, J=8.2, 2.4 Hz, 1H), 7.58 (dd, J=9.6, 2.3 Hz, 1H), 6.96 (s, 1H), 6.78 (d, J=7.6 Hz, 1H), 5.48 (s, 2H), 3.90 (s, 3H); MS (ESI+) m/z=353.1 (M+H)$^+$.

Example 38

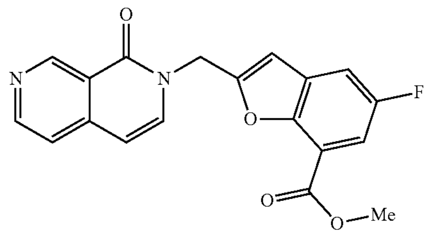 [SMILES: COC(=O)c1cc(F)cc2cc(Cn3ccc4ccncc4c3=O)oc12]

Methyl 5-fluoro-2-((1-oxo-2,7-naphthyridin-2(1H)-yl)methyl)benzofuran-7-carboxylate Methyl 4-methylnicotinate (35.9 mg, 0.237 mmol) and N,N-dimethylformamide dimethyl acetal (0.127 mL, 0.949 mmol) were taken up in DMF (0.5 mL) in a 0.5-2 mL microwave vial. The vial was sealed and heated 160° C. for 40 minutes in a microwave reactor. After 40 minutes, the reaction mixture was cooled and concentrated in vacuo. The resulting residue was dissolved in DCM and concentrated again in vacuo. To this residue was added Acetic Acid (0.5 mL) and methyl 2-(aminomethyl)-5-fluorobenzofuran-7-carboxylate, TFA (40 mg, 0.119 mmol, Step C of Example 35). The vial was then sealed and heated at 110° C. for 25 minutes in a microwave reactor. After 25 minutes, the reaction was again cooled and concentrated in vacuo. The residue was taken up in DMF and MeOH, filtered, and purified via HPLC (method B) to give the title compound (21 mg, 50% yield). $^1$H NMR (500 MHz, DMSO-$d_6$) δ 9.36 (br s, 1H), 8.73 (br s, 1H), 7.85 (d, J=7.3 Hz, 1H), 7.73 (dd, J=8.1, 2.3 Hz, 1H), 7.63 (br d, J=4.3 Hz, 1H), 7.57 (dd, J=9.5, 2.4 Hz, 1H), 6.92 (s, 1H), 6.75 (d, J=7.3 Hz, 1H), 5.42 (s, 2H), 3.86 (s, 3H); MS (ESI+) m/z=352.9 (M+H)$^+$.

Example 39

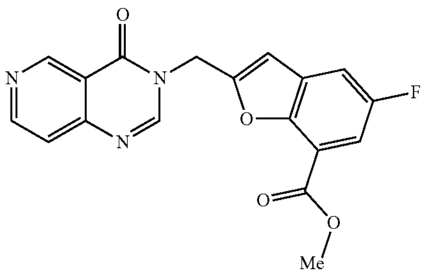 [SMILES: COC(=O)c1cc(F)cc2cc(Cn3cnc4ccncc4c3=O)oc12]

Methyl 5-fluoro-2-((4-oxopyrido[4,3-d]pyrimidin-3(4H)-yl)methyl)benzofuran-7-carboxylate 4-Aminonicotinic acid (40 mg, 0.290 mmol) and N,N-dimethylfromamide dimethyl acetal (0.116 mL, 0.869 mmol) were taken up in DMF (0.5 mL) in a 0.2-5 mL of microwave vial. The vial was sealed and heated to 100° C. for 15 minutes in a microwave reactor. After 15 minutes, the reaction mixture was cooled and concentrated in vacuo. To this residue was added 1 mL of acetic acid and methyl 2-(aminomethyl)-5-fluorobenzofuran-7-carboxylate (64.6 mg, 0.290 mmol, Step C of Example 35). The vial was then sealed and heated to 120° C. for an additional 15 min in a microwave reactor. The reaction was again cooled and concentrated in vacuo. The residue was diluted with ethyl acetate and saturated $NaHCO_3$ solution. The organic layer was separated and concentrated in vacuo. The residue was taken up in DMF, filtered, and purified via HPLC (method B) to give the title compound (11.8 mg, 11% yield). $^1$H NMR (500 MHz, DMSO-$d_6$) δ 9.34 (s, 1H), 8.88 (d, J=5.6 Hz, 1H), 8.76 (s, 1H), 7.73 (dd, J=8.2, 2.6 Hz, 1H), 7.64 (d, J=5.6 Hz, 1H), 7.57 (dd, J=9.6, 2.6 Hz, 1H), 7.03 (s, 1H), 5.48 (s, 2H), 3.88 (s, 3H); MS (ESI+) m/z=354.0 $(M+H)^+$.

Example 40

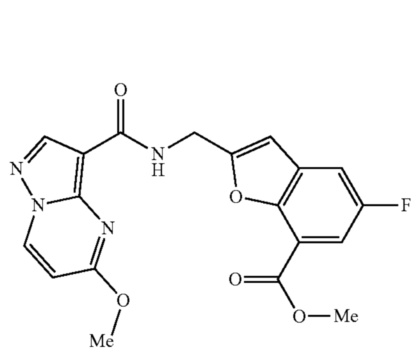 [SMILES: COC(=O)c1cc(F)cc2cc(CNC(=O)c3cnn4ccc(OC)nc34)oc12]

Methyl 5-fluoro-2-((5-methoxypyrazolo[1,5-a]pyrimidine-3-carboxamido)methyl)benzofuran-7-carboxylate 5-Methoxypyrazolo[1,5-a]pyrimidine-3-carboxylic acid (25 mg, 0.129 mmol) (WO 2016/177658 A1) was dissolved in DMF (260 μl). DIPEA (90 μl, 0.518 mmol) and methyl 2-(aminomethyl)-5-fluorobenzofuran-7-carboxylate, TFA salt (49.9 mg, 0.155 mmol, Step C of Example 35) were added. BOP (86 mg, 0.194 mmol) was added and the reaction was stirred at room temperature. After 3 hours, a solid formed and the reaction was diluted with 1.5 mL DMSO and precipitate went back into solution. The reaction was stirred an additional 3 hours before it was filtered and purified directly via preparative HPLC (Method B) to give methyl 5-fluoro-2-((5-methoxypyrazolo[1,5-a]pyrimidine-3-carboxamido)methyl)benzofuran-7-carboxylate (9.6 mg, 0.024 mmol, 18.51% yield). $^1$H NMR (500 MHz, DMSO-$d_6$) δ 9.01 (d, J=7.6 Hz, 1H), 8.40 (s, 1H), 8.23 (br t, J=5.6 Hz, 1H), 7.73 (dd, J=8.2, 2.4 Hz, 1H), 7.55 (dd, J=9.6, 2.6 Hz, 1H), 6.89 (s, 1H), 6.73 (d, J=7.3 Hz, 1H), 4.79 (br d, J=5.8 Hz, 2H), 4.03 (s, 3H), 3.90 (s, 3H); MS (ESI+) m/z=399.2 $(M+H)^+$.

Example 41

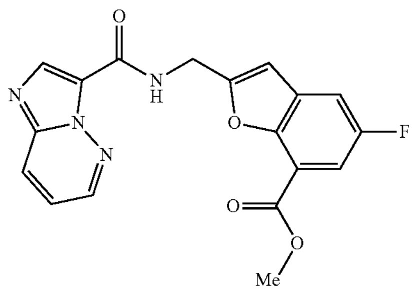 [SMILES: COC(=O)c1cc(F)cc2cc(CNC(=O)c3cnc4cccnn34)oc12]

Methyl 5-fluoro-2-((imidazo[1,2-b]pyridazine-3-carboxamido)methyl)benzofuran-7-carboxylate A suspension of imidazo[1,2-b]pyridazine-3-carboxylic acid (94 mg, 0.58 mmol) and BOP (275 mg, 0.62 mmol) in DMF (3 mL) was stirred at room temperature for 10 min. A solution of methyl 2-(aminomethyl)-5-fluorobenzofuran-7-carboxylate, TFA salt (150 mg, 0.445 mmol, Step C of Example 35) in THE (2 mL) and DIPEA (0.31 mL, 1.78 mmol) was added. The reaction mixture became clear and was stirred at room temperature for 1 hour. The reaction was diluted with ethyl acetate and saturated aqueous $NaHCO_3$ solution. The organic layer was separated, washed with brine, and dried over $MgSO_4$. The filtrate was concentrated in vacuo. A portion (1/10) of the residue was dissolved in DMF, filtered and purified by preparative HPLC (Method A). Fractions containing the desired product were combined and dried via centrifugal evaporation to give the title compound as a TFA salt (9.7 mg, 4.5% yield). $^1$H NMR (500 MHz, DMSO-$d_6$) δ 9.24 (br t, J=5.6 Hz, 1H), 8.79 (d, J=3.4 Hz, 1H), 8.46-8.24 (m, 2H), 7.72 (dd, J=8.2, 2.4 Hz, 1H), 7.56 (dd, J=9.6, 2.6 Hz, 1H), 7.49 (dd, J=9.2, 4.6 Hz, 1H), 6.91 (s, 1H), 4.84 (d, J=5.8 Hz, 2H), 3.90 (s, 3H); MS (ESI+) m/z=369.1 $(M+H)^+$.

Example 42

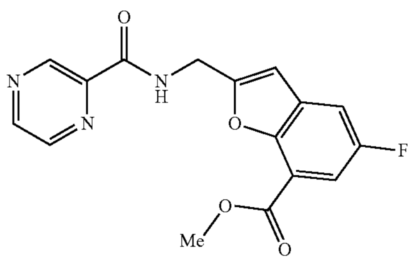 [SMILES: COC(=O)c1cc(F)cc2cc(CNC(=O)c3cnccn3)oc12]

Methyl 5-fluoro-2-((pyrazine-2-carboxamido) methyl)benzofuran-7-carboxylate

To a solution of pyrazine-2-carboxylic acid (8.8 mg, 0.071 mmol) in DMF (1 mL) were added BOP (34.1 mg, 0.077 mmol), methyl 2-(aminomethyl)-5-fluorobenzofuran-7-carboxylate TFA salt (20 mg, 0.059 mmol) (step C of Example 35) and DIPEA (0.03 mL, 0.178 mmol). The reaction mixture was stirred at rt for 1 h. LC-MS showed new peak at tr=0.78 min, $[M+H]^+=330.2$ as the desired product peak. The reaction mixture was diluted with ethyl acetate and saturated aqueous $NaHCO_3$ solution. The organic layer was separated, dried over $MgSO_4$, and filtered. The filtrate was concentrated in vacuo and the residue was dissolved in DMF, filtered and purified by preparative HPLC (Method B). Fractions containing the desired product were combined and dried via centrifugal evaporation to give the title compound (7.9 mg, 40%). $^1H$ NMR (500 MHz, DMSO-$d_6$) δ 9.45 (br s, 1H), 9.23 (s, 1H), 8.89 (s, 1H), 8.76 (s, 1H), 7.78-7.66 (m, 1H), 7.55 (dd, J=9.6, 2.1 Hz, 1H), 6.86 (s, 1H), 4.74 (br d, J=6.0 Hz, 2H), 3.92 (s, 3H); MS (ESI+) m/z=330.2 $(M+H)^+$.

Example 43

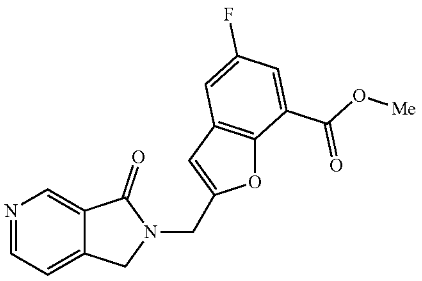 [SMILES: COC(=O)c1cc(F)cc2cc(CN3Cc4ccncc4C3=O)oc12]

Methyl 5-fluoro-2-((3-oxo-1,3-dihydro-2H-pyrrolo [3,4-c]pyridin-2-yl)methyl)benzofuran-7-carboxylate To a mixture of methyl 4-methylnicotinate (0.15 g, 0.99 mmol) and NBS (0.20 g, 1.14 mmol) in carbon tetrachloride (10 mL) was added AIBN (0.021 g, 0.13 mmol). The vial was purged with nitrogen and sealed. The resulting mixture was heated at 90° C. for 1.5 hours. The reaction was cooled (brown solid forms during reaction and cooling) and the liquid was decanted off. The decanted liquid was concentrated in vacuo to give the crude benzyl bromide intermediate which used immediately. To methyl 2-(aminomethyl)-5-fluorobenzofuran-7-carboxylate (43.7 mg, 0.196 mmol, Step C of Example 35) in THF (1 mL) was added TEA (0.136 mL, 0.978 mmol) followed by a solution of crude methyl 4-(bromomethyl)nicotinate (150 mg, 0.098 mmol) in THE (1 mL). The reaction mixture was stirred at room temperature for 1 hour and then heated at 70° C. for 2 hours. The reaction mixture was concentrated in vacuo. The residue was dissolved in MeOH, filtered, and purified by preparative HPLC (Method A). Fractions containing the desired product were combined and dried via centrifugal evaporation to give the title compound as a TFA salt (5.1 mg, 11%). $^1H$ NMR (500 MHz, DMSO-$d_6$) δ 8.97 (s, 1H), 8.78 (br d, J=4.9 Hz, 1H), 7.77 (dd, J=8.2, 2.4 Hz, 1H), 7.72 (br s, 1H), 7.59 (dd, J=9.6, 2.3 Hz, 1H), 7.02 (br d, J=13.4 Hz, 1H), 4.99 (s, 2H), 4.69 (s, 2H), 3.88 (s, 3H); MS (ESI+) m/z=341.0 $(M+H)^+$.

Example 44

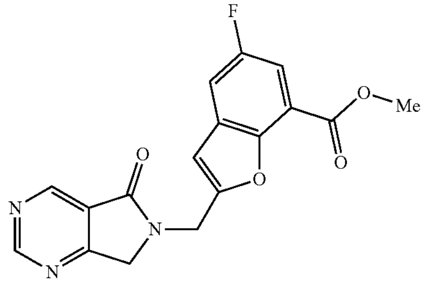 [SMILES: COC(=O)c1cc(F)cc2cc(CN3Cc4ncncc4C3=O)oc12]

Methyl 5-fluoro-2-((5-oxo-5,7-dihydro-6H-pyrrolo [3,4-d]pyrimidin-6-yl)methyl)benzofuran-7-carboxylate Ethyl 4-formylpyrimidine-5-carboxylate (28 mg, 0.155 mmol) in THE (0.8 mL) and methyl 2-(aminomethyl)-5-fluorobenzofuran-7-carboxylate (34.7 mg, 0.155 mmol, Step C of Example 35) in THE (1 mL) was stirred at room temperature for 40 minutes. After 40 minutes, acetic acid (0.1 mL, 1.747 mmol) and sodium triacetoxyborohydride (49.4 mg, 0.233 mmol) were added. The resulting mixture was stirred at room temperature for 20 hours. After 20 hours, saturated $NaHCO_3$ solution was added and the mixture was stirred at room temperature for 5 min. The mixture was diluted with water and extracted with ethyl acetate. The organic layer was separated, washed with brine, dried over sodium sulfate, and filtered. The filtrate was concentrated in vacuo. The residue was taken up in DMF, filtered, and purified via HPLC (method B) to give the title compound (3.1 mg, 6%). $^1H$ NMR (500 MHz, DMSO-$d_6$) δ 9.40 (s, 1H), 9.20 (s, 1H), 7.87-7.72 (m, 1H), 7.59 (dd, J=9.6, 2.4 Hz, 1H), 7.05 (s, 1H), 5.02 (s, 2H), 4.76 (s, 2H), 3.90 (s, 3H); MS (ESI+) m/z=342.1 $(M+H)^+$.

Example 45

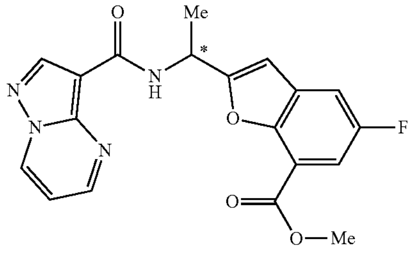 [SMILES: COC(=O)c1cc(F)cc2cc(C(C)NC(=O)c3cnn4cccnc34)oc12]

Methyl-5-fluoro-2-(1-(pyrazolo[1,5-a]pyrimidine-3-carboxamido)ethyl)benzofuran-7-carboxylate

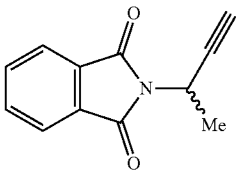

A) 2-(But-3-yn-2-yl)isoindoline-1,3-dione

To a solution of 1-pentyn-3-ol (2.1 mL, 22.2 mmol) in THE (35 mL) was added isoindoline-1,3-dione (3.92 g, 26.7 mmol) and triphenylphosphine (6.70 g, 25.6 mmol). The reaction mixture was cooled with an ice bath and then DEAD (4.22 mL, 26.7 mmol) was added dropwise. The resulting mixture was then warmed up to room temperature and stirred overnight. The reaction mixture was diluted with ethyl acetate and saturated aqueous $NaHCO_3$ solution. The organic layer was separated and washed with brine and 1 N aqueous HCl solution successively. The organic layer was separated, dried over $MgSO_4$, and filtered. The filtrate was concentrated in vacuo. The residue was dissolved in DCM and purified by flash chromatography (ISCO column 80 g, 0-30% ethyl acetate in hexanes) to give the title compound (1.5 g, 70%) as a white solid. $^1$H NMR (500 MHz, CHLOROFORM-d) δ 7.89 (dd, J=5.5, 3.0 Hz, 2H), 7.80-7.67 (m, 2H), 5.24 (dd, J=7.2, 2.5 Hz, 1H), 2.37 (d, J=2.5 Hz, 1H), 1.74 (d, J=7.1 Hz, 3H).

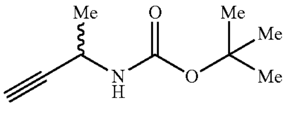

B) tert-Butyl but-3-yn-2-ylcarbamate

To a suspension of 2-(but-3-yn-2-yl)isoindoline-1,3-dione (3.0 g, 15.06 mmol) in ethanol (50 mL) and $H_2O$ (2 mL) was added hydrazine (0.52 mL, 16.6 mmol). The reaction mixture was heated at 76° C. for 60 min. The reaction mixture turned into clear solution in the beginning and after 30 min, a solid crashed out. The reaction mixture was filtered. To the filtrate was added $Boc_2O$ (4.55 mL, 19.6 mmol) and DIPEA (5.26 mL, 30.1 mmol). The reaction mixture was stirred at rt for 2 h. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-30% ethyl acetate in hexanes) to give the title compound (2.0 g, 78%) as a white solid. $^1$H NMR (400 MHz, CHLOROFORM-d) δ 4.88-4.63 (m, 1H), 4.57-4.35 (m, 1H), 2.27 (d, J=2.2 Hz, 1H), 1.47 (s, 9H), 1.42 (d, J=6.9 Hz, 3H).

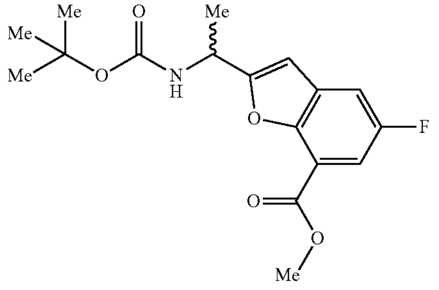 [SMILES: COC(=O)c1cc(F)cc2cc(C(C)NC(=O)OC(C)(C)C)oc12]

C) Methyl 2-(1-((tert-butoxycarbonyl)amino)ethyl)-5-fluorobenzofuran-7-carboxylate A mixture of methyl 5-fluoro-2-hydroxy-3-iodobenzoate (1.0 g, 3.38 mmol, Step A of Example 35), tert-butyl but-3-yn-2-ylcarbamate (0.66 g, 3.88 mmol), TEA (7.06 mL, 50.7 mmol), and copper(I) iodide (0.064 g, 0.338 mmol) in DMF (8 mL) was purged with a nitrogen stream for 5 mins. Bis(triphenylphosphine)palladium(II) chloride (0.119 g, 0.169 mmol) was then added. The resulting mixture was heated at 80° C. for 2 hours. The reaction mixture was cooled down. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.0 g, 88%) as a light brown solid. $^1$H NMR (400 MHz, Chloroform-d) δ 7.63 (dd, J=9.6, 2.6 Hz, 1H), 7.40 (dd, J=7.9, 2.7 Hz, 1H), 6.61 (s, 1H), 5.20-4.86 (m, 1H), 3.99 (s, 3H), 1.60-1.58 (m, 3H), 1.48 (s, 9H); MS (ESI+) m/z=282.2 $(M-55+H)^+$.

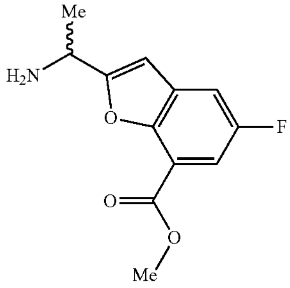 [SMILES: COC(=O)c1cc(F)cc2cc(C(C)N)oc12]

D) Methyl 2-(1-aminoethyl)-5-fluorobenzofuran-7-carboxylate

To a solution of methyl 2-(1-((tert-butoxycarbonyl) amino)ethyl)-5-fluorobenzofuran-7-carboxylate (1.1 g, 2.61 mmol) in DCE (10 mL) was added TFA (2.01 mL, 26.1 mmol). The reaction mixture was stirred at room temperature for 2 hours. The reaction mixture was concentrated in vacuo to give the crude title compound (TFA salt) as light brown solid (1.1 g, 96%). $^1$H NMR (400 MHz, DMSO-$d_6$) δ 7.90 (dd, J=8.2, 2.7 Hz, 1H), 7.67 (dd, J=9.6, 2.7 Hz, 1H), 7.13 (s, 1H), 4.96-4.69 (m, 1H), 4.02 (s, 3H), 1.63 (d, J=6.8 Hz, 3H); MS (ESI+) m/z=221.3 (M−16+H)$^+$.

E) Methyl (S)-5-fluoro-2-(1-(pyrazolo[1,5-a]pyrimidine-3-carboxamido) ethyl)benzofuran-7-carboxylate A mixture of pyrazolo[1,5-a]pyrimidine-3-carboxylic acid (178 mg, 1.09 mmol) and BOP (524 mg, 1.18 mmol) in DMF (10 mL) was stirred at rt for 10 min. A solution of methyl 2-(1-aminoethyl)-5-fluorobenzofuran-7-carboxylate, TFA salt (400 mg, 0.911 mmol) in THF (2 mL) and DIPEA (0.95 mL, 5.47 mmol) were added. The reaction mixture was stirred at rt for 2 h. The reaction mixture was diluted with ethyl acetate and saturated aqueous $NaHCO_3$ solution. The organic layer was separated, washed with brine, dried over $MgSO_4$, and filtered. The filtrate was concentrated in vacuo. Roughly ⅓ of the crude product was dissolved in DMF, filtered and purified by preparative HPLC (Method B). Fractions containing the desired product were combined and dried via centrifugal evaporation to give the racemic product (21.4 mg, 36% yield). A portion of the material (20 mg) was further purified using SFC-chiral chromatography (Method H) to give two isomers. The first isomer as the titled compound (8.1 mg, 13%). $^1$H NMR (500 MHz, DMSO-$d_6$) δ 9.45-9.21 (m, 1H), 8.84 (d, J=2.7 Hz, 1H), 8.64 (s, 1H), 8.38 (br d, J=8.2 Hz, 1H), 7.74 (dd, J=8.2, 2.4 Hz, 1H), 7.57 (dd, J=9.6, 2.6 Hz, 1H), 7.29 (dd, J=6.7, 4.3 Hz, 1H), 6.93 (s, 1H), 5.50 (br t, J=7.3 Hz, 1H), 3.89 (s, 3H), 3.18 (d, J=5.2 Hz, 1H), 1.66 (d, J=7.0 Hz, 3H); MS (ESI+) m/z=383.0 (M+H)$^+$.

Example 46

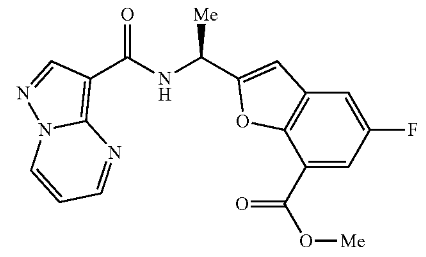 [SMILES: COC(=O)c1cc(F)cc2cc([C@H](C)NC(=O)c3cnn4cccnc34)oc12]

Methyl (S)-5-fluoro-2-(1-(pyrazolo[1,5-a]pyrimidine-3-carboxamido)ethyl)benzofuran-7-carboxylate

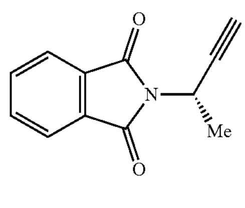

A) (S)-2-(But-3-yn-2-yl)isoindoline-1,3-dione

To a solution of 1-pentyn-3-ol (2.1 mL, 22.2 mmol) in THF (35 mL) was added isoindoline-1,3-dione (3.92 g, 26.7 mmol) and triphenylphosphine (6.70 g, 25.6 mmol). The reaction mixture was cooled with an ice bath and then DEAD (4.22 mL, 26.7 mmol) was added dropwise. The resulting mixture was then warmed up to room temperature and stirred overnight. The reaction mixture was diluted with ethyl acetate and saturated aqueous $NaHCO_3$ solution. The organic layer was separated and washed with brine and 1 N aqueous HCl solution successively. The organic layer was separated, dried over $MgSO_4$, and filtered. The filtrate was concentrated in vacuo. The residue was dissolved in DCM and purified by flash chromatography (ISCO column 80 g, 0-30% ethyl acetate in hexanes) to give the title compound (1.5 g, 70%) as a white solid. $^1$H NMR (500 MHz, Chloroform-d) δ 7.89 (dd, J=5.5, 3.0 Hz, 2H), 7.80-7.67 (m, 2H), 5.24 (dd, J=7.2, 2.5 Hz, 1H), 2.37 (d, J=2.5 Hz, 1H), 1.74 (d, J=7.1 Hz, 3H).

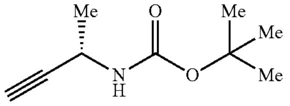

B) tert-butyl (S)-but-3-yn-2-ylcarbamate

To a suspension of (S)-2-(but-3-yn-2-yl)isoindoline-1,3-dione (1.5 g, 7.53 mmol) in Ethanol (30 mL) and $H_2O$ (1 mL) was added hydrazine (0.260 mL, 8.28 mmol). The reaction mixture was heated at 76° C. for 60 min. The reaction mixture turned into clear solution in the beginning and after 30 min, solid crashed out. The reaction mixture was cooled down and filtered. To the filtrate was added $Boc_2O$ (2.273 mL, 9.79 mmol) and DIPEA (2.63 mL, 15.06 mmol). The reaction mixture was stirred at rt for 16 h. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-30% ethyl acetate in hexanes) to give the title compound (0.8 g, 63%) as a white solid. $^1$H NMR (400 MHz, Chloroform-d) δ 4.84-4.59 (m, 1H), 4.56-4.35 (m, 1H), 2.28 (d, J=2.2 Hz, 1H), 1.52-1.46 (s, 9H), 1.43 (d, J=6.8 Hz, 3H).

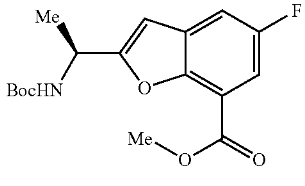 [SMILES: COC(=O)c1cc(F)cc2cc([C@H](C)NC(=O)OC(C)(C)C)oc12]

C) Methyl (S)-2-(1-((tert-butoxycarbonyl)amino) ethyl)-5-fluorobenzofuran-7-carboxylate The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution.

The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

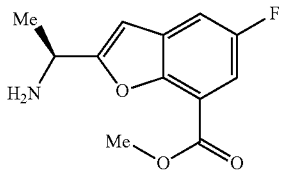 [SMILES: COC(=O)c1cc(F)cc2cc([C@H](C)N)oc12]

D) Methyl (S)-2-(1-aminoethyl)-5-fluorobenzofuran-7-carboxylate

To a solution of methyl (S)-2-(1-((tert-butoxycarbonyl)amino)ethyl)-5-fluorobenzofuran-7-carboxylate (1.2 g, 3.56 mmol) in DCM (10 mL) was added TFA (2.192 mL, 28.5 mmol). The reaction mixture was stirred at rt for 3 h. The reaction mixture was concentrated in vacuo and dried on high vacuum over night to give the title compound TFA salt (1.2 g, 96%) as brown oil. MS (ESI+) m/z=221.1 $(M-17+H)^+$.

E) Methyl (S)-5-fluoro-2-(1-(pyrazolo[1,5-a]pyrimidine-3-carboxamido)ethyl)benzofuran-7-carboxylate The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

Example 47

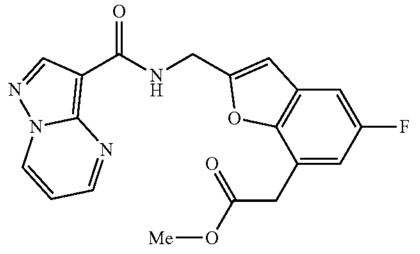 [SMILES: COC(=O)Cc1cc(F)cc2cc(CNC(=O)c3cnn4cccnc34)oc12]

Methyl 2-(5-fluoro-2-((pyrazolo[1,5-a]pyrimidine-3-carboxamido)methyl)benzofuran-7-yl)acetate

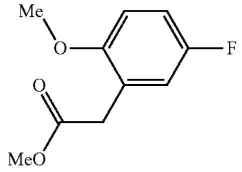 [SMILES: COC(=O)Cc1cc(F)ccc1OC]

A) Methyl 2-(5-fluoro-2-methoxyphenyl)acetate

To a solution of 2-(5-fluoro-2-methoxyphenyl)acetic acid (3 g, 16.3 mmol) in DCM (40 mL) and MeOH (8 mL) at 0° C. was added (diazomethyl)trimethylsilane, 2 M in diethyl ether (9.8 mL, 19.6 mmol). The reaction mixture was stirred at 0° C. for 30 minutes and room temperature for 1 hour. The reaction mixture was concentrated and purified by ISCO, 120 g column, eluting with 0-20% EtOAc in hexanes to give the desired product (3.11 g, 96% yield). $^1H$ NMR (400 MHz, Chloroform-d) δ 7.00-6.92 (m, 2H), 6.85-6.78 (m, 1H), 3.82 (s, 3H), 3.72 (s, 3H), 3.64 (s, 2H); MS (ESI+) m/z=199.2 $(M+H)^+$.

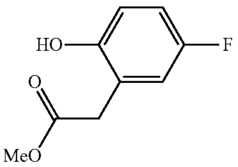 [SMILES: COC(=O)Cc1cc(F)ccc1O]

B) Methyl 2-(5-fluoro-2-hydroxyphenyl)acetate

To a solution of methyl 2-(5-fluoro-2-methoxyphenyl)acetate (3.11 g, 15.7 mmol) in DCM (50 mL) at 0° C. was added tribromoborane (2.27 mL, 23.5 mmol). The reaction mixture was stirred at 0° C. for 1 h and room temperature for 1 h. The reaction mixture was concentrated and purified by ISCO, 120 g column, eluting with 0-40% EtOAc in hexanes to give the desired product as a white solid (2.61 g, 90%). $^1H$ NMR (400 MHz, Chloroform-d) δ 7.16 (s, 1H), 6.95-6.89 (m, 1H), 6.85 (dd, J=8.2, 1.5 Hz, 1H), 3.79 (s, 3H), 3.67 (s, 2H); MS (ESI+) m/z=185.1 $(M+H)^+$.

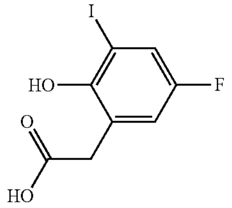 [SMILES: O=C(O)Cc1cc(F)cc(I)c1O]

C) 2-(5-Fluoro-2-hydroxy-3-iodophenyl)acetic acid

To a solution of methyl 2-(5-fluoro-2-hydroxyphenyl) acetate (0.2 g, 1.09 mmol) in THE (5 mL) and MeOH (5 mL) at room temperature was added 3 M aqueous sodium hydroxide solution (1.09 mL, 3.26 mmol). The reaction mixture was stirred at room temperature for 18 hours, acidified to pH 2-3 with 1 N aqueous HCl solution and extracted with DCM. The organic layer was dried over sodium sulfate, filtered, and concentrated to give the hydrolyzed product. To a solution of the above acid (0.1 g, 0.588 mmol) in $CH_3CN$ (2 mL) at room temperature was added NIS (0.132 g, 0.588 mmol). The reaction mixture was stirred at room temperature for 18 hours. The reaction mixture was concentrated and purified by ISCO, 24 g column, eluting with 0-5% MeOH in DCM to give the desired product (100 mg, 58% yield). $^1$H NMR (400 MHz, Chloroform-d) δ 7.30 (dd, J=7.7, 3.0 Hz, 1H), 6.81 (dd, J=8.7, 3.0 Hz, 1H), 3.57 (s, 2H); MS (ESI+) m/z=296.8 $(M+H)^+$.

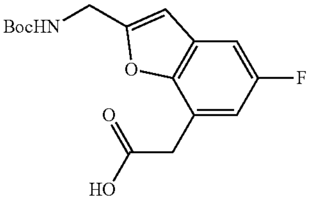 [SMILES: CC(C)(C)OC(=O)NCc1cc2cc(F)cc(CC(=O)O)c2o1]

D) 2-(2-(((tert-Butoxycarbonyl)amino)methyl)-5-fluorobenzofuran-7-yl)acetic acid To a solution of 2-(5-fluoro-2-hydroxy-3-iodophenyl)acetic acid (100 mg, 0.338 mmol) in DMF (0.5 mL) and TEA (0.5 mL) was added copper(I) iodide (6.4 mg, 0.034 mmol), tert-butyl prop-2-yn-1-ylcarbamate (79 mg, 0.507 mmol) and bis(triphenylphosphine)palladium(II) chloride (23.7 mg, 0.034 mmol). The reaction mixture was degassed by bubbling Ar through and stirred at 80° C. for 3 hours. The reaction mixture was concentrated and the residue was dissolved in MeOH and purified by prep HPLC, Method C, to give the desired product as a brown semi-solid (35 mg, 32% yield). $^1$H NMR (400 MHz, Chloroform-d) δ 7.12 (dd, J=8.3, 2.5 Hz, 1H), 6.96 (dd, J=9.7, 2.4 Hz, 1H), 6.59 (br s, 1H), 5.04 (br s, 1H), 4.44 (br s, 2H), 3.93 (s, 2H), 1.48 (s, 9H); MS (ESI+) m/z=322.1 $(M-H)^+$.

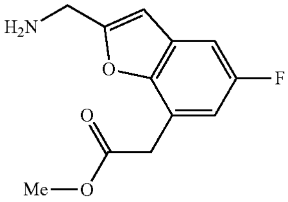 [SMILES: COC(=O)Cc1cc(F)cc2cc(CN)oc12]

E) Methyl 2-(2-(aminomethyl)-5-fluorobenzofuran-7-yl)acetate

To a solution of 2-(2-(((tert-butoxycarbonyl)amino) methyl)-5-fluorobenzofuran-7-yl)acetic acid (35 mg, 0.108 mmol) in DCM (2 mL) and MeOH (0.4 mL) at 0° C. was added (diazomethyl)trimethylsilane, 2 M in diethyl ether (0.081 mL, 0.162 mmol). The reaction mixture was stirred at 0° C. for 30 min and then room temperature for 18 hours. The reaction mixture was concentrated and purified by ISCO, 12 g column, eluting with 0-30% EtOAc in hexanes to give the desired product.

To a solution of the above product (30 mg, 0.089 mmol) in DCM (1.5 mL) was added TFA (0.5 mL). The reaction mixture was stirred at room temperature for 1 hour and concentrated in vacuo to give the desired product (21 mg, 100% yield). $^1$H NMR (400 MHz, Chloroform-d) δ 7.11 (dd, J=8.3, 2.5 Hz, 1H), 6.95 (dd, J=9.8, 2.5 Hz, 1H), 6.59 (s, 1H), 4.45 (br d, J=5.7 Hz, 2H), 3.90 (s, 2H), 3.75 (s, 3H); MS (ESI+) m/z=221.0 $(M+H)^+$.

F) Methyl 2-(5-fluoro-2-((pyrazolo[1,5-a]pyrimidine-3-carboxamido)methyl)benzofuran-7-yl)acetate To a solution of methyl 2-(2-(aminomethyl)-5-fluorobenzofuran-7-yl)acetate (21 mg, 0.089 mmol) in DMF (1 mL) was added pyrazolo[1,5-a]pyrimidine-3-carboxylic acid (14.4 mg, 0.089 mmol), BOP (58.7 mg, 0.133 mmol) and DIPEA (0.046 mL, 0.266 mmol). The reaction mixture was stirred at room temperature for 2 hours. The reaction mixture was concentrated in vacuo and purified by preparative HPLC, Method B, to give the desired product (18.8 mg, 54% yield). $^1$H NMR (500 MHz, DMSO-$d_6$) δ 9.29 (br d, J=7.0 Hz, 1H), 8.82 (br d, J=3.4 Hz, 1H), 8.62 (s, 1H), 8.50 (br t, J=5.6 Hz, 1H), 7.37-7.21 (m, 2H), 7.05 (dd, J=9.9, 2.0 Hz, 1H), 6.78 (s, 1H), 4.74 (br d, J=5.8 Hz, 2H), 3.93 (s, 2H), 3.63 (s, 3H); MS (ESI+) m/z=383.1 $(M+H)^+$.

Example 48

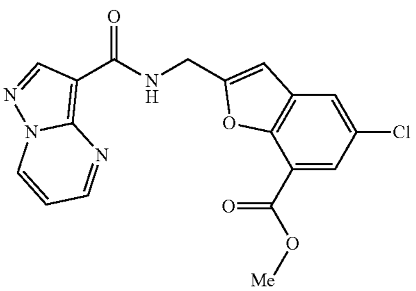 [SMILES: COC(=O)c1cc(Cl)cc2cc(CNC(=O)c3cnn4cccnc34)oc12]

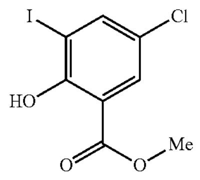 [SMILES: COC(=O)c1cc(Cl)cc(I)c1O]

A) Methyl 5-chloro-2-hydroxy-3-iodobenzoate

To a solution of methyl 5-chloro-2-hydroxybenzoate (5.0 g, 26.8 mmol) in N,N-dimethylformamide (50 mL) was added sodium iodide (4.82 g, 32.2 mmol), followed by chloramine T trihydrate (8.68 g, 30.8 mmol) in several batches. The resulting mixture turned into a brown solution and was stirred at room temperature for 18 hours. The reaction mixture was diluted with ethyl acetate and saturated aqueous $NaHCO_3$ solution. The organic layer was separated, washed with brine followed by $Na_2S_2O_3$ solution, dried over $MgSO_4$, and filtered. The filtrate was concentrated in vacuo to give a light yellow solid. The crude solid was mixed with MeOH and filtered to give the title compound (4.6 g, 69%) as a white solid. $^1$H NMR (400 MHz, Chloroform-d) δ 11.56 (s, 1H), 7.93 (d, J=2.5 Hz, 1H), 7.86 (d, J=2.5 Hz, 1H), 4.01 (s, 3H); MS (ESI+) m/z=313 $(M+H)^+$.

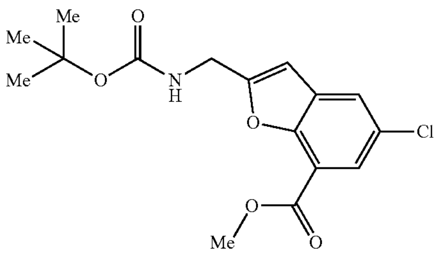 [SMILES: COC(=O)c1cc(Cl)cc2cc(CNC(=O)OC(C)(C)C)oc12]

B) Methyl 2-(((tert-butoxycarbonyl)amino)methyl)-5-chlorobenzofuran-7-carboxylate A mixture of methyl 5-chloro-2-hydroxy-3-iodobenzoate (1.5 g, 4.8 mmol), tert-butyl prop-2-yn-1-ylcarbamate (0.86 g, 5.5 mmol), TEA (11.4 mL, 82 mmol), and copper(I) iodide (0.091 g, 0.48 mmol) in DMF (10 mL) was purged with a stream of nitrogen for 5 mins. Bis(triphenylphosphine)palladium(II) chloride (0.17 g, 0.24 mmol) was then added. The resulting mixture was heated at 80° C. for 2 hours. The reaction was diluted with ethyl acetate and saturated aqueous $NaHCO_3$ solution. The organic layer was separated, washed with brine, dried over $MgSO_4$, and filtered. The filtrate was concentrated in vacuo and the residue was dissolved in DCM and then purified by flash chromatography (ISCO 80 g column, 0-20% ethyl acetate in hexanes) to give the title compound (0.86 g, 72%) as a light brown oily solid. $^1$H NMR (400 MHz, Chloroform-d) δ 7.88-7.81 (m, 1H), 7.67-7.62 (m, 1H), 6.61 (br s, 1H), 5.26-5.11 (m, 1H), 4.50 (br d, J=5.7 Hz, 2H), 3.99 (d, J=1.0 Hz, 3H), 1.47 (s, 9H); MS (ESI+) m/z=284.1 $(M-55+H)^+$.

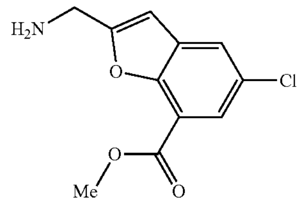 [SMILES: COC(=O)c1cc(Cl)cc2cc(CN)oc12]

C) Methyl 2-(aminomethyl)-5-chlorobenzofuran-7-carboxylate

To a solution of methyl 2-(((tert-butoxycarbonyl)amino)methyl)-5-chlorobenzofuran-7-carboxylate (0.6 g, 1.77 mmol) in DCM (8 mL) was added TFA (1.91 mL, 24.7 mmol). The reaction was stirred at room temperature for 1 hour. The reaction mixture was concentrated in vacuo to give the title compound (TFA salt) as a brown solid (0.6 g, 96%). $^1$H NMR (400 MHz, Chloroform-d) δ 7.92 (d, J=2.2 Hz, 1H), 7.76 (d, J=2.2 Hz, 1H), 6.88 (s, 1H), 4.44 (s, 2H), 3.97 (s, 3H); MS (ESI+) m/z=240.1 $(M+H)^+$.

D) Methyl 5-chloro-2-((pyrazolo[1,5-a]pyrimidine-3-carboxamido) methyl)benzofuran-7-carboxylate To a suspension of pyrazolo[1,5-a]pyrimidine-3-carboxylic acid (12 mg, 0.074 mmol) and BOP (25 mg, 0.057 mmol) in DMF (2 mL) was added methyl 2-(aminomethyl)-5-chlorobenzofuran-7-carboxylate, TFA (20 mg, 0.057 mmol) and DIPEA (0.040 mL, 0.226 mmol). The reaction was stirred at room temperature for 2 hours. The reaction mixture was concentrated in vacuo and the residue was dissolved in DMF, filtered and purified by preparative HPLC (Method B). Fractions containing the desired product were combined and dried via centrifugal evaporation to give the title compound (8.5 mg, 36% yield). $^1$H NMR (500 MHz, DMSO-$d_6$) δ 9.28 (br d, J=6.9 Hz, 1H), 8.83 (br d, J=2.7 Hz, 1H), 8.62 (s, 1H), 8.55-8.46 (m, 1H), 7.94 (s, 1H), 7.74 (s, 1H), 7.31-7.13 (m, 1H), 6.87 (s, 1H), 4.82 (br d, J=5.9 Hz, 2H), 3.92 (s, 3H); MS (ESI+) m/z=385.1 $(M+H)^+$.

Examples 49-62

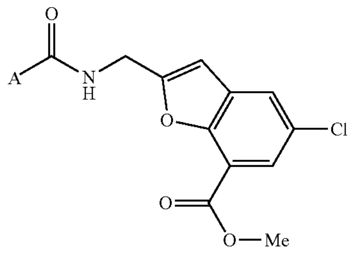

Examples 49 to 62 were prepared according to the procedures described in the synthesis of Example 48 from the required 5-Cl benzofuran amine (Step C in Example 48) and a carboxylic acid.

| Ex. No. | A | Name | $^1$H NMR | LC/MS $(M + H)^+$ |
|---|---|---|---|---|
| 49 | 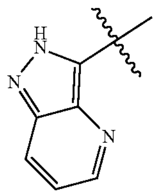 [SMILES: *c1[nH]nc2cccnc12] | Methyl 2-((2H-pyrazolo[4,3-b]pyridine-3-carboxamido)methyl)-5-chlorobenzofuran-7-carboxylate | $^1$H NMR (500 MHz, DMSO-$d_6$) δ 9.27 (br s, 1H), 8.70 (br d, J = 4.0 Hz, 1H), 8.19 (br d, J = 8.2 Hz, 1H), 7.97 (d, J = 1.8 Hz, 1H), 7.74 (d, J = 1.8 Hz, 1H), 7.52 (dd, J = 8.5, 4.3 Hz, 1H), 6.89 (s, 1H), 4.87 (br d, J = 6.1 Hz, 2H), 3.90 (s, 3H) | 385.1 |
| 50 | 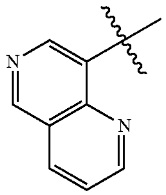 [SMILES: *c1cncc2cccnc12] | Methyl 2-((1,6-naphthyridine-8-carboxamido)methyl)-5-chlorobenzofuran-7-carboxylate | $^1$H NMR (500 MHz, DMSO-$d_6$) δ 10.96 (br t, J = 5.3 Hz, 1H), 9.60 (s, 1H), 9.34 (s, 1H), 9.29 (br d, J = 2.4 Hz, 1H), 8.79 (br d, J = 8.2 Hz, 1H), 7.97 (d, J = 2.1 Hz, 1H), 7.87 (dd, J = 8.2, 4.3 Hz, 1H), 7.74 (d, J = 1.8 Hz, 1H), 6.96 (s, 1H), 4.91 (br d, J = 5.5 Hz, 2H), 3.90 (s, 3H) | 396.2 |
| 51 | 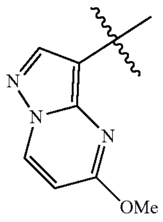 [SMILES: *c1cnn2ccc(OC)nc12] | Methyl 5-chloro-2-((5-methoxypyrazolo[1,5-a]pyrimidine-3-carboxamido)methyl)benzofuran-7-carboxylate | $^1$H NMR (500 MHz, DMSO-$d_6$) δ 8.98 (d, J = 7.5 Hz, 1H), 8.39 (s, 1H), 8.19 (br t, J = 5.4 Hz, 1H), 7.94 (d, J = 1.9 Hz, 1H), 7.74 (d, J = 1.9 Hz, 1H), 6.88 (s, 1H), 6.71 (d, J = 7.5 Hz, 1H), 4.80 (d, J = 5.8 Hz, 2H), 4.04 (s, 3H), 3.91 (s, 3H) | 415.2 |
| 52 | 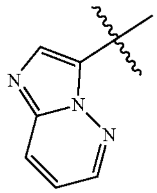 [SMILES: *c1cnc2cccnn12] | Methyl 5-chloro-2-((imidazo[1,2-b]pyridazine-3-carboxamido)methyl)benzofuran-7-carboxylate | $^1$H NMR (500 MHz, DMSO-$d_6$) δ 9.40-9.14 (m, 1H), 8.80 (br d, J = 4.3 Hz, 1H), 8.49-8.22 (m, 2H), 7.97 (d, J = 1.8 Hz, 1H), 7.76 (d, J = 1.8 Hz, 1H), 7.50 (dd, J = 9.3, 4.4 Hz, 1H), 6.91 (s, 1H), 4.85 (br d, J = 5.8 Hz, 2H), 4.01-3.82 (m, 3H) | 385.0 |
| 53 | 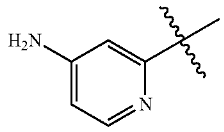 [SMILES: *c1cc(N)ccn1] | Methyl 2-((4-aminopicolinamido)methyl)-5-chlorobenzofuran-7-carboxylate | $^1$H NMR (500 MHz, DMSO-$d_6$) δ 9.68 (br s, 1H), 8.09 (br d, J = 6.4 Hz, 1H), 7.97 (s, 1H), 7.77 (d, J = 1.2 Hz, 1H), 7.33 (s, 1H), 6.91 (s, 1H), 6.84 (br d, J = 5.6 Hz, 1H), 4.73 (br d, J = 5.5 Hz, 2H), 3.93 (s, 3H) | 360.2 |

-continued

| Ex. No. | A | Name | $^1H$ NMR | LC/MS $(M + H)^+$ |
|---|---|---|---|---|
| 54 | 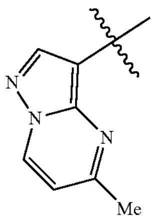 [SMILES: *c1cnn2ccc(C)nc12] | Methyl 5-chloro-2-((5-methyl pyrazolo[1,5-a]pyrimidine-3-carboxamido)methyl) benzofuran-7-carboxylate | $^1H$ NMR (400 MHz, CHLOROFORM-d) δ 8.67-8.62 (m, 2H), 8.52 (br t, J = 5.8 Hz, 1H), 7.91-7.86 (m, 1H), 7.70-7.66 (m, 1H), 6.87 (d, J = 7.2 Hz, 1H), 6.74 (s, 1H), 4.97-4.92 (m, 2H), 4.02 (s, 3H), 2.75-2.65 (m, 3H) | 399.0 |
| 55 | 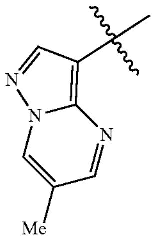 | Methyl 5-chloro-2-((6-methyl pyrazolo[1,5-a]pyrimidine-3-carboxamido)methyl) benzofuran-7-carboxylate | $^1H$ NMR (400 MHz, CHLOROFORM-d) δ 8.66-8.64 (m, 1H), 8.62-8.59 (m, 1H), 8.55 (d, J = 2.0 Hz, 1H), 8.42 (br t, J = 5.5 Hz, 1H), 7.88 (d, J = 2.2 Hz, 1H), 7.68 (d, J = 2.1 Hz, 1H), 6.74 (s, 1H), 4.93 (d, J = 6.0 Hz, 2H), 4.02 (s, 3H), 2.48 (d, J = 0.9 Hz, 3H) | 399.0 |
| 56 | 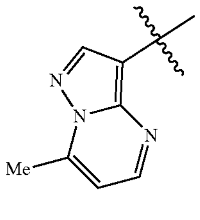 [SMILES: *c1cnn2c(C)ccnc12] | Methyl 5-chloro-2-((7-methyl pyrazolo[1,5-a]pyrimidine-3-carboxamido)methyl) benzofuran-7-carboxylate | $^1H$ NMR (500 MHz, DMSO-$d_6$) δ 8.76-8.69 (m, 1H), 8.68-8.59 (m, 2H), 8.01-7.92 (m, 1H), 7.78-7.71 (m, 1H), 7.29-7.20 (m, 1H), 6.89-6.83 (m, 1H), 4.88-4.76 (m, 2H), 3.96-3.84 (m, 3H), 2.87-2.76 (m, 3H) | 398.9 |
| 57 | 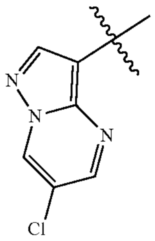 | Methyl 5-chloro-2-((6-chloropyrazolo[1,5-a]pyrimidine-3-carboxamido)methyl) benzofuran-7-carboxylate | $^1H$ NMR (500 MHz, DMSO-$d_6$) δ 9.68 (s, 1H), 8.87 (s, 1H), 8.64 (s, 1H), 8.52 (br s, 1H), 7.95 (s, 1H), 7.74 (s, 1H), 6.86 (s, 1H), 4.78 (br d, J = 5.8 Hz, 2H), 3.90 (s, 3H) | 419.3 |
| 58 | 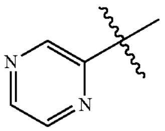 [SMILES: *c1cnccn1] | Methyl 5-chloro-2-((pyrazine-2-carboxamido)methyl) benzofuran-7-carboxylate | $^1H$ NMR (400 MHz, DMSO-$d_6$) δ 9.61 (t, J = 6.1 Hz, 1H), 9.23 (d, J = 1.5 Hz, 1H), 8.91 (d, J = 2.5 Hz, 1H), 8.78 (dd, J = 2.5, 1.5 Hz, 1H), 7.96 (d, J = 2.2 Hz, 1H), 7.75 (d, J = 2.2 Hz, 1H), 6.84 (s, 1H), 4.72 (d, J = 5.4 Hz, 2H), 3.91 (s, 3H) | 346.1 |
| 59 | 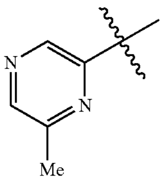 [SMILES: *c1cncc(C)n1] | Methyl 5-chloro-2-((6-methylpyrazine-2-carboxamido)methyl) benzofuran-7-carboxylate | $^1H$ NMR (400 MHz, DMSO-$d_6$) δ 9.47 (t, J = 6.0 Hz, 1H), 9.02 (s, 1H), 8.80 (s, 1H), 7.97 (d, J = 2.2 Hz, 1H), 7.75 (d, J = 2.2 Hz, 1H), 6.84 (s, 1H), 4.72 (d, J = 5.8 Hz, 2H), 3.91 (s, 3H), 2.62 (s, 3H) | 360.1 |

-continued

| Ex. No. | A | Name | $^1$H NMR | LC/MS $(M + H)^+$ |
|---|---|---|---|---|
| 60 | 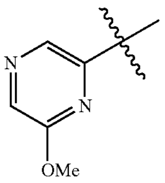 [SMILES: *c1cncc(OC)n1] | Methyl 5-chloro-2-((6-methoxypyrazine-2-carboxamido)methyl) benzofuran-7-carboxylate | $^1$H NMR (500 MHz, DMSO-$d_6$) δ 9.31 (br t, J = 5.7 Hz, 1H), 8.74 (s, 1H), 8.48 (d, J = 1.9 Hz, 1H), 7.93 (d, J = 2.1 Hz, 1H), 7.73 (s, 1H), 6.85 (s, 1H), 4.73 (d, J = 6.1 Hz, 2H), 4.05 (s, 3H), 3.90 (s, 3H) | 376.1 |
| 61 | 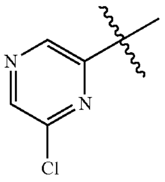 [SMILES: *c1cncc(Cl)n1] | Methyl 5-chloro-2-((6-chloropyrazine-2-carboxamido)methyl) benzofuran-7-carboxylate | $^1$H NMR (400 MHz, DMSO-$d_6$) δ 9.60 (t, J = 6.0 Hz, 1H), 9.17 (s, 1H), 9.05 (s, 1H), 7.96 (d, J = 2.2 Hz, 1H), 7.74 (d, J = 2.2 Hz, 1H), 6.86 (s, 1H), 4.70 (d, J = 6.0 Hz, 2H), 3.91 (s, 3H) | 380.2 |
| 62 | 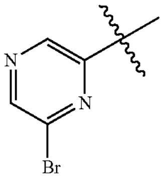 [SMILES: *c1cncc(Br)n1] | Methyl 2-((6-bromopyrazine-2-carboxamido)methyl)-5-chlorobenzofuran-7-carboxylate | $^1$H NMR (500 MHz, DMSO-$d_6$) δ 9.56 (br t, J = 5.6 Hz, 1H), 9.17 (s, 1H), 9.08 (s, 1H), 7.95 (s, 1H), 7.74 (s, 1H), 6.87 (s, 1H), 4.70 (br d, J = 5.8 Hz, 2H), 3.90 (s, 3H) | 423.9 |

Example 63

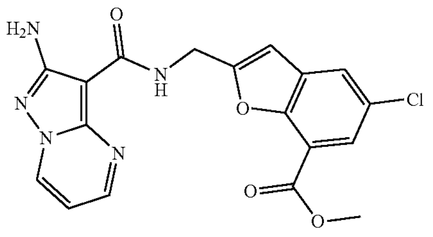 [SMILES: COC(=O)c1cc(Cl)cc2cc(CNC(=O)c3c(N)nn4cccnc34)oc12]

Methyl 2-((2-aminopyrazolo[1,5-a]pyrimidine-3-carboxamido)methyl)-5-chlorobenzofuran-7-carboxylate

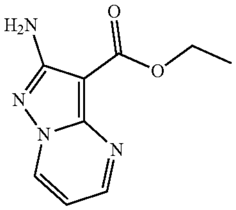

A) Ethyl 2-(amino)pyrazolo[1,5-a]pyrimidine-3-carboxylate

To a solution of ethyl 3,5-diamino-1H-pyrazole-4-carboxylate (15.11 g, 89 mmol, Example 1 in WO 2015/073267) in HCl (60.5 ml, 121 mmol) was added 1,1,3,3-tetramemethoxypropane (13.29 ml, 81 mmol). The reaction was heated at 55° C. for 24 hours. The reaction was quenched with 2N NaOH to pH 9, then extracted with 10% MeOH/DCM (2×). The combined organic extracts were dried with anhydrous sodium sulfate and concentrated in vacuo to give the crude product mixture. The crude product mixture was purified by a silica gel ISCO 80 g column eluting with 0-5% methanol/DCM over a 15 minute gradient. The appropriate fractions were isolated and concentrated in vacuo to afford the title compound (9.2 g, 55.3% yield) as a solid. $^1$H NMR (400 MHz, Chloroform-d) δ 8.59 (dd, J=4.3, 1.8 Hz, 1H), 8.45 (dd, J=6.7, 1.8 Hz, 1H), 6.85 (dd, J=6.8, 4.4 Hz, 1H), 4.50 (q, J=7.1 Hz, 2H), 1.47 (t, J=7.1 Hz, 3H); MS (ESI+) m/z=207.1 $(M+H)^+$.

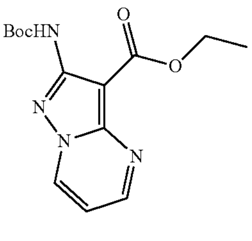 [SMILES: CCOC(=O)c1c(NC(=O)OC(C)(C)C)nn2cccnc12]

B) Ethyl 2-((tert-butoxycarbonyl)amino)pyrazolo[1,5-a]pyrimidine-3-carboxylate

In a vial was added ethyl 2-aminopyrazolo[1,5-a]pyrimidine-3-carboxylate (500 mg, 2.425 mmol), BOC-anhydride (1.126 mL, 4.85 mmol), TEA (1.014 mL, 7.27 mmol), catalytic DMAP in DCM (5 mL). The solution was stirred at room temperature for 24 hours. The solution was quenched with water, washed with saturated sodium bicarbonate, water, saturated sodium chloride solution, dried with anhydrous sodium sulfate, and concentrated in vacuo. The crude product mixture was purified by a silica gel ISCO 12 g column eluting with 0-40% EA/DCM over a 15 minute gradient. The appropriate fractions were isolated and concentrated in vacuo to afford the title compound (640 mg, 86% yield). 1H NMR (400 MHz, Chloroform-d) δ 8.87-8.77 (m, 1H), 8.75-8.64 (m, 1H), 7.14-6.99 (m, 1H), 4.49-4.33 (m, 2H), 1.52-1.43 (m, 9H), 1.41 (t, J=7.1 Hz, 3H); MS (ESI+) m/z=307.1 $(M+H)^+$.

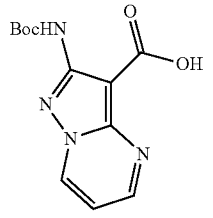 [SMILES: CC(C)(C)OC(=O)Nc1nn2cccnc2c1C(=O)O]

C) 2-((Tert-butoxycarbonyl)amino)pyrazolo[1,5-a] pyrimidine-3-carboxylic acid

The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution.

The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

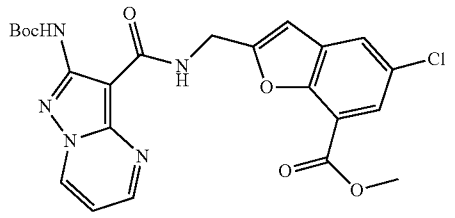 [SMILES: COC(=O)c1cc(Cl)cc2cc(CNC(=O)c3c(NC(=O)OC(C)(C)C)nn4cccnc34)oc12]

D) Methyl 2-((2-((tert-butoxycarbonyl)amino)pyrazolo[1,5-a]pyrimidine-3-carboxamido)methyl)-5-chlorobenzofuran-7-carboxylate The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

E) Methyl 2-((2-aminopyrazolo[1,5-a]pyrimidine-3-carboxamido)methyl)-5-chlorobenzofuran-7-carboxylate The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

Example 64

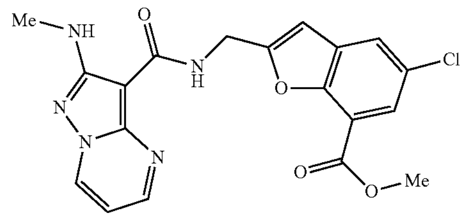 [SMILES: CNc1nn2cccnc2c1C(=O)NCc1cc2cc(Cl)cc(C(=O)OC)c2o1]

Methyl 5-chloro-2-((2-(methylamino)pyrazolo[1,5-a]pyrimidine-3-carboxamido)methyl)benzofuran-7-carboxylate

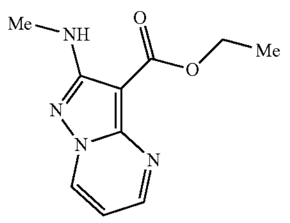 [SMILES: CCOC(=O)c1c(NC)nn2cccnc12]

A) Ethyl 2-(methylamino)pyrazolo[1,5-a]pyrimidine-3-carboxylate

In a vial was added ethyl 2-aminopyrazolo[1,5-a]pyrimidine-3-carboxylate (520 mg, 2.52 mmol, Step A of Example 63), potassium carbonate (349 mg, 2.52 mmol), methyl iodide (0.158 mL, 2.52 mmol) in DMF (4 mL). The solution was stirred at 140° C. for 16 hours. The solution was quenched with DCM and water. The separated organics were washed with saturated sodium bicarbonate, water, and saturated sodium chloride. The washed organics were then dried with anhydrous sodium sulfate, filtered, and concentrated in vacuo. The crude product mixture was purified by a silica gel ISCO 12 g column eluting with 0-5% Methanol/DCM over a 15 minute gradient. The appropriate fractions were isolated and concentrated in vacuo to afford the title compound (160 mg, 28.8% yield). 1H NMR (400 MHz, Methanol-d4) δ 8.75 (dd, J=6.7, 1.7 Hz, 1H), 8.51 (dd, J=4.4, 1.6 Hz, 1H), 7.00 (dd, J=6.7, 4.6 Hz, 1H), 4.41 (q, J=7.1 Hz, 2H), 3.04 (s, 3H), 1.40 (t, J=7.1 Hz, 3H); MS (ESI+) m/z=221.0 $(M+H)^+$.

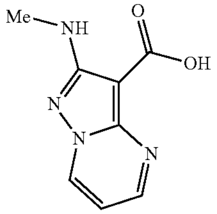 [SMILES: CNc1nn2cccnc2c1C(=O)O]

B) 2-(Methylamino)pyrazolo[1,5-a]pyrimidine-3-carboxylic acid

A vial was charged with ethyl 2-(methylamino)pyrazolo[1,5-a]pyrimidine-3-carboxylate (75 mg, 0.341 mmol), methanol (4 mL) and tetrahydrofuran (2 mL). To the solution was added lithium hydroxide (0.341 mL, 0.681 mmol, 2M) and the reaction stirred at 80° C. for 16 hours. The reaction was concentrated in vacuo, acidified with 1N HCl and extracted with DCM, the organic layer was dried with anhydrous sodium sulfate and concentrated in vacuo to give the title compound (45 mg, 68.8% yield), used as is in the next reaction. 1H NMR (400 MHz, Methanol-d4) δ 8.78-8.67 (m, 1H), 8.52-8.45 (m, 1H), 7.07-6.91 (m, 1H), 3.03 (s, 3H); MS (ESI+) m/z=192.9 $(M-55)^+$.

C) Methyl 2-((2-aminopyrazolo[1,5-a]pyrimidine-3-carboxamido)methyl)-5-chlorobenzofuran-7-carboxylate To a solution of 2-(methylamino)pyrazolo[1,5-a]pyrimidine-3-carboxylic acid (45 mg, 0.234 mmol) and methyl 2-(aminomethyl)-5-chlorobenzofuran-7-carboxylate, TFA (83 mg, 0.234 mmol, Step C of Example 48) in DMF (5 mL) were added BOP (155 mg, 0.351 mmol) and DIPEA (0.123 mL, 0.702 mmol). The reaction mixture was stirred at room temperature for 16 hours. The sample was quenched with water, the resulting product precipitate was filtered. The crude product was purified via preparative HPLC (Method C) to yield the title compound (5 mg, 4.85% yield). 1H NMR (400 MHz, Methanol-d4) δ 8.99-8.91 (m, 1H), 8.85-8.76 (m, 1H), 8.23-8.15 (m, 1H), 8.09-8.02 (m, 1H), 7.91-7.84 (m, 2H), 7.31-7.20 (m, 1H), 7.13-7.07 (m, 1H), 5.20 (s, 2H), 4.49-4.25 (m, 3H), 3.48-3.21 (m, 3H); MS (ESI+) m/z=414.0 $(M+H)^+$.

Example 65

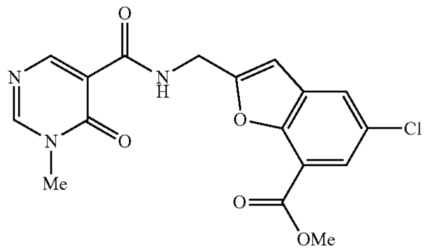 [SMILES: COC(=O)c1cc(Cl)cc2cc(CNC(=O)c3cncn(C)c3=O)oc12]

Methyl 5-chloro-2-((1-methyl-6-oxo-1,6-dihydropyrimidine-5-carboxamido)methyl)benzofuran-7-carboxylate

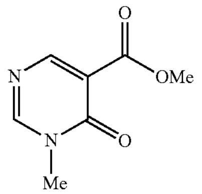 [SMILES: COC(=O)c1cncn(C)c1=O]

A) Methyl 1-methyl-6-oxo-1,6-dihydropyrimidine-5-carboxylate

To a solution of methyl 4-hydroxypyrimidine-5-carboxylate (100 mg, 0.649 mmol) in NMP (3.2 mL) under N2 was added NaH (31.1 mg, 0.779 mmol). The reaction mixture was stirred for 15 min, iodomethane (138 mg, 0.973 mmol) was added, and the reaction mixture was stirred for 14 hours. The reaction mixture was quenched with a saturated aqueous solution of $NH_4Cl$ and extracted with a 3:1 (v/v) solution of $CHCl_3$:iPrOH. The organic layers were combined, washed with a 10% aqueous solution of LiCl, washed with brine, dried over $MgSO_4$, filtered, and concentrated in vacuo. The residue was dissolved in DCM and purified by flash chromatography (ISCO 40 g column, 0-10% MeOH in DCM) to give the title compound (30.2 mg, 27%). $^1H$ NMR (500 MHz, Chloroform-d) δ 8.65 (s, 1H), 8.31 (s, 1H), 3.92 (s, 3H), 3.59 (s, 3H); MS (ESI+) m/z=169.1 $(M+H)^+$.

B) Methyl 5-chloro-2-((1-methyl-6-oxo-1,6-dihydropyrimidine-5-carboxamido)methyl)benzofuran-7-carboxylate To a solution of methyl 1-methyl-6-oxo-1,6-dihydropyrimidine-5-carboxylate (30.2 mg, 0.180 mmol) in THE (72 μL), water (72 μL), and MeOH (36 μL) was added lithium hydroxide monohydrate (7.54 mg, 0.180 mmol). The reaction mixture was stirred at room temperature for 16 hours. An additional portion of lithium hydroxide monohydrate (7.54 mg, 0.180 mmol) was added and the reaction mixture was stirred for 6 hours at room temperature. The reaction mixture was concentrated in vacuo to obtain a residue that was used without further purification.

To the obtained residue was added methyl 2-(aminomethyl)-5-chlorobenzofuran-7-carboxylate, TFA (57.9 mg, 0.164 mmol, Step C of Example 48) and ((1H-benzo[d][1, 2,3]triazol-1-yl)oxy)tris(dimethylamino)phosphonium hexafluorophosphate(V) (80 mg, 0.180 mmol). DMF (818 μL) and DIPEA (57.0 μL, 0.327 mmol) were added and the reaction mixture was stirred at room temperature for 15 h. The reaction mixture was diluted with water and extracted with EtOAc. The organic layers were combined, washed with brine, dried over $MgSO_4$, filtered, and concentrated in vacuo. A sixth of the obtained residue was dissolved in 2 mL DMSO, filtered through a syringe filter, and purified by preparative LC/MS (Method B). Fractions containing the desired product were combined and dried via centrifugal evaporation to give the title compound (1.2 mg, 2%). The remaining obtained residue contained additional semipure title compound (45.7 mg) that was used without further purification. $^1H$ NMR (500 MHz, DMSO-$d_6$) δ 9.64 (br s, 1H), 8.74 (s, 1H), 8.69 (s, 1H), 7.98 (d, J=2.1 Hz, 1H), 7.75 (d, J=1.8 Hz, 1H), 6.84 (s, 1H), 4.76 (br d, J=5.8 Hz, 2H), 3.92 (s, 3H), 3.40 (br s, 3H); MS (ESI+) m/z=376.0 $(M+H)^+$.

Example 66

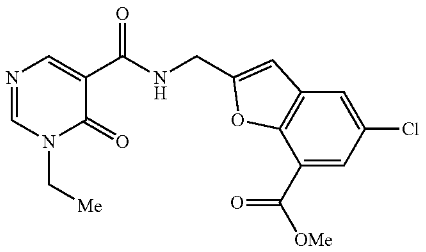 [SMILES: CCn1cncc(C(=O)NCc2cc3cc(Cl)cc(C(=O)OC)c3o2)c1=O]

Methyl 5-chloro-2-((1-ethyl-6-oxo-1,6-dihydropyrimidine-5-carboxamido)methyl)benzofuran-7-carboxylate

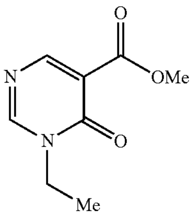 [SMILES: CCn1cncc(C(=O)OC)c1=O]

A) Methyl 1-ethyl-6-oxo-1,6-dihydropyrimidine-5-carboxylate

To a solution of methyl 4-hydroxypyrimidine-5-carboxylate (100 mg, 0.649 mmol) in NMP (3.2 mL) under N2 was added NaH (31.1 mg, 0.779 mmol). The reaction mixture was stirred for 30 min, iodoethane (78 μL, 0.973 mmol) was added, and the reaction mixture was stirred for 15 h. The reaction mixture was quenched with MeOH and then concentrated in vacuo. The residue was dissolved in DCM and purified by flash chromatography (ISCO 12 g column, 0-100% EtOAc in hexanes, followed by 0-10% MeOH in DCM) to give the title compound (73.4 mg, 62%). $^1H$ NMR (500 MHz, Chloroform-d) δ 8.64-8.59 (m, 1H), 8.28 (s, 1H), 4.07-4.00 (m, 2H), 3.92-3.88 (m, 3H), 1.44-1.38 (m, 3H); MS (ESI+) m/z=183.1 $(M+H)^+$.

B) Methyl 5-chloro-2-((1-ethyl-6-oxo-1,6-dihydropyrimidine-5-carboxamido)methyl)benzofuran-7-carboxylate To a solution of methyl 1-ethyl-6-oxo-1,6-dihydropyrimidine-5-carboxylate (73.4 mg, 0.403 mmol) in THF (1.6 mL), water (1.6 mL), and MeOH (0.81 mL) was added lithium hydroxide monohydrate (33.8 mg, 0.806 mmol). The reaction mixture was stirred at room temperature for 3 h. The reaction mixture was filtered through a fritted funnel and concentrated in vacuo to obtain a residue that was used without further purification.

To half of the obtained residue (41.7 mg) was added methyl 2-(aminomethyl)-5-chlorobenzofuran-7-carboxylate, TFA (64.3 mg, 0.182 mmol, Step C of Example 48) and ((1H-benzo[d][1,2,3]triazol-1-yl)oxy)tris(dimethylamino)phosphonium hexafluorophosphate(V) (88 mg, 0.200 mmol). DMF (909 μL) and DIPEA (95 μL, 0.545 mmol) were added and the reaction mixture was stirred at room temperature for 4 h. The reaction mixture was diluted with water and extracted with EtOAc. The organic layers were combined, washed with brine, dried over $MgSO_4$, filtered, and concentrated in vacuo. A third of the obtained residue was dissolved in 2 mL DMSO, filtered through a syringe filter, and purified by preparative LC/MS (Method B). Fractions containing the desired product were combined and dried via centrifugal evaporation to give the title compound (5.9 mg, 8%). The remaining obtained residue contained additional semipure title compound (43.3 mg) that was used without further purification. $^1H$ NMR (500 MHz, DMSO-$d_6$) δ 9.59 (br s, 1H), 8.75 (s, 1H), 8.70 (s, 1H), 7.95 (s, 1H), 7.75 (s, 1H), 6.86 (s, 1H), 4.76 (br d, J=5.7 Hz, 2H), 4.06 (q, J=7.1 Hz, 2H), 3.93 (s, 3H), 1.32 (t, J=7.1 Hz, 3H); MS (ESI+) m/z=389.8 $(M+H)^+$.

Example 67

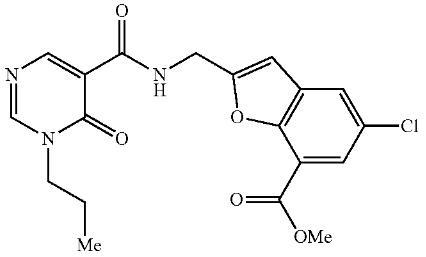 [SMILES: CCCn1cncc(C(=O)NCc2cc3cc(Cl)cc(C(=O)OC)c3o2)c1=O]

Methyl 5-chloro-2-((1-propyl-6-oxo-1,6-dihydropyrimidine-5-carboxamido)methyl)benzofuran-7-carboxylate

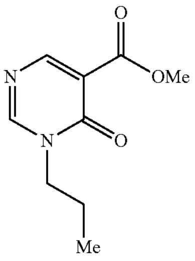 [SMILES: CCCn1cncc(C(=O)OC)c1=O]

A) Methyl 1-propyl-6-oxo-1,6-dihydropyrimidine-5-carboxylate

To a solution of methyl 4-hydroxypyrimidine-5-carboxylate (100 mg, 0.649 mmol) in NMP (3.2 mL) under N2 was added NaH (31.1 mg, 0.779 mmol). The reaction mixture was stirred for 40 min, 1-iodopropane (95 μL, 0.973 mmol) was added, and the reaction mixture was stirred for 15 h. The reaction mixture was quenched with MeOH and then concentrated in vacuo. The residue was dissolved in DCM and purified by flash chromatography (ISCO 12 g column, 0-100% EtOAc in hexanes) to give the title compound (57.4 mg, 45%). $^1$H NMR (500 MHz, Chloroform-d) δ 8.63 (s, 1H), 8.24 (s, 1H), 3.94 (t, J=7.3 Hz, 2H), 3.91 (s, 3H), 1.83 (sxt, J=7.4 Hz, 2H), 0.98 (t, J=7.4 Hz, 3H); MS (ESI+) m/z=197.0 $(M+H)^+$.

B) Methyl 5-chloro-2-((1-propyl-6-oxo-1,6-dihydropyrimidine-5-carboxamido)methyl)benzofuran-7-carboxylate To a solution of methyl 1-propyl-6-oxo-1,6-dihydropyrimidine-5-carboxylate (57.4 mg, 0.293 mmol) in THF (1.2 mL), water (1.2 mL), and MeOH (0.59 mL) was added lithium hydroxide monohydrate (24.6 mg, 0.585 mmol). The reaction mixture was stirred at room temperature for 22 h. The reaction mixture was filtered through a fritted funnel and concentrated in vacuo to obtain a residue that was used without further purification.

To half of the obtained residue (37.1 mg) was added methyl 2-(aminomethyl)-5-chlorobenzofuran-7-carboxylate, TFA (76 mg, 0.215 mmol, Step C of Example 48) and ((1H-benzo[d][1,2,3]triazol-1-yl)oxy)tris(dimethylamino)phosphonium hexafluorophosphate(V) (105 mg, 0.237 mmol). DMF (1.1 mL) and DIPEA (112 μL, 0.645 mmol) were added and the reaction mixture was stirred at room temperature for 3.5 h. The reaction mixture was diluted with water and extracted with EtOAc. The organic layers were combined, washed with brine, dried over $MgSO_4$, filtered, and concentrated in vacuo. A third of the obtained residue was dissolved in 2 mL DMSO, filtered through a syringe filter, and purified by preparative LC/MS (Method B). Fractions containing the desired product were combined and dried via centrifugal evaporation to give the title compound (7.1 mg, 8%). The remaining obtained residue contained additional semipure title compound (58.8 mg) that was used without further purification. $^1$H NMR (500 MHz, DMSO-$d_6$) δ 9.67-9.59 (m, 1H), 8.74 (s, 1H), 8.69 (s, 1H), 7.96 (s, 1H), 7.74 (d, J=1.5 Hz, 1H), 6.85 (s, 1H), 4.74 (br d, J=5.8 Hz, 2H), 3.96 (br t, J=7.2 Hz, 2H), 3.91 (s, 3H), 1.76-1.64 (m, 2H), 0.87 (t, J=7.3 Hz, 3H); MS (ESI+) m/z=404.1 $(M+H)^+$.

Example 68

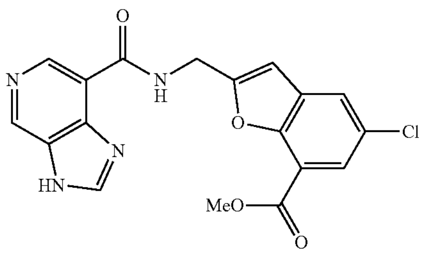 [SMILES: COC(=O)c1cc(Cl)cc2cc(CNC(=O)c3cncc4[nH]cnc34)oc12]

Methyl 2-((3H-imidazo[4,5-c]pyridine-7-carboxamido)methyl)-5-chlorobenzofuran-7-carboxylate

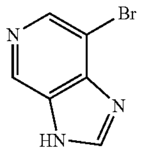

A) 7-Bromo-3H-imidazo[4,5-c]pyridine

To the suspension of 5-bromopyridine-3,4-diamine (0.2 g, 1.064 mmol) in triethoxymethane (1.77 ml, 10.6 mmol) was added (1R)-(−)-camphor-10-sulfonic acid (0.012 g, 0.053 mmol). The reaction mixture was stirred at 150° C. for 2 hours and cooled to room temperature. The solid formed was collected by filtration and washed with DCM to give the desired product as a brown solid (0.19 g, 90% yield). $^1$H NMR (400 MHz, Methanol-$d_4$) δ 8.89 (s, 1H), 8.49 (s, 1H), 8.47 (s, 1H); MS (ESI+) m/z=199.8 $(M+H)^+$.

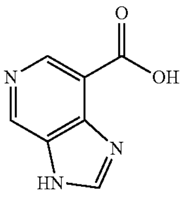 [SMILES: O=C(O)c1cncc2[nH]cnc12]

B) 3H-Imidazo[4,5-c]pyridine-7-carboxylic acid

To a solution of 7-bromo-3H-imidazo[4,5-c]pyridine (190 mg, 0.959 mmol) in DMF (1 mL) and MeOH (0.5 mL) was added triethylamine (485 mg, 4.80 mmol), diacetoxypalladium (21.5 mg, 0.096 mmol), and 1,3-bis(diphenylphosphanyl)propane (39.6 mg, 0.096 mmol). The reaction mixture was degassed by bubbling argon through and heated under CO at 100° C. for 16 hours. The reaction mixture was concentrated. The residue was washed with MeOH. The solid which is insoluble in MeOH was collected by filtration to give the methyl ester product as a brown solid.

To the solution of the above solid (70 mg, 0.395 mmol) in THF (1 mL) and MeOH (1 mL) was added 3 M aqueous sodium hydroxide solution (0.66 mL, 1.98 mmol). The reaction mixture was stirred at room temperature for 18 hours. The reaction mixture was acidified with 2 M aqueous HCl solution to pH ~2, and concentrated. The residue was dissolved in MeOH and purified with prep HPLC, Method C, to give the desired product as a light yellow TFA salt (81 mg, 74% yield). $^1$H NMR (400 MHz, Deuterium Oxide) δ 9.16 (s, 1H), 8.75 (s, 1H), 8.64 (s, 1H); MS (ESI+) m/z=164.0 $(M+H)^+$.

C) Methyl 2-((3H-imidazo[4,5-c]pyridine-7-carboxamido)methyl)-5-chlorobenzofuran-7-carboxylate To a solution of 3H-imidazo[4,5-c]pyridine-7-carboxylic acid, TFA salt (25 mg, 0.090 mmol) in DMF (1 mL) was added methyl 2-(aminomethyl)-5-chlorobenzofuran-7-carboxylate (21.6 mg, 0.090 mmol, Step C in Example 48), BOP (59.8 mg, 0.135 mmol) and DIPEA (0.095 mL, 0.541 mmol). The reaction mixture was stirred at room temperature for 2 hours. The reaction mixture was concentrated and purified with prep HPLC (Method A) to give the desired product (13.2 mg, 37% yield). $^1$H NMR (500 MHz, DMSO-$d_6$) δ 9.78 (br s, 1H), 9.09 (s, 1H), 8.90 (s, 1H), 8.55 (br s, 1H), 7.96 (d, J=1.8 Hz, 1H), 7.74 (d, J=1.8 Hz, 1H), 6.92 (s, 1H), 4.85 (br d, J=4.9 Hz, 2H), 3.89 (s, 3H); MS (ESI+) m/z=384.8 $(M+H)^+$.

Example 69

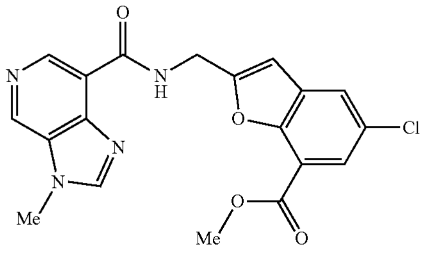 [SMILES: COC(=O)c1cc(Cl)cc2cc(CNC(=O)c3cncc4c3ncn4C)oc12]

Methyl 5-chloro-2-((3-methyl-3H-imidazo[4,5-c]pyridine-7-carboxamido)methyl)benzofuran-7-carboxylate

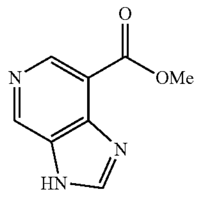 [SMILES: COC(=O)c1cncc2[nH]cnc12]

A) Methyl 3H-imidazo[4,5-c]pyridine-7-carboxylate

To a solution of 7-bromo-3H-imidazo[4,5-c]pyridine (420 mg, 2.121 mmol) in DMF (3 mL) and MeOH (1 mL) were added triethylamine (1073 mg, 10.60 mmol), diacetoxypalladium (47.6 mg, 0.212 mmol), and 1,3-bis(diphenylphosphanyl)propane (87 mg, 0.212 mmol). The reaction mixture was degassed by bubbling Ar through and heated under CO (20 psi) at 100° C. for 16 h. The reaction mixture was concentrated in vacuo. The residue was washed with MeOH. The solid was collected by filtration to give the desired product (270 mg, 72%). $^1$H NMR (400 MHz, Methanol-d4) δ 9.42 (s, 1H), 9.09 (s, 1H), 8.79 (s, 1H), 4.13 (s, 3H); MS (ESI+) m/z=178.0 $(M+H)^+$.

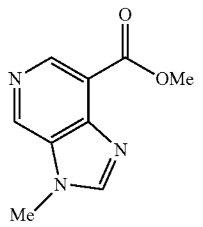 [SMILES: COC(=O)c1cncc2c1ncn2C]

B) Methyl 3-methyl-3H-imidazo[4,5-c]pyridine-7-carboxylate

To a solution of methyl 3H-imidazo[4,5-c]pyridine-7-carboxylate (100 mg, 0.564 mmol) in DMF (1 mL) were added cesium carbonate (368 mg, 1.129 mmol) and iodomethane (0.071 mL, 1.129 mmol). The reaction mixture was stirred at rt for 2 h. The reaction mixture was concentrated. MeOH was added to the residue and filtered to remove the solid. The filtrate was purified by prep HPLC (Method C) to give the desired product (12 mg, 11%) as the TFA salt. $^1$H NMR (400 MHz, Methanol-d4) δ 9.40 (s, 1H), 9.03 (s, 1H), 8.70 (s, 1H), 4.26 (s, 3H), 4.10 (s, 3H); MS (ESI+) m/z=191.9 $(M+H)^+$.

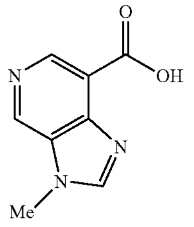 [SMILES: Cn1cnc2c(C(=O)O)cncc21]

C) 3-Methyl-3H-imidazo[4,5-c]pyridine-7-carboxylic acid

To the solution of methyl 3-methyl-3H-imidazo[4,5-c]pyridine-7-carboxylate (50 mg, 0.262 mmol) in MeOH (1 mL) and THE (1 mL) was added 3 M sodium hydroxide (0.262 mL, 0.785 mmol). The reaction mixture was stirred at rt for 4 h. The reaction mixture was neutralized with 2 N HCl and concentrated in vacuo, and used for next reaction without purification. MS (ESI+) m/z=177.9 $(M+H)^+$.

D) Methyl 5-chloro-2-((3-methyl-3H-imidazo[4,5-c]pyridine-7-carboxamido)methyl)benzofuran-7-carboxylate To a solution of methyl 2-(aminomethyl)-5-chlorobenzofuran-7-carboxylate, TFA (19.96 mg, 0.056 mmol, Step A of Example 48) in DMF (1 mL) were added 3-methyl-3H-imidazo[4,5-c]pyridine-7-carboxylic acid (10 mg, 0.056 mmol), BOP (37.4 mg, 0.085 mmol) and DIPEA (36.5 mg, 0.282 mmol). The reaction mixture was stirred at rt for 18 h. The reaction mixture was concentrated in vacuo. The residue was dissolved with MeOH and purified by prep HPLC (Method C) (3.5 mg, 11%) as the TFA salt. $^1$H NMR (400 MHz, Methanol-$d_4$) δ 9.38 (s, 1H), 9.07 (s, 1H), 8.80 (s, 1H), 7.94-7.79 (m, 2H), 6.90 (s, 1H), 5.05-4.94 (m, 2H), 4.16 (s, 3H), 3.92 (s, 3H); MS (ESI+) m/z=399.1 $(M+H)^+$.

Example 70

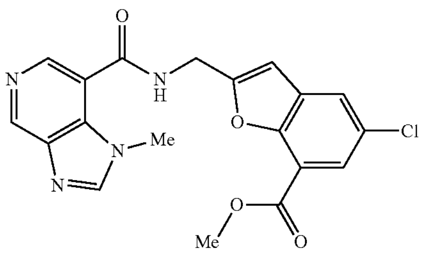 [SMILES: COC(=O)c1cc(Cl)cc2cc(CNC(=O)c3cncc4ncn(C)c34)oc12]

Methyl 5-chloro-2-((1-methyl-1H-imidazo[4,5-c]pyridine-7-carboxamido)methyl)benzofuran-7-carboxylate

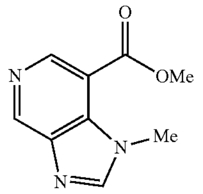 [SMILES: COC(=O)c1cncc2ncn(C)c12]

A) Methyl 3-methyl-3H-imidazo[4,5-c]pyridine-7-carboxylate

To a solution of methyl 3H-imidazo[4,5-c]pyridine-7-carboxylate (100 mg, 0.564 mmol, Step A of Example 69) in DMF (1 mL) were added cesium carbonate (368 mg, 1.129 mmol), and iodomethane (0.071 mL, 1.129 mmol). The reaction mixture was stirred at rt for 2 h. The reaction mixture was concentrated. MeOH was added to the residue and filtered to remove the solid. The filtrate was purified by prep HPLC (Method C) to give the desired product (31 mg, 29%) as the TFA salt. $^1$H NMR (400 MHz, Methanol-d4) 9.42 (s, 1H), 9.09 (s, 1H), 8.96 (s, 1H), 4.18 (s, 3H), 4.08 (s, 3H); MS (ESI+) m/z=191.9 $(M+H)^+$.

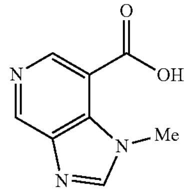 [SMILES: Cn1cnc2cncc(C(=O)O)c21]

B) 1-Methyl-1H-imidazo[4,5-c]pyridine-7-carboxylic acid

To the solution of methyl 3-methyl-3H-imidazo[4,5-c]pyridine-7-carboxylate (50 mg, 0.262 mmol) in MeOH (1 mL) and THE (1 mL) was added 3 M sodium hydroxide (0.262 mL, 0.785 mmol). The reaction mixture was stirred at rt for 4 h. The reaction mixture was neutralized with 2 N HCl, concentrated in vacuo, and used for next reaction without purification. MS (ESI+) m/z=177.9 $(M+H)^+$.

C) Methyl 5-chloro-2-((1-methyl-1H-imidazo[4,5-c]pyridine-7-carboxamido)methyl)benzofuran-7-carboxylate To a solution of methyl 2-(aminomethyl)-5-chlorobenzofuran-7-carboxylate, TFA (19.96 mg, 0.056 mmol, Step A of Example 48) in DMF (1 mL) were added 1-methyl-1H-imidazo[4,5-c]pyridine-7-carboxylic acid (10 mg, 0.056 mmol), BOP (37.4 mg, 0.085 mmol) and DIPEA (36.5 mg, 0.282 mmol). The reaction mixture was stirred at rt for 18 h. The reaction mixture was concentrated in vacuo. The residue was dissolved with MeOH and purified by prep HPLC (Method C) (4.6 mg, 15%) as the TFA salt. $^1$H NMR (400 MHz, Methanol-d4) δ 9.33 (s, 1H), 8.76 (s, 1H), 8.65 (s, 1H), 7.89 (s, 2H), 6.97 (s, 1H), 4.91 (s, 2H), 4.05 (s, 3H), 4.00 (s, 3H); MS (ESI+) m/z=399.0 $(M+H)^+$.

Example 71

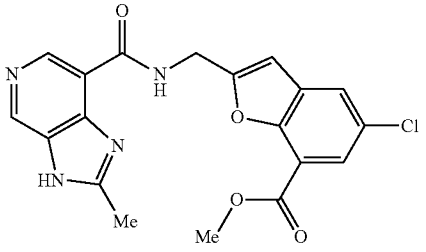 [SMILES: COC(=O)c1cc(Cl)cc2cc(CNC(=O)c3cncc4[nH]c(C)nc34)oc12]

Methyl 5-chloro-2-((2-methyl-3H-imidazo[4,5-c]pyridine-7-carboxamido)methyl)benzofuran-7-carboxylate

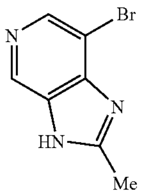 [SMILES: Cc1nc2c(Br)cncc2[nH]1]

A) 7-Bromo-2-methyl-3H-imidazo[4,5-c]pyridine

To a suspension of 5-bromopyridine-3,4-diamine (0.2 g, 1.064 mmol) in 1,1,1-triethoxyethane (1.035 g, 6.38 mmol) was added acetic acid (0.365 mL, 6.38 mmol). The reaction mixture was stirred at 120° C. for 2 h, and concentrated in vacuo. The residue was washed with DCM. The solid was collected by filtration, and washed with DCM to give the desired product as an off-white solid (125 mg, 43% yield). $^1$H NMR (400 MHz, Chloroform-d) δ 8.71 (s, 1H), 8.38 (s, 1H), 2.66 (s, 3H); MS (ESI+) m/z=211.8 $(M+H)^+$.

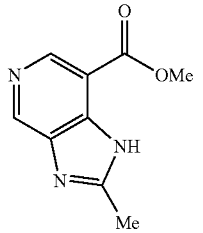 [SMILES: COC(=O)c1cncc2nc(C)[nH]c12]

B) Methyl 2-methyl-1H-imidazo[4,5-c]pyridine-7-carboxylate

To a solution of 7-bromo-2-methyl-3H-imidazo[4,5-c]pyridine (770 mg, 2.83 mmol) in DMF (10 mL) and MeOH (2 mL) were added triethylamine (859 mg, 8.49 mmol), diacetoxypalladium (63.5 mg, 0.283 mmol), and 1,3-bis(diphenylphosphanyl)propane (117 mg, 0.283 mmol). The reaction mixture was degassed with argon and heated at 100°

C. under CO (30 psi) for 16 h. The reaction mixture was concentrated in vacuo and the residue was purified by a flash chromatography (ISCO 120 g column, eluting with 0-10% MeOH in DCM over a 25 minute gradient) to give the desired product as an off white solid (460 mg, 85% yield). $^1$H NMR (400 MHz, Chloroform-d) δ 9.13 (s, 1H), 8.98 (s, 1H), 4.06 (s, 3H), 2.74 (s, 3H); MS (ESI+) m/z=191.9 $(M+H)^+$.

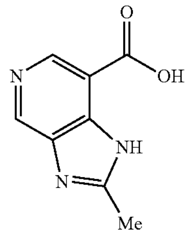 [SMILES: Cc1nc2cncc(C(=O)O)c2[nH]1]

C) 2-Methyl-1H-imidazo[4,5-c]pyridine-7-carboxylic acid

To the solution of methyl 2-methyl-3H-imidazo[4,5-c] pyridine-7-carboxylate (175 mg, 0.915 mmol) in MeOH (1 mL) and THE (1 mL) was added sodium hydroxide, 3 M in water (0.915 mL, 2.75 mmol). The reaction mixture was stirred at rt for 18 h, and neutralized to pH ~7 with 1 N HCl. The mixture was extracted with 20% MeOH in DCM. The combined organic extracts were dried and concentrated in vacuo to give the desired product as a white solid (177 mg, 100% yield). MS (ESI+) m/z=177.9 $(M+H)^+$.

D) Methyl 5-chloro-2-((2-methyl-3H-imidazo[4,5-c] pyridine-7-carboxamido)methyl)benzofuran-7-carboxylate To a solution of methyl 2-(aminomethyl)-5-chlorobenzofuran-7-carboxylate, TFA (19.96 mg, 0.056 mmol, Step C in Example 48) in DMF (1 mL) were added 2-methyl-3H-imidazo[4,5-c]pyridine-7-carboxylic acid (10 mg, 0.056 mmol), BOP (37.4 mg, 0.085 mmol) and DIPEA (36.5 mg, 0.282 mmol). The reaction mixture was stirred at rt for 18 h. The reaction mixture was concentrated in vacuo. The residue was purified by prep HPLC (Method B) to give the product (4.4 mg, 20% yield). $^1$H NMR (500 MHz, DMSO-d6) δ 8.91 (s, 1H), 8.84 (s, 1H), 7.96 (d, J=2.0 Hz, 1H), 7.75 (d, J=2.0 Hz, 1H), 6.91 (s, 1H), 4.86 (br d, J=5.2 Hz, 2H), 3.92 (s, 3H), 2.63 (s, 3H); MS (ESI+) m/z=399.1 $(M+H)^+$.

Example 72

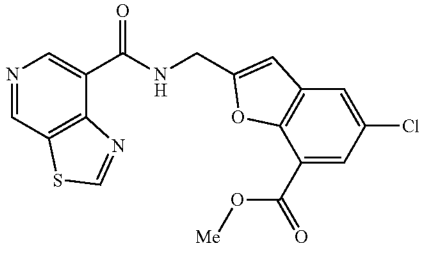 [SMILES: COC(=O)c1cc(Cl)cc2cc(CNC(=O)c3cncc4scnc34)oc12]

Methyl 5-chloro-2-((thiazolo[5,4-c]pyridine-7-carboxamido)methyl)benzofuran-7-carboxylate

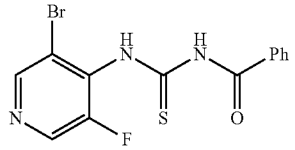 [SMILES: O=C(NC(=S)Nc1c(F)cncc1Br)c1ccccc1]

A) N-((3-Bromo-5-fluoropyridin-4-yl)carbamothioyl)benzamide

To a solution of 3-bromo-5-fluoropyridin-4-amine (900 mg, 4.71 mmol) in acetone (15 mL) was added benzoyl isothiocyanate (1153 mg, 7.07 mmol). The reaction mixture was stirred at 60° C. for 24 h. The reaction mixture was concentrated in vacuo and purified by flash chromatography (120 g ISCO column, 0-30% ethyl acetate in DCM) to give the title compound (1.08 g, 65% yield) as a yellow solid. $^1$H NMR (400 MHz, Methanol-d4) δ 8.70 (s, 1H), 8.56 (d, J=1.2 Hz, 1H), 8.02 (dd, J=8.4, 1.2 Hz, 2H), 7.73-7.67 (m, 1H), 7.62-7.54 (m, 2H); MS (ESI+) m/z=355.9 $(M+H)^+$.

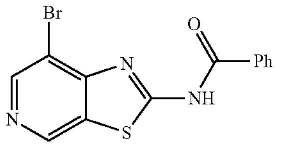 [SMILES: O=C(Nc1nc2c(Br)cncc2s1)c1ccccc1]

B) N-(7-Bromothiazolo[5,4-c]pyridin-2-yl)benzamide

To a solution of N-((3-bromo-5-fluoropyridin-4-yl)carbamothioyl)benzamide (1080 mg, 3.05 mmol) in DMF (10 mL) was added cesium carbonate (1987 mg, 6.10 mmol). The reaction mixture was heated at 85° C. for 2 h. The reaction mixture was diluted with cold water. The solid formed was collected by filtration and dried under vacuum to give the product (750 mg, 74% yield). $^1$H NMR (400 MHz, Methanol-d4) δ 8.72 (s, 1H), 8.43 (s, 1H), 8.25-8.16 (m, 2H), 7.52-7.40 (m, 3H); MS (ESI+) m/z=335.9 $(M+H)^+$.

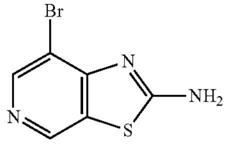 [SMILES: Nc1nc2c(Br)cncc2s1]

C) 7-Bromothiazolo[5,4-c]pyridin-2-amine

A suspension of N-(7-bromothiazolo[5,4-c]pyridin-2-yl) benzamide (750 mg, 2.244 mmol) in hydrochloric acid, 37% (10 mL) was heated at 90° C. for 8 h. The reaction mixture was concentrated in vacuo. To the residue was washed with DCM. The solid was collected by filtration and dried under vacuum to give the desired product as a tan solid (340 mg, 66% yield). $^1$H NMR (400 MHz, Chloroform-d) δ 8.84 (s, 1H), 8.57 (s, 1H); MS (ESI+) m/z=229.8 $(M+H)^+$.

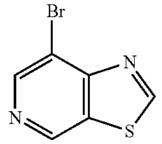

D) 7-Bromothiazolo[5,4-c]pyridine

To a suspension of 7-bromothiazolo[5,4-c]pyridin-2-amine (200 mg, 0.869 mmol) in THE (10 mL) was added isopentyl nitrite (509 mg, 4.35 mmol). The reaction mixture was heated at 85° C. for 4 h. The reaction mixture was concentrated in vacuo and purified by flash chromatography (40 g ISCO column, 0-10% MeOH in DCM) to give the title compound as a light yellow solid (151 mg, 81%). $^1$H NMR (400 MHz, Chloroform-d) δ 9.33 (s, 1H), 9.22 (s, 1H), 8.83 (s, 1H); MS (ESI+) m/z=229.8 $(M+H)^+$.

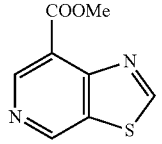 [SMILES: COC(=O)c1cncc2scnc12]

E) Methyl thiazolo[5,4-c]pyridine-7-carboxylate

To a solution of 7-bromothiazolo[5,4-c]pyridine (100 mg, 0.465 mmol) in DMF (2 mL) and MeOH (0.5 mL) were added triethylamine (235 mg, 2.325 mmol), diacetoxypalladium (10.44 mg, 0.046 mmol), and 1,3-bis(diphenylphosphanyl) propane (19.18 mg, 0.046 mmol). The reaction mixture was degassed by bubbling Ar through and heated under 30 psi CO at 100° C. for 16 h. The reaction mixture was filtered and concentrated in vacuo. The residue was purified with prep HPLC (Method C) to give the desired product (51 mg, 57%) as the TFA salt. $^1$H NMR (400 MHz, Methanol-$d_4$) Shift 9.71 (s, 1H), 9.55 (s, 1H), 9.22 (s, 1H), 3.99 (s, 3H); MS (ESI+) m/z=194.9 $(M+H)^+$.

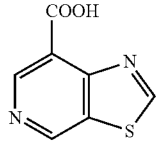 [SMILES: O=C(O)c1cncc2scnc12]

F) Thiazolo[5,4-c]pyridine-7-carboxylic acid

To the solution of methyl thiazolo[5,4-c]pyridine-7-carboxylate (51 mg, 0.263 mmol) in THE (1 mL) and MeOH (1 mL) was added sodium hydroxide, 3 M in water (0.438 mL, 1.313 mmol). The reaction mixture was stirred at rt for 2 h and neutralized to pH ~7 with 1 N HCl. The mixture was extracted with 20% MeOH in DCM. The combined organic extracts were dried over sodium sulfate, filtered, and concentrated in vacuo to give the desired product (34 mg, 71% yield). MS (ESI+) m/z=180.9 $(M+H)^+$.

G) Methyl 5-chloro-2-((thiazolo[5,4-c]pyridine-carboxamido)methyl)benzofuran-7-carboxylate To a solution of methyl 2-(aminomethyl)-5-chlorobenzofuran-7-carboxylate, TFA (20 mg, 0.057 mmol, Step C of Example 48) in DMF (1 mL) were added thiazolo[5,4-c]pyridine-7-carboxylic acid (10.19 mg, 0.057 mmol), BOP (37.5 mg, 0.085 mmol) and DIPEA (36.5 mg, 0.283 mmol). The reaction mixture was stirred at rt for 18 h. The reaction mixture was filtered and concentrated in vacuo. The residue was purified by prep HPLC (Method B) to give the desired product (4.7 mg, 19%). $^1$H NMR (500 MHz, DMSO-d6) δ 9.92 (s, 2H), 9.65 (s, 1H), 9.15 (s, 1H), 7.97 (s, 1H), 7.74 (s, 1H), 6.94 (s, 1H), 4.90 (br d, J=5.8 Hz, 2H), 3.90 (s, 3H); MS (ESI+) m/z=402.0 $(M+H)^+$.

Example 73

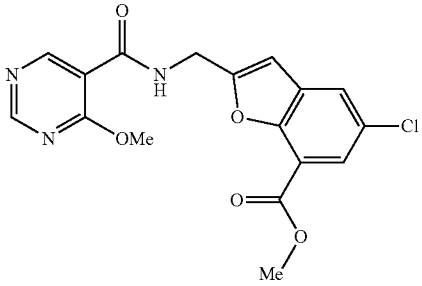 [SMILES: COC(=O)c1cc(Cl)cc2cc(CNC(=O)c3cncnc3OC)oc12]

Methyl 5-chloro-2-((4-methoxypyrimidine-5-carboxamido)methyl)benzofuran-7-carboxylate A mixture of methyl 2-(aminomethyl)-5-chlorobenzofuran-7-carboxylate, TFA (50.5 mg, 0.143 mmol, Step C in Example 48), 4-methoxypyrimidine-5-carboxylic acid (20 mg, 0.130 mmol), HATU (54.3 mg, 0.143 mmol) and Hunig's base (0.091 mL, 0.519 mmol) in DMF (1 mL) was stirred at room temperature for 1 hour. The reaction mixture was quenched with 1:1 DMF/AcOH and purified by preparative HPLC (Method B). The appropriate fractions were combined and dried via centrifugal evaporation to afford the title compound (6.4 mg, 13.13% yield). $^1$H NMR (500 MHz, DMSO-$d_6$) δ 9.01 (br t, J=5.5 Hz, 1H), 8.91 (s, 1H), 8.85 (s, 1H), 7.98 (d, J=1.8 Hz, 1H), 7.75 (d, J=1.8 Hz, 1H), 6.87 (s, 1H), 4.70 (br d, J=5.8 Hz, 2H), 4.06 (s, 3H), 3.92 (s, 3H); MS (ESI+) m/z=376.1 $(M+H)^+$.

Example 74

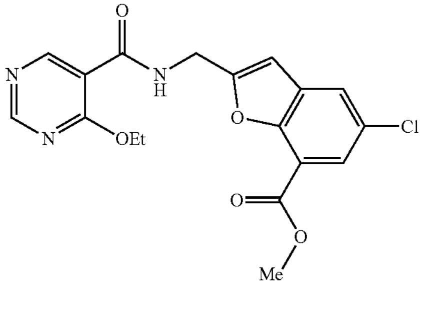 [SMILES: CCOc1ncncc1C(=O)NCc1cc2cc(Cl)cc(C(=O)OC)c2o1]

Methyl 5-chloro-2-((4-ethoxypyrimidine-5-carboxamido)methyl)benzofuran-7-carboxylate

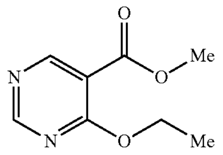 [SMILES: CCOc1ncncc1C(=O)OC]

A) Methyl 4-ethoxypyrimidine-5-carboxylate

A mixture of methyl 4-hydroxypyrimidine-5-carboxylate (200 mg, 1.3 mmol), Hunig's base (240 μl, 1.43 mmol) and $POCl_3$ (133 μl, 1.43 mmol) was heated to 80° C. for 2 h. The reaction was transferred to a flask containing EtOH (20 mL). The solvent was evaporated and the residue was suspended in ice cold saturated sodium bicarbonate solution. The aqueous layer was extracted with EtOAc (3×). The organic layer was separated, dried over sodium sulfate, filtered, and concentrated. The residue was purified by silica gel chromatography eluting with 0-40% EtOAc in hexanes. The appropriate fractions were combined and concentrated in vacuo to afford the product (103 mg, 43.6% yield). MS (ESI+) m/z=183.0 $(M+H)^+$.

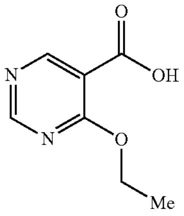

B) 4-Ethoxypyrimidine-5-carboxylic acid

A mixture of methyl 4-ethoxypyrimidine-5-carboxylate (100 mg, 0.549 mmol) and lithium hydroxide monohydrate (46.1 mg, 1.098 mmol) in THE (2.2 mL) and water (0.55 mL) was stirred at room temperature for 1.5 hours. The reaction mixture was quenched with 1N aqueous HCl solution (1.1 mL, 1.1 mmol). The mixture was concentrated and dried on high vacuum to afford the product as an HCl salt (111 mg, 99% yield). MS (ESI+) m/z=169.0 $(M+H)^+$.

C) Methyl 5-chloro-2-((4-ethoxypyrimidine-5-carboxamido)methyl)benzofuran-7-carboxylate A mixture of methyl 2-(aminomethyl)-5-chlorobenzofuran-7-carboxylate, TFA (41.6 mg, 0.118 mmol, Step C in Example 48), 4-ethoxypyrimidine-5-carboxylic acid (18 mg, 0.107 mmol), HATU (44.8 mg, 0.118 mmol) and Hunig's base (0.075 mL, 0.428 mmol) in DMF (1 mL) was stirred at room temperature for 1 hour. The reaction mixture was quenched with 1:1 DMF/AcOH and purified by preparative HPLC (Method B). The appropriate fractions were combined and dried via centrifugal evaporation to afford the title compound (4.8 mg, 11.50% yield). $^1H$ NMR (500 MHz, DMSO-$d_6$) δ 8.83 (br d, J=11.0 Hz, 2H), 8.79 (br d, J=5.8 Hz, 1H), 7.94 (s, 1H), 7.74 (s, 1H), 6.87 (s, 1H), 4.71 (d, J=5.8 Hz, 2H), 4.54 (q, J=7.1 Hz, 2H), 3.91 (s, 3H), 1.36 (td, J=7.0, 1.6 Hz, 3H); MS (ESI+) m/z=390.2 $(M+H)^+$.

Example 75

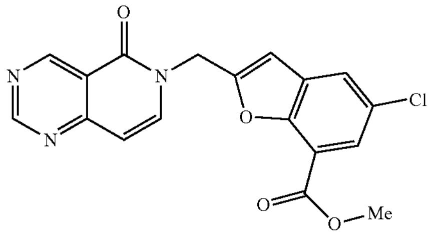 [SMILES: COC(=O)c1cc(Cl)cc2cc(Cn3ccc4ncncc4c3=O)oc12]

Methyl 5-chloro-2-((5-oxopyrido[4,3-d]pyrimidin-6(5H)-yl)methyl)benzofuran-7-carboxylate A mixture of ethyl 4-methylpyrimidine-5-carboxylate (35.7 mg, 0.215 mmol), and 1,1-dimethoxy-N,N-dimethylmethanamine (0.12 mL, 0.91 mmol) in DMF (0.5 mL) in a microwave tube was heated in a microwave reactor at 160° C. for 40 min. The reaction mixture was concentrated in vacuo. To the residue was added 1 mL of acetic acid and methyl 2-(aminomethyl)-5-chlorobenzofuran-7-carboxylate TFA salt (38 mg, 0.107 mmol, Step C in Example 48) and the mixture was again heated in a microwave at 110° C. for 25 min. The reaction mixture was concentrated in vacuo. The residue was dissolved in DMF, filtered and purified by preparative HPLC (Method B). Fractions containing the desired product were combined and dried via centrifugal evaporation to give the title compound (28 mg, 67%). $^1H$ NMR (500 MHz, DMSO-$d_6$) δ 9.49 (s, 1H), 9.36 (s, 1H), 8.14 (d, J=7.7 Hz, 1H), 7.96 (s, 1H), 7.76 (s, 1H), 6.95 (s, 1H), 6.77 (d, J=7.6 Hz, 1H), 5.47 (s, 2H), 3.90 (s, 3H); MS (ESI+) m/z=370.1 $(M+H)^+$.

Example 76

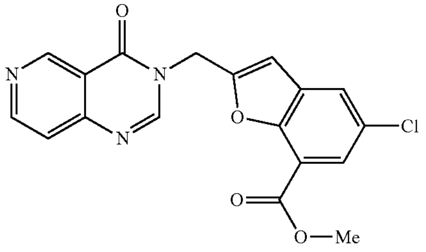 [SMILES: COC(=O)c1cc(Cl)cc2cc(Cn3cnc4ccncc4c3=O)oc12]

Methyl 5-chloro-2-((4-oxopyrido[4,3-d]pyrimidin-3(4H)-yl)methyl)benzofuran-7-carboxylate 4-Aminonicotinic acid (19.92 mg, 0.144 mmol) and N,N-dimethylformamide dimethyl acetal (0.114 mL, 0.848 mmol) were taken up in DMF (4 mL) in a microwave vial. The vial was sealed and heated to 110° C. for 40 minutes in a microwave reactor. The reaction mixture was cooled and concentrated in vacuo. To the residue was added 1 mL of acetic acid and methyl 2-(aminomethyl)-5-chlorobenzofuran-7-carboxylate, TFA (30 mg, 0.085 mmol, Step C in Example 48). The reaction was sealed and again heated in a microwave reactor to 110° C. for 35 minutes. The reaction mixture was cooled and concentrated in vacuo. The residue was dissolved in MeOH and 0.1 mL of DMF, filtered, and purified via HPLC (method B) to give the title compound (7.6 mg, 24% yield). $^1$H NMR (500 MHz, DMSO-$d_6$) δ 9.33 (s, 1H), 8.88 (d, J=5.5 Hz, 1H), 8.78 (s, 1H), 7.98 (d, J=2.1 Hz, 1H), 7.76 (d, J=1.8 Hz, 1H), 7.65 (d, J=5.8 Hz, 1H), 7.02 (s, 1H), 5.48 (s, 2H), 3.87 (s, 3H); MS (ESI+) m/z=370.3 $(M+H)^+$.

Example 77

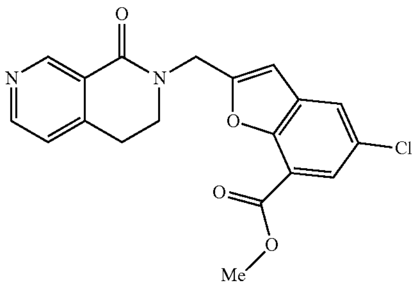 [SMILES: COC(=O)c1cc(Cl)cc2cc(CN3CCc4ccncc4C3=O)oc12]

Methyl 5-chloro-2-((1-oxo-3,4-dihydro-2,7-naphthyridin-2(1H)-yl)methyl)benzofuran-7-carboxylate A mixture of 3,4-dihydro-1H-pyrano[3,4-c]pyridin-1-one, HCl (87 mg, 0.47 mmol) (WO 2005063768) and methyl 2-(aminomethyl)-5-chlorobenzofuran-7-carboxylate TFA salt (150 mg, 0.424 mmol, Step C of Example 48) in pyridine (2 mL) was heated at 128° C. for 5 hours in a vial with pressure relief septum. The reaction was concentrated in vacuo. A portion of the sample was taken up in DMF, filtered, and purified by preparative HPLC (Method B). Fractions containing the desired product were combined and dried via centrifugal evaporation to give the title compound (7.4 mg, 18%). $^1$H NMR (500 MHz, DMSO-$d_6$) δ 8.94 (s, 1H), 8.58 (br d, J=4.6 Hz, 1H), 7.92 (s, 1H), 7.73 (s, 1H), 7.36 (br d, J=4.9 Hz, 1H), 6.93 (s, 1H), 4.91 (s, 2H), 3.86 (s, 3H), 3.61-3.47 (m, 2H), 3.08-3.00 (m, 2H); MS (ESI+) m/z=371.0 $(M+H)^+$.

Example 78

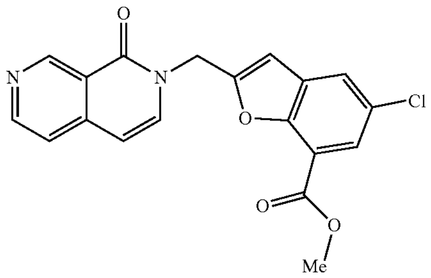 [SMILES: COC(=O)c1cc(Cl)cc2cc(Cn3ccc4ccncc4c3=O)oc12]

Methyl 5-chloro-2-((1-oxo-2,7-naphthyridin-2(1H)-yl)methyl)benzofuran-7-carboxylate Methyl 4-methylnicotinate (34.2 mg, 0.226 mmol) and N,N-dimethylformamide dimethylacetal (0.121 mL, 0.905 mmol) were taken up in DMF in a microwave vial. The vial was sealed and heated to 160° C. for 40 minutes in a microwave reactor. The reaction mixture was cooled and concentrated in vacuo. The residue was dissolved in DCM and concentrated in vacuo once again. To the resulting residue was added acetic acid (0.5 mL) and methyl 2-(aminomethyl)-5-chlorobenzofuran-7-carboxylate, TFA (40 mg, 0.113 mmol, Step C in Example 48). The vial was then sealed and heated to 110° C. for 25 minutes in a microwave reactor. The reaction was again cooled and concentrated in vacuo. The residue was dissolved in DMF and MeOH, filtered, and purified via HPLC (method B) to give the title compound (29 mg, 69% yield). $^1$H NMR (500 MHz, DMSO-$d_6$) δ 9.35 (s, 1H), 8.73 (d, J=5.2 Hz, 1H), 7.96 (d, J=2.1 Hz, 1H), 7.86 (d, J=7.3 Hz, 1H), 7.75 (d, J=1.8 Hz, 1H), 7.63 (d, J=5.5 Hz, 1H), 6.91 (s, 1H), 6.75 (d, J=7.3 Hz, 1H), 5.43 (s, 2H), 3.87 (s, 3H); MS (ESI+) m/z=368.9 $(M+H)^+$.

Example 79

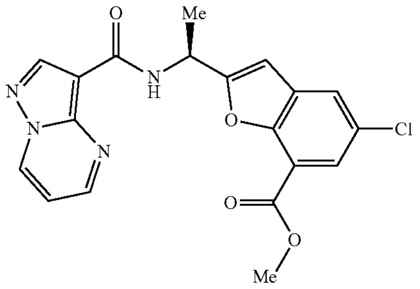 [SMILES: COC(=O)c1cc(Cl)cc2cc([C@H](C)NC(=O)c3cnn4cccnc34)oc12]

Methyl (S)-5-chloro-2-(1-(pyrazolo[1,5-a]pyrimidine-3-carboxamido)ethyl)benzofuran-7-carboxylate

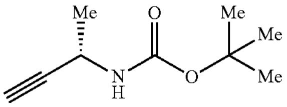

A) tert-Butyl (S)-but-3-yn-2-ylcarbamate

To a suspension of (S)-2-(but-3-yn-2-yl)isoindoline-1,3-dione (1.6 g, 8.03 mmol) in ethanol (30 mL) and $H_2O$ (1 mL) was added hydrazine (0.30 mL, 9.64 mmol). The reaction mixture was heated at 76° C. for 60 min. The reaction mixture turned into clear solution and after 30 min, a solid crashed out. The reaction mixture was cooled down and filtered. To the filtrate was added $Boc_2O$ (2.42 mL, 10.44 mmol) and DIPEA (2.81 mL, 16.06 mmol). The reaction mixture was stirred at room temperature for 16 hours. The reaction mixture was concentrated in vacuo. The residue was dissolved in DCM and purified by flash chromatography (ISCO column 40 g, 0-20% ethyl acetate in hexanes) to give the title compound (1.2 g, 88%) as a white solid. $^1$H NMR (499 MHz, CHLOROFORM-d) δ 4.87-4.59 (m, 1H), 4.58-4.33 (m, 1H), 2.28 (d, J=2.2 Hz, 1H), 1.47 (s, 9H), 1.42 (d, J=6.9 Hz, 3H).

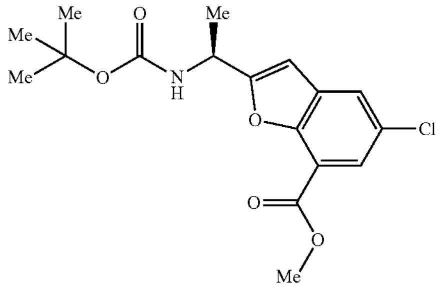 [SMILES: COC(=O)c1cc(Cl)cc2cc([C@H](C)NC(=O)OC(C)(C)C)oc12]

B) Methyl (S)-2-(1-((tert-butoxycarbonyl)amino) ethyl)-5-chlorobenzofuran-7-carboxylate A mixture of methyl 5-chloro-2-hydroxy-3-iodobenzoate (1.95 g, 6.24 mmol, Step A of Example 94), tert-butyl (S)-but-3-yn-2-ylcarbamate (1.21 g, 7.18 mmol), TEA (14.8 mL, 106 mmol), and copper(I) iodide (0.12 g, 0.62 mmol) in DMF (15 mL) was purged with a nitrogen stream for 5 mins. Bis(triphenylphosphine)-palladium(II) chloride (0.219 g, 0.312 mmol) was then added. The resulting mixture was heated at 80° C. for 2 hours. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 80 g, 0-20% ethyl acetate in hexanes) to give the title compound (2.0 g, 91%) as a light brown solid. $^1$H NMR (400 MHz, Chloroform-d) δ 7.89 (d, J=2.1 Hz, 1H), 7.68 (d, J=2.2 Hz, 1H), 6.58 (s, 1H), 5.18-4.89 (m, 2H), 4.02 (s, 3H), 1.65-1.59 (m, 3H), 1.48 (s, 9H); MS (ESI+) m/z=298.2 $(M-55+H)^+$.

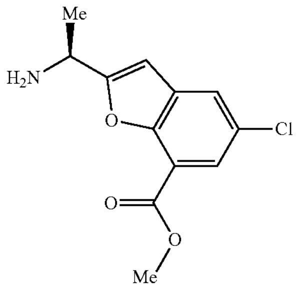 [SMILES: COC(=O)c1cc(Cl)cc2cc([C@H](C)N)oc12]

C) Methyl (S)-2-(1-aminoethyl)-5-chlorobenzofuran-7-carboxylate

To a solution of methyl (S)-2-(1-((tert-butoxycarbonyl)amino)ethyl)-5-chlorobenzofuran-7-carboxylate (0.26 g, 0.735 mmol) in DCM (3 mL) was added TFA (0.57 mL, 7.35 mmol). The reaction mixture was stirred at room temperature for 2 hours. The reaction mixture was concentrated in vacuo to give the title compound (TFA salt) as a brown solid (250 mg, 93%). MS (ESI+) m/z=237.1 $(M-16+H)^+$.

D) Methyl (S)-5-chloro-2-(1-(pyrazolo[1,5-a]pyrimidine-3-carboxamido) ethyl)benzofuran-7-carboxylate A mixture of pyrazolo[1,5-a]pyrimidine-3-carboxylic acid (144 mg, 0.884 mmol) and BOP (421 mg, 0.952 mmol) in DMF (4 mL) was stirred at rt for 15 min. A solution of methyl (S)-2-(1-aminoethyl)-5-chlorobenzofuran-7-carboxylate, TFA salt (250 mg, 0.680 mmol) in THE (2 mL) and DIPEA (0.71 mL, 4.08 mmol) were added. The reaction mixture turned into clear solution after addition of the amine and was stirred at rt for 3 h. The reaction mixture was diluted with ethyl acetate and saturated aqueous $NaHCO_3$ solution. The organic layer was separated, washed with brine, dried over $MgSO_4$, and filtered. The filtrate was concentrated in vacuo to give the title compound as a white solid (220 mg, 81%). A portion of the sample was dissolved in DMF and purified by preparative HPLC (Method B). Fractions containing the desired product were combined and dried via centrifugal evaporation to give the title compound. $^1$H NMR (500 MHz, DMSO-$d_6$) δ 9.31-9.18 (m, 1H), 8.82 (br d, J=4.1 Hz, 1H), 8.61 (s, 1H), 8.36 (br d, J=8.1 Hz, 1H), 7.95 (s, 1H), 7.74 (d, J=1.1 Hz, 1H), 7.27 (dd, J=6.6, 4.5 Hz, 1H), 6.91 (s, 1H), 5.50 (br t, J=7.3 Hz, 1H), 3.89 (s, 3H), 1.67 (d, J=6.9 Hz, 3H); MS (ESI+) m/z=399.1 $(M+H)^+$.

Example 80

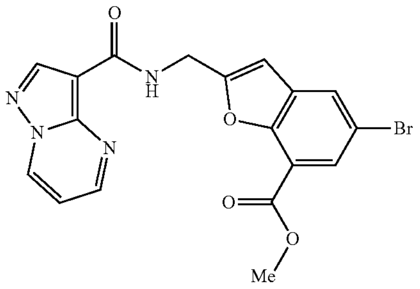 [SMILES: COC(=O)c1cc(Br)cc2cc(CNC(=O)c3cnn4cccnc34)oc12]

Methyl 5-bromo-2-((pyrazolo[1,5-a]pyrimidine-3-carboxamido)methyl)benzofuran-7-carboxylate

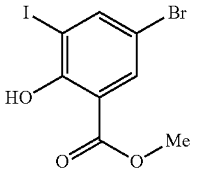 [SMILES: COC(=O)c1cc(Br)cc(I)c1O]

A) Methyl 5-bromo-2-hydroxy-3-iodobenzoate

To a solution of methyl 5-bromo-2-hydroxybenzoate (4.0 g, 17.3 mmol) in N,N-dimethylformamide (50 mL) was added sodium iodide (3.11 g, 20.8 mmol), followed by chloramine T trihydrate (5.36 g, 19.0 mmol) slowly. The resulting mixture was stirred at room temperature for 20 hours. The reaction mixture was diluted with ethyl acetate and 1 N aqueous HCl solution. The organic layer was separated, washed with brine followed by $Na_2S_2O_3$ solution, dried over $MgSO_4$, and filtered. The filtrate was concentrated in vacuo to give a light yellow oil. To the residue was added MeOH and the resulting precipitate was filtered to give the title compound as a white solid (5.1 g, 83%). $^1$H NMR (400 MHz, CHLOROFORM-d) δ 11.59 (s, 1H), 8.06 (d, J=2.3 Hz, 1H), 7.99 (d, J=2.3 Hz, 1H), 4.01 (s, 3H).

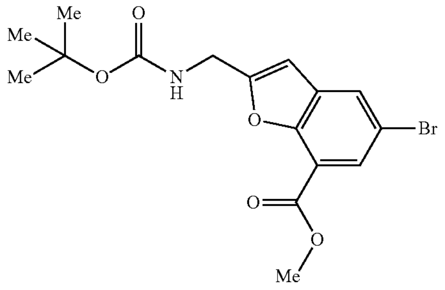 [SMILES: COC(=O)c1cc(Br)cc2cc(CNC(=O)OC(C)(C)C)oc12]

B) Methyl 5-bromo-2-(((tert-butoxycarbonyl)amino) methyl) benzofuran-7-carboxylate A mixture of methyl 5-bromo-2-hydroxy-3-iodobenzoate (5.1 g, 14.3 mmol), tert-butyl prop-2-yn-1-ylcarbamate (2.55 g, 16.4 mmol), TEA (23.9 mL, 171 mmol), and copper(I) iodide (0.272 g, 1.43 mmol) in DMF (20 mL) was purged with a nitrogen stream for 5 mins, then bis(triphenylphosphine)palladium(II) chloride (0.85 g, 1.21 mmol) was added. The resulting mixture was heated at 80° C. for 2 hours. The reaction was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO 80 g column, 0-25% ethyl acetate in hexanes) to give the title compound (4.2 g, 77% yield) as a light brown solid. $^1H$ NMR (400 MHz, Chloroform-d) δ 8.01 (d, J=2.0 Hz, 1H), 7.83 (d, J=2.0 Hz, 1H), 6.63 (s, 1H), 5.20-5.03 (m, 1H), 4.52 (br d, J=5.9 Hz, 2H), 4.01 (s, 3H), 1.48 (s, 9H); MS (ESI+) m/z=330 $(M-54+H)^+$.

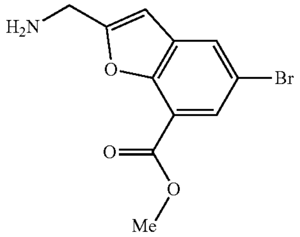 [SMILES: COC(=O)c1cc(Br)cc2cc(CN)oc12]

C) Methyl 2-(aminomethyl)-5-bromobenzofuran-7-carboxylate

To a solution of methyl 5-bromo-2-(((tert-butoxycarbonyl)amino)methyl) benzofuran-7-carboxylate (260 mg, 0.677 mmol) in DCE (3 mL) was added TFA (1.04 mL, 13.5 mmol). The reaction mixture was stirred at room temperature for 3 hours. The reaction mixture was concentrated in vacuo to give the crude title compound (TFA salt) as a brown solid (260 mg, 87%). MS (ESI+) m/z=269.1 $(M-17+H)^+$.

D) Methyl 5-bromo-2-((pyrazolo[1,5-a]pyrimidine-3-carboxamido)methyl) benzofuran-7-carboxylate To a suspension of pyrazolo[1,5-a]pyrimidine-3-carboxylic acid (12.3 mg, 0.075 mmol) and BOP (33.3 mg, 0.075 mmol) in DMF (1 mL) was added methyl 2-(aminomethyl)-5-bromobenzofuran-7-carboxylate, TFA (25 mg, 0.063 mmol) and DIPEA (0.04 mL, 0.25 mmol). The reaction mixture turned into a clear solution and was stirred at room temperature for 3 hours. Solid formed in the reaction mixture. The reaction mixture was concentrated in vacuo. The residue was dissolved in DMF, filtered and purified by preparative HPLC (Method B). Fractions containing the desired product were combined and dried via centrifugal evaporation to give the title compound (5.6 mg, 16.3%). 1H NMR (500 MHz, DMSO-$d_6$) δ 9.35 (br s, 1H), 9.01-8.76 (m, 1H), 8.65 (s, 2H), 8.10 (d, J=1.5 Hz, 1H), 7.86 (d, J=1.5 Hz, 1H), 7.46-7.22 (m, 1H), 6.86 (s, 1H), 4.82 (br d, J=5.2 Hz, 2H), 3.92 (s, 3H); MS (ESI+) m/z=429.1 $(M+H)^+$.

Example 81

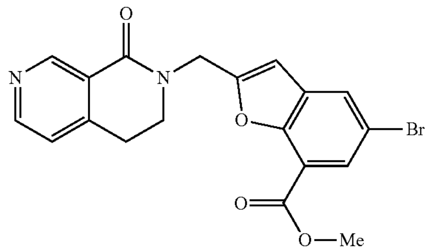 [SMILES: COC(=O)c1cc(Br)cc2cc(CN3CCc4ccncc4C3=O)oc12]

Methyl 5-bromo-2-((1-oxo-3,4-dihydro-2,7-naphthyridin-2(1H)-yl)methyl)benzofuran-7-carboxylate 3,4-Dihydro-1H-pyrano[3,4-c]pyridin-1-one (20 mg, 0.134 mmol) (WO 2005063768) and methyl 2-(aminomethyl)-5-bromobenzofuran-7-carboxylate (76 mg, 0.27 mmol, Step C in Example 80) were added to a pressure relief vial and heated neat at 120° C. After 4 hours, the reaction was cooled, taken up in 2 mL DMF, filtered, and purified via HPLC (Method B) to give methyl 5-bromo-2-((1-oxo-3,4-dihydro-2,7-naphthyridin-2(1H)-yl)methyl)benzofuran-7-carboxylate (9.5 mg, 0.022 mmol, 16.2% yield). $^1H$ NMR (500 MHz, DMSO-$d_6$) δ 8.96 (s, 1H), 8.62 (d, J=4.9 Hz, 1H), 8.09 (d, J=1.8 Hz, 1H), 7.86 (d, J=1.8 Hz, 1H), 7.38 (d, J=5.2 Hz, 1H), 6.96 (s, 1H), 4.94 (s, 2H), 3.88 (s, 3H), 3.75 (t, J=6.6 Hz, 2H), 3.09 (t, J=6.4 Hz, 2H); MS (ESI+) m/z 415.0 $(M+H)^+$.

Example 82

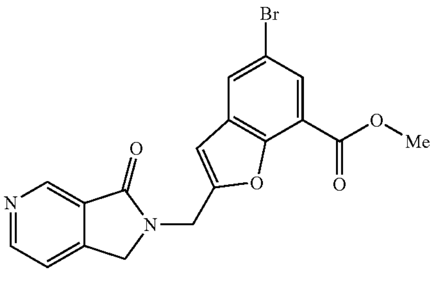 [SMILES: COC(=O)c1cc(Br)cc2cc(CN3Cc4ccncc4C3=O)oc12]

Methyl 5-bromo-2-((3-oxo-1,3-dihydro-2H-pyrrolo[3,4-c]pyridin-2-yl)methyl)benzofuran-7-carboxylate

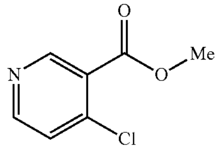 [SMILES: COC(=O)c1cnccc1Cl]

A) Methyl 4-chloronicotinate

To a suspension of 4-chloronicotinic acid (4.0 g, 25.4 mmol) in DMF (35 mL) were added $K_2CO_3$ (5.26 g, 38.1 mmol) and iodomethane (1.75 mL, 27.9 mmol). The reaction mixture was stirred at room temperature overnight. The reaction mixture was diluted with ethyl acetate and water. The organic layer was separated, washed with brine, dried over $MgSO_4$, and filtered. The filtrate was concentrated in vacuo. The residue was dissolved in DCM and purified by flash chromatography (ISCO column 80 g, 0-25% ethyl acetate in DCM) to give the title compound (3.1 g, 71%) as a colorless oil. $^1$H NMR (400 MHz, Chloroform-d) δ 9.06 (s, 1H), 8.61 (d, J=5.3 Hz, 1H), 7.44 (d, J=5.3 Hz, 1H), 4.00 (s, 3H); MS (ESI+) m/z=172.1 $(M+H)^+$.

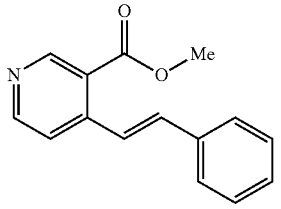 [SMILES: COC(=O)c1cnccc1/C=C/c1ccccc1]

B) Methyl (E)-4-styrylnicotinate

A mixture of (E)-4,4,5,5-tetramethyl-2-styryl-1,3,2-dioxaborolane (8.37 g, 36.4 mmol), methyl 4-chloronicotinate (5.2 g, 30.3 mmol) in 1,4-dioxane (35 mL) and water (8 mL) was purged with a nitrogen stream for 5 min. $PdCl_2$(dppf) (1.33 g, 1.82 mmol) was then added. The reaction mixture was heated at 95° C. under nitrogen atmosphere for 5 hours. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 120 g, 0-35% ethyl acetate in hexanes) to give the title compound (5.2 g, 72%) as a brown oil. $^1$H NMR (499 MHz, Chloroform-d) δ 9.15 (d, J=0.6 Hz, 1H), 8.69 (d, J=5.3 Hz, 1H), 8.05 (d, J=16.3 Hz, 1H), 7.71-7.57 (m, 3H), 7.47-7.39 (m, 2H), 7.38-7.33 (m, 1H), 7.26 (d, J=16.3 Hz, 1H), 4.00 (s, 3H); MS (ESI+) m/z=240.2 $(M+H)^+$.

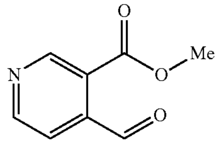 [SMILES: COC(=O)c1cnccc1C=O]

C) Methyl 4-formylnicotinate

The reaction mixture of methyl (E)-4-styrylnicotinate (1.0 g, 4.18 mmol) and pyridine (1.0 mL, 12.5 mmol) in DCM (15 mL) was cooled to −78° C. A stream of $O_3/O_2$ was bubbled through the reaction solution for 10 minutes. The brown reaction mixture changed from yellow to colorless and purple. The $O_3$ generator was turned off and $O_2$ was bubbled for a few minutes until the purple color dissipated and the solution returned to light yellow in color. The reaction mixture was purged with nitrogen for 3 min and stirred at −78° C. for 20 minutes. The reaction was diluted with DCM and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-50% ethyl acetate in hexanes) to give the title compound (0.34 g, 49%) as a white solid. $^1$H NMR (500 MHz, $CDCl_3$) δ 10.74 (d, J=0.6 Hz, 1H), 9.30 (s, 1H), 8.97 (d, J=4.9 Hz, 1H), 7.72 (dd, J=4.9, 0.7 Hz, 1H), 4.04 (s, 3H); MS (ESI+) m/z=166.1 $(M+H)^+$.

D) Methyl 5-bromo-2-((3-oxo-1,3-dihydro-2H-pyrrolo[3,4-c]pyridin-2-yl)methyl)benzofuran-7-carboxylate A mixture of methyl 4-formylnicotinate (20 mg, 0.112 mmol) in THE (0.8 mL) was charged with a solution of methyl 2-(aminomethyl)-5-bromobenzofuran-7-carboxylate (33.3 mg, 0.117 mmol, Step C in Example 80) in THE (2 mL). After stirring at room temperature for 40 min, acetic acid (0.1 mL, 1.75 mmol) and sodium triacetoxyborohydride (35.5 mg, 0.167 mmol) were added. The resulting mixture was stirred at room temperature for 20 hours. After 20 hours, more ethyl 4-formylnicotinate (15 mg) in THE (1 mL) was added. The reaction mixture was stirred at room temperature for an additional hour, and then sodium triacetoxyborohydride (35.5 mg, 0.167 mmol) was added. The reaction mixture was stirred at room temperature for another 4 hours before being diluted with saturated aqueous $NaHCO_3$ solution. After stirring the quenched reaction for 5 minutes, the resulting mixture was extracted with ethyl acetate. The organic layer was separated and concentrated in vacuo. The residue was dissolved in DMF and purified by preparative HPLC (Method B). Fractions containing the desired product were combined and dried via centrifugal evaporation to give the title compound (7.5 mg, 12%). $^1$H NMR (500 MHz, DMSO-$d_6$) δ 8.97 (s, 1H), 8.78 (d, J=5.0 Hz, 1H), 8.13 (d, J=1.9 Hz, 1H), 7.88 (d, J=2.0 Hz, 1H), 7.73 (br d, J=4.8 Hz, 1H), 7.00 (s, 1H), 5.00 (s, 2H), 4.69 (s, 2H), 3.91 (s, 3H); MS (ESI+) m/z=400.9 $(M+H)^+$.

Example 83

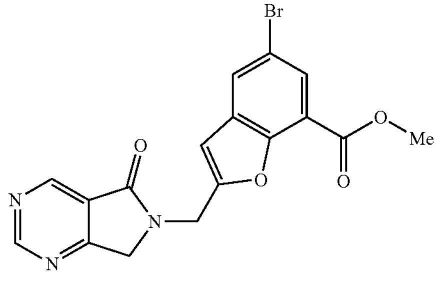 [SMILES: COC(=O)c1cc(Br)cc2cc(CN3Cc4ncncc4C3=O)oc12]

Methyl 5-bromo-2-((5-oxo-5,7-dihydro-6H-pyrrolo[3,4-d]pyrimidin-6-yl)methyl)benzofuran-7-carboxylate

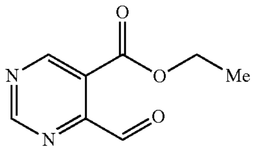 [SMILES: CCOC(=O)c1cncnc1C=O]

A) Ethyl 4-formylpyrimidine-5-carboxylate

A mixture of ethyl 4-methylpyrimidine-5-carboxylate (1.0 g, 6.02 mmol) and selenium dioxide (0.708 g, 6.38 mmol) in 1,4-dioxane (10 mL) in a sealed tube was heated at 95° C. overnight. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-50% ethyl acetate in hexanes) to give the title compound (0.21 g, 19%) as a brown oil. $^1H$ NMR (500 MHz, Chloroform-d) δ 10.38 (s, 1H), 9.49 (s, 1H), 9.27 (s, 1H), 4.47 (q, J=7.2 Hz, 2H), 1.42 (t, J=7.2 Hz, 3H); MS (ESI+) m/z=181.1 $(M+H)^+$.

B) Methyl 5-bromo-2-((5-oxo-5,7-dihydro-6H-pyrrolo[3,4-d]pyrimidin-6-yl)methyl)benzofuran-7-carboxylate A mixture of of ethyl 4-formylpyrimidine-5-carboxylate (20 mg, 0.111 mmol) and methyl 2-(aminomethyl)-5-bromobenzofuran-7-carboxylate (37.8 mg, 0.133 mmol, Step C of Example 80) in THE (2 mL) was stirred at room temperature for 40 min. Acetic acid (0.1 mL, 1.75 mmol) and sodium triacetoxyborohydride (35 mg, 0.167 mmol) were added. The resulting mixture was stirred at room temperature for 7 hours. To the reaction mixture was added saturated aqueous $NaHCO_3$ solution and the mixture was stirred for 5 min. The mixture was then extracted with ethyl acetate. The organic layer was separated, washed with brine, dried over $MgSO_4$, and filtered. The filtrate was concentrated in vacuo. The residue was dissolved in DMF and purified by preparative HPLC (Method B). Fractions containing the desired product were combined and dried via centrifugal evaporation to give the title compound (4.1 mg, 9%). $^1H$ NMR (500 MHz, DMSO-$d_6$) δ 9.40 (s, 1H), 9.20 (s, 1H), 8.13 (d, J=1.8 Hz, 1H), 7.89 (d, J=1.8 Hz, 1H), 7.04 (s, 1H), 5.03 (s, 2H), 4.76 (s, 2H), 3.91 (s, 3H); MS (ESI+) m/z=403.9 $(M+H)^+$.

Example 84

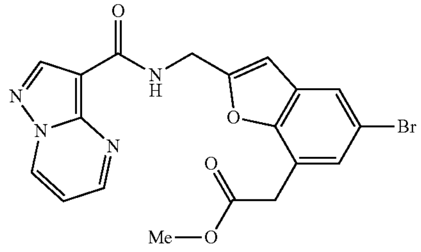 [SMILES: COC(=O)Cc1cc(Br)cc2cc(CNC(=O)c3cnn4cccnc34)oc12]

Methyl 2-(5-bromo-2-((pyrazolo[1,5-a]pyrimidine-3-carboxamido) methyl)benzofuran-7-yl)acetate

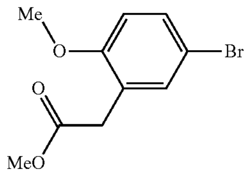 [SMILES: COC(=O)Cc1cc(Br)ccc1OC]

A) Methyl 2-(5-bromo-2-methoxyphenyl)acetate

To a solution of 2-(5-bromo-2-methoxyphenyl)acetic acid (1.5 g, 6.12 mmol) in DCM (20 mL) and MeOH (4 mL) at 0° C. was added (diazomethyl)trimethylsilane, 2 M in diethyl ether (3.67 mL, 7.34 mmol). The reaction mixture was stirred at 0° C. for 30 min and room temperature for 1 hour. The reaction mixture was concentrated and purified by ISCO, 80 g column, eluting with 0-20% EtOAc in hexanes to give the desired product as a colorless oil (1.41 g, 89% yield). $^1H$ NMR (400 MHz, CHLOROFORM-d) δ 7.37 (dd, J=8.7, 2.4 Hz, 1H), 7.32 (d, J=2.5 Hz, 1H), 6.77 (d, J=8.7 Hz, 1H), 3.82 (s, 3H), 3.72 (s, 3H), 3.61 (s, 2H).

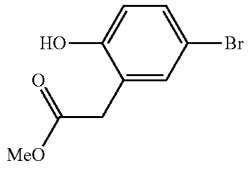 [SMILES: COC(=O)Cc1cc(Br)ccc1O]

B) Methyl 2-(5-bromo-2-hydroxyphenyl)acetate

To a solution of methyl 2-(5-bromo-2-methoxyphenyl) acetate (1.41 g, 5.44 mmol) in DCM (30 mL) at 0° C. was added tribromoborane (0.787 mL, 8.16 mmol). The reaction mixture was stirred at 0° C. for 1 hour and then at room temperature for 1 hour. The reaction mixture was concentrated in vacuo and purified by ISCO, 80 g column, eluting with 0-40% EtOAc in hexanes to give the desired product as a white solid (1.30 g, 97% yield). $^1H$ NMR (400 MHz, Chloroform-d) δ 7.32-7.21 (m, 2H), 6.79 (d, J=8.4 Hz, 1H), 3.77 (s, 3H), 3.65 (s, 2H); MS (ESI+) m/z=245.0 $(M+H)^+$.

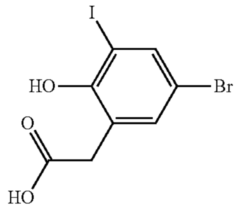 [SMILES: O=C(O)Cc1cc(Br)cc(I)c1O]

C) 2-(5-Bromo-2-hydroxy-3-iodophenyl)acetic acid

To a solution of methyl 2-(5-bromo-2-hydroxyphenyl) acetate (1.3 g, 5.30 mmol) in THE (10 mL) and MeOH (10 mL) at room temperature was added 3 N aqueous sodium hydroxide solution (5.30 mL, 15.9 mmol). The reaction mixture was stirred at room temperature for 1 hour. The reaction mixture was acidified with 3 N aqueous HCl solution to pH 2-3 and extracted with EtOAc. The organic layer was dried over sodium sulfate, filtered, and concentrated to give the desired acid.

To a solution of the above acid (1.22 g, 5.28 mmol) in $CH_3CN$ (2 mL) at room temperature was added NIS (1.19 g, 5.28 mmol). The reaction mixture was stirred at room temperature for 18 hours. The reaction mixture was concentrated and purified by ISCO, 24 g column, eluting with 0-5% MeOH in DCM to give the desired product (1.18 g, 63% yield). $^1$H NMR (400 MHz, Chloroform-d) δ 7.76 (d, J=2.2 Hz, 1H), 7.31 (d, J=2.2 Hz, 1H), 3.73 (s, 2H); MS (ESI+) m/z=356.8 $(M-H)^+$.

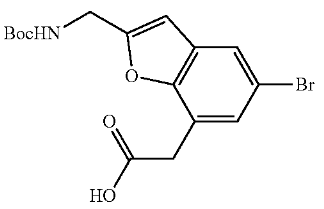 [SMILES: CC(C)(C)OC(=O)NCc1cc2cc(Br)cc(CC(=O)O)c2o1]

D) 2-(5-Bromo-2-(((tert-butoxycarbonyl)amino) methyl)benzofuran-7-yl)acetic acid To a solution of 2-(5-bromo-2-hydroxy-3-iodophenyl) acetic acid (1.18 g, 3.31 mmol) in DMF (5 mL) and TEA (5 mL) was added copper(I) iodide (63.0 mg, 0.331 mmol), tert-butyl prop-2-yn-1-ylcarbamate (770 mg, 4.96 mmol) and bis(triphenylphosphine)palladium(II) chloride (232 mg, 0.331 mmol). The reaction mixture was degassed by bubbling Ar through and stirred at 80° C. for 2 h. The reaction mixture was concentrated in vacuo and the residue was dissolved in EtOAc and washed with 10% aqueous citric acid solution. The organic layer was dried over sodium sulfate, filtered, concentrated in vacuo, and purified by ISCO, 80 g column, eluting with 0-50% EtOAc in DCM to give the desired product as a brown semi-solid (805 mg, 63% yield). $^1$H NMR (400 MHz, Chloroform-d) δ 7.58 (d, J=1.9 Hz, 1H), 7.31 (d, J=1.8 Hz, 1H), 6.56 (br s, 1H), 5.04 (br s, 1H), 4.45 (br d, J=4.4 Hz, 2H), 3.90 (s, 2H), 1.48 (s, 9H); MS (ESI+) m/z=327.9 $(M-55+H)^+$.

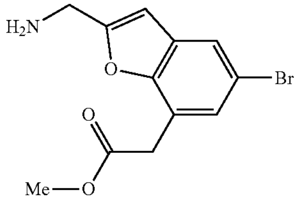 [SMILES: COC(=O)Cc1cc(Br)cc2cc(CN)oc12]

E) Methyl 2-(2-(aminomethyl)-5-bromobenzofuran-7-yl)acetate

To a solution of 2-(5-bromo-2-(((tert-butoxycarbonyl) amino)methyl) benzofuran-7-yl)acetic acid (800 mg, 2.08 mmol) in DCM (20 mL) and MeOH (4 mL) at 0° C. was added (diazomethyl)trimethylsilane, 2 M in diethyl ether (1.25 mL, 2.5 mmol). The reaction mixture was stirred at rt for 1 h. The reaction mixture was concentrated and purified by ISCO, 80 g column, eluting with 0-30% EtOAc in hexanes to give the desired product (740 mg, 89%).

To a solution of the above compound (740 mg, 1.86 mmol) in DCM (1.5 mL) was added TFA (0.5 mL). The reaction mixture was stirred at room temperature for 1 hour and concentrated to give the desired product (765 mg, 100% yield). $^1$H NMR (400 MHz, Chloroform-d) δ 7.58 (d, J=1.9 Hz, 1H), 7.31 (d, J=1.9 Hz, 1H), 6.56 (s, 1H), 4.45 (br d, J=5.6 Hz, 2H), 3.88 (s, 2H), 3.74 (s, 3H); MS (ESI+) m/z=297.9 $(M+H)^+$.

F) Methyl 2-(5-bromo-2-((pyrazolo[1,5-a]pyrimidine-3-carboxamido)methyl)benzofuran-7-yl)acetate To a solution of methyl 2-(2-(aminomethyl)-5-bromobenzofuran-7-yl)acetate, TFA (400 mg, 0.970 mmol) in DMF (1 mL) was added pyrazolo[1,5-a]pyrimidine-3-carboxylic acid (158 mg, 0.970 mmol), BOP (644 mg, 1.456 mmol) and DIPEA (0.509 mL, 2.91 mmol). The reaction mixture was stirred at room temperature for 2 hours. The reaction mixture was concentrated and purified with ISCO, 40 g column, eluting with 50-100% EtOAc in DCM to give the desired product as a white solid (310 mg, 72% yield). $^1$H NMR (400 MHz, Chloroform-d) δ 8.81 (dd, J=7.0, 1.8 Hz, 1H), 8.73 (s, 1H), 8.67 (dd, J=4.2, 1.8 Hz, 1H), 8.37 (br t, J=5.4 Hz, 1H), 7.57 (d, J=1.9 Hz, 1H), 7.31 (d, J=2.0 Hz, 1H), 7.03 (dd, J=7.0, 4.1 Hz, 1H), 6.66 (s, 1H), 4.87 (dd, J=5.8, 0.7 Hz, 2H), 3.91 (s, 2H), 3.72 (s, 3H); MS (ESI+) m/z=444.8 $(M+H)^+$.

Example 85

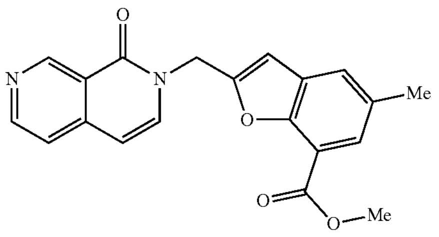 [SMILES: COC(=O)c1cc(C)cc2cc(Cn3ccc4ccncc4c3=O)oc12]

Methyl 5-methyl-2-((1-oxo-2,7-naphthyridin-2(1H)-yl)methyl)benzofuran-7-carboxylate

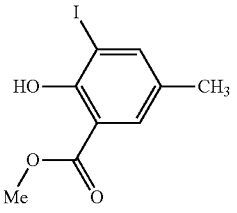

A) Methyl-2-hydroxy-3-iodo-5-methylbenzoate

To a solution of methyl 5-methylsalicylate (5 g, 30.1 mmol) in N,N-dimethylformamide (40 mL) was added sodium iodide (5.41 g, 36.1 mmol) followed by chloramine T trihydrate (10.17 g, 36.1 mmol) slowly in portions. The reaction was stirred at room temperature for 3 hours. The reaction mixture was quenched with ethyl acetate and 1N aqueous HCl solution. The organic layer was separated, washed with saturated aqueous sodium chloride solution followed by 10% aqueous $Na_2S_2O_3$ solution, and dried with anhydrous sodium sulfate. The dried organic extracts were filtered and concentrated in vacuo. The crude product mixture was purified by a silica gel ISCO 120 g column eluting with 0-20% ethyl acetate/hexane over a 15 minute gradient. The appropriate fractions were isolated and concentrated in vacuo to afford the product (8.2 g, 93% yield) as a solid. $^1$H NMR (400 MHz, Chloroform-d) δ 11.52-11.27 (m, 1H), 7.86-7.72 (m, 1H), 7.72-7.52 (m, 1H), 4.09-3.89 (m, 3H), 2.39-2.08 (m, 3H); MS (ESI+) m/z=293.1 $(M+H)^+$.

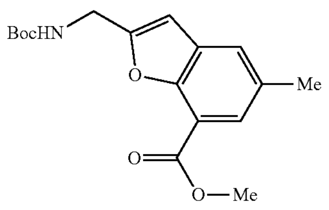 [SMILES: COC(=O)c1cc(C)cc2cc(CNC(=O)OC(C)(C)C)oc12]

B) Methyl 2-(((tert-butoxycarbonyl)amino)methyl)-5-methylbenzofuran-7-carboxylate A 100 ml flask was charged with methyl 2-hydroxy-3-iodo-5-methylbenzoate (8.2 g, 28.1 mmol), tert-butyl prop-2-yn-1-ylcarbamate (5.01 g, 32.3 mmol), and copper(I) iodide (0.428 g, 2.25 mmol) in DMF (20 mL) and TEA (30 mL). The reaction was purged with nitrogen, then bis (triphenylphosphine)palladium(II) chloride (0.985 g, 1.404 mmol) was added. The resulting mixture was heated at 80° C. for 4 hours. After cooling to room temperature, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 80 g column eluting with 0-35% ethyl acetate/hexane over a 15 minute gradient. The appropriate fractions were isolated and concentrated in vacuo to afford the title compound (6 g, 67% yield) as a light brown solid. $^1$H NMR (400 MHz, Chloroform-d) δ 7.86-7.66 (m, 1H), 7.63-7.38 (m, 1H), 6.75-6.43 (m, 1H), 4.62-4.43 (m, 2H), 4.20-3.75 (m, 3H), 2.70-2.16 (m, 3H), 1.55-1.28 (m, 9H); MS (ESI+) m/z=264.1 $(M-55+H)^+$.

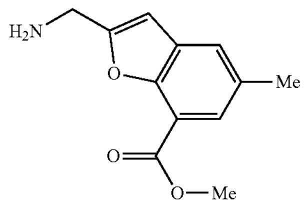 [SMILES: COC(=O)c1cc(C)cc2cc(CN)oc12]

C) Methyl 2-(aminomethyl)-5-methylbenzofuran-7-carboxylate, TFA salt

To a solution of methyl 2-(((tert-butoxycarbonyl)amino) methyl)-5-methylbenzofuran-7-carboxylate (0.5 g, 1.57 mmol, Step B of Example 230) in $CH_2Cl_2$ (8 mL) was added TFA (1.21 mL, 15.7 mmol). The reaction mixture was stirred at room temperature for 2 hours. The reaction mixture was concentrated in vacuo to afford the product methyl 2-(aminomethyl)-5-methylbenzofuran-7-carboxylate as a TFA salt (250 mg, 47.9% yield). $^1$H NMR (400 MHz, Methanol-$d_4$) δ 7.94-7.75 (m, 1H), 7.77-7.65 (m, 1H), 7.10-6.87 (m, 1H), 4.49-4.26 (m, 2H), 4.10-3.78 (m, 3H), 2.61-2.30 (m, 3H); MS (ESI+) m/z=203.1 $(M-16)^+$.

D) Methyl 5-methyl-2-((1-oxo-2,7-naphthyridin-2 (1H)-yl)methyl)benzofuran-7-carboxylate The reaction mixture of methyl 4-methylnicotinate (68.0 mg, 0.450 mmol), N,N-dimethylformamide dimethyl acetal (0.321 mL, 2.401 mmol) in DMF (0.5 mL) was heated in the microwave at 150° C. for 60 minutes. The reaction solution was concentrated in vacuo. The residue was mixed with acetic acid (0.5 mL) and methyl 2-(aminomethyl)-5-methylbenzofuran-7-carboxylate, TFA salt (50 mg, 0.150 mmol) and heated at 120° C. in the microwave for 30 minutes. The reaction mixture was concentrated in vacuo. The crude material was purified via preparative HPLC (Method C), to afford the product (25 mg, 45% yield) as a solid. $^1$H NMR (400 MHz, Chloroform-d) δ 9.64 (s, 1H), 8.74 (d, J=5.4 Hz, 1H), 7.77 (s, 1H), 7.60 (d, J=7.3 Hz, 1H), 7.56-7.51 (m, 1H), 7.41-7.30 (m, 1H), 6.79 (s, 1H), 6.52 (d, J=7.5 Hz, 1H), 5.39 (s, 2H), 3.99 (s, 3H), 2.46 (s, 3H); MS (ESI+) m/z=349.0 $(M+H)^+$.

Example 86

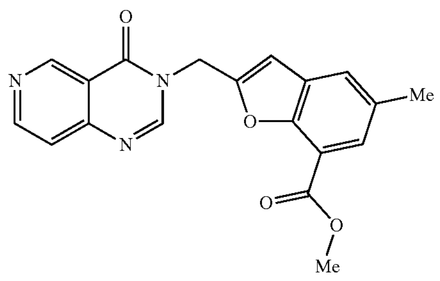 [SMILES: COC(=O)c1cc(C)cc2cc(Cn3cnc4ccncc4c3=O)oc12]

Methyl 5-methyl-2-((4-oxopyrido[4,3-d]pyrimidin-3 (4H)-yl)methyl)benzofuran-7-carboxylate 4-Aminonicotinic acid (40 mg, 0.290 mmol) and N,N-dimethylformamide dimethyl acetal (0.116 mL, 0.869 mmol) were taken up in DMF (1 mL) in a 0.5-2 mL microwave vial. The vial was sealed and heated to 100° C. for 15 minutes in a microwave reactor. After 15 minutes, the reaction mixture was cooled and concentrated in vacuo. To this residue was added 1 mL of acetic acid and methyl 2-(aminomethyl)-5-methylbenzofuran-7-carboxylate (63.5 mg, 0.290 mmol, Step C in Example 85). The vial was sealed and heated to 120° C. for 15 min in a microwave reactor. The reaction mixture was again cooled and concentrated in vacuo. The residue was diluted with water and extracted with EtOAc. The combined organic extracts were dried over sodium sulfate, filtered, and concentrated in vacuo. The residue was taken up in DMF and MeOH, filtered, and purified via HPLC (method B) to give the title compound (18 mg, 18% yield). 1H NMR (500 MHz, DMSO-d6) δ 9.35 (s, 1H), 8.89 (d, J=5.8 Hz, 1H), 8.81 (s, 1H), 7.81-7.50 (m, 3H), 6.95 (s, 1H), 5.47 (s, 2H), 3.87 (s, 3H), 2.42 (s, 3H); MS (ESI+) m/z=350.0 $(M+H)^+$.

Example 87

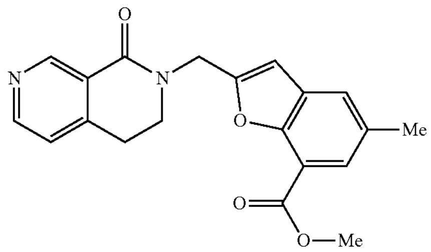 [SMILES: COC(=O)c1cc(C)cc2cc(CN3CCc4ccncc4C3=O)oc12]

Methyl 5-methyl-2-((1-oxo-3,4-dihydro-2,7-naphthyridin-2(1H)-yl)methyl)benzofuran-7-carboxylate 3,4-Dihydro-1H-pyrano[3,4-c]pyridin-1-one (15 mg, 0.101 mmol) (WO 2005063768) and methyl 2-(aminomethyl)-5-methylbenzofuran-7-carboxylate (26.5 mg, 0.121 mmol, Step C of Example 85) were added to a pressure relief vial and heated neat at 120° C. After 4 hours, the reaction was cooled, diluted with 2 mL DMF, filtered, and purified via HPLC (Method B) to give methyl 5-methyl-2-((1-oxo-3,4-dihydro-2,7-naphthyridin-2(1H)-yl)methyl)benzofuran-7-carboxylate (9.0 mg, 0.025 mmol, 25.0% yield). $^1$H NMR (500 MHz, DMSO-$d_6$) δ 8.96 (s, 1H), 8.62 (d, J=4.9 Hz, 1H), 7.65 (s, 1H), 7.63 (s, 1H), 7.37 (d, J=4.9 Hz, 1H), 6.88 (s, 1H), 4.91 (s, 2H), 3.86 (s, 3H), 3.74 (t, J=6.6 Hz, 2H), 3.08 (br t, J=6.4 Hz, 2H), 2.41 (s, 3H); MS (ESI+) m/z 351.1 $(M+H)^+$.

Example 88

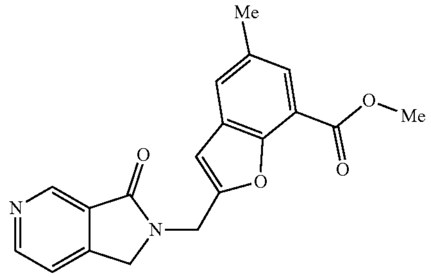 [SMILES: COC(=O)c1cc(C)cc2cc(CN3Cc4ccncc4C3=O)oc12]

Methyl 5-methyl-2-((3-oxo-1,3-dihydro-2H-pyrrolo[3,4-c]pyridin-2-yl)methyl)benzofuran-7-carboxylate Methyl 2-(aminomethyl)-5-methylbenzofuran-7-carboxylate (34.3 mg, 0.156 mmol, Step C in Example 85) was taken up in THF (1 mL). TEA (0.109 mL, 0.782 mmol) was added followed by the addition of a solution of crude methyl 4-(bromomethyl)nicotinate (120 mg, 0.078 mmol, as prepared in Example 2) in THF (1 mL). The reaction mixture was stirred at room temperature for 1 hour, then heated at 70° C. for 16 hours. The reaction mixture was then concentrated in vacuo. The crude residue was dissolved in MeOH, filtered, and purified via HPLC (method B) to give the title compound (3.5 mg, 13% yield). $^1$H NMR (500 MHz, DMSO-d6) δ 9.30-8.74 (m, 2H), 7.80-7.72 (m, 1H), 7.69 (s, 1H), 7.67-7.64 (m, 1H), 6.92 (s, 1H), 4.97 (s, 2H), 4.68 (s, 2H), 3.89-3.85 (m, 3H), 2.43 (s, 3H); MS (ESI+) m/z 337.1 $(M+H)^+$.

Example 89

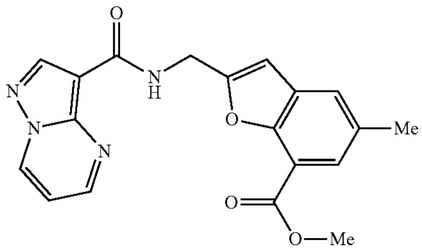 [SMILES: COC(=O)c1cc(C)cc2cc(CNC(=O)c3cnn4cccnc34)oc12]

Methyl 5-methyl-2-((pyrazolo[1,5-a]pyrimidine-3-carboxamido)methyl)benzofuran-7-carboxylate To a suspension of pyrazole[1,5-a]pyrimidine-3-carboxylic acid (20 mg, 0.123 mmol) and BOP (41.7 mg, 0.094 mmol) in DMF (2 mL) was added methyl 2-(aminomethyl)-5-methylbenzofuran-7-carboxylate, TFA salt (31.4 mg, 0.094 mmol, Step C of Example 85) and DIPEA (0.066 mL, 0.377 mmol). The reaction mixture was stirred at room temperature for 2 hours. The reaction mixture was quenched with water, extracted with DCM, dried with anhydrous sodium sulfate, filtered and concentrated in vacuo. The crude material was purified via preparative HPLC (Method C) to give the title compound as a solid (21 mg, 58% yield). $^1$H NMR (400 MHz, Methanol-$d_4$) δ 9.09 (dd, J=7.0, 1.7 Hz, 1H), 8.80 (dd, J=4.2, 1.7 Hz, 1H), 8.62 (s, 1H), 7.71 (d, J=1.2 Hz, 1H), 7.65-7.56 (m, 1H), 7.22 (dd, J=7.0, 4.2 Hz, 1H), 6.75 (s, 1H), 4.87 (br m, 2H), 3.97 (s, 3H), 2.45 (s, 3H); MS (ESI+) m/z=365 $(M+H)^+$.

Example 90-91

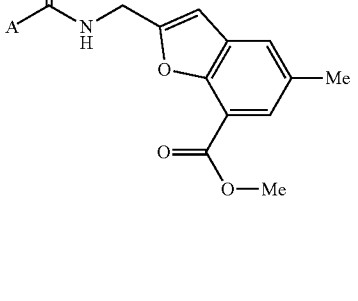

Example 90-91 were prepare according to the procedure described for the synthesis of Example 89 from the benzofuran intermediate synthesized in Step C in Example 85 and a carboxylic acid.

| Ex. No. | A | Name | $^1$H NMR | LC/MS [M + H]+ |
|---|---|---|---|---|
| 90 | 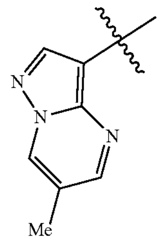 [SMILES: *c1cnn2cc(C)cnc12] | Methyl 5-methyl-2-((6-methyl pyrazolo[1,5-a]pyrimidine-3-carboxamido)methyl)benzofuran-7-carboxylate | $^1$H NMR (500 MHz, DMSO-$d_6$) δ 9.10 (s, 1H), 8.72 (s, 1H), 8.53 (s, 1H), 8.41 (br t, J = 5.6 Hz, 2H), 7.63 (br d, J = 9.3 Hz, 2H), 6.77 (s, 1H), 4.78 (br d, J = 5.8 Hz, 2H), 3.92-3.87 (m, 3H), 2.41 (s, 3H), 2.39 (m, 3H) | 379.2 |
| 91 | 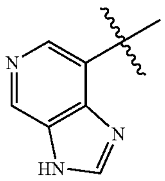 [SMILES: *c1cncc2[nH]cnc12] | Methyl 2-((3H-imidazo[4,5-c]pyridine-7-carboxamido)methyl)-5-methylbenzofuran-7-carboxylate | $^1$H NMR (500 MHz, DMSO-$d_6$) δ 9.74 (br s, 1H), 9.09 (s, 1H), 8.91 (s, 1H), 8.56 (br s, 1H), 7.67 (s, 1H), 7.64 (s, 1H), 6.84 (s, 1H), 4.83 (br d, J = 4.3 Hz, 2H), 3.88 (s, 3H), 2.42 (s, 3H) | 364.9 |

Example 92

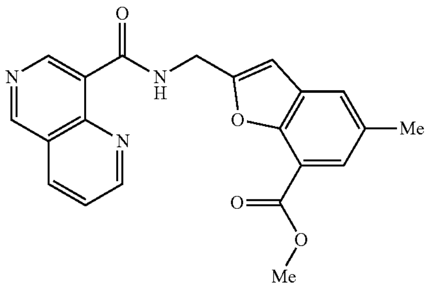 [SMILES: COC(=O)c1cc(C)cc2cc(CNC(=O)c3cncc4cccnc34)oc12]

methyl 2-((1,6-naphthyridine-8-carboxamido)methyl)-5-methylbenzofuran-7-carboxylate A mixture of 1,6-naphthyridine-8-carboxylic acid, HCl (10 mg, 0.047 mmol), methyl 2-(aminomethyl)-5-methylbenzofuran-7-carboxylate, TFA (15.82 mg, 0.047 mmol, Step C of Example 85), HATU (18.05 mg, 0.047 mmol) and Hunig's Base (0.033 mL, 0.190 mmol) in DMF (0.5 mL) was stirred at rt for 48 h. The reaction was quenched with 1:1 DMF/AcOH and purified by preparative LC/MS (Method B) to give the title compound (2.5 mg, 6.66 μmol, 14.03% yield). $^1$H NMR (500 MHz, DMSO-$d_6$) δ 10.95 (br s, 1H), 9.59 (s, 1H), 9.36 (s, 1H), 9.29 (br s, 1H), 8.78 (br d, J=7.9 Hz, 1H), 7.86 (br dd, J=8.1, 4.4 Hz, 1H), 7.66 (s, 1H), 7.64-7.60 (m, 1H), 6.87 (s, 1H), 4.88 (br d, J=5.5 Hz, 2H), 3.88 (s, 3H), 2.41 (s, 3H); MS (ESI+) m/z=376.0 $(M+H)^+$.

Example 93

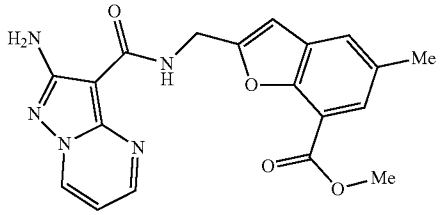 [SMILES: COC(=O)c1cc(C)cc2cc(CNC(=O)c3c(N)nn4cccnc34)oc12]

Methyl 2-((2-aminopyrazolo[1,5-a]pyrimidine-3-carboxamido)methyl)-5-methylbenzofuran-7-carboxylate

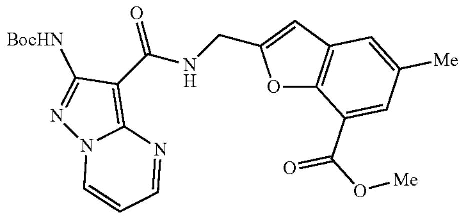 [SMILES: COC(=O)c1cc(C)cc2cc(CNC(=O)c3c(NC(=O)OC(C)(C)C)nn4cccnc34)oc12]

A) Methyl 2-((2-((tert-butoxycarbonyl)amino)pyrazolo[1,5-a]pyrimidine-3-carboxamido)methyl)-5-methylbenzofuran-7-carboxylate To a solution of 2-((tert-butoxycarbonyl)amino)pyrazolo[1,5-a]pyrimidine-3-carboxylic acid (75 mg, 0.270 mmol, Step C of Example 63) and methyl 2-(aminomethyl)-5-methylbenzofuran-7-carboxylate, TFA (90 mg, 0.270 mmol, Step A of Example 85) in DMF (5 mL) were added BOP (179 mg, 0.404 mmol) and DIPEA (0.141 mL, 0.809 mmol). The reaction mixture was stirred at RT for 16 hours. The sample was quenched with water, the resulting product precipitate was filtered. The crude product was purified via preparative HPLC (Method C) to yield methyl 2-((2-((tert-butoxycarbonyl)amino)pyrazolo[1,5-a]pyrimidine-3-carboxamido)methyl)-5-methylbenzofuran-7-carboxylate (55 mg, 42.4% yield). 1H NMR (400 MHz, Chloroform-d) δ 9.84-9.70 (m, 1H), 8.87-8.80 (m, 1H), 8.61-8.57 (m, 1H), 8.48-8.40 (m, 1H), 7.75 (d, J=1.3 Hz, 1H), 7.57-7.48 (m, 1H), 6.98-6.88 (m, 1H), 6.72-6.67 (m, 1H), 4.93-4.80 (m, 2H), 4.05-3.96 (m, 3H), 2.45 (s, 3H), 1.63-1.53 (m, 9H); MS (ESI+) m/z=480 $(M+H)^+$.

B) Methyl 2-((2-aminopyrazolo[1,5-a]pyrimidine-3-carboxamido)methyl)-5-methylbenzofuran-7-carboxylate In a vial was added methyl 2-((2-((tert-butoxycarbonyl)amino)pyrazolo[1,5-a]pyrimidine-3-carboxamido)methyl)-5-methylbenzofuran-7-carboxylate (10 mg, 0.208 mmol) DCM (5 mL) and TFA (0.5 mL). The reaction solution was stirred at room temperature for 2 hours. The solution was concentrated in vacuo and purified purified via preparative HPLC (Method C) to yield the title compound (6 mg, 75% yield). 1H NMR (400 MHz, Chloroform-d) δ 8.50-8.44 (m, 1H), 8.44-8.37 (m, 1H), 8.32-8.22 (m, 1H), 7.77-7.72 (m, 1H), 7.53-7.48 (m, 1H), 6.84-6.76 (m, 1H), 6.71-6.65 (m, 1H), 5.78-5.65 (m, 2H), 4.95-4.86 (m, 2H), 4.04-3.97 (m, 3H), 2.46 (s, 3H); MS (ESI+) m/z=380 $(M+H)^+$.

Example 94

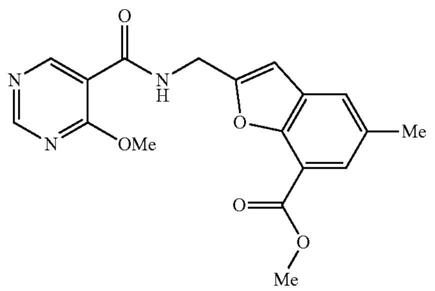 [SMILES: COC(=O)c1cc(C)cc2cc(CNC(=O)c3cncnc3OC)oc12]

Methyl 2-((4-methoxypyrimidine-5-carboxamido)methyl)-5-methylbenzofuran-7-carboxylate A mixture of methyl 2-(aminomethyl)-5-methylbenzofuran-7-carboxylate, TFA (47.6 mg, 0.143 mmol, Step C of Example 85), 4-methoxypyrimidine-5-carboxylic acid (20 mg, 0.130 mmol), HATU (54.3 mg, 0.143 mmol) and Hunig's base (0.091 mL, 0.519 mmol) in DMF (1 mL) was stirred at room temperature for 1 hour. The reaction mixture was quenched with 1:1 DMF/AcOH and purified by preparative HPLC (Method B). The appropriate fractions were combined and dried via centrifugal evaporation to afford the title compound (5.1 mg, 10.93% yield). $^1H$ NMR (500 MHz, DMSO-$d_6$) δ 8.86 (br d, J=16.3 Hz, 3H), 7.64 (d, J=16.2 Hz, 2H), 6.77 (s, 1H), 4.68 (d, J=5.7 Hz, 2H), 4.07 (s, 3H), 3.90 (s, 3H), 2.41 (s, 3H); MS (ESI+) m/z=356.1 $(M+H)^+$.

Example 95

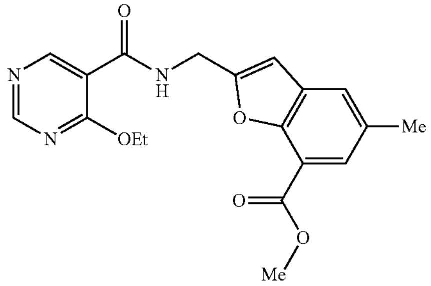 [SMILES: CCOc1ncncc1C(=O)NCc1cc2cc(C)cc(C(=O)OC)c2o1]

Methyl 2-((4-ethoxypyrimidine-5-carboxamido)methyl)-5-methylbenzofuran-7-carboxylate A mixture of methyl 2-(aminomethyl)-5-methylbenzofuran-7-carboxylate, TFA (21.80 mg, 0.065 mmol, Step C of Example 85), 4-ethoxypyrimidine-5-carboxylic acid (10 mg, 0.059 mmol), HATU (24.9 mg, 0.065 mmol) and Hunig's base (0.042 mL, 0.238 mmol) in DMF (1 mL) was stirred at room temperature for 1 hour. The reaction mixture was quenched with 1:1 DMF/AcOH and purified by preparative HPLC (Method B). The appropriate fractions were combined and dried via centrifugal evaporation to afford the title compound (0.7 mg, 3.06% yield). $^1H$ NMR (500 MHz, DMSO-$d_6$) δ 8.85 (d, J=14.8 Hz, 3H), 7.65 (br d, J=12.5 Hz, 2H), 6.81 (s, 1H), 4.70 (d, J=5.7 Hz, 2H), 4.55 (q, J=7.0 Hz, 2H), 3.91 (s, 3H), 1.72 (br s, 3H), 1.38 (t, J=7.0 Hz, 3H); MS (ESI+) m/z=370.2 $(M+H)^+$.

Example 96

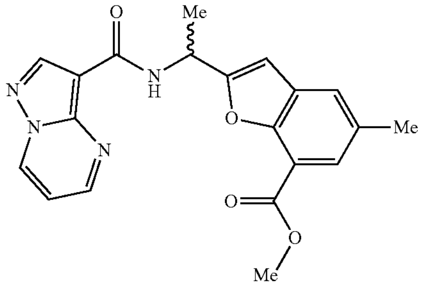 [SMILES: COC(=O)c1cc(C)cc2cc(C(C)NC(=O)c3cnn4cccnc34)oc12]

Methyl 5-methyl-2-(1-(pyrazolo[1,5-a]pyrimidine-3-carboxamido)ethyl)benzofuran-7-carboxylate (racemic)

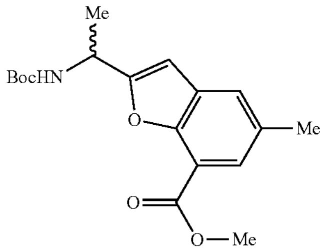 [SMILES: COC(=O)c1cc(C)cc2cc(C(C)NC(=O)OC(C)(C)C)oc12]

A) Methyl 2-(1-((tert-butoxycarbonyl)amino)ethyl)-5-methylbenzofuran-7-carboxylate The reaction mixture of methyl 2-hydroxy-3-iodo-5-methylbenzoate (1.0 g, 3.42 mmol, Step A in Example 85), tert-butyl but-3-yn-2-ylcarbamate (0.66 g, 3.94 mmol, Step B in Example 45), TEA (7.16 mL, 51.4 mmol), and copper(I) iodide (0.065 g, 0.342 mmol) in DMF (8 mL) was purged with a nitrogen stream for 5 mins, then bis(triphenylphosphine)palladium(II) chloride (0.120 g, 0.171 mmol) was added. The resulting mixture was heated at 80° C. for 2 hours. After cooling to RT, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO column eluting with 0-25% ethyl acetate in hexanes over a 15 minute gradient. The appropriate fractions were isolated and concentrated in vacuo to afford the product (0.804 g, 70% yield) as a solid. 1H NMR (400 MHz, Chloroform-d) δ 7.78-7.67 (m, 1H), 7.56-7.47 (m, 1H), 6.66-6.37 (m, 1H), 5.16-4.98 (m, 1H), 4.07-3.87 (m, 3H), 2.55-2.36 (m, 3H), 1.66-1.54 (m, 3H), 1.54-1.40 (m, 9H); MS (ESI+) m/z=278.1 $(M-55+H)^+$.

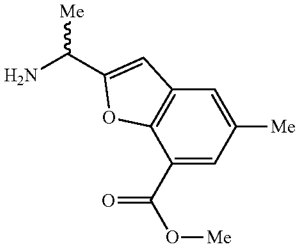 [SMILES: COC(=O)c1cc(C)cc2cc(C(C)N)oc12]

B) Methyl 2-(1-aminoethyl)-5-methylbenzofuran-7-carboxylate

A vial was charged methyl 2-(((tert-butoxycarbonyl)amino)methyl)-3-chlorobenzofuran-7-carboxylate (0.4 g, 1.2 mmol), DCM (20 mL) and TFA (2 mL). The reaction solution was stirred at room temperature for 2 hours. The reaction mixture was concentrated in vacuo to afford methyl 2-(1-aminoethyl)-5-methylbenzofuran-7-carboxylate as a TFA salt (0.4 g, 96% yield) as a solid. $^1$H NMR (400 MHz, Chloroform-d) δ 7.86-7.61 (m, 1H), 7.54 (d, J=0.8 Hz, 1H), 6.75 (s, 1H), 4.84-4.67 (m, 1H), 3.90 (s, 3H), 2.52-2.41 (m, 3H), 1.84-1.73 (m, 3H); MS (ESI+) m/z=217.1 $(M-16)^+$.

C) Methyl 5-methyl-2-(1-(pyrazolo[1,5-a]pyrimidine-3-carboxamido)ethyl)benzofuran-7-carboxylate To a solution of pyrazolo[1,5-a]pyrimidine-3-carboxylic acid (188 mg, 1.152 mmol) and BOP (764 mg, 1.728 mmol) in DMF (10 mL), was added methyl 2-(1-aminoethyl)-5-methylbenzofuran-7-carboxylate TFA salt (0.4 g, 1.15 mmol) and DIPEA (0.805 mL, 4.61 mmol) The reaction mixture was stirred at room temperature for 16 hours. The solution was diluted with ethyl acetate, and washed with saturated sodium bicarbonate, water and saturated sodium chloride. The organic layer was dried with anhydrous sodium sulfate, filtered, and concentrated in vacuo. The crude product mixture was purified by a silica gel ISCO 24 g column eluting with 0-10% methanol in DCM over a 15 minute gradient. The appropriate fractions were isolated and concentrated in vacuo to afford the product (450 mg, 103% yield, 90% pure). A portion of the product mixture (70 mg) was purified via preparative HPLC (Method A) to afford the racemate product as a TFA salt (25 mg, 67% yield). 1H NMR (500 MHz, DMSO-d6) δ 9.27 (br d, J=6.6 Hz, 1H), 8.82 (br d, J=3.3 Hz, 1H), 8.61 (s, 1H), 8.33 (br d, J=8.2 Hz, 1H), 7.66 (s, 1H), 7.63 (s, 1H), 7.27 (dd, J=6.6, 4.3 Hz, 1H), 6.83 (s, 1H), 5.53-5.45 (m, 1H), 3.87 (s, 3H), 2.42 (s, 3H), 1.66 (d, J=6.9 Hz, 3H); MS (ESI+) m/z=379.0 $(M+H)^+$.

Example 97

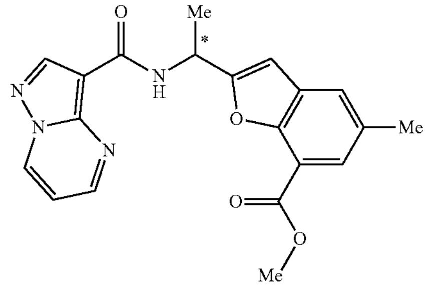 [SMILES: COC(=O)c1cc(C)cc2cc(C(C)NC(=O)c3cnn4cccnc34)oc12]

Methyl-5-methyl-2-(1-(pyrazolo[1,5-a]pyrimidine-3-carboxamido)ethyl)benzofuran-7-carboxylate The racemic mixture of methyl 5-methyl-2-(1-(pyrazolo[1,5-a]pyrimidine-3-carboxamido)ethyl)benzofuran-7-carboxylate (25 mg, 0.066 mmol, Example 96) was separated into the two enantiomers using chiral SFC (Method K) to give the first eluting enantiomer as the title compound (9.8 mg, 39%) (white solid). $^1$H NMR (500 MHz, DMSO-$d_6$) δ 9.29 (br d, J=6.7 Hz, 1H), 8.85-8.80 (m, 1H), 8.63 (s, 1H), 8.37 (br d, J=8.2 Hz, 1H), 7.68-7.65 (m, 1H), 7.63 (s, 1H), 7.30-7.25 (m, 1H), 6.84 (s, 1H), 5.52-5.43 (m, 1H), 3.86 (s, 3H), 2.41 (s, 3H), 1.65 (br d, J=6.7 Hz, 3H); MS (ESI+) m/z=379.2 (M+H)+; Chiral purity >95% ee.

Example 98

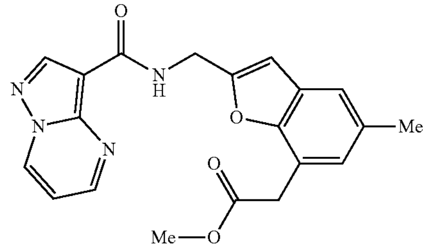 [SMILES: COC(=O)Cc1cc(C)cc2cc(CNC(=O)c3cnn4cccnc34)oc12]

Methyl 2-(5-methyl-2-((pyrazolo[1,5-a]pyrimidine-3-carboxamido)methyl)benzofuran-7-yl)acetate To a solution of methyl 2-(5-bromo-2-((pyrazolo[1,5-a]pyrimidine-3-carboxamido)methyl)benzofuran-7-yl)acetate (20 mg, 0.045 mmol, Example 84) in dioxane (4 mL) and water (0.4 mL) was added methylboronic acid (5.4 mg, 0.09 mmol), $K_2CO_3$ (18.7 mg, 0.135 mmol) and $PdCl_2$(dppf)-

$CH_2Cl_2$ (3.7 mg, 4.51 μmol). The reaction mixture was degassed by bubbling argon through it and heated at 80° C. for 6 hours. The reaction mixture was concentrated. The residue was purified with prep HPLC, Method B, to give the desired product (2.6 mg, 15% yield). $^1$H NMR (400 MHz, Chloroform-d) δ 8.84-8.75 (m, 1H), 8.66-8.57 (m, 2H), 8.42 (br s, 1H), 7.15 (s, 1H), 7.06-6.97 (m, 1H), 6.90 (s, 1H), 6.56 (s, 1H), 4.76 (br d, J=5.6 Hz, 2H), 3.82 (s, 2H), 3.62 (s, 3H), 2.33 (s, 3H); MS (ESI+) m/z=379.2 (M+H)$^+$.

Example 99

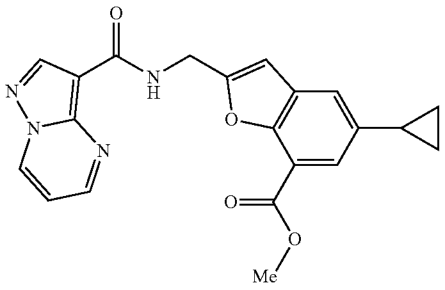 [SMILES: COC(=O)c1cc(C2CC2)cc2cc(CNC(=O)c3cnn4cccnc34)oc12]

Methyl 5-cyclopropyl-2-((pyrazolo[1,5-a]pyrimidine-3-carboxamido)methyl)benzofuran-7-carboxylate

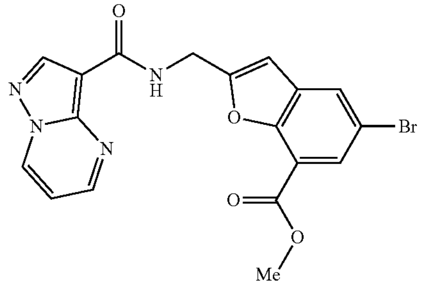 [SMILES: COC(=O)c1cc(Br)cc2cc(CNC(=O)c3cnn4cccnc34)oc12]

A) Methyl 5-bromo-2-((pyrazolo[1,5-a]pyrimidine-3-carboxamido)methyl)benzofuran-7-carboxylate To a solution of methyl 2-(aminomethyl)-5-bromobenzofuran-7-carboxylate, TFA (1.3 g, 2.29 mmol, Step C of Example 80) and pyrazolo[1,5-a]pyrimidine-3-carboxylic acid (0.373 g, 2.29 mmol) in DMF (2 mL) was added BOP (1.52 g, 3.43 mmol) and DIPEA (1.6 mL, 9.14 mmol). The reaction mixture was stirred at room temperature for 16 hours. The solution was diluted with ethyl acetate and washed with saturated sodium bicarbonate, water, and saturated sodium chloride, dried with anhydrous sodium sulfate and concentrated in vacuo. The crude product mixture was purified by a silica gel ISCO 80 g column eluting with 0-10% methanol in DCM over a 15 minute gradient. The appropriate fractions were isolated and concentrated in vacuo to afford the product as a solid (0.38 g, 38.7% yield). $^1$H NMR (400 MHz, Chloroform-d) δ 8.85-8.80 (m, 1H), 8.73 (s, 1H), 8.70-8.66 (m, 1H), 8.54-8.45 (m, 1H), 8.05-7.99 (m, 1H), 7.86-7.81 (m, 1H), 7.05 (dd, J=7.0, 4.2 Hz, 1H), 6.76-6.70 (m, 1H), 4.94 (dd, J=6.0, 0.7 Hz, 2H), 4.02 (s, 3H); MS (ESI+) m/z=431.1 (M+H)$^+$.

B) Methyl 5-cyclopropyl-2-((pyrazolo[1,5-a]pyrimidine-3-carboxamido)methyl)benzofuran-7-carboxylate A vial was charged with methyl 5-bromo-2-((pyrazolo[1,5-a]pyrimidine-3-carboxamido)methyl)benzofuran-7-carboxylate (45 mg, 0.105 mmol), 2-cyclopropyl-6-methyl-1,2,6,2-dioxazaborocane-4,8-dione (41.3 mg, 0.210 mmol), potassium phosphate tribasic (0.140 mL, 0.419 mmol, 3M aqueous solution), and 1,1'-bis(diphenylphosphino)ferrocene-palladium (II) dichloride dichloromethane (17.12 mg, 0.021 mmol) in toluene (2 mL). The solution was degassed and heated to 90° C. for 16 hours. The solution was diluted with ethyl acetate and washed with saturated sodium bicarbonate, water, and saturated sodium chloride, dried with anhydrous sodium sulfate, filtered, and concentrated in vacuo. The crude material was purified via preparative HPLC (Method A) to afford the product as a TFA salt (1.5 mg, 3% yield). 1H NMR (500 MHz, DMSO-d6) δ 9.16-9.10 (m, 1H), 8.81-8.76 (m, 1H), 8.64 (br t, J=5.8 Hz, 1H), 8.58 (s, 1H), 7.52 (s, 1H), 7.51-7.46 (m, 1H), 7.24 (dd, J=6.9, 4.4 Hz, 1H), 6.77 (s, 1H), 4.74 (br d, J=5.8 Hz, 2H), 3.84 (s, 3H), 2.14-1.90 (m, 1H), 1.06-0.86 (m, 2H), 0.70-0.53 (m, 2H); MS (ESI+) m/z=391.3 (M+H)$^+$.

Example 100

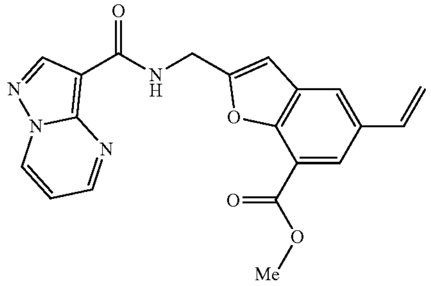 [SMILES: C=Cc1cc(C(=O)OC)c2oc(CNC(=O)c3cnn4cccnc34)cc2c1]

Methyl 2-((pyrazolo[1,5-a]pyrimidine-3-carboxamido)methyl)-5-vinylbenzofuran-7-carboxylate The reaction mixture of methyl 5-fluoro-2-hydroxy-3-iodobenzoate (1.539 g, 5.20 mmol), tert-butyl (S)-but-3-yn-2-ylcarbamate (0.8 g, 4.73 mmol), TEA (9.88 mL, 70.9 mmol), copper(I) iodide (0.090 g, 0.473 mmol) in DMF (8 mL) was purged with nitrogen stream for 5 mins, then bis(triphenylphosphine)palladium(II) chloride (0.166 g, 0.236 mmol) was added. The resulting mixture was heated at 80° C. for 4 h. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO column 40 g, 0-20% ethyl acetate in hexanes) to give the title compound (1.25 g g, 78%) as light yellow oil. 1H NMR (400 MHz, Chloroform-d) δ 7.63 (dd, J=9.6, 2.7 Hz, 2H), 7.40 (dd, J=7.9, 2.7 Hz, 1H), 6.61 (s, 1H), 5.17-4.89 (m, 2H), 4.02-3.98 (m, 3H), 1.61 (br d, J=6.9 Hz, 3H), 1.48 (s, 9H); MS (ESI+) m/z=282.0 $(M-55+H)^+$.

Example 101

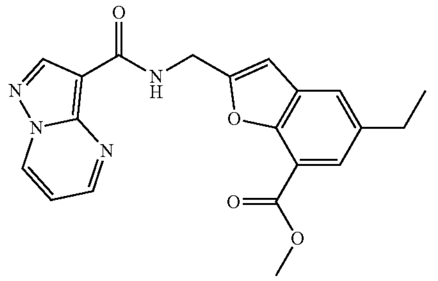 [SMILES: CCc1cc(C(=O)OC)c2oc(CNC(=O)c3cnn4cccnc34)cc2c1]

Methyl 5-ethyl-2-((pyrazolo[1,5-a]pyrimidine-3-carboxamido)methyl)benzofuran-7-carboxylate A flask was charged with methyl 2-((pyrazolo[1,5-a]pyrimidine-3-carboxamido)methyl)-5-vinylbenzofuran-7-carboxylate (50 mg, 0.133 mmol, Example 100), ethyl acetate (5 mL), Pd/C (2.83 mg, 0.027 mmol). The reaction was purged with nitrogen, and then charged with hydrogen (balloon) for 3 hours. The solution was flushed with nitrogen, filtered through celite and concentrated in vacuo. The crude material was purified via preparative HPLC (Method B) to yield the title compound (4.2 mg, 8.4% yield). 1H NMR (500 MHz, DMSO-d6) δ 9.28 (br d, J=6.7 Hz, 1H), 8.82 (br d, J=3.4 Hz, 1H), 8.62 (s, 1H), 8.52 (br t, J=5.6 Hz, 1H), 7.68 (s, 1H), 7.66-7.62 (m, 1H), 7.27 (dd, J=6.7, 4.3 Hz, 1H), 6.80 (s, 1H), 4.78 (br d, J=5.8 Hz, 2H), 3.88 (s, 2H), 2.71 (q, J=7.3 Hz, 2H), 1.20 (t, J=7.5 Hz, 3H); MS (ESI+) m/z=379.2 $(M+H)^+$.

Example 102

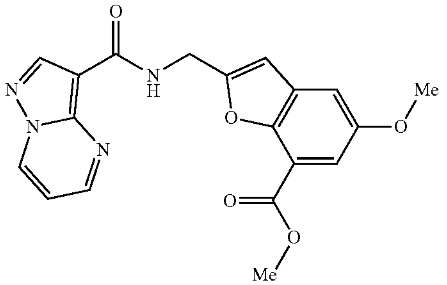 [SMILES: COC(=O)c1cc(OC)cc2cc(CNC(=O)c3cnn4cccnc34)oc12]

Methyl 5-methoxy-2-((pyrazolo[1,5-a]pyrimidine-3-carboxamido)methyl)benzofuran-7-carboxylate

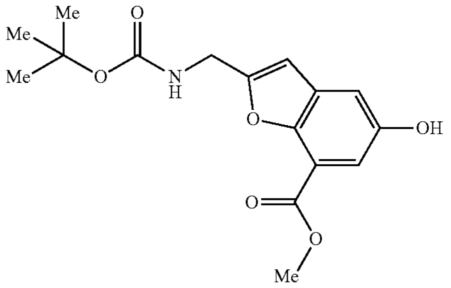 [SMILES: COC(=O)c1cc(O)cc2cc(CNC(=O)OC(C)(C)C)oc12]

A) Methyl 2-(((tert-butoxycarbonyl)amino)methyl)-5-hydroxybenzofuran-7-carboxylate A mixture of methyl 5-bromo-2-(((tert-butoxycarbonyl)amino)methyl) benzofuran-7-carboxylate (1.05 g, 2.73 mmol, Step B of Example 80), potassium acetate (0.54 g, 5.47 mmol), 4,4,4',4',5,5,5',5'-octamethyl-2,2'-bi(1,3,2-dioxaborolane) (2.08 g, 8.20 mmol) in 1,4-dioxane (25 mL) was purged with nitrogen for 5 min. X-PHOS (0.13 g, 0.27 mmol) and $Pd_2(dba)_3$ (0.125 g, 0.137 mmol) were then added. The reaction mixture was heated at 90° C. for 20 hours. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. To the residue was added THE (20 mL), water (8 mL), and sodium perborate tetrahydrate (1.26 g, 8.20 mmol). The resulting mixture was stirred at room temperature overnight. To the reaction mixture was added water and 1 N aqueous HCl solution and ethyl acetate. The organic layer was separated, washed with brine, dried over $MgSO_4$, and filtered. The filtrate was concentrated in vacuo. The residue was dissolved in DCM and purified by flash chromatography (ISCO 80 g column, 0-40% ethyl acetate in hexanes) to give the title compound (0.88 g, 99% yield) as a viscous solid. $^1$H NMR (400 MHz, Chloroform-d) δ 7.43 (d, J=2.6 Hz, 1H), 7.17 (d, J=2.6 Hz, 1H), 6.57 (s, 1H), 5.28-5.06 (m, 1H), 4.50 (br d, J=5.9 Hz, 2H), 4.01 (s, 3H), 1.49 (s, 9H); MS (ESI+) m/z=266.1 $(M-55+H)^+$.

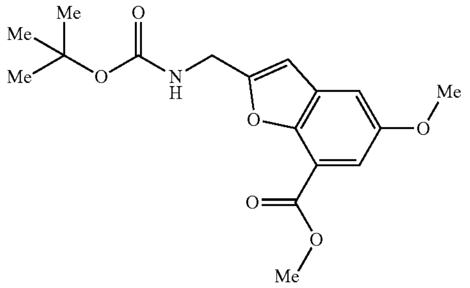 [SMILES: COC(=O)c1cc(OC)cc2cc(CNC(=O)OC(C)(C)C)oc12]

B) Methyl 2-(((tert-butoxycarbonyl)amino)methyl)-5-methoxybenzofuran-7-carboxylate To a solution of methyl 2-(((tert-butoxycarbonyl)amino)methyl)-5-hydroxybenzofuran-7-carboxylate (0.4 g, 1.25 mmol) in DMF (8 mL) was added $K_2CO_3$ (0.43 g, 3.11 mmol) and methyl iodide (0.09 mL, 1.49 mmol). The reaction mixture was stirred at room temperature for 4 hours. The reaction mixture was diluted with ethyl acetate and saturated aqueous $NaHCO_3$ solution. The organic layer was separated, washed with brine, dried over $MgSO_4$, and filtered. The filtrate was concentrated in vacuo to give the crude title compound (0.41 g, 98%) as a white solid. $^1H$ NMR (400 MHz, Chloroform-d) δ 7.51 (d, J=2.7 Hz, 1H), 7.23 (d, J=2.7 Hz, 1H), 6.61 (s, 1H), 5.10 (br s, 1H), 4.50 (br d, J=5.9 Hz, 2H), 4.01 (s, 3H), 3.89 (s, 3H), 1.49 (s, 9H); MS (ESI+) m/z=280.2 $(M-55+H)^+$.

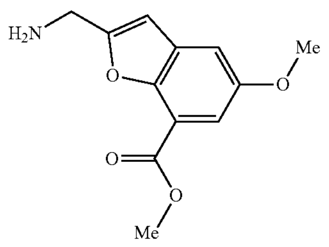 [SMILES: COC(=O)c1cc(OC)cc2cc(CN)oc12]

C) Methyl 2-(aminomethyl)-5-methoxybenzofuran-7-carboxylate

To a solution of methyl 2-(((tert-butoxycarbonyl)amino) methyl)-5-methoxybenzofuran-7-carboxylate (0.41 g, 1.223 mmol) in DCM (8 mL) was added TFA (0.94 mL, 12.23 mmol). The reaction mixture was stirred at room temperature for 2 hours. The reaction mixture was concentrated in vacuo to give the title compound (0.42 g, 93%, TFA salt) as a light brown solid. $^1H$ NMR (400 MHz, Methanol-d4) δ 7.56 (d, J=2.6 Hz, 1H), 7.46 (d, J=2.6 Hz, 1H), 7.02 (s, 1H), 4.39 (s, 2H), 4.01 (s, 3H), 3.89 (s, 3H); MS (ESI+) m/z=219.1 $(M-16+H)^+$.

D) Methyl 5-methoxy-2-((pyrazolo[1,5-a]pyrimidine-3-carboxamido) methyl)benzofuran-7-carboxylate To a suspension of pyrazolo[1,5-a]pyrimidine-3-carboxylic acid (15.2 mg, 0.093 mmol) and BOP (31.7 mg, 0.072 mmol) in DMF (2 mL) was added methyl 2-(aminomethyl)-5-methoxybenzofuran-7-carboxylate, TFA (25 mg, 0.072 mmol) and DIPEA (0.05 mL, 0.29 mmol). The reaction mixture turned into a clear solution and was stirred at room temperature for 1 hour. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DMF, filtered and purified by preparative HPLC (Method B). Fractions containing the desired product were combined and dried via centrifugal evaporation to give the title compound (17.6 mg, 65%). $^1H$ NMR (500 MHz, DMSO-$d_6$) δ 9.31 (br d, J=6.1 Hz, 1H), 8.84 (br d, J=2.7 Hz, 1H), 8.64 (s, 1H), 8.53 (br t, J=5.8 Hz, 1H), 7.43 (d, J=2.4 Hz, 1H), 7.33 (d, J=2.4 Hz, 1H), 7.29 (dd, J=6.9, 4.1 Hz, 1H), 6.80 (s, 1H), 4.78 (br d, J=5.8 Hz, 2H), 3.90 (s, 3H), 3.81 (s, 3H); MS (ESI+) m/z=381.1 $(M+H)^+$.

Example 103

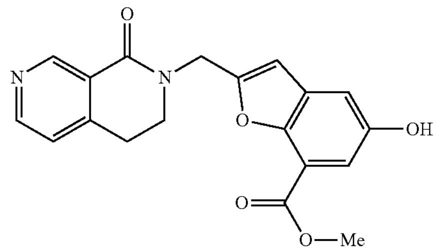 [SMILES: COC(=O)c1cc(O)cc2cc(CN3CCc4ccncc4C3=O)oc12]

Methyl 5-hydroxy-2-((1-oxo-3,4-dihydro-2,7-naphthyridin-2(1H)-yl)methyl)benzofuran-7-carboxylate

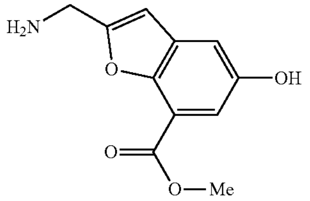 [SMILES: COC(=O)c1cc(O)cc2cc(CN)oc12]

A) Methyl 2-(aminomethyl)-5-hydroxybenzofuran-7-carboxylate

To a solution of methyl 2-(((tert-butoxycarbonyl)amino) methyl)-5-hydroxybenzofuran-7-carboxylate (0.5 g, 1.556 mmol, Step A of Example 102) in DCM (8 mL) was added TFA (3 mL, 39 mmol). The reaction mixture was stirred at room temperature for 3 hours. The reaction mixture was then concentrated in vacuo. The residue was mixed with ethyl acetate and extracted with saturated aqueous $NaHCO_3$ solution. The organic layer was separated, washed with brine, dried over $MgSO_4$, and filtered. The filtrate was concentrated in vacuo to give methyl 2-(aminomethyl)-5-hydroxybenzofuran-7-carboxylate (0.20 g, 58% yield) as a light yellow solid. $^1H$ NMR (400 MHz, Methanol-$d_4$) δ 7.33 (d, J=2.4 Hz, 1H), 7.16 (d, J=2.6 Hz, 1H), 6.64 (s, 1H), 3.98 (s, 2H), 3.96 (s, 3H); MS (ESI+) m/z=443.1 $(2M+H)^+$.

B) Methyl 5-hydroxy-2-((1-oxo-3,4-dihydro-2,7-naphthyridin-2(1H)-yl)methyl)benzofuran-7-carboxylate 3,4-Dihydro-1H-pyrano[3,4-c]pyridin-1-one (15 mg, 0.101 mmol) (WO 2005063768) and methyl 2-(aminomethyl)-5-hydroxybenzofuran-7-carboxylate (27 mg, 0.12 mmol) were added to a pressure relief vial and heated neat at 120° C. After heating for 4 hours, the reaction was cooled, then diluted with 2 mL DMF, filtered and purified via HPLC (Method B) to give methyl 5-hydroxy-2-((1-oxo-3,4-dihydro-2,7-naphthyridin-2(1H)-yl)methyl)benzofuran-7-carboxylate (10 mg, 0.028 mmol, 27.9% yield). $^1H$ NMR (500 MHz, DMSO-$d_6$) δ 8.96 (s, 1H), 8.62 (br d, J=4.9 Hz, 1H), 7.37 (d, J=4.9 Hz, 1H), 7.24 (d, J=2.4 Hz, 1H), 7.18 (d, J=2.4 Hz, 1H), 6.80 (s, 1H), 4.87 (s, 2H), 3.84 (s, 3H), 3.73 (t, J=6.6 Hz, 2H), 3.08 (br t, J=6.6 Hz, 2H); MS (ESI+) m/z=353.0 $(M+H)^+$.

Example 104

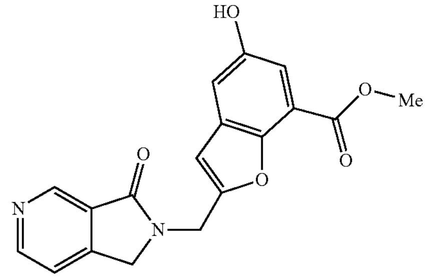 [SMILES: COC(=O)c1cc(O)cc2cc(CN3Cc4ccncc4C3=O)oc12]

Methyl 5-hydroxy-2-((3-oxo-1,3-dihydro-2H-pyrrolo[3,4-c]pyridin-2-yl)methyl)benzofuran-7-carboxylate Ethyl 4-formylnicotinate (80 mg, 0.446 mmol) and methyl 2-(aminomethyl)-5-hydroxybenzofuran-7-carboxylate (104 mg, 0.469 mmol, Step A in Example 103) were taken up in THF (3 mL) was stirred at rt for 40 min. After 40 minutes, acetic acid (0.1 mL, 1.747 mmol) and sodium triacetoxyborohydride (142 mg, 0.670 mmol) were added. The resulting mixture was stirred at room temperature for 4 hours. After 4 hours, the reaction mixture was diluted with saturated $NaHCO_3$ solution and the mixture was stirred at rt for 5 min. The mixture was further diluted with water and extracted with ethyl acetate. The organics were separated and combined. The combined organics were washed with brine, dried over magnesium sulfate, filtered, and concentrated in vacuo. The residue was purified via ISCO (12 g column, eluting with 0-10% MeOH in DCM) to give the title compound (46 mg, 30%). $^1H$ NMR (499 MHz, DMSO-d6) δ 9.52 (s, 1H), 8.96 (d, J=1.1 Hz, 1H), 8.78 (d, J=5.0 Hz, 1H), 7.71 (dd, J=5.1, 0.8 Hz, 1H), 7.27 (d, J=2.6 Hz, 1H), 7.19 (d, J=2.4 Hz, 1H), 6.83 (s, 1H), 4.93 (s, 2H), 4.67 (s, 2H), 3.86 (s, 3H); MS (ESI+) m/z=339.1 $(M+H)^+$.

Example 105

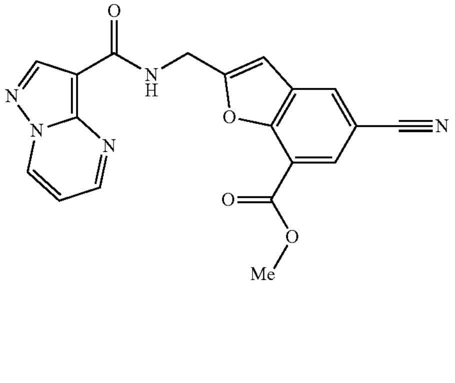 [SMILES: COC(=O)c1cc(C#N)cc2cc(CNC(=O)c3cnn4cccnc34)oc12]

Methyl 5-cyano-2-((pyrazolo[1,5-a]pyrimidine-3-carboxamido)methyl)benzofuran-7-carboxylate

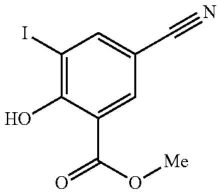 [SMILES: COC(=O)c1cc(C#N)cc(I)c1O]

A) Methyl 5-cyano-2-hydroxy-3-iodobenzoate

To a solution of methyl 5-cyano-2-hydroxybenzoate (3.0 g, 16.9 mmol) in N,N-dimethylformamide (30 mL) was added sodium iodide (3.05 g, 20.3 mmol), followed by chloramine T trihydrate (5.25 g, 18.6 mmol) slowly. The resulting mixture was stirred at room temperature for 2 hours, then heated at 95° C. overnight. The reaction mixture was diluted with ethyl acetate and 1 N aqueous HCl solution. The organic layer was separated, washed with brine followed by $Na_2S_2O_3$ solution, dried over $MgSO_4$, and filtered. The filtrate was concentrated in vacuo to give a light yellow oil. To the residue was added MeOH and the solid was filtered to give the title compound as a white solid (2.1 g, 41%). $^1H$ NMR (400 MHz, CHLOROFORM-d) δ 12.19 (s, 1H), 8.22-8.14 (m, 2H), 4.05 (s, 3H).

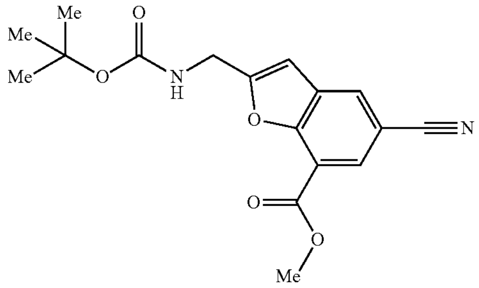 [SMILES: COC(=O)c1cc(C#N)cc2cc(CNC(=O)OC(C)(C)C)oc12]

B) Methyl 2-(((tert-butoxycarbonyl)amino)methyl)-5-cyanobenzofuran-7-carboxylate A mixture of methyl 5-cyano-2-hydroxy-3-iodobenzoate (2.1 g, 6.93 mmol), tert-butyl prop-2-yn-1-ylcarbamate (1.24 g, 7.97 mmol), TEA (11.6 mL, 83 mmol), and copper (I) iodide (0.132 g, 0.693 mmol) in DMF (15 mL) was purged with a nitrogen stream for 5 mins. Bis(triphenylphosphine)palladium(II) chloride (0.29 g, 0.416 mmol) was added and the resulting mixture was heated at 80° C. for 2 h. The reaction mixture was cooled down and diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO 80 g column, 0-40% ethyl acetate in hexanes) to give the title compound (1.8 g, 79% yield) as a light brown solid. $^1H$ NMR (400 MHz, Chloroform-d) δ 8.21 (d, J=1.6 Hz, 1H), 8.04 (d, J=1.6 Hz, 1H), 7.29 (s, 1H), 6.76 (s, 1H), 4.56 (br d, J=6.1 Hz, 2H), 4.05 (s, 3H), 1.49 (s, 9H); MS (ESI+) m/z=275.2 $(M-55+H)^+$.

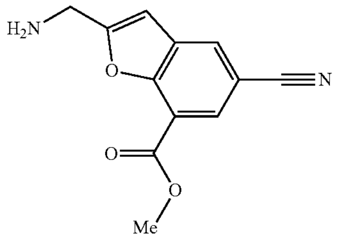 [SMILES: COC(=O)c1cc(C#N)cc2cc(CN)oc12]

C) Methyl 2-(aminomethyl)-5-cyanobenzofuran-7-carboxylate

To a solution of methyl 2-(((tert-butoxycarbonyl)amino)methyl)-5-cyanobenzofuran-7-carboxylate (0.3 g, 0.91 mmol) in DCM (3 mL) was added TFA (1.05 mL, 13.6 mmol). The reaction mixture was stirred at room temperature for 2 hours. The reaction mixture was concentrated in vacuo to give the title compound (0.3 g, 86% yield, TFA salt) as a light brown solid. MS (ESI+) m/z=231.1 $(M+H)^+$.

D) Methyl 5-cyano-2-((pyrazolo[1,5-a]pyrimidine-3-carboxamido)methyl) benzofuran-7-carboxylate To a suspension of pyrazolo[1,5-a]pyrimidine-3-carboxylic acid (14 mg, 0.087 mmol) and BOP (39 mg, 0.087 mmol) in DMF (1 mL) was added methyl 2-(aminomethyl)-5-cyanobenzofuran-7-carboxylate, TFA salt (25 mg, 0.073 mmol) and DIPEA (0.05 mL, 0.29 mmol). The reaction mixture turned into a clear solution and was stirred at room temperature for 20 hours. The reaction mixture was concentrated in vacuo and and the residue was dissolved in DMF, filtered and purified by preparative HPLC (Method B). Fractions containing the desired product were combined and dried via centrifugal evaporation to give the title compound (7.7 mg, 27%). $^1H$ NMR (500 MHz, DMSO-$d_6$) δ 9.29 (d, J=7.0 Hz, 1H), 8.84 (d, J=4.0 Hz, 1H), 8.62 (s, 1H), 8.53 (br t, J=5.9 Hz, 1H), 8.38 (s, 1H), 8.14 (s, 1H), 7.28 (dd, J=6.9, 4.2 Hz, 1H), 6.99 (s, 1H), 4.86 (d, J=5.9 Hz, 2H), 3.94 (s, 3H); MS (ESI+) m/z=376.1 $(M+H)^+$.

Example 106

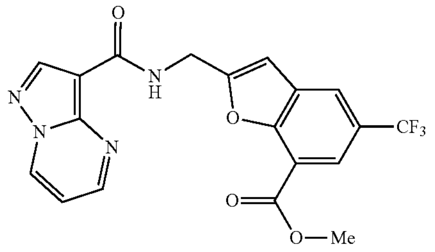 [SMILES: COC(=O)c1cc(C(F)(F)F)cc2cc(CNC(=O)c3cnn4cccnc34)oc12]

Methyl 2-((pyrazolo[1,5-a]pyrimidine-3-carboxamido)methyl)-5-(trifluoromethyl) benzofuran-7-carboxylate 2-((Pyrazolo[1,5-a]pyrimidine-3-carboxamido)methyl)-5-(trifluoromethyl)benzofuran-7-carboxylic acid (20 mg, 0.049 mmol, Example 180) was dissolved in DMF (198 µl) and DIPEA (34.6 µl, 0.198 mmol) and methanol (4.76 mg, 0.148 mmol) were added. BOP (32.8 mg, 0.074 mmol) was added and the reaction was stirred at room temperature overnight. The reaction was diluted with DMF, filtered, and purified via preparative HPLC (method B) to give the title compound (12.1 mg, 58% yield). $^1H$ NMR (500 MHz, DMSO-$d_6$) δ 9.31 (br d, J=6.7 Hz, 1H), 8.83 (br d, J=2.1 Hz, 1H), 8.63 (s, 1H), 8.57 (br t, J=5.5 Hz, 1H), 8.30 (s, 1H), 8.02 (s, 1H), 7.29 (br dd, J=6.3, 4.4 Hz, 1H), 7.00 (s, 1H), 4.85 (br d, J=5.8 Hz, 2H), 3.93 (s, 3H); MS (ESI+) m/z=419.1 $(M+H)^+$.

Example 107

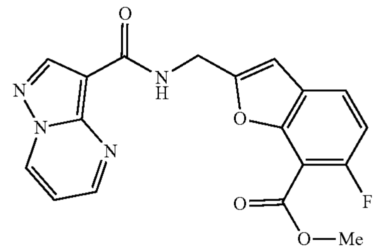 [SMILES: COC(=O)c1c(F)ccc2cc(CNC(=O)c3cnn4cccnc34)oc12]

Methyl 6-fluoro-2-((pyrazolo[1,5-a]pyrimidine-3-carboxamido)methyl)benzofuran-7-carboxylate

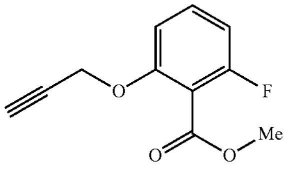

A) Methyl 2-fluoro-6-(prop-2-yn-1-yloxy)benzoate

To a solution of methyl 2-fluoro-6-hydroxybenzoate (3.6 g, 21.2 mmol) and 3-bromoprop-1-yne (2.77 g, 23.3 mmol) in DMF (25 mL) was added $K_2CO_3$ (4.39 g, 31.7 mmol). The reaction mixture was stirred at rt for 5 h. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (80 g column, 0-20% ethyl acetate in hexanes) to give the title compound (3.4 g, 77%) as oil. $^1H$ NMR (400 MHz, Chloroform-d) δ 7.37 (td, J=8.5, 6.5 Hz, 1H), 6.91 (d, J=8.5 Hz, 1H), 6.80 (t, J=8.7 Hz, 1H), 4.77 (d, J=2.4 Hz, 2H), 3.95 (s, 3H), 2.55 (t, J=2.4 Hz, 1H); MS (ESI+) m/z=209.1 $(M+H)^+$.

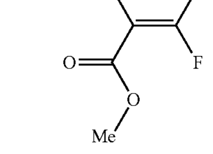

B) Methyl 6-fluoro-2-methylbenzofuran-7-carboxylate

A mixture of methyl 2-fluoro-6-(prop-2-yn-1-yloxy)benzoate (3.3 g, 15.9 mmol) and cesium fluoride (3.61 g, 23.8 mmol) in N,N-diethylaniline (20.3 ml, 127 mmol) was heated at 230° C. for 6 h and then at 200° C. overnight. The reaction mixture was cooled down and diluted with ethyl acetate and saturated aqueous $NaHCO_3$ solution. The organic layer was separated, washed with 1N aqueous HCl solution followed by brine, dried over $MgSO_4$, and filtered. The filtrate was concentrated in vacuo. The residue was dissolved in DCM and purified by flash chromatography (80 g column, 0-16% ethyl acetate in hexanes) to give the title compound (1.1 g, 33%) as light brown solid. $^1H$ NMR (400 MHz, Chloroform-d) δ 7.53 (dd, J=8.5, 5.0 Hz, 1H), 7.03 (dd, J=11.0, 8.5 Hz, 1H), 6.40 (d, J=1.1 Hz, 1H), 4.04 (s, 3H), 2.52 (s, 3H); MS (ESI+) m/z=209.2 $(M+H)^+$.

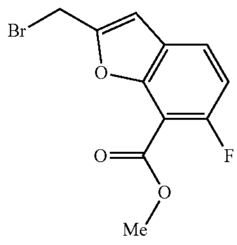 [SMILES: COC(=O)c1c(F)ccc2cc(CBr)oc12]

C) Methyl 2-(bromomethyl)-6-fluorobenzofuran-7-carboxylate

To a mixture of methyl 6-fluoro-2-methylbenzofuran-7-carboxylate (1.1 g, 5.28 mmol) and NBS (1.08 g, 6.08 mmol) in $CCl_4$ (25 mL) was added AIBN (0.087 g, 0.528 mmol). The resulting mixture was heated at 70° C. overnight. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (40 g column, 0-20% ethyl acetate in hexanes) to give the title compound (0.96 g, 63%) as light brown solid. $^1H$ NMR (400 MHz, DMSO-$d_6$) δ 7.90 (dd, J=8.6, 5.2 Hz, 1H), 7.33-7.25 (m, 1H), 7.14 (s, 1H), 4.94 (s, 2H), 3.96-3.92 (m, 3H); MS (ESI+) m/z=289 $(M+H)^+$.

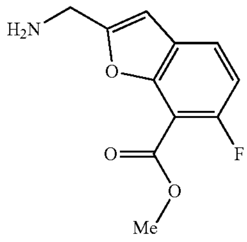 [SMILES: COC(=O)c1c(F)ccc2cc(CN)oc12]

D) Methyl 2-(aminomethyl)-6-fluorobenzofuran-7-carboxylate

To a solution of methyl 2-(bromomethyl)-6-fluorobenzofuran-7-carboxylate (0.95 g, 3.31 mmol) in DMF (15 mL) was added $K_2CO_3$ (0.46 g, 3.31 mmol) and sodium azide (0.24 g, 3.64 mmol). The reaction mixture was stirred at rt for 24 h. The reaction mixture was diluted with ethyl acetate and saturated aqeuous $NaHCO_3$ solution. The organic layer was separated, washed with brine, dried over $MgSO_4$, and filtered. The filtrate was concentrated in vacuo. To the crude intermediate (methyl 2-(azidomethyl)-6-fluorobenzofuran-7-carboxylate) was added MeOH (15 mL) and Pd/C (0.68 g, 0.32 mmol). The reaction mixture was evacuated and then filled with hydrogen (balloon). The reaction mixture was stirred under a hydrogen atmosphere at room temperature for 2 hours. The reaction mixture was filtered through a celite pad. The filtrate was concentrated in vacuo. The residue was dissolved in DCM and purified by flash chromatography (40 g column, 0-15% MeOH in DCM) to give the title compound (0.21 g, 29%) as light yellow oil. $^1H$ NMR (400 MHz, DMSO-$d_6$) δ 7.81 (dd, J=8.6, 5.2 Hz, 1H), 7.23 (dd, J=11.3, 8.6 Hz, 1H), 6.80 (s, 1H), 3.93 (s, 3H), 3.87 (s, 2H); MS (ESI+) m/z=447.3 $(2M+H)^+$.

E) Methyl 6-fluoro-2-((pyrazolo[1,5-a]pyrimidine-3-carboxamido)methyl) benzofuran-7-carboxylate A mixture of pyrazolo[1,5-a]pyrimidine-3-carboxylic acid (0.184 g, 1.13 mmol) and BOP (0.54 g, 1.22 mmol) in DMF (5 mL) was stirred at room temperature for 10 min. A solution of methyl 2-(aminomethyl)-6-fluorobenzofuran-7-carboxylate (0.21 g, 0.94 mmol) in THE (2 mL) and DIPEA (0.49 mL, 2.82 mmol) was then added. The reaction mixture was stirred at room temperature for 24 hours. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (24 g column, 0-60% ethyl acetate in DCM) to give the title compound (0.225 g, 72%) as a white solid. $^1H$ NMR (500 MHz, DMSO-$d_6$) δ 9.27 (br d, J=6.1 Hz, 1H), 8.82 (br d, J=3.1 Hz, 1H), 8.61 (s, 1H), 8.46 (br t, J=5.3 Hz, 1H), 7.80 (dd, J=8.5, 5.2 Hz, 1H), 7.40-7.15 (m, 2H), 6.86 (s, 1H), 4.78 (br d, J=5.8 Hz, 2H), 3.91 (s, 3H); MS (ESI+) m/z=369.2 $(M+H)^+$.

Example 108

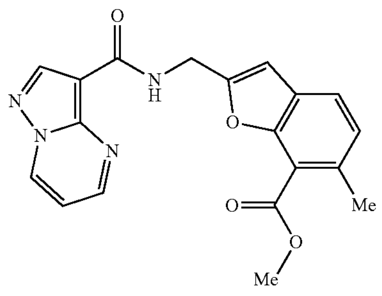 [SMILES: COC(=O)c1c(C)ccc2cc(CNC(=O)c3cnn4cccnc34)oc12]

Methyl 6-methyl-2-((pyrazolo[1,5-a]pyrimidine-3-carboxamido)methyl)benzofuran-7-carboxylate To a solution of 6-methyl-2-((pyrazolo[1,5-a]pyrimidine-3-carboxamido) methyl) benzofuran-7-carboxylic acid (30 mg, 0.086 mmol, Example 182) and BOP (37.9 mg, 0.086 mmol) in DMF (1.5 mL) was added methanol (27.4 mg, 0.856 mmol) and DIPEA (0.060 mL, 0.343 mmol). The reaction mixture was stirred at room temperature for 4 hours. The reaction mixture was concentrated in vacuo and the residue was dissolved in DMF, filtered and purified by preparative LC/MS (Method B). Fractions containing the desired product were combined and dried via centrifugal evaporation to give the title compound (5 mg, 16%). $^1$H NMR (500 MHz, DMSO-$d_6$) δ 9.27 (br d, J=6.8 Hz, 1H), 8.82 (br d, J=3.0 Hz, 1H), 8.61 (s, 1H), 8.48-8.38 (m, 1H), 7.61 (d, J=7.9 Hz, 1H), 7.27 (dd, J=6.8, 4.3 Hz, 1H), 7.16 (d, J=8.0 Hz, 1H), 6.78 (s, 1H), 4.77 (d, J=5.9 Hz, 2H), 3.90 (s, 3H), 2.48 (s, 3H); MS (ESI+) m/z=365.0 $(M+H)^+$.

Example 109

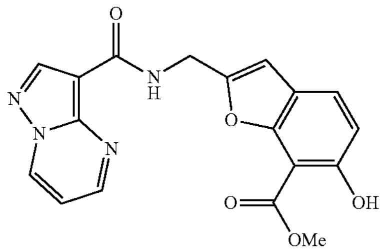 [SMILES: COC(=O)c1c(O)ccc2cc(CNC(=O)c3cnn4cccnc34)oc12]

Methyl 6-hydroxy-2-((pyrazolo[1,5-a]pyrimidine-3-carboxamido)methyl)benzofuran-7-carboxylate

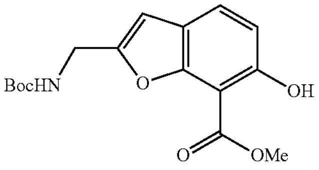 [SMILES: COC(=O)c1c(O)ccc2cc(CNC(=O)OC(C)(C)C)oc12]

A) Methyl 2-(((tert-butoxycarbonyl)amino)methyl)-6-hydroxybenzofuran-7-carboxylate To a solution of tert-butyl prop-2-yn-1-ylcarbamate (68.0 mg, 0.438 mmol), methyl 2,6-dihydroxy-3-iodobenzoate (112.1 mg, 0.381 mmol) (Bioorg. Med. Chem. Lett. 2003, 13, 4015-4017), and copper(I) iodide (7.26 mg, 0.038 mmol) in DMF (477 μL) was added $Et_3N$ (638 μL, 4.57 mmol). The mixture was sparged with N2 for 3 min and then bis (triphenylphosphine)palladium(II) chloride (13.38 mg, 0.019 mmol) was added. The reaction mixture was sparged with N2 for an additional 1 min, sealed, and heated to 80° C. for 2 h. The reaction mixture was cooled to room temperature and concentrated in vacuo. The residue was dissolved in DCM and purified by flash chromatography (ISCO 12 g column, 0-50% EtOAc in hexanes) to give the title compound (10.4 mg, 8%). $^1$H NMR (400 MHz, Chloroform-d) δ 11.16 (s, 1H), 7.58 (d, J=8.6 Hz, 1H), 6.91 (d, J=8.6 Hz, 1H), 6.56 (s, 1H), 4.99 (br s, 1H), 4.48 (br d, J=5.7 Hz, 2H), 4.08 (s, 3H), 1.50 (s, 9H); MS (ESI+) m/z=344.3 $(M+Na)^+$.

B) Methyl 6-hydroxy-2-((pyrazolo[1,5-a]pyrimidine-3-carboxamido)methyl)benzofuran-7-carboxylate To a solution of methyl 2-(((tert-butoxycarbonyl)amino)methyl)-6-hydroxybenzofuran-7-carboxylate (10.4 mg, 0.032 mmol) in DCM (485 μL) was added TFA (162 μL). The reaction mixture was stirred for 3 h and then concentrated in vacuo to obtain a residue that was used without further purification.

To this residue was added pyrazolo[1,5-a]pyrimidine-3-carboxylic acid (7.49 mg, 0.046 mmol) and ((1H-benzo[d][1,2,3]triazol-1-yl)oxy)tris(dimethylamino) phosphonium hexafluorophosphate(V) (20.3 mg, 0.046 mmol). DMF (0.21 mL) and DIPEA (21.8 μL, 0.125 mmol) were added and the reaction mixture was stirred at room temperature for 16 h. The reaction mixture was diluted with water and a precipitate formed. The slurry was filtered and the filter cake was rinsed with water. The solid was collected and placed on high vacuum to give the title compound (8.5 mg, 55%). $^1$H NMR (400 MHz, DMSO-$d_6$) δ 10.70 (s, 1H), 9.34 (dd, J=7.0, 1.6 Hz, 1H), 8.84 (dd, J=4.2, 1.6 Hz, 1H), 8.63 (s, 1H), 8.44 (t, J=5.9 Hz, 1H), 7.67 (d, J=8.5 Hz, 1H), 7.29 (dd, J=6.9, 4.2 Hz, 1H), 6.88 (d, J=8.6 Hz, 1H), 6.74 (s, 1H), 4.75 (d, J=5.8 Hz, 2H), 3.94 (s, 3H); MS (ESI+) m/z=367.0 $(M+H)^+$.

Example 110

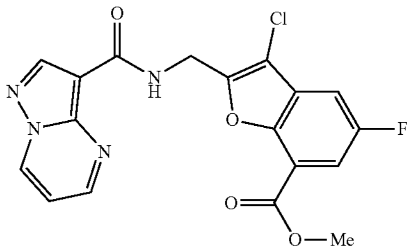 [SMILES: COC(=O)c1cc(F)cc2c(Cl)c(CNC(=O)c3cnn4cccnc34)oc12]

Methyl 3-chloro-5-fluoro-2-((pyrazolo[1,5-a]pyrimidine-3-carboxamido)methyl)benzofuran-7-carboxylate

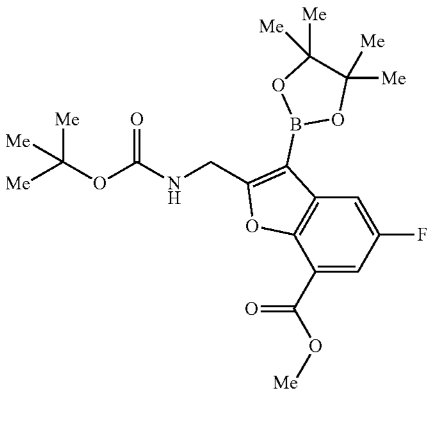 [SMILES: COC(=O)c1cc(F)cc2c(B3OC(C)(C)C(C)(C)O3)c(CNC(=O)OC(C)(C)C)oc12]

A) Methyl 2-(((tert-butoxycarbonyl)amino)methyl)-5-fluoro-3-(4,4,5,5-tetramethyl-1,3,2-dioxaborolan-2-yl)benzofuran-7-carboxylate A mixture of methyl 2-(((tert-butoxycarbonyl)amino)methyl)-5-fluorobenzofuran-7-carboxylate (0.66 g, 2.041 mmol, Step B of Example 35), 4,4'-di-tert-butyl-2,2'-bipyridine (0.055 g, 0.20 mmol), and bis(pinacolato)diboron (0.62 g, 2.45 mmol) in hexane (30 mL) was sonicated and purged with a nitrogen stream for 5 min. Next, (1,5-cyclooctadiene) (methoxy) iridium (I) dimer (0.081 g, 0.122 mmol) was added. The resulting mixture was heated at 80° C. under a nitrogen atmosphere overnight. The reaction mixture was cooled down and filtered through a celite pad. The pad was washed with ethyl acetate. The filtrate was concentrated in vacuo. The residue was dissolved in DCM and purified by flash chromatography (ISCO column 40 g, 0-30% ethyl acetate in hexanes) to give the title compound (0.52 g, 57%) as a white solid. $^1$H NMR (400 MHz, Chloroform-d) 7.79 (dd, J=8.1, 2.7 Hz, 1H), 7.64 (dd, J=9.6, 2.7 Hz, 1H), 5.99-5.62 (m, 1H), 4.95-4.64 (m, 2H), 4.02 (s, 3H), 1.48 (s, 9H), 1.41 (s, 12H); MS (ESI+) m/z=450.4 $(M+H)^+$.

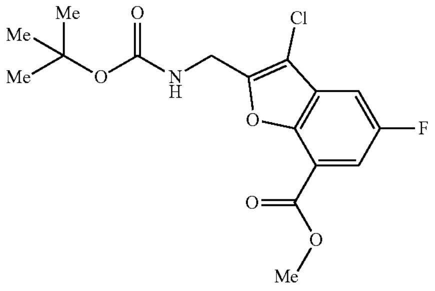 [SMILES: COC(=O)c1cc(F)cc2c(Cl)c(CNC(=O)OC(C)(C)C)oc12]

B) Methyl 2-(((tert-butoxycarbonyl)amino)methyl)-3-chloro-5-fluorobenzofuran-7-carboxylate To a solution of methyl 2-(((tert-butoxycarbonyl)amino) methyl)-5-fluoro-3-(4,4,5,5-tetramethyl-1,3,2-dioxaborolan-2-yl)benzofuran-7-carboxylate (0.52 g, 1.16 mmol) in MeOH (15 mL) was added copper(II) chloride (0.31 g, 2.31 mmol). The reaction mixture was heated at 50° C. for 4 hours and then stirred at room temperature overnight. The reaction mixture was filtered through a celite pad and the pad was washed with ethyl acetate. The filtrate was concentrated in vacuo. The residue was dissolved in DCM and purified by flash chromatography (ISCO column 40 g, 0-20% ethyl acetate in hexanes) to give the title compound (0.29 g, 70%) as a white solid. $^1$H NMR (400 MHz, Chloroform-d) δ 7.71 (dd, J=9.4, 2.7 Hz, 1H), 7.43 (dd, J=7.3, 2.7 Hz, 1H), 5.33-4.96 (m, 1H), 4.59 (br d, J=5.1 Hz, 2H), 4.02 (s, 3H), 1.49 (s, 9H); MS (ESI+) m/z=302.1 $(M+H)^+$.

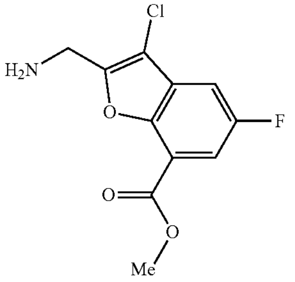 [SMILES: COC(=O)c1cc(F)cc2c(Cl)c(CN)oc12]

C) Methyl 2-(aminomethyl)-3-chloro-5-fluorobenzofuran-7-carboxylate

To a solution of methyl 2-(((tert-butoxycarbonyl)amino) methyl)-3-chloro-5-fluorobenzofuran-7-carboxylate (0.29 g, 0.81 mmol) in DCM (5 mL) was added TFA (0.94 mL, 12.2 mmol). The reaction mixture was stirred at room temperature overnight. The reaction mixture was concentrated in vacuo to give the crude title compound (TFA salt) as a white solid (0.3 g, 95%). $^1$H NMR (400 MHz, DMSO-$d_6$) δ 8.56 (br s, 2H), 7.90 (dd, J=7.6, 2.7 Hz, 1H), 7.82 (dd, J=9.5, 2.7 Hz, 1H), 4.38 (s, 2H), 3.97 (s, 3H); MS (ESI+) m/z=241.1 $(M-16+H)^+$.

D) Methyl 3-chloro-5-fluoro-2-((pyrazolo[1,5-a]pyrimidine-3-carboxamido)methyl)benzofuran-7-carboxylate A mixture of pyrazolo[1,5-a]pyrimidine-3-carboxylic acid (163 mg, 1.0 mmol) and BOP (516 mg, 1.17 mmol) in DMF (7 mL) was stirred at room temperature for 10 minutes. A solution of methyl 2-(aminomethyl)-3-chloro-5-fluorobenzofuran-7-carboxylate, TFA salt (310 mg, 0.834 mmol) in THE (2 mL) and DIPEA (0.874 mL, 5.00 mmol) were then added. The reaction mixture was stirred at room temperature for 2 hours. The reaction mixture was diluted with ethyl acetate and saturated aqueous $NaHCO_3$ solution. The organic layer was separated, washed with brine and 1 N aqueous HCl solution successively, dried over $MgSO_4$, and filtered. The filtrate was concentrated in vacuo to give the title compound as a light tan solid (315 mg, 94%). A portion of the sample was dissolved in DMF and purified by preparative HPLC (Method B). Fractions containing the desired product were combined and dried via centrifugal evaporation to give the title compound. $^1$H NMR (500 MHz, DMSO-$d_6$) δ 9.26 (br d, J=6.9 Hz, 1H), 8.83 (br d, J=3.5 Hz, 1H), 8.60 (s, 1H), 8.54-8.38 (m, 1H), 7.83-7.55 (m, 2H), 7.39-7.15 (m, 1H), 4.88 (br d, J=5.7 Hz, 2H), 3.88 (s, 3H); MS (ESI+) m/z=402.9 $(M+H)^+$.

Example 111

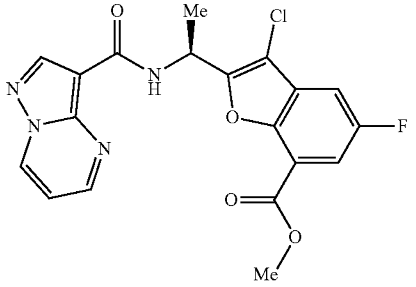 [SMILES: COC(=O)c1cc(F)cc2c(Cl)c([C@H](C)NC(=O)c3cnn4cccnc34)oc12]

Methyl (S)-3-chloro-5-fluoro-2-(1-(pyrazolo[1,5-a]pyrimidine-3-carboxamido)ethyl)benzofuran-7-carboxylate

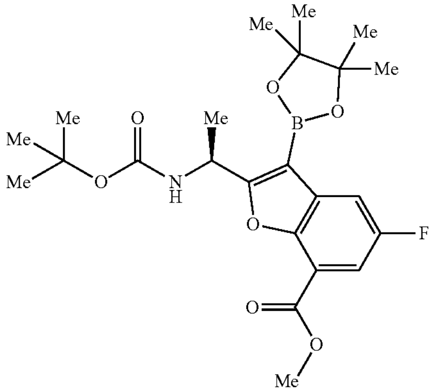 [SMILES: COC(=O)c1cc(F)cc2c(B3OC(C)(C)C(C)(C)O3)c([C@H](C)NC(=O)OC(C)(C)C)oc12]

A) Methyl (S)-2-(1-((tert-butoxycarbonyl)amino)ethyl)-5-fluoro-3-(4,4,5,5-tetramethyl-1,3,2-dioxaborolan-2-yl)benzofuran-7-carboxylate A mixture of methyl (S)-2-(1-((tert-butoxycarbonyl)amino)ethyl)-5-fluorobenzofuran-7-carboxylate (0.8 g, 2.371 mmol, Step C of Example 46), 4,4'-di-tert-butyl-2,2'-bipyridine (0.064 g, 0.237 mmol), bis(pinacolato)diboron (0.723 g, 2.85 mmol) in hexane (30 mL) was sonicated and purged with a nitrogen stream for 5 min. (1,5-Cyclooctadiene)(methoxy) iridium(I) dimer (0.094 g, 0.142 mmol) was then added. The resulting mixture was heated at 80° C. under a nitrogen atmosphere overnight. The reaction mixture was cooled down, filtered through a celite pad and the pad was washed with ethyl acetate. The filtrate was concentrated in vacuo. The residue was dissolved in DCM and purified by flash chromatography (ISCO column 40 g, 0-20% ethyl acetate in hexanes) to give the title compound (0.26 g, 24%) as a white solid. $^1$H NMR (400 MHz, CHLOROFORM-d) δ 7.80 (dd, J=8.2, 2.8 Hz, 1H), 7.62 (dd, J=9.5, 2.8 Hz, 1H), 6.27 (br d, J=8.2 Hz, 1H), 5.47-5.19 (m, 1H), 4.01 (s, 3H), 1.55 (d, J=7.0 Hz, 3H), 1.45 (s, 9H), 1.43-1.38 (m, 12H); MS (ESI+) m/z=408.3 $(M-55+H)^+$.

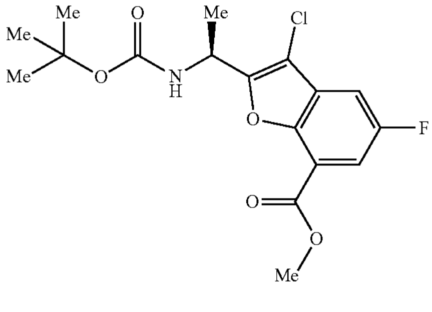 [SMILES: COC(=O)c1cc(F)cc2c(Cl)c([C@H](C)NC(=O)OC(C)(C)C)oc12]

B) Methyl (S)-2-(1-((tert-butoxycarbonyl)amino)ethyl)-3-chloro-5-fluorobenzofuran-7-carboxylate To a solution of methyl (S)-2-(1-((tert-butoxycarbonyl)amino)ethyl)-5-fluoro-3-(4,4,5,5-tetramethyl-1,3,2-dioxaborolan-2-yl)benzofuran-7-carboxylate (0.26 g, 0.561 mmol) in MeOH (8 mL) was added copper(II) chloride (0.15 g, 1.12 mmol). The reaction mixture was heated at 50° C. overnight. The reaction mixture was filtered through a celite pad and the pad was washed with ethyl acetate. The filtrate was concentrated in vacuo.

The residue was dissolved in DCM and purified by flash chromatography (ISCO column 24 g, 0-15% ethyl acetate in hexanes) to give the title compound (0.1 g, 48%) as a white solid. $^1$H NMR (400 MHz, Chloroform-d) δ 7.67 (dd, J=9.4, 2.7 Hz, 1H), 7.40 (dd, J=7.4, 2.7 Hz, 1H), 5.29-5.08 (m, 2H), 4.01 (s, 3H), 1.59 (d, J=6.8 Hz, 3H), 1.45 (s, 9H); MS (ESI+) m/z=316.2 $(M-55+H)^+$.

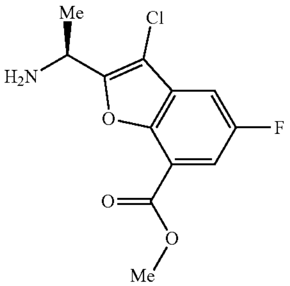 [SMILES: COC(=O)c1cc(F)cc2c(Cl)c([C@H](C)N)oc12]

C) Methyl (S)-2-(1-aminoethyl)-3-chloro-5-fluorobenzofuran-7-carboxylate

To a solution of methyl (S)-2-(1-((tert-butoxycarbonyl)amino)ethyl)-3-chloro-5-fluorobenzofuran-7-carboxylate (100 mg, 0.269 mmol) in DCM (3 mL) was added TFA (0.21 mL, 2.69 mmol). The reaction mixture was stirred at rt for 2 h. The reaction mixture was concentrated in vacuo and dried on high vacuum overnight to give the title compound (TFA salt) as a white solid (100 mg, 96%); MS (ESI+) m/z=255 $(M-16+H)^+$.

D) Methyl (S)-3-chloro-5-fluoro-2-(1-(pyrazolo[1,5-a]pyrimidine-3-carboxamido)ethyl)benzofuran-7-carboxylate The reaction mixture of pyrazolo[1,5-a]pyrimidine-3-carboxylic acid (55.0 mg, 0.337 mmol) and BOP (161 mg, 0.363 mmol) in DMF (2 mL) was stirred at rt for 15 min, followed by addition of a solution of methyl (S)-2-(1-aminoethyl)-3-chloro-5-fluorobenzofuran-7-carboxylate TFA salt (100 mg, 0.259 mmol) in THE (2 mL) and DIPEA (0.27 mL, 1.556 mmol). The reaction mixture turned into clear solution after addition of amine and was stirred at rt for 3 h. The reaction mixture was diluted with ethyl acetate and saturated $NaHCO_3$ solution. The organic layer was separated, washed with brine, and dried over $MgSO_4$. The organic layer was filtered and the filtrate was concentrated in vacuo to give the title compound as white solid (82 mg, 80%). A portion of the residue was dissolved in DMF, filtered and purified by preparative HPLC (Method B). Fractions containing the desired product were combined and dried via centrifugal evaporation to give the title compound (11.1 mg. 43%). $^1$H NMR (500 MHz, DMSO-$d_6$) δ 9.31 (d, J=7.3 Hz, 1H), 8.87 (br d, J=3.1 Hz, 1H), 8.60 (s, 1H), 8.49 (br d, J=7.6 Hz, 1H), 7.74 (dd, J=7.6, 2.4 Hz, 1H), 7.69 (dd, J=9.5, 2.4 Hz, 1H), 7.30 (dd, J=6.7, 4.3 Hz, 1H), 5.57 (br t, J=7.3 Hz, 1H), 3.90 (s, 3H), 1.67 (d, J=7.0 Hz, 3H); MS (ESI+) m/z=417.2 $(M+H)^+$.

Example 112

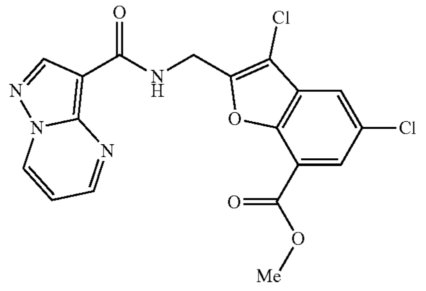 [SMILES: COC(=O)c1cc(Cl)cc2c(Cl)c(CNC(=O)c3cnn4cccnc34)oc12]

Methyl 3,5-dichloro-2-((pyrazolo[1,5-a]pyrimidine-3-carboxamido)methyl)benzofuran-7-carboxylate

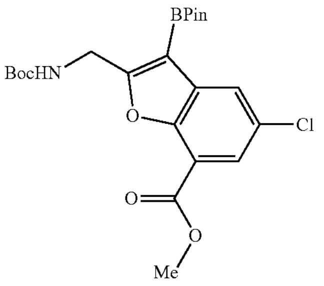

A) Methyl 2-(((tert-butoxycarbonyl)amino)methyl)-5-chloro-3-(4,4,5,5-tetramethyl-1,3,2-dioxaborolan-2-yl)benzofuran-7-carboxylate A mixture of methyl 2-(((tert-butoxycarbonyl)amino)methyl)-5-chlorobenzofuran-7-carboxylate (1.3 g, 3.83 mmol, Step B of Example 48), 4,4'-di-tert-butyl-2,2'-bipyridine (0.103 g, 0.383 mmol), and bis(pinacolato)diboron (1.17 g, 4.59 mmol) in hexane (50 mL) was sonicated and purged with a nitrogen stream for 5 min. Then, (1,5-cyclooctadiene) (methoxy) iridium (I) dimer (0.152 g, 0.230 mmol) was added. The resulting mixture was heated at 80° C. under a nitrogen atmosphere overnight. The reaction mixture was cooled down, filtered through a celite pad, and the pad was washed with ethyl acetate. The filtrate was concentrated in vacuo. The residue was dissolved in DCM and purified by flash chromatography (ISCO column 40 g, 0-20% ethyl acetate in hexanes) to give the title compound (1.25 g, 70%) as a white solid. $^1$H NMR (400 MHz, Chloroform-d) δ 8.06 (d, J=2.2 Hz, 1H), 7.90 (d, J=2.2 Hz, 1H), 5.91-5.66 (m, 1H), 4.72 (br d, J=4.7 Hz, 2H), 4.01 (s, 3H), 1.48 (s, 9H), 1.41 (s, 12H); MS (ESI+) m/z=410.3 $(M-55+H)^+$.

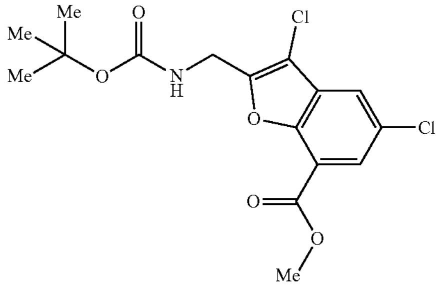 [SMILES: COC(=O)c1cc(Cl)cc2c(Cl)c(CNC(=O)OC(C)(C)C)oc12]

B) Methyl 2-(((tert-butoxycarbonyl)amino)methyl)-3,5-dichlorobenzofuran-7-carboxylate To a solution of methyl 2-(((tert-butoxycarbonyl)amino)methyl)-5-chloro-3-(4,4,5,5-tetramethyl-1,3,2-dioxaborolan-2-yl)benzofuran-7-carboxylate (0.56 g, 1.20 mmol) in MeOH (20 mL) was added copper(II) chloride (0.323 g, 2.4 mmol). The reaction mixture was heated at 50° C. overnight. The reaction mixture was filtered through a celite pad and the pad was washed with ethyl acetate. The filtrate was concentrated in vacuo. The residue was dissolved in DCM and purified by flash chromatography (ISCO column 40 g, 0-20% ethyl acetate in hexanes) to give the title compound (0.36 g, 80%) as a white solid. $^1$H NMR (400 MHz, Chloroform-d) δ 7.97 (d, J=2.2 Hz, 1H), 7.73 (d, J=2.2 Hz, 1H), 5.20-4.96 (m, 1H), 4.59 (br d, J=4.9 Hz, 2H), 4.02 (s, 3H), 1.49 (s, 9H); MS (ESI+) m/z=396.1 $(M+Na)^+$.

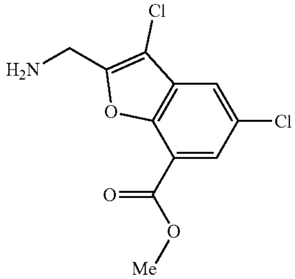 [SMILES: COC(=O)c1cc(Cl)cc2c(Cl)c(CN)oc12]

C) Methyl 2-(aminomethyl)-3,5-dichlorobenzofuran-7-carboxylate

To a solution of methyl 2-(((tert-butoxycarbonyl)amino)methyl)-3,5-dichlorobenzofuran-7-carboxylate (0.36 g, 0.96 mmol) in DCM (6 mL) was added TFA (0.9 mL, 11.5 mmol). The reaction mixture was stirred at room temperature for 2 hours. The reaction mixture was concentrated in vacuo to give the crude title compound (TFA salt, 0.37 g, 99%) and as a white solid. MS (ESI+) m/z=257 $(M+H)^+$.

D) Methyl 3,5-dichloro-2-((pyrazolo[1,5-a]pyrimidine-3-carboxamido) methyl)benzofuran-7-carboxylate A reaction mixture of pyrazolo[1,5-a]pyrimidine-3-carboxylic acid (0.187 g, 1.14 mmol) and BOP (0.55 g, 1.24 mmol) in DMF (7 mL) was stirred at room temperature for 15 minutes. A solution of methyl 2-(aminomethyl)-3,5-dichlorobenzofuran-7-carboxylate, TFA salt (0.37 g, 0.953 mmol) in THE (7 mL) and DIPEA (0.67 mL, 3.81 mmol)

were then added. The reaction mixture turned into a clear solution after addition of the amine and was stirred at room temperature for 16 hours. The reaction mixture was diluted with ethyl acetate and saturated aqueous $NaHCO_3$ solution. The organic layer was separated, washed with brine, dried over $MgSO_4$, and filtered. The filtrate was concentrated in vacuo to give a solid. The solid was triturated with MeOH and the solid was isolated via filtration to give the title compound as a white solid (0.39 g, 93%). $^1H$ NMR (400 MHz, DMSO-$d_6$) δ 9.34 (dd, J=7.0, 1.6 Hz, 1H), 8.85 (dd, J=4.2, 1.7 Hz, 1H), 8.62 (s, 1H), 8.54 (t, J=5.9 Hz, 1H), 7.95 (d, J=2.2 Hz, 1H), 7.87 (d, J=2.2 Hz, 1H), 7.30 (dd, J=7.0, 4.2 Hz, 1H), 4.88 (d, J=5.9 Hz, 2H), 3.88 (s, 3H); MS (ESI+) m/z=419.1 $(M+H)^+$.

Example 113

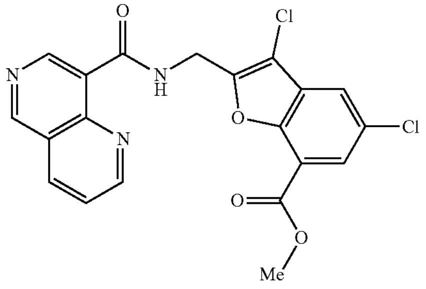 [SMILES: COC(=O)c1cc(Cl)cc2c(Cl)c(CNC(=O)c3cncc4cccnc34)oc12]

methyl 2-((1,6-naphthyridine-8-carboxamido) methyl)-3,5-dichlorobenzofuran-7-carboxylate A mixture of 1,6-naphthyridine-8-carboxylic acid, HCl (10 mg, 0.047 mmol), methyl 2-(aminomethyl)-3,5-dichlorobenzofuran-7-carboxylate, TFA (18.43 mg, 0.047 mmol, Step C of Example 112), HATU (18.05 mg, 0.047 mmol) and Hunig's Base (0.033 mL, 0.190 mmol) in DMF (0.5 mL) was stirred at rt for 24 h. The reaction was quenched with 1:1 DMF/AcOH and purified by preparative HPLC (Method B) to give the title compound (2.7 mg, 6.20 μmol, 13.06% yield). $^1H$ NMR (500 MHz, DMSO-$d_6$) δ 11.15-11.04 (m, 1H), 9.61 (s, 1H), 9.36 (s, 1H), 9.30 (br d, J=2.4 Hz, 1H), 8.80 (br d, J=8.2 Hz, 1H), 7.96 (s, 1H), 7.87 (br s, 2H), 4.97 (br d, J=5.5 Hz, 2H), 3.86 (s, 3H); MS (ESI+) m/z=430.2 $(M+H)^+$.

Example 114

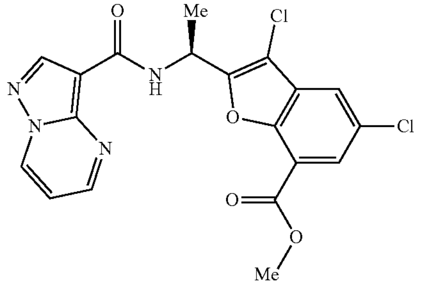 [SMILES: COC(=O)c1cc(Cl)cc2c(Cl)c([C@H](C)NC(=O)c3cnn4cccnc34)oc12]

Methyl (S)-3,5-dichloro-2-(1-(pyrazolo[1,5-a]pyrimidine-3-carboxamido)ethyl)benzofuran-7-carboxylate

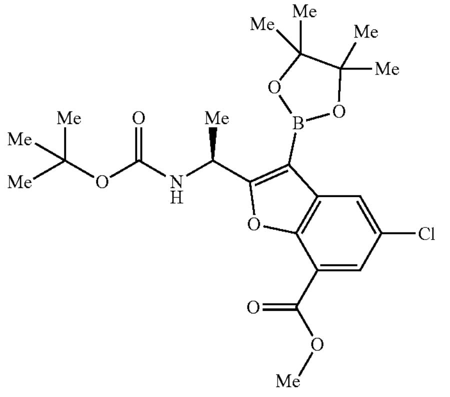 [SMILES: COC(=O)c1cc(Cl)cc2c(B3OC(C)(C)C(C)(C)O3)c([C@H](C)NC(=O)OC(C)(C)C)oc12]

A) Methyl (S)-2-(1-((tert-butoxycarbonyl)amino) ethyl)-5-chloro-3-(4,4,5,5-tetramethyl-1,3,2-dioxaborolan-2-yl)benzofuran-7-carboxylate A mixture of methyl (S)-2-(1-((tert-butoxycarbonyl) amino)ethyl)-5-chlorobenzofuran-7-carboxylate (1.7 g, 4.80 mmol, Step B of Example 79), 4,4'-di-tert-butyl-2,2'-bipyridine (0.129 g, 0.480 mmol), and bis(pinacolato)diboron (1.464 g, 5.77 mmol) in hexane (50 mL) was sonicated and purged with a nitrogen stream for 5 min. (1,5-Cyclooctadiene)(methoxy) iridium(I) dimer (0.191 g, 0.288 mmol) was then added. The resulting mixture was heated at 80° C. under a nitrogen atmosphere overnight. The reaction mixture was filtered through a celite pad and the pad was washed with ethyl acetate. The filtrate was concentrated in vacuo. The residue was dissolved in DCM and purified by flash chromatography (ISCO column 80 g, 0-20% ethyl acetate in hexanes) to give the title compound (1.2 g, 52%) as a white solid. $^1H$ NMR (400 MHz, Chloroform-d) δ 8.07 (d, J=2.2 Hz, 1H), 7.89 (d, J=2.2 Hz, 1H), 6.41-6.13 (m, 1H), 5.46-5.21 (m, 1H), 4.01 (s, 3H), 1.55 (d, J=7.0 Hz, 3H), 1.45 (s, 9H), 1.44-1.39 (m, 12H); MS (ESI+) m/z=480.5 $(M+H)^+$.

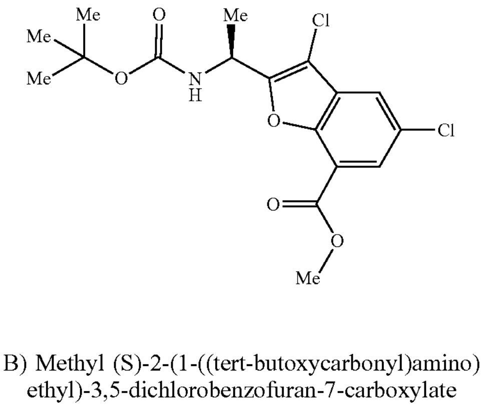

B) Methyl (S)-2-(1-((tert-butoxycarbonyl)amino) ethyl)-3,5-dichlorobenzofuran-7-carboxylate To a solution of methyl (S)-2-(1-((tert-butoxycarbonyl) amino)ethyl)-5-chloro-3-(4,4,5,5-tetramethyl-1,3,2-dioxaborolan-2-yl)benzofuran-7-carboxylate (0.7 g, 1.46 mmol) in methanol (20 mL) was added copper(II) chloride (0.392 g, 2.92 mmol). The resulting reaction mixture was heated at 50° C. overnight. The reaction mixture was filtered through a celite pad and the pad was washed with ethyl acetate. The filtrate was concentrated in vacuo. The residue was dissolved in DCM and purified by flash chromatography (ISCO column 40 g, 0-20% ethyl acetate in hexanes) to give the title compound (0.48 g, 85%) as a white solid. $^1$H NMR (400 MHz, Chloroform-d) δ 7.96 (d, J=2.2 Hz, 1H), 7.72 (d, J=2.2 Hz, 1H), 5.32-5.19 (m, 1H), 5.18-4.98 (m, 1H), 4.03 (s, 3H), 1.65-1.57 (m, 3H), 1.46 (s, 9H); MS (ESI+) m/z=332.1 $(M-55+H)^+$.

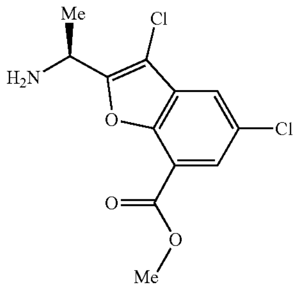 [SMILES: COC(=O)c1cc(Cl)cc2c(Cl)c([C@H](C)N)oc12]

C) Methyl (S)-2-(1-aminoethyl)-3,5-dichlorobenzofuran-7-carboxylate

To a solution of methyl (S)-2-(1-((tert-butoxycarbonyl)amino)ethyl)-3,5-dichlorobenzofuran-7-carboxylate (0.48 g, 1.24 mmol) in DCM (6 mL) was added TFA (1.14 mL, 14.8 mmol). The reaction mixture was stirred at room temperature for 2 hours. The reaction mixture was concentrated in vacuo and dried on high vacuum overnight to give the title compound (TFA salt, 0.48 g, 97%) as a white solid. $^1$H NMR (400 MHz, DMSO-$d_6$) δ 8.64 (br s, 2H), 8.09 (d, J=2.1 Hz, 1H), 7.97 (d, J=2.2 Hz, 1H), 4.86 (br d, J=5.9 Hz, 1H), 3.97 (s, 3H), 1.66 (d, J=6.9 Hz, 3H); MS (ESI) m/z=271.0 $(M-17+H)^+$.

D) Methyl (S)-3,5-dichloro-2-(1-(pyrazolo[1,5-a]pyrimidine-3-carboxamido)ethyl)benzofuran-7-carboxylate A mixture of pyrazolo[1,5-a]pyrimidine-3-carboxylic acid (142 mg, 0.873 mmol) and BOP (416 mg, 0.94 mmol) in DMF (4 mL) was stirred at room temperature for 15 minutes. A solution of methyl (S)-2-(1-aminoethyl)-3,5-dichlorobenzofuran-7-carboxylate TFA salt (270 mg, 0.671 mmol) in THF (2 mL) and DIPEA (0.70 mL, 4.03 mmol) were then added. The reaction mixture turned into a clear solution after addition of the amine and was stirred at room temperature for 2 hours. The reaction mixture was diluted with ethyl acetate and saturated aqueous $NaHCO_3$ solution. The organic layer was separated, washed with brine, dried over $MgSO_4$, and filtered. The filtrate was concentrated in vacuo to give the crude title compound as a white solid (200 mg, 70%). A portion of the material was purified by preparative HPLC (Method A). Fractions containing the desired product were combined and dried via centrifugal evaporation to give the title compound as a TFA salt. $^1$H NMR (500 MHz, DMSO-$d_6$) δ 9.27 (dd, J=6.9, 1.1 Hz, 1H), 8.93-8.81 (m, 1H), 8.58 (s, 1H), 8.47 (br d, J=7.6 Hz, 1H), 7.84 (d, J=2.1 Hz, 1H), 7.79 (d, J=2.1 Hz, 1H), 7.28 (dd, J=7.0, 4.3 Hz, 1H), 5.56 (br t, J=7.2 Hz, 1H), 3.89 (s, 3H), 1.67 (br d, J=7.0 Hz, 3H); MS (ESI+): m/z=433.2 $(M+H)^+$.

Example 115

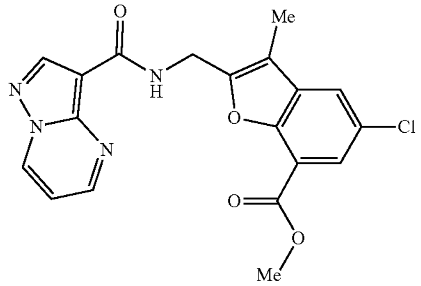 [SMILES: COC(=O)c1cc(Cl)cc2c(C)c(CNC(=O)c3cnn4cccnc34)oc12]

Methyl 5-chloro-3-methyl-2-((pyrazolo[1,5-a]pyrimidine-3-carboxamido)methyl)benzofuran-7-carboxylate

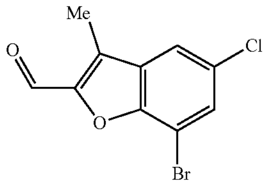 [SMILES: Cc1c(C=O)oc2c(Br)cc(Cl)cc12]

A) 7-Bromo-5-chloro-3-methylbenzofuran-2-carbaldehyde

To a solution of 1-(3-bromo-5-chloro-2-hydroxyphenyl)ethan-1-one (3.5 g, 14.03 mmol) in THF (70 mL) were added 1,1-dichloroethene (2.242 mL, 28.1 mmol) and potassium tert-butoxide (6.30 g, 56.1 mmol) slowly at ice bath temperature. The resulting reaction mixture was stirred at rt for 18 h. The reaction mixture was diluted with DCM and 1 N HCl solution. The organic layer was separated and washed with brine, dried over $MgSO_4$ and filtered. The filtrate was concentrated in vacuo. To the residue was added DCE (20 mL) and sulfuric acid (0.748 mL, 14.03 mmol). The reaction mixture was stirred at rt for 2 h. Then to the reaction mixture was added water and more DCM. The resulting mixture was stirred for 5 min vigorously, then poured into the separational funnel. The organic layer was separated, washed with brine, dried over $MgSO_4$ and filtered. The filtrate was concentrated in vacuo. The residue was dissolved in DCM and purified by silica gel column chromatography (80 g column, 0-20% ethyl acetate in hexanes) to give 7-bromo-5-chloro-3-methylbenzofuran-2-carbaldehyde (1.8 g, 47% yield) as a yellow solid. $^1$H NMR (400 MHz, Chloroform-d) δ 10.10 (s, 1H), 7.70 (d, J=1.9 Hz, 1H), 7.64 (d, J=2.0 Hz, 1H), 2.61 (s, 3H); MS (ESI+) m/z=273.1, 275.1 $(M+H)^+$.

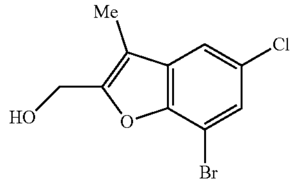 [SMILES: Cc1c(CO)oc2c(Br)cc(Cl)cc12]

B) (7-Bromo-5-chloro-3-methylbenzofuran-2-yl)methanol

To a solution of 7-bromo-5-chloro-3-methylbenzofuran-2-carbaldehyde (0.6 g, 2.194 mmol) in THE (6 mL) and MeOH (10 mL) was added sodium borohydride (0.166 g, 4.39 mmol). The reaction mixture was stirred at rt for 1 h. The reaction mixture was quenched with water and the resulting mixture was diluted with ethyl acetate. The organic layer was separated, washed with brine, dried over $MgSO_4$, and filtered. The filtrate was concentrated in vacuo to give (7-bromo-5-chloro-3-methylbenzofuran-2-yl)methanol (0.5 g, 83% yield) as a light yellow solid. $^1$H NMR (400 MHz, Chloroform-d) δ 7.47 (d, J=1.9 Hz, 1H), 7.43 (d, J=2.0 Hz, 1H), 4.80 (br d, J=4.9 Hz, 2H), 2.25 (s, 3H), 2.03-1.90 (m, 1H); MS (ESI+) m/z=256.9 $(M-17+H)^+$.

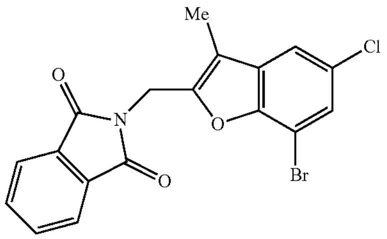 [SMILES: Cc1c(CN2C(=O)c3ccccc3C2=O)oc2c(Br)cc(Cl)cc12]

C) 2-((7-Bromo-5-chloro-3-methylbenzofuran-2-yl)methyl)isoindoline-1,3-dione

To a solution of (7-bromo-5-chloro-3-methylbenzofuran-2-yl)methanol (0.5 g, 1.815 mmol) in THE (15 mL) were added isoindoline-1,3-dione (0.320 g, 2.178 mmol) and triphenylphosphine (0.547 g, 2.087 mmol). The resulting reaction mixture was cooled to ice bath temperature and to the mixture was added DEAD (0.35 mL, 2.18 mmol) dropwise. The resulting mixture was allowed to warm up to rt and stirred at rt for 4 h. The reaction mixture was diluted with ethyl acetate and saturated $NaHCO_3$ solution. The organic layer was separated, washed with brine, 1 N HCl solution successively. The organic layer was separated, dried over $MgSO_4$, and filtered. The filtrate was concentrated in vacuo. The residue was dissolved in DCM and purified by silica gel column chromatography (40 g column, 0-30% ethyl acetate in DCM) to give 2-((7-bromo-5-chloro-3-methylbenzofuran-2-yl)methyl)isoindoline-1,3-dione (0.3 g, 41% yield) as a light brown solid. $^1$H NMR (400 MHz, Chloroform-d) δ 7.90 (dd, J=5.5, 3.0 Hz, 2H), 7.75 (dd, J=5.5, 3.1 Hz, 2H), 7.44-7.38 (m, 2H), 5.01 (s, 2H), 2.37 (s, 3H).

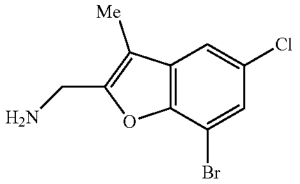 [SMILES: Cc1c(CN)oc2c(Br)cc(Cl)cc12]

D) (7-Bromo-5-chloro-3-methylbenzofuran-2-yl)methanamine

To a suspension of 2-((7-bromo-5-chloro-3-methylbenzofuran-2-yl)methyl)isoindoline-1,3-dione (0.3 g, 0.741 mmol) in ethanol (7 mL) was added hydrazine (0.035 mL, 1.112 mmol). The reaction mixture was stirred at rt for 16 h. The reaction mixture was diluted with ethyl acetate and filtered to remove solid impurity. The filtrate was diluted with ethyl acetate and saturated $NaHCO_3$ solution. The organic layer was separated, washed with brine, dried over $MgSO_4$ and filtered. The filtrate was concentrated in vacuo to give (7-bromo-5-chloro-3-methylbenzofuran-2-yl)methanamine (0.16 g, 79%) as a light brown solid. MS (ESI+) m/z=257.0, 259.0 $(M-17+H)^+$.

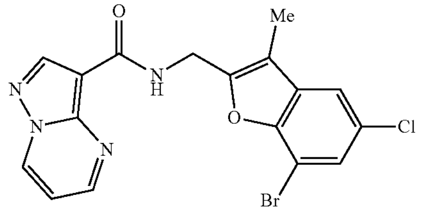 [SMILES: Cc1c(CNC(=O)c2cnn3cccnc23)oc2c(Br)cc(Cl)cc12]

E) N-((7-Bromo-5-chloro-3-methylbenzofuran-2-yl)methyl)pyrazolo[1,5-a]pyrimidine-3-carboxamide The reaction mixture of pyrazolo[1,5-a]pyrimidine-3-carboxylic acid (116 mg, 0.710 mmol) and BOP (314 mg, 0.710 mmol) in DMF (3 mL) was stirred at rt for 10 min, followed by addition of a solution of (7-bromo-5-chloro-3-methylbenzofuran-2-yl)methanamine (150 mg, 0.546 mmol) in DMF (2 mL) and DIPEA (0.286 mL, 1.639 mmol). The reaction mixture was stirred at rt for 2 h. The reaction mixture was diluted with ethyl acetate and saturated $NaHCO_3$ solution. The organic layer was separated, washed with brine, dried over $MgSO_4$ and filtered. The filtrate was concentrated in vacuo. The crude residue was purified via silica gel column chromatography (24 g column, 0-40% EtOAc in DCM) to give N-((7-bromo-5-chloro-3-methylbenzofuran-2-yl)methyl)pyrazolo[1,5-a]pyrimidine-3-carboxamide (105 mg, 60% purity, 27% yield) as a pale yellow solid. Analytical sample was purified with preparative HPLC (Method B). $^1$H NMR (400 MHz, DMSO-$d_6$) δ 9.32 (dd, J=7.0, 1.7 Hz, 1H), 8.83 (dd, J=4.2, 1.7 Hz, 1H), 8.62 (s, 1H), 8.47 (t, J=5.8 Hz, 1H), 7.72 (d, J=2.0 Hz, 1H), 7.62 (d, J=2.0 Hz, 1H), 7.28 (dd, J=7.0, 4.2 Hz, 1H), 4.77 (d, J=5.9 Hz, 2H), 2.28 (s, 3H); MS (ESI+) m/z=419.1, 421.1 $(M+H)^+$.

F) Methyl 5-chloro-3-methyl-2-((pyrazolo[1,5-a]pyrimidine-3-carboxamido)methyl)benzofuran-7-carboxylate The reaction mixture of N-((7-bromo-5-chloro-3-methylbenzofuran-2-yl)methyl)pyrazolo[1,5-a]pyrimidine-3-carboxamide (50 mg, 0.119 mmol), palladium(II) acetate (4.01 mg, 0.018 mmol), 1,3-bis(diphenylphosphino)propane (9.9 mg, 0.024 mmol) and TEA (0.166 mL, 1.191 mmol) in MeOH (4 mL) and DMF (1 mL) was vacated and then filled with nitrogen. The reaction mixture was vacated, filled with nitrogen again. The reaction mixture was heated under CO atmosphere (balloon) at 70° C. over night. The reaction mixture was filtered through a celite pad and the filtrate was concentrated in vacuo. The residue was diluted with ethyl acetate and saturated $NaHCO_3$ solution. The organic layer was separated, dried over $MgSO_4$ and filtered. The filtrate was concentrated in vacuo. The residue was taken up in DMF, filtered, and purified with preparative HPLC (Method B) to give methyl 5-chloro-3-methyl-2-((pyrazolo[1,5-a]pyrimidine-3-carboxamido)methyl)benzofuran-7-carboxylate (2.4 mg, 4.9% yield). 1H NMR (500 MHz, DMSO-d6) δ 9.28 (d, J=7.0 Hz, 1H), 8.82 (br d, J=4.0 Hz, 1H), 8.60 (s, 1H), 8.41 (br s, 1H), 7.94 (d, J=1.9 Hz, 1H), 7.75 (d, J=1.9 Hz, 1H), 7.27 (dd, J=6.9, 4.3 Hz, 1H), 4.80 (d, J=5.8 Hz, 2H), 3.90 (s, 3H), 2.30 (s, 3H); MS (ESI+) m/z=398.9 $(M+H)^+$.

Example 116

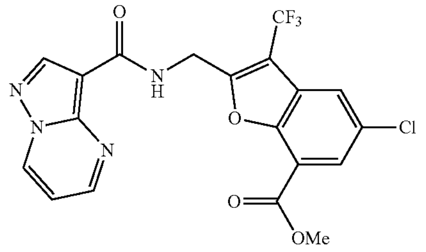 [SMILES: COC(=O)c1cc(Cl)cc2c(C(F)(F)F)c(CNC(=O)c3cnn4cccnc34)oc12]

Methyl 5-chloro-2-((pyrazolo[1,5-a]pyrimidine-3-carboxamido)methyl)-3-(trifluoromethyl)benzofuran-7-carboxylate

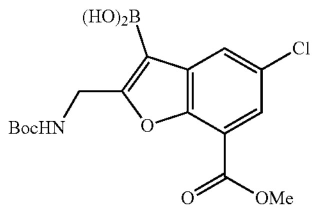 [SMILES: COC(=O)c1cc(Cl)cc2c(B(O)O)c(CNC(=O)OC(C)(C)C)oc12]

A) (2-(((tert-Butoxycarbonyl)amino)methyl)-7-(methoxycarbonyl)-5-chlorobenzofuran-3-yl)boronic acid To a suspension of methyl 2-(((tert-butoxycarbonyl)amino)methyl)-5-chloro-3-(4,4,5,5-tetramethyl-1,3,2-dioxaborolan-2-yl)benzofuran-7-carboxylate (108.9 mg, 0.234 mmol, Step A of Example 112) in acetone (1.2 mL) and water (1.2 mL) was added ammonium acetate (90 mg, 1.169 mmol), followed by sodium periodate (250 mg, 1.169 mmol). The reaction mixture was stirred for 3 h and then concentrated in vacuo. The slurry was sonicated with water and filtered. The filter cake was rinsed with water, collected, and dried on high vacuum to give the title compound (82.3 mg, 92%). 1H NMR (400 MHz, Chloroform-d) δ 8.16 (d, J=2.2 Hz, 1H), 7.92 (d, J=2.2 Hz, 1H), 6.94 (br s, 2H), 5.54 (br t, J=6.0 Hz, 1H), 4.49 (d, J=6.7 Hz, 2H), 4.01 (s, 3H), 1.44 (s, 9H); MS (ESI+) m/z=327.9 $(M-tBu+H)^+$.

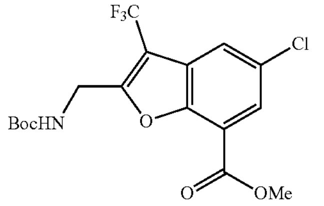 [SMILES: COC(=O)c1cc(Cl)cc2c(C(F)(F)F)c(CNC(=O)OC(C)(C)C)oc12]

B) Methyl 2-(((tert-butoxycarbonyl)amino)methyl)-5-chloro-3-(trifluoromethyl)benzofuran-7-carboxylate A solution of (2-(((tert-butoxycarbonyl)amino)methyl)-7-(methoxycarbonyl)-5-chlorobenzofuran-3-yl)boronic acid (82.3 mg, 0.215 mmol), 3,3-dimethyl-1-(trifluoromethyl)-1,3-dihydro-113-benzo[d][1,2]iodaoxole (142 mg, 0.429 mmol), 1,10-phenanthroline (3.87 mg, 0.021 mmol), and potassium carbonate (59.3 mg, 0.429 mmol) in diglyme (2.1 mL) was sparged with N2 for 5 min. Copper(I) iodide (2.04 mg, 0.011 mmol) was added and the reaction mixture was sparged with N2 for an additional 5 min, sealed, and heated to 35° C. The reaction mixture was cooled to room temperature and diluted with water and extracted with EtOAc. The organic layers were combined, washed with a 10% aqueous solution of LiCl, washed with brine, dried over $MgSO_4$, filtered, and concentrated in vacuo. The residue was dissolved in MeCN and purified by flash chromatography (ISCO 12 g column, 0-25% EtOAc in hexanes) to give the title compound (36.0 mg, 41%). $^1H$ NMR (400 MHz, Chloroform-d) δ 7.81 (s, 1H), 7.61 (s, 1H), 5.18 (br s, 1H), 4.66 (br s, 2H), 3.99 (s, 3H), 2.48 (s, 3H), 1.46 (s, 9H); MS (ESI+) m/z=332.1 $(M-tBu+H)^+$.

C) Methyl 5-chloro-2-((pyrazolo[1,5-a]pyrimidine-3-carboxamido)methyl)-3-(trifluoromethyl)benzofuran-7-carboxylate To a solution of methyl 2-(((tert-butoxycarbonyl)amino)methyl)-5-chloro-3-(trifluoromethyl)benzofuran-7-carboxylate (36.0 mg, 0.088 mmol) in DCM (0.66 mL) was added TFA (0.22 mL). The reaction mixture was stirred for 20 min and then concentrated in vacuo to obtain a residue that was used without further purification.

To this residue was added pyrazolo[1,5-a]pyrimidine-3-carboxylic acid (32.6 mg, 0.200 mmol) and ((1H-benzo[d][1,2,3]triazol-1-yl)oxy)tris(dimethylamino)phosphonium hexafluorophosphate(V) (88 mg, 0.200 mmol). DMF (1.5 mL) and DIPEA (96 μL, 0.553 mmol) and the reaction mixture was stirred at room temperature for 2.5 hours. The reaction mixture was diluted with water and extracted with EtOAc. The organic layers were combined, washed with a 10% aqueous solution of LiCl, washed with brine, dried over $MgSO_4$, filtered, and concentrated in vacuo. A third of the obtained residue was dissolved in 2 mL MeOH, filtered through a syringe filter, and purified by preparative LC/MS (Method B). Fractions containing the desired product were combined and dried via centrifugal evaporation to give the title compound (3.3 mg, 5%). The remaining obtained residue contained additional semipure title compound (72.8 mg) that was used without further purification. $^{1}$H NMR (500 MHz, DMSO-$d_6$) δ 9.32 (br d, J=5.8 Hz, 1H), 8.85 (br d, J=2.7 Hz, 1H), 8.66-8.55 (m, 2H), 7.96 (s, 1H), 7.89 (br d, J=1.8 Hz, 1H), 7.30 (br dd, J=6.9, 4.4 Hz, 1H), 4.98 (br d, J=5.5 Hz, 2H), 3.78 (s, 3H); MS (ESI+) m/z=453.0 $(M+H)^+$.

Example 117

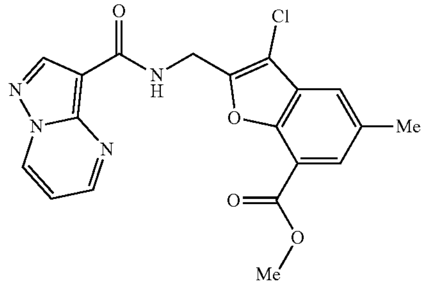 [SMILES: COC(=O)c1cc(C)cc2c(Cl)c(CNC(=O)c3cnn4cccnc34)oc12]

Methyl 3-chloro-5-methyl-2-((pyrazolo[1,5-a]pyrimidine-3-carboxamido)methyl)benzofuran-7-carboxylate

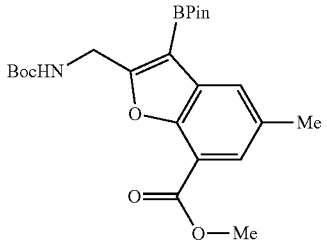

A) Methyl 2-(((tert-butoxycarbonyl)amino)methyl)-5-methyl-3-(4,4,5,5-tetramethyl-1,3,2-dioxaborolan-2-yl)benzofuran-7-carboxylate A vial-was charged with methyl 2-(((tert-butoxycarbonyl) amino)methyl)-5-methylbenzofuran-7-carboxylate (3.2 g, 102 mmol, Step B of Example 85), 4,4'-di-tert-butyl-2,2'-bipyridine (0.269 g, 1.002 mmol), bis(pinacolato)diboron (2.90 g, 11.42 mmol) and (1,5-cyclooctadiene)(methoxy) iridium (I) dimer (0.4 g, 0.60 mmol) in hexane (45 ml). The reaction mixture was purged with nitrogen and heated to 80° C. for 5 hours. The reaction mixture was filtered and concentrated in vacuo. The crude product mixture was purified by a silica gel ISCO 120 g column eluting with 0-20% ethyl acetate in hexanes over a 15 minute gradient. The appropriate fractions were isolated and concentrated in vacuo to afford the product (2.5 g, 56% yield) as a solid. $^{1}$H NMR (400 MHz, Chloroform-d) δ 8.00-7.78 (m, 1H), 7.76-7.59 (m, 1H), 4.97-4.52 (m, 2H), 4.22-3.79 (m, 3H), 2.78-2.25 (m, 3H), 1.60-1.35 (m, 21H); MS (ESI+) m/z=390 $(M-55+H)^+$.

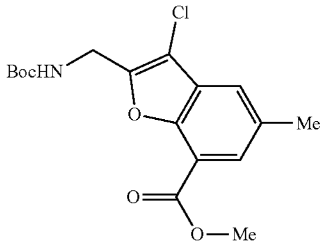 [SMILES: COC(=O)c1cc(C)cc2c(Cl)c(CNC(=O)OC(C)(C)C)oc12]

B) Methyl 2-(((tert-butoxycarbonyl)amino)methyl)-3-chloro-5-methylbenzofuran-7-carboxylate A vial was charged with methyl 2-(((tert-butoxycarbonyl) amino)methyl)-5-methyl-3-(4,4,5,5-tetramethyl-1,3,2-dioxaborolan-2-yl)benzofuran-7-carboxylate (300 mg, 0.674 mmol), copper(II) chloride (181 mg, 1.347 mmol) and MeOH (3 mL). The reaction mixture was heated to 50° C. for 16 hours. The solution was filtered through celite and concentrated in vacuo. The crude product mixture was purified by a silica gel ISCO 24 g column eluting with 0-20% ethyl acetate/hexane over a 15 minute gradient. The appropriate fractions were isolated and concentrated in vacuo to afford the title compound (1.12 g, 69.8% yield) as a solid. $^{1}$H NMR (400 MHz, Chloroform-d) δ 8.04 (d, J=0.6 Hz, 1H), 7.84 (d, J=6.5 Hz, 1H), 7.27 (dd, J=6.5, 0.8 Hz, 1H), 3.97 (s, 3H), 3.74-3.65 (m, 2H), 2.48 (s, 3H), 1.57-1.50 (m, 9H); MS (ESI+) m/z=298.0 $(M-55+H)^+$.

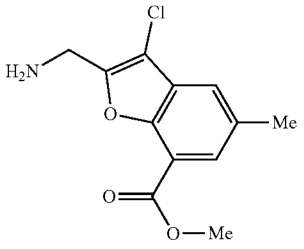 [SMILES: COC(=O)c1cc(C)cc2c(Cl)c(CN)oc12]

C) Methyl 2-(aminomethyl)-3-chlorobenzofuran-7-carboxylate, TFA

A vial was charged methyl 2-(((tert-butoxycarbonyl) amino)methyl)-3-chlorobenzofuran-7-carboxylate (1.12 g, 3.17 mmmol), DCM (20 mL) and TFA (2 mL). The reaction solution was stirred at RT for 2 hours. The reaction mixture was concentrated in vacuo to afford the crude product (0.98 g, 85% yield) as a solid. $^{1}$H NMR (400 MHz, Chloroform-d) δ 7.86-7.81 (m, 1H), 7.61-7.54 (m, 1H), 4.31 (s, 2H), 3.97 (s, 3H), 2.48 (s, 3H); MS (ESI+) m/z=237.0 $(M-16)^+$.

D) Methyl 3-chloro-5-methyl-2-((pyrazolo[1,5-a] pyrimidine-3-carboxamido)methyl)benzofuran-7-carboxylate A flask was charged with a suspension of pyrazolo[1,5-a]pyrimidine-3-carboxylic acid (88 mg, 0.537 mmol) and BOP (238 mg, 0.537 mmol) in DMF (2 mL). To the reaction mixture was added methyl 2-(aminomethyl)-3-chloro-5-methylbenzofuran-7-carboxylate, TFA (158 mg, 0.430 mmol) and DIPEA (0.300 mL, 1.719 mmol). The reaction mixture was stirred at rt for 16 hours. The solution was quenched with water and the precipitate was collected by vacuum filtration. The crude material was purified via preparative HPLC (Method B) to yield the title compound (156 mg, 35% yield. $^{1}H$ NMR (500 MHz, DMSO-$d_6$) δ 9.32 (d, J=6.1 Hz, 1H), 8.85 (br d, J=2.7 Hz, 1H), 8.62 (s, 1H), 8.51 (br t, J=5.5 Hz, 1H), 7.75 (s, 1H), 7.65 (s, 1H), 7.29 (dd, J=7.0, 4.3 Hz, 1H), 4.86 (d, J=5.8 Hz, 2H), 3.86 (s, 3H), 2.49-2.46 (m, 3H); MS (ESI+) m/z=399.0 $(M+H)^+$.

Example 118

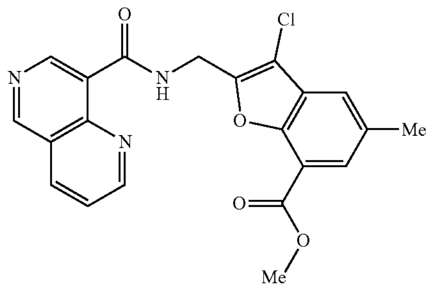 [SMILES: COC(=O)c1cc(C)cc2c(Cl)c(CNC(=O)c3cncc4cccnc34)oc12]

methyl 2-((1,6-naphthyridine-8-carboxamido)methyl)-3-chloro-5-methylbenzofuran-7-carboxylate A mixture of 1,6-naphthyridine-8-carboxylic acid, HCl (7 mg, 0.033 mmol), methyl 2-(aminomethyl)-3-chloro-5-methylbenzofuran-7-carboxylate, TFA (12.22 mg, 0.033 mmol, Step C Example 117), HATU (12.64 mg, 0.033 mmol) and Hunig's Base (0.023 mL, 0.133 mmol) in DMF (0.5 mL) was stirred at rt for 3 h. The reaction was quenched with 1:1 DMF/AcOH and purified by preparative LC/MS (Method B) to give the title compound (2.5 mg, 5.84 μmol, 17.57% yield). $^{1}H$ NMR (500 MHz, DMSO-$d_6$) δ 11.06 (br s, 1H), 9.60 (s, 1H), 9.36 (s, 1H), 9.33-9.26 (m, 1H), 8.79 (br d, J=7.3 Hz, 1H), 7.87 (dd, J=8.2, 4.3 Hz, 1H), 7.75 (s, 1H), 7.70-7.60 (m, 1H), 4.95 (br d, J=5.5 Hz, 2H), 3.85 (s, 3H); MS (ESI+) m/z=410.1 $(M+H)^+$.

Example 119

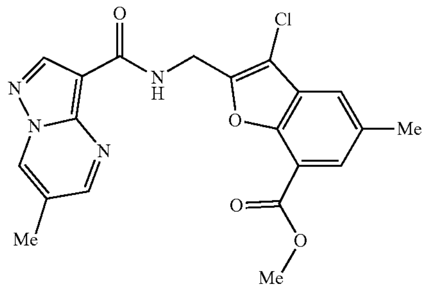 [SMILES: COC(=O)c1cc(C)cc2c(Cl)c(CNC(=O)c3cnn4cc(C)cnc34)oc12]

Methyl 3-chloro-5-methyl-2-((6-methylpyrazolo[1,5-a]pyrimidine-3-carboxamido)methyl)benzofuran-7-carboxylate To a suspension of 6-methylpyrazolo[1,5-a]pyrimidine-3-carboxylic acid (20 mg, 0.113 mmol) and BOP (62.4 mg, 0.141 mmol) in DMF (2 mL) was added methyl 2-(aminomethyl)-3-chloro-5-methylbenzofuran-7-carboxylate, TFA (41.5 mg, 0.113 mmol, Step C of Example 264) and DIPEA (0.079 mL, 0.452 mmol). The reaction mixture turned into clear solution and was stirred at rt for 16 hours. The reaction was quenched with water, the precipitate that formed was filtered, and then dissolved in 2 mL of DMF for purification. The crude material was purified via preparative HPLC (Method B) to afford the product (15.4 mg, 33% yield). 1H NMR (500 MHz, DMSO-d6) δ 9.13 (s, 1H), 8.73 (s, 1H), 8.54-8.50 (m, 1H), 8.50-8.45 (m, 1H), 7.73 (s, 1H), 7.64-7.61 (m, 1H), 4.84 (br d, J=5.8 Hz, 2H), 3.85 (s, 3H), 2.48-2.43 (m, 3H), 2.40-2.35 (m, 3H); MS (ESI+) m/z=413.1 $(M+H)^+$.

Example 120

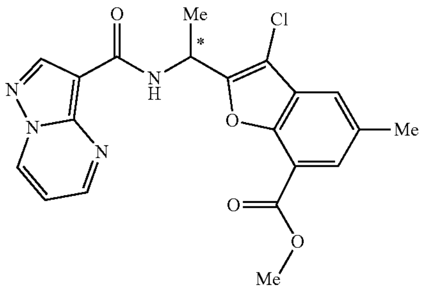 [SMILES: COC(=O)c1cc(C)cc2c(Cl)c(C(C)NC(=O)c3cnn4cccnc34)oc12]

Methyl-3-chloro-5-methyl-2-(1-(pyrazolo[1,5-a]pyrimidine-3-carboxamido)ethyl)benzofuran-7-carboxylate

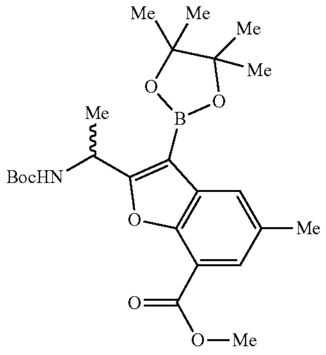 [SMILES: COC(=O)c1cc(C)cc2c(B3OC(C)(C)C(C)(C)O3)c(C(C)NC(=O)OC(C)(C)C)oc12]

A) Methyl 2-(1-((tert-butoxycarbonyl)amino)ethyl)-5-methyl-3-(4,4,5,5-tetramethyl-1,3,2-dioxaborolan-2-yl)benzofuran-7-carboxylate A vial was charged with methyl 2-(1-((tert-butoxycarbonyl)amino)ethyl)-5-methylbenzofuran-7-carboxylate (2 g, 6.00 mmol, Step A of Example 96), 4,4'-di-tert-butyl-2,2'-bipyridine (0.161 g, 0.6 mmol), bis(pinacolato)diboron (1.74 g, 6.84 mmol) and (1,5-cyclooctadiene)(methoxy)iridium (I) dimer (0.24 g, 0.360 mmol) in hexanes (45 ml). The reaction mixture was purged with nitrogen and heated to 80° C. for 16 hours. The reaction mixture was filtered and concentrated in vacuo. The crude product mixture was purified by a silica gel ISCO 80 g column eluting with 0-20% ethyl acetate in hexanes over a 15 minute gradient. The appropriate fractions were isolated and concentrated in vacuo to afford the product (1.21 g, 44% yield) as a solid. $^1$H NMR (400 MHz, Chloroform-d) δ 7.97-7.79 (m, 1H), 7.79-7.66 (m, 1H), 6.46-6.08 (m, 1H), 5.61-5.21 (m, 1H), 3.86 (s, 3H), 2.50 (s, 3H), 1.55 (d, J=6.9 Hz, 3H), 1.50-1.32 (m, 21H); MS (ESI+) m/z=404.1 (M−55+H)$^+$.

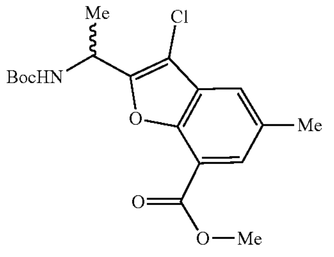 [SMILES: COC(=O)c1cc(C)cc2c(Cl)c(C(C)NC(=O)OC(C)(C)C)oc12]

B) Methyl 2-(1-((tert-butoxycarbonyl)amino)ethyl)-3-chloro-5-methylbenzofuran-7-carboxylate A vial was charged with methyl 2-(1-((tert-butoxycarbonyl)amino)ethyl)-5-methyl-3-(4,4,5,5-tetramethyl-1,3,2-dioxaborolan-2-yl)benzofuran-7-carboxylate (1.2 g, 2.61 mmol), copper(II) chloride (0.70 g, 5.22 mmol) and MeOH (10 mL). The reaction mixture was heated to 50° C. for 3 hours. The solution was filtered through celite and concentrated in vacuo. The crude product mixture was purified by a silica gel ISCO 40 g column eluting with 0-30% ethyl acetate in hexanes over a 15 minute gradient. The appropriate fractions were isolated and concentrated in vacuo to afford the title compound (0.697, 72% yield) as a solid. $^1$H NMR (400 MHz, Chloroform-d) δ 7.84-7.80 (m, 1H), 7.57-7.51 (m, 1H), 4.15 (q, J=7.1 Hz, 1H), 4.02-4.01 (m, 3H), 2.54-2.51 (m, 3H), 1.62-1.58 (m, 3H), 1.49-1.45 (m, 9H); MS (ESI+) m/z=312.0 (M−55+H)$^+$.

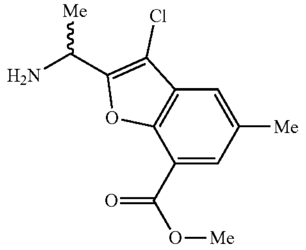 [SMILES: COC(=O)c1cc(C)cc2c(Cl)c(C(C)N)oc12]

C) Methyl 2-(aminomethyl)-3-chlorobenzofuran-7-carboxylate, TFA

A vial was charged methyl 2-(1-((tert-butoxycarbonyl)amino)ethyl)-3-chloro-5-methylbenzofuran-7-carboxylate (0.7 g, 1.9 mmol), DCM (20 mL) and TFA (2 mL). The reaction solution was stirred at room temperature for 2 hours. The reaction mixture was concentrated in vacuo to afford crude methyl 2-(aminomethyl)-3-chlorobenzofuran-7-carboxylate, TFA (0.72 g, 100% yield). $^1$H NMR (400 MHz, DMSO-d$_6$) δ 7.94-7.59 (m, 2H), 4.83 (q, J=6.9 Hz, 1H), 4.10-3.72 (m, 3H), 2.54-2.51 (m, 3H), 1.85-1.52 (m, 3H); MS (ESI+) m/z=251.0 (M−16)$^+$.

D) Methyl-3-chloro-5-methyl-2-(1-(pyrazolo[1,5-a]pyrimidine-3-carboxamido)ethyl)benzofuran-7-carboxylate The above product was added to a mixture of pyrazolo[1,5-a]pyrimidine-3-carboxylic acid (338 mg, 2.075 mmol), BOP (1.25 g, 2.83 mmol) and DIPEA (1.32 mL, 7.54 mmol) in DMF (10 mL). The reaction mixture was stirred at room temperature for 16 hours. The solution was diluted with water, and a precipitate formed which was isolated via filtration. This crude product was purified by a silica gel ISCO 24 g column eluting with 0-10% methanol in DCM over a 15 minute gradient. The appropriate fractions were isolated and concentrated in vacuo to afford the title compound (0.643 g, 83% yield) as a solid. The racemic product mixture was separated using chiral SFC (Method L) to give the first eluting enantiomer as the title compound (245 mg, 32%)$^1$H NMR (400 MHz, Methanol-d$_4$) δ 9.09 (dd, J=7.0, 1.7 Hz, 1H), 8.84 (dd, J=4.2, 1.7 Hz, 1H), 8.58 (s, 1H), 7.81 (d, J=1.8 Hz, 1H), 7.60 (dd, J=1.8, 0.8 Hz, 1H), 7.23 (dd, J=7.1, 4.2 Hz, 1H), 5.72 (d, J=7.1 Hz, 1H), 3.97 (s, 3H), 2.50 (s, 3H), 1.76 (d, J=7.0 Hz, 3H); MS (ESI+) m/z=413.2 (M+H)+; Chiral purity >99.8% ee.

Example 121

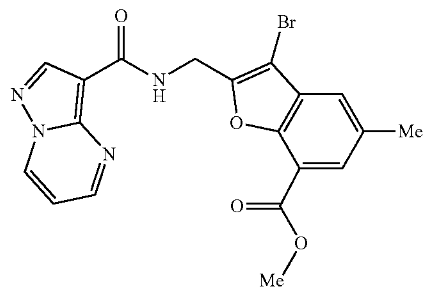 [SMILES: COC(=O)c1cc(C)cc2c(Br)c(CNC(=O)c3cnn4cccnc34)oc12]

Methyl 3-bromo-5-methyl-2-((pyrazolo[1,5-a]pyrimidine-3-carboxamido)methyl)benzofuran-7-carboxylate

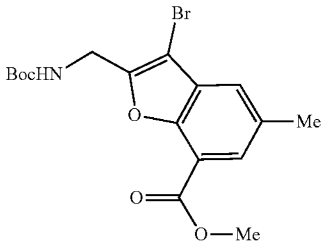 [SMILES: COC(=O)c1cc(C)cc2c(Br)c(CNC(=O)OC(C)(C)C)oc12]

A) Methyl-3-bromo-2-(((tert-butoxycarbonyl)amino)methyl)-5-methylbenzofuran-7-carboxylate A vial was charged methyl 2-(((tert-butoxycarbonyl)amino)methyl)-5-methyl-3-(4,4,5,5-tetramethyl-1,3,2-dioxaborolan-2-yl)benzofuran-7-carboxylate (400 mg, 0.9 mmol, Step A of Example 117), copper(II) bromide (410 mg, 1.796 mmol) and MeOH (5 mL). The reaction mixture was heated to 50° C. for 16 hours. The solution was filtered through celite and concentrated in vacuo. The crude product mixture was purified by a silica gel ISCO 24 g column eluting with 0-20% ethyl acetate in hexanes over a 15 minute gradient. The appropriate fractions were isolated and concentrated in vacuo to afford the title compound (177 mg, 50% yield) as a solid. $^1$H NMR (400 MHz, Chloroform-d) δ 7.75 (d, J=1.3 Hz, 1H), 7.55-7.51 (m, 1H), 6.61 (s, 1H), 4.52 (br d, J=5.8 Hz, 2H), 4.01 (s, 3H), 2.48 (s, 3H), 1.49 (s, 9H); MS (ESI+) m/z=341.9 $(M-55)^+$.

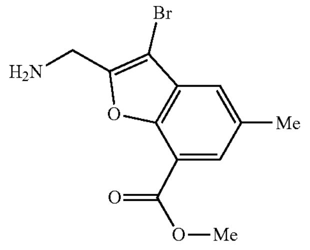 [SMILES: COC(=O)c1cc(C)cc2c(Br)c(CN)oc12]

B) Methyl 2-(aminomethyl)-3-bromo-5-methylbenzofuran-7-carboxylate

A vial was charged methyl 2-(((tert-butoxycarbonyl)amino)methyl)-3-bromobenzofuran-7-carboxylate (177 mg, 0.44 mmmol), DCM (10 mL) and TFA (1 mL). The reaction solution was stirred at room temperature for 2 hours. The reaction mixture was concentrated in vacuo to afford methyl 2-(aminomethyl)-3-bromo-5-methylbenzofuran-7-carboxylate (183 mg, 49% yield) as a solid. $^1$H NMR (400 MHz, Methanol-$d_4$) δ 7.87-7.72 (m, 1H), 7.53-7.44 (m, 1H), 4.58-4.42 (m, 2H), 4.04-3.84 (m, 3H), 2.63-2.35 (m, 3H); MS (ESI+) m/z=281.0 $(M-16)^+$.

C) Methyl 3-bromo-5-methyl-2-((pyrazolo[1,5-a]pyrimidine-3-carboxamido)methyl)benzofuran-7-carboxylate A flask was charged with a suspension of pyrazolo[1,5-a]pyrimidine-3-carboxylic acid (91 mg, 0.555 mmol) BOP (245 mg, 0.555 mmol), methyl 2-(aminomethyl)-3-bromo-5-methylbenzofuran-7-carboxylate, TFA salt (183 mg, 0.444 mmol) and DIPEA (0.310 mL, 1.776 mmol) in DMF (5 mL). The reaction mixture was stirred at room temperature for 16 hours. The solution was quenched with water and a precipitate formed which was collected by vacuum filtration. The crude material was purified via preparative HPLC (Method B) to yield the title compound (156 mg, 35% yield). $^1$H NMR (500 MHz, DMSO-d6) δ 9.28 (br d, J=6.7 Hz, 1H), 8.84 (br d, J=4.0 Hz, 1H), 8.62 (s, 1H), 8.58-8.49 (m, 1H), 7.74 (s, 1H), 7.57 (s, 1H), 7.28 (dd, J=6.9, 4.1 Hz, 1H), 4.84 (br d, J=5.8 Hz, 2H), 3.85 (s, 3H), 2.48-2.45 (m, 3H); MS (ESI+) m/z=443.1 $(M+H)^+$.

Example 122

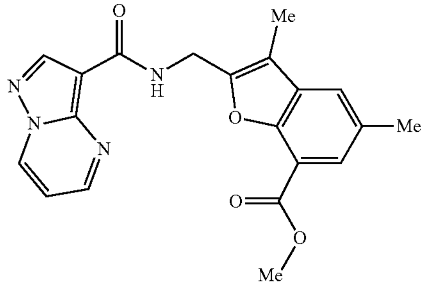 [SMILES: COC(=O)c1cc(C)cc2c(C)c(CNC(=O)c3cnn4cccnc34)oc12]

Methyl 3,5-dimethyl-2-((pyrazolo[1,5-a]pyrimidine-3-carboxamido)methyl)benzofuran-7-carboxylate A vial was charged with methyl 3-bromo-5-methyl-2-((pyrazolo[1,5-a]pyrimidine-3-carboxamido)methyl)benzofuran-7-carboxylate (50 mg, 0.113 mmol, Example 121), methylboronic acid (13.50 mg, 0.226 mmol), $Pd(OAc)_2$ (2.53 mg, 0.011 mmol), tricyclohexylphosphine (3.16 mg, 0.011 mmol) and a potassium phosphate tribasic aqueous solution (0.112 mL, 0.338 mmol, 3M) in toluene (2 mL). The solution was degassed and heated to 100° C. for 16 hours. The reaction mixture was filtered and concentrated in vacuo. The crude material was purified via preparative HPLC (Method B) to yield the title compound (2.2 mg, 5% yield). $^1$H NMR (500 MHz, DMSO-$d_6$) δ 9.25 (d, J=7.0 Hz, 1H), 8.81 (br d, J=3.1 Hz, 1H), 8.60 (s, 1H), 8.46 (br s, 1H), 7.63 (s, 2H), 7.26 (dd, J=7.0, 4.3 Hz, 1H), 4.75 (br d, J=5.8 Hz, 2H), 3.85 (s, 3H), 2.43 (s, 3H), 2.26 (s, 3H); MS (ESI+) m/z=379.2 $(M+H)^+$.

Example 123

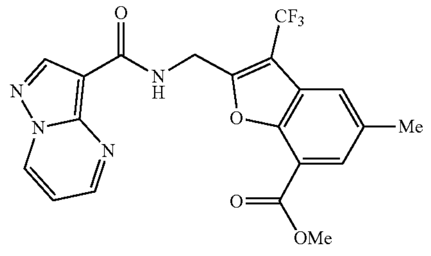 [SMILES: COC(=O)c1cc(C)cc2c(C(F)(F)F)c(CNC(=O)c3cnn4cccnc34)oc12]

Methyl 5-methyl-2-((pyrazolo[1,5-a]pyrimidine-3-carboxamido)methyl)-3-(trifluoromethyl)benzofuran-7-carboxylate

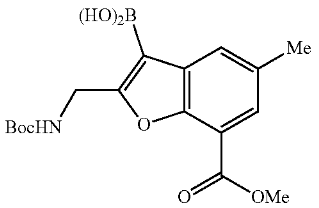 [SMILES: COC(=O)c1cc(C)cc2c(B(O)O)c(CNC(=O)OC(C)(C)C)oc12]

A) (2-(((tert-Butoxycarbonyl)amino)methyl)-7-(methoxycarbonyl)-5-methylbenzofuran-3-yl)boronic acid To a suspension of methyl 2-(((tert-butoxycarbonyl)amino)methyl)-5-methyl-3-(4,4,5,5-tetramethyl-1,3,2-dioxaborolan-2-yl)benzofuran-7-carboxylate (220.1 mg, 0.494 mmol, Step A of Example 117) in acetone (2.5 mL) and water (2.5 mL) was added ammonium acetate (190 mg, 2.471 mmol), followed by sodium periodate (529 mg, 2.471 mmol). The reaction mixture was stirred for 15 h and then concentrated in vacuo. The slurry was sonicated with water and filtered. The filter cake was rinsed with water, collected, and dried on high vacuum to give the title compound (174.4 mg, 97%). 1H NMR (400 MHz, Chloroform-d) δ 7.95 (s, 1H), 7.76 (d, J=1.3 Hz, 1H), 7.00 (br s, 2H), 5.56 (br t, J=6.6 Hz, 1H), 4.47 (d, J=6.6 Hz, 2H), 3.99 (s, 3H), 2.48 (s, 3H), 1.42 (s, 9H); MS (ESI+) m/z=386.1 $(M+Na)^+$.

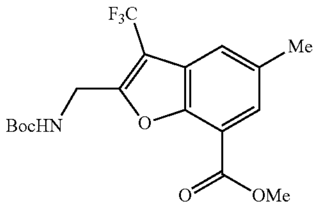 [SMILES: COC(=O)c1cc(C)cc2c(C(F)(F)F)c(CNC(=O)OC(C)(C)C)oc12]

B) Methyl 2-(((tert-butoxycarbonyl)amino)methyl)-5-methyl-3-(trifluoromethyl)benzofuran-7-carboxylate A solution of (2-(((tert-butoxycarbonyl)amino)methyl)-7-(methoxycarbonyl)-5-methylbenzofuran-3-yl)boronic acid (100 mg, 0.275 mmol), 3,3-dimethyl-1-(trifluoromethyl)-1,3-dihydro-113-benzo[d][1,2]iodaoxole (109 mg, 0.330 mmol), 1,10-phenanthroline (4.96 mg, 0.028 mmol), and potassium carbonate (76 mg, 0.551 mmol) in diglyme (2754 μL) was sparged with N2 for 5 min. Copper(I) iodide (2.62 mg, 0.014 mmol) was added and the reaction mixture was sparged with N2 for an additional 5 min, sealed, and heated to 35° C. The reaction mixture was cooled to room temperature and diluted with water and extracted with EtOAc. The organic layers were combined, washed with a 10% aqueous solution of LiCl, washed with brine, dried over $MgSO_4$, filtered, and concentrated in vacuo. The residue was dissolved in MeCN and purified by flash chromatography (Gold C18 ISCO 50 g column, 5-95% MeCN in water with TFA) to give the title compound (65.2 mg, 61%). $^{1}$H NMR (400 MHz, Chloroform-d) δ 7.81 (s, 1H), 7.61 (s, 1H), 5.18 (br s, 1H), 4.66 (br s, 2H), 3.99 (s, 3H), 2.48 (s, 3H), 1.46 (s, 9H); MS (ESI+) m/z=332.1 $(M-tBu+H)^+$.

C) Methyl 5-methyl-2-((pyrazolo[1,5-a]pyrimidine-3-carboxamido)methyl)-3-(trifluoromethyl)benzofuran-7-carboxylate To a solution of methyl 2-(((tert-butoxycarbonyl)amino)methyl)-5-methyl-3-(trifluoromethyl)benzofuran-7-carboxylate (65.2 mg, 0.168 mmol) in DCM (1.3 mL) was added TFA (0.42 mL). The reaction mixture was stirred for 20 min and then concentrated in vacuo to obtain a residue that was used without further purification.

To this residue was added pyrazolo[1,5-a]pyrimidine-3-carboxylic acid (30.1 mg, 0.185 mmol) and ((1H-benzo[d][1,2,3]triazol-1-yl)oxy)tris(dimethylamino) phosphonium hexafluorophosphate(V) (82 mg, 0.185 mmol). DMF (1.7 mL) and DIPEA (88 μL, 0.504 mmol) were added and the reaction mixture was stirred at room temperature for 15 hours. An additional portion of pyrazolo[1,5-a]pyrimidine-3-carboxylic acid (6 mg, 0.037 mmol), ((1H-benzo[d][1,2,3]triazol-1-yl)oxy)tris(dimethylamino)phosphonium hexafluorophosphate(V) (16 mg, 0.054 mmol), and DIPEA (18 μL, 0.188 mmol) were added and the reaction mixture was stirred for 20 min. The reaction mixture was diluted with water and extracted with EtOAc. The organic layers were combined, washed with a 10% aqueous solution of LiCl, washed with brine, dried over $MgSO_4$, filtered, and concentrated in vacuo. A fourth of the obtained residue was dissolved in 2 mL MeOH, filtered through a syringe filter, and purified by preparative LC/MS (Method B). Fractions containing the desired product were combined and dried via centrifugal evaporation to give the title compound (11.4 mg, 16%). The remaining obtained residue contained additional semipure title compound (71.0 mg) that was used without further purification. $^{1}$H NMR (500 MHz, DMSO-$d_6$) δ 9.32 (br d, J=7.0 Hz, 1H), 8.85 (br d, J=2.4 Hz, 1H), 8.64-8.55 (m, 2H), 7.77 (s, 1H), 7.72 (s, 1H), 7.33-7.25 (m, 1H), 4.96 (br d, J=5.2 Hz, 2H), 3.76 (s, 3H), 2.47 (s, 3H); MS (ESI+) m/z=433.1 $(M+H)^+$.

Example 124

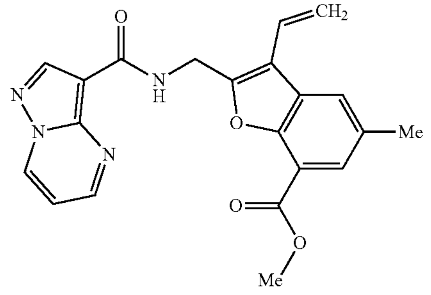 [SMILES: C=Cc1c(CNC(=O)c2cnn3cccnc23)oc2c(C(=O)OC)cc(C)cc12]

Methyl 5-methyl-2-((pyrazolo[1,5-a]pyrimidine-3-carboxamido)methyl)-3-vinylbenzofuran-7-carboxylate

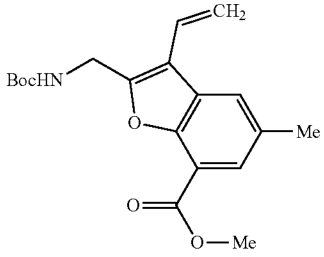 [SMILES: C=Cc1c(CNC(=O)OC(C)(C)C)oc2c(C(=O)OC)cc(C)cc12]

A) Methyl 2-(((tert-butoxycarbonyl)amino)methyl)-5-methyl-3-vinylbenzofuran-7-carboxylate A vial was charged with methyl 2-(((tert-butoxycarbonyl)amino)methyl)-5-methyl-3-(4,4,5,5-tetramethyl-1,3,2-dioxaborolan-2-yl)benzofuran-7-carboxylate (300 mg, 0.674 mmol, Step A of Example 117), bromoethene (1.347 mL, 1.347 mmol), 1,1'-bis(di-tert-butylphospino)ferrocene palladium dichloride (43.9 mg, 0.067 mmol) and a potassium phosphate tribasic aqueous solution (0.674 mL, 2.021 mmol, 3M) in toluene (5 mL). The solution was degassed and heated to 50° C. for 1 hour. The reaction solution was diluted with ethyl acetate, washed with saturated sodium bicarbonate, water, and saturated sodium chloride, dried with anhydrous sodium sulfate, filtered, and concentrated in vacuo. The crude product mixture was purified by a silica gel ISCO 40 g column eluting with 0-20% ethyl acetate/hexane over a 15 minute gradient. The appropriate fractions were isolated and concentrated in vacuo to afford the title compound (85 mg, 36.5% yield) as a solid. $^1$H NMR (400 MHz, Chloroform-d) δ 7.85-7.68 (m, 2H), 7.05-6.72 (m, 1H), 5.98-5.68 (m, 1H), 5.56-5.39 (m, 1H), 5.26-5.01 (m, 1H), 4.75-4.40 (m, 2H), 4.06-3.82 (m, 3H), 2.66-2.39 (m, 3H), 1.56-1.36 (m, 9H); MS (ESI+) m/z=290.1 (M−55)$^+$.

B) Methyl 5-methyl-2-((pyrazolo[1,5-a]pyrimidine-3-carboxamido)methyl)-3-vinylbenzofuran-7-carboxylate A vial was charged methyl 2-(((tert-butoxycarbonyl)amino)methyl)-5-methyl-3-vinylbenzofuran-7-carboxylate (85 mg, 0.25 mmol), DCM (5 mL) and TFA (0.5 mL). The reaction solution was stirred at room temperature for 2 hours. The reaction mixture was concentrated in vacuo to afford methyl-2-(aminomethyl)-5-methyl-3-vinylbenzofuran-7-carboxylate, TFA (88 mg, 0.25 mmol, 100% yield) as a solid. To a solution of methyl 2-(aminomethyl)-5-methyl-3-vinylbenzofuran-7-carboxylate, TFA (88 mg, 0.25 mmol) in DMF (5 mL) was added pyrazolo[1,5-a]pyrimidine-3-carboxylic acid (30.3 mg, 0.186 mmol), BOP (123 mg, 0.279 mmol) and DIPEA (0.097 mL, 0.558 mmol). The reaction mixture was stirred at RT for 16 hours. The solution was quenched with water and the precipitated product was collected by vacuum filtration. The crude material was purified via preparative HPLC (Method B) to yield the title compound (11.6 mg, 16% yield). $^1$H NMR (500 MHz, DMSO-d$_6$) δ 9.32-9.22 (m, 1H), 8.87-8.78 (m, 1H), 8.64-8.57 (m, 1H), 8.52-8.44 (m, 1H), 8.00-7.96 (m, 1H), 7.68 (s, 1H), 7.30-7.25 (m, 1H), 7.10-7.02 (m, 1H), 5.94 (d, J=17.7 Hz, 1H), 5.47 (d, J=11.9 Hz, 1H), 4.86 (br d, J=5.5 Hz, 2H), 3.88-3.82 (m, 3H), 2.48-2.43 (m, 3H); MS (ESI+) m/z=391.2 (M+H)$^+$.

Example 125

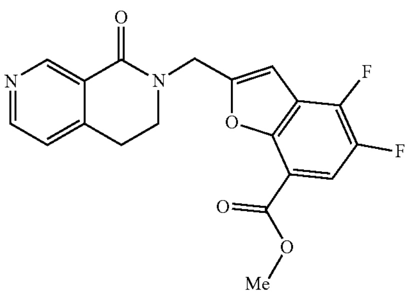 [SMILES: COC(=O)c1cc(F)c(F)c2cc(CN3CCc4ccncc4C3=O)oc12]

Methyl 4,5-difluoro-2-((1-oxo-3,4-dihydro-2,7-naphthyridin-2(1H)-yl)methyl)benzofuran-7-carboxylate 3,4-Dihydro-1H-pyrano[3,4-c]pyridin-1-one, HCl (22.99 mg, 0.124 mmol) and methyl 2-(aminomethyl)-4,5-difluorobenzofuran-7-carboxylate, TFA (40 mg, 0.113 mmol, Step E in Example 138) were taken up in Pyridine (1 mL). The reaction was sealed and heated at 125° C. for 18 hours. The reaction mixture was diluted with saturated $NaHCO_3$ solution, diluted with water, and extracted with ethyl acetate. The organic layers were separated, combined, and concentrated in vacuo. The residue was dissolved in MeOH, filtered, and purified via HPLC (method B) to give the title compound (2.3 mg, 5%). $^1$H NMR (500 MHz, DMSO-d$_6$) δ 8.95 (s, 1H), 8.61 (d, J=4.9 Hz, 1H), 7.81 (dd, J=11.3, 7.9 Hz, 1H), 7.38 (d, J=4.9 Hz, 1H), 7.18 (s, 1H), 4.93 (s, 2H), 3.86 (s, 3H), 3.76 (t, J=6.6 Hz, 2H), 3.10 (t, J=6.6 Hz, 2H); MS (ESI+) m/z=373.0 (M+H)$^+$.

Example 126

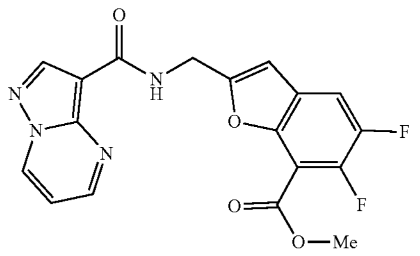 [SMILES: COC(=O)c1c(F)c(F)cc2cc(CNC(=O)c3cnn4cccnc34)oc12]

Methyl 5,6-difluoro-2-((pyrazolo[1,5-a]pyrimidine-3-carboxamido)methyl)benzofuran-7-carboxylate

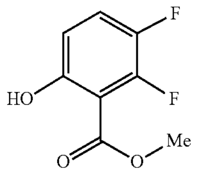 [SMILES: COC(=O)c1c(O)ccc(F)c1F]

A) Methyl 2,3-difluoro-6-hydroxybenzoate

To a solution of 2,3-difluoro-6-hydroxybenzoic acid (2 g, 11.49 mmol) in thionyl chloride (2.52 mL, 34.5 mmol) was added a few drops of DMF. The reaction mixture was stirred at rt over night. The reaction was then concentrated in vacuo and azeotroped three times with toluene to remove excess thionyl chloride. To the residue were added DCM (10 mL), MeOH (10 mL) and TEA (6.40 mL, 45.9 mmol). The reaction mixture was stirred at rt for 5 h. The solvents were removed under reduced pressure and the residue was diluted with ethyl acetate and brine. The organic layer was separated, washed with brine, dried over $MgSO_4$ and filtered. The filtrate was concentrated in vacuo. to give methyl 2,3-difluoro-6-hydroxybenzoate (1.85 g, 86% yield) as a light brown solid. $^1$H NMR (400 MHz, CHLOROFORM-d)

δ 10.78 (d, J=1.2 Hz, 1H), 7.66 (dd, J=10.4, 9.0 Hz, 1H), 6.80 (dd, J=11.4, 6.7 Hz, 1H), 3.98 (s, 3H).

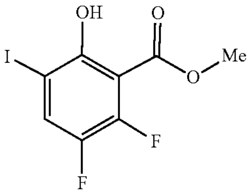 [SMILES: COC(=O)c1c(O)c(I)cc(F)c1F]

B) Methyl 2,3-difluoro-6-hydroxy-5-iodobenzoate

To a solution of methyl 2,3-difluoro-6-hydroxybenzoate (1.8 g, 9.57 mmol) in DMF (20 mL) were added sodium iodide (1.793 g, 11.96 mmol) and chloramine T trihydrate (3.23 g, 11.48 mmol) slowly. The reaction mixture was stirred at rt over night. The reaction mixture was diluted with ethyl acetate and 1 N aqueous HCl solution. The organic layer was separated and washed with brine, $Na_2S_2O_3$ solution, dried over $MgSO_4$, and filtered. The filtrate was concentrated in vacuo to give a light yellow oil. The crude residue was dissolved in DCM and purified by silica gel column chromatography (40 g column, 0-20% ethyl acetate in hexanes) to give methyl 2,3-difluoro-6-hydroxy-5-iodobenzoate (1.5 g, 50%) as a white solid. $^1$H NMR (400 MHz, Chloroform-d) δ 11.70 (d, J=2.0 Hz, 1H), 10.78 (d, J=1.4 Hz, 1H), 7.74 (dd, J=10.0, 8.8 Hz, 1H), 7.66 (dd, J=10.4, 9.0 Hz, 1H), 6.80 (dd, J=11.4, 6.6 Hz, 1H), 4.01 (s, 3H), 3.98 (s, 3H).

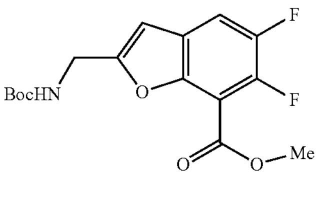 [SMILES: COC(=O)c1c(F)c(F)cc2cc(CNC(=O)OC(C)(C)C)oc12]

C) Methyl 2-(((tert-butoxycarbonyl)amino)methyl)-5,6-difluorobenzofuran-7-carboxylate To the reaction mixture of methyl 2,3-difluoro-6-hydroxy-5-iodobenzoate (1.5 g, 4.78 mmol), tert-butyl prop-2-yn-1-ylcarbamate (0.815 g, 5.25 mmol) in DMF (12 mL) were added TEA (5.33 mL, 38.2 mmol) and copper(I) iodide (0.091 g, 0.478 mmol). The reaction mixture was purged with nitrogen stream for 5 min, then bis(triphenylphosphine) palladium(II) chloride (0.335 g, 0.478 mmol) was added. The resulting mixture was heated at 80° C. under nitrogen stream for 2 h. The reaction mixture was cooled down, diluted with ethyl acetate and 1N aqueous HCl solution. The organic layer was separated, washed with brine, $Na_2S_2O_3$ solution, dried over $MgSO_4$, and filtered. The filtrate was concentrated in vacuo. The crude residue was dissolved in DCM and purified by silica gel column chromatography (40 g column, 0-20% ethyl acetate in hexanes) to give methyl 2-(((tert-butoxycarbonyl)amino) methyl)-5,6-difluorobenzofuran-7-carboxylate (0.8 g, 49.1%) as a light yellow solid. 1H NMR (400 MHz, CHLOROFORM-d) 67.79 (dd, J=11.1, 7.7 Hz, 1H), 6.81 (s, 1H), 5.23-5.00 (m, 1H), 4.53 (br d, J=5.8 Hz, 2H), 4.01 (s, 3H), 1.49 (s, 9H).

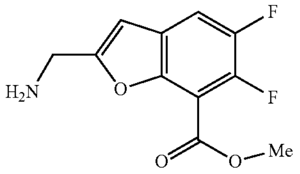 [SMILES: COC(=O)c1c(F)c(F)cc2cc(CN)oc12]

D) Methyl 2-(aminomethyl)-5,6-difluorobenzofuran-7-carboxylate

To a solution of methyl 2-(((tert-butoxycarbonyl)amino) methyl)-5,6-difluorobenzofuran-7-carboxylate (0.42 g, 1.231 mmol) in DCM (5 mL) was added TFA (0.948 mL, 12.31 mmol). The reaction mixture was stirred at rt for 2 h. The reaction was then concentrated in vacuo and azeotroped three times with toluene to remove excess TFA. The crude product was placed under high vacuum overnight to give methyl 2-(aminomethyl)-5,6-difluorobenzofuran-7-carboxylate TFA salt (0.43 g, 98% yield) as a brown solid. $^1$H NMR (400 MHz, Methanol-d$_4$) δ 7.95 (dd, J=11.3, 7.8 Hz, 1H), 7.24 (t, J=0.7 Hz, 1H), 4.45 (s, 2H), 4.02 (s, 3H); MS (ESI+) m/z=242.1 (M+H)$^+$.

E) Methyl 5,6-difluoro-2-((pyrazolo[1,5-a]pyrimidine-3-carboxamido)methyl)benzofuran-7-carboxylate To a suspension of pyrazolo[1,5-a]pyrimidine-3-carboxylic acid (185 mg, 1.135 mmol) in DMF (10 mL) was added BOP (540 mg, 1.222 mmol). The reaction mixture was stirred at rt for 20 min, then a solution of methyl 2-(aminomethyl)-5,6-difluorobenzofuran-7-carboxylate TFA salt (310 mg, 0.873 mmol) in THE (3 mL) and DIPEA (0.610 mL, 3.49 mmol) were added. The resulting mixture was stirred at rt for 1 h. The reaction mixture turned into clear solution after addition of DIPEA and solid crashed out after 10 min. After 1 h, the reaction mixture was diluted with water and filtered to give light brown solid as the pure product methyl 5,6-difluoro-2-((pyrazolo[1,5-a]pyrimidine-3-carboxamido)methyl)benzofuran-7-carboxylate (300 mg, 85% yield). The solid was not soluble in DMF. $^1$H NMR (400 MHz, DMSO-d$_6$) δ 9.35 (br d, J=6.6 Hz, 1H), 8.85 (br d, J=2.6 Hz, 1H), 8.64 (s, 1H), 8.56 (br t, J=5.5 Hz, 1H), 7.84 (br dd, J=11.4, 7.9 Hz, 1H), 7.31 (br dd, J=6.3, 4.5 Hz, 1H), 7.05 (s, 1H), 4.83 (br d, J=5.6 Hz, 2H), 3.91 (s, 3H); MS (ESI+) m/z=387.2 (M+H)$^+$.

Example 127

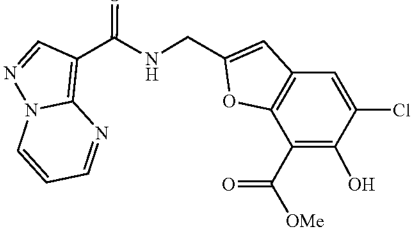

Methyl 5-chloro-6-hydroxy-2-((pyrazolo[1,5-a]pyrimidine-3-carboxamido)methyl)benzofuran-7-carboxylate

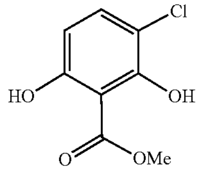

A) Methyl 3-chloro-2,6-dihydroxybenzoate

To a flask charged with methyl 2,6-dihydroxybenzoate (1.5 g, 8.92 mmol) was added sulfuryl chloride, 1 M in DCM (13.38 mL, 13.38 mmol) under N2. The mixture was cooled to 0° C. and $Et_2O$ (1.391 mL, 13.38 mmol) was added. The reaction mixture was warmed to room temperature and stirred for 70 min. Additional portions of sulfuryl chloride, 1 M in DCM (4.5 mL, 4.5 mmol) and $Et_2O$ (0.47 mL, 4.5 mmol) were added and the reaction mixture was stirred for 30 min. Additional portions of sulfuryl chloride, 1 M in DCM (2.3 mL, 2.3 mmol) and $Et_2O$ (0.24 mL, 2.3 mmol) were added and the reaction mixture was stirred for 15 min. The reaction mixture was concentrated in vacuo to give the title compound (1.7856 g, 99%). $^1$H NMR (400 MHz, CHLOROFORM-d) δ 10.31 (br s, 1H), 9.51 (br s, 1H), 7.44 (d, J=9.0 Hz, 1H), 6.51 (d, J=8.9 Hz, 1H), 4.14 (s, 3H).

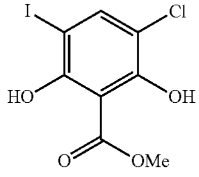

B) Methyl 3-chloro-2,6-dihydroxy-5-iodobenzoate

To a suspension of methyl 3-chloro-2,6-dihydroxybenzoate (1.7856 g, 8.81 mmol) in AcOH (5.04 mL) was added NIS (2.97 g, 13.22 mmol). The headspace was flushed with N2 and the vessel was sealed and heated to 65° C. for 30 min. The reaction mixture was cooled to rt, quenched with a saturated aqueous solutions of $NaHCO_3$ and $Na_2S_2O_3$, and extracted with EtOAc. The organic layers were combined, washed with brine, dried over $MgSO_4$, filtered, and concentrated in vacuo. The residue was dissolved in DCM and purified by flash chromatography (ISCO 80 g column, 0-40% EtOAc in hexanes) to give the title compound (1.6310 g, 56%). $^1$H NMR (400 MHz, CHLOROFORM-d) δ 10.47 (s, 1H), 10.20 (br s, 1H), 7.91 (s, 1H), 4.17 (s, 3H).

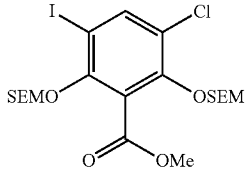

C) Methyl 3-chloro-5-iodo-2,6-bis((2-(trimethylsilyl)ethoxy)methoxy)benzoate

To a solution of methyl 3-chloro-2,6-dihydroxy-5-iodobenzoate (1.7366 g, 5.29 mmol) in DCM (26.4 mL) was added Hunig's Base (5.54 mL, 31.7 mmol) at 0° C. SEMCl (2.344 mL, 13.22 mmol) was added and the reaction vessel was flushed with N2, sealed, and warmed to room temperature and stirred for 5 h. An additional portion of SEMCl (0.47 mL, 2.65 mmoL) was added and the reaction mixture was stirred for 1.5 h. The reaction mixture was quenched with water and extracted with EtOAc. The organic layers were combined, washed with brine, dried over $MgSO_4$, filtered, and concentrated in vacuo. The residue was dissolved in DCM and purified by flash chromatography (ISCO 80 g column, 0-10% EtOAc in hexanes) to give the title compound (3.0224 g, 97%). $^1$H NMR (400 MHz, CHLOROFORM-d) δ 7.88 (s, 1H), 5.19 (s, 2H), 5.15 (s, 2H), 3.93 (s, 3H), 3.91-3.81 (m, 4H), 1.05-0.99 (m, 4H), 0.06 (s, 9H), 0.05 (s, 9H).

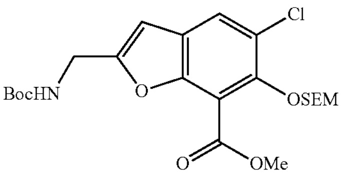

D) Methyl 2-(((tert-butoxycarbonyl)amino)methyl)-5-chloro-6-((2-(trimethylsilyl)ethoxy)methoxy)benzofuran-7-carboxylate To a solution of tert-butyl prop-2-yn-1-ylcarbamate (916 mg, 5.90 mmol) and methyl 3-chloro-5-iodo-2,6-bis((2-(trimethylsilyl)ethoxy)methoxy)benzoate (3.0224 g, 5.13 mmol) in DMF (477 μl) was added $Et_3N$ (638 μl, 4.57 mmol). The mixture was sparged with N2 for 13 min and then copper(I) iodide (98 mg, 0.513 mmol) and bis(triphenylphosphine)palladium(II) chloride (180 mg, 0.257 mmol) was added. The reaction mixture was sparged with N2 for an additional 3 min, sealed, and heated to 80° C. for 2.5 h. The reaction mixture was cooled to room temperature and concentrated in vacuo. The residue was dissolved in DCM and purified by flash chromatography (ISCO 120 g column, 0-30% EtOAc in hexanes) to give the title compound (1.3544 g, 54%). $^1$H NMR (400 MHz, Chloroform-d) δ 7.66 (s, 1H), 6.57 (s, 1H), 5.22 (s, 2H), 5.00 (br d, J=2.9 Hz, 1H), 4.45 (br d, J=5.9 Hz, 2H), 4.03 (s, 3H), 3.94-3.87 (m, 2H), 1.48 (s, 9H), 1.02 (d, J=17.2 Hz, 2H), 0.06 (s, 9H); MS (ESI+) m/z=524.0 $(M+K)^+$.

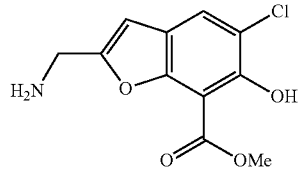 [SMILES: COC(=O)c1c(O)c(Cl)cc2cc(CN)oc12]

E) Methyl 2-(aminomethyl)-5-chloro-6-hydroxybenzofuran-7-carboxylate

To a solution of methyl 2-(((tert-butoxycarbonyl)amino)methyl)-5-chloro-6-((2-(trimethylsilyl)ethoxy)methoxy)

benzofuran-7-carboxylate (184 mg, 0.379 mmol) in DCM (2839 μL) was added TFA (946 μL). The reaction mixture was stirred for 2 h and then concentrated in vacuo and placed on high vacuum. The residue was dissolved in MeCN and purified by flash chromatography (Gold C18 ISCO 50 g column, 5-95% MeCN in water with TFA) to give the title compound (39.5 mg, 28%) as the TFA salt. $^1$H NMR (400 MHz, Methanol-$d_4$) δ 7.85 (s, 1H), 6.78 (s, 1H), 4.11 (d, J=0.7 Hz, 2H), 4.09 (s, 3H); MS (ESI+) m/z=238.9 $(M-NH_2)^+$.

F) Methyl 5-chloro-6-hydroxy-2-((pyrazolo[1,5-a]pyrimidine-3-carboxamido)methyl)benzofuran-7-carboxylate To a flask charged with methyl 2-(aminomethyl)-5-chloro-6-hydroxybenzofuran-7-carboxylate, TFA (39.5 mg, 0.107 mmol), pyrazolo[1,5-a]pyrimidine-3-carboxylic acid (22.7 mg, 0.139 mmol) and ((1H-benzo[d][1,2,3]triazol-1-yl)oxy)tris(dimethylamino)phosphonium hexafluorophosphate(V) (61.4 mg, 0.139 mmol) was added DMF (1.1 mL) and DIPEA (67 μL, 0.385 mmol) and the reaction mixture was stirred at room temperature for 45 min. The reaction mixture was diluted with water and extracted with EtOAc. The organic layers were combined, washed with a 10% aqueous solution of LiCl, washed with brine, dried over $MgSO_4$, filtered, and concentrated in vacuo. A third of the obtained residue was dissolved in 2 mL MeOH, filtered through a syringe filter, and purified by preparative LC/MS (Method B). Fractions containing the desired product were combined and dried via centrifugal evaporation to give the title compound (2.0 mg, 5%). The remaining obtained residue contained additional semipure title compound (72.8 mg) that was used without further purification. $^1$H NMR (500 MHz, DMSO-$d_6$) δ 9.26 (br d, J=6.7 Hz, 1H), 8.80 (br s, 1H), 8.59 (s, 1H), 8.46 (br s, 1H), 7.91 (s, 1H), 7.25 (br dd, J=6.7, 4.3 Hz, 1H), 6.71 (s, 1H), 4.72 (br d, J=5.5 Hz, 2H), 3.94 (s, 3H); MS (ESI+) m/z=401.0 $(M+H)^+$.

Example 128

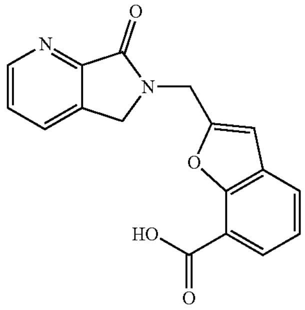 [SMILES: O=C(O)c1cccc2cc(CN3Cc4cccnc4C3=O)oc12]

2-((7-Oxo-5,7-dihydro-6H-pyrrolo[3,4-b]pyridin-6-yl)methyl)benzofuran-7-carboxylic acid Methyl 2-((3-oxo-1,3-dihydro-2H-pyrrolo[3,4-c]pyridin-2-yl)methyl)benzofuran-7-carboxylate (1.39 g, 4.31 mmol, Example 2) was taken up in THE (17.25 ml), methanol (8.62 ml), and water (17.25 ml). LiOH (1.03 g, 43.1 mmol) was added and reaction stirred was at room temperature for 1 hour. The solvent was removed under reduced pressure and water was added. The pH value of the mixture was adjusted to 4-5 with acetic acid and the aqueous layer turned cloudy. The aqueous layer was extracted with EtOAc. The combined organic extracts were dried with sodium sulfate, filtered, and concentrated in vacuo to give 2-((3-oxo-1,3-dihydro-2H-pyrrolo[3,4-c]pyridin-2-yl)methyl)benzofuran-7-carboxylic acid (590 mg, 1.91 mmol, 44.4% yield). $^1$H NMR (400 MHz, Methanol-$d_4$) δ 8.98 (s, 1H), 8.72 (d, J=5.3 Hz, 1H), 7.89 (dd, J=7.6, 1.2 Hz, 1H), 7.80 (dd, J=7.7, 1.2 Hz, 1H), 7.71-7.66 (m, 1H), 7.31 (t, J=7.7 Hz, 1H), 6.90 (s, 1H), 5.04 (s, 2H), 4.77 (s, 2H); MS (ESI+) m/z=309.3 $(M+H)^+$.

Examples 129-184

The following acids were synthesized from the corresponding methyl esters according to the hydrolysis procedure outlined in Example 128.

| Ex. No. | Structure | Name | $^1$H NMR | LC/MS $(M + H)^+$ |
|---|---|---|---|---|
| 130 | 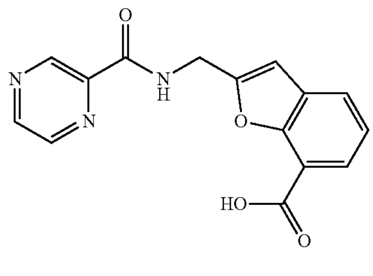 [SMILES: O=C(NCc1cc2cccc(C(=O)O)c2o1)c1cnccn1] | 2-((Pyrazine-2-carboxamido)methyl)benzofuran-7-carboxylic acid | $^1$H NMR (500 MHz, DMSO-$d_6$) δ 9.36 (s, 1H), 8.73 (d, J = 5.2 Hz, 1H), 7.88-7.77 (m, 3H), 7.62 (d, J = 5.2 Hz, 1H), 7.32 (t, J = 7.6 Hz, 1H), 6.88 (s, 1H), 6.73 (d, J = 7.3 Hz, 1H), 5.43 (s, 2H) | 298.1 |
| 131 | 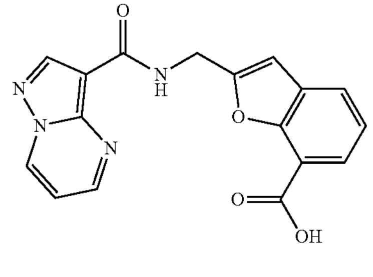 [SMILES: O=C(O)c1cccc2cc(CNC(=O)c3cnn4cccnc34)oc12] | 2-((pyrazolo[1,5-a]pyrimidine-3-carboxamido)methyl)benzofuran-7-carboxylic acid | $^1$H NMR (500 MHz, DMSO-$d_6$) δ 9.25 (br d, J = 6.7 Hz, 1H), 8.81 (br d, J = 3.1 Hz, 1H), 8.61 (s, 1H), 8.59-8.53 (m, 1H), 7.82 (br d, J = 7.3 Hz, 1H), 7.80-7.75 (m, 1H), 7.31 (br t, J = 7.6 Hz, 1H), 7.29-7.24 (m, 1H), 6.84 (s, 1H), 4.79 (br d, J = 5.5 Hz, 2H), 3.67 (br s, 2H) | 337.0 |

-continued

| Ex. No. | Structure | Name | $^1$H NMR | LC/MS (M + H)$^+$ |
|---|---|---|---|---|
| 132 | 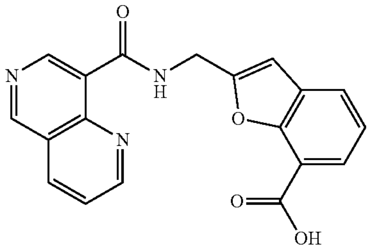 [SMILES: O=C(NCc1cc2cccc(C(=O)O)c2o1)c1cncc2cccnc12] | 2-((1,6-naphthyridine-8-carboxamido)methyl)benzofuran-7-carboxylic acid | $^1$H NMR (500 MHz, DMSO-$d_6$) δ 10.97 (br s, 1H), 9.60 (s, 1H), 9.36 (s, 1H), 9.34-9.26 (m, 1H), 8.79 (br d, J = 8.2 Hz, 1H), 7.98-7.82 (m, 2H), 7.80 (br d, J = 7.6 Hz, 1H), 7.33 (br t, J = 7.6 Hz, 1H), 6.95 (s, 1H), 4.91 (br d, J = 5.5 Hz, 2H) | 348.1 |
| 133 | 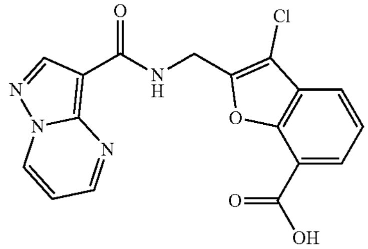 [SMILES: O=C(O)c1cccc2c(Cl)c(CNC(=O)c3cnn4cccnc34)oc12] | 3-Chloro-2-((pyrazolo[1,5-a]pyrimidine-3-carboxamido)methyl)benzofuran-7-carboxylic acid | $^1$H NMR (500 MHz, DMSO-$d_6$) δ 9.30-9.26 (m, 1H), 8.85-8.81 (m, 1H), 8.61 (s, 1H), 8.53 (br t, J = 5.6 Hz, 1H), 7.84 (d, J = 7.3 Hz, 1H), 7.71 (d, J = 7.6 Hz, 1H), 7.41 (t, J = 7.6 Hz, 1H), 7.27 (dd, J = 7.0, 4.3 Hz, 1H), 4.85 (d, J = 5.8 Hz, 2H) | 371.1 |
| 134 | 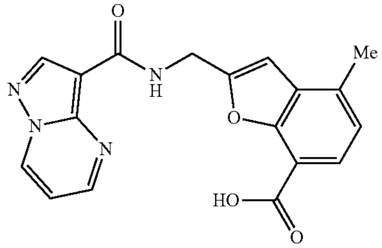 [SMILES: Cc1ccc(C(=O)O)c2oc(CNC(=O)c3cnn4cccnc34)cc12] | 4-Methyl-2-((pyrazolo[1,5-a]pyrimidine-3-carboxamido)methyl)benzofuran-7-carboxylic acid | $^1$H NMR (500 MHz, DMSO-$d_6$) δ 9.29-9.23 (m, 1H), 8.82 (d, J = 2.7 Hz, 1H), 8.62 (s, 1H), 8.57-8.51 (m, 1H), 7.70 (d, J = 7.6 Hz, 1H), 7.27 (dd, J = 6.9, 4.1 Hz, 1H), 7.13 (d, J = 7.9 Hz, 1H), 6.88 (s, 1H), 4.79 (br d, J = 5.8 Hz, 2H), 2.48 (s, 3H) | 351.0 |
| 135 | 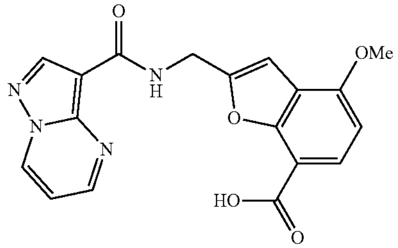 [SMILES: COc1ccc(C(=O)O)c2oc(CNC(=O)c3cnn4cccnc34)cc12] | 4-Methoxy-2-((pyrazolo[1,5-a]pyrimidine-3-carboxamido)methyl)benzofuran-7-carboxylic acid | $^1$H NMR (500 MHz, DMSO-$d_6$) δ 9.22 (br d, J = 7.0 Hz, 1H), 8.80 (br d, J = 3.4 Hz, 1H), 8.60 (s, 1H), 8.54 (br t, J = 5.6 Hz, 1H), 7.81 (d, J = 8.5 Hz, 1H), 7.25 (dd, J = 7.0, 4.3 Hz, 1H), 6.88 (d, J = 8.5 Hz, 1H), 6.77 (s, 1H), 4.75 (br d, J = 5.8 Hz, 2H), 3.92 (s, 3H) | 367.1 |
| 136 | 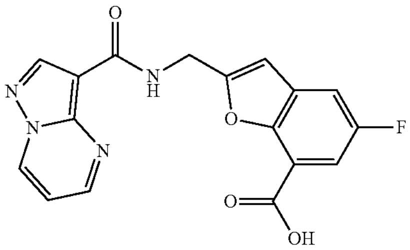 | 5-Fluoro-2-((pyrazolo[1,5-a]pyrimidine-3-carboxamido)methyl)benzofuran-7-carboxylic acid | $^1$H NMR (400 MHz, DMSO-d6) δ 9.34 (dd, J = 7.0, 1.6 Hz, 1H), 8.84 (dd, J = 4.2, 1.6 Hz, 1H), 8.64 (s, 1H), 8.53 (t, J = 5.9 Hz, 1H), 7.69 (dd, J = 8.4, 2.7 Hz, 1H), 7.52 (dd, J = 9.7, 2.7 Hz, 1H), 7.30 (dd, J = 7.0, 4.2 Hz, 1H), 6.85 (s, 1H), 4.80 (d, J = 5.8 Hz, 2H) | 355.2 |
| 137 | 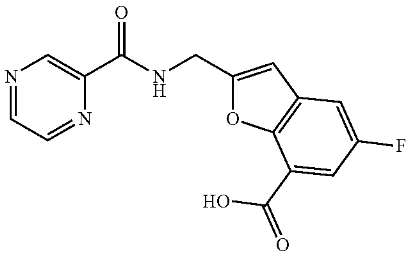 [SMILES: O=C(NCc1cc2cc(F)cc(C(=O)O)c2o1)c1cnccn1] | 5-fluoro-2-((pyrazine-2-carboxamido)methyl)benzofuran-7-carboxylic acid | $^1$H NMR (500 MHz, DMSO-$d_6$) δ 9.60 (br t, J = 5.8 Hz, 1H), 9.22 (s, 1H), 8.90 (br d, J = 2.1 Hz, 1H), 8.77 (s, 1H), 7.74-7.57 (m, 1H), 7.50 (br d, J = 9.8 Hz, 1H), 6.82 (s, 1H), 4.71 (br d, J = 5.8 Hz, 2H) | 316.2 |

-continued

| Ex. No. | Structure | Name | $^1$H NMR | LC/MS (M + H)$^+$ |
|---|---|---|---|---|
| 138 | 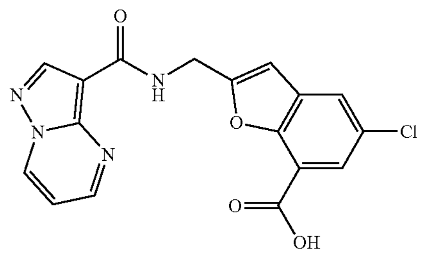 | 5-Chloro-2-((pyrazolo[1,5-a]pyrimidine-3-carboxamido)methyl)benzofuran-7-carboxylic acid | $^1$H NMR (500 MHz, DMSO-$d_6$) δ 9.32 (br d, J = 6.7 Hz, 1H), 8.84 (br d, J = 3.4 Hz, 1H), 8.64 (s, 1H), 8.53 (br t, J = 5.5 Hz, 1H), 7.76 (s, 1H), 7.62 (s, 1H), 7.38-7.20 (m, 1H), 6.78 (s, 1H), 4.79 (br d, J = 5.5 Hz, 2H) | 371.0 |
| 139 | 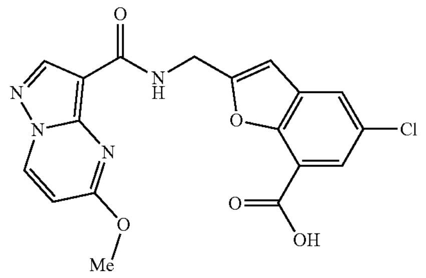 | 5-Chloro-2-((5-methoxypyrazolo[1,5-a]pyrimidine-3-carboxamido)methyl)benzofuran-7-carboxylic acid | $^1$H NMR (500 MHz, DMSO-$d_6$) δ 8.97 (d, J = 7.5 Hz, 1H), 8.38 (s, 1H), 8.19 (br t, J = 5.5 Hz, 1H), 7.86 (s, 1H), 7.69 (s, 1H), 6.86 (s, 1H), 6.70 (d, J = 7.5 Hz, 1H), 4.79 (d, J = 5.8 Hz, 2H), 4.03 (s, 3H) | 401.1 |
| 140 | 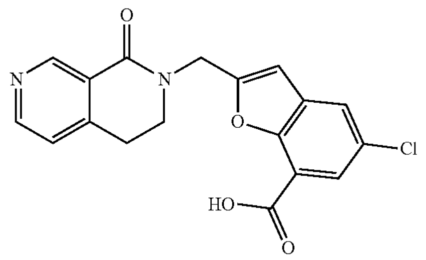 [SMILES: O=C(O)c1cc(Cl)cc2cc(CN3CCc4ccncc4C3=O)oc12] | 5-Chloro-2-((1-oxo-3,4-dihydro-2,7-naphthyridin-2(1H)-yl)methyl)benzofuran-7-carboxylic acid | $^1$H NMR (500 MHz, DMSO-$d_6$) δ 8.94 (br s, 1H), 8.60 (br d, J = 4.0 Hz, 1H), 7.86 (d, J = 1.6 Hz, 1H), 7.69 (d, J = 1.8 Hz, 1H), 7.49 (br d, J = 5.0 Hz, 1H), 6.90 (s, 1H), 4.89 (s, 2H), 3.73 (t, J = 6.6 Hz, 2H), 3.11 (t, J = 6.6 Hz, 2H) | 357.2 |
| 141 | 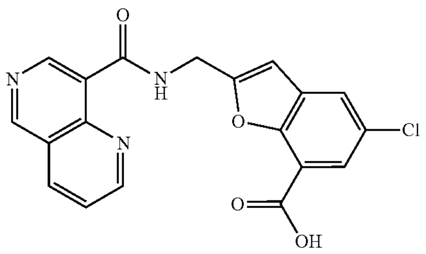 [SMILES: O=C(NCc1cc2cc(Cl)cc(C(=O)O)c2o1)c1cncc2cccnc12] | 2-((1,6-8-carboxamido)methyl)-5-chlorobenzofuran-7-carboxylic acid | $^1$H NMR (500 MHz, DMSO-$d_6$) δ 10.90 (br t, J = 5.5 Hz, 1H), 9.54 (s, 1H), 9.29 (s, 1H), 9.27-9.21 (m, 1H), 8.73 (br d, J = 8.2 Hz, 1H), 7.86 (s, 1H), 7.81 (dd, J = 8.1, 4.4 Hz, 1H), 7.65 (d, J = 1.8 Hz, 1H), 6.89 (s, 1H), 4.85 (br d, J = 5.5 Hz, 2H) | 382.0 |
| 142 | 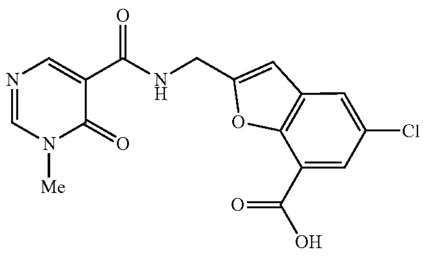 [SMILES: Cn1cncc(C(=O)NCc2cc3cc(Cl)cc(C(=O)O)c3o2)c1=O] | 5-Chloro-2-((1-methyl-6-oxo-1,6-dihydropyrimidine-5-carboxamido)methyl)benzofuran-7-carboxylic acid | $^1$H NMR (500 MHz, DMSO-$d_6$) δ 9.61 (br t, J = 5.3 Hz, 1H), 8.75 (s, 1H), 8.70 (s, 1H), 7.92 (s, 1H), 7.71 (s, 1H), 6.82 (s, 1H), 4.75 (br d, J = 5.8 Hz, 2H), 3.53 (s, 3H) | 362.0 |
| 143 | 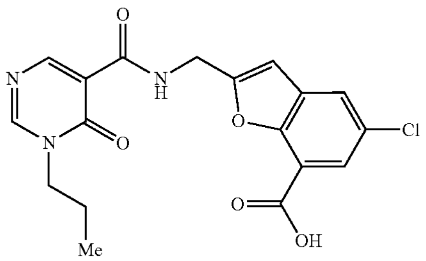 [SMILES: CCCn1cncc(C(=O)NCc2cc3cc(Cl)cc(C(=O)O)c3o2)c1=O] | 5-Chloro-2-((1-propyl-6-oxo-1,6-dihydropyrimidine-5-carboxamido)methyl)benzofuran-7-carboxylic acid | $^1$H NMR (500 MHz, DMSO-$d_6$) δ 9.62-9.53 (m, 1H), 8.76 (s, 1H), 8.69 (s, 1H), 7.90 (s, 1H), 7.70 (s, 1H), 6.82 (s, 1H), 4.73 (br d, J = 5.8 Hz, 2H), 3.97 (br t, J = 7.2 Hz, 2H), 1.79-1.64 (m, 2H), 0.88 (br t, J = 7.3 Hz, 3H) | 390.3 |

-continued

| Ex. No. | Structure | Name | $^1$H NMR | LC/MS (M + H)$^+$ |
|---|---|---|---|---|
| 144 | 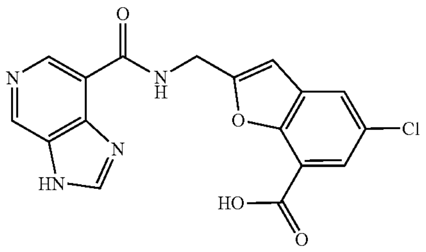 [SMILES: O=C(NCc1cc2cc(Cl)cc(C(=O)O)c2o1)c1cncc2[nH]cnc12] | 2-((3H-Imidazo[4,5-c]pyridine-7-carboxamido)methyl)-5-chlorobenzofuran-7-carboxylic acid | $^1$H NMR (500 MHz, DMSO-$d_6$) δ 9.75 (br s, 1H), 9.09 (s, 1H), 8.90 (s, 1H), 8.54 (br s, 1H), 7.85 (s, 1H), 7.68 (s, 1H), 6.86 (s, 1H), 4.83 (br d, J = 4.9 Hz, 2H) | 371.2 |
| 147 | 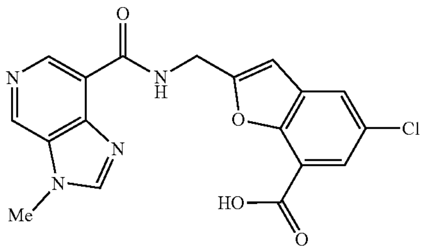 [SMILES: Cn1cnc2c(C(=O)NCc3cc4cc(Cl)cc(C(=O)O)c4o3)cncc21] | 5-Chloro-2-((1-methyl-1H-imidazo[4,5-c]pyridine-7-carboxamido)methyl)benzofuran-7-carboxylic acid | $^1$H NMR (500 MHz, DMSO-d6) δ 9.81-9.70 (m, 1H), 9.18 (s, 1H), 8.95 (s, 1H), 8.63 (s, 1H), 7.92 (d, J = 2.0 Hz, 1H), 7.72 (d, J = 2.0 Hz, 1H), 6.89 (s, 1H), 4.91 (d, J = 5.6 Hz, 2H), 4.04 (s, 3H) | 385.0 |
| 148 | 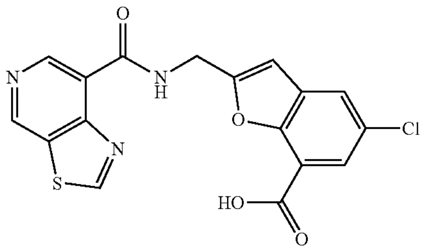 [SMILES: O=C(NCc1cc2cc(Cl)cc(C(=O)O)c2o1)c1cncc2scnc12] | 5-Chloro-2-((thiazolo[5,4-c]pyridine-7-carboxamido)methyl)benzofuran-7-carboxylic acid | $^1$H NMR (500 MHz, DMSO-d6) δ 9.79 (s, 1H), 9.74 (br s, 1H), 9.50 (s, 1H), 9.03 (s, 1H), 7.34 (m, 3H), 6.62 (s, 1H), 4.70 (br d, J = 5.2 Hz, 2H) | 388.0 |
| 149 | 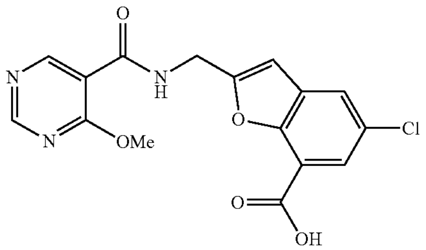 [SMILES: COc1ncncc1C(=O)NCc1cc2cc(Cl)cc(C(=O)O)c2o1] | 5-Chloro-2-((4-methoxypyrimidine-5-carboxamido)methyl)benzofuran-7-carboxylic acid | $^1$H NMR (500 MHz, DMSO-$d_6$) δ 9.01 (br t, J = 5.3 Hz, 1H), 8.90 (s, 1H), 8.87-8.83 (m, 1H), 7.73 (s, 1H), 7.60 (s, 1H), 6.78 (s, 1H), 4.68 (br d, J = 5.8 Hz, 2H), 4.06 (s, 3H) | 362.1 |
| 150 | 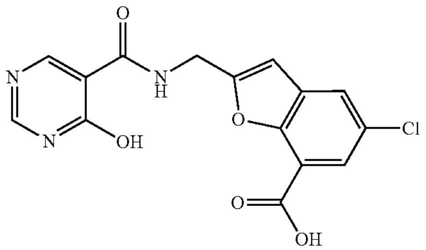 [SMILES: O=C(NCc1cc2cc(Cl)cc(C(=O)O)c2o1)c1cncnc1O] | 5-Chloro-2-((4-hydroxypyrimidine-5-carboxamido)methyl)benzofuran-7-carboxylic acid | $^1$H NMR (500 MHz, DMSO-$d_6$) δ 9.71 (br s, 1H), 8.65 (s, 1H), 8.43 (s, 1H), 7.90 (d, J = 1.5 Hz, 1H), 7.70 (d, J = 1.5 Hz, 1H), 6.81 (s, 1H), 4.72 (br d, J = 5.5 Hz, 2H) | 346.2 |
| 151 | 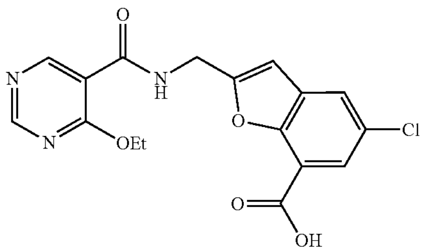 | 5-Chloro-2-((4-ethoxypyrimidine-5-carboxamido)methyl)benzofuran-7-carboxylic acid | $^1$H NMR (500 MHz, DMSO-$d_6$) δ 8.84 (s, 1H), 8.82-8.73 (m, 2H), 7.81 (s, 1H), 7.67 (s, 1H), 6.82 (s, 1H), 4.70 (br d, J = 5.6 Hz, 2H), 4.54 (q, J = 6.9 Hz, 2H), 1.36 (t, J = 7.0 Hz, 3H) | 376.2 |

-continued

| Ex. No. | Structure | Name | $^1$H NMR | LC/MS $(M + H)^+$ |
|---|---|---|---|---|
| 152 | 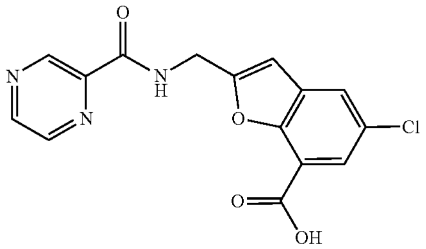 [SMILES: O=C(NCc1cc2cc(Cl)cc(C(=O)O)c2o1)c1cnccn1] | 5-Chloro-2-((pyrazine-2-carboxamido)methyl)benzofuran-7-carboxylic acid | $^1$H NMR (500 MHz, DMSO-$d_6$) δ 9.60 (br t, J = 5.6 Hz, 1H), 9.20 (s, 1H), 8.88 (d, J = 2.1 Hz, 1H), 8.75 (s, 1H), 7.91 (d, J = 1.5 Hz, 1H), 7.70 (d, J = 1.5 Hz, 1H), 6.83 (s, 1H), 4.71 (br d, J = 6.1 Hz, 2H) | 332.0 |
| 153 | 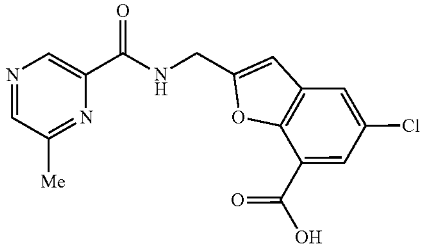 [SMILES: Cc1cncc(C(=O)NCc2cc3cc(Cl)cc(C(=O)O)c3o2)n1] | 5-Chloro-2-((6-methylpyrazine-2-carboxamido)methyl)benzofuran-7-carboxylic acid | $^1$H NMR (500 MHz, DMSO-$d_6$) δ 9.46 (br t, J = 6.0 Hz, 1H), 9.01 (s, 1H), 8.79 (s, 1H), 7.92 (d, J = 1.8 Hz, 1H), 7.71 (d, J = 1.8 Hz, 1H), 6.82 (s, 1H), 4.71 (br d, J = 6.1 Hz, 2H), 2.61 (s, 3H) | 346.1 |
| 154 | 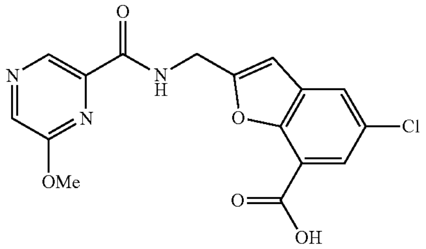 [SMILES: COc1cncc(C(=O)NCc2cc3cc(Cl)cc(C(=O)O)c3o2)n1] | 5-Chloro-2-((6-methoxypyrazine-2-carboxamido)methyl)benzofuran-7-carboxylic acid | $^1$H NMR (500 MHz, DMSO-$d_6$) δ 9.31 (br t, J = 5.8 Hz, 1H), 8.73 (s, 1H), 8.48 (s, 1H), 7.85 (d, J = 1.9 Hz, 1H), 7.68 (d, J = 2.0 Hz, 1H), 6.82 (s, 1H), 4.72 (d, J = 6.0 Hz, 2H), 4.05 (s, 3H) | 362.1 |
| 155 | 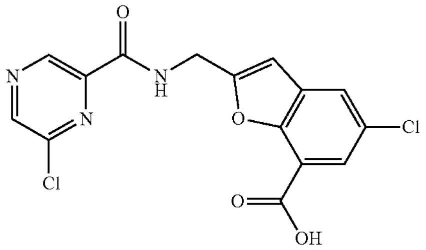 [SMILES: O=C(NCc1cc2cc(Cl)cc(C(=O)O)c2o1)c1cncc(Cl)n1] | 5-Chloro-2-((6-chloropyrazine-2-carboxamido)methyl)benzofuran-7-carboxylic acid | $^1$H NMR (500 MHz, DMSO-$d_6$) δ 9.59 (br t, J = 5.8 Hz, 1H), 9.15 (s, 1H), 9.01 (s, 1H), 7.74 (s, 1H), 7.61 (d, J = 1.5 Hz, 1H), 6.77 (s, 1H), 4.70-4.65 (m, 2H) | 366.2 |
| 156 | 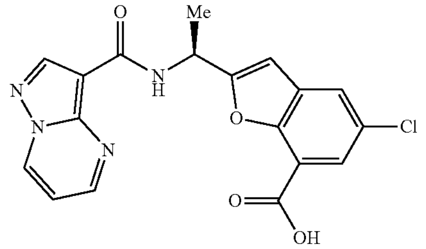 | (S)-5-Chloro-2-(1-(pyrazolo[1,5-a]pyrimidine-3-carboxamido)ethyl)benzofuran-7-carboxylic acid | $^1$H NMR (500 MHz, DMSO-$d_6$) δ 9.28-9.16 (m, 1H), 8.86-8.73 (m, 1H), 8.60 (s, 1H), 8.37 (br d, J = 8.0 Hz, 1H), 7.85 (d, J = 1.2 Hz, 1H), 7.68 (s, 1H), 7.33-7.13 (m, 1H), 6.87 (s, 1H), 5.47 (br t, J = 7.4 Hz, 1H), 1.65 (d, J = 6.9 Hz, 3H) | 384.9 |
| 157 | 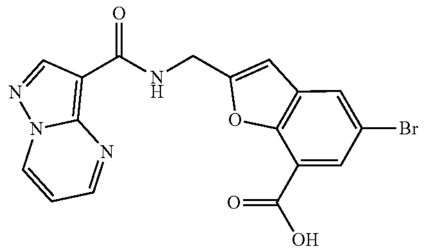 | 5-Bromo-2-((pyrazolo[1,5-a]pyrimidine-3-carboxamido)methyl)benzofuran-7-carboxylic acid | $^1$H NMR (400 MHz, DMSO-d6) δ 13.49 (br s, 1H), 9.34 (dd, J = 7.0, 1.7 Hz, 1H), 8.84 (dd, J = 4.2, 1.7 Hz, 1H), 8.64 (s, 1H), 8.53 (t, J = 5.9 Hz, 1H), 8.06 (d, J = 2.1 Hz, 1H), 7.84 (d, J = 2.1 Hz, 1H), 7.30 (dd, J = 7.0, 4.2 Hz, 1H), 6.84 (s, 1H), 4.81 (d, J = 5.7 Hz, 2H) | 417.1 |

-continued

| Ex. No. | Structure | Name | $^1$H NMR | LC/MS (M + H)$^+$ |
|---|---|---|---|---|
| 158 | 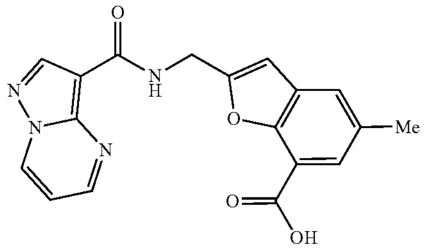 | 5-Methyl-2-((pyrazolo[1,5-a]pyrimidine-3-carboxamido)methyl)benzofuran-7-carboxylic acid | $^1$H NMR (500 MHz, DMSO-$d_6$) δ 9.26 (br d, J = 6.7 Hz, 1H), 8.81 (br d, J = 2.7 Hz, 1H), 8.61 (s, 1H), 8.53 (br t, J = 5.8 Hz, 1H), 7.59 (br d, J = 5.5 Hz, 2H), 7.27 (dd, J = 7.0, 4.3 Hz, 1H), 6.76 (s, 1H), 4.76 (br d, J = 5.8 Hz, 2H), 2.39 (s, 3H) | 351.0 |
| 159 | 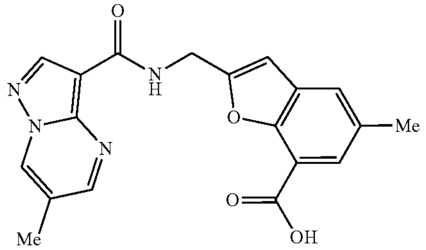 | 5-Methyl-2-((6-methyl pyrazolo[1,5-a]pyrimidine-3-carboxamido)methyl)benzofuran-7-carboxylic acid | $^1$H NMR (500 MHz, DMSO-d6) δ 9.09 (s, 1H), 8.71 (s, 1H), 8.52 (s, 1H), 8.41 (br t, J = 5.6 Hz, 1H), 7.63-7.57 (m, 2H), 6.76 (s, 1H), 4.77 (d, J = 5.8 Hz, 2H), 2.44-2.37 (m, 6H) | 365.2 |
| 160 | 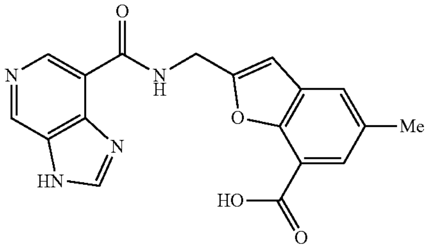 [SMILES: Cc1cc(C(=O)O)c2oc(CNC(=O)c3cncc4[nH]cnc34)cc2c1] | 2-((3H-Imidazo[4,5-c]pyridine-7-carboxamido)methyl)-5-methylbenzofuran-7-carboxylic acid | $^1$H NMR (500 MHz, DMSO-$d_6$) δ 9.72 (br d, J = 5.8 Hz, 1H), 9.09 (s, 1H), 8.92 (s, 1H), 8.55 (br s, 1H), 7.62 (br s, 2H), 6.82 (s, 1H), 4.82 (br d, J = 4.0 Hz, 2H), 2.41 (s, 3H) | 351.2 |
| 161 | 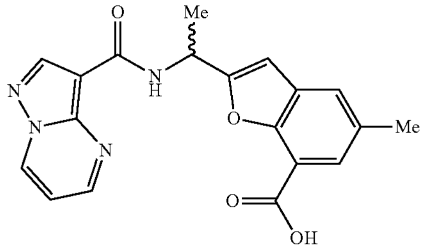 | 5-Methyl-2-(1-(pyrazolo[1,5-a]pyrimidine-3-carboxamido)ethyl)benzofuran-7-carboxylic acid (racemic) | $^1$H NMR (500 MHz, DMSO-$d_6$) δ 9.39-9.15 (m, 1H), 8.96-8.73 (m, 1H), 8.69-8.52 (m, 1H), 8.46-8.22 (m, 1H), 7.71-7.49 (m, 2H), 7.32-7.18 (m, 1H), 6.87-6.74 (m, 1H), 5.56-5.38 (m, 1H), 2.45-2.28 (m, 3H), 1.80-1.49 (m, 3H) | 365.1 |
| 162 | 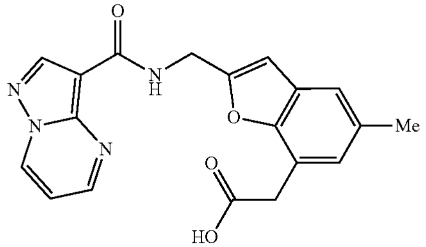 | 2-(5-Methyl-2-((pyrazolo[1,5-a]pyrimidine-3-carboxamido)methyl)benzofuran-7-yl)acetic acid | $^1$H NMR (400 MHz, Methanol-d4) δ 9.10 (dd, J = 7.0, 1.7 Hz, 1H), 8.81 (dd, J = 4.2, 1.7 Hz, 1H), 8.62 (s, 1H), 7.26 (s, 1H), 7.24-7.19 (m, 1H), 7.01 (s, 1H), 6.67 (s, 1H), 4.83 (br d, J = 5.0 Hz, 2H), 3.86 (s, 2H), 2.41 (s, 3H) | 365.1 |
| 163 | 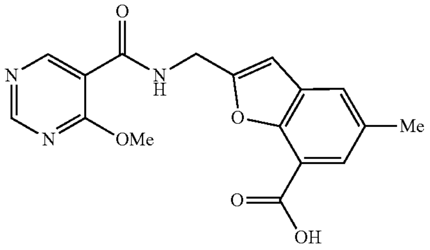 [SMILES: COc1ncncc1C(=O)NCc1cc2cc(C)cc(C(=O)O)c2o1] | 2-((4-Methoxypyrimidine-5-carboxamido)methyl)-5-methylbenzofuran-7-carboxylic acid | $^1$H NMR (500 MHz, DMSO-$d_6$) δ 8.97 (br s, 1H), 8.94-8.88 (m, 1H), 8.88-8.82 (m, 1H), 7.63 (br d, J = 9.2 Hz, 3H), 4.68 (br d, J = 5.8 Hz, 2H), 4.06 (s, 3H), 2.42 (s, 3H) | 342.0 |

-continued

| Ex. No. | Structure | Name | $^1$H NMR | LC/MS (M + H)$^+$ |
| --- | --- | --- | --- | --- |
| 164 | 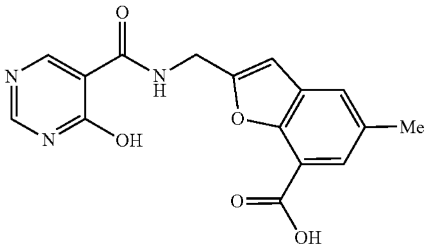 [SMILES: Cc1cc(C(=O)O)c2oc(CNC(=O)c3cncnc3O)cc2c1] | 2-((4-Hydroxypyrimidine-5-carboxamido)methyl)-5-methylbenzofuran-7-carboxylic acid | $^1$H NMR (500 MHz, DMSO-$d_6$) δ 9.79 (br s, 1H), 8.65 (s, 1H), 8.42 (s, 1H), 7.61 (br d, J = 7.0 Hz, 2H), 6.75 (s, 1H), 4.70 (br d, J = 5.8 Hz, 2H), 2.40 (s, 3H) | 328.3 |
| 165 | 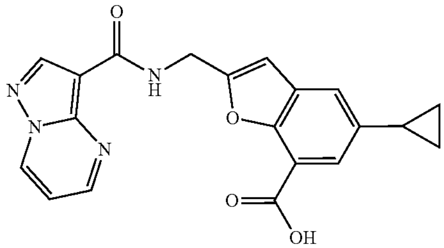 | 5-Cyclopropyl-2-((pyrazolo[1,5-a]pyrimidine-3-carboxamido)methyl)benzofuran-7-carboxylic acid | $^1$H NMR (500 MHz, DMSO-$d_6$) δ 9.30 (d, J = 6.1 Hz, 1H), 8.82 (br d, J = 3.1 Hz, 1H), 8.62 (s, 1H), 8.49 (br t, J = 5.8 Hz, 1H), 7.50 (s, 2H), 7.28 (dd, J = 7.0, 4.3 Hz, 1H), 6.75 (s, 1H), 4.77 (br d, J = 5.8 Hz, 2H), 2.08-2.01 (m, 1H), 0.97 (br d, J = 6.7 Hz, 2H), 0.67 (br d, J = 4.3 Hz, 2H) | 377.2 |
| 166 | 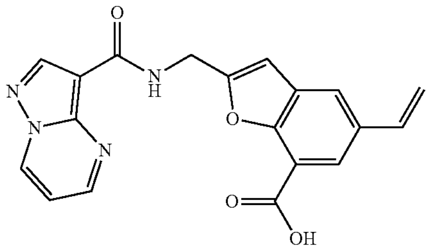 | 2-((Pyrazolo[1,5-a]pyrimidine-3-carboxamido)methyl)-5-vinylbenzofuran-7-carboxylic acid | $^1$H NMR (500 MHz, DMSO-$d_6$) δ 9.30 (br d, J = 7.0 Hz, 1H), 8.83 (br d, J = 3.7 Hz, 1H), 8.63 (s, 1H), 8.53 (br t, J = 5.6 Hz, 1H), 7.93 (s, 1H), 7.90-7.83 (m, 1H), 7.31-7.25 (m, 1H), 6.89-6.80 (m, 2H), 5.83 (d, J = 17.7 Hz, 1H), 5.28 (d, J = 11.0 Hz, 1H), 4.79 (br d, J = 5.5 Hz, 2H) | 363.1 |
| 167 | 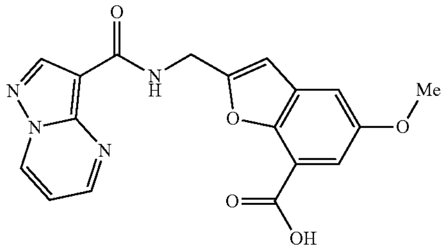 | 5-Methoxy-2-((pyrazolo[1,5-a]pyrimidine-3-carboxamido)methyl)benzofuran-7-carboxylic acid | $^1$H NMR (400 MHz, DMSO-d6) δ 9.34 (br d, J = 6.9 Hz, 1H), 8.83 (br s, 1H), 8.64 (s, 1H), 8.49 (br s, 1H), 7.38 (d, J = 2.6 Hz, 1H), 7.31 (d, J = 2.6 Hz, 2H), 6.77 (s, 1H), 4.77 (d, J = 5.8 Hz, 2H), 3.80 (s, 3H) | 367.3 |
| 168 | 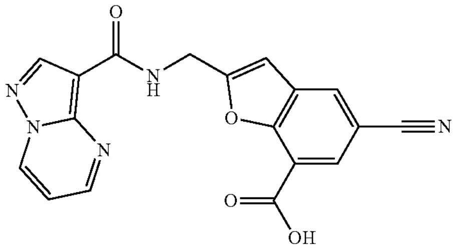 | 5-Cyano-2-((pyrazolo[1,5-a]pyrimidine-3-carboxamido)methyl)benzofuran-7-carboxylic acid | $^1$H NMR (500 MHz, DMSO-$d_6$) δ 9.28 (br d, J = 7.0 Hz, 1H), 8.82 (br d, J = 4.0 Hz, 1H), 8.61 (s, 1H), 8.52 (br t, J = 5.7 Hz, 1H), 8.33 (s, 1H), 8.09 (s, 1H), 7.28 (dd, J = 6.8, 4.2 Hz, 1H), 6.97 (s, 1H), 4.85 (d, J = 5.8 Hz, 2H) | 362.0 |
| 169 | 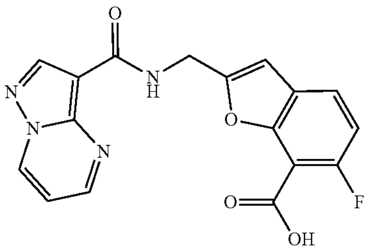 | 6-Fluoro-2-((pyrazolo[1,5-a]pyrimidine-3-carboxamido)methyl)benzofuran-7-carboxylic acid | $^1$H NMR (400 MHz, DMSO-$d_6$) δ 13.77 (s, 1H), 9.34 (dd, J = 7.0, 1.7 Hz, 1H), 8.84 (dd, J = 4.2, 1.7 Hz, 1H), 8.64 (s, 1H), 8.49 (t, J = 5.8 Hz, 1H), 7.74 (dd, J = 8.6, 5.2 Hz, 1H), 7.30 (dd, J = 7.0, 4.2 Hz, 1H), 7.20 (dd, J = 10.9, 8.6 Hz, 1H), 6.84 (s, 1H), 4.78 (d, J = 5.9 Hz, 2H) | 355.0 |

-continued

| Ex. No. | Structure | Name | $^1H$ NMR | LC/MS (M + H)$^+$ |
|---|---|---|---|---|
| 170 | 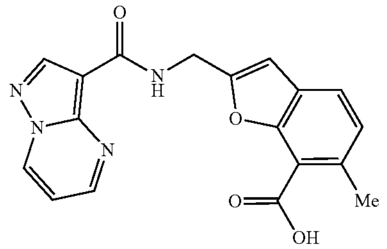 | 6-Methyl-2-((pyrazolo[1,5-a]pyrimidine-3-carboxamido)methyl)benzofuran-7-carboxylic acid | $^1H$ NMR (500 MHz, DMSO-$d_6$) δ 9.27 (br d, J = 6.2 Hz, 1H), 8.81 (br d, J = 3.8 Hz, 1H), 8.61 (s, 1H), 8.42 (br s, 1H), 7.50 (d, J = 7.9 Hz, 1H), 7.27 (dd, J = 6.6, 4.5 Hz, 1H), 7.10 (d, J = 7.8 Hz, 1H), 6.74 (s, 1H), 4.76 (br d, J = 5.7 Hz, 2H), 2.52 (s, 3H) | 351.0 |
| 171 | 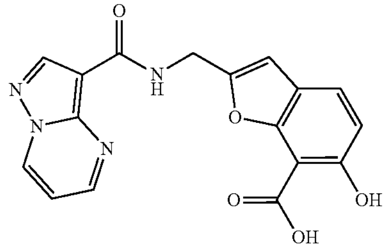 | 6-Hydroxy-2-((pyrazolo[1,5-a]pyrimidine-3-carboxamido)methyl)benzofuran-7-carboxylic acid | $^1H$ NMR (500 MHz, DMSO-$d_6$) δ 9.30 (br d, J = 7.0 Hz, 1H), 8.82 (br d, J = 3.4 Hz, 1H), 8.62 (s, 1H), 8.39 (br t, J = 5.3 Hz, 1H), 7.38 (d, J = 8.5 Hz, 1H), 7.27 (dd, J = 6.7, 4.3 Hz, 1H), 6.64 (d, J = 8.2 Hz, 1H), 6.59 (s, 1H), 4.70 (br d, J = 5.5 Hz, 2H) | 353.0 |
| 172 | 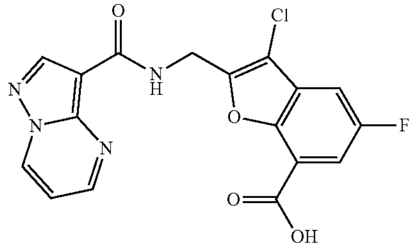 | 3-Chloro-5-fluoro-2-((pyrazolo[1,5-a]pyrimidine-3-carboxamido)methyl)benzofuran-7-carboxylic acid | $^1H$ NMR (500 MHz, DMSO-$d_6$) δ 9.29 (br d, J = 5.8 Hz, 1H), 8.83 (br d, J = 2.7 Hz, 1H), 8.60 (s, 1H), 8.54 (br t, J = 5.5 Hz, 1H), 7.72-7.51 (m, 2H), 7.28 (dd, J = 6.7, 4.3 Hz, 1H), 4.85 (br d, J = 5.8 Hz, 2H) | 389.1 |
| 173 | 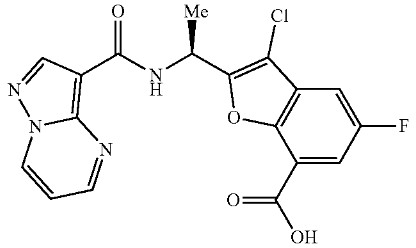 | (S)-3-Chloro-5-fluoro-2-(1-(pyrazolo[1,5-a]pyrimidine-3-carboxamido)ethyl)benzofuran-7-carboxylic acid | $^1H$ NMR (500 MHz, DMSO-d6) δ 9.26 (d, J = 7.0 Hz, 1H), 8.84 (br d, J = 3.1 Hz, 1H), 8.59 (s, 1H), 8.52 (br d, J = 7.6 Hz, 1H), 7.69-7.57 (m, 2H), 7.28 (dd, J = 7.0, 4.3 Hz, 1H), 5.54 (br t, J = 7.3 Hz, 1H), 1.66 (d, J = 7.0 Hz, 3H) | 403.0 |
| 174 | 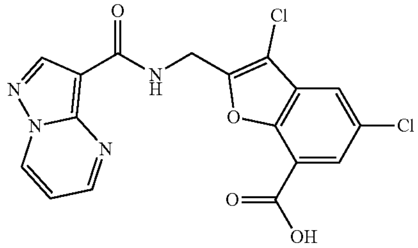 | 3,5-Dichloro-2-((pyrazolo[1,5-a]pyrimidine-3-carboxamido)methyl)benzofuran-7-carboxylic acid | $^1H$ NMR (400 MHz, DMSO-$d_6$) δ 9.32 (dd, J = 7.0, 1.6 Hz, 1H), 8.84 (dd, J = 4.1, 1.5 Hz, 1H), 8.61 (s, 1H), 8.51 (br t, J = 5.7 Hz, 1H), 7.75 (s, 2H), 7.29 (dd, J = 7.0, 4.2 Hz, 1H), 4.85 (d, J = 5.8 Hz, 2H) | 407.0 |
| 175 | 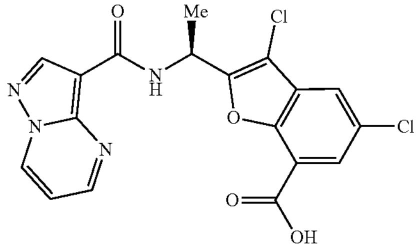 | (S)-3,5-Dichloro-2-(1-(pyrazolo[1,5-a]pyrimidine-3-carboxamido)ethyl)benzofuran-7-carboxylic acid | $^1H$ NMR (500 MHz, DMSO-$d_6$) δ 9.27 (br d, J = 7.0 Hz, 1H), 8.86 (br d, J = 3.7 Hz, 1H), 8.59 (s, 1H), 8.53 (br d, J = 7.6 Hz, 1H), 7.77 (s, 2H), 7.28 (dd, J = 6.9, 4.4 Hz, 1H), 5.55 (br t, J = 7.2 Hz, 1H), 1.66 (br d, J = 7.0 Hz, 3H) | 418.9 |

-continued

| Ex. No. | Structure | Name | $^1$H NMR | LC/MS (M + H)$^+$ |
|---|---|---|---|---|
| 176 | 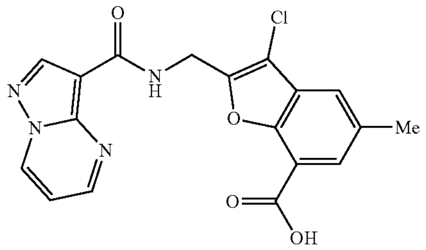 | 3-Chloro-5-methyl-2-((pyrazolo[1,5-a]pyrimidine-3-carboxamido)methyl)benzofuran-7-carboxylic acid | $^1$H NMR (400 MHz, Methanol-d4) δ 9.01 (dd, J = 7.0, 1.7 Hz, 1H), 8.77 (dd, J = 4.2, 1.7 Hz, 1H), 8.60 (s, 1H), 7.79-7.73 (m, 2H), 7.48 (d, J = 1.0 Hz, 1H), 7.18 (dd, J = 7.0, 4.2 Hz, 1H), 4.96-4.91 (m, 2H), 2.49 (s, 3H) | 385.0 |
| 177 | 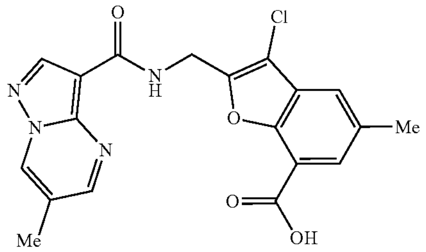 | 3-Chloro-5-methyl-2-((6-methyl pyrazolo[1,5-a]pyrimidine-3-carboxamido)methyl)benzofuran-7-carboxylic acid | $^1$H NMR (500 MHz, DMSO-$d_6$) δ 9.13 (s, 1H), 8.72 (s, 1H), 8.51 (s, 1H), 8.47 (br t, J = 5.5 Hz, 1H), 7.71 (s, 1H), 7.60 (s, 1H), 4.83 (br d, J = 5.5 Hz, 2H), 2.45 (s, 3H), 2.38 (s, 3H) | 398.9 |
| 178 | 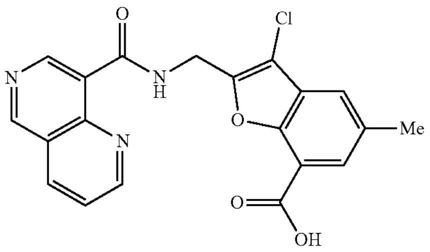 [SMILES: Cc1cc(C(=O)O)c2oc(CNC(=O)c3cncc4cccnc34)c(Cl)c2c1] | 2-((1,6-naphthyridine-8-carboxamido)methyl)-3-chloro-5-methylbenzofuran-7-carboxylic acid | $^1$H NMR (500 MHz, DMSO-$d_6$) δ 11.04 (br t, J = 4.9 Hz, 1H), 9.52 (s, 1H), 9.30 (s, 1H), 9.25 (br d, J = 3.1 Hz, 1H), 8.70 (br d, J = 8.2 Hz, 1H), 7.77 (dd, J = 7.9, 4.3 Hz, 1H), 7.61 (s, 1H), 7.44 (s, 1H), 4.88 (br d, J = 5.5 Hz, 2H), 2.39 (s, 3H) | 396.1 |
| 179 | 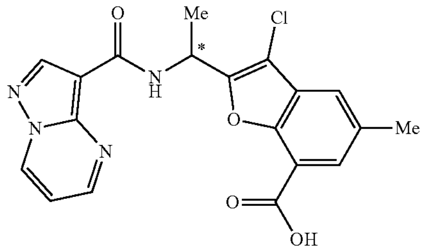 | 3-Chloro-5-methyl-2-(1-(pyrazolo[1,5-a]pyrimidine-3-carboxamido)ethyl)benzofuran-7-carboxylic acid | $^1$H NMR (400 MHz, Methanol-$d_4$) δ 9.06 (dd, J = 7.0, 1.6 Hz, 1H), 8.80 (dd, J = 4.1, 1.5 Hz, 1H), 8.57 (s, 1H), 7.80 (d, J = 1.8 Hz, 1H), 7.56 (dd, J = 1.7, 0.8 Hz, 1H), 7.21 (dd, J = 7.0, 4.3 Hz, 1H), 5.72 (q, J = 7.1 Hz, 1H), 2.49 (s, 3H), 1.75 (d, J = 7.0 Hz, 3H) | 399.1 |
| 180 | 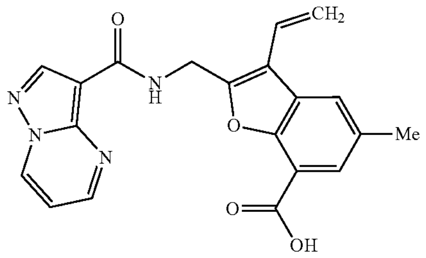 | 5-Methyl-2-((pyrazolo[1,5-a]pyrimidine-3-carboxamido)methyl)-3-vinylbenzofuran-7-carboxylate | $^1$H NMR (400 MHz, Methanol-$d_4$) δ 9.05-9.00 (m, 1H), 8.79-8.75 (m, 1H), 8.62-8.56 (m, 1H), 7.90-7.84 (m, 1H), 7.82-7.79 (m, 2H), 7.78-7.75 (m, 1H), 7.21-7.16 (m, 1H), 7.12-7.02 (m, 1H), 5.93-5.86 (m, 1H), 5.52-5.47 (m, 1H), 4.97-4.91 (m, 2H), 2.50 (s, 3H) | 377.1 |
| 182 | 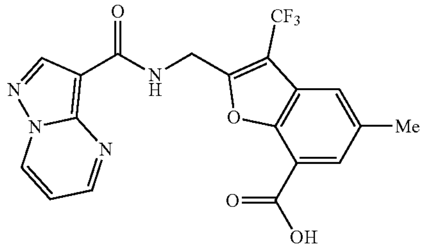 | 5-Methyl-2-((pyrazolo[1,5-a]pyrimidine-3-carboxamido)methyl)-3-(trifluoromethyl)benzofuran-7-carboxylic acid | $^1$H NMR (500 MHz, DMSO-$d_6$) δ 9.29 (d, J = 7.0 Hz, 1H), 8.83 (br d, J = 3.0 Hz, 1H), 8.59 (s, 1H), 8.55 (br t, J = 5.4 Hz, 1H), 7.77 (s, 1H), 7.69 (s, 1H), 7.28 (dd, J = 6.9, 4.2 Hz, 1H), 4.97 (br d, J = 5.5 Hz, 2H), 2.48 (s, 3H) | 419.1 |

-continued

| Ex. No. | Structure | Name | $^1$H NMR | LC/MS (M + H)$^+$ |
|---|---|---|---|---|
| 183 | 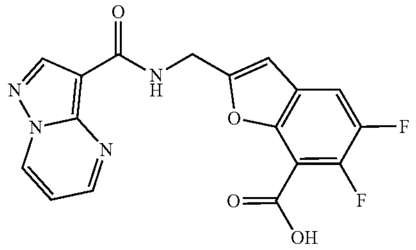 | 5,6-Difluoro-2-((pyrazolo[1,5-a]pyrimidine-3-carboxamido)methyl)benzofuran-7-carboxylic acid | $^1$H NMR (400 MHz, DMSO-$d_6$) δ 9.34 (dd, J = 7.0, 1.6 Hz, 1H), 8.84 (dd, J = 4.3, 1.7 Hz, 1H), 8.64 (s, 1H), 8.55 (t, J = 6.0 Hz, 1H), 7.76 (dd, J = 11.5, 7.9 Hz, 1H), 7.30 (dd, J = 7.0, 4.2 Hz, 1H), 7.02 (s, 1H), 4.82 (d, J = 5.9 Hz, 2H) | 373.1 |
| 184 | 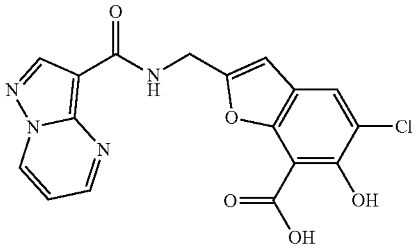 | 5-Chloro-6-hydroxy-2-((pyrazolo[1,5-a]pyrimidine-3-carboxamido)methyl)benzofuran-7-carboxylic acid | $^1$H NMR (500 MHz, DMSO-$d_6$) δ 9.27 (br d, J = 7.0 Hz, 1H), 8.79 (br s, 1H), 8.59 (s, 1H), 8.44 (br s, 1H), 7.80 (s, 1H), 7.25 (br d, J = 4.3 Hz, 1H), 6.66 (s, 1H), 4.71 (br d, J = 5.5 Hz, 2H) | 386.9 |

Examples 185-186

The following acids were synthesized from the corresponding racemic methyl esters according to the hydrolysis procedure outlined in Example 128 and resolved according to the methods listed.

| Ex. No. | Structure | Name | $^1$H NMR | LC/MS (M + H)$^+$ | Method |
|---|---|---|---|---|---|
| 185 | 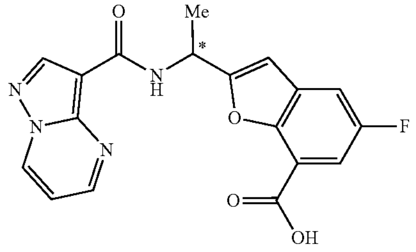 (Isomer 1) | 5-Fluoro-2-(1-(pyrazolo[1,5-a]pyrimidine-3-carboxamido)ethyl)benzofuran-7-carboxylic acid | $^1$H NMR (500 MHz, DMSO-$d_6$) δ 9.25 (dd, J = 7.0, 1.2 Hz, 1H), 8.81 (dd, J = 4.0, 1.2 Hz, 1H), 8.61 (s, 1H), 8.41 (d, J = 8.2 Hz, 1H), 7.68 (dd, J = 8.2, 2.4 Hz, 1H), 7.51 (dd, J = 9.6, 2.6 Hz, 1H), 7.26 (dd, J = 7.0, 4.3 Hz, 1H), 6.91 (s, 1H), 5.46 (br t, J = 7.3 Hz, 1H), 1.64 (d, J = 7.0 Hz, 3H) | 369.2 | Method G |
| 186 | 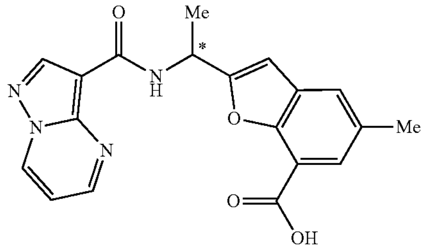 (Isomer 1) | 5-Methyl-2-(1-(pyrazolo[1,5-a]pyrimidine-3-carboxamido)ethyl)benzofuran-7-carboxylic acid | $^1$H NMR (400 MHz, Methanol-$d_4$) δ 9.17-8.99 (m, 1H), 8.91-8.66 (m, 1H), 8.60 (s, 1H), 7.69 (s, 1H), 7.56 (s, 1H), 7.32-7.11 (m, 1H), 6.73 (s, 1H), 5.57 (br d, J = 6.0 Hz, 1H), 2.44 (s, 3H), 1.75 (br d, J = 6.1 Hz, 3H) | 365.1 | Method L |

Example 187

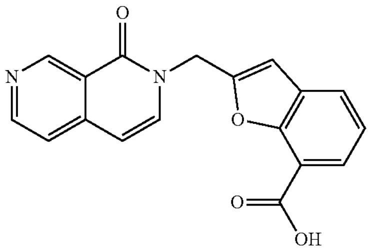 [SMILES: O=C(O)c1cccc2cc(Cn3ccc4ccncc4c3=O)oc12]

2-((1-Oxo-2,7-naphthyridin-2(1H)-yl)methyl)benzofuran-7-carboxylic acid 2,7-Naphthyridin-1(2H)-one (15 mg, 0.103 mmol, Step A of Example 7) was taken up in dry DMF (1.0 mL) and cooled to O ° C. Sodium hydride (6.16 mg, 0.154 mmol) (60% dispersion in mineral oil) was added and after 30 minutes, methyl 2-(bromomethyl)benzofuran-7-carboxylate (38.7 mg, 0.144 mmol, Step D of Example 7) was added. Once the addition was complete, the reaction was allowed to warm to room temperature. The reaction was stirred at room temperature for 30 minutes, after which time, LCMS indicated that some of the methyl ester had been cleaved. The reaction was quenched with a few drops of ammonium chloride solution, filtered, and purified via preparative HPLC (Method B) to give 2-((1-oxo-2,7-naphthyridin-2(1H)-yl)methyl)benzofuran-7-carboxylic acid (16.9 mg, 0.046 mmol, 45.2% yield). $^1$H NMR (500 MHz, DMSO-$d_6$) δ 9.36 (s, 1H), 8.73 (d, J=5.2 Hz, 1H), 7.88-7.77 (m, 3H), 7.62 (d, J=5.2 Hz, 1H), 7.32 (t, J=7.6 Hz, 1H), 6.88 (s, 1H), 6.73 (d, J=7.3 Hz, 1H), 5.43 (s, 2H); MS (ESI+) m/z=321.0 $(M+H)^+$.

Example 188

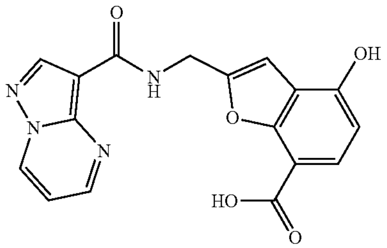 [SMILES: O=C(O)c1ccc(O)c2cc(CNC(=O)c3cnn4cccnc34)oc12]

4-Hydroxy-2-((pyrazolo[1,5-a]pyrimidine-3-carboxamido)methyl)benzofuran-7-carboxylic acid To a solution of methyl 4-methoxy-2-((pyrazolo[1,5-a]pyrimidine-3-carboxamido)methyl)benzofuran-7-carboxylate (10 mg, 0.026 mmol, Example 33) in DCM (1 mL) at 0° C. was added tribromoborane (5.07 µl, 0.053 mmol). The reaction mixture was stirred at room temperature for 4 hours. The reaction mixture was acidified with 1 N aqueous HCl solution to pH 2-3 and extracted with DCM. The organic layer was dried over sodium sulfate, filtered, concentrated, and purified with prep HPLC, Method C, to give the product (5.1 mg, 38% yield). $^1$H NMR (400 MHz, Chloroform-d) δ 9.01 (dd, J=7.0, 1.8 Hz, 1H), 8.78 (dd, J=4.1, 1.6 Hz, 1H), 8.62 (s, 1H), 7.80 (d, J=8.5 Hz, 1H), 7.19 (dd, J=7.1, 4.3 Hz, 1H), 6.86 (s, 1H), 6.64 (d, J=8.5 Hz, 1H), 5.41 (s, 2H); MS (ESI+) m/z=353.1 $(M+H)^+$.

Example 189

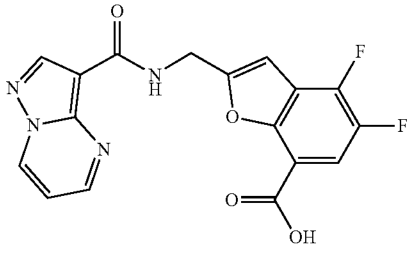 [SMILES: O=C(O)c1cc(F)c(F)c2cc(CNC(=O)c3cnn4cccnc34)oc12]

4,5-Difluoro-2-((pyrazolo[1,5-a]pyrimidine-3-carboxamido)methyl)benzofuran-7-carboxylic acid

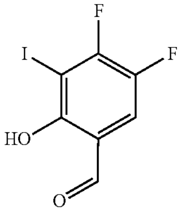 [SMILES: O=Cc1cc(F)c(F)c(I)c1O]

A) 4,5-Difluoro-2-hydroxy-3-iodobenzaldehyde

To a solution of 4,5-difluoro-2-hydroxybenzaldehyde (3.0 g, 19.0 mmol) in N,N-dimethylformamide (30 mL) was added sodium iodide (3.41 g, 22.8 mmol), followed by chloramine T trihydrate (5.88 g, 20.9 mmol) slowly. The resulting mixture was stirred at room temperature overnight. The reaction was not complete by LCMS, so the reaction mixture was stirred at room temperature for another 24 hours. The reaction mixture was diluted with ethyl acetate and 1 N aqueous HCl solution. The organic layer was separated, washed with brine followed by $Na_2S_2O_3$ solution, dried over $MgSO_4$, and filtered. The filtrate was concentrated in vacuo to give light a yellow solid. The residue was dissolved in DCM and purified by flash chromatography (80 g column, 0-15% ethyl acetate in hexanes) to give the title compound (3.0 g, 56% yield) as a white solid. $^1$H NMR (400 MHz, CHLOROFORM-d) δ 12.02 (d, J=1.9 Hz, 1H), 9.74 (s, 1H), 7.56-7.39 (m, 1H).

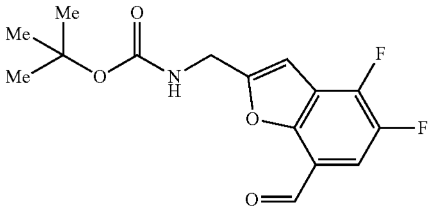 [SMILES: CC(C)(C)OC(=O)NCc1cc2c(F)c(F)cc(C=O)c2o1]

B) tert-Butyl ((4,5-difluoro-7-formylbenzofuran-2-yl)methyl)carbamate

A mixture of 4,5-difluoro-2-hydroxy-3-iodobenzaldehyde (3.0 g, 10.6 mmol), tert-butyl prop-2-yn-1-ylcarbamate (1.89 g, 12.2 mmol), TEA (17.7 mL, 127 mmol), and copper(I) iodide (0.16 g, 0.85 mmol) in DMF (20 mL) was purged with a nitrogen stream for 5 mins. Bis(triphenylphosphine)palladium(II) chloride (0.37 g, 0.53 mmol) was then added. The resulting mixture was heated at 80° C. for 2 hours. The reaction mixture was cooled down and diluted with ethyl acetate and saturated aqueous $NaHCO_3$ solution. The organic layer was separated, washed with brine followed by saturated aqueous $NH_4Cl$ solution, dried over $MgSO_4$, and filtered. The filtrate was concentrated in vacuo to give an oil. The oil was dissolved in DCM and purified by flash chromatography (80 g column, 0-25% ethyl acetate in hexanes) to give the title compound (2.44 g, 74% yield) as a white solid. $^1$H NMR (400 MHz, Chloroform-d) δ 10.39 (d, J=2.0 Hz, 1H), 7.65 (dd, J=10.4, 7.6 Hz, 1H), 6.84 (s, 1H), 5.19-4.99 (m, 1H), 4.54 (br d, J=6.0 Hz, 2H), 1.50 (s, 9H).

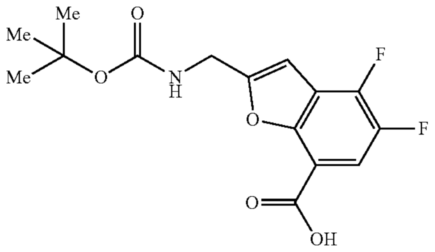 [SMILES: CC(C)(C)OC(=O)NCc1cc2c(F)c(F)cc(C(=O)O)c2o1]

C) 2-(((tert-Butoxycarbonyl)amino)methyl)-4,5-difluorobenzofuran-7-carboxylic acid To a solution of tert-butyl ((4,5-difluoro-7-formylbenzofuran-2-yl)methyl) carbamate (2.4 g, 7.71 mmol) in tert-butanol (24 mL) was added 2-methyl-2-butene (2.0 M solution in THF) (19.3 mL, 38.5 mmol) and a solution of potassium dihydrogen phosphate (4.20 g, 30.8 mmol) in water (24 mL). A solution of sodium chlorite (1.74 g, 15.4 mmol) in water (2 mL) was then added slowly. The reaction mixture was stirred at room temperature for 3 hours. To the reaction mixture was added water and then acetic acid was added to adjust the pH to 4-5. The resulting mixture was extracted with ethyl acetate. The organic layer was separated, washed with brine, dried over $MgSO_4$, and filtered. The filtrate was concentrated in vacuo. A solid crashed out from the residue upon standing. To the residue was added MeOH and the resulting precipitate was filtered to give the crude title compound (0.8 g) as a pale yellow solid. The filtrate was concentrated in vacuo. The residue was dissolved in DCM and purified by flash chromatography (ISCO 40 g column, 0-50% ethyl acetate in DCM) to give a white solid. The combined yield of the title compound was 2.2 g or 87% yield. $^1$H NMR (400 MHz, DMSO-$d_6$) δ 7.78 (dd, J=11.5, 7.9 Hz, 1H), 7.60-7.52 (m, 1H), 6.92 (s, 1H), 4.34 (br d, J=5.7 Hz, 2H), 1.41 (s, 9H); MS (ESI+) m/z=272.1 $(M-55+H)^+$.

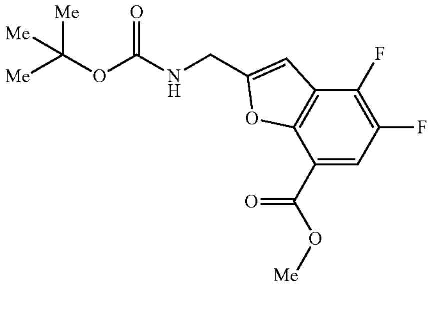 [SMILES: COC(=O)c1cc(F)c(F)c2cc(CNC(=O)OC(C)(C)C)oc12]

D) Methyl 2-(((tert-butoxycarbonyl)amino)methyl)-4,5-difluorobenzofuran-7-carboxylate To a solution of 2-(((tert-butoxycarbonyl)amino)methyl)-4,5-difluorobenzofuran-7-carboxylic acid (1.3 g, 3.97 mmol) in DMF (12 mL) was added BOP (2.11 g, 4.77 mmol). The reaction mixture was stirred at rt for 5 min. Methanol (5 mL, 3.97 mmol) and DIPEA (1.4 mL, 7.94 mmol) were the added. The reaction mixture was stirred at rt overnight. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was triturated with MeOH and filtered to give the title compound as a white solid (0.85 g, 63%). $^1$H NMR (400 MHz, Chloroform-d) δ 7.79 (dd, J=11.1, 7.7 Hz, 1H), 6.80 (s, 1H), 5.58-4.93 (m, 1H), 4.53 (br d, J=6.0 Hz, 2H), 4.01 (s, 3H), 1.49 (s, 9H); MS (ESI+) m/z=286.2 $(M-55+H)^+$.

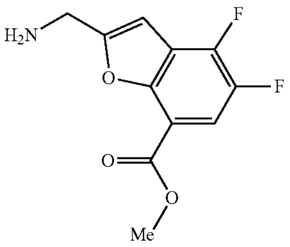 [SMILES: COC(=O)c1cc(F)c(F)c2cc(CN)oc12]

E) Methyl 2-(aminomethyl)-4,5-difluorobenzofuran-7-carboxylate

To a solution of methyl 2-(((tert-butoxycarbonyl)amino) methyl)-4,5-difluorobenzofuran-7-carboxylate (0.9 g, 2.64 mmol) in DCE (10 mL) was added TFA (2.44 mL, 31.6 mmol). The reaction mixture was stirred at room temperature for 2 hours. The reaction mixture was concentrated in vacuo and dried on high vacuum overnight to give the crude title compound (TFA salt) as a white solid (0.98 g, 99%). $^1$H NMR (400 MHz, DMSO-$d_6$) δ 8.54 (br s, 1H), 7.96 (dd, J=11.4, 7.9 Hz, 1H), 4.38 (br s, 2H), 3.95 (s, 3H); MS (ESI+) m/z=225.2 $(M-17+H)^+$.

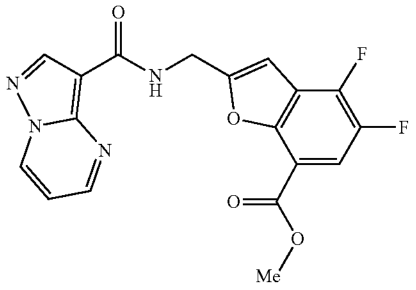

F) Methyl 4,5-difluoro-2-((pyrazolo[1,5-a]pyrimidine-3-carboxamido) methyl)benzofuran-7-carboxylate A suspension of pyrazolo[1,5-a]pyrimidine-3-carboxylic acid (248 mg, 1.52 mmol) and BOP (672 mg, 1.52 mmol) in DMF (8 mL) was stirred at room temperature for 10 minutes. A solution of methyl 2-(aminomethyl)-4,5-difluorobenzofuran-7-carboxylate, TFA (450 mg, 1.27 mmol) in THE (4 mL) and DIPEA (0.9 mL, 5.1 mmol) were added. The reaction mixture turned into a clear solution after addition of the amine and was stirred at room temperature for 1.5 h. During this time a solid crashed out. To the reaction mixture was added water and the solid was filtered to give the crude title compound (440 mg, 85%). $^1$H NMR (400 MHz, DMSO-$d_6$) δ 9.35 (dd, J=7.0, 1.6 Hz, 1H), 8.85 (dd, J=4.2, 1.7 Hz, 1H), 8.64 (s, 1H), 8.56 (t, J=6.0 Hz, 1H), 7.84 (dd, J=11.4, 7.8 Hz, 1H), 7.31 (dd, J=7.0, 4.2 Hz, 1H), 7.05 (s, 1H), 4.83 (d, J=5.8 Hz, 2H), 3.91 (s, 3H); MS (ESI+) m/z=387.3 $(M+H)^+$.

G) 4,5-Difluoro-2-((pyrazolo[1,5-a]pyrimidine-3-carboxamido)methyl)benzofuran-7-carboxylic acid To a suspension of methyl 4,5-difluoro-2-((pyrazolo[1,5-a]pyrimidine-3-carboxamido)methyl)benzofuran-7-carboxylate (380 mg, 0.984 mmol) in THE (6 mL) and MeOH (6 mL) was added 2M LiOH aqueous solution (4.92 mL, 9.84 mmol). The resulting mixture was stirred at room temperature for 24 hours. To the reaction mixture was added water and then acetic acid was added to adjust the pH to 4-5. A white solid crashed out and the mixture was filtered to give the title compound as a white solid (340 mg, 88%). $^1$H NMR (400 MHz, DMSO-$d_6$) δ 9.34 (dd, J=7.0, 1.7 Hz, 1H), 8.84 (dd, J=4.2, 1.6 Hz, 1H), 8.64 (s, 1H), 8.55 (t, J=6.1 Hz, 1H), 7.77 (dd, J=11.5, 7.9 Hz, 1H), 7.30 (dd, J=7.0, 4.2 Hz, 1H), 7.02 (s, 1H), 4.82 (d, J=5.9 Hz, 2H); MS (ESI+) m/z=373.2 $(M+H)^+$.

Example 190

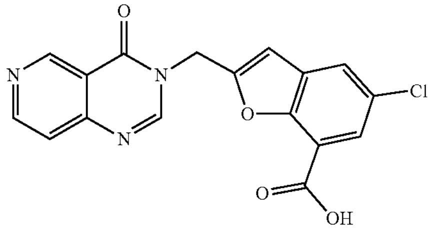 [SMILES: O=C(O)c1cc(Cl)cc2cc(Cn3cnc4ccncc4c3=O)oc12]

5-Chloro-2-((4-oxopyrido[4,3-d]pyrimidin-3(4H)-yl) methyl)benzofuran-7-carboxylic acid 4-Aminonicotinic acid (65.1 mg, 0.471 mmol) and N,N-dimethylformamide dimethyl acetal (0.221 mL, 1.649 mmol) were taken up in DMF (0.5 mL) in a microwave vial. The vial was sealed and heated at 110° C. for 20 min. The reaction mixture was cooled and concentrated in vacuo. To the residue was added 1 mL of acetic acid and 2-(aminomethyl)-5-chlorobenzofuran-7-carboxylic acid, TFA (80 mg, 0.236 mmol). The mixture was heated at 110° C. for another 20 minutes in a microwave reactor. The reaction mixture was cooled and concentrated in vacuo. To the residue was added MeOH, and a solid crashed out. The mixture was filtered to give a grey solid as the title compound (34 mg, 41% yield). $^1$H NMR (500 MHz, DMSO-$d_6$) δ 9.33 (s, 1H), 8.86 (br d, J=5.5 Hz, 1H), 8.74 (s, 1H), 7.85 (s, 1H), 7.69 (s, 1H), 7.63 (d, J=5.6 Hz, 1H), 6.96 (s, 1H), 5.45 (s, 2H); MS (ESI+) m/z=356.2 $(M+H)^+$.

Example 191

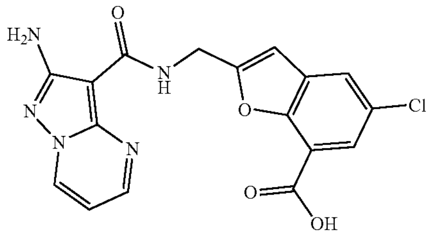 [SMILES: Nc1nn2cccnc2c1C(=O)NCc1cc2cc(Cl)cc(C(=O)O)c2o1]

2-((2-Aminopyrazolo[1,5-a]pyrimidine-3-carboxamido)methyl)-5-chlorobenzofuran-7-carboxylic acid A vial was charged with methyl 2-((2-((tert-butoxycarbonyl)amino)pyrazolo[1,5-a]pyrimidine-3-carboxamido) methyl)-5-chlorobenzofuran-7-carboxylate (35 mg, 0.070 mmol, Step D of Example 63) in methanol (4 mL) and tetrahydrofuran (2 mL). To the solution was added lithium hydroxide (0.047 mL, 0.140 mmol, 3M) and the reaction was stirred at room temperature for 3 hours. The solution was concentrated in vacuo and the residue acidified with 1N HCl. The product precipitate, 2-((2-((tert-butoxycarbonyl) amino)pyrazolo[1,5-a]pyrimidine-3-carboxamido)methyl)-5-chlorobenzofuran-7-carboxylic acid, was filtered, pumped dried by vacuum and used as is in next step.

The above product was dissolved in DCM (5 mL) and TFA (0.5 mL) was added. The solution was stirred at room temperature for 2 hours. The solution was concentrated in vacuo, dissolved in 2 mL of DMF and purified via preparative HPLC (Method A) to yield the title compound (7.8 mg, 28.8% yield). 1H NMR (500 MHz, DMSO-$d_6$) δ 8.97-8.88 (m, 1H), 8.55-8.47 (m, 1H), 8.29-8.19 (m, 1H), 7.95-7.87 (m, 1H), 7.74-7.67 (m, 1H), 7.05-6.95 (m, 1H), 6.84-6.73 (m, 1H), 6.57-6.43 (m, 2H), 4.85-4.72 (m, 2H); MS (ESI+) m/z=386.1 $(M+H)^+$.

Example 192

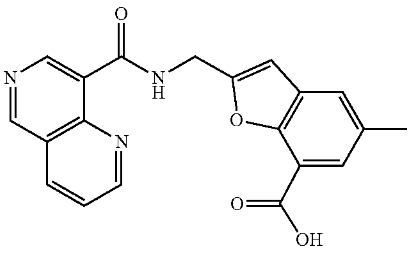 [SMILES: Cc1cc(C(=O)O)c2oc(CNC(=O)c3cncc4cccnc34)cc2c1]

2-((1,6-naphthyridine-8-carboxamido)methyl)-5-methylbenzofuran-7-carboxylic acid A mixture of 1,6-naphthyridine-8-carboxylic acid, HCl (10 mg, 0.047 mmol), methyl 2-(aminomethyl)-5-methylbenzofuran-7-carboxylate, TFA (15.82 mg, 0.047 mmol, Step C of Example 85), HATU (18.05 mg, 0.047 mmol) and Hunig's Base (0.033 mL, 0.190 mmol) in THE (0.5 mL) was stirred at rt for 48 h. The solvent was evaporated and the residue was suspended in Water (0.500 mL) and THE (0.5 mL). Lithium hydroxide dihydrate (19.47 mg, 0.475 mmol) was added and the reaction was stirred at rt for 48 h. The solvent was evaporated and the residue was dissolved in 1:1 DMF/AcOH and and purified by preparative LC/MS (Method B) to give the title compound (2.7 mg, 7.28 μmol, 15.33% yield). $^{1}$H NMR (500 MHz, DMSO-$d_6$) δ 10.97 (br s, 1H), 9.59 (s, 1H), 9.36 (s, 1H), 9.33-9.28 (m, 1H), 8.78 (br d, J=8.2 Hz, 1H), 7.86 (br dd, J=8.1, 4.1 Hz, 1H), 7.55 (br d, J=10.1 Hz, 2H), 6.83 (s, 1H), 4.87 (br d, J=5.5 Hz, 2H), 2.39 (s, 3H); MS (ESI+) m/z=362.0 $(M+H)^+$.

Example 194

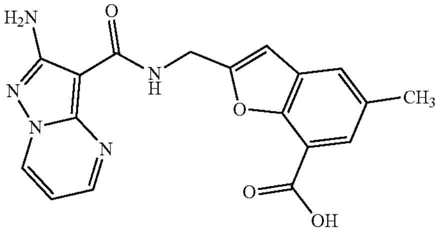 [SMILES: Cc1cc(C(=O)O)c2oc(CNC(=O)c3c(N)nn4cccnc34)cc2c1]

2-((2-Aminopyrazolo[1,5-a]pyrimidine-3-carboxamido)methyl)-5-methylbenzofuran-7-carboxylic acid A vial was charged with methyl 2-((2-((tert-butoxycarbonyl)amino) pyrazolo[1,5-a]pyrimidine-3-carboxamido)methyl)-5-methylbenzofuran-7-carboxylate (45 mg, 0.094 mmol, Step A of Example 93) in methanol (4 mL) and tetrahydrofuran (2 mL). To the solution was added lithium hydroxide (0.063 mL, 0.188 mmol, 3M) and the reaction was stirred at room temperature for 3 hours. The solution was concentrated in vacuo and the residue acidified with 1N HCl. The product precipitate 2-((2-((tert-butoxycarbonyl)amino)pyrazolo[1,5-a]pyrimidine-3-carboxamido)methyl)-5-methylbenzofuran-7-carboxylic acid was filtered, pumped dried by vacuum and used as is in next step The above product was dissolved in DCM (5 mL) and TFA (0.5 mL) was added. The solution was stirred at RT for 2 hours. The solution was concentrated in vacuo, dissolved in 2 mL of DMF and purified via preparative HPLC (Method B) to yield the title compound (14 mg, 40.8% yield). 1H NMR (500 MHz, DMSO-d6) δ 8.91-8.84 (m, 1H), 8.49-8.44 (m, 1H), 8.21-8.15 (m, 1H), 7.60-7.51 (m, 2H), 6.99-6.92 (m, 1H), 6.73-6.67 (m, 1H), 6.52-6.44 (m, 1H), 4.77-4.66 (m, 2H), 2.35 (s, 3H); MS (ESI+) m/z=366.1 $(M+H)^+$.

Example 195

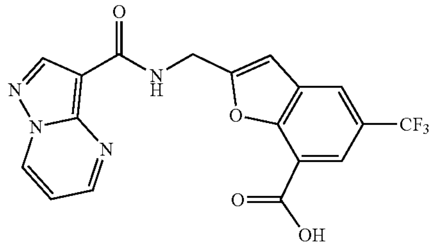 [SMILES: O=C(O)c1cc(C(F)(F)F)cc2cc(CNC(=O)c3cnn4cccnc34)oc12]

2-((Pyrazolo[1,5-a]pyrimidine-3-carboxamido)methyl)-5-(trifluoromethyl)benzofuran-7-carboxylic acid

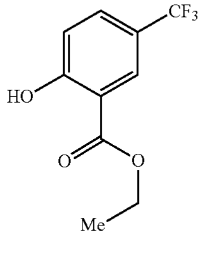

A) Ethyl 2-hydroxy-5-(trifluoromethyl)benzoate

To a solution of 2-hydroxy-5-(trifluoromethyl)benzonitrile (3.45 g, 18.4 mmol) in ethanol (35 mL) was added sulfuric acid (6.9 mL, 130 mmol). The reaction mixture was heated at 85° C. overnight. After 16 hours, additional sulfuric acid (6.9 mL, 130 mmol) and the reaction mixture was heated at 92° C. for another 72 hours. The reaction mixture was cooled down and the mixture was poured into ice. The resulting mixture was extracted with ethyl acetate. The organic layer was separated and washed with brine, dried over $MgSO_4$ and filtered. The filtrate was concentrated in vacuo. The residue was dissolved in DCM and purified by ISCO (80 g column, 0-30% ethyl acetate in hexanes) to give ethyl 2-hydroxy-5-(trifluoromethyl)benzoate (1.2 g, 28% yield). $^{1}$H NMR (400 MHz, Chloroform-d) δ 11.20 (s, 1H), 8.14 (d, J=1.8 Hz, 1H), 7.69 (dd, J=8.8, 2.3 Hz, 1H), 7.08 (d, J=8.8 Hz, 1H), 4.47 (q, J=7.1 Hz, 2H), 1.46 (t, J=7.1 Hz, 3H); MS (ESI+) m/z=335.1 $(M+H)^+$.

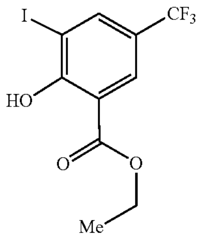 [SMILES: CCOC(=O)c1cc(C(F)(F)F)cc(I)c1O]

B) Ethyl 2-hydroxy-3-iodo-5-(trifluoromethyl)benzoate

To a solution of ethyl 2-hydroxy-5-(trifluoromethyl)benzoate (1.2 g, 5.12 mmol) in N,N-dimethylformamide (20 mL) was added sodium iodide (0.92 g, 6.15 mmol) followed by chloramine T trihydrate (1.59 g, 5.64 mmol) slowly. The resulting mixture was stirred at room temperature overnight. The reaction mixture was diluted with ethyl acetate and 1 N aqueous HCl solution. The organic layer was separated and washed with brine, $Na_2S_2O_3$ solution, dried over $MgSO_4$, and filtered. The filtrate was concentrated in vacuo to give a light yellow oil. The crude residue was dissolved in DCM and purified by silica gel column chromatography (80 g column, 0-10% ethyl acetate in hexanes) to give ethyl 2-hydroxy-3-iodo-5-(trifluoromethyl)benzoate (0.83 g, 45%). $^1H$ NMR (400 MHz, CHLOROFORM-d) δ 12.11 (s, 1H), 8.18 (d, J=2.0 Hz, 1H), 8.15 (d, J=1.5 Hz, 1H), 4.50 (q, J=7.1 Hz, 2H), 1.47 (t, J=7.1 Hz, 3H).

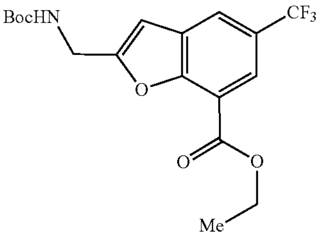 [SMILES: CCOC(=O)c1cc(C(F)(F)F)cc2cc(CNC(=O)OC(C)(C)C)oc12]

C) Ethyl 2-(((tert-butoxycarbonyl)amino)methyl)-5-(trifluoromethyl) benzofuran-7-carboxylate The reaction mixture of ethyl 2-hydroxy-3-iodo-5-(trifluoromethyl)benzoate (0.83 g, 2.31 mmol), tert-butyl prop-2-yn-1-ylcarbamate (0.43 g, 2.77 mmol), TEA (4.82 mL, 34.6 mmol), and copper(I) iodide (0.044 g, 0.23 mmol) in DMF (10 mL) was purged with a nitrogen stream for 5 mins, then bis(triphenylphosphine) palladium(II) chloride (0.097 g, 0.14 mmol) was added. The resulting mixture was sealed and heated at 80° C. for 2 hours. The reaction mixture was cooled down and diluted with ethyl acetate and saturated aqueous $NaHCO_3$ solution. The organic layer was separated and washed with brine, dried over $MgSO_4$, and filtered. The filtrate was concentrated in vacuo. The crude residue was dissolved in DCM and purified by silica gel column chromatography (40 g column, 0-25% ethyl acetate in hexanes) to give ethyl 2-(((tert-butoxycarbonyl)amino)methyl)-5-(trifluoromethyl) benzofuran-7-carboxylate (0.80 g, 90% yield). $^1H$ NMR (400 MHz, Chloroform-d) δ 8.19 (d, J=1.3 Hz, 1H), 8.00 (s, 1H), 6.76 (s, 1H), 5.22-5.06 (m, 1H), 4.60-4.54 (m, 2H), 4.52-4.46 (m, 2H), 1.50-1.45 (m, 12H); MS (ESI+) m/z=332.3 $(M+H-tBu)^+$.

TFA

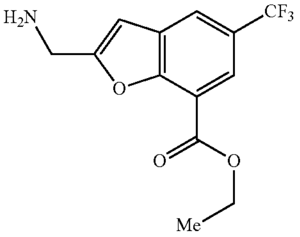

D) Ethyl 2-(aminomethyl)-5-(trifluoromethyl)benzofuran-7-carboxylate·TFA

Ethyl 2-(((tert-butoxycarbonyl)amino)methyl)-5-(trifluoromethyl)benzofuran-7-carboxylate (400 mg, 1.03 mmol) was taken up in DCM (3.9 mL) and cooled to 0° C. TFA (1.3 mL) was added and the reaction was stirred at room temperature for 2 hours. The reaction was then concentrated in vacuo and azeotroped three times with toluene to remove excess TFA. The crude product was placed under high vacuum overnight to give ethyl 2-(aminomethyl)-5-(trifluoromethyl)benzofuran-7-carboxylate as a TFA salt (418 mg, 1.08 mmol, 100% yield). $^1H$ NMR (400 MHz, Chloroform-d) δ 8.18 (d, J=1.3 Hz, 1H), 8.05 (s, 1H), 6.98 (s, 1H), 4.46 (s, 2H), 4.42 (q, J=7.1 Hz, 2H), 1.42 (t, J=7.1 Hz, 3H); MS (ESI+) m/z=575.4 $(2M+H)^+$.

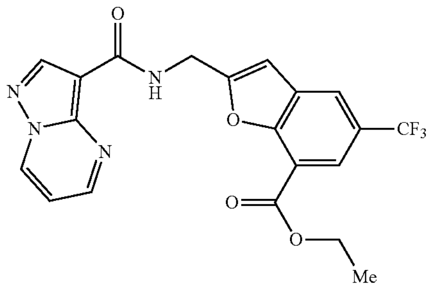 [SMILES: CCOC(=O)c1cc(C(F)(F)F)cc2cc(CNC(=O)c3cnn4cccnc34)oc12]

E) Ethyl 2-((pyrazolo[1,5-a]pyrimidine-3-carboxamido)methyl)-5-(trifluoromethyl)benzofuran-7-carboxylate Pyrazolo[1,5-a]pyrimidine-3-carboxylic acid (212 mg, 1.30 mmol) was dissolved in DMF (2.2 mL). DIPEA (760 μl, 4.34 mmol) and ethyl 2-(aminomethyl)-5-(trifluoromethyl) benzofuran-7-carboxylate, TFA salt (418 mg, 1.09 mmol) were added. BOP (720 mg, 1.63 mmol) was then added and the reaction was stirred at room temperature overnight. After 16 hours, the reaction was diluted with water and extracted with EtOAc and DCM (solubility of product in organic solvent is poor). Organics were dried over sodium sulfate, filtered, and concentrated in vacuo. The crude residue was purified via silica gel column chromatography (24 g column, 0-100% EtOAc in hexanes, product elutes at ~60% EtOAc) to give ethyl 2-((pyrazolo[1,5-a]pyrimidine-3-carboxamido) methyl)-5-(trifluoromethyl)benzofuran-7-carboxylate (472 mg, 0.873 mmol, 80% yield) as a pale yellow solid. MS (ESI+) m/z=433.3 $(M+H)^+$.

F) 2-((Pyrazolo[1,5-a]pyrimidine-3-carboxamido) methyl)-5-(trifluoromethyl)benzofuran-7-carboxylic acid Ethyl 2-((pyrazolo[1,5-a]pyrimidine-3-carboxamido) methyl)-5-(trifluoromethyl)benzofuran-7-carboxylate (472 mg, 1.09 mmol) was taken up in THE (3.3 mL), methanol (2.2 mL), and water (4.4 mL). LiOH (261 mg, 10.9 mmol) was added and the reaction was stirred at room temperature for 1 hour. The solvent was then removed under reduced pressure and water was added. The pH value of the mixture was adjusted to 4-5 with acetic acid and a precipitate formed. The precipitate was filtered to give 2-((pyrazolo[1, 5-a]pyrimidine-3-carboxamido)methyl)-5-(trifluoromethyl) benzofuran-7-carboxylic acid (210 mg, 0.519 mmol, 47.6% yield). $^1H$ NMR (500 MHz, DMSO-$d_6$) δ 9.30 (br d, J=6.4 Hz, 1H), 8.83 (br d, J=3.1 Hz, 1H), 8.62 (s, 1H), 8.59-8.52 (m, 1H), 8.10 (s, 1H), 7.93 (s, 1H), 7.28 (br dd, J=6.3, 4.4 Hz, 1H), 6.92 (s, 1H), 4.82 (br d, J=5.5 Hz, 2H); MS (ESI+) m/z=405.1 $(M+H)^+$.

Example 196

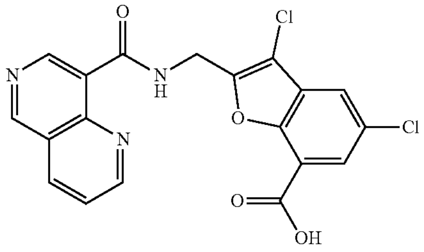 [SMILES: O=C(NCc1oc2c(C(=O)O)cc(Cl)cc2c1Cl)c1cncc2cccnc12]

2-((1,6-naphthyridine-8-carboxamido)methyl)-3,5-dichlorobenzofuran-7-carboxylic acid A mixture of 1,6-naphthyridine-8-carboxylic acid, HCl (10 mg, 0.047 mmol), methyl 2-(aminomethyl)-3,5-dichlorobenzofuran-7-carboxylate, TFA (18.43 mg, 0.047 mmol, Example 113), HATU (18.05 mg, 0.047 mmol) and Hunig's Base (0.033 mL, 0.190 mmol) in THF (0.5 mL) was stirred at rt for 3 h. To the reaction, lithium hydroxide hydrate (38.9 mg, 0.950 mmol) and water (0.500 mL) were added. The reaction was stirred at rt for 12 h. The solvent was evaporated and the residue was dissolved in 1:1 DMF/AcOH. The suspension was filtered and purified by preparative LC/MS (Method B) to give the title compound (3.1 mg, 7.37 μmol, 15.51% yield). $^1H$ NMR (500 MHz, DMSO-$d_6$) δ 11.10 (br s, 1H), 11.06 (br s, 1H), 9.58 (s, 1H), 9.34 (s, 1H), 9.29 (br s, 1H), 9.05 (br d, J=4.0 Hz, 1H), 8.63 (br d, J=7.6 Hz, 1H), 8.77 (br d, J=8.2 Hz, 1H), 8.26 (s, 1H), 8.03-7.38 (m, 4H), 4.99-4.83 (m, 2H); MS (ESI+) m/z=415.9 $(M+H)^+$.

Example 197

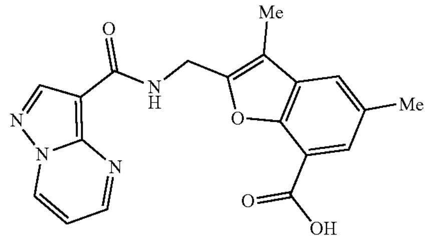 [SMILES: Cc1cc(C(=O)O)c2oc(CNC(=O)c3cnn4cccnc34)c(C)c2c1]

3,5-Dimethyl-2-((pyrazolo[1,5-a]pyrimidine-3-carboxamido)methyl)benzofuran-7-carboxylic acid

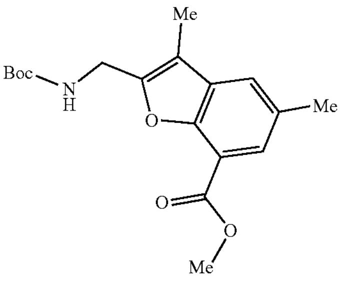 [SMILES: COC(=O)c1cc(C)cc2c(C)c(CNC(=O)OC(C)(C)C)oc12]

A) Methyl 2-(((tert-butoxycarbonyl)amino)methyl)-3,5-dimethylbenzofuran-7-carboxylate

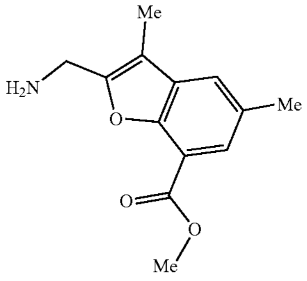 [SMILES: COC(=O)c1cc(C)cc2c(C)c(CN)oc12]

A vial was charged with methyl 2-(((tert-butoxycarbonyl) amino)methyl)-5-methyl-3-(4,4,5,5-tetramethyl-1,3,2-dioxaborolan-2-yl)benzofuran-7-carboxylate (850 mg, 1.909 mmol, Step A of Example 117), methyl iodide (0.239 mL, 3.82 mmol), 1,1'-bis(di-tert-butylphospino)ferrocene palladium dichloride (124 mg, 0.191 mmol) and potassium phosphate tribasic aqueous solution (1.909 mL, 5.73 mmol, 3M) in toluene (5 mL). The solution was degassed and heated to 50° C. for 1 hour. LCMS of the reaction showed 30% of the title product and 70% of the des-boronated material. The reaction solution was cooled, diluted with ethyl acetate, washed with saturated sodium bicarbonate, water, and saturated sodium chloride, dried with anhydrous sodium sulfate, filtered, and concentrated in vacuo. The crude product mixture was purified via preparative HPLC (Method C) to yield the title compound (197 mg, 31% yield). 1H NMR (400 MHz, Chloroform-d) δ 7.81-7.68 (m, 1H), 7.47 (dd, J=1.7, 0.7 Hz, 1H), 4.58-4.36 (m, 2H), 4.02 (s, 3H), 2.48 (s, 3H), 2.34 (s, 3H), 1.56-1.33 (m, 9H); MS (ESI+) m/z=278.1 $(M-55)^+$.

B) Methyl 2-(aminomethyl)-3,5-dimethylbenzofuran-7-carboxylate, TFA

A flask was charged with methyl 2-(((tert-butoxycarbonyl)amino)methyl)-3,5-dimethylbenzofuran-7-carboxylate (197 mg, 0.591 mmol), DCM (5 mL) and TFA (0.5 mL). The reaction solution was stirred at room temperature for 2 hours. The solution was concentrated in vacuo to give methyl 3-allyl-2-(aminomethyl)-5-methylbenzofuran-7-carboxylate, TFA (202 mg, 98% yield), which was used in the next step without further purification. $^1$H NMR (400 MHz, Methanol-$d_4$) δ 7.79-7.70 (m, 1H), 7.67-7.58 (m, 1H), 6.94-6.86 (m, 1H), 4.35-4.26 (m, 2H), 3.93 (s, 3H), 2.49 (s, 3H), 2.35 (s, 3H); MS (ESI+) m/z=217.0 $(M-16)^+$.

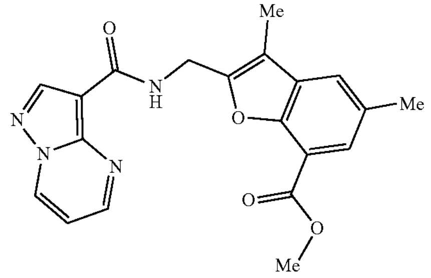 [SMILES: COC(=O)c1cc(C)cc2c(C)c(CNC(=O)c3cnn4cccnc34)oc12]

C) Methyl 3,5-dimethyl-2-((pyrazolo[1,5-a]pyrimidine-3-carboxamido)methyl)benzofuran-7-carboxylate To a vial was added pyrazolo[1,5-a]pyrimidine-3-carboxylic acid (95 mg, 0.582 mmol), methyl 2-(aminomethyl)-3,5-dimethylbenzofuran-7-carboxylate, TFA (202 mg, 0.582 mmol), and DIEA (0.406 mL, 2.327 mmol) in acetonitrile (2 mL). To the solution was added BOP (386 mg, 0.872 mmol) and the reaction stirred at room temperature for 16 hours. The reaction was quenched with water. The resulting product precipitate was filtered and dissolved in 2 mL of DMF, and purified via preparative HPLC (Method B) to yield the title compound (150 mg, 68.2% yield). $^1$H NMR (400 MHz, Chloroform-d) δ 8.80-8.75 (m, 1H), 8.73-8.70 (m, 1H), 8.67-8.64 (m, 1H), 8.48-8.36 (m, 1H), 7.76-7.73 (m, 1H), 7.50-7.46 (m, 1H), 7.03-6.98 (m, 1H), 4.89 (d, J=5.7 Hz, 2H), 4.02-3.95 (m, 3H), 2.49 (s, 3H), 2.35 (s, 3H); MS (ESI+) m/z=379.1 $(M+H)^+$.

D) 3,5-Dimethyl-2-((pyrazolo[1,5-a]pyrimidine-3-carboxamido)methyl)benzofuran-7-carboxylic acid, TFA A flask was charged with methyl 3,5-dimethyl-2-((pyrazolo[1,5-a]pyrimidine-3-carboxamido)methyl)benzofuran-7-carboxylate (24 mg, 0.063 mmol), lithium hydroxide (0.063 mL, 0.127 mmol, 2M) in methanol (2 mL) and tetrahydrofuran (2 mL). The reaction solution was stirred at room temperature for 3 hours. The reaction was concentrated in vacuo and acidified with 1N HCl. The product was extracted with DCM, the organic phase was dried with anhydrous sodium sulfate and concentrated in vacuo. The crude product mixture was purified via preparative HPLC (Method C) to yield the title compound (10 mg, 0.020 mmol, 31.3% yield). $^1$H NMR (400 MHz, DMSO-d6) δ 7.88-7.84 (m, 1H), 7.83-7.77 (m, 2H), 7.70-7.64 (m, 1H), 7.25-7.19 (m, 1H), 6.97-6.89 (m, 1H), 6.84-6.75 (m, 1H), 4.12-3.99 (m, 2H), 1.72 (s, 3H), 1.57 (s, 3H); MS (ESI+) m/z=365 $(M+H)^+$.

Example 201

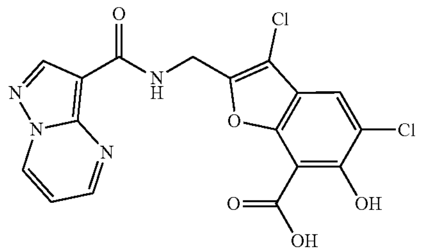 [SMILES: O=C(O)c1c(O)c(Cl)cc2c(Cl)c(CNC(=O)c3cnn4cccnc34)oc12]

3,5-Dichloro-6-hydroxy-2-((pyrazolo[1,5-a]pyrimidine-3-carboxamido)methyl)benzofuran-7-carboxylic acid

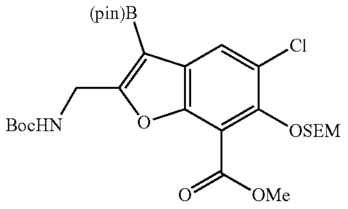

A) Methyl 2-(((tert-butoxycarbonyl)amino)methyl)-5-chloro-3-(4,4,5,5-tetramethyl-1,3,2-dioxaborolan-2-yl)-6-((2-(trimethylsilyl)ethoxy)methoxy)benzofuran-7-carboxylate To a vial charged with methyl 2-(((tert-butoxycarbonyl)amino)methyl)-5-chloro-6-((2-(trimethylsilyl)ethoxy)methoxy)benzofuran-7-carboxylate (200.5 mg, 0.413 mmol, Step D in Example 127), bis(pinacolato)diboron (119 mg, 0.470 mmol), and 4,4'-di-tert-butyl-2,2'-bipyridine (11.1 mg, 0.041 mmol) was added hexanes (1.85 mL). The mixture was sparged with N2 for 3 min and then (1,5-cyclooctadiene)(methoxy)iridium(I) dimer (16.41 mg, 0.025 mmol) was added. The reaction mixture was sparged with N2 for an additional 30 seconds, sealed, and heated to 80° C. for 6 h. The reaction mixture was cooled to room temperature and concentrated in vacuo. The residue was dissolved in DCM and purified by flash chromatography (ISCO 12 g column, 0-30% EtOAc in hexanes) to give the title compound (115.7 mg, 46%). $^1$H NMR (400 MHz, Chloroform-d) δ 7.99 (s, 1H), 5.67 (br s, 1H), 5.20 (s, 2H), 4.64 (br d, J=4.7 Hz, 2H), 4.00 (s, 3H), 3.95-3.87 (m, 2H), 1.47 (s, 9H), 1.39 (s, 12H), 1.06-0.96 (m, 2H), 0.05 (s, 9H); MS (ESI+) m/z=612.1 $(M+H)^+$.

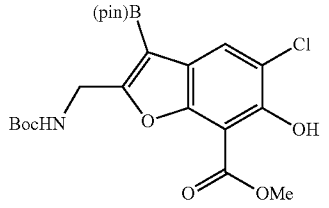

B) Methyl 2-(((tert-butoxycarbonyl)amino)methyl)-5-chloro-6-hydroxy-3-(4,4,5,5-tetramethyl-1,3,2-dioxaborolan-2-yl)benzofuran-7-carboxylate A solution of methyl 2-(((tert-butoxycarbonyl)amino) methyl)-5-chloro-3-(4,4,5,5-tetramethyl-1,3,2-dioxaborolan-2-yl)-6-((2-(trimethylsilyl)ethoxy) methoxy)benzofuran-7-carboxylate (115.7 mg, 0.189 mmol) and copper(II) chloride (50.8 mg, 0.378 mmol) in MeOH was heated to 50° C. under N2 for 80 min. The reaction mixture was cooled to room temperature and water was added. The resultant slurry was filtered and the filter cake was rinsed with water. The solid was collected and dried on high vacuum to give the title compound (76.4 mg, 84%). $^1$H NMR (400 MHz, Chloroform-d) δ 11.75 (s, 1H), 8.08 (s, 1H), 5.70 (br s, 1H), 4.66 (br d, J=5.3 Hz, 2H), 4.09 (s, 3H), 1.49 (s, 9H), 1.40 (s, 12H); MS (ESI+) m/z=520.0 $(M+K)^+$.

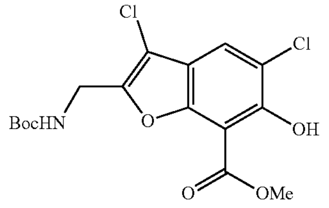 [SMILES: COC(=O)c1c(O)c(Cl)cc2c(Cl)c(CNC(=O)OC(C)(C)C)oc12]

C) Methyl 2-(((tert-butoxycarbonyl)amino)methyl)-3,5-dichloro-6-hydroxybenzofuran-7-carboxylate A solution of methyl 2-(((tert-butoxycarbonyl)amino) methyl)-5-chloro-6-hydroxy-3-(4,4,5,5-tetramethyl-1,3,2-dioxaborolan-2-yl)benzofuran-7-carboxylate (76.4 mg, 0.159 mmol) and copper(II) chloride (42.6 mg, 0.317 mmol) in MeOH was heated to 50° C. under N2 for 22 h. The reaction mixture was cooled to room temperature and water was added. The resultant slurry was filtered and the filter cake was rinsed with water. The solid was collected and dried on high vacuum to give the title compound (56.0 mg, 90%). $^1$H NMR (400 MHz, Chloroform-d) δ 11.86 (s, 1H), 7.75 (s, 1H), 4.93 (br s, 1H), 4.55 (br d, J=2.5 Hz, 2H), 4.11 (s, 3H), 1.50 (s, 9H); MS (ESI+) m/z=390.1 $(M+H)^+$.

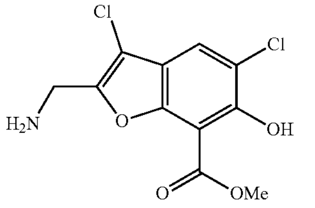 [SMILES: COC(=O)c1c(O)c(Cl)cc2c(Cl)c(CN)oc12]

D) Methyl 2-(aminomethyl)-3,5-dichloro-6-hydroxybenzofuran-7-carboxylate

To a solution of methyl 2-(((tert-butoxycarbonyl)amino) methyl)-3,5-dichloro-6-hydroxybenzofuran-7-carboxylate (56.0 mg, 0.144 mmol) in DCM (807 μL) was added TFA (269 μL). The reaction mixture was stirred for 3 h and then concentrated in vacuo and placed on high vacuum. The residue was dissolved in DMSO and purified by flash chromatography (Gold C18 ISCO 50 g column, 5-95% MeCN in water with TFA) to give the title compound (30.3 mg, 52%) as the TFA salt. $^1$H NMR (400 MHz, Methanol-$d_4$) δ 7.83 (s, 1H), 4.92-4.83 (m, 2H), 4.11 (s, 3H); MS (ESI+) m/z=272.9 $(M-NH_2)^+$.

E) Methyl 3,5-dichloro-6-hydroxy-2-((pyrazolo[1,5-a]pyrimidine-3-carboxamido)methyl)benzofuran-7-carboxylate To a flask charged with methyl 2-(aminomethyl)-3,5-dichloro-6-hydroxybenzofuran-7-carboxylate, TFA (30.3 mg, 0.075 mmol), pyrazolo[1,5-a]pyrimidine-3-carboxylic acid (15.9 mg, 0.097 mmol) and ((1H-benzo[d][1,2,3]triazol-1-yl)oxy)tris(dimethylamino)phosphonium hexafluorophosphate(V) (43.1 mg, 0.097 mmol) was added DMF (0.75 mL) and DIPEA (47 μL, 0.270 mmol) and the reaction mixture was stirred at room temperature for 3 h. Additional portions of pyrazolo[1,5-a]pyrimidine-3-carboxylic acid (4 mg, 0.025 mmol), ((1H-benzo[d][1,2,3]triazol-1-yl)oxy)tris (dimethylamino) phosphonium hexafluorophosphate(V) (10 mg, 0.023 mmol), and DIPEA (10 μL, 0.058 mmol) were added and the reaction mixture was stirred for 30 min. The reaction mixture was diluted with water and a precipitate formed. The slurry was filtered and the filter cake was rinsed with water. The solid was collected and placed on high vacuum to give the title compound (9.8 mg, 29%). The filtrate was extracted with EtOAc. The organic layers were combined, washed with a 10% aqueous solution of LiCl, washed with brine, dried over $MgSO_4$, filtered, and concentrated in vacuo. The residue was dissolved in DCM and purified by flash chromatography (ISCO 4 g column, 0-10% MeOH in DCM) to give additional semipure title compound (25.0 mg) that was used without further purification. $^1$H NMR (400 MHz, DMSO-$d_6$) δ 11.35 (br s, 1H), 9.33 (dd, J=7.0, 1.7 Hz, 1H), 8.84 (dd, J=4.1, 1.5 Hz, 1H), 8.62 (s, 1H), 8.47 (t, J=5.8 Hz, 1H), 7.90 (s, 1H), 7.29 (dd, J=7.0, 4.2 Hz, 1H), 4.81 (d, J=5.9 Hz, 2H), 3.93 (s, 3H); MS (ESI+) m/z=435.0 $(M+H)^+$.

F) 3,5-Dichloro-6-hydroxy-2-((pyrazolo[1,5-a]pyrimidine-3-carboxamido)methyl)benzofuran-7-carboxylic acid Semipure methyl 3,5-dichloro-6-hydroxy-2-((pyrazolo[1,5-a]pyrimidine-3-carboxamido)methyl)benzofuran-7-carboxylate (25 mg) was suspended in THE (460 μL), water (460 μL), and MeOH (230 μL). Lithium hydroxide monohydrate (12.1 mg, 0.287 mmol) was added and the reaction mixture was stirred for 2.5 h. The reaction mixture was transferred to a vial and rinsed with 2.5 mL of a 1:2:2 (v/v/v) solution of MeOH, THF, and water. The vial was flushed with N2, sealed, and heated to 160° C. for 15 min. The reaction mixture was cooled to room temperature and concentrated in vacuo. The residue was dissolved in 2 mL DMSO, filtered through a syringe filter, and purified by preparative LC/MS (Method A). Fractions containing the desired product were combined and dried via centrifugal evaporation to give the title compound (5.4 mg, 21%) as the TFA salt. $^1$H NMR (500 MHz, DMSO-$d_6$) δ 9.30 (br d, J=6.7 Hz, 1H), 8.82 (br s, 1H), 8.61 (s, 1H), 8.41 (br s, 1H), 7.64 (s, 1H), 7.27 (br s, 1H), 4.77 (br d, J=5.2 Hz, 2H); MS (ESI+) m/z=420.9 $(M+H)^+$.

Example 202

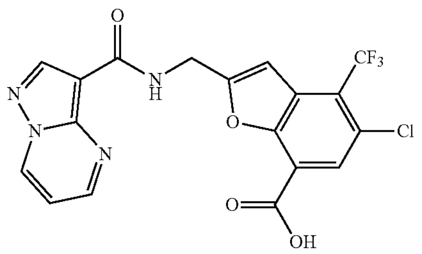 [SMILES: O=C(O)c1cc(Cl)c(C(F)(F)F)c2cc(CNC(=O)c3cnn4cccnc34)oc12]

5-Chloro-2-((pyrazolo[1,5-a]pyrimidine-3-carboxamido)methyl)-4-(trifluoromethyl)benzofuran-7-carboxylic acid

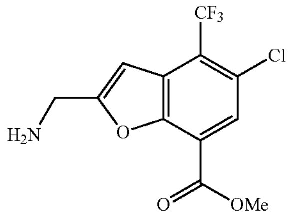 [SMILES: COC(=O)c1cc(Cl)c(C(F)(F)F)c2cc(CN)oc12]

A) Methyl 2-(aminomethyl)-5-chloro-4-(trifluoromethyl)benzofuran-7-carboxylate To a biphasic mixture of methyl 2-(aminomethyl)-5-chlorobenzofuran-7-carboxylate, TFA (50 mg, 0.141 mmol, Step C of Example 48) and sodium trifluoromethanesulfinate (66.2 mg, 0.424 mmol) in DCM (561 μL) and water (224 μL) was slowly added tert-butyl hydroperoxide, 70% in water (98 μL, 0.707 mmol) at 0° C. The reaction mixture was warmed to room temperature and stirred for 2 h. The reaction mixture was cooled to 0° C. and additional portions of sodium trifluoromethanesulfinate (66.2 mg, 0.424 mmol) and tert-butyl hydroperoxide, 70% in water (98 μL, 0.707 mmol) were added. The reaction mixture was warmed to room temperature and stirred for 14 h. The reaction mixture was quenched with a saturated aqueous solution of $NaHCO_3$ and extracted with EtOAc. The organic layers were combined and washed with brine, dried over $MgSO_4$, filtered, and concentrated in vacuo. The residue was dissolved in DCM and purified by flash chromatography (ISCO 4 g column, 0-10% MeOH in DCM) to give the title compound (17.8 mg, 41%). $^1$H NMR (400 MHz, Chloroform-d) δ 7.98 (s, 1H), 6.90 (br s, 1H), 4.04 (m, 5H); MS (ESI+) m/z=307.9 $(M+H)^+$.

B) Methyl 5-chloro-2-((pyrazolo[1,5-a]pyrimidine-3-carboxamido)methyl)-4-(trifluoromethyl)benzofuran-7-carboxylate To a flask charged with methyl 2-(aminomethyl)-5-chloro-4-(trifluoromethyl)benzofuran-7-carboxylate (17.8 mg, 0.058 mmol), pyrazolo[1,5-a]pyrimidine-3-carboxylic acid (10.4 mg, 0.064 mmol), and ((1H-benzo[d][1,2,3]triazol-1-yl)oxy)tris(dimethylamino)phosphonium hexafluorophosphate(V) (28.1 mg, 0.064 mmol) was added DMF (0.58 mL) and DIPEA (30 μL, 0.174 mmol) and the reaction mixture was stirred at room temperature for 1.5 h. The reaction mixture was diluted with water and extracted with EtOAc. The organic layers were combined, washed with a 10% aqueous solution of LiCl, washed with brine, dried over $MgSO_4$, filtered, and concentrated in vacuo. The residue was dissolved in DCM and purified by flash chromatography (ISCO 4 g column, 0-10% MeOH in DCM) to give the title compound (15.2 mg, 58%). $^1$H NMR (500 MHz, DMSO-$d_6$) δ 9.33 (br d, J=7.0 Hz, 1H), 8.84 (br d, J=3.7 Hz, 1H), 8.64 (s, 1H), 8.58 (br t, J=5.6 Hz, 1H), 7.95 (s, 1H), 7.30 (dd, J=6.7, 4.3 Hz, 1H), 7.01 (br s, 1H), 4.87 (br d, J=5.8 Hz, 2H), 3.94 (s, 3H); MS (ESI+) m/z=453.1 $(M+H)^+$.

C) 5-Chloro-2-((pyrazolo[1,5-a]pyrimidine-3-carboxamido)methyl)-4-(trifluoromethyl)benzofuran-7-carboxylic acid Methyl 5-chloro-2-((pyrazolo[1,5-a]pyrimidine-3-carboxamido)methyl)-4-(trifluoromethyl)benzofuran-7-carboxylate (15.2 mg, 0.034 mmol) was suspended in THF (537 μL), water (537 μL), and MeOH (269 μL). Lithium hydroxide monohydrate (7.0 mg, 0.168 mmol) was added and the reaction mixture was stirred for 8 h. The reaction mixture was concentrated in vacuo. The residue was dissolved in 2 mL DMSO, filtered through a syringe filter, and purified by preparative LC/MS (Method B). Fractions containing the desired product were combined and dried via centrifugal evaporation to give the title compound (2.3 mg, 15%). $^1$H NMR (500 MHz, DMSO-$d_6$) δ 9.33-9.24 (m, 1H), 8.86-8.78 (m, 1H), 8.62 (s, 1H), 8.55-8.44 (m, 1H), 7.68 (s, 1H), 7.27 (dd, J=7.0, 4.2 Hz, 1H), 6.88 (br d, J=2.2 Hz, 1H), 4.83 (br d, J=5.7 Hz, 2H); MS (ESI+) m/z=439.1 $(M+H)^+$.

Example 203

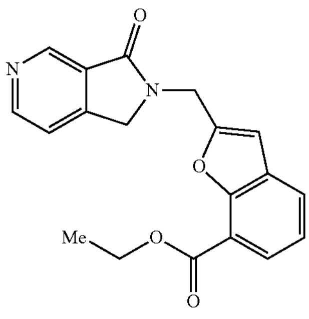 [SMILES: CCOC(=O)c1cccc2cc(CN3Cc4ccncc4C3=O)oc12]

Ethyl 2-((3-oxo-1,3-dihydro-2H-pyrrolo[3,4-c]pyridin-2-yl)methyl)benzofuran-7-carboxylate

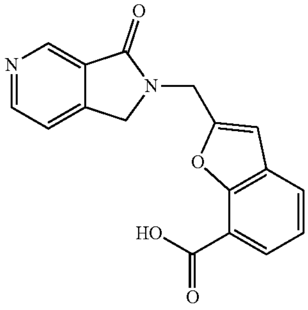 [SMILES: O=C(O)c1cccc2cc(CN3Cc4ccncc4C3=O)oc12]

A) 2-((3-Oxo-1,3-dihydro-2H-pyrrolo[3,4-c]pyridin-2-yl)methyl)benzofuran-7-carboxylic acid Methyl 2-((3-oxo-1,3-dihydro-2H-pyrrolo[3,4-c]pyridin-2-yl)methyl)benzofuran-7-carboxylate (347 mg, 1.08 mmol, Example 2) was taken up in THE (4.31 mL), methanol (2.15 mL), and water (4.31 mL). LiOH (258 mg, 10.8 mmol) was added and the reaction stirred at room temperature. After 1 hour, the solvent was removed under reduced pressure and water was added. The pH of the reaction mixture was adjusted to 4-5 with acetic acid and the aqueous layer turned cloudy. The resulting precipitate was extracted with EtOAc. The combined organic extracts were dried with sodium sulfate, filtered, and concentrated in vacuo to give 2-((3-oxo-1,3-dihydro-2H-pyrrolo[3,4-c]pyridin-2-yl)methyl) benzofuran-7-carboxylic acid (97 mg, 0.315 mmol, 29.2% yield). $^1$H NMR (400 MHz, Methanol-$d_4$) δ 8.98 (s, 1H), 8.72 (d, J=5.3 Hz, 1H), 7.89 (dd, J=7.6, 1.2 Hz, 1H), 7.80 (dd, J=7.7, 1.2 Hz, 1H), 7.71-7.66 (m, 1H), 7.31 (t, J=7.7 Hz, 1H), 6.90 (s, 1H), 5.04 (s, 2H), 4.77 (s, 2H); MS (ESI+) m/z=309.3 $(M+H)^+$.

B) Ethyl 2-((3-oxo-1,3-dihydro-2H-pyrrolo[3,4-c]pyridin-2-yl)methyl)benzofuran-7-carboxylate 2-((3-Oxo-1,3-dihydro-2H-pyrrolo[3,4-c]pyridin-2-yl) methyl)benzofuran-7-carboxylic acid (10 mg, 0.032 mmol) was dissolved in DMF (162 μl) and DIPEA (23 μl, 0.130 mmol) and ethanol (14.9 mg, 0.162 mmol) were added. BOP (21.5 mg, 0.049 mmol) was added and the reaction was stirred at room temperature for 2 hours. The reaction was then diluted with 1.5 mL DMF, filtered, and purified via HPLC (Method A) to give ethyl 2-((3-oxo-1,3-dihydro-2H-pyrrolo[3,4-c]pyridin-2-yl)methyl)benzofuran-7-carboxylate (3.7 mg, 10.9 μmol, 33.6% yield). $^1$H NMR (500 MHz, DMSO-$d_6$) δ 8.94 (s, 1H), 8.76 (br d, J=4.9 Hz, 1H), 7.88 (br d, J=7.6 Hz, 1H), 7.82 (d, J=7.6 Hz, 1H), 7.69 (br d, J=4.6 Hz, 1H), 7.35 (t, J=7.6 Hz, 1H), 7.01 (s, 1H), 4.98 (s, 2H), 4.68 (s, 2H), 4.31 (q, J=7.1 Hz, 2H), 1.27 (t, J=7.0 Hz, 3H); MS (ESI+) m/z=337.2 $(M+H)^+$.

Example 204

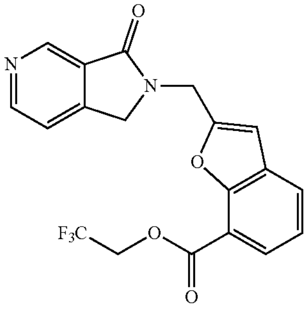

2,2,2-Trifluoroethyl 2-((3-oxo-1,3-dihydro-2H-pyrrolo[3,4-c]pyridin-2-yl)methyl)benzofuran-7-carboxylate 2-((3-Oxo-1,3-dihydro-2H-pyrrolo[3,4-c]pyridin-2-yl) methyl)benzofuran-7-carboxylic acid (15 mg, 0.049 mmol, Step A of Example 203) was dissolved in DMF (243 μl). DIPEA (34.0 μl, 0.195 mmol) and 2,2,2-trifluoroethan-1-ol (24.3 mg, 0.243 mmol) were added. BOP (32.3 mg, 0.073 mmol) was added and the reaction was stirred at room temperature for 1 hour. The reaction was diluted with 1.5 mL DMF, filtered, and purified via HPLC (Method B) to give 2,2,2-trifluoroethyl 2-((3-oxo-1,3-dihydro-2H-pyrrolo[3,4-c]pyridin-2-yl)methyl)benzofuran-7-carboxylate (2.6 mg, 6.59 μmol, 13.6% yield). $^1$H NMR (500 MHz, DMSO-$d_6$) δ 8.94 (s, 1H), 8.76 (d, J=4.9 Hz, 1H), 7.97 (d, J=7.6 Hz, 1H), 7.88 (d, J=7.6 Hz, 1H), 7.67 (d, J=4.9 Hz, 1H), 7.41 (t, J=7.6 Hz, 1H), 7.05 (s, 1H), 5.06-4.94 (m, 4H), 4.67 (s, 2H); MS (ESI+) m/z=391.0 $(M+H)^+$.

Examples 205-306

The following examples were synthesized from the corresponding esters according to the procedure outlined in Example 204.

| Ex. No. | Structure | Name | $^1$H NMR | LCMS $(M + H)^+$ |
|---|---|---|---|---|
| 205 | 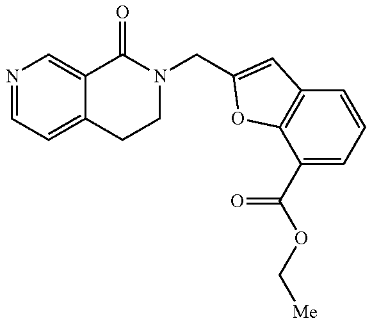 [SMILES: CCOC(=O)c1cccc2cc(CN3CCc4ccncc4C3=O)oc12] | Ethyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.95 (s, 1H), 8.61 (d, J = 4.9 Hz, 1H), 7.87 (d, J = 7.6 Hz, 1H), 7.81 (d, J = 7.3 Hz, 1H), 7.40-7.30 (m, 2H), 6.97 (s, 1H), 4.93 (s, 2H), 4.31 (q, J = 7.0 Hz, 2H), 3.74 (t, J = 6.6 Hz, 2H), 3.07 (t, J = 6.6 Hz, 2H), 1.26 (t, J = 7.2 Hz, 3H) | 351.0 |

-continued

| Ex. No. | Structure | Name | $^1$H NMR | LCMS $(M + H)^+$ |
|---|---|---|---|---|
| 206 | 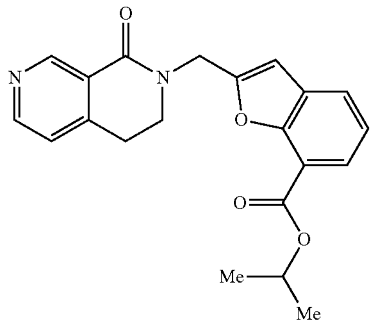 [SMILES: CC(C)OC(=O)c1cccc2cc(CN3CCc4ccncc4C3=O)oc12] | Isopropyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.96 (s, 1H), 8.59 (br d, J = 4.8 Hz, 1H), 7.85 (d, J = 7.6 Hz, 1H), 7.77 (d, J = 7.5 Hz, 1H), 7.39-7.29 (m, 2H), 6.95 (s, 1H), 5.15 (dt, J = 12.4, 6.2 Hz, 1H), 4.93 (s, 2H), 3.72 (t, J = 6.6 Hz, 2H), 3.05 (t, J = 6.6 Hz, 2H), 1.26 (d, J = 6.2 Hz, 6H) | 365.0 |
| 207 | 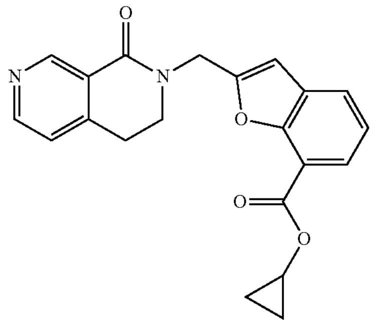 [SMILES: O=C(OC1CC1)c1cccc2cc(CN3CCc4ccncc4C3=O)oc12] | Cyclopropyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.96 (s, 1H), 8.60 (br d, J = 4.9 Hz, 1H), 7.87 (d, J = 7.3 Hz, 1H), 7.77 (d, J = 7.3 Hz, 1H), 7.39-7.30 (m, 2H), 6.96 (s, 1H), 4.92 (s, 2H), 4.32 (tt, J = 6.1, 3.2 Hz, 1H), 3.69 (t, J = 6.7 Hz, 2H), 3.05 (t, J = 6.6 Hz, 2H), 0.77-0.67 (m, 4H) | 363.0 |
| 208 | 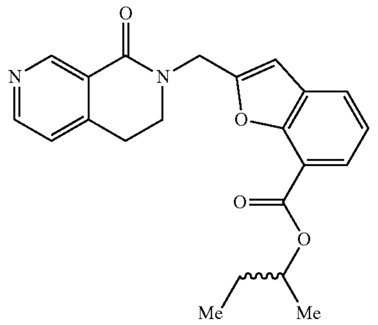 [SMILES: CCC(C)OC(=O)c1cccc2cc(CN3CCc4ccncc4C3=O)oc12] | Sec-butyl 2-((1-oxo-3,4-dihydro-2,7-naphthyridin-2(1H)-yl)methyl)benzofuran-7-carboxylate (racemic) | $^1$H NMR (500 MHz, DMSO-$d_6$) δ 8.97 (s, 1H), 8.60 (d, J = 4.9 Hz, 1H), 7.86 (d, J = 7.2 Hz, 1H), 7.79 (d, J = 7.6 Hz, 1H), 7.39-7.30 (m, 2H), 6.97 (s, 1H), 5.07-5.00 (m, 1H), 4.94 (q, J = 15.9 Hz, 2H), 3.71 (t, J = 6.6 Hz, 2H), 3.05 (t, J = 6.6 Hz, 2H), 1.68-1.52 (m, 2H), 1.24 (d, J = 6.3 Hz, 3H), 0.84 (t, J = 7.4 Hz, 3H) | 379.0 |
| 209 | 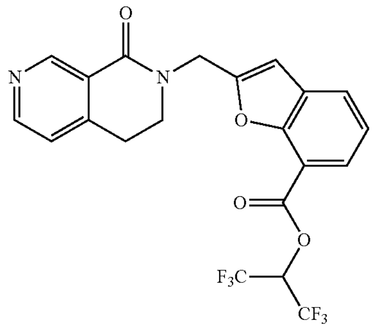 [SMILES: O=C(OC(C(F)(F)F)C(F)(F)F)c1cccc2cc(CN3CCc4ccncc4C3=O)oc12] | 1,1,1-Trifluoropropan-2-yl 2-((1-oxo-3,4-dihydro-2,7-naphthyridin-2(1H)-yl)methyl)benzofuran-7-carboxylate | $^1$H NMR (500 MHz, DMSO-$d_6$) δ 8.95 (s, 1H), 8.61 (d, J = 4.9 Hz, 1H), 8.04 (d, J = 7.6 Hz, 1H), 7.93 (d, J = 7.6 Hz, 1H), 7.45 (t, J = 7.6 Hz, 1H), 7.36 (d, J = 4.9 Hz, 1H), 7.12-7.07 (m, 1H), 7.06 (s, 1H), 4.94 (s, 2H), 3.72 (t, J = 6.6 Hz, 2H), 3.04 (t, J = 6.6 Hz, 2H) | 473.1 |

-continued

| Ex. No. | Structure | Name | $^1$H NMR | LCMS (M + H)$^+$ |
|---|---|---|---|---|
| 210 | 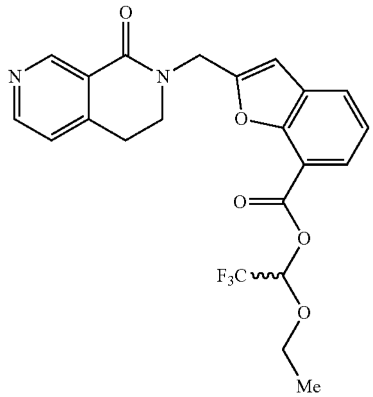 [SMILES: CCOC(OC(=O)c1cccc2cc(CN3CCc4ccncc4C3=O)oc12)C(F)(F)F] | 1-Ethoxy-2,2,2-trifluoroethyl 2-((1-oxo-3,4-dihydro-2,7-naphthyridin-2(1H)-yl)methyl)benzofuran-7-carboxylate (racemic) | $^1$H NMR (500 MHz, DMSO-$d_6$) δ 8.95 (s, 1H), 8.61 (d, J = 4.9 Hz, 1H), 7.98 (d, J = 7.3 Hz, 1H), 7.88 (d, J = 7.6 Hz, 1H), 7.42 (t, J = 7.8 Hz, 1H), 7.37 (d, J = 4.9 Hz, 1H), 7.03 (s, 1H), 6.65-6.59 (m, 1H), 4.93 (s, 2H), 3.98-3.86 (m, 2H), 3.74 (t, J = 6.6 Hz, 2H), 3.06 (t, J = 6.6 Hz, 2H), 1.16 (t, J = 7.0 Hz, 3H) | 449.1 |
| 211 | 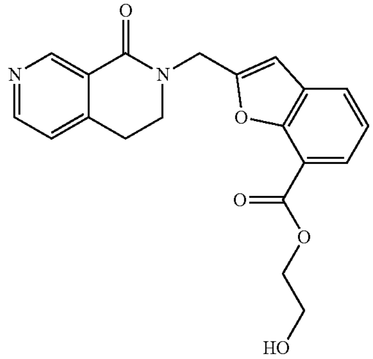 [SMILES: O=C(OCCO)c1cccc2cc(CN3CCc4ccncc4C3=O)oc12] | 2-Hydroxyethyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.94 (br s, 1H), 8.60 (br s, 1H), 7.87 (d, J = 7.7 Hz, 1H), 7.85 (br d, J = 7.6 Hz, 1H), 7.41-7.32 (m, 2H), 6.96 (s, 1H), 4.92 (s, 2H), 4.30 (t, J = 4.9 Hz, 2H), 3.82-3.69 (m, 4H), 3.07 (br t, J = 6.5 Hz, 2H) | 367.1 |
| 212 | 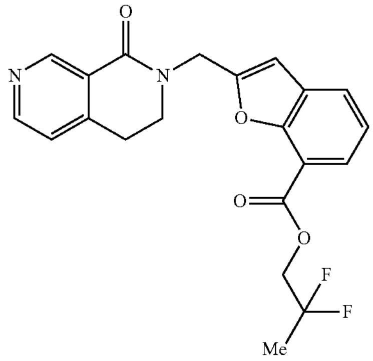 [SMILES: CC(F)(F)COC(=O)c1cccc2cc(CN3CCc4ccncc4C3=O)oc12] | 2,2-Difluoropropyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.94 (br s, 1H), 8.58 (br s, 1H), 7.91 (d, J = 7.7 Hz, 1H), 7.85 (d, J = 7.6 Hz, 1H), 7.37 (t, J = 7.7 Hz, 1H), 7.34 (br d, J = 4.6 Hz, 1H), 6.98 (s, 1H), 4.91 (s, 2H), 4.55 (t, J = 12.9 Hz, 2H), 3.69 (br t, J = 6.6 Hz, 2H), 3.08-2.99 (m, 2H), 1.69 (br t, J = 19.2 Hz, 3H) | 401.1 |
| 213 | 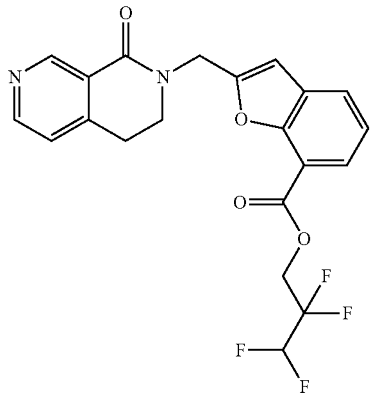 [SMILES: O=C(OCC(F)(F)C(F)F)c1cccc2cc(CN3CCc4ccncc4C3=O)oc12] | 2,2,3,3-Tetrafluoropropyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.96 (s, 1H), 8.59 (br d, J = 4.8 Hz, 1H), 7.94 (d, J = 7.7 Hz, 1H), 7.88 (d, J = 7.7 Hz, 1H), 7.39 (t, J = 7.7 Hz, 1H), 7.34 (d, J = 4.9 Hz, 1H), 7.00 (s, 1H), 6.73-6.46 (m, 1H), 4.93 (s, 2H), 4.86 (br t, J = 13.7 Hz, 2H), 3.72 (br t, J = 6.6 Hz, 2H), 3.05 (br t, J = 6.5 Hz, 2H) | 437.0 |

-continued

| Ex. No. | Structure | Name | $^1$H NMR | LCMS (M + H)$^+$ |
|---|---|---|---|---|
| 214 | 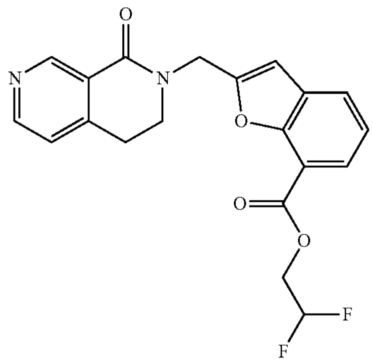 [SMILES: O=C(OCC(F)F)c1cccc2cc(CN3CCc4ccncc4C3=O)oc12] | 2,2-Difluoroethyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.94 (br s, 1H), 8.58 (br s, 1H), 7.91 (d, J = 7.7 Hz, 1H), 7.84 (d, J = 7.7 Hz, 1H), 7.42-7.31 (m, 2H), 6.96 (s, 1H), 6.48-6.17 (m, 1H), 4.91 (s, 2H), 4.58 (td, J = 15.2, 2.9 Hz, 2H), 3.73 (t, J = 6.6 Hz, 2H), 3.05 (t, J = 6.6 Hz, 2H) | 386.9 |
| 215 | 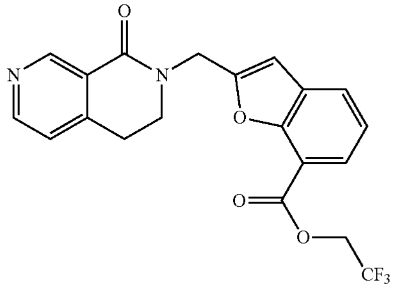 [SMILES: O=C(OCC(F)(F)F)c1cccc2cc(CN3CCc4ccncc4C3=O)oc12] | 2,2,2-Trifluoroethyl 2-((1-oxo-3,4-dihydro-2,7-naphthyridin-2(1H)-yl)methyl)benzofuran-7-carboxylate | $^1$H NMR (500 MHz, DMSO-$d_6$) δ 8.94 (s, 1H), 8.57 (br d, J = 4.6 Hz, 1H), 7.91 (d, J = 7.7 Hz, 1H), 7.83 (d, J = 7.6 Hz, 1H), 7.36 (t, J = 7.7 Hz, 1H), 7.32 (d, J = 4.8 Hz, 1H), 6.96 (s, 1H), 4.96 (q, J = 9.0 Hz, 2H), 4.90 (s, 2H), 3.72 (t, J = 6.6 Hz, 2H), 3.03 (t, J = 6.6 Hz, 2H) | 405.0 |
| 216 | 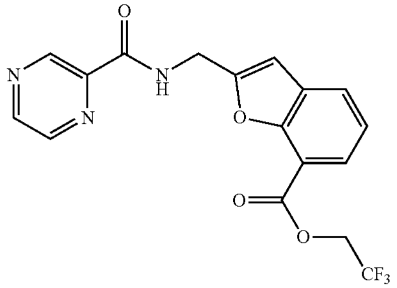 [SMILES: O=C(NCc1cc2cccc(C(=O)OCC(F)(F)F)c2o1)c1cnccn1] | 2,2,2-Trifluoroethyl 2-((pyrazine-2-carboxamido)methyl)benzofuran-7-carboxylate | $^1$H NMR (500 MHz, DMSO-$d_6$) δ 9.37 (br s, 1H), 9.20 (s, 1H), 8.86 (s, 1H), 8.72 (s, 1H), 7.92 (d, J = 7.6 Hz, 1H), 7.84 (d, J = 7.7 Hz, 1H), 7.38 (t, J = 7.7 Hz, 1H), 6.87 (s, 1H), 4.97 (q, J = 8.9 Hz, 2H), 4.74 (d, J = 6.0 Hz, 2H) | 380.1 |
| 217 | 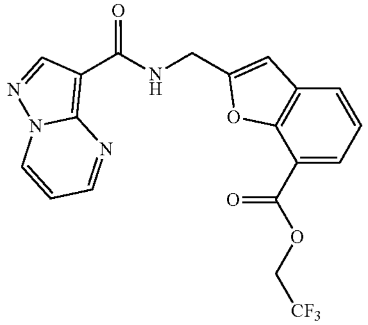 | 2,2,2-Trifluoroethyl 2-((pyrazolo[1,5-a]pyrimidine-3-carboxamido)methyl)benzofuran-7-carboxylate | $^1$H NMR (500 MHz, DMSO-$d_6$) δ 9.23 (br d, J = 6.9 Hz, 1H), 8.79 (br d, J = 3.6 Hz, 1H), 8.59 (s, 1H), 8.48 (br t, J = 5.4 Hz, 1H), 7.92 (d, J = 7.6 Hz, 1H), 7.84 (d, J = 7.6 Hz, 1H), 7.38 (t, J = 7.7 Hz, 1H), 7.25 (dd, J = 6.8, 4.3 Hz, 1H), 6.90 (s, 1H), 4.98 (q, J = 8.9 Hz, 2H), 4.80 (d, J = 5.8 Hz, 2H) | 419.0 |

-continued

| Ex. No. | Structure | Name | $^1$H NMR | LCMS $(M + H)^+$ |
|---|---|---|---|---|
| 218 | 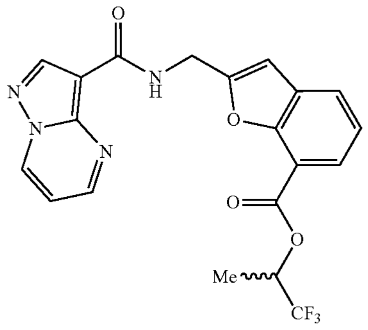 | 1,1,1-Trifluoropropan-2-yl 2-((pyrazolo[1,5-a]pyrimidine-3-carboxamido)methyl)benzofuran-7-carboxylate | $^1$H NMR (500 MHz, DMSO-$d_6$) δ 9.26 (br d, J = 7.1 Hz, 1H), 8.79 (br d, J = 3.9 Hz, 1H), 8.60 (s, 1H), 8.50-8.41 (m, 1H), 7.92 (d, J = 7.6 Hz, 1H), 7.83 (d, J = 7.7 Hz, 1H), 7.38 (t, J = 7.7 Hz, 1H), 7.26 (dd, J = 6.7, 4.2 Hz, 1H), 6.90 (s, 1H), 5.70 (dt, J = 13.4, 6.7 Hz, 1H), 4.81 (br d, J = 5.8 Hz, 2H), 1.49 (d, J = 6.6 Hz, 3H) | 433.2 |
| 219 | 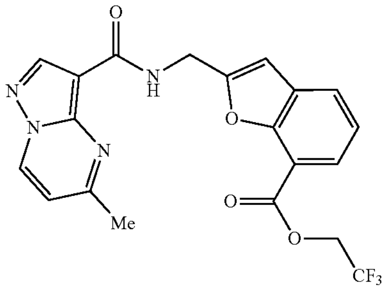 | 2,2,2-Trifluoroethyl 2-((5-methyl pyrazolo[1,5-a]pyrimidine-3-carboxamido)methyl)benzofuran-7-carboxylate | $^1$H NMR (500 MHz, DMSO-$d_6$) δ 9.10 (d, J = 7.2 Hz, 1H), 8.56-8.47 (m, 2H), 7.94 (d, J = 7.7 Hz, 1H), 7.86 (d, J = 7.7 Hz, 1H), 7.40 (t, J = 7.7 Hz, 1H), 7.15 (d, J = 7.1 Hz, 1H), 6.91 (s, 1H), 5.02 (q, J = 8.9 Hz, 2H), 4.82 (br d, J = 5.7 Hz, 2H), 2.66 (s, 3H) | 433.1 |
| 220 | 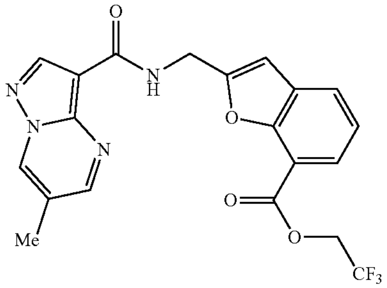 | 2,2,2-Trifluoroethyl 2-((6-methyl pyrazolo[1,5-a]pyrimidine-3-carboxamido)methyl)benzofuran-7-carboxylate | $^1$H NMR (500 MHz, DMSO-$d_6$) δ 9.13 (br s, 1H), 8.71 (s, 1H), 8.53 (s, 1H), 8.42 (br t, J = 5.5 Hz, 1H), 7.93 (d, J = 7.7 Hz, 1H), 7.86 (d, J = 7.6 Hz, 1H), 7.39 (t, J = 7.7 Hz, 1H), 6.90 (s, 1H), 5.02 (q, J = 8.9 Hz, 2H), 4.82 (d, J = 5.8 Hz, 2H), 2.40 (s, 3H) | 433.1 |
| 221 | 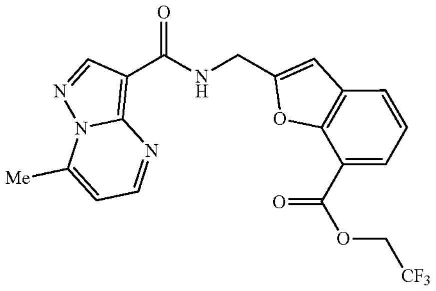 | 2,2,2-Trifluoroethyl 2-((7-methyl pyrazolo[1,5-a]pyrimidine-3-carboxamido)methyl)benzofuran-7-carboxylate | $^1$H NMR (500 MHz, DMSO-$d_6$) δ 8.72 (d, J = 4.3 Hz, 1H), 8.66 (s, 1H), 8.63-8.55 (m, 1H), 7.95 (br d, J = 7.6 Hz, 1H), 7.87 (br d, J = 7.6 Hz, 1H), 7.41 (br t, J = 7.8 Hz, 1H), 7.26 (br d, J = 4.0 Hz, 1H), 6.91 (s, 1H), 5.09-5.00 (m, 2H), 4.87-4.79 (m, 2H), 2.83 (s, 3H) | 433.1 |
| 222 | 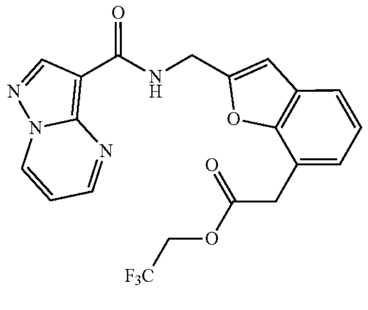 | 2,2,2-Trifluoroethyl 2-(2-((pyrazolo[1,5-a]pyrimidine-3-carboxamido)methyl)benzofuran-7-yl)acetate | $^1$H NMR (500 MHz, DMSO-$d_6$) δ 9.26 (d, J = 6.9 Hz, 1H), 8.85-8.74 (m, 1H), 8.60 (s, 1H), 8.42 (br s, 1H), 7.60-7.47 (m, 1H), 7.27 (dd, J = 7.0, 4.2 Hz, 1H), 7.21-7.14 (m, 2H), 6.79 (s, 1H), 4.84-4.63 (m, 4H), 4.06 (s, 2H) | 433.2 |

-continued

| Ex. No. | Structure | Name | $^1$H NMR | LCMS (M + H)$^+$ |
|---|---|---|---|---|
| 223 | 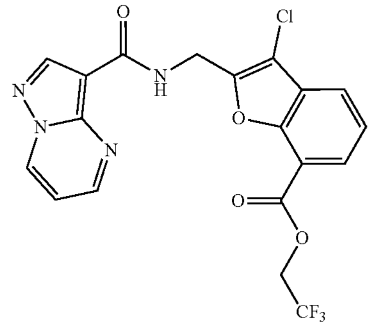 | 2,2,2-Trifluoroethyl 3-chloro-2-((pyrazolo[1,5-a]pyrimidine-3-carboxamido)methyl)benzofuran-7-carboxylate | $^1$H NMR (500 MHz, DMSO-$d_6$) δ 9.30 (d, J = 5.8 Hz, 1H), 8.82 (d, J = 3.1 Hz, 1H), 8.60 (s, 1H), 8.53 (br t, J = 5.6 Hz, 1H), 7.98 (d, J = 7.3 Hz, 1H), 7.93 (d, J = 7.6 Hz, 1H), 7.54 (t, J = 7.6 Hz, 1H), 7.31-7.27 (m, 1H), 4.99 (q, J = 8.9 Hz, 2H), 4.88 (d, J = 5.8 Hz, 2H) | 453.1 |
| 224 | 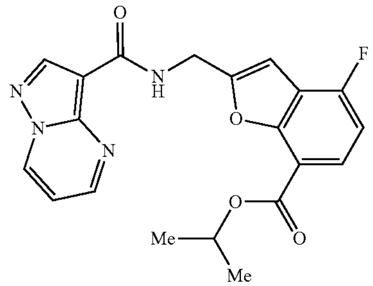 | Isopropyl 4-fluoro-2-((pyrazolo[1,5-a]pyrimidine-3-carboxamido)methyl)benzofuran-7-carboxylate | 1H NMR (500 MHz, DMSO-$d_6$) δ 9.29 (dd, J = 7.0, 1.2 Hz, 1H), 8.82 (dd, J = 4.1, 1.4 Hz, 1H), 8.62 (s, 1H), 8.54 (br t, J = 6.0 Hz, 1H), 7.84 (dd, J = 8.5, 5.5 Hz, 1H), 7.35-7.10 (m, 2H), 6.96 (s, 1H), 5.13 (dt, J = 12.4, 6.3 Hz, 1H), 4.83 (d, J = 6.1 Hz, 2H), 1.26 (d, J = 6.1 Hz, 6H) | 397.0 |
| 225 | 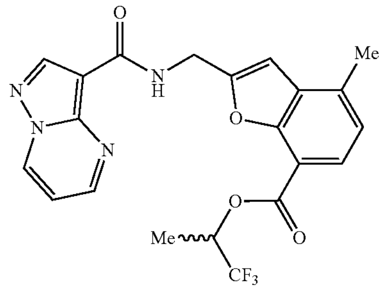 | 1,1,1-Trifluoropropan-2-yl 4-methyl-2-((pyrazolo[1,5-a]pyrimidine-3-carboxamido)methyl)benzofuran-7-carboxylate | $^1$H NMR (500 MHz, DMSO-$d_6$) δ 9.23 (br d, J = 5.7 Hz, 1H), 8.94-8.72 (m, 1H), 8.60 (s, 1H), 8.51 (br s, 1H), 7.73 (d, J = 7.8 Hz, 1H), 7.28 (br s, 1H), 7.19 (d, J = 7.8 Hz, 1H), 6.93 (s, 1H), 5.66 (dt, J = 13.3, 6.6 Hz, 1H), 4.80 (br d, J = 5.5 Hz, 2H), 2.54 (s, 3H), 1.46 (d, J = 6.5 Hz, 3H) | 447.1 |
| 226 | 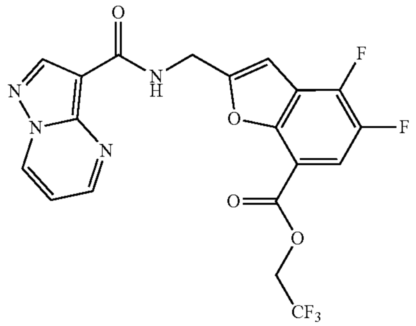 | 2,2,2-Trifluoroethyl 4,5-difluoro-2-((pyrazolo[1,5-a]pyrimidine-3-carboxamido)methyl)benzofuran-7-carboxylate | $^1$H NMR (500 MHz, DMSO-$d_6$) δ 9.27 (br d, J = 6.8 Hz, 1H), 8.81 (br d, J = 3.2 Hz, 1H), 8.61 (s, 1H), 8.51 (br t, J = 5.6 Hz, 1H), 7.84 (dd, J = 11.1, 7.7 Hz, 1H), 7.28 (dd, J = 6.9, 4.2 Hz, 1H), 7.07 (s, 1H), 5.01 (q, J = 8.9 Hz, 2H), 4.83 (d, J = 5.8 Hz, 2H) | 455.2 |
| 227 | 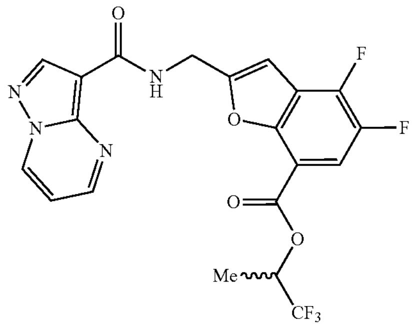 | 1,1,1-Trifluoropropan-2-yl 4,5-difluoro-2-((pyrazolo[1,5-a]pyrimidine-3-carboxamido)methyl)benzofuran-7-carboxylate | $^1$H NMR (500 MHz, DMSO-$d_6$) δ 9.29 (d, J = 7.0 Hz, 1H), 8.82 (br d, J = 4.0 Hz, 1H), 8.61 (s, 1H), 8.55-8.38 (m, 1H), 7.84 (dd, J = 11.1, 7.7 Hz, 1H), 7.28 (dd, J = 6.9, 4.2 Hz, 1H), 7.08 (s, 1H), 5.81-5.60 (m, 1H), 4.84 (d, J = 5.9 Hz, 2H), 1.49 (d, J = 6.6 Hz, 3H) | 469.3 |

-continued

| Ex. No. | Structure | Name | $^1$H NMR | LCMS (M + H)$^+$ |
|---|---|---|---|---|
| 228 | 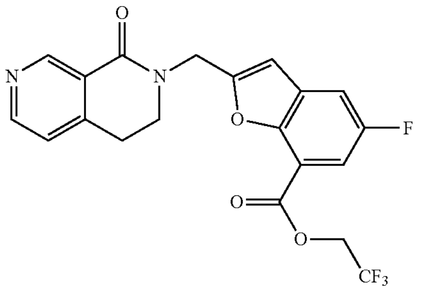 [SMILES: O=C(OCC(F)(F)F)c1cc(F)cc2cc(CN3CCc4ccncc4C3=O)oc12] | 2,2,2-Trifluoroethyl 5-fluoro-2-((1-oxo-3,4-dihydro-2,7-naphthyridin-2(1H)-yl)methyl)benzofuran-7-carboxylate | $^1$H NMR (500 MHz, DMSO-$d_6$) δ 8.95 (s, 1H), 8.61 (br d, J = 4.9 Hz, 1H), 7.83 (dd, J = 8.2, 2.4 Hz, 1H), 7.60 (dd, J = 9.5, 2.4 Hz, 1H), 7.37 (d, J = 4.9 Hz, 1H), 7.03 (s, 1H), 5.03 (q, J = 9.1 Hz, 2H), 4.93 (s, 2H), 3.74 (t, J = 6.6 Hz, 2H), 3.06 (t, J = 6.6 Hz, 2H) | 423.2 |
| 229 | 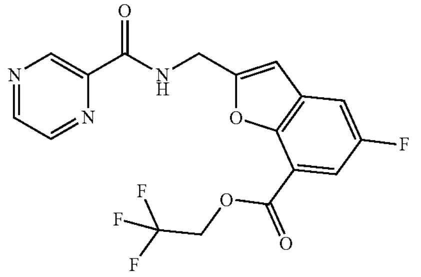 [SMILES: O=C(NCc1cc2cc(F)cc(C(=O)OCC(F)(F)F)c2o1)c1cnccn1] | 2,2,2-Trifluoroethyl 5-fluoro-2-((pyrazine-2-carboxamido)methyl)benzofuran-7-carboxylate | $^1$H NMR (500 MHz, DMSO-$d_6$) δ 9.57 (br t, J = 5.6 Hz, 1H), 9.23 (s, 1H), 8.91 (d, J = 2.1 Hz, 1H), 8.77 (s, 1H), 7.81 (dd, J = 8.2, 2.4 Hz, 1H), 7.59 (dd, J = 9.5, 2.4 Hz, 1H), 6.90 (s, 1H), 5.04 (q, J = 9.1 Hz, 2H), 4.73 (br d, J = 5.8 Hz, 2H) | 398.2 |
| 230 | 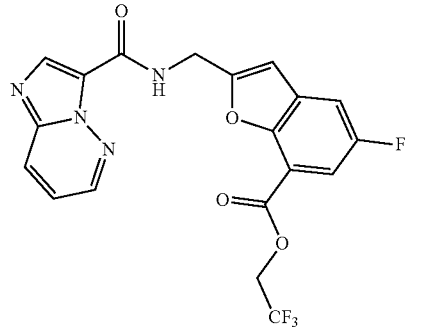 [SMILES: O=C(OCC(F)(F)F)c1cc(F)cc2cc(CNC(=O)c3cnc4cccnn34)oc12] | 2,2,2-Trifluoroethyl 5-fluoro-2-((imidazo[1,2-b]pyridazine-3-carboxamido)methyl)benzofuran-7-carboxylate | $^1$H NMR (500 MHz, DMSO-$d_6$) δ 9.22 (br t, J = 5.6 Hz, 1H), 8.78 (br d, J = 3.1 Hz, 1H), 8.52-8.13 (m, 2H), 7.81 (dd, J = 8.2, 2.4 Hz, 1H), 7.59 (dd, J = 9.5, 2.4 Hz, 1H), 7.49 (dd, J = 9.2, 4.6 Hz, 1H), 6.95 (s, 1H), 5.02 (q, J = 8.9 Hz, 2H), 4.85 (br d, J = 5.8 Hz, 2H) | 437.2 |
| 231 | 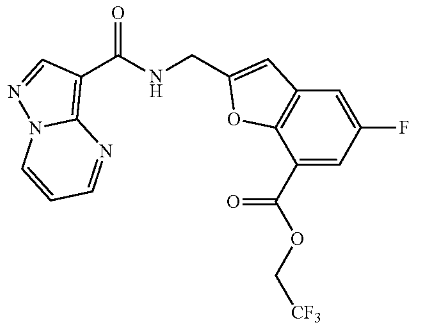 | 2,2,2-Trifluoroethyl 5-fluoro-2-((pyrazolo[1,5-a]pyrimidine-3-carboxamido)methyl)benzofuran-7-carboxylate | $^1$H NMR (500 MHz, DMSO-d6) δ 9.30 (br d, J = 6.7 Hz, 1H), 8.85 (br d, J = 3.1 Hz, 1H), 8.72-8.54 (m, 2H), 7.83 (br d, J = 6.7 Hz, 1H), 7.62 (br d, J = 8.9 Hz, 1H), 7.32 (br dd, J = 6.3, 4.4 Hz, 1H), 6.94 (s, 1H), 5.04 (br d, J = 8.9 Hz, 2H), 4.83 (br d, J = 5.5 Hz, 2H) | 437.3 |

-continued

| Ex. No. | Structure | Name | $^1$H NMR | LCMS (M + H)$^+$ |
|---|---|---|---|---|
| 232 | 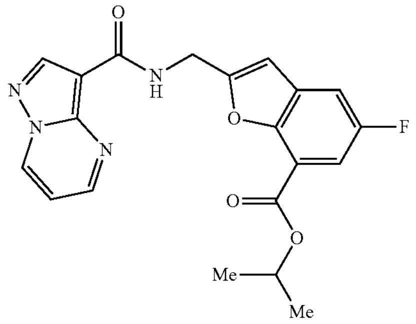 | Isopropyl 5-fluoro-2-((pyrazolo[1,5-a]pyrimidine-3-carboxamido)methyl)benzofuran-7-carboxylate | $^1$H NMR (500 MHz, DMSO-$d_6$) δ 9.27 (br d, J = 6.8 Hz, 1H), 8.81 (br d, J = 3.8 Hz, 1H), 8.61 (s, 1H), 8.52-8.40 (m, 1H), 7.69 (dd, J = 8.3, 2.3 Hz, 1H), 7.51 (dd, J = 9.6, 2.4 Hz, 1H), 7.27 (dd, J = 6.9, 4.4 Hz, 1H), 6.88 (s, 1H), 5.17 (dt, J = 12.4, 6.1 Hz, 1H), 4.82 (d, J = 5.9 Hz, 2H), 1.30 (d, J = 6.2 Hz, 6H) | 397.3 |
| 233 | 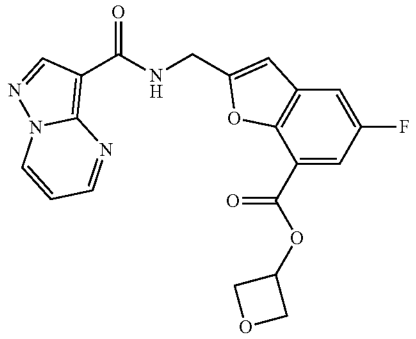 | Oxetan-3-yl 5-fluoro-2-((pyrazolo[1,5-a]pyrimidine-3-carboxamido)methyl)benzofuran-7-carboxylate | $^1$H NMR (500 MHz, DMSO-$d_6$) δ 9.33 (br d, J = 6.4 Hz, 1H), 8.85 (br d, J = 3.1 Hz, 1H), 8.65 (s, 1H), 8.58 (br t, J = 5.5 Hz, 1H), 7.80 (dd, J = 8.4, 2.3 Hz, 1H), 7.65 (dd, J = 9.8, 2.1 Hz, 1H), 7.31 (dd, J = 7.0, 4.3 Hz, 1H), 6.93 (s, 1H), 5.68 (br t, J = 5.5 Hz, 1H), 5.01-4.78 (m, 4H), 4.73-4.54 (m, 2H) | 411.3 |
| 234 | 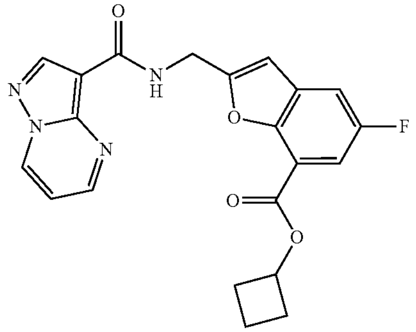 | Cyclobutyl 5-fluoro-2-((pyrazolo[1,5-a]pyrimidine-3-carboxamido)methyl)benzofuran-7-carboxylate | $^1$H NMR (500 MHz, DMSO-$d_6$) δ 9.20 (br d, J = 6.6 Hz, 1H), 8.79 (br d, J = 2.9 Hz, 1H), 8.59 (s, 1H), 8.52 (br t, J = 5.5 Hz, 1H), 7.67 (dd, J = 8.2, 2.4 Hz, 1H), 7.50 (dd, J = 9.6, 2.4 Hz, 1H), 7.25 (dd, J = 6.9, 4.1 Hz, 1H), 6.87 (s, 1H), 5.15 (br t, J = 7.3 Hz, 1H), 4.81 (br d, J = 5.9 Hz, 2H), 2.32 (br d, J = 7.5 Hz, 2H), 2.17-2.03 (m, 2H), 1.82-1.53 (m, 2H) | 409.3 |
| 235 | 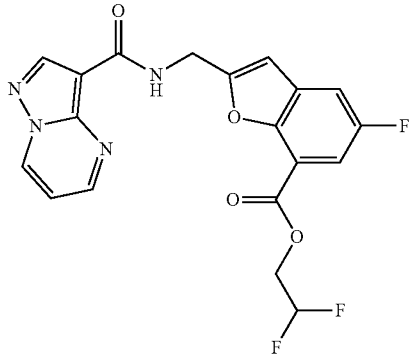 | 2,2-Difluoroethyl 5-fluoro-2-((pyrazolo[1,5-a]pyrimidine-3-carboxamido)methyl)benzofuran-7-carboxylate | $^1$H NMR (500 MHz, DMSO-$d_6$) δ 9.23 (br d, J = 6.6 Hz, 1H), 8.81 (br d, J = 2.8 Hz, 1H), 8.60 (s, 1H), 8.52 (br s, 1H), 7.75 (dd, J = 8.2, 2.4 Hz, 1H), 7.57 (dd, J = 9.5, 2.4 Hz, 1H), 7.26 (dd, J = 6.9, 4.2 Hz, 1H), 6.90 (s, 1H), 6.51-6.19 (m, 1H), 4.80 (br d, J = 5.9 Hz, 2H), 4.62 (td, J = 15.0, 3.0 Hz, 2H) | 419.3 |

-continued

| Ex. No. | Structure | Name | $^1$H NMR | LCMS (M + H)$^+$ |
|---|---|---|---|---|
| 236 | 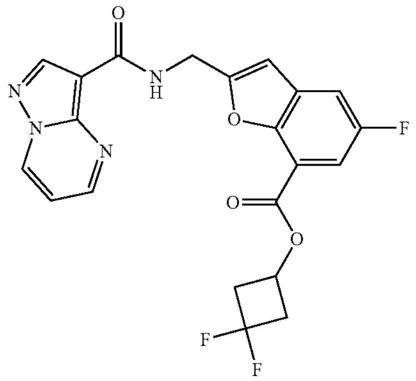 | 3,3-Difluorocyclobutyl 5-fluoro-2-((pyrazolo[1,5-a]pyrimidine-3-carboxamido)methyl)benzofuran-7-carboxylate | $^1$H NMR (500 MHz, DMSO-d$_6$) δ 9.33 (br d, J = 6.7 Hz, 1H), 8.83 (br d, J = 3.4 Hz, 1H), 8.63 (s, 1H), 8.53 (br t, J = 5.6 Hz, 1H), 7.77 (dd, J = 8.2, 2.4 Hz, 1H), 7.61 (dd, J = 9.8, 2.4 Hz, 1H), 7.30 (dd, J = 6.7, 4.3 Hz, 1H), 6.91 (s, 1H), 5.26-5.05 (m, 1H), 4.84 (br d, J = 5.8 Hz, 2H), 3.24-3.05 (m, 2H), 2.89 (qd, J = 14.4, 4.9 Hz, 2H) | 445.3 |
| 237 | 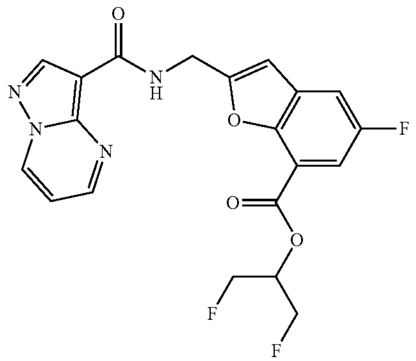 | 1,3-Difluoropropan-2-yl 5-fluoro-2-((pyrazolo[1,5-a]pyrimidine-3-carboxamido)methyl)benzofuran-7-carboxylate | $^1$H NMR (500 MHz, DMSO-d$_6$) δ 9.24 (br d, J = 6.6 Hz, 1H), 8.90-8.75 (m, 1H), 8.60 (s, 1H), 8.50 (br s, 1H), 7.84-7.69 (m, 1H), 7.58 (dd, J = 9.5, 2.2 Hz, 1H), 7.26 (dd, J = 6.8, 4.2 Hz, 1H), 6.90 (s, 1H), 5.70-5.46 (m, 1H), 4.89-4.74 (m, 4H), 4.69 (br d, J = 5.5 Hz, 2H) | 433.3 |
| 238 | 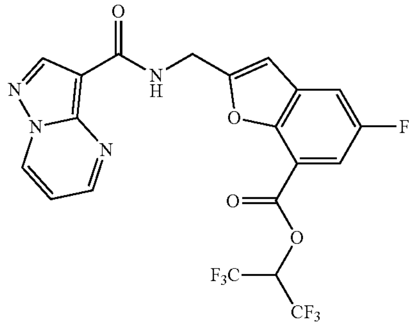 | 1,1,1,3,3,3-Hexafluoropropan-2-yl 5-fluoro-2-((pyrazolo[1,5-a]pyrimidine-3-carboxamido)methyl)benzofuran-7-carboxylate | $^1$H NMR (500 MHz, DMSO-d$_6$) δ 9.35-9.23 (m, 1H), 8.80 (d, J = 3.1 Hz, 1H), 8.61 (s, 1H), 8.54 (br t, J = 5.8 Hz, 1H), 7.88 (dd, J = 8.2, 2.4 Hz, 1H), 7.64 (dd, J = 9.3, 2.6 Hz, 1H), 7.28 (dd, J = 7.0, 4.3 Hz, 1H), 7.11-7.01 (m, 1H), 6.94 (s, 1H), 4.80 (d, J = 5.8 Hz, 2H) | 505.3 |
| 239 | 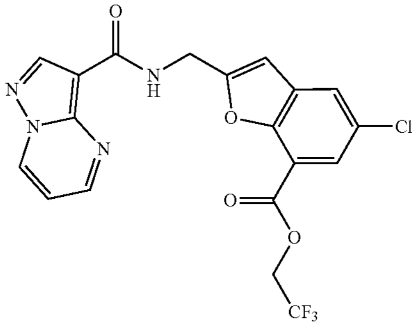 | 2,2,2-Trifluoroethyl 5-chloro-2-((pyrazolo[1,5-a]pyrimidine-3-carboxamido)methyl)benzofuran-7-carboxylate | $^1$H NMR (500 MHz, DMSO-d$_6$) δ 9.28 (br d, J = 6.9 Hz, 1H), 8.82 (br d, J = 3.7 Hz, 1H), 8.61 (s, 1H), 8.49 (br t, J = 5.6 Hz, 1H), 8.02 (d, J = 1.6 Hz, 1H), 7.76 (d, J = 1.6 Hz, 1H), 7.28 (dd, J = 6.9, 4.3 Hz, 1H), 6.90 (s, 1H), 5.02 (q, J = 9.0 Hz, 2H), 4.82 (d, J = 5.9 Hz, 2H) | 453.1 |

-continued

| Ex. No. | Structure | Name | $^1$H NMR | LCMS (M + H)$^+$ |
|---|---|---|---|---|
| 240 | 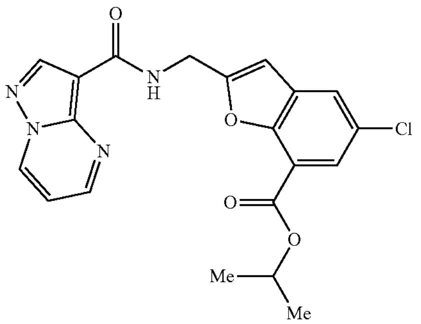 | Isopropyl 5-chloro-2-((pyrazolo[1,5-a]pyrimidine-3-carboxamido)methyl)benzofuran-7-carboxylate | $^1$H NMR (500 MHz, DMSO-$d_6$) δ 9.27 (d, J = 6.9 Hz, 1H), 8.82 (br d, J = 3.1 Hz, 1H), 8.61 (s, 1H), 8.48 (br t, J = 5.7 Hz, 1H), 7.93 (d, J = 1.9 Hz, 1H), 7.70 (d, J = 1.9 Hz, 1H), 7.28 (dd, J = 6.9, 4.2 Hz, 1H), 6.87 (s, 1H), 5.17 (dt, J = 12.4, 6.1 Hz, 1H), 4.83 (d, J = 5.9 Hz, 2H), 1.31 (d, J = 6.2 Hz, 6H) | 413.3 |
| 241 | 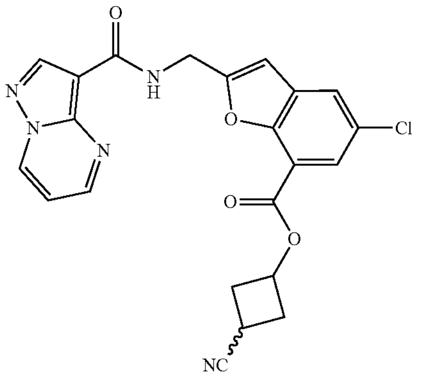 | 3-Cyanocyclobutyl 5-chloro-2-((pyrazolo[1,5-a]pyrimidine-3-carboxamido)methyl)benzofuran-7-carboxylate | $^1$H NMR (500 MHz, DMSO-$d_6$) δ 9.37-9.27 (m, 1H), 8.84 (d, J = 3.1 Hz, 1H), 8.64 (s, 1H), 8.53 (br t, J = 6.0 Hz, 1H), 7.98 (d, J = 2.1 Hz, 1H), 7.79 (d, J = 2.1 Hz, 1H), 7.29 (dd, J = 6.9, 4.1 Hz, 1H), 6.88 (s, 1H), 5.16 (t, J = 7.3 Hz, 1H), 4.83 (br d, J = 5.8 Hz, 2H), 3.25-3.08 (m, 1H), 2.84 (br dd, J = 7.6, 1.8 Hz, 2H), 2.58-2.53 (m, 2H) | 450.3 |
| 242 | 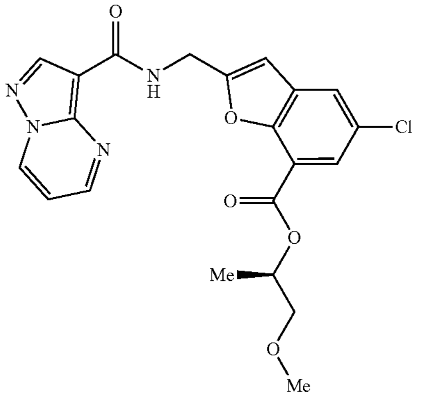 | (R)-1-Methoxypropan-2-yl 5-chloro-2-((pyrazolo[1,5-a]pyrimidine-3-carboxamido)methyl)benzofuran-7-carboxylate | $^1$H NMR (500 MHz, DMSO-$d_6$) δ 9.24 (br d, J = 6.8 Hz, 1H), 8.81 (br d, J = 2.9 Hz, 1H), 8.61 (s, 1H), 8.49 (br s, 1H), 7.93 (d, J = 1.9 Hz, 1H), 7.70 (d, J = 1.9 Hz, 1H), 7.27 (dd, J = 6.9, 4.2 Hz, 1H), 6.87 (s, 1H), 5.24 (td, J = 6.4, 3.9 Hz, 1H), 4.81 (br d, J = 5.9 Hz, 2H), 3.50-3.42 (m, 5H), 1.25 (d, J = 6.5 Hz, 3H) | 443.0 |
| 243 | 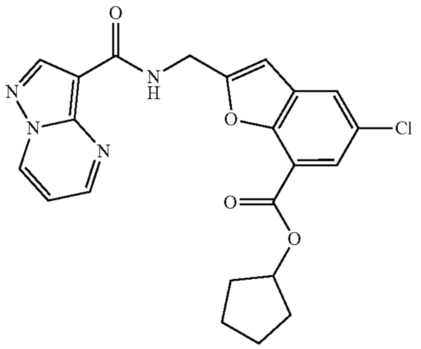 | Cyclopentyl 5-chloro-2-((pyrazolo[1,5-a]pyrimidine-3-carboxamido)methyl)benzofuran-7-carboxylate | $^1$H NMR (500 MHz, DMSO-$d_6$) δ 9.23 (br d, J = 6.9 Hz, 1H), 8.79 (br d, J = 4.0 Hz, 1H), 8.60 (s, 1H), 8.47 (br t, J = 5.6 Hz, 1H), 7.91 (s, 1H), 7.67 (s, 1H), 7.26 (dd, J = 6.6, 4.5 Hz, 1H), 6.87 (s, 1H), 5.34 (br s, 1H), 4.81 (d, J = 5.8 Hz, 2H), 1.95-1.80 (m, 2H), 1.79-1.69 (m, 2H), 1.64 (br d, J = 4.0 Hz, 2H), 1.50 (br s, 2H) | 439.3 |

-continued

| Ex. No. | Structure | Name | $^1$H NMR | LCMS (M + H)$^+$ |
|---|---|---|---|---|
| 244 | 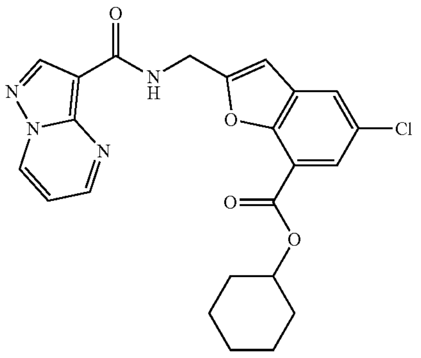 | Cyclohexyl 5-chloro-2-((pyrazolo[1,5-a]pyrimidine-3-carboxamido)methyl)benzofuran-7-carboxylate | $^1$H NMR (500 MHz, DMSO-$d_6$) δ 9.25 (br d, J = 6.6 Hz, 1H), 8.80 (br d, J = 3.7 Hz, 1H), 8.60 (s, 1H), 8.46 (br t, J = 5.6 Hz, 1H), 7.93 (s, 1H), 7.70 (s, 1H), 7.27 (dd, J = 6.5, 4.5 Hz, 1H), 6.88 (s, 1H), 4.99 (br s, 1H), 4.82 (br d, J = 5.8 Hz, 2H), 1.80 (br s, 2H), 1.66 (br d, J = 3.2 Hz, 2H), 1.57-1.15 (m, 6H) | 453.4 |
| 245 | 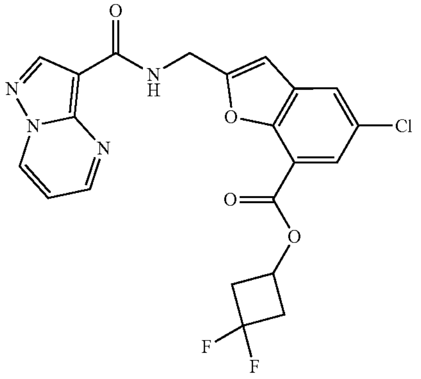 | 3,3-Difluorocyclobutyl 5-chloro-2-((pyrazolo[1,5-a]pyrimidine-3-carboxamido)methyl)benzofuran-7-carboxylate | $^1$H NMR (500 MHz, DMSO-d6) δ 9.29 (d, J = 6.7 Hz, 1H), 8.81 (br d, J = 3.4 Hz, 1H), 8.61 (s, 1H), 8.54 (br t, J = 5.8 Hz, 1H), 7.98 (d, J = 1.5 Hz, 1H), 7.77 (d, J = 1.5 Hz, 1H), 7.28 (dd, J = 7.0, 4.3 Hz, 1H), 6.88 (s, 1H), 5.14 (br dd, J = 7.2, 4.4 Hz, 1H), 4.82 (br d, J = 5.8 Hz, 2H), 3.22-3.07 (m, 2H), 2.87 (br dd, J = 14.8, 4.4 Hz, 2H) | 461.3 |
| 246 | 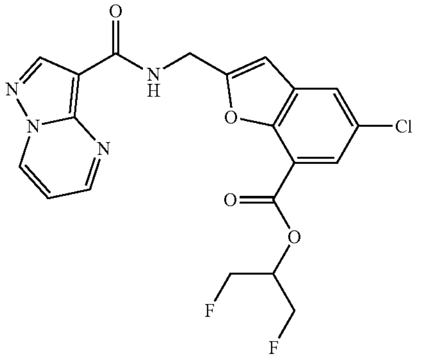 | 1,3-Difluoropropan-2-yl 5-chloro-2-((pyrazolo[1,5-a]pyrimidine-3-carboxamido)methyl)benzofuran-7-carboxylate | $^1$H NMR (500 MHz, DMSO-d6) δ 9.26 (br d, J = 6.7 Hz, 1H), 8.81 (br d, J = 3.7 Hz, 1H), 8.62 (s, 1H), 8.56 (br t, J = 5.8 Hz, 1H), 7.77 (d, J = 1.2 Hz, 1H), 7.27 (dd, J = 6.9, 4.1 Hz, 1H), 6.89 (s, 1H), 5.63-5.44 (m, 1H), 4.85-4.74 (m, 4H), 4.73-4.62 (m, 2H) | 449.3 |
| 247 | 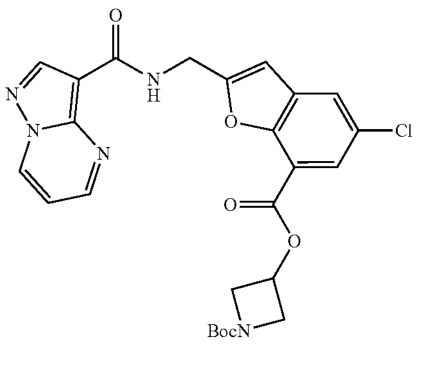 | Tert-butyl 3-((5-chloro-2-((pyrazolo[1,5-a]pyrimidine-3-carboxamido)methyl)benzofuran-7-carbonyl)oxy)azetidine-1-carboxylate | $^1$H NMR (400 MHz, CHLOROFORM-d) δ 8.81 (dd, J = 7.0, 1.7 Hz, 1H), 8.76-8.69 (m, 2H), 8.49 (br t, J = 5.9 Hz, 1H), 7.90 (d, J = 2.1 Hz, 1H), 7.72 (d, J = 2.1 Hz, 1H), 7.04 (dd, J = 7.0, 4.2 Hz, 1H), 6.76 (s, 1H), 5.44 (ddd, J = 6.8, 4.3, 2.4 Hz, 1H), 4.93 (d, J = 6.0 Hz, 2H), 4.40 (ddd, J = 10.1, 6.9, 1.0 Hz, 2H), 4.19-4.13 (m, 2H), 1.49 (s, 9H) | 526.2 |

-continued

| Ex. No. | Structure | Name | $^1$H NMR | LCMS $(M + H)^+$ |
|---|---|---|---|---|
| 248 | 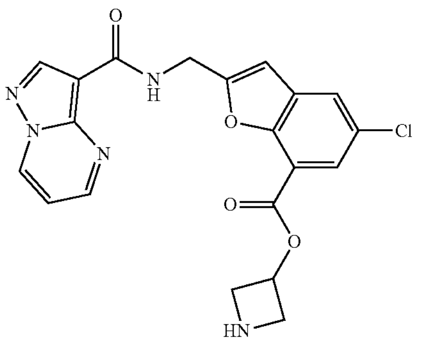 | Azetidin-3-yl 5-chloro-2-((pyrazolo[1,5-a]pyrimidine-3-carboxamido)methyl)benzofuran-7-carboxylate | $^1$H NMR (500 MHz, DMSO-$d_6$) δ 9.34-9.19 (m, 1H), 8.91-8.74 (m, 1H), 8.63 (d, J = 1.2 Hz, 1H), 8.52 (br s, 1H), 8.01 (s, 1H), 7.85 (s, 1H), 7.37-7.18 (m, 1H), 6.91 (s, 1H), 5.52 (br t, J = 5.9 Hz, 1H), 4.83 (br d, J = 5.8 Hz, 2H), 4.45 (br dd, J = 12.3, 6.9 Hz, 2H), 4.26 (br dd, J = 11.7, 4.7 Hz, 2H) | 426.1 |
| 249 | 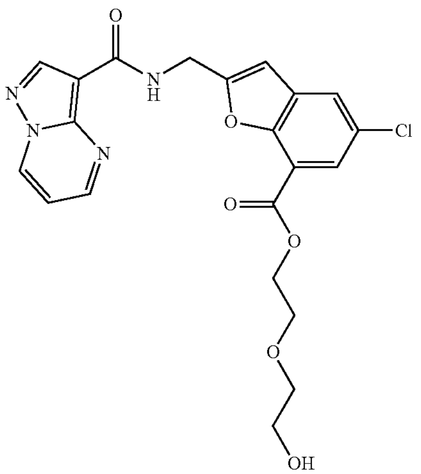 | 2-(2-Hydroxyethoxy)ethyl 5-chloro-2-((pyrazolo[1,5-a]pyrimidine-3-carboxamido)methyl)benzofuran-7-carboxylate | $^1$H NMR (500 MHz, DMSO-$d_6$) δ 9.26 (d, J = 7.0 Hz, 1H), 8.91-8.78 (m, 1H), 8.61 (s, 1H), 8.55 (br t, J = 5.8 Hz, 1H), 7.94 (d, J = 2.1 Hz, 1H), 7.72 (d, J = 2.1 Hz, 1H), 7.27 (dd, J = 7.0, 4.3 Hz, 1H), 6.85 (s, 1H), 4.79 (br d, J = 5.8 Hz, 2H), 4.50-4.38 (m, 2H), 3.77-3.70 (m, 2H), 3.65-3.53 (m, 4H) | 459.2 |
| 250 | 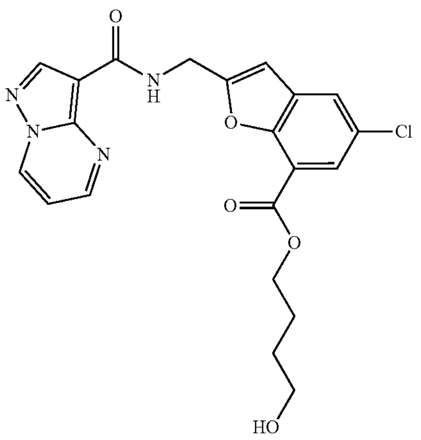 | 4-Hydroxybutyl 5-chloro-2-((pyrazolo[1,5-a]pyrimidine-3-carboxamido)methyl)benzofuran-7-carboxylate | $^1$H NMR (500 MHz, DMSO-$d_6$) δ 9.34-9.20 (m, 1H), 8.81 (br d, J = 2.7 Hz, 1H), 8.61 (s, 1H), 8.53 (br t, J = 5.8 Hz, 1H), 7.93 (d, J = 2.1 Hz, 1H), 7.70 (d, J = 2.1 Hz, 1H), 7.27 (dd, J = 7.0, 4.3 Hz, 1H), 6.85 (s, 1H), 4.79 (br d, J = 5.8 Hz, 2H), 4.55 (t, J = 5.0 Hz, 1H), 4.31 (t, J = 6.4 Hz, 2H), 3.40 (q, J = 6.1 Hz, 2H), 1.76-1.67 (m, 2H), 1.60-1.49 (m, 2H) | 443.3 |

-continued

| Ex. No. | Structure | Name | $^1$H NMR | LCMS $(M + H)^+$ |
|---|---|---|---|---|
| 251 | 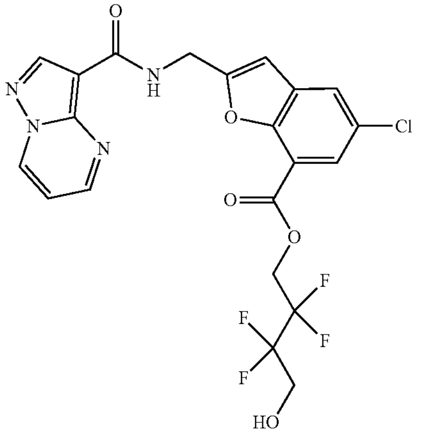 | 2,2,3,3-Tetrafluoro-4-hydroxybutyl 5-chloro-2-((pyrazolo[1,5-a]pyrimidine-3-carboxamido)methyl)benzofuran-7-carboxylate | $^1$H NMR (500 MHz, DMSO-$d_6$) δ 9.19 (br d, J = 6.8 Hz, 1H), 8.75 (br d, J = 3.5 Hz, 1H), 8.55 (s, 1H), 8.46 (br t, J = 5.8 Hz, 1H), 7.94 (s, 1H), 7.70 (d, J = 1.5 Hz, 1H), 7.21 (dd, J = 6.8, 4.3 Hz, 1H), 6.84 (s, 1H), 4.87 (br t, J = 14.8 Hz, 2H), 4.76 (d, J = 5.9 Hz, 2H), 3.87 (td, J = 14.6, 5.8 Hz, 2H) | 515.3 |
| 252 | 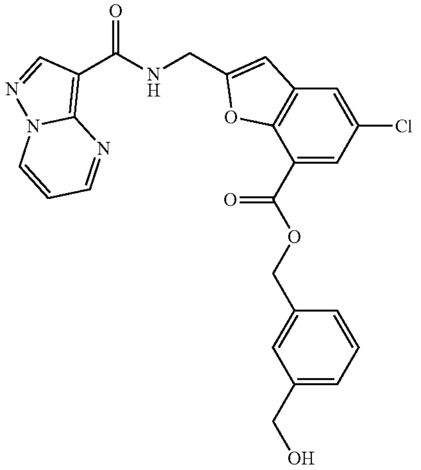 | 3-(Hydroxymethyl)benzyl 5-chloro-2-((pyrazolo[1,5-a]pyrimidine-3-carboxamido)methyl)benzofuran-7-carboxylate | $^1$H NMR (500 MHz, DMSO-$d_6$) δ 9.29 (dd, J = 7.0, 1.2 Hz, 1H), 8.83-8.69 (m, 1H), 8.62 (s, 1H), 8.54 (br t, J = 5.8 Hz, 1H), 7.96 (d, J = 2.1 Hz, 1H), 7.74 (d, J = 2.1 Hz, 1H), 7.46 (s, 1H), 7.41-7.21 (m, 4H), 6.86 (s, 1H), 5.41 (s, 2H), 4.82 (br d, J = 5.8 Hz, 2H), 4.50 (d, J = 5.5 Hz, 2H) | 491.2 |
| 253 | 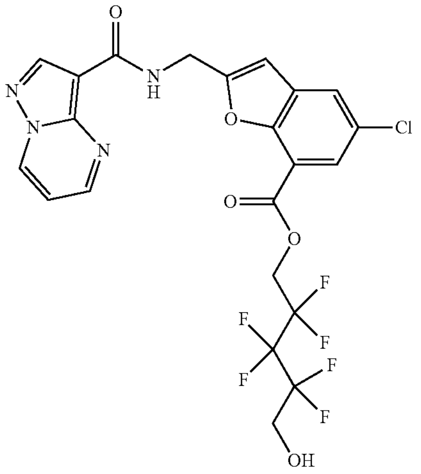 | 2,2,3,3,4,4-Hexafluoro-5-hydroxypentyl 5-chloro-2-((pyrazolo[1,5-a]pyrimidine-3-carboxamido)methyl)benzofuran-7-carboxylate | $^1$H NMR (500 MHz, DMSO-$d_6$) δ 9.24 (dd, J = 7.0, 1.2 Hz, 1H), 8.82-8.72 (m, 1H), 8.59 (s, 1H), 8.57-8.53 (m, 1H), 8.01 (d, J = 2.1 Hz, 1H), 7.73 (d, J = 2.1 Hz, 1H), 7.26 (dd, J = 6.7, 4.3 Hz, 1H), 6.88 (s, 1H), 4.99 (br t, J = 14.3 Hz, 2H), 4.78 (br d, J = 5.8 Hz, 2H), 3.98-3.84 (m, 2H) | 565.2 |

-continued

| Ex. No. | Structure | Name | $^1$H NMR | LCMS $(M + H)^+$ |
|---|---|---|---|---|
| 254 | 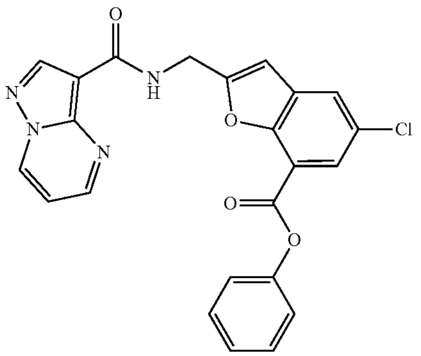 | Phenyl 5-chloro-2-((pyrazolo[1,5-a]pyrimidine-3-carboxamido)methyl)benzofuran-7-carboxylate | $^1$H NMR (500 MHz, DMSO-$d_6$) δ 9.24 (br d, J = 6.4 Hz, 1H), 8.72 (br s, 1H), 8.63-8.53 (m, 2H), 8.03 (br s, 1H), 7.90 (br s, 1H), 7.49-7.39 (m, 2H), 7.36-7.19 (m, 4H), 6.90 (s, 1H), 4.81 (br d, J = 5.2 Hz, 2H) | 447.2 |
| 255 | 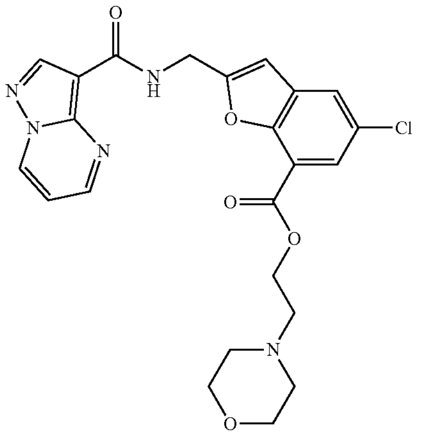 | 2-Morpholinoethyl 5-chloro-2-((pyrazolo[1,5-a]pyrimidine-3-carboxamido)methyl)benzofuran-7-carboxylate | $^1$H NMR (500 MHz, DMSO-$d_6$) δ 9.18 (br d, J = 6.9 Hz, 1H), 8.78 (br d, J = 3.8 Hz, 1H), 8.58 (s, 1H), 8.50 (br t, J = 5.8 Hz, 1H), 7.90 (s, 1H), 7.71 (d, J = 1.8 Hz, 1H), 7.24 (dd, J = 6.7, 4.3 Hz, 1H), 6.86 (s, 1H), 4.77 (br d, J = 5.8 Hz, 2H), 4.41 (t, J = 5.5 Hz, 2H), 3.50-3.44 (m, 4H), 2.67 (t, J = 5.5 Hz, 2H), 2.44-2.39 (m, 4H) | 484.1 |
| 256 | 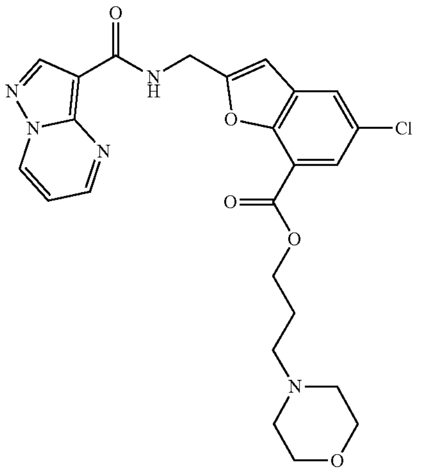 | 3-Morpholinopropyl 5-chloro-2-((pyrazolo[1,5-a]pyrimidine-3-carboxamido)methyl)benzofuran-7-carboxylate | $^1$H NMR (500 MHz, DMSO-$d_6$) δ 9.20 (br d, J = 7.0 Hz, 1H), 8.79 (br d, J = 4.0 Hz, 1H), 8.58 (s, 1H), 8.49 (br t, J = 5.6 Hz, 1H), 7.91 (s, 1H), 7.71 (s, 1H), 7.25 (dd, J = 6.8, 4.3 Hz, 1H), 6.86 (s, 1H), 4.78 (d, J = 5.8 Hz, 2H), 4.34 (t, J = 6.2 Hz, 2H), 3.50-3.44 (m, 4H), 2.39 (br t, J = 7.0 Hz, 2H), 2.29 (br s, 4H), 1.84 (quin, J = 6.6 Hz, 2H) | 498.3 |

-continued

| Ex. No. | Structure | Name | $^1$H NMR | LCMS (M + H)$^+$ |
|---|---|---|---|---|
| 257 | 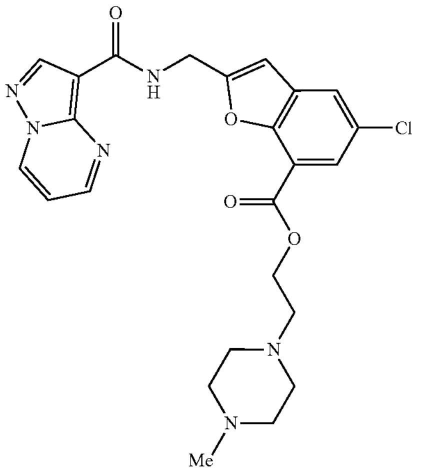 | 2-(4-Methylpiperazin-1-yl)ethyl 5-chloro-2-((pyrazolo[1,5-a]pyrimidine-3-carboxamido)methyl)benzofuran-7-carboxylate | $^1$H NMR (500 MHz, DMSO-$d_6$) δ 9.26 (br d, J = 7.1 Hz, 1H), 8.81 (br d, J = 2.7 Hz, 1H), 8.60 (s, 1H), 8.46 (br t, J = 5.7 Hz, 1H), 7.93 (d, J = 1.9 Hz, 1H), 7.72 (d, J = 2.0 Hz, 1H), 7.27 (dd, J = 6.9, 4.1 Hz, 1H), 6.87 (s, 1H), 4.80 (br d, J = 5.8 Hz, 2H), 4.41 (t, J = 5.6 Hz, 2H), 2.68 (br t, J = 5.6 Hz, 2H), 2.44 (br s, 4H), 2.25 (br s, 4H), 2.09 (s, 3H) | 497.1 |
| 258 | 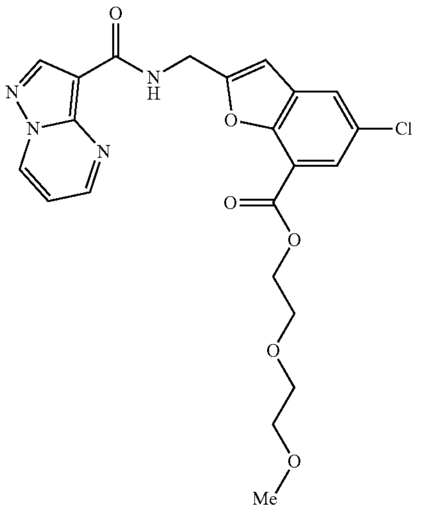 | 2-(2-Methoxyethoxy)ethyl 5-chloro-2-((pyrazolo[1,5-a]pyrimidine-3-carboxamido)methyl)benzofuran-7-carboxylate | $^1$H NMR (500 MHz, DMSO-$d_6$) δ 9.26 (d, J = 5.8 Hz, 1H), 8.81 (br d, J = 3.1 Hz, 1H), 8.61 (s, 1H), 8.54 (br t, J = 5.8 Hz, 1H), 7.94 (d, J = 2.1 Hz, 1H), 7.72 (d, J = 2.1 Hz, 1H), 7.27 (dd, J = 6.9, 4.1 Hz, 1H), 6.86 (s, 1H), 4.79 (br d, J = 5.8 Hz, 2H), 4.46-4.37 (m, 2H), 3.75-3.70 (m, 2H), 3.55-3.52 (m, 2H), 3.40-3.35 (m, 2H), 3.16 (s, 3H) | 473.3 |
| 259 | 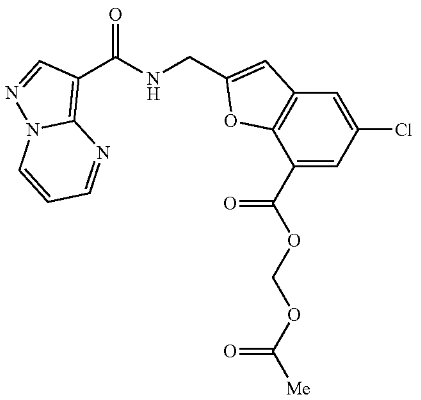 | Acetoxymethyl 5-chloro-2-((pyrazolo[1,5-a]pyrimidine-3-carboxamido)methyl)benzofuran-7-carboxylate | $^1$H NMR (500 MHz, DMSO-$d_6$) δ 9.27 (br d, J = 6.7 Hz, 1H), 8.85-8.79 (m, 1H), 8.61 (s, 1H), 8.56 (br t, J = 5.8 Hz, 1H), 8.00 (d, J = 2.1 Hz, 1H), 7.73 (d, J = 1.8 Hz, 1H), 7.27 (dd, J = 7.0, 4.3 Hz, 1H), 6.87 (s, 1H), 5.94 (s, 2H), 4.79 (br d, J = 5.8 Hz, 2H), 2.07 (s, 3H) | 443.2 |

-continued

| Ex. No. | Structure | Name | $^1$H NMR | LCMS (M + H)$^+$ |
|---|---|---|---|---|
| 260 | 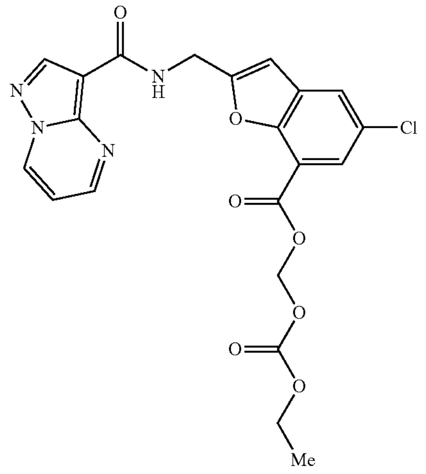 | ((Ethoxycarbonyl)oxy)methyl 5-chloro-2-((pyrazolo[1,5-a]pyrimidine-3-carboxamido)methyl)benzofuran-7-carboxylate | $^1$H NMR (500 MHz, DMSO-$d_6$) δ 9.29-9.21 (m, 1H), 8.82-8.79 (m, 1H), 8.59 (d, J = 1.4 Hz, 1H), 8.50 (br s, 1H), 7.98 (t, J = 2.1 Hz, 1H), 7.74 (t, J = 1.8 Hz, 1H), 7.26 (t, J = 4.6, 1H), 6.87 (s, 1H), 5.97 (s, 2H), 4.80 (br d, J = 5.6 Hz, 2H), 4.17 (q, J = 7.0, 2H), 1.21 (t, J = 7.0 Hz, 3H) | 473.0 |
| 261 | 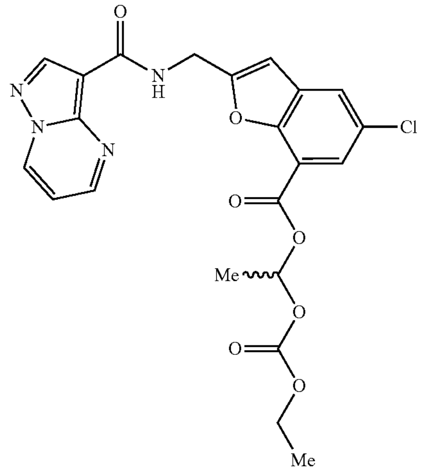 | 1-((Ethoxycarbonyl)oxy)ethyl 5-chloro-2-((pyrazolo[1,5-a]pyrimidine-3-carboxamido)methyl)benzofuran-7-carboxylate (racemic) | $^1$H NMR (500 MHz, DMSO-$d_6$) δ 9.26 (br d, J = 6.7 Hz, 1H), 8.81 (br d, J = 3.4 Hz, 1H), 8.60 (s, 1H), 8.56 (br t, J = 5.6 Hz, 1H), 7.99 (s, 1H), 7.72 (s, 1H), 7.26 (dd, J = 6.7, 4.3 Hz, 1H), 6.90-6.85 (m, 2H), 4.79 (br d, J = 5.8 Hz, 2H), 4.17-4.07 (m, 2H), 1.55 (d, J = 5.2 Hz, 3H), 1.17 (t, J = 7.2 Hz, 3H) | 487.3 |
| 262 | 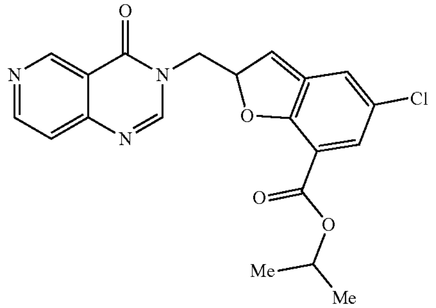 | Isopropyl 5-chloro-2-((4-oxopyrido[4,3-d]pyrimidin-3(4H)-yl)methyl)benzofuran-7-carboxylate | $^1$H NMR (500 MHz, DMSO-$d_6$) δ 9.33 (s, 1H), 8.88 (d, J = 5.5 Hz, 1H), 8.80 (s, 1H), 7.99 (d, J = 1.8 Hz, 1H), 7.72 (d, J = 1.8 Hz, 1H), 7.65 (d, J = 5.5 Hz, 1H), 7.07 (s, 1H), 5.50 (s, 2H), 5.27-5.03 (m, 1H), 1.25 (d, J = 6.1 Hz, 6H) | 398.2 |
| 263 | 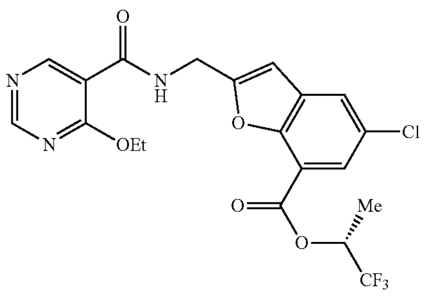 [SMILES: CCOc1ncncc1C(=O)NCc1cc2cc(Cl)cc(C(=O)O[C@H](C)C(F)(F)F)c2o1] | (R)-1,1,1-trifluoropropan-2-yl 5-chloro-2-((4-ethoxypyrimidine-5-carboxamido)methyl)benzofuran-7-carboxylate | $^1$H NMR (500 MHz, DMSO-$d_6$) δ 8.87 (s, 1H), 8.84 (s, 1H), 8.80-8.70 (m, 1H), 8.04 (d, J = 1.9 Hz, 1H), 7.76 (d, J = 1.9 Hz, 1H), 6.92 (s, 1H), 5.74 (dt, J = 13.3, 6.6 Hz, 1H), 4.74 (br d, J = 5.7 Hz, 3H), 4.55 (q, J = 7.0 Hz, 3H), 1.53 (d, J = 6.6 Hz, 4H), 1.37 (t, J = 7.0 Hz, 3H) | 472.3 |

-continued

| Ex. No. | Structure | Name | $^1$H NMR | LCMS $(M + H)^+$ |
|---|---|---|---|---|
| 264 | 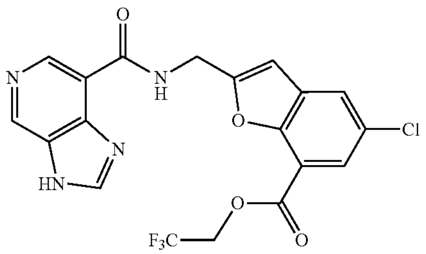 [SMILES: O=C(NCc1cc2cc(Cl)cc(C(=O)OCC(F)(F)F)c2o1)c1cncc2[nH]cnc12] | 2,2,2-Trifluoroethyl 2-((3H-imidazo[4,5-c]pyridine-7-carboxamido)methyl)-5-chlorobenzofuran-7-carboxylate | $^1$H NMR (500 MHz, DMSO-d6) δ 9.70 (br d, J = 3.1 Hz, 1H), 9.11 (s, 1H), 8.93 (s, 1H), 8.55 (br s, 1H), 8.04 (s, 1H), 7.78 (s, 1H), 6.96 (s, 1H), 5.03 (q, J = 8.9 Hz, 2H), 4.87 (br d, J = 5.0 Hz, 2H) | 453.1 |
| 265 | 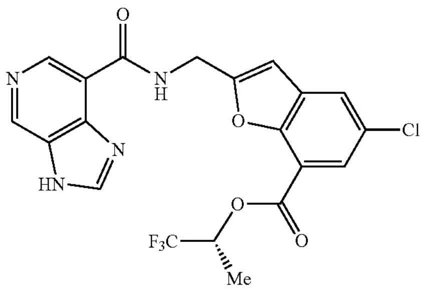 [SMILES: C[C@@H](OC(=O)c1cc(Cl)cc2cc(CNC(=O)c3cncc4[nH]cnc34)oc12)C(F)(F)F] | (R)-1,1,1-Trifluoropropan-2-yl 2-((3H-imidazo[4,5-c]pyridine-7-carboxamido)methyl)-5-chlorobenzofuran-7-carboxylate | $^1$H NMR (500 MHz, DMSO-d6) δ 9.71 (br s, 1H), 9.20 (s, 1H), 8.96 (s, 1H), 8.63 (s, 1H), 8.04 (d, J = 2.0 Hz, 1H), 7.76 (d, J = 2.1 Hz, 1H), 6.97 (s, 1H), 5.72 (dt, J = 13.3, 6.7 Hz, 1H), 4.88 (br d, J = 5.6 Hz, 2H) | 467.1 |
| 266 | 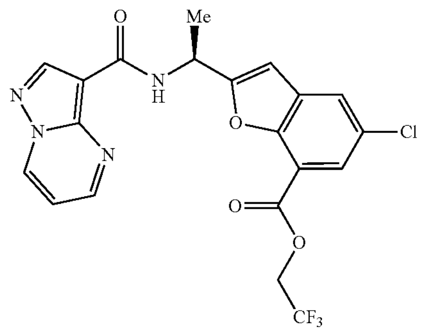 | 2,2,2-Trifluoroethyl (S)-5-chloro-2-(1-(pyrazolo[1,5-a]pyrimidine-3-carboxamido)ethyl)benzofuran-7-carboxylate | $^1$H NMR (500 MHz, DMSO-d6) δ 9.31 (d, J = 6.1 Hz, 1H), 8.82 (br d, J = 3.4 Hz, 1H), 8.62 (s, 1H), 8.39 (br d, J = 7.9 Hz, 1H), 8.04 (d, J = 1.8 Hz, 1H), 7.77 (d, J = 1.8 Hz, 1H), 7.29 (dd, J = 7.0, 4.3 Hz, 1H), 6.94 (s, 1H), 5.50 (br t, J = 7.3 Hz, 1H), 5.04 (q, J = 8.9 Hz, 2H), 1.66 (d, J = 6.7 Hz, 3H) | 467.3 |
| 267 | 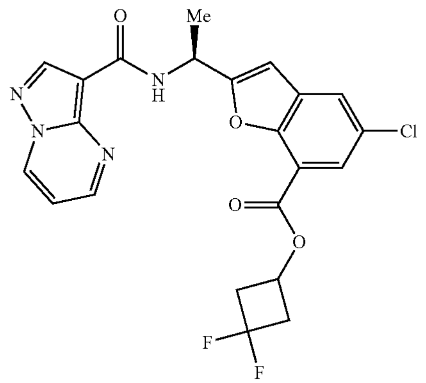 | 3,3-Difluorocyclobutyl (S)-5-chloro-2-(1-(pyrazolo[1,5-a]pyrimidine-3-carboxamido)ethyl)benzofuran-7-carboxylate | $^1$H NMR (500 MHz, DMSO-$d_6$) δ 9.31 (br d, J = 7.0 Hz, 1H), 8.82 (br d, J = 3.4 Hz, 1H), 8.62 (s, 1H), 8.37 (br d, J = 8.2 Hz, 1H), 8.00 (s, 1H), 7.78 (s, 1H), 7.29 (dd, J = 6.7, 4.3 Hz, 1H), 6.93 (s, 1H), 5.53 (br t, J = 7.2 Hz, 1H), 5.16 (br dd, J = 7.6, 4.9 Hz, 1H), 3.25-3.05 (m, 2H), 2.84 (br dd, J = 13.3, 9.6 Hz, 2H), 1.67 (br d, J = 6.7 Hz, 3H) | 475.3 |

-continued

| Ex. No. | Structure | Name | $^1$H NMR | LCMS $(M + H)^+$ |
|---|---|---|---|---|
| 268 | 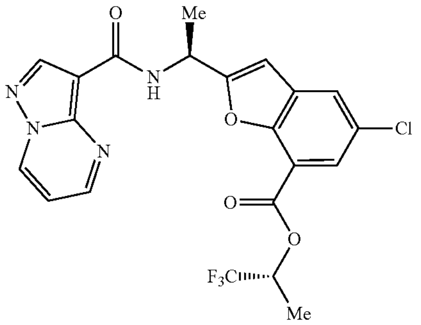 | (R)-1,1,1-Trifluoropropan-2-yl 5-chloro-2-((S)-1-(pyrazolo[1,5-a]pyrimidine-3-carboxamido)ethyl)benzofuran-7-carboxylate | $^1$H NMR (500 MHz, DMSO-$d_6$) δ 9.32 (br d, J = 6.7 Hz, 1H), 8.81 (br d, J = 3.1 Hz, 1H), 8.62 (s, 1H), 8.37 (br d, J = 8.2 Hz, 1H), 8.04 (d, J = 1.5 Hz, 1H), 7.77 (d, J = 1.8 Hz, 1H), 7.29 (dd, J = 6.9, 4.4 Hz, 1H), 6.94 (s, 1H), 5.85-5.61 (m, 1H), 5.51 (br t, J = 7.3 Hz, 1H), 1.66 (br d, J = 7.0 Hz, 3H), 1.49 (br d, J = 6.4 Hz, 3H) | 481.2 |
| 269 | 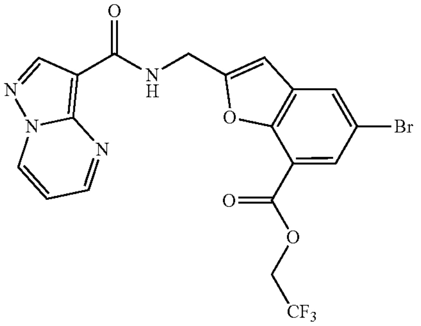 | 2,2,2-Trifluoroethyl 5-bromo-2-((pyrazolo[1,5-a]pyrimidine-3-carboxamido)methyl)benzofuran-7-carboxylate | $^1$H NMR (500 MHz, DMSO-$d_6$) δ 9.32 (br d, J = 6.7 Hz, 1H), 8.84 (br d, J = 3.4 Hz, 1H), 8.64 (s, 1H), 8.58 (br t, J = 5.8 Hz, 1H), 8.19 (s, 1H), 7.90 (d, J = 1.5 Hz, 1H), 7.31 (dd, J = 6.9, 4.1 Hz, 1H), 6.92 (s, 1H), 5.04 (q, J = 8.9 Hz, 2H), 4.83 (br d, J = 5.8 Hz, 2H) | 497.1 |
| 270 | 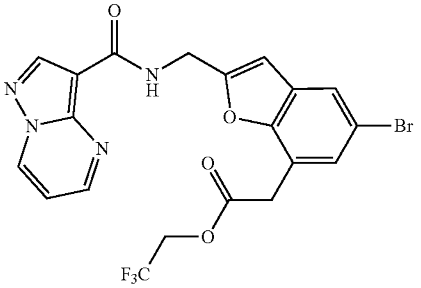 | 2,2,2-Trifluoroethyl 2-(5-bromo-2-((pyrazolo[1,5-a]pyrimidine-3-carboxamido)methyl)benzofuran-7-yl)acetate | $^1$H NMR (500 MHz, DMSO-$d_6$) δ 9.22 (br d, J = 7.0 Hz, 1H), 8.79 (br d, J = 3.1 Hz, 1H), 8.59 (s, 1H), 8.53 (br t, J = 5.8 Hz, 1H), 7.72 (d, J = 1.2 Hz, 1H), 7.35 (s, 1H), 7.26 (dd, J = 6.7, 4.3 Hz, 1H), 6.77 (s, 1H), 4.72 (br d, J = 5.8 Hz, 2H), 4.67 (q, J = 9.1 Hz, 2H), 4.05 (s, 2H) | 513.1 |
| 271 | 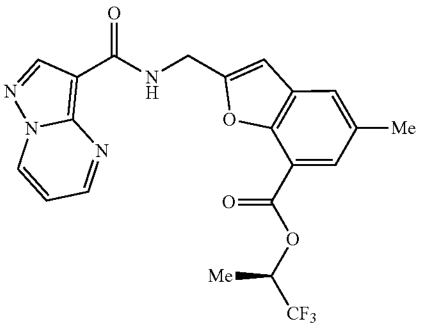 | (R)-1,1,1-Trifluoropropan-2-yl 5-methyl-2-((pyrazolo[1,5-a]pyrimidine-3-carboxamido)methyl)-benzofuran-7-carboxylate | $^1$H NMR (500 MHz, DMSO-$d_6$) δ 9.31 (br d, J = 7.0 Hz, 1H), 8.82 (br d, J = 2.7 Hz, 1H), 8.63 (s, 1H), 8.50 (br s, 1H), 7.73 (s, 1H), 7.64 (s, 1H), 7.31-7.26 (m, 1H), 6.83 (s, 1H), 5.77-5.68 (m, 1H), 4.80 (br d, J = 5.2 Hz, 2H), 2.43 (s, 3H), 1.48 (br d, J = 6.4 Hz, 3H) | 447.2 |

-continued

| Ex. No. | Structure | Name | $^1H$ NMR | LCMS $(M + H)^+$ |
|---|---|---|---|---|
| 272 | 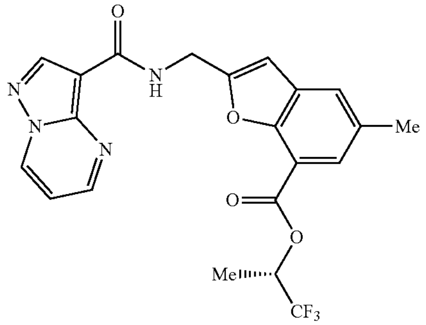 | (S)-1,1,1-Trifluoropropan-2-yl 5-methyl-2-((pyrazolo[1,5-a]pyrimidine-3-carboxamido)methyl)-benzofuran-7-carboxylate | $^1H$ NMR (500 MHz, DMSO-$d_6$) δ 9.31 (br d, J = 6.7 Hz, 1H), 8.82 (br d, J = 2.1 Hz, 1H), 8.80-8.59 (m, 1H), 8.50 (br t, J = 5.5 Hz, 1H), 7.73 (s, 1H), 7.64 (s, 1H), 7.32-7.26 (m, 1H), 6.83 (s, 1H), 5.77-5.67 (m, 1H), 4.80 (br d, J = 5.2 Hz, 2H), 2.43 (s, 3H), 1.48 (br d, J = 6.4 Hz, 3H) | 447.1 |
| 273 | 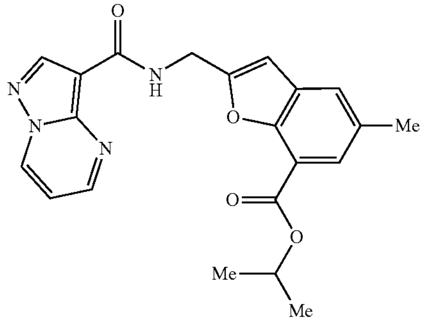 | Isopropyl 5-methyl-2-((pyrazolo[1,5-a]pyrimidine-3-carboxamido)methyl)-benzofuran-7-carboxylate | $^1H$ NMR (400 MHz, METHANOL-$d_4$) δ 9.08 (dd, J = 7.0, 1.7 Hz, 1H), 8.78 (dd, J = 4.2, 1.7 Hz, 1H), 8.61 (s, 1H), 8.54-8.48 (m, 1H), 7.66 (d, J = 1.2 Hz, 1H), 7.58 (dd, J = 1.6, 0.7 Hz, 1H), 7.21 (dd, J = 7.0, 4.2 Hz, 1H), 6.74 (s, 1H), 5.26 (dt, J = 12.5, 6.2 Hz, 1H), 4.87 (d, J = 0.6 Hz, 2H), 2.45 (s, 3H), 1.38 (d, J = 6.2 Hz, 6H) | 393.1 |
| 274 | 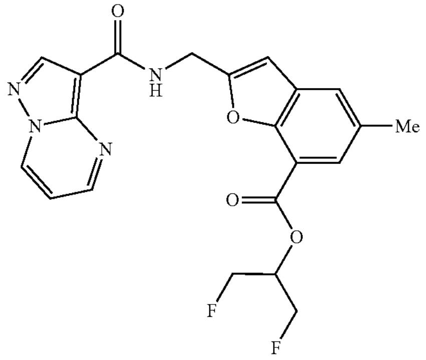 | 1,3-Difluoropropan-2-yl 5-methyl-2-((pyrazolo[1,5-a]pyrimidine-3-carboxamido)methyl)-benzofuran-7-carboxylate | $^1H$ NMR (500 MHz, DMSO-$d_6$) δ 9.30-9.24 (m, 1H), 8.81 (br d, J = 3.1 Hz, 1H), 8.64-8.59 (m, 1H), 8.55-8.46 (m, 1H), 7.74-7.67 (m, 1H), 7.67-7.61 (m, 1H), 7.30-7.23 (m, 1H), 6.86-6.75 (m, 1H), 5.61-5.47 (m, 1H), 4.84-4.74 (m, 4H), 4.74-4.62 (m, 2H), 2.42 (s, 3H) | 429.2 |
| 275 | 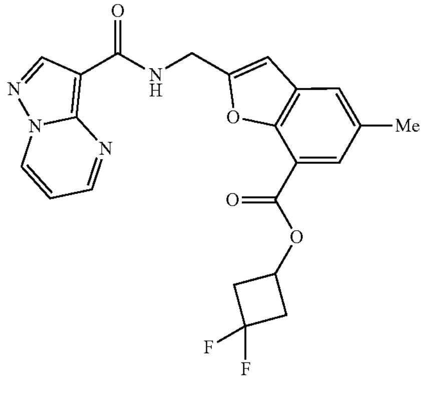 | 3,3-Difluorocyclobutyl 5-methyl-2-((pyrazolo[1,5-a]pyrimidine-3-carboxamido)methyl)-benzofuran-7-carboxylate | $^1H$ NMR (500 MHz, DMSO-$d_6$) δ 9.29 (br d, J = 6.7 Hz, 1H), 8.81 (br d, J = 3.7 Hz, 1H), 8.62 (s, 1H), 8.51 (br t, J = 5.8 Hz, 1H), 7.68 (s, 1H), 7.64 (s, 1H), 6.81 (s, 1H), 5.12 (br s, 1H), 4.80 (br d, J = 5.8 Hz, 2H), 3.18-3.08 (m, 2H), 2.82 (qd, J = 14.3, 4.7 Hz, 2H), 2.41 (s, 3H) | 441.0 |

-continued

| Ex. No. | Structure | Name | $^1$H NMR | LCMS (M + H)$^+$ |
|---|---|---|---|---|
| 276 | 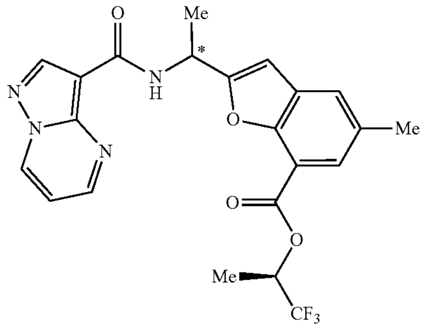 | (R)-1,1,1-Trifluoropropan-2-yl 5-methyl-2-(1-(pyrazolo[1,5-a]pyrimidine-3-carboxamido)ethyl)benzofuran-7-carboxylate | $^1$H NMR (500 MHz, DMSO-$d_6$) δ 9.25 (br d, J = 7.0 Hz, 1H), 8.81-8.75 (m, 1H), 8.60 (s, 1H), 8.35-8.30 (m, 1H), 7.73 (s, 1H), 7.64 (s, 1H), 7.26 (dd, J = 6.9, 4.2 Hz, 1H), 6.85 (s, 1H), 5.73-5.66 (m, 1H), 5.54-5.44 (m, 1H), 2.43 (s, 3H), 1.66 (d, J = 7.0 Hz, 3H), 1.51-1.47 (m, 3H) | 461.3 |
| 277 | 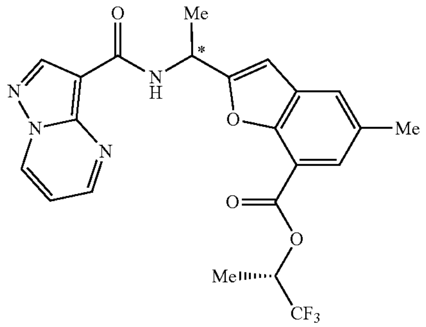 | (S)-1,1,1-Trifluoropropan-2-yl 5-methyl-2-(1-(pyrazolo[1,5-a]pyrimidine-3-carboxamido)ethyl)benzofuran-7-carboxylate | $^1$H NMR (500 MHz, DMSO-$d_6$) δ 9.25 (br d, J = 7.0 Hz, 1H), 8.81-8.75 (m, 1H), 8.60 (s, 1H), 8.35-8.30 (m, 1H), 7.73 (s, 1H), 7.64 (s, 1H), 7.26 (dd, J = 6.9, 4.2 Hz, 1H), 6.85 (s, 1H), 5.73-5.66 (m, 1H), 5.54-5.44 (m, 1H), 2.43 (s, 3H), 1.66 (d, J = 7.0 Hz, 3H), 1.51-1.47 (m, 3H) | 461.3 |
| 278 | 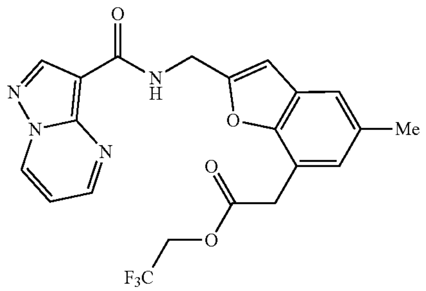 | 2,2,2-Trifluoroethyl 2-(5-methyl-2-((pyrazolo[1,5-a]pyrimidine-3-carboxamido)methyl)benzofuran-7-yl)acetate | $^1$H NMR (500 MHz, DMSO-$d_6$) δ 9.21 (d, J = 6.1 Hz, 1H), 8.78 (br d, J = 2.7 Hz, 1H), 8.59 (s, 1H), 8.49 (br t, J = 5.6 Hz, 1H), 7.28 (s, 1H), 7.25 (dd, J = 7.0, 4.3 Hz, 1H), 6.97 (s, 1H), 6.69 (s, 1H), 4.78-4.61 (m, 4H), 3.97 (s, 2H), 2.33 (s, 3H) | 447.2 |
| 279 | 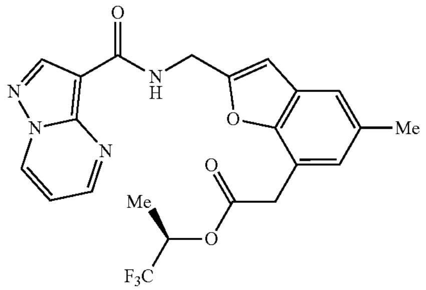 | (R)-1,1,1-Trifluoropropan-2-yl 2-(5-methyl-2-((pyrazolo[1,5-a]pyrimidine-3-carboxamido)methyl)benzofuran-7-yl)acetate | $^1$H NMR (500 MHz, DMSO-$d_6$) δ 9.31 (br d, J = 6.4 Hz, 1H), 8.82 (br d, J = 3.1 Hz, 1H), 8.62 (s, 1H), 8.44 (br t, J = 5.3 Hz, 1H), 7.29 (br s, 2H), 6.99 (s, 1H), 6.70 (s, 1H), 5.50-5.31 (m, 1H), 4.73 (br d, J = 5.8 Hz, 2H), 3.98 (s, 2H), 2.35 (s, 3H), 1.30 (br d, J = 6.4 Hz, 3H) | 461.2 |
| 280 | 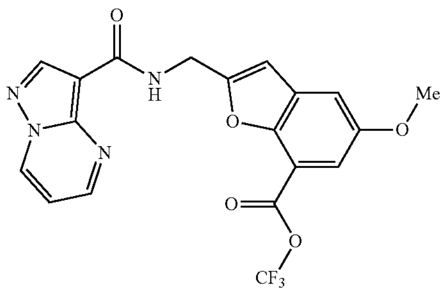 | 2,2,2-Trifluoroethyl 5-methoxy-2-((pyrazolo[1,5-a]pyrimidine-3-carboxamido)methyl)benzofuran-7-carboxylate | $^1$H NMR (500 MHz, DMSO-$d_6$) δ 9.32 (br s, 1H), 8.84 (br s, 1H), 8.65 (s, 1H), 8.55 (br s, 1H), 7.53 (d, J = 2.1 Hz, 1H), 7.42-7.23 (m, 2H), 6.86 (s, 1H), 5.03 (q, J = 8.9 Hz, 2H), 4.80 (br d, J = 4.9 Hz, 2H), 3.84 (s, 3H) | 448.9 |

-continued

| Ex. No. | Structure | Name | $^1$H NMR | LCMS $(M + H)^+$ |
|---|---|---|---|---|
| 281 | 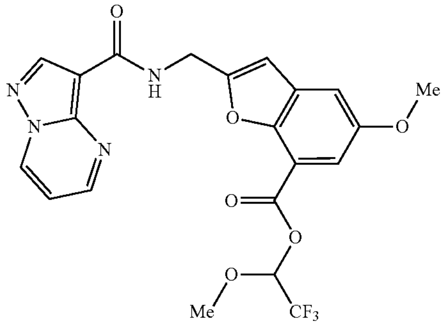 | 2,2,2-Trifluoro-1-methoxyethyl 5-methoxy-2-((pyrazolo[1,5-a]pyrimidine-3-carboxamido)methyl)benzofuran-7-carboxylate (racemate) | $^1$H NMR (500 MHz, DMSO-$d_6$) δ 9.33 (d, J = 7.0 Hz, 1H), 8.82 (br d, J = 2.7 Hz, 1H), 8.63 (s, 1H), 8.50 (br t, J = 5.6 Hz, 1H), 7.55 (d, J = 2.4 Hz, 1H), 7.35 (d, J = 2.4 Hz, 1H), 7.30 (dd, J = 7.0, 4.3 Hz, 1H), 6.84 (s, 1H), 6.56 (br d, J = 3.7 Hz, 1H), 4.79 (br d, J = 6.1 Hz, 2H), 3.84 (s, 3H), 3.65 (s, 3H) | 479.3 |
| 282 | 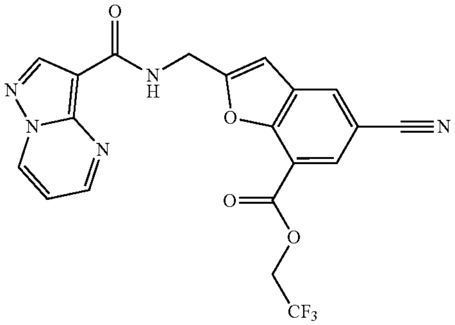 | 2,2,2-Trifluoroethyl 5-cyano-2-((pyrazolo[1,5-a]pyrimidine-3-carboxamido)methyl)benzofuran-7-carboxylate | $^1$H NMR (500 MHz, DMSO-$d_6$) δ 9.30 (br d, J = 7.1 Hz, 1H), 8.82 (br d, J = 3.0 Hz, 1H), 8.62 (s, 1H), 8.56-8.49 (m, 1H), 8.45 (s, 1H), 8.18 (s, 1H), 7.29 (br dd, J = 6.8, 4.4 Hz, 1H), 7.02 (s, 1H), 5.05 (br d, J = 8.8 Hz, 2H), 4.86 (br d, J = 6.1 Hz, 2H) | 444.2 |
| 283 | 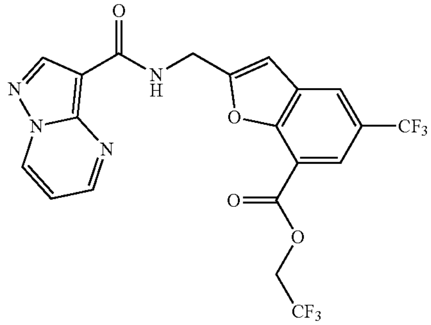 | 2,2,2-Trifluoroethyl 2-((pyrazolo[1,5-a]pyrimidine-3-carboxamido)methyl)-5-(trifluoromethyl)benzofuran-7-carboxylate | $^1$H NMR (500 MHz, DMSO-$d_6$) δ 9.26 (br d, J = 6.1 Hz, 1H), 8.80 (br d, J = 3.8 Hz, 1H), 8.60 (s, 1H), 8.52 (br s, 1H), 8.35 (s, 1H), 8.04 (s, 1H), 7.33-7.22 (m, 1H), 7.04 (s, 1H), 5.04 (q, J = 8.7 Hz, 2H), 4.85 (br d, J = 5.8 Hz, 2H) | 487.2 |
| 284 | 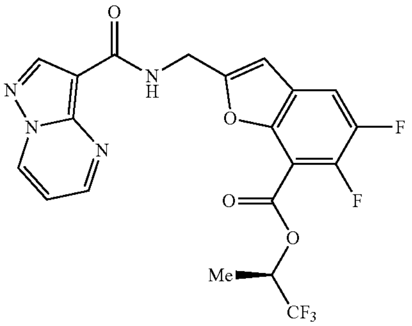 | (R)-1,1,1-Trifluoropropan-2-yl 5,6-difluoro-2-((pyrazolo[1,5-a]pyrimidine-3-carboxamido)methyl)benzofuran-7-carboxylate | $^1$H NMR (500 MHz, DMSO-$d_6$) δ 9.33 (br d, J = 6.7 Hz, 1H), 8.82 (br d, J = 3.1 Hz, 1H), 8.62 (s, 1H), 8.53 (br t, J = 5.6 Hz, 1H), 7.85 (br dd, J = 10.8, 7.8 Hz, 1H), 7.29 (dd, J = 6.6, 4.4 Hz, 1H), 7.09 (s, 1H), 5.85-5.59 (m, 1H), 4.83 (br d, J = 5.8 Hz, 2H), 1.47 (br d, J = 6.4 Hz, 3H) | 469.3 |

-continued

| Ex. No. | Structure | Name | $^1H$ NMR | LCMS $(M + H)^+$ |
|---|---|---|---|---|
| 285 | 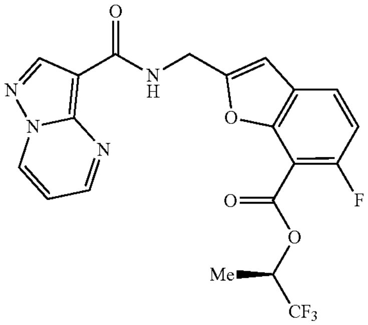 | (R)-1,1,1-Trifluoropropan-2-yl 6-fluoro-2-((pyrazolo[1,5-a]pyrimidine-3-carboxamido)methyl)benzofuran-7-carboxylate | $^1H$ NMR (500 MHz, DMSO-$d_6$) δ 9.23 (d, J = 6.1 Hz, 1H), 8.79 (d, J = 3.1 Hz, 1H), 8.60 (s, 1H), 8.52 (br t, J = 5.8 Hz, 1H), 7.87 (dd, J = 8.5, 5.2 Hz, 1H), 7.35-7.18 (m, 2H), 6.89 (s, 1H), 5.84-5.62 (m, 1H), 4.76 (br d, J = 4.0 Hz, 2H), 1.45 (d, J = 6.4 Hz, 3H) | 451.2 |
| 286 | 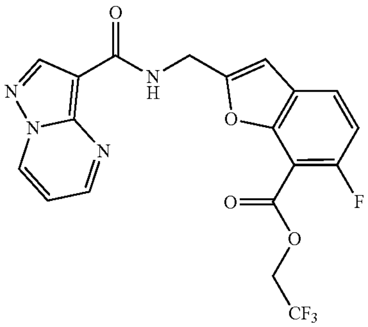 | 2,2,2-Trifluoroethyl 6-fluoro-2-((pyrazolo[1,5-a]pyrimidine-3-carboxamido)methyl)benzofuran-7-carboxylate | $^1H$ NMR (500 MHz, DMSO-$d_6$) δ 9.29 (br d, J = 6.9 Hz, 1H), 8.81 (br d, J = 3.8 Hz, 1H), 8.61 (s,1H), 8.45 (br s, 1H), 7.89 (dd, J = 8.6, 5.2 Hz, 1H), 7.38-7.15 (m, 2H), 6.90 (s, 1H), 5.05 (q, J = 8.9 Hz, 2H), 4.79 (br d, J = 5.8 Hz, 2H) | 437.3 |
| 287 | 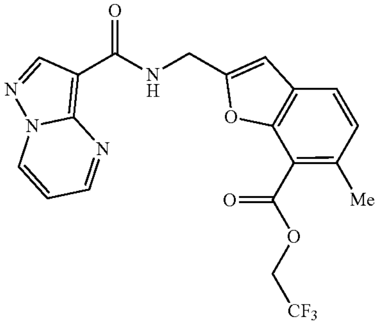 | 2,2,2-Trifluoroethyl 6-methyl-2-((pyrazolo[1,5-a]pyrimidine-3-carboxamido)methyl)benzofuran-7-carboxylate | $^1H$ NMR (500 MHz, DMSO-$d_6$) δ 9.24 (br d, J = 5.9 Hz, 1H), 8.79 (br d, J = 2.9 Hz, 1H), 8.60 (s, 1H), 8.43 (br t, J = 5.4 Hz, 1H), 7.69 (d, J = 7.9 Hz, 1H), 7.26 (dd, J = 6.9, 4.2 Hz, 1H), 7.21 (d, J = 7.9 Hz, 1H), 6.81 (s, 1H), 5.00 (q, J = 9.0 Hz, 2H), 4.75 (d, J = 5.8 Hz, 2H), 2.52 (s, 3H) | 433.1 |
| 288 | 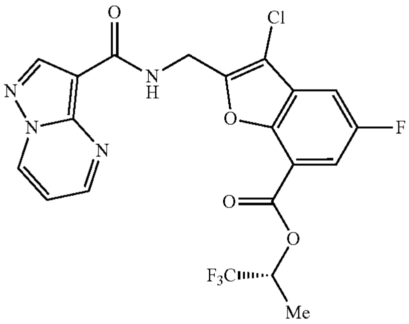 | (R)-1,1,1-Trifluoropropan-2-yl 3-chloro-5-fluoro-2-((pyrazolo[1,5-a]pyrimidine-3-carboxamido)methyl)benzofuran-7-carboxylate | $^1H$ NMR (500 MHz, DMSO-d6) δ 9.31 (dd, J = 6.9, 1.4 Hz, 1H), 8.82 (dd, J = 4.0, 1.2 Hz, 1H), 8.60 (s, 1H), 8.56-8.45 (m, 1H), 7.82 (dd, J = 7.6, 2.7 Hz, 1H), 7.70 (dd, J = 9.5, 2.4 Hz, 1H), 7.29 (dd, J = 7.0, 4.3 Hz, 1H), 5.85-5.54 (m, 1H), 4.87 (dd, J = 5.8, 1.8 Hz, 2H), 1.42 (d, J = 6.7 Hz, 3H) | 485.3 |

-continued

| Ex. No. | Structure | Name | $^{1}H$ NMR | LCMS $(M + H)^{+}$ |
|---|---|---|---|---|
| 289 | 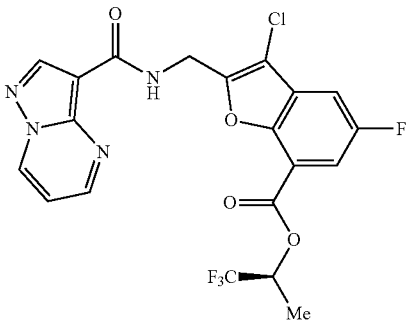 | (S)-1,1,1-Trifluoropropan-2-yl 3-chloro-5-fluoro-2-((pyrazolo[1,5-a]pyrimidine-3-carboxamido)methyl)benzofuran-7-carboxylate | $^{1}H$ NMR (500 MHz, DMSO-$d_6$) δ 9.28 (d, J = 6.1 Hz, 1H), 8.81 (br d, J = 2.7 Hz, 1H), 8.62-8.47 (m, 2H), 7.81 (dd, J = 7.6, 2.4 Hz, 1H), 7.70 (dd, J = 9.2, 2.4 Hz, 1H), 7.28 (dd, J = 7.0, 4.3 Hz, 1H), 5.81-5.56 (m, 1H), 4.91-4.75 (m, 2H), 1.40 (d, J = 6.7 Hz, 3H) | 485.3 |
| 290 | 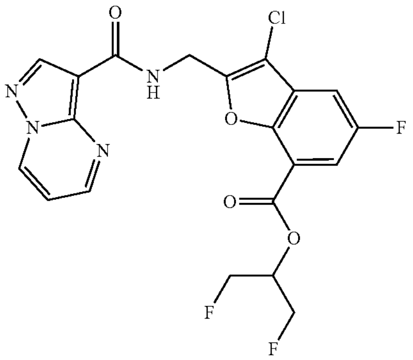 | 1,3-Difluoropropan-2-yl 3-chloro-5-fluoro-2-((pyrazolo[1,5-a]pyrimidine-3-carboxamido)methyl)benzofuran-7-carboxylate | $^{1}H$ NMR (500 MHz, DMSO-$d_6$) δ 9.32 (dd, J = 7.0, 1.2 Hz, 1H), 8.83 (br d, J = 2.7 Hz, 1H), 8.61 (s, 1H), 8.55 (br t, J = 5.8 Hz, 1H), 7.80 (dd, J = 7.6, 2.4 Hz, 1H), 7.72 (dd, J = 9.5, 2.7 Hz, 1H), 7.29 (dd, J = 7.0, 4.3 Hz, 1H), 5.74-5.39 (m, 1H), 4.88 (d, J = 5.8 Hz, 2H), 4.80-4.54 (m, 4H) | 467.3 |
| 291 | 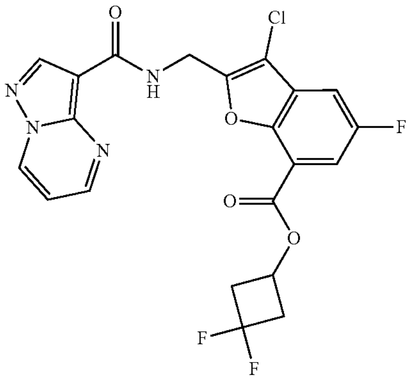 | 3,3-Difluorocyclobutyl 3-chloro-5-fluoro-2-((pyrazolo[1,5-a]pyrimidine-3-carboxamido)methyl)benzofuran-7-carboxylate | $^{1}H$ NMR (500 MHz, DMSO-d6) δ 9.32 (dd, J = 7.0, 1.2 Hz, 1H), 8.83 (dd, J = 4.0, 1.5 Hz, 1H), 8.68-8.49 (m, 2H), 7.77 (dd, J = 7.6, 2.4 Hz, 1H), 7.72 (dd, J = 9.5, 2.4 Hz, 1H), 7.29 (dd, J = 6.7, 4.3 Hz, 1H), 5.12 (br dd, J = 7.3, 4.3 Hz, 1H), 4.88 (d, J = 6.1 Hz, 2H), 3.06 (td, J = 7.6, 4.3 Hz, 2H), 2.81 (br dd, J = 14.8, 4.4 Hz, 2H) | 479.3 |
| 292 | 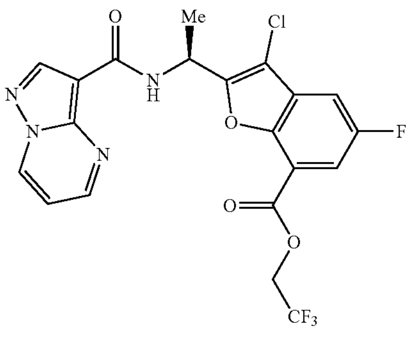 | 2,2,2-Trifluoroethyl (S)-3-chloro-5-fluoro-2-(1-(pyrazolo[1,5-a]pyrimidine-3-carboxamido)ethyl)benzofuran-7-carboxylate | $^{1}H$ NMR (500 MHz, DMSO-d6) δ 9.28 (br d, J = 6.4 Hz, 1H), 8.82 (br d, J = 3.1 Hz, 1H), 8.58 (s, 1H), 8.44 (br d, J = 7.6 Hz, 1H), 7.81 (dd, J = 7.5, 2.3 Hz, 1H), 7.72 (dd, J = 9.2, 2.4 Hz, 1H), 7.29 (dd, J = 6.9, 4.4 Hz, 1H), 5.56 (br t, J = 7.2 Hz, 1H), 5.03 (q, J = 8.9 Hz, 2H), 1.67 (br d, J = 7.0 Hz, 3H) | 485.0 |

-continued

| Ex. No. | Structure | Name | $^1$H NMR | LCMS $(M + H)^+$ |
|---|---|---|---|---|
| 293 | 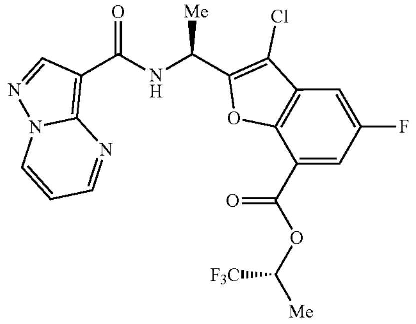 | (R)-1,1,1-Trifluoropropan-2-yl 3-chloro-5-fluoro-2-((S)-1-(pyrazolo[1,5-a]pyrimidine-3-carboxamido)ethyl)benzofuran-7-carboxylate | $^1$H NMR (500 MHz, DMSO-d6) δ 9.29 (br d, J = 6.4 Hz, 1H), 8.81 (br d, J = 3.1 Hz, 1H), 8.58 (s, 1H), 8.42 (br d, J = 7.6 Hz, 1H), 7.81 (dd, J = 7.6, 2.1 Hz, 1H), 7.72 (dd, J = 9.3, 2.3 Hz, 1H), 7.29 (dd, J = 6.7, 4.3 Hz, 1H), 5.82-5.67 (m, 1H), 5.57 (br t, J = 7.2 Hz, 1H), 1.66 (br d, J = 7.0 Hz, 3H), 1.46 (br d, J = 6.7 Hz, 3H) | 499.3 |
| 294 | 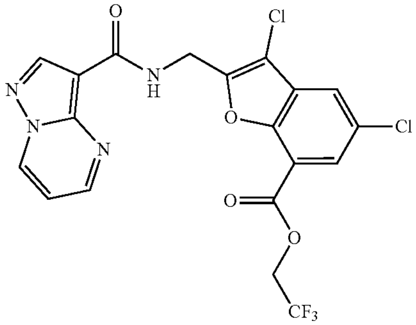 | 2,2,2-Trifluoroethyl 3,5-dichloro-2-((pyrazolo[1,5-a]pyrimidine-3-carboxamido)methyl)benzofuran-7-carboxylate | $^1$H NMR (400 MHz, DMSO-$d_6$) δ 9.30 (d, J = 7.0 Hz, 1H), 8.82 (br d, J = 3.1 Hz, 1H), 8.60 (s, 1H), 8.55 (s, 1H), 8.02 (d, J = 1.8 Hz, 1H), 7.88 (d, J = 1.8 Hz, 1H), 7.29 (dd, J = 6.7, 4.3 Hz, 1H), 4.99 (br d, J = 9.2 Hz, 2H), 4.87 (br d, J = 5.8 Hz, 2H) | 487.1 |
| 295 | 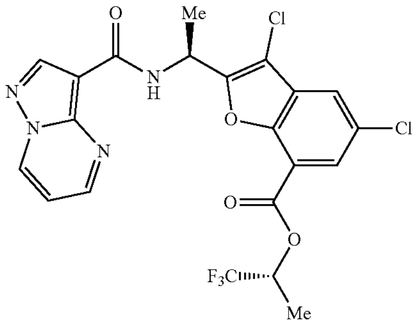 | (R)-1,1,1-Trifluoropropan-2-yl 3,5-dichloro-2-((pyrazolo[1,5-a]pyrimidine-3-carboxamido)methyl)benzofuran-7-carboxylate | $^1$H NMR (500 MHz, DMSO-$d_6$) δ 9.23 (br d, J = 6.7 Hz, 1H), 8.80 (br d, J = 2.9 Hz, 1H), 8.58 (s, 1H), 8.53-8.43 (m, 1H), 7.96 (s, 1H), 7.85 (s, 1H), 7.26 (dd, J = 6.8, 4.3 Hz, 1H), 5.79-5.50 (m, 1H), 4.87 (br d, J = 5.7 Hz, 2H), 1.43 (br d, J = 6.6 Hz, 3H) | 501.1 |
| 296 | 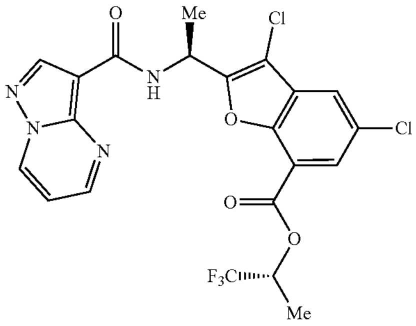 | (R)-1,1,1-Trifluoropropan-2-yl 3,5-dichloro-2-((S)-1-(pyrazolo[1,5-a]pyrimidine-3-carboxamido)ethyl)benzofuran-7-carboxylate | $^1$H NMR (500 MHz, DMSO-$d_6$) δ 9.31 (d, J = 6.7 Hz, 1H), 8.82 (br d, J = 3.4 Hz, 1H), 8.59 (s, 1H), 8.42 (br d, J = 7.6 Hz, 1H), 8.02 (d, J = 1.5 Hz, 1H), 7.89 (d, J = 1.5 Hz, 1H), 7.30 (dd, J = 6.7, 4.3 Hz, 1H), 5.84-5.68 (m, 1H), 5.58 (br t, J = 7.3 Hz, 1H), 1.67 (br d, J = 7.0 Hz, 3H), 1.47 (d, J = 6.4 Hz, 3H) | 515.1 |

-continued

| Ex. No. | Structure | Name | $^1$H NMR | LCMS (M + H)$^+$ |
|---|---|---|---|---|
| 297 | 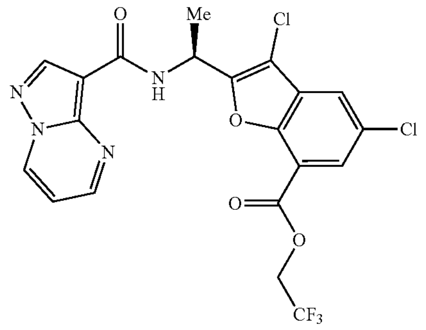 | 2,2,2-Trifluoroethyl (S)-3,5-dichloro-2-(1-(pyrazolo[1,5-a]pyrimidine-3-carboxamido)ethyl)benzofuran-7-carboxylate | $^1$H NMR (500 MHz, DMSO-$d_6$) δ 9.30 (d, J = 6.7 Hz, 1H), 8.82 (br d, J = 3.4 Hz, 1H), 8.59 (s, 1H), 8.44 (br d, J = 7.3 Hz, 1H), 8.01 (s, 1H), 7.89 (d, J = 1.5 Hz, 1H), 7.30 (dd, J = 6.9, 4.4 Hz, 1H), 5.57 (br t, J = 7.2 Hz, 1H), 5.16-4.96 (m, 2H), 1.67 (br d, J = 7.0 Hz, 3H) | 500.9 |
| 298 | 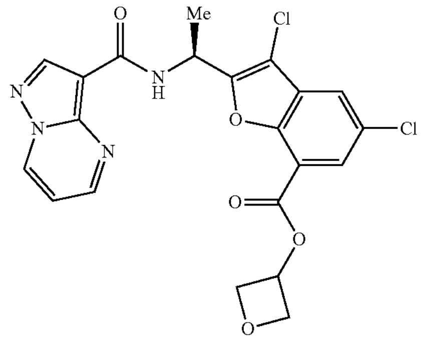 | Oxetan-3-yl (S)-3,5-dichloro-2-(1-(pyrazolo[1,5-a]pyrimidine-3-carboxamido)ethyl)benzofuran-7-carboxylate | $^1$H NMR (500 MHz, DMSO-$d_6$) δ 9.29 (br d, J = 5.8 Hz, 1H), 8.84 (br d, J = 2.7 Hz, 1H), 8.59 (s, 1H), 8.48 (br d, J = 7.6 Hz, 1H), 7.97 (d, J = 2.1 Hz, 1H), 7.92 (d, J = 1.8 Hz, 1H), 7.29 (dd, J = 7.0, 4.3 Hz, 1H), 5.68 (br t, J = 5.3 Hz, 1H), 5.58 (br t, J = 7.3 Hz, 1H), 4.95-4.77 (m, 2H), 4.70-4.54 (m, 2H), 1.68 (br d, J = 7.0 Hz, 3H) | 475.1 |
| 299 | 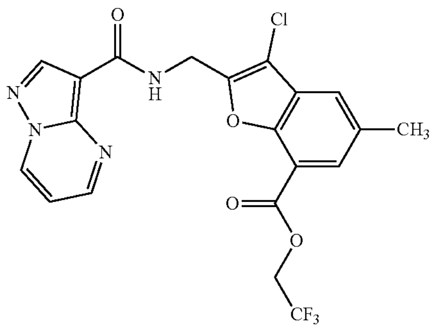 | 2,2,2-Trifluoroethyl 3-chloro-5-methyl-2-((pyrazolo[1,5-a]pyrimidine-3-carboxamido)methyl)benzofuran-7-carboxylate | $^1$H NMR (500 MHz, DMSO-$d_6$) δ 9.25 (d, J = 7.0 Hz, 1H), 8.80 (br d, J = 3.1 Hz, 1H), 8.59 (s, 1H), 8.53 (br t, J = 5.8 Hz, 1H), 7.75 (s, 1H), 7.70 (s, 1H), 7.27 (dd, J = 7.0, 4.3 Hz, 1H), 4.95 (q, J = 9.1 Hz, 2H), 4.84 (d, J = 5.8 Hz, 2H), 2.48-2.44 (m, 3H) | 467.2 |
| 300 | 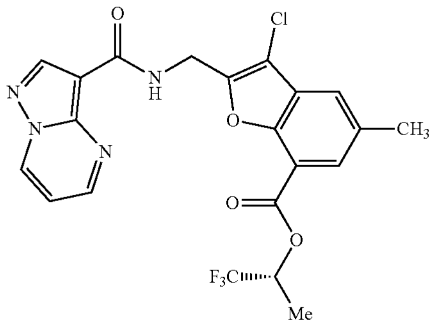 | (R)-1,1,1-Trifluoropropan-2-yl 3-chloro-5-methyl-2-((pyrazolo[1,5-a]pyrimidine-3-carboxamido)methyl)benzofuran-7-carboxylate | $^1$H NMR (500 MHz, DMSO-$d_6$) δ 9.24 (br d, J = 6.1 Hz, 1H), 8.79 (br d, J = 2.7 Hz, 1H), 8.58 (s, 1H), 8.55-8.51 (m, 1H), 7.73 (s, 1H), 7.70-7.67 (m, 1H), 7.27 (dd, J = 7.0, 4.3 Hz, 1H), 5.71-5.62 (m, 1H), 4.84 (br d, J = 4.3 Hz, 2H), 2.48-2.44 (m, 3H), 1.40 (d, J = 6.7 Hz, 3H) | 481.2 |

-continued

| Ex. No. | Structure | Name | $^1$H NMR | LCMS (M + H)$^+$ |
|---|---|---|---|---|
| 301 | 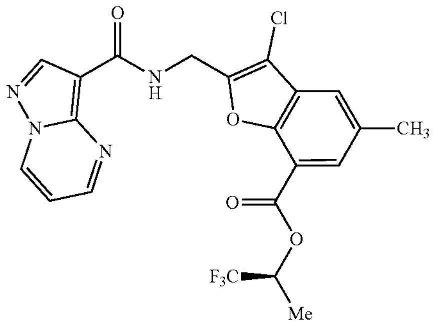 | (S)-1,1,1-Trifluoropropan-2-yl 3-chloro-5-methyl-2-((pyrazolo[1,5-a]pyrimidine-3-carboxamido)methyl)benzofuran-7-carboxylate | $^1$H NMR (500 MHz, DMSO-$d_6$) δ 9.31 (d, J = 6.1 Hz, 1H), 8.81 (d, J = 3.1 Hz, 1H), 8.60 (s, 1H), 8.50 (br t, J = 5.6 Hz, 1H), 7.75 (s, 1H), 7.72-7.69 (m, 1H), 7.29 (dd, J = 7.0, 4.3 Hz, 1H), 5.74-5.66 (m, 1H), 4.86 (br d, J = 5.5 Hz, 2H), 2.48 (s, 3H), 1.42 (d, J = 6.7 Hz, 3H) | 481.2 |
| 302 | 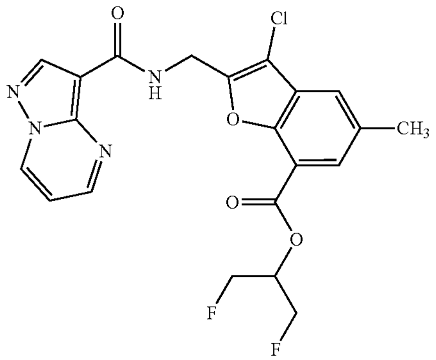 | 1,3-Difluoropropan-2-yl 3-chloro-5-methyl-2-((pyrazolo[1,5-a]pyrimidine-3-carboxamido)methyl)benzofuran-7-carboxylate | $^1$H NMR (400 MHz, METHANOL-$d_4$) δ 9.12 (dd, J = 7.0, 1.7 Hz, 1H), 8.88 (dd, J = 4.2, 1.8 Hz, 1H), 8.75 (s, 1H), 7.95 (d, J = 1.8 Hz, 1H), 7.73 (dd, J = 1.8, 0.8 Hz, 1H), 7.31 (dd, J = 7.0, 4.3 Hz, 1H), 5.64 (tquin, J = 19.5, 4.6 Hz, 1H), 5.08 (s, 2H), 4.93-4.89 (m, 2H), 4.81-4.77 (m, 4H), 2.64 (s, 3H) | 463.1 |
| 303 | 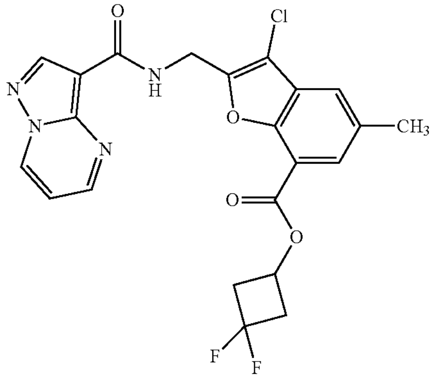 | 3,3-Difluorocyclobutyl 3-chloro-5-methyl-2-((pyrazolo[1,5-a]pyrimidine-3-carboxamido)methyl)benzofuran-7-carboxylate | $^1$H NMR (500 MHz, DMSO-$d_6$) δ 9.27 (br d, J = 7.0 Hz, 1H), 8.81 (br s, 1H), 8.54 (br t, J = 5.6 Hz, 1H), 7.77-7.72 (m, 1H), 7.68-7.64 (m, 1H), 7.28 (br d, J = 4.6 Hz, 1H), 5.14-5.06 (m, 1H), 4.88-4.82 (m, 2H), 3.12-2.99 (m, 2H), 2.84-2.69 (m, 2H), 2.48-2.43 (m, 3H) | 475.3 |
| 304 | 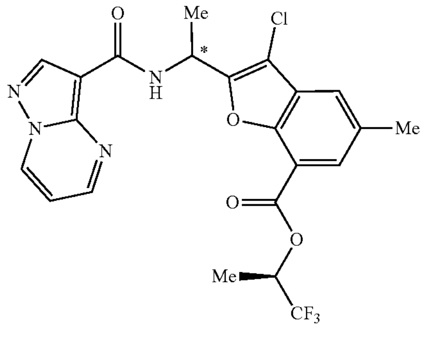 | (R)-1,1,1-Trifluoropropan-2-yl 3-chloro-5-methyl-2-(1-(pyrazolo[1,5-a]pyrimidine-3-carboxamido)ethyl)benzofuran-7-carboxylate | $^1$H NMR (500 MHz, DMSO-$d_6$) δ 9.23 (d, J = 6.4 Hz, 1H), 8.78 (br d, J = 3.4 Hz, 1H), 8.57 (s, 1H), 8.44 (br d, J = 7.6 Hz, 1H), 7.78-7.72 (m, 1H), 7.70-7.67 (m, 1H), 7.27 (dd, J = 7.0, 4.3 Hz, 1H), 5.76-5.66 (m, 1H), 5.62-5.51 (m, 1H), 2.45 (s, 3H), 1.68-1.59 (m, 3H), 1.48-1.41 (m, 3H) | 495.3 |

-continued

| Ex. No. | Structure | Name | $^1$H NMR | LCMS (M + H)$^+$ |
|---|---|---|---|---|
| 305 | 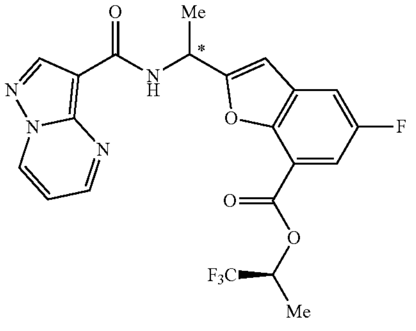 enantiopure | (S)-1,1,1-Trifluoropropan-2-yl 5-fluoro-2-(1-(pyrazolo[1,5-a]pyrimidine-3-carboxamido)ethyl)benzofuran-7-carboxylate | $^1$H NMR (500 MHz, DMSO-d6) δ 9.30 (br d, J = 6.4 Hz, 1H), 8.81 (br d, J = 3.1 Hz, 1H), 8.62 (s, 1H), 8.38 (br d, J = 8.2 Hz, 1H), 7.81 (dd, J = 8.2, 2.4 Hz, 1H), 7.59 (dd, J = 9.5, 2.4 Hz, 1H), 7.29 (dd, J = 6.7, 4.3 Hz, 1H), 6.94 (s, 1H), 5.81-5.65 (m, 1H), 5.56-5.40 (m, 1H), 1.66 (br d, J = 7.0 Hz, 3H), 1.48 (d, J = 6.7 Hz, 3H) | 465.1 |
| 306 | 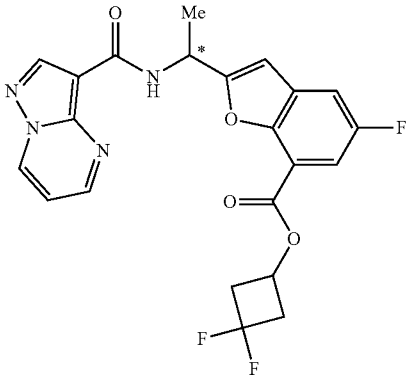 enantiopure | 3,3-Difluorocyclobutyl 5-fluoro-2-(1-(pyrazolo[1,5-a]pyrimidine-3-carboxamido)ethyl)benzofuran-7-carboxylate | $^1$H NMR (500 MHz, DMSO-$d_6$) δ 9.22 (br d, J = 6.7 Hz, 1H), 8.78 (br d, J = 2.7 Hz, 1H), 8.59 (s, 1H), 8.39 (br d, J = 8.2 Hz, 1H), 7.73 (dd, J = 8.1, 2.6 Hz, 1H), 7.56 (dd, J = 9.5, 2.4 Hz, 1H), 7.25 (dd, J = 6.7, 4.3 Hz, 1H), 6.92 (s, 1H), 5.49 (br t, J = 7.3 Hz, 1H), 5.13 (br dd, J = 7.5, 4.4 Hz, 1H), 3.16-3.00 (m, 2H), 2.85-2.67 (m, 2H), 1.65 (br d, J = 6.7 Hz, 3H) | 459.3 |

Examples 307-352

The following esters were synthesized from the acids according to the procedure outlined in Example 204 and asymmetrically resolved according to the methods listed.

| Ex. No. | Structure | Name | $^1$H NMR | LC/MS (M + H)$^+$ | Method |
|---|---|---|---|---|---|
| 307 | 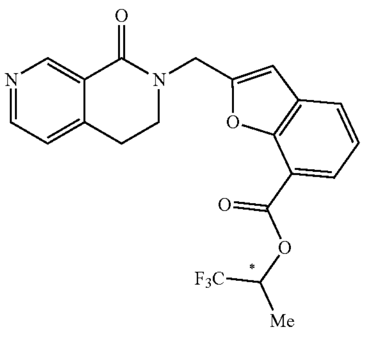 [SMILES: CC(OC(=O)c1cccc2cc(CN3CCc4ccncc4C3=O)oc12)C(F)(F)F] (Isomer-1) | 1,1,1-Trifluoropropan-2-yl 2-((1-oxo-3,4-dihydro-2,7-naphthyridin-2(1H)-yl)methyl)benzofuran-7-carboxylate | $^1$H NMR (500 MHz, DMSO-$d_6$) δ 8.97 (s, 1H), 8.63 (br d, J = 4.6 Hz, 1H), 7.97 (d, J = 7.6 Hz, 1H), 7.87 (d, J = 7.6 Hz, 1H), 7.51-7.31 (m, 2H), 7.04 (s, 1H), 5.75 (dt, J = 13.4, 6.7 Hz, 1H), 5.05-4.79 (m, 2H), 3.75 (br t, J = 6.6 Hz, 2H), 3.07 (br t, J = 6.6 Hz, 2H), 1.48 (d, J = 6.4 Hz, 3H) | 419.3 | Method F |

-continued

| Ex. No. | Structure | Name | $^1$H NMR | LC/MS (M + H)$^+$ | Method |
|---|---|---|---|---|---|
| 308 | 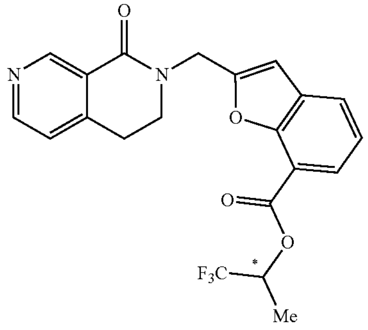 [SMILES: CC(OC(=O)c1cccc2cc(CN3CCc4ccncc4C3=O)oc12)C(F)(F)F] (Isomer-2) | 1,1,1-Trifluoropropan-2-yl 2-((1-oxo-3,4-dihydro-2,7-naphthyridin-2(1H)-yl)methyl)benzofuran-7-carboxylate | $^1$H NMR (500 MHz, DMSO-$d_6$) δ 8.97 (s, 1H), 8.63 (br d, J = 4.6 Hz, 1H), 7.97 (d, J = 7.6 Hz, 1H), 7.87 (d, J = 7.6 Hz, 1H), 7.51-7.31 (m, 2H), 7.04 (s, 1H), 5.75 (dt, J = 13.4, 6.7 Hz, 1H), 5.05-4.79 (m, 2H), 3.75 (br t, J = 6.6 Hz, 2H), 3.07 (br t, J = 6.6 Hz, 2H), 1.48 (d, J = 6.4 Hz, 3H) | 419.3 | Method F |
| 309 | 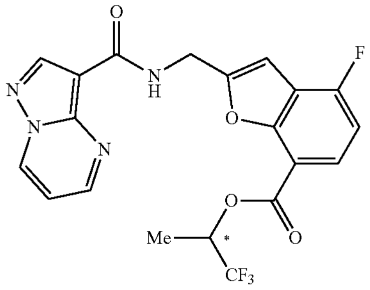 [SMILES: CC(OC(=O)c1ccc(F)c2cc(CNC(=O)c3cnn4cccnc34)oc12)C(F)(F)F] (Isomer-1) | 1,1,1-Trifluoropropan-2-yl 4-fluoro-2-((pyrazolo[1,5-a]pyrimidine-3-carboxamido)methyl) benzofuran-7-carboxylate | $^1$H NMR (500 MHz, DMSO-$d_6$) δ 9.36-9.26 (m, 1H), 8.82 (d, J = 3.1 Hz, 1H), 8.62 (s, 1H), 8.54 (br t, J = 5.8 Hz, 1H), 7.91 (dd, J = 8.5, 5.2 Hz, 1H), 7.37-7.19 (m, 2H), 7.00 (s, 1H), 5.79-5.63 (m, 1H), 4.83 (br d, J = 5.5 Hz, 2H), 1.47 (d, J = 6.7 Hz, 3H) | 451.1 | Method F |
| 310 | 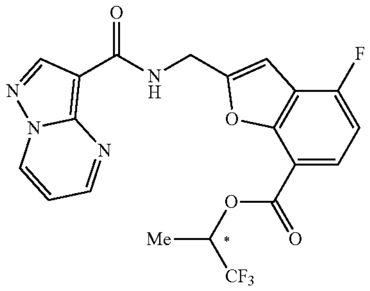 [SMILES: CC(OC(=O)c1ccc(F)c2cc(CNC(=O)c3cnn4cccnc34)oc12)C(F)(F)F] (Isomer-2) | 1,1,1-Trifluoropropan-2-yl 4-fluoro-2-((pyrazolo[1,5-a]pyrimidine-3-carboxamido)methyl) benzofuran-7-carboxylate | $^1$H NMR (500 MHz, DMSO-$d_6$) δ 9.36-9.26 (m, 1H), 8.82 (d, J = 3.1 Hz, 1H), 8.62 (s, 1H), 8.54 (br t, J = 5.8 Hz, 1H), 7.91 (dd, J = 8.5, 5.2 Hz, 1H), 7.37-7.19 (m, 2H), 7.00 (s, 1H), 5.79-5.63 (m, 1H), 4.83 (br d, J = 5.5 Hz, 2H), 1.47 (d, J = 6.7 Hz, 3H) | 451.1 | Method F |
| 311 | 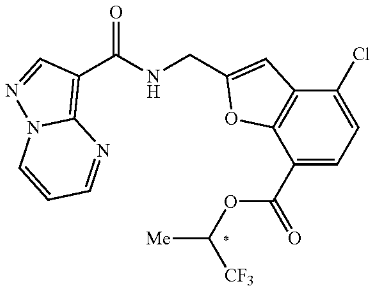 [SMILES: CC(OC(=O)c1ccc(Cl)c2cc(CNC(=O)c3cnn4cccnc34)oc12)C(F)(F)F] | 1,1,1-Trifluoropropan-2-yl 4-chloro-2-((pyrazolo[1,5-a]pyrimidine-3-carboxamido)methyl) benzofuran-7-carboxylate | $^1$H NMR (500 MHz, DMSO-$d_6$) δ 9.39-9.24 (m, 1H), 8.86-8.77 (m, 1H), 8.63 (s, 1H), 8.55 (br t, J = 5.8 Hz, 1H), 7.85 (d, J = 8.2 Hz, 1H), 7.51 (d, J = 8.2 Hz, 1H), 7.30 (dd, J = 6.9, 4.1 Hz, 1H), 6.94 (s, 1H), 5.81-5.63 (m, 1H), 4.85 (br d, J = 5.8 Hz, 2H), 1.48 (d, J = 6.4 Hz, 3H) | 467.0 | Method M |

-continued

| Ex. No. | Structure | Name | $^1$H NMR | LC/MS (M + H)$^+$ | Method |
|---|---|---|---|---|---|
| 312 | 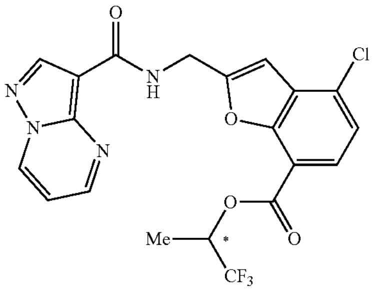 [SMILES: CC(OC(=O)c1ccc(Cl)c2cc(CNC(=O)c3cnn4cccnc34)oc12)C(F)(F)F] | 1,1,1-Trifluoropropan-2-yl 4-chloro-2-((pyrazolo[1,5-a]pyrimidine-3-carboxamido)methyl) benzofuran-7-carboxylate | $^1$H NMR (500 MHz, DMSO-$d_6$) δ 9.39-9.24 (m, 1H), 8.86-8.77 (m, 1H), 8.63 (s, 1H), 8.55 (br t, J = 5.8 Hz, 1H), 7.85 (d, J = 8.2 Hz, 1H), 7.51 (d, J = 8.2 Hz, 1H), 7.30 (dd, J = 6.9, 4.1 Hz, 1H), 6.94 (s, 1H), 5.81-5.63 (m, 1H), 4.85 (br d, J = 5.8 Hz, 2H), 1.48 (d, J = 6.4 Hz, 3H) | 467.0 | Method M |
| 313 | 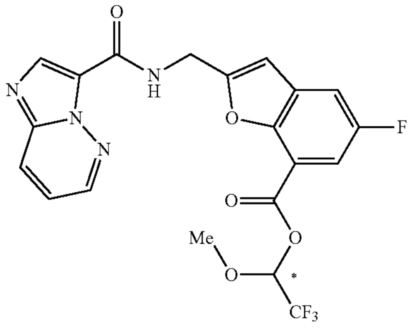 [SMILES: COC(OC(=O)c1cc(F)cc2cc(CNC(=O)c3cnc4cccnn34)oc12)C(F)(F)F] (Isomer-1) | 2,2,2-Trifluoro-1-methoxyethyl 5-fluoro-2-((imidazo[1,2-b]pyridazine-3-carboxamido)methyl) benzofuran-7-carboxylate | $^1$H NMR (500 MHz, DMSO-$d_6$) δ 9.23 (br t, J = 5.5 Hz, 1H), 8.77 (br d, J = 3.4 Hz, 1H), 8.44-8.23 (m, 2H), 7.84 (dd, J = 8.1, 2.6 Hz, 1H), 7.60 (br dd, J = 9.5, 2.4 Hz, 1H), 7.49 (dd, J = 9.2, 4.6 Hz, 1H), 6.96 (s, 1H), 6.55 (br d, J = 3.7 Hz, 1H), 4.85 (br d, J = 5.8 Hz, 2H), 3.74-3.44 (m, 3H) | 467.1 | Method F |
| 314 | 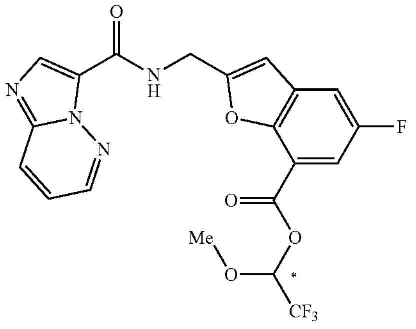 [SMILES: COC(OC(=O)c1cc(F)cc2cc(CNC(=O)c3cnc4cccnn34)oc12)C(F)(F)F] (Isomer-2) | 2,2,2-Trifluoro-1-methoxyethyl 5-fluoro-2-((imidazo[1,2-b]pyridazine-3-carboxamido)methyl) benzofuran-7-carboxylate | $^1$H NMR (500 MHz, DMSO-$d_6$) δ 9.23 (br t, J = 5.5 Hz, 1H), 8.77 (br d, J = 3.4 Hz, 1H), 8.44-8.23 (m, 2H), 7.84 (dd, J = 8.1, 2.6 Hz, 1H), 7.60 (br dd, J = 9.5, 2.4 Hz, 1H), 7.49 (dd, J = 9.2, 4.6 Hz, 1H), 6.96 (s, 1H), 6.55 (br d, J = 3.7 Hz, 1H), 4.85 (br d, J = 5.8 Hz, 2H), 3.74-3.44 (m, 3H) | 467.1 | Method F |
| 315 | 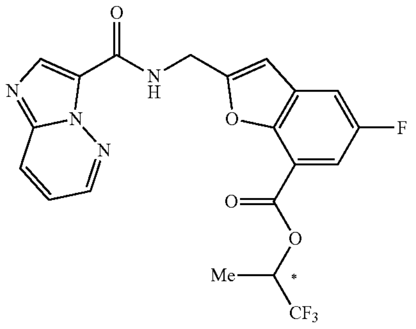 [SMILES: CC(OC(=O)c1cc(F)cc2cc(CNC(=O)c3cnc4cccnn34)oc12)C(F)(F)F] (Isomer-1) | 1,1,1-Trifluoropropan-2-yl 5-fluoro-2-((imidazo[1,2-b]pyridazine-3-carboxamido)methyl) benzofuran-7-carboxylate | $^1$H NMR (500 MHz, DMSO-$d_6$) δ 9.12 (br t, J = 5.3 Hz, 1H), 8.76 (br d, J = 4.2 Hz, 1H), 8.43-8.29 (m, 2H), 7.79 (dd, J = 8.2, 2.4 Hz, 1H), 7.57 (dd, J = 9.4, 2.4 Hz, 1H), 7.48 (dd, J = 9.2, 4.5 Hz, 1H), 6.95 (s, 1H), 5.72 (dt, J = 13.2, 6.6 Hz, 1H), 4.87 (br d, J = 5.8 Hz, 2H), 1.49 (d, J = 6.6 Hz, 3H) | 451.3 | Method D |

-continued

| Ex. No. | Structure | Name | $^1$H NMR | LC/MS $(M + H)^+$ | Method |
|---|---|---|---|---|---|
| 316 | 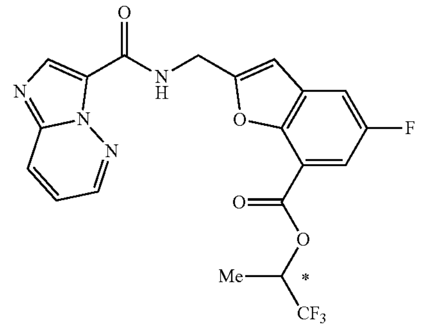 [SMILES: CC(OC(=O)c1cc(F)cc2cc(CNC(=O)c3cnc4cccnn34)oc12)C(F)(F)F] (Isomer-2) | 1,1,1-Trifluoropropan-2-yl 5-fluoro-2-((imidazo[1,2-b]pyridazine-3-carboxamido)methyl) benzofuran-7-carboxylate | $^1$H NMR (500 MHz, DMSO-$d_6$) δ 9.12 (br t, J = 5.3 Hz, 1H), 8.76 (br d, J = 4.2 Hz, 1H), 8.43-8.29 (m, 2H), 7.79 (dd, J = 8.2, 2.4 Hz, 1H), 7.57 (dd, J = 9.4, 2.4 Hz, 1H), 7.48 (dd, J = 9.2, 4.5 Hz, 1H), 6.95 (s, 1H), 5.72 (dt, J = 13.2, 6.6 Hz, 1H), 4.87 (br d, J = 5.8 Hz, 2H), 1.49 (d, J = 6.6 Hz, 3H) | 451.3 | Method D |
| 317 | 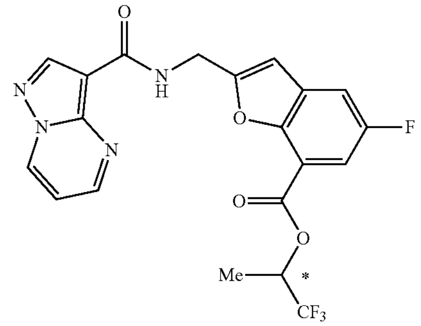 [SMILES: CC(OC(=O)c1cc(F)cc2cc(CNC(=O)c3cnn4cccnc34)oc12)C(F)(F)F] (Isomer-1) | 1,1,1-Trifluoropropan-2-yl 5-fluoro-2-((pyrazolo[1,5-a]pyrimidine-3-carboxamido)methyl) benzofuran-7-carboxylate | $^1$H NMR (500 MHz, DMSO-$d_6$) δ 9.34 (br d, J = 7.0 Hz, 1H), 8.84 (br d, J = 2.7 Hz, 1H), 8.65 (s, 1H), 8.55 (br t, J = 5.6 Hz, 1H), 7.83 (dd, J = 8.2, 2.4 Hz, 1H), 7.60 (dd, J = 9.3, 2.6 Hz, 1H), 7.31 (dd, J = 6.9, 4.1 Hz, 1H), 6.93 (s, 1H), 5.83-5.68 (m, 1H), 4.84 (br d, J = 5.8 Hz, 2H), 1.51 (d, J = 6.4 Hz, 3H) | 451.3 | Method D |
| 318 | 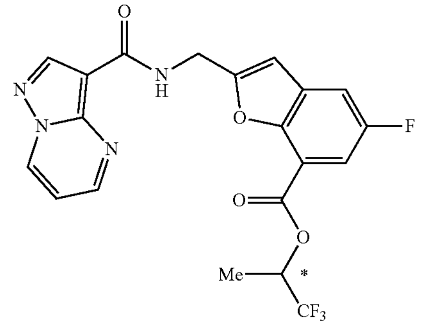 [SMILES: CC(OC(=O)c1cc(F)cc2cc(CNC(=O)c3cnn4cccnc34)oc12)C(F)(F)F] (Isomer-2) | 1,1,1-Trifluoropropan-2-yl 5-fluoro-2-((pyrazolo[1,5-a]pyrimidine-3-carboxamido)methyl) benzofuran-7-carboxylate | $^1$H NMR (500 MHz, DMSO-$d_6$) δ 9.34 (br d, J = 7.0 Hz, 1H), 8.84 (br d, J = 2.7 Hz, 1H), 8.65 (s, 1H), 8.55 (br t, J = 5.6 Hz, 1H), 7.83 (dd, J = 8.2, 2.4 Hz, 1H), 7.60 (dd, J = 9.3, 2.6 Hz, 1H), 7.31 (dd, J = 6.9, 4.1 Hz, 1H), 6.93 (s, 1H), 5.83-5.68 (m, 1H), 4.84 (br d, J = 5.8 Hz, 2H), 1.51 (d, J = 6.4 Hz, 3H) | 451.3 | Method D |
| 319 | 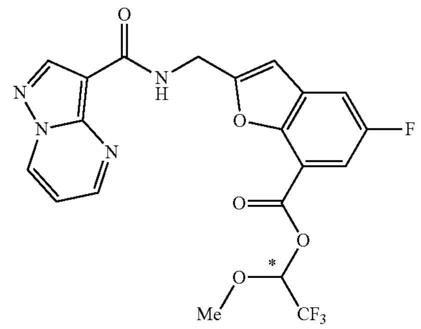 [SMILES: COC(OC(=O)c1cc(F)cc2cc(CNC(=O)c3cnn4cccnc34)oc12)C(F)(F)F] (Isomer-1) | 2,2,2-Trifluoro-1-methoxyethyl 5-fluoro-2-((pyrazolo[1,5-a]pyrimidine-3-carboxamido)methyl) benzofuran-7-carboxylate | $^1$H NMR (500 MHz, DMSO-d6) δ 9.34 (br d, J = 6.7 Hz, 1H), 8.83 (br d, J = 3.1 Hz, 1H), 8.64 (s, 1H), 8.54 (br t, J = 5.6 Hz, 1H), 7.85 (dd, J = 8.2, 2.4 Hz, 1H), 7.61 (dd, J = 9.2, 2.4 Hz, 1H), 7.31 (dd, J = 7.0, 4.3 Hz, 1H), 6.93 (s, 1H), 6.59 (br d, J = 3.7 Hz, 1H), 4.82 (br d, J = 5.8 Hz, 2H), 3.67 (s, 3H) | 467.3 | Method F |

-continued

| Ex. No. | Structure | Name | $^1$H NMR | LC/MS (M + H)$^+$ | Method |
|---|---|---|---|---|---|
| 320 | 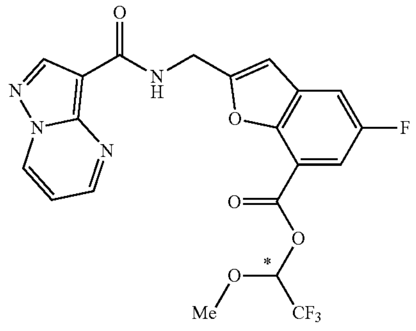 [SMILES: COC(OC(=O)c1cc(F)cc2cc(CNC(=O)c3cnn4cccnc34)oc12)C(F)(F)F] (Isomer-2) | 2,2,2-Trifluoro-1-methoxyethyl 5-fluoro-2-((pyrazolo[1,5-a]pyrimidine-3-carboxamido)methyl) benzofuran-7-carboxylate | $^1$H NMR (500 MHz, DMSO-d6) δ 9.34 (br d, J = 6.7 Hz, 1H), 8.83 (br d, J = 3.1 Hz, 1H), 8.64 (s, 1H), 8.54 (br t, J = 5.6 Hz, 1H), 7.85 (dd, J = 8.2, 2.4 Hz, 1H), 7.61 (dd, J = 9.2, 2.4 Hz, 1H), 7.31 (dd, J = 7.0, 4.3 Hz, 1H), 6.93 (s, 1H), 6.59 (br d, J = 3.7 Hz, 1H), 4.82 (br d, J = 5.8 Hz, 2H), 3.67 (s, 3H) | 467.3 | Method F |
| 321 | 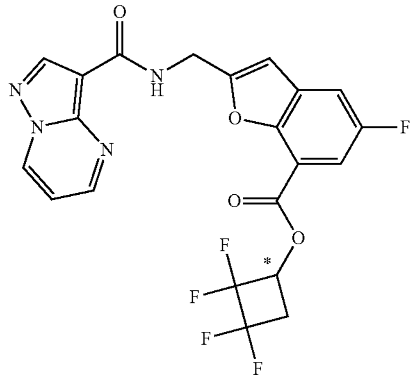 [SMILES: O=C(OC1CC(F)(F)C1(F)F)c1cc(F)cc2cc(CNC(=O)c3cnn4cccnc34)oc12] (Isomer-1) | 2,2,3,3-Tetrafluorocyclobutyl 5-fluoro-2-((pyrazolo[1,5-a]pyrimidine-3-carboxamido)methyl) benzofuran-7-carboxylate | $^1$H NMR (500 MHz, DMSO-$d_6$) δ 9.24 (br d, J = 6.9 Hz, 1H), 8.80 (br d, J = 3.9 Hz, 1H), 8.60 (s, 1H), 8.50 (br t, J = 5.6 Hz, 1H), 7.78 (dd, J = 8.2, 2.1 Hz, 1H), 7.63 (dd, J = 9.4, 2.1 Hz, 1H), 7.26 (dd, J = 6.8, 4.3 Hz, 1H), 6.92 (s, 1H), 5.62 (br d, J = 7.2 Hz, 1H), 4.82 (br dd, J = 8.4, 6.5 Hz, 2H), 3.39-3.14 (m, 1H), 3.12-2.93 (m, 1H) | 481.1 | Method D |
| 322 | 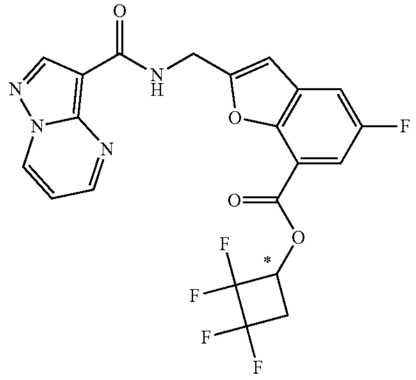 [SMILES: O=C(OC1CC(F)(F)C1(F)F)c1cc(F)cc2cc(CNC(=O)c3cnn4cccnc34)oc12] (Isomer-2) | 2,2,3,3-Tetrafluorocyclobutyl 5-fluoro-2-((pyrazolo[1,5-a]pyrimidine-3-carboxamido)methyl) benzofuran-7-carboxylate | $^1$H NMR (500 MHz, DMSO-$d_6$) δ 9.24 (br d, J = 6.9 Hz, 1H), 8.80 (br d, J = 3.9 Hz, 1H), 8.60 (s, 1H), 8.50 (br t, J = 5.6 Hz, 1H), 7.78 (dd, J = 8.2, 2.1 Hz, 1H), 7.63 (dd, J = 9.4, 2.1 Hz, 1H), 7.26 (dd, J = 6.8, 4.3 Hz, 1H), 6.92 (s, 1H), 5.62 (br d, J = 7.2 Hz, 1H), 4.82 (br dd, J = 8.4, 6.5 Hz, 2H), 3.39-3.14 (m, 1H), 3.12-2.93 (m, 1H) | 481.1 | Method D |
| 323 | 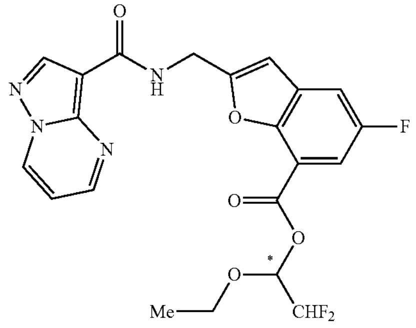 [SMILES: CCOC(OC(=O)c1cc(F)cc2cc(CNC(=O)c3cnn4cccnc34)oc12)C(F)F] (Isomer-1) | 1-Ethoxy-2,2-difluoroethyl 5-fluoro-2-((pyrazolo[1,5-a]pyrimidine-3-carboxamido)methyl) benzofuran-7-carboxylate | $^1$H NMR (500 MHz, DMSO-$d_6$) δ 9.32 (dd, J = 7.0, 1.2 Hz, 1H), 8.83 (d, J = 2.7 Hz, 1H), 8.63 (s, 1H), 8.54 (br t, J = 5.8 Hz, 1H), 7.81 (dd, J = 8.2, 2.7 Hz, 1H), 7.60 (dd, J = 9.5, 2.4 Hz, 1H), 7.29 (dd, J = 6.9, 4.1 Hz, 1H), 6.91 (s, 1H), 6.42-6.07 (m, 2H), 4.82 (d, J = 6.1 Hz, 2H), 4.05-3.69 (m, 2H), 1.16 (t, J = 7.2 Hz, 3H) | 463.3 | Method D |

-continued

| Ex. No. | Structure | Name | $^1$H NMR | LC/MS $(M + H)^+$ | Method |
|---|---|---|---|---|---|
| 324 | 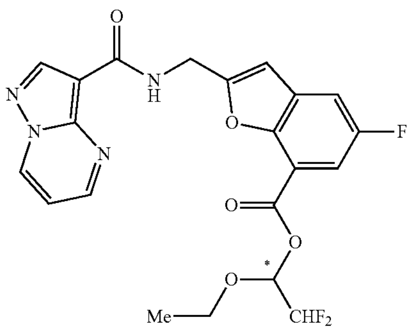 [SMILES: CCOC(OC(=O)c1cc(F)cc2cc(CNC(=O)c3cnn4cccnc34)oc12)C(F)F] (Isomer-2) | 1-Ethoxy-2,2-difluoroethyl 5-fluoro-2-((pyrazolo[1,5-a]pyrimidine-3-carboxamido)methyl) benzofuran-7-carboxylate | $^1$H NMR (500 MHz, DMSO-$d_6$) δ 9.32 (dd, J = 7.0, 1.2 Hz, 1H), 8.83 (d, J = 2.7 Hz, 1H), 8.63 (s, 1H), 8.54 (br t, J = 5.8 Hz, 1H), 7.81 (dd, J = 8.2, 2.7 Hz, 1H), 7.60 (dd, J = 9.5, 2.4 Hz, 1H), 7.29 (dd, J = 6.9, 4.1 Hz, 1H), 6.91 (s, 1H), 6.42-6.07 (m, 2H), 4.82 (d, J = 6.1 Hz, 2H), 4.05-3.69 (m, 2H), 1.16 (t, J = 7.2 Hz, 3H) | 463.3 | Method D |
| 325 | 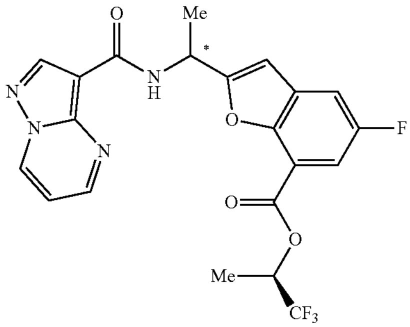 [SMILES: CC(NC(=O)c1cnn2cccnc12)c1cc2cc(F)cc(C(=O)O[C@H](C)C(F)(F)F)c2o1] | (R)-1,1,1-Trifluoropropan-2-yl 5-fluoro-2-(1-(pyrazolo[1,5-a]pyrimidine-3-carboxamido)ethyl) benzofuran-7-carboxylate | $^1$H NMR (500 MHz, DMSO-$d_6$) δ 9.25 (br d, J = 6.9 Hz, 1H), 8.79 (br s, 1H), 8.60 (s, 1H), 8.35 (br d, J = 8.1 Hz, 1H), 7.78 (br d, J = 8.2 Hz, 1H), 7.57 (br d, J = 9.3 Hz, 1H), 7.34-7.08 (m, 1H), 6.94 (s, 1H), 5.81-5.65 (m, 1H), 5.50 (br t, J = 7.3 Hz, 1H), 1.66 (br d, J = 7.0 Hz, 3H), 1.49 (br d, J = 6.3 Hz, 3H) | 465.3 | Method H |
| 326 | 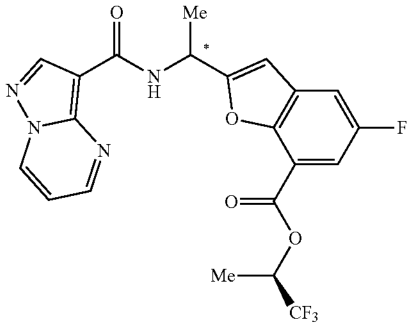 [SMILES: CC(NC(=O)c1cnn2cccnc12)c1cc2cc(F)cc(C(=O)O[C@H](C)C(F)(F)F)c2o1] | (R)-1,1,1-Trifluoropropan-2-yl 5-fluoro-2-(1-(pyrazolo[1,5-a]pyrimidine-3-carboxamido)ethyl) benzofuran-7-carboxylate | $^1$H NMR (500 MHz, DMSO-$d_6$) δ 9.25 (br d, J = 6.9 Hz, 1H), 8.79 (br s, 1H), 8.60 (s, 1H), 8.35 (br d, J = 8.1 Hz, 1H), 7.78 (br d, J = 8.2 Hz, 1H), 7.57 (br d, J = 9.3 Hz, 1H), 7.34-7.08 (m, 1H), 6.94 (s, 1H), 5.81-5.65 (m, 1H), 5.50 (br t, J = 7.3 Hz, 1H), 1.66 (br d, J = 7.0 Hz, 3H), 1.49 (br d, J = 6.3 Hz, 3H) | 465.2 | Method H |
| 327 | 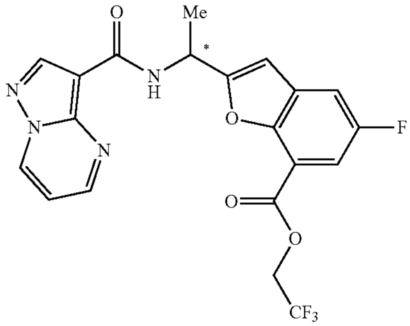 [SMILES: CC(NC(=O)c1cnn2cccnc12)c1cc2cc(F)cc(C(=O)OCC(F)(F)F)c2o1] (Isomer-1) | 2,2,2-Trifluoroethyl 5-fluoro-2-(1-(pyrazolo[1,5-a]pyrimidine-3-carboxamido)ethyl) benzofuran-7-carboxylate | $^1$H NMR (500 MHz, DMSO-$d_6$) δ 9.27 (d, J = 7.0 Hz, 1H), 8.80 (br d, J = 3.1 Hz, 1H), 8.61 (s, 1H), 8.41 (br d, J = 8.2 Hz, 1H), 7.80 (dd, J = 8.1, 2.3 Hz, 1H), 7.59 (dd, J = 9.5, 2.4 Hz, 1H), 7.27 (dd, J = 7.0, 4.3 Hz, 1H), 6.94 (s, 1H), 5.48 (br t, J = 7.3 Hz, 1H), 5.01 (q, J = 8.9 Hz, 2H), 1.65 (d, J = 6.7 Hz, 3H) | 451.3 | Method J |

-continued

| Ex. No. | Structure | Name | $^1$H NMR | LC/MS $(M + H)^+$ | Method |
|---|---|---|---|---|---|
| 328 | 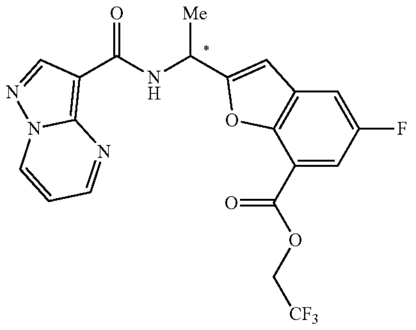 [SMILES: CC(NC(=O)c1cnn2cccnc12)c1cc2cc(F)cc(C(=O)OCC(F)(F)F)c2o1] (Isomer-2) | 2,2,2-Trifluoroethyl 5-fluoro-2-(1-(pyrazolo[1,5-a]pyrimidine-3-carboxamido)ethyl) benzofuran-7-carboxylate | $^1$H NMR (500 MHz, DMSO-$d_6$) δ 9.27 (d, J = 7.0 Hz, 1H), 8.80 (br d, J = 3.1 Hz, 1H), 8.61 (s, 1H), 8.41 (br d, J = 8.2 Hz, 1H), 7.80 (dd, J = 8.1, 2.3 Hz, 1H), 7.59 (dd, J = 9.5, 2.4 Hz, 1H), 7.27 (dd, J = 7.0, 4.3 Hz, 1H), 6.94 (s, 1H), 5.48 (br t, J = 7.3 Hz, 1H), 5.01 (q, J = 8.9 Hz, 2H), 1.65 (d, J = 6.7 Hz, 3H) | 451.3 | Method J |
| 329 | 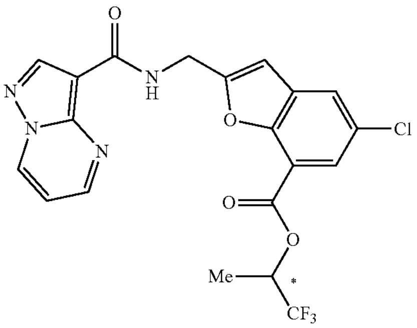 [SMILES: CC(OC(=O)c1cc(Cl)cc2cc(CNC(=O)c3cnn4cccnc34)oc12)C(F)(F)F] (Isomer-1) | 1,1,1-Trifluoropropan-2-yl 5-chloro-2-((pyrazolo[1,5-a]pyrimidine-3-carboxamido)methyl) benzofuran-7-carboxylate | $^1$H NMR (500 MHz, DMSO-$d_6$) δ 9.34 (br d, J = 6.7 Hz, 1H), 8.85 (br d, J = 2.7 Hz, 1H), 8.65 (s, 1H), 8.56 (br t, J = 5.8 Hz, 1H), 8.05 (d, J = 1.8 Hz, 1H), 7.77 (d, J = 1.8 Hz, 1H), 7.32 (dd, J = 7.0, 4.3 Hz, 1H), 6.92 (s, 1H), 5.86-5.67 (m, 1H), 4.84 (br d, J = 5.8 Hz, 2H), 1.51 (br d, J = 6.4 Hz, 3H) | 467.2 | Method D |
| 330 | 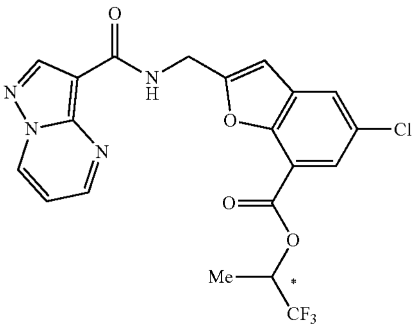 (Isomer-2) | 1,1,1-Trifluoropropan-2-yl 5-chloro-2-((pyrazolo[1,5-a]pyrimidine-3-carboxamido)methyl) benzofuran-7-carboxylate | $^1$H NMR (500 MHz, DMSO-$d_6$) δ 9.34 (br d, J = 6.7 Hz, 1H), 8.85 (br d, J = 2.7 Hz, 1H), 8.65 (s, 1H), 8.56 (br t, J = 5.8 Hz, 1H), 8.05 (d, J = 1.8 Hz, 1H), 7.77 (d, J = 1.8 Hz, 1H), 7.32 (dd, J = 7.0, 4.3 Hz, 1H), 6.92 (s, 1H), 5.86-5.67 (m, 1H), 4.84 (br d, J = 5.8 Hz, 2H), 1.51 (br d, J = 6.4 Hz, 3H) | 467.2 | Method D |
| 331 | 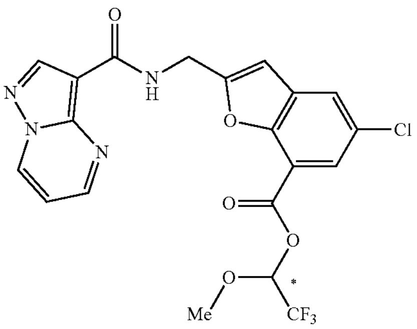 (Isomer-1) | 2,2,2-Trifluoro-1-methoxyethyl 5-chloro-2-((pyrazolo[1,5-a]pyrimidine-3-carboxamido)methyl) benzofuran-7-carboxylate | $^1$H NMR (500 MHz, DMSO-d6) δ 9.35 (br d, J = 7.0 Hz, 1H), 8.84 (br d, J = 3.1 Hz, 1H), 8.64 (s, 1H), 8.54 (br t, J = 5.5 Hz, 1H), 8.08 (d, J = 1.8 Hz, 1H), 7.78 (d, J = 1.8 Hz, 1H), 7.31 (dd, J = 6.9, 4.1 Hz, 1H), 6.92 (s, 1H), 6.60 (br d, J = 3.7 Hz, 1H), 4.83 (br d, J = 5.8 Hz, 2H), 3.67 (s, 3H) | 482.9 | Method F |

-continued

| Ex. No. | Structure | Name | $^1$H NMR | LC/MS (M + H)$^+$ | Method |
|---|---|---|---|---|---|
| 332 | 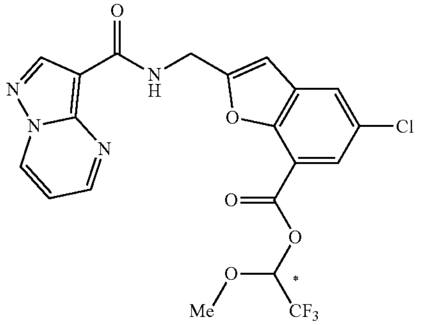 [SMILES: COC(OC(=O)c1cc(Cl)cc2cc(CNC(=O)c3cnn4cccnc34)oc12)C(F)(F)F] (Isomer-2) | 2,2,2-Trifluoro-1-methoxyethyl 5-chloro-2-((pyrazolo[1,5-a]pyrimidine-3-carboxamido)methyl) benzofuran-7-carboxylate | $^1$H NMR (500 MHz, DMSO-d6) δ 9.35 (br d, J = 7.0 Hz, 1H), 8.84 (br d, J = 3.1 Hz, 1H), 8.64 (s, 1H), 8.54 (br t, J = 5.5 Hz, 1H), 8.08 (d, J = 1.8 Hz, 1H), 7.78 (d, J = 1.8 Hz, 1H), 7.31 (dd, J = 6.9, 4.1 Hz, 1H), 6.92 (s, 1H), 6.60 (br d, J = 3.7 Hz, 1H), 4.83 (br d, J = 5.8 Hz, 2H), 3.67 (s, 3H) | 482.9 | Method F |
| 333 | 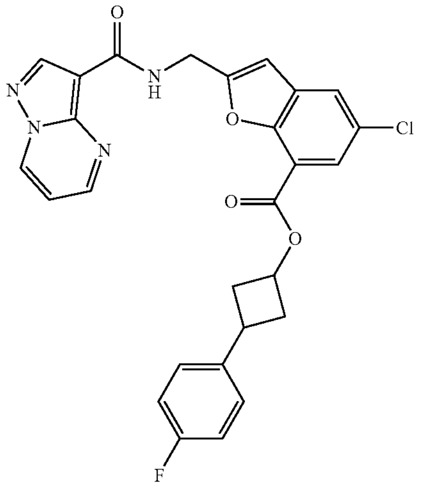 [SMILES: O=C(OC1CC(c2ccc(F)cc2)C1)c1cc(Cl)cc2cc(CNC(=O)c3cnn4cccnc34)oc12] (Isomer-1) (cis- trans- not determined) | 3-(4-Fluorophenyl) cyclobutyl 5-chloro-2-((pyrazolo[1,5-a]pyrimidine-3-carboxamido)methyl) benzofuran-7-carboxylate | $^1$H NMR (500 MHz, DMSO-d6) δ 9.24 (br d, J = 5.8 Hz, 1H), 8.74 (br d, J = 2.7 Hz, 1H), 8.58-8.45 (m, 2H), 7.96 (d, J = 1.8 Hz, 1H), 7.76 (d, J = 1.8 Hz, 1H), 7.37-7.16 (m, 3H), 7.08 (br t, J = 8.9 Hz, 2H), 6.88 (s, 1H), 5.17 (br t, J = 7.3 Hz, 1H), 4.82 (br d, J = 5.8 Hz, 2H), 3.28-3.06 (m, 1H), 2.88-2.73 (m, 2H), 2.19 (br d, J = 9.2 Hz, 2H) | 519.4 | Method G |
| 334 | 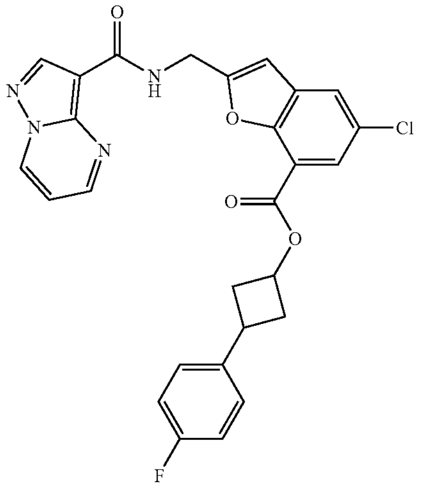 [SMILES: O=C(OC1CC(c2ccc(F)cc2)C1)c1cc(Cl)cc2cc(CNC(=O)c3cnn4cccnc34)oc12] (Isomer-2) (cis- trans- not determined) | 3-(4-Fluorophenyl) cyclobutyl 5-chloro-2-((pyrazolo[1,5-a]pyrimidine-3-carboxamido)methyl) benzofuran-7-carboxylate | $^1$H NMR (500 MHz, DMSO-d6) δ 9.24 (br d, J = 5.8 Hz, 1H), 8.74 (br d, J = 2.7 Hz, 1H), 8.58-8.45 (m, 2H), 7.96 (d, J = 1.8 Hz, 1H), 7.76 (d, J = 1.8 Hz, 1H), 7.37-7.16 (m, 3H), 7.08 (br t, J = 8.9 Hz, 2H), 6.88 (s, 1H), 5.17 (br t, J = 7.3 Hz, 1H), 4.82 (br d, J = 5.8 Hz, 2H), 3.28-3.06 (m, 1H), 2.88-2.73 (m, 2H), 2.19 (br d, J = 9.2 Hz, 2H) | 519.4 | Method G |

-continued

| Ex. No. | Structure | Name | $^1$H NMR | LC/MS $(M + H)^+$ | Method |
| --- | --- | --- | --- | --- | --- |
| 335 | 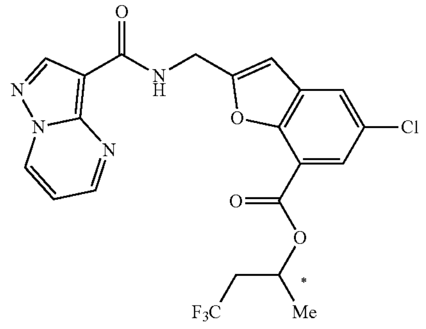 [SMILES: CC(CC(F)(F)F)OC(=O)c1cc(Cl)cc2cc(CNC(=O)c3cnn4cccnc34)oc12] (Isomer-1) (Method D) | 4,4,4-Trifluorobutan-2-yl 5-chloro-2-((pyrazolo[1,5-a]pyrimidine-3-carboxamido)methyl) benzofuran-7-carboxylate | $^1$H NMR (500 MHz, DMSO-$d_6$) δ 9.33 (dd, J = 7.0, 1.5 Hz, 1H), 8.83 (dd, J = 4.1, 1.4 Hz, 1H), 8.63 (s, 1H), 8.52 (br t, J = 6.0 Hz, 1H), 7.98 (d, J = 2.1 Hz, 1H), 7.74 (d, J = 2.1 Hz, 1H), 7.30 (dd, J = 7.0, 4.3 Hz, 1H), 6.88 (s, 1H), 5.50-5.34 (m, 1H), 4.82 (br t, J = 5.5 Hz, 2H), 2.90-2.66 (m, 2H), 1.38 (d, J = 6.4 Hz, 3H) | 481.3 | Method D |
| 336 | 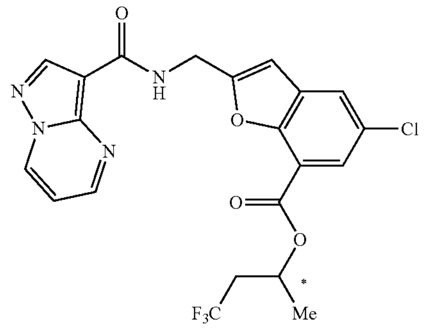 [SMILES: CC(CC(F)(F)F)OC(=O)c1cc(Cl)cc2cc(CNC(=O)c3cnn4cccnc34)oc12] (Isomer-2) | 4,4,4-Trifluorobutan-2-yl 5-chloro-2-((pyrazolo[1,5-a]pyrimidine-3-carboxamido)methyl) benzofuran-7-carboxylate | $^1$H NMR (500 MHz, DMSO-$d_6$) δ 9.33 (dd, J = 7.0, 1.5 Hz, 1H), 8.83 (dd, J = 4.1, 1.4 Hz, 1H), 8.63 (s, 1H), 8.52 (br t, J = 6.0 Hz, 1H), 7.98 (d, J = 2.1 Hz, 1H), 7.74 (d, J = 2.1 Hz, 1H), 7.30 (dd, J = 7.0, 4.3 Hz, 1H), 6.88 (s, 1H), 5.50-5.34 (m, 1H), 4.82 (br t, J = 5.5 Hz, 2H), 2.90-2.66 (m, 2H), 1.38 (d, J = 6.4 Hz, 3H) | 481.3 | Method D |
| 337 | 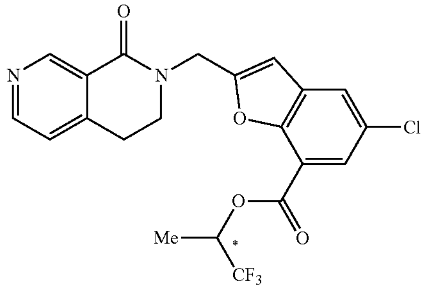 [SMILES: CC(OC(=O)c1cc(Cl)cc2cc(CN3CCc4ccncc4C3=O)oc12)C(F)(F)F] | 1,1,1-Trifluoropropan-2-yl 5-chloro-2-((1-oxo-3,4-dihydro-2,7-naphthyridin-2(1H)-yl)methyl) benzofuran-7-carboxylate | $^1$H NMR (500 MHz, DMSO-$d_6$) δ 8.98 (s, 1H), 8.64 (br d, J = 4.9 Hz, 1H), 8.08 (d, J = 1.5 Hz, 1H), 7.80 (d, J = 1.8 Hz, 1H), 7.40 (br d, J = 4.9 Hz, 1H), 7.04 (s, 1H), 5.84-5.70 (m, 1H), 5.11-4.87 (m, 2H), 3.75 (br t, J = 6.6 Hz, 2H), 3.08 (br t, J = 6.6 Hz, 2H), 1.49 (br d, J = 6.7 Hz, 3H) | 453.3 | Method F |
| 338 | 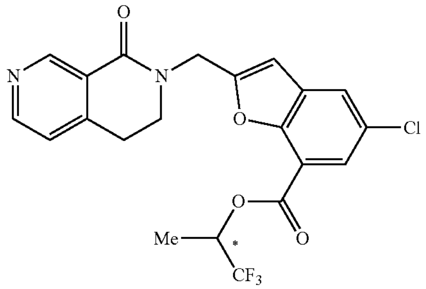 [SMILES: CC(OC(=O)c1cc(Cl)cc2cc(CN3CCc4ccncc4C3=O)oc12)C(F)(F)F] | 1,1,1-Trifluoropropan-2-yl 5-chloro-2-((1-oxo-3,4-dihydro-2,7-naphthyridin-2(1H)-yl)methyl) benzofuran-7-carboxylate | $^1$H NMR (500 MHz, DMSO-$d_6$) δ 8.98 (s, 1H), 8.64 (br d, J = 4.9 Hz, 1H), 8.08 (d, J = 1.5 Hz, 1H), 7.80 (d, J = 1.8 Hz, 1H), 7.40 (br d, J = 4.9 Hz, 1H), 7.04 (s, 1H), 5.84-5.70 (m, 1H), 5.11-4.87 (m, 2H), 3.75 (br t, J = 6.6 Hz, 2H), 3.08 (br t, J = 6.6 Hz, 2H), 1.49 (br d, J = 6.7 Hz, 3H) | 453.3 | Method F |

-continued

| Ex. No. | Structure | Name | $^1$H NMR | LC/MS (M + H)$^+$ | Method |
|---|---|---|---|---|---|
| 339 | 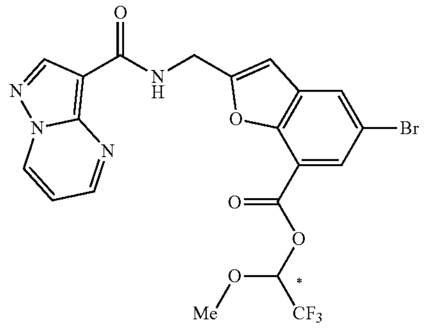 [SMILES: COC(OC(=O)c1cc(Br)cc2cc(CNC(=O)c3cnn4cccnc34)oc12)C(F)(F)F] (Isomer-1) | 2,2,2-Trifluoro-1-methoxyethyl 5-bromo-2-((pyrazolo[1,5-a]pyrimidine-3-carboxamido)methyl) benzofuran-7-carboxylate | $^1$H NMR (500 MHz, DMSO-$d_6$) δ 9.25 (br d, J = 6.0 Hz, 1H), 8.80 (br d, J = 3.2 Hz, 1H), 8.60 (s, 1H), 8.54-8.42 (m, 1H), 8.17 (s, 1H), 7.88 (s, 1H), 7.27 (dd, J = 6.8, 4.3 Hz, 1H), 6.91 (s, 1H), 6.51 (br s, 1H), 4.82 (br d, J = 5.7 Hz, 2H), 3.65 (s, 3H | 529.2 | Method F |
| 340 | 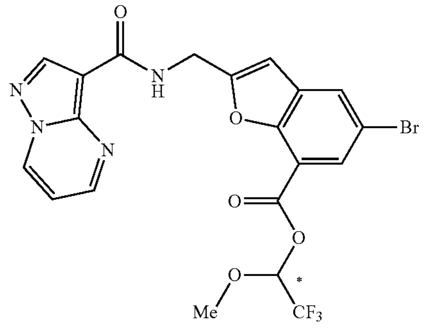 [SMILES: COC(OC(=O)c1cc(Br)cc2cc(CNC(=O)c3cnn4cccnc34)oc12)C(F)(F)F] (Isomer-2) | 2,2,2-Trifluoro-1-methoxyethyl 5-bromo-2-((pyrazolo[1,5-a]pyrimidine-3-carboxamido)methyl) benzofuran-7-carboxylate | $^1$H NMR (500 MHz, DMSO-$d_6$) δ 9.25 (br d, J = 6.0 Hz, 1H), 8.80 (br d, J = 3.2 Hz, 1H), 8.60 (s, 1H), 8.54-8.42 (m, 1H), 8.17 (s, 1H), 7.88 (s, 1H), 7.27 (dd, J = 6.8, 4.3 Hz, 1H), 6.91 (s, 1H), 6.51 (br s, 1H), 4.82 (br d, J = 5.7 Hz, 2H), 3.65 (s, 3H) | 529.2 | Method F |
| 341 | 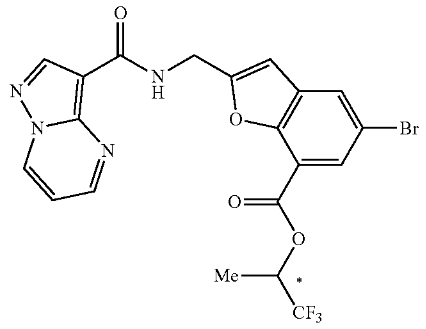 [SMILES: CC(OC(=O)c1cc(Br)cc2cc(CNC(=O)c3cnn4cccnc34)oc12)C(F)(F)F] (Isomer-1) | 1,1,1-Trifluoropropan-2-yl 5-bromo-2-((pyrazolo[1,5-a]pyrimidine-3-carboxamido)methyl) benzofuran-7-carboxylate | $^1$H NMR (500 MHz, DMSO-d6) δ 9.24 (d, J = 7.0 Hz, 1H), 8.80 (br d, J = 3.1 Hz, 1H), 8.64-8.51 (m, 2H), 8.13 (d, J = 1.5 Hz, 1H), 7.84 (d, J = 1.5 Hz, 1H), 7.27 (dd, J = 6.7, 4.3 Hz, 1H), 6.89 (s, 1H), 5.78-5.54 (m, 1H), 4.80 (br d, J = 4.3 Hz, 2H), 1.46 (d, J = 6.7 Hz, 3H) | 513.2 | |
| 342 | 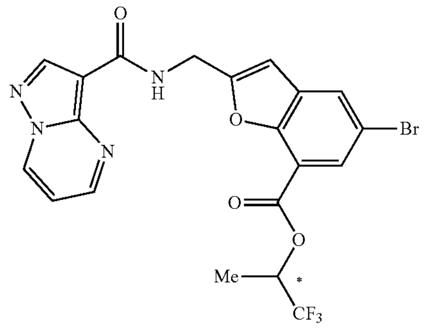 (Isomer-2) | 1,1,1-Trifluoropropan-2-yl 5-bromo-2-((pyrazolo[1,5-a]pyrimidine-3-carboxamido)methyl) benzofuran-7-carboxylate | $^1$H NMR (500 MHz, DMSO-d6) δ 9.24 (d, J = 7.0 Hz, 1H), 8.80 (br d, J = 3.1 Hz, 1H), 8.64-8.51 (m, 2H), 8.13 (d, J = 1.5 Hz, 1H), 7.84 (d, J = 1.5 Hz, 1H), 7.27 (dd, J = 6.7, 4.3 Hz, 1H), 6.89 (s, 1H), 5.78-5.54 (m, 1H), 4.80 (br d, J = 4.3 Hz, 2H), 1.46 (d, J = 6.7 Hz, 3H) | 513.2 | Method D |

-continued

| Ex. No. | Structure | Name | $^1$H NMR | LC/MS $(M + H)^+$ | Method |
|---|---|---|---|---|---|
| 343 | 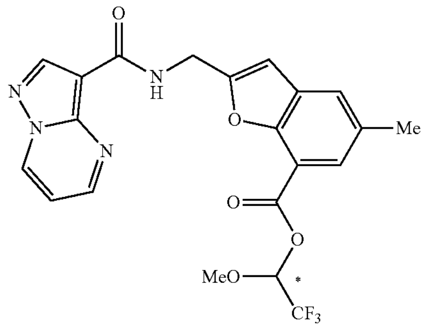 [SMILES: COC(OC(=O)c1cc(C)cc2cc(CNC(=O)c3cnn4cccnc34)oc12)C(F)(F)F] (Isomer-1) | 2,2,2-Trifluoro-1-methoxyethyl 5-methyl-2-((pyrazolo[1,5-a]pyrimidine-3-carboxamido)methyl) benzofuran-7-carboxylate | $^1$H NMR (500 MHz, DMSO-$d_6$) δ 9.24 (br d, J = 6.9 Hz, 1H), 8.78 (br d, J = 3.8 Hz, 1H), 8.59 (s, 1H), 8.45 (br t, J = 5.6 Hz, 1H), 7.74 (s, 1H), 7.65 (s, 1H), 7.25 (dd, J = 6.8, 4.3 Hz, 1H), 6.82 (s, 1H), 6.48 (br d, J = 3.4 Hz, 1H), 4.78 (d, J = 5.8 Hz, 2H), 3.63 (s, 3H), 2.43 (s, 3H) | 463.1 | Method F |
| 344 | 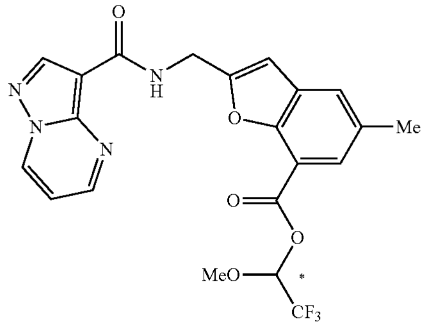 [SMILES: COC(OC(=O)c1cc(C)cc2cc(CNC(=O)c3cnn4cccnc34)oc12)C(F)(F)F] (Isomer-2) | 2,2,2-Trifluoro-1-methoxyethyl 5-methyl-2-((pyrazolo[1,5-a]pyrimidine-3-carboxamido)methyl) benzofuran-7-carboxylate | $^1$H NMR (500 MHz, DMSO-$d_6$) δ 9.28 (br d, J = 6.6 Hz, 1H), 8.79 (br d, J = 3.1 Hz, 1H), 8.60 (s, 1H), 8.44 (br t, J = 5.6 Hz, 1H), 7.75 (s, 1H), 7.66 (s, 1H), 7.27 (dd, J = 6.7, 4.4 Hz, 1H), 6.83 (s, 1H), 6.51 (br d, J = 3.7 Hz, 1H), 4.79 (br d, J = 5.8 Hz, 2H), 3.65 (s, 3H), 2.43 (s, 3H) | 463.1 | Method F |
| 345 | 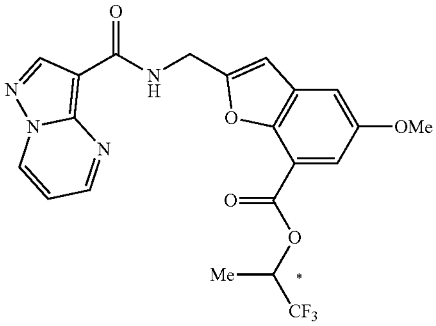 [SMILES: COc1cc(C(=O)OC(C)C(F)(F)F)c2oc(CNC(=O)c3cnn4cccnc34)cc2c1] (Isomer-1) | 1,1,1-Trifluoropropan-2-yl 5-methoxy-2-((pyrazolo[1,5-a]pyrimidine-3-carboxamido)methyl) benzofuran-7-carboxylate | $^1$H NMR (500 MHz, DMSO-$d_6$) δ 9.24 (br d, J = 6.8 Hz, 1H), 8.79 (br d, J = 3.3 Hz, 1H), 8.60 (s, 1H), 8.46 (br t, J = 5.4 Hz, 1H), 7.49 (d, J = 2.1 Hz, 1H), 7.32 (d, J = 2.1 Hz, 1H), 7.26 (dd, J = 6.7, 4.4 Hz, 1H), 6.83 (s, 1H), 5.83-5.52 (m, 1H), 4.78 (br d, J = 5.8 Hz, 2H), 3.82 (s, 3H), 1.48 (d, J = 6.6 Hz, 3H) | 463.3 | Method G |
| 346 | 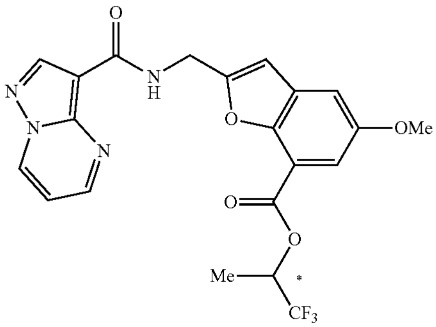 [SMILES: COc1cc(C(=O)OC(C)C(F)(F)F)c2oc(CNC(=O)c3cnn4cccnc34)cc2c1] (Isomer-2) | 1,1,1-Trifluoropropan-2-yl 5-methoxy-2-((pyrazolo[1,5-a]pyrimidine-3-carboxamido)methyl) benzofuran-7-carboxylate | $^1$H NMR (500 MHz, DMSO-$d_6$) δ 9.24 (br d, J = 6.8 Hz, 1H), 8.79 (br d, J = 3.3 Hz, 1H), 8.60 (s, 1H), 8.46 (br t, J = 5.4 Hz, 1H), 7.49 (d, J = 2.1 Hz, 1H), 7.32 (d, J = 2.1 Hz, 1H), 7.26 (dd, J = 6.7, 4.4 Hz, 1H), 6.83 (s, 1H), 5.83-5.52 (m, 1H), 4.78 (br d, J = 5.8 Hz, 2H), 3.82 (s, 3H), 1.48 (d, J = 6.6 Hz, 3H) | 463.3 | Method G |

-continued

| Ex. No. | Structure | Name | $^1$H NMR | LC/MS (M + H)$^+$ | Method |
|---|---|---|---|---|---|
| 347 | 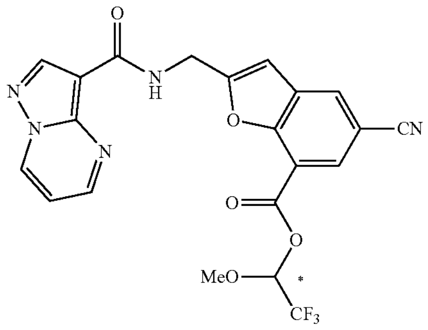 [SMILES: COC(OC(=O)c1cc(C#N)cc2cc(CNC(=O)c3cnn4cccnc34)oc12)C(F)(F)F] (Isomer-1) | 2,2,2-Trifluoro-1-methoxyethyl 5-cyano-2-((pyrazolo[1,5-a]pyrimidine-3-carboxamido)methyl) benzofuran-7-carboxylate | $^1$H NMR (500 MHz, DMSO-$d_6$) δ 9.27 (br d, J = 6.7 Hz, 1H), 8.81 (br d, J = 3.9 Hz, 1H), 8.69-8.58 (m, 1H), 8.52 (br t, J = 5.8 Hz, 1H), 8.46 (s, 1H), 8.18 (s, 1H), 7.28 (dd, J = 6.7, 4.3 Hz, 1H), 7.03 (s, 1H), 6.55 (br s, 1H), 4.85 (br d, J = 5.8 Hz, 2H), 3.67 (s, 3H) | 474.3 | Method F |
| 348 | 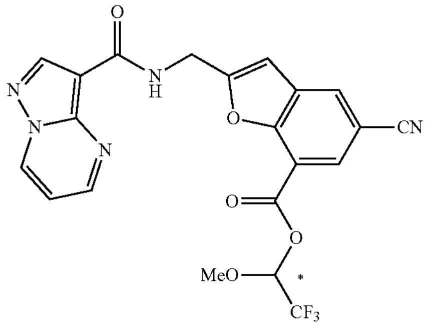 [SMILES: COC(OC(=O)c1cc(C#N)cc2cc(CNC(=O)c3cnn4cccnc34)oc12)C(F)(F)F] (Isomer-2) | 2,2,2-Trifluoro-1-methoxyethyl 5-cyano-2-((pyrazolo[1,5-a]pyrimidine-3-carboxamido)methyl) benzofuran-7-carboxylate | $^1$H NMR (500 MHz, DMSO-$d_6$) δ 9.27 (br d, J = 6.7 Hz, 1H), 8.81 (br d, J = 3.9 Hz, 1H), 8.69-8.58 (m, 1H), 8.52 (br t, J = 5.8 Hz, 1H), 8.46 (s, 1H), 8.18 (s, 1H), 7.28 (dd, J = 6.7, 4.3 Hz, 1H), 7.03 (s, 1H), 6.55 (br s, 1H), 4.85 (br d, J = 5.8 Hz, 2H), 3.67 (s, 3H) | 474.3 | Method F |
| 349 | 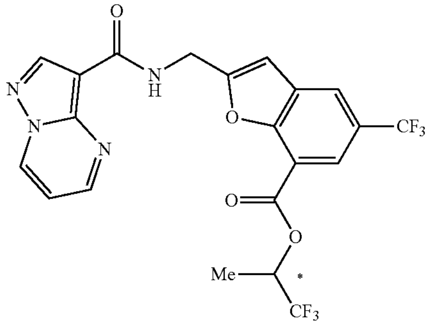 [SMILES: CC(OC(=O)c1cc(C(F)(F)F)cc2cc(CNC(=O)c3cnn4cccnc34)oc12)C(F)(F)F] (Isomer-1) | 1,1,1-Trifluoropropan-2-yl 2-((pyrazolo[1,5-a]pyrimidine-3-carboxamido)methyl)-5-(trifluoromethyl) benzofuran-7-carboxylate | $^1$H NMR (500 MHz, DMSO-$d_6$) δ 9.28 (br d, J = 6.3 Hz, 1H), 8.80 (br d, J = 2.9 Hz, 1H), 8.60 (s, 1H), 8.50 (br t, J = 5.4 Hz, 1H), 8.35 (s, 1H), 8.03 (s, 1H), 7.27 (dd, J = 6.8, 4.3 Hz, 1H), 7.04 (s, 1H), 5.74 (dt, J = 13.1, 6.6 Hz, 1H), 4.86 (br d, J = 5.8 Hz, 2H), 1.51 (br d, J = 6.5 Hz, 3H) | 501.1 | Method D |
| 350 | 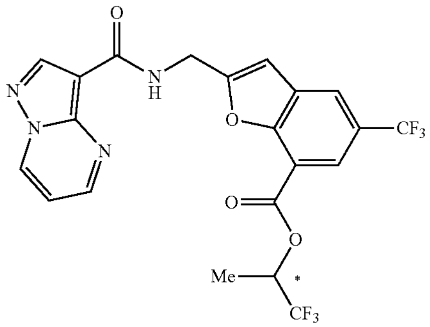 [SMILES: CC(OC(=O)c1cc(C(F)(F)F)cc2cc(CNC(=O)c3cnn4cccnc34)oc12)C(F)(F)F] (Isomer-2) | 1,1,1-Trifluoropropan-2-yl 2-((pyrazolo[1,5-a]pyrimidine-3-carboxamido)methyl)-5-(trifluoromethyl) benzofuran-7-carboxylate | $^1$H NMR (500 MHz, DMSO-$d_6$) δ 9.28 (dd, J = 7.0, 1.2 Hz, 1H), 8.80 (dd, J = 4.1, 1.4 Hz, 1H), 8.61 (s, 1H), 8.56 (br t, J = 5.8 Hz, 1H), 8.36 (s, 1H), 8.01 (s, 1H), 7.27 (dd, J = 6.7, 4.3 Hz, 1H), 7.03 (s, 1H), 5.74 (quin, J = 6.6 Hz, 1H), 4.84 (br d, J = 5.8 Hz, 2H), 1.48 (d, J = 6.4 Hz, 3H) | 501.3 | Method D |

-continued

| Ex. No. | Structure | Name | $^1H$ NMR | LC/MS $(M + H)^+$ | Method |
|---|---|---|---|---|---|
| 351 | 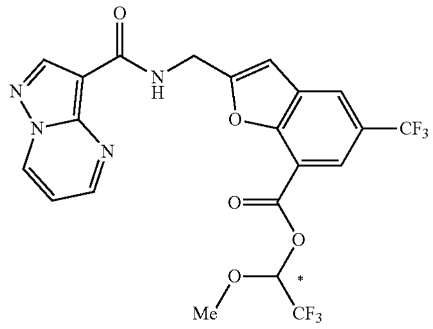 [SMILES: COC(OC(=O)c1cc(C(F)(F)F)cc2cc(CNC(=O)c3cnn4cccnc34)oc12)C(F)(F)F] (Isomer-1) | 2,2,2-Trifluoro-1-methoxyethyl 2-((pyrazolo[1,5-a]pyrimidine-3-carboxamido)methyl)-5-(trifluoromethyl) benzofuran-7-carboxylate | $^1H$ NMR (500 MHz, DMSO-d6) δ 9.23 (br d, J = 6.7 Hz, 1H), 8.79 (br d, J = 2.7 Hz, 1H), 8.59 (s, 2H), 8.37 (s, 1H), 8.02 (s, 1H), 7.26 (br dd, J = 6.6, 4.1 Hz, 1H), 7.04 (s, 1H), 6.54 (br d, J = 3.4 Hz, 1H), 4.82 (br d, J = 5.5 Hz, 2H), 3.67 (s, 3H) | 517.2 | Method E |
| 352 | 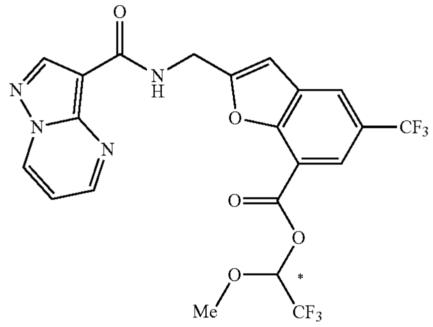 [SMILES: COC(OC(=O)c1cc(C(F)(F)F)cc2cc(CNC(=O)c3cnn4cccnc34)oc12)C(F)(F)F] (Isomer-2) | 2,2,2-Trifluoro-1-methoxyethyl 2-((pyrazolo[1,5-a]pyrimidine-3-carboxamido)methyl)-5-(trifluoromethyl) benzofuran-7-carboxylate | $^1H$ NMR (500 MHz, DMSO-$d_6$) δ 9.26 (br d, J = 6.6 Hz, 1H), 8.80 (br d, J = 3.2 Hz, 1H), 8.60 (s, 1H), 8.51 (br t, J = 5.6 Hz, 1H), 8.38 (s, 1H), 8.05 (s, 1H), 7.27 (dd, J = 6.6, 4.4 Hz, 1H), 7.05 (s, 1H), 6.55 (br d, J = 2.9 Hz, 1H), 4.85 (br d, J = 5.8 Hz, 2H), 3.67 (s, 3H) | 517.2 | Method E |

Example 353

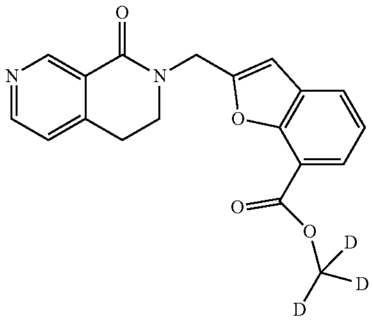 [SMILES: [2H]C([2H])([2H])OC(=O)c1cccc2cc(CN3CCc4ccncc4C3=O)oc12]

Methyl-D3 2-((1-oxo-3,4-dihydro-2,7-naphthyridin-2(1H)-yl)methyl)benzofuran-7-carboxylate A mixture of 2-((1-oxo-3,4-dihydro-2,7-naphthyridin-2(1H)-yl)methyl)benzofuran-7-carboxylic acid (15 mg, 0.047 mmol, Example 129), Methanol-D3 (16.3 mg, 0.465 mmol), HATU (35.4 mg, 0.093 mmol) and Hunig's base (24.4 μl, 0.140 mmol) in DMF (465 μl) was stirred at room temperature for 2 hours. The reaction mixture was quenched with 1:1 DMF/AcOH and purified by preparative HPLC (Method B). The appropriate fractions were combined and dried via centrifugal evaporation to afford the title compound (8 mg, 50.7% yield). $^1H$ NMR (500 MHz, DMSO-$d_6$) δ 8.97 (s, 1H), 8.63 (d, J=5.2 Hz, 1H), 7.88 (d, J=7.6 Hz, 1H), 7.83 (d, J=7.6 Hz, 1H), 7.43-7.33 (m, 2H), 6.98 (s, 1H), 4.94 (s, 2H), 3.82-3.70 (m, 2H), 3.10 (t, J=6.6 Hz, 2H); MS (ESI+) m/z=340.0 $(M+H)^+$.

Example 354

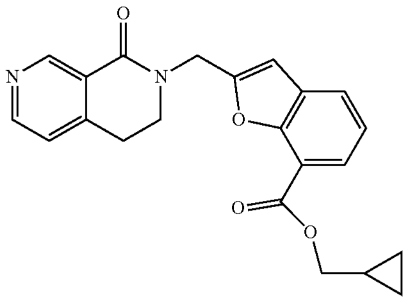 [SMILES: O=C(OCC1CC1)c1cccc2cc(CN3CCc4ccncc4C3=O)oc12]

Cyclopropylmethyl 2-((1-oxo-3,4-dihydro-2,7-naphthyridin-2(1H)-yl)methyl)benzofuran-7-carboxylate A mixture of 2-((1-oxo-3,4-dihydro-2,7-naphthyridin-2(1H)-yl)methyl)benzofuran-7-carboxylic acid (10 mg, 0.031 mmol, Example 129), Hunig's base (21.7 μl, 0.124 mmol), PyBOP (32.3 mg, 0.062 mmol) and cyclopropanemethanol (11.2 mg, 0.155 mmol) in DMF (310 μl) was stirred at room temperature for 72 hours. The reaction mixture was quenched with 1:1 DMF/AcOH and purified by preparative HPLC (Method B). The appropriate fractions were combined and dried via centrifugal evaporation to afford the title compound (6 mg, 51.4% yield). $^1$H NMR (500 MHz, DMSO-$d_6$) δ 8.72 (s, 1H), 8.36 (d, J=5.0 Hz, 1H), 7.63 (d, J=7.7 Hz, 1H), 7.61-7.48 (m, 1H), 7.20-7.04 (m, 2H), 6.72 (s, 1H), 4.69 (s, 2H), 3.90 (d, J=7.0 Hz, 2H), 3.50 (t, J=6.6 Hz, 2H), 2.83 (t, J=6.6 Hz, 2H), 0.95-0.86 (m, 1H), 0.30-0.18 (m, 2H), 0.07 (br d, J=4.9 Hz, 2H); MS (ESI+) m/z=377.1 $(M+H)^+$.

Example 355

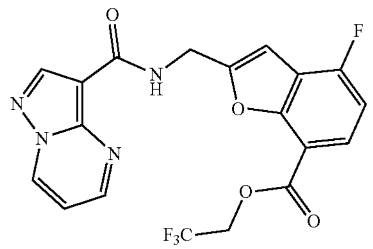 [SMILES: O=C(OCC(F)(F)F)c1ccc(F)c2cc(CNC(=O)c3cnn4cccnc34)oc12]

2,2,2-Trifluoroethyl 4-fluoro-2-((pyrazolo[1,5-a] pyrimidine-3-carboxamido)methyl)benzofuran-7-carboxylate

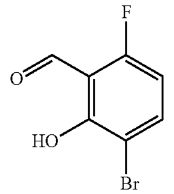 [SMILES: O=Cc1c(F)ccc(Br)c1O]

A) 3-Bromo-6-fluoro-2-hydroxybenzaldehyde

To the solution of 2-bromo-5-fluorophenol (2.70 g, 14.14 mmol) in THF (80 mL) was added triethylamine (3.94 mL, 28.3 mmol) and magnesium chloride (2.69 g, 28.3 mmol). The reaction mixture was stirred at room temperature for 15 min and then paraformaldehyde (1.27 g, 42.4 mmol) was added. The reaction mixture was stirred at 80° C. for 16 h. The reaction mixture was concentrated in vacuo. The residue was dissolved in hydrochloric acid, 10% aqueous (40 mL) and stirred at room temperature for 30 minutes. Ethyl acetate (80 mL) was added and the layers were separated. The organic layer was dried over sodium sulfate and concentrated in vacuo. The residue was purified through a silica gel ISCO 120 g column, eluted with 0-20% EtOAc in hexane over 30 min to give the desired product as a light yellow solid (1.86 g, 60.1% yield). 1H NMR (400 MHz, Chloroform-d) δ 10.19 (s, 1H), 7.79-7.67 (m, 1H), 6.61 (m, 1H); MS (ESI+) m/z=217.9 $(M+H)^+$.

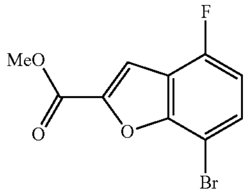 [SMILES: COC(=O)c1cc2c(F)ccc(Br)c2o1]

B) Methyl 7-bromo-4-fluorobenzofuran-2-carboxylate

To a solution of 3-bromo-6-fluoro-2-hydroxybenzaldehyde (7.0 g, 32.0 mmol) in DMF (100 mL) was added ethyl 2-bromoacetate (8.01 g, 47.9 mmol) and potassium carbonate (11 g, 80 mmol). The reaction mixture was stirred at 120° C. for 6 hours. After cooling to room temperature, 100 ml of cold water was added. The mixture was extracted with EtOAc three times. The combined organic extracts were dried over sodium sulfate, concentrated in vacuo and purified through a silica gel ISCO 220 g column, eluting with 0-5% MeOH in DCM to give a brown solid (6.8 g, 80%). The above brown solid (6.8 g, 26.3 mmol) was dissolved in DCM (100 mL) and MeOH (20 mL) and (diazomethyl) trimethylsilane, 2 M in diethyl ether (15.75 mL, 31.5 mmol) was added at room temperature dropwise. The reaction mixture was stirred at room temperature for 2 hours and concentrated in vacuo. The residue was purified with ISCO 220 g silica gel column, eluting with 0-30% EtOAc in DCM to give the desired product as a light yellow solid (3.01 g, 42%). $^1$H NMR (400 MHz, Chloroform-d) δ 7.68 (s, 1H), 7.58 (dd, J=8.6, 4.7 Hz, 1H), 6.96 (t, J=8.7 Hz, 1H), 4.02 (s, 3H); MS (ESI+) m/z=275.1 $(M+H)^+$.

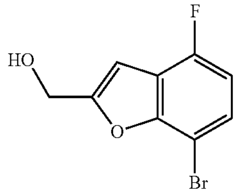 [SMILES: OCc1cc2c(F)ccc(Br)c2o1]

C) (7-Bromo-4-fluorobenzofuran-2-yl)methanol

To a −20° C. stirred solution of methyl 7-bromo-4-fluorobenzofuran-2-carboxylate (3.0 g, 11 mmol) in tetrahydrofuran (80 mL) under N2 was added lithium aluminum hydride (11.0 mL, 11.0 mmol, 1.0 M in THF) dropwise via syringe over 5 min. The reaction mixture was stirred at this temperature for 30 min. The reaction was quenched with Fieser Method (at −20° C. add 0.5 ml of water, add 1 ml of 15% NaOH, add 1.5 ml of water, and stirred at rt for 30 min). Some anhydrous magnesium sulfate was added and the reaction was stirred at rt for 15 min and then filtered over celite. The filtrate was concentrated in vacuo and purified by ISCO silica gel 120 g column, eluting with 0-30% EtOAc in DCM, to give the product as a light yellow solid (1.82 g, 67.4% yield). $^1$H NMR (400 MHz, Chloroform-d) δ 7.39 (dd, J=8.6, 4.7 Hz, 1H), 6.91-6.82 (m, 2H), 4.84 (d, J=6.2 Hz, 2H), 2.07 (t, J=6.4 Hz, 1H); MS (ESI+) m/z=229.0 $(M-OH)^+$.

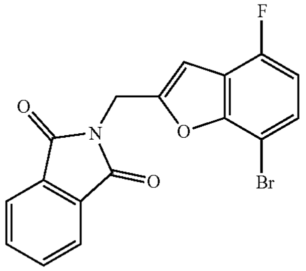

D) 2-((7-Bromo-4-fluorobenzofuran-2-yl)methyl) isoindoline-1,3-dione

To a stirred solution of (7-bromo-4-fluorobenzofuran-2-yl)methanol (1.82 g, 7.43 mmol) and phthalimide (1.09 g, 7.43 mmol) in tetrahydrofuran (60 mL) under N2 was added triphenylphosphine (2.338 g, 8.91 mmol) and DIAD (1.73 mL, 8.91 mmol). The reaction mixture was stirred at room temperature for 2 hours and was concentrated in vacuo. The residue was purified by flash chromatography to give the desired product (2.2 g, 79% yield). $^1$H NMR (400 MHz, Chloroform-d) δ 7.91 (dd, J=5.4, 3.1 Hz, 2H), 7.76 (dd, J=5.5, 3.1 Hz, 2H), δ 7.39 (dd, J=8.6, 4.7 Hz, 1H), 6.91-6.82 (m, 2H), 5.07 (s, 2H).

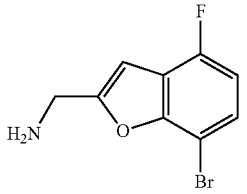 [SMILES: NCc1cc2c(F)ccc(Br)c2o1]

E) (7-Bromo-4-fluorobenzofuran-2-yl)methanamine

To a stirred suspension of 2-((7-bromo-4-fluorobenzofuran-2-yl)methyl)isoindoline-1,3-dione (2.20 g, 5.88 mmol) in ethanol (70 mL) was added hydrazine (4.22 mL, 47.0 mmol, Aldrich). The reaction was heated at 50° C. with stirring for 45 min. After cooling to rt, $Et_2O$ (50 mL) was added and the mixture was stirred for 10 min. The solid was removed by filtration and washed with $Et_2O$. The filtrate was concentrated in vacuo to give an oil. To the oil was added 50 ml of ether and a solid formed. The solid was removed by filtration and washed with ether. The filtrate was concentrated again to give a white solid as the desired product solid (1.02 g, 71% yield). $^1$H NMR (400 MHz, Chloroform-d) δ 7.33 (dd, J=8.6, 4.7 Hz, 1H), 6.83 (t, J=8.8 Hz, 1H), 6.70 (s, 1H), 4.02 (s, 2H); MS (ESI+) m/z=226.9 $(M+H)^+$.

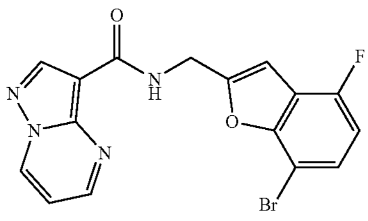 [SMILES: O=C(NCc1cc2c(F)ccc(Br)c2o1)c1cnn2cccnc12]

F) N-((7-Bromo-4-fluorobenzofuran-2-yl)methyl) pyrazolo[1,5-a]pyrimidine-3-carboxamide To a solution of (7-bromo-4-fluorobenzofuran-2-yl)methanamine (400 mg, 1.64 mmol) and pyrazolo[1,5-a]pyrimidine-3-carboxylic acid (321 mg, 1.967 mmol) in DMF (4 mL) was added BOP (1087 mg, 2.458 mmol) and DIPEA (1.145 mL, 6.56 mmol). The reaction mixture turned into a clear solution and was stirred at room temperature for 16 h. The reaction mixture was diluted with cold water and the solid that formed was collected by filtration. The solid was purified by flash chromatography with an ISCO 80 g column eluting with 0-5% MeOH in DCM to give the desired product as a white solid (0.55 g, 87% yield). MS (ESI+) m/z=391.0 $(M+H)^+$.

G) 2,2,2-Trifluoroethyl 4-fluoro-2-((pyrazolo[1,5-a] pyrimidine-3-carboxamido)methyl)benzofuran-7-carboxylate To the solution of N-((7-bromo-4-fluorobenzofuran-2-yl) methyl)pyrazolo[1,5-a]pyrimidine-3-carboxamide (25 mg, 0.064 mmol) in DMSO (1 mL) was added 2,2,2-trifluoroethan-1-ol (129 mg, 1.285 mmol), palladium(II) acetate (1.44 mg, 6.42 μmol), DPPP (2.65 mg, 6.42 μmol) and triethylamine (0.090 mL, 0.642 mmol). The reaction mixture was degassed by bubbling argon through it and heated at 120° C. under a CO atmosphere for 18 h. The reaction mixture was cooled, dissolved in MeOH and purified by prep HPLC (Method A) to give the desired product (6.0 mg, 21%). 1H NMR (500 MHz, DMSO-d6) δ 9.26 (dd, J=7.0, 1.2 Hz, 1H), 8.85-8.77 (m, 1H), 8.61 (s, 1H), 8.58 (br t, J=6.0 Hz, 1H), 7.92 (dd, J=8.5, 5.2 Hz, 1H), 7.32-7.21 (m, 2H), 6.99 (s, 1H), 5.05-4.92 (m, 2H), 4.81 (d, J=5.8 Hz, 2H); MS (ESI+) m/z=437.0 $(M+H)^+$.

Example 356

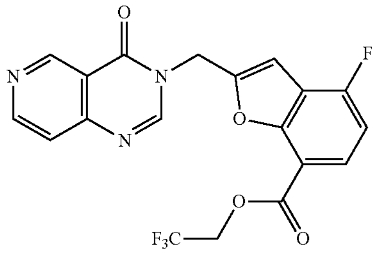 [SMILES: O=C(OCC(F)(F)F)c1ccc(F)c2cc(Cn3cnc4ccncc4c3=O)oc12]

2,2,2-Trifluoroethyl 4-fluoro-2-((4-oxo-3,4-dihydropyrido[4,3-d]pyrimidine-3-carboxamido)methyl) benzofuran-7-carboxylate

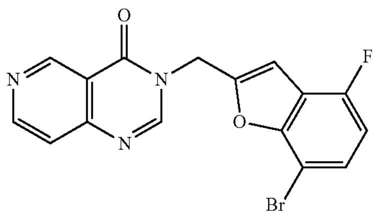 [SMILES: O=c1c2cnccc2ncn1Cc1cc2c(F)ccc(Br)c2o1]

A) N-((7-Bromo-4-fluorobenzofuran-2-yl)methyl)-4-oxopyrido[4,3-d]pyrimidine-3(4H)-carboxamide A mixture of 4-aminonicotinic acid (212 mg, 1.54 mmol) and N,N-dimethylformamide dimethylacetal (0.514 mL, 3.84 mmol) in DMF (2 mL) in a microwave vial was heated in a microwave at 100° C. for 20 min. The reaction mixture was concentrated in vacuo. To the residue was added acetic acid (1 mL) and (7-bromo-4-fluorobenzofuran-2-yl)methanamine (250 mg, 1.02 mmol, Step E of Example 355) and the mixture was heated at 100° C. in a microwave for 20 min. The reaction mixture was concentrated in vacuo and purified with ISCO, 24 g column, eluted with 0-50% acetone in DCM to give the desired product (140 mg, 37%). $^1H$ NMR (400 MHz, Chloroform-d) δ 9.55 (s, 1H), 8.90 (d, J=5.6 Hz, 1H), 8.50 (s, 1H), 7.59 (dd, J=5.6, 0.7 Hz, 1H), 7.40 (dd, J=8.5, 4.6 Hz, 1H), 7.05 (s, 1H), 6.87 (t, J=8.7 Hz, 1H), 5.38 (s, 2H); MS (ESI+) m/z=373.9 $(M+H)^+$.

B) 2,2,2-Trifluoroethyl 4-fluoro-2-((4-oxo-3,4-dihydropyrido[4,3-d]pyrimidine-3-carboxamido)methyl)benzofuran-7-carboxylate To a solution of 3-((7-bromo-4-fluorobenzofuran-2-yl)methyl)pyrido[4,3-d]pyrimidin-4(3H)-one (14 mg, 0.0374 mmol) in DMSO (1 mL) was added 2,2,2-trifluoroethan-1-ol (74.9 mg, 0.748 mmol), palladium(II) acetate (0.840 mg, 0.0037 mmol) and triethylamine (0.52 mL, 3.74 mmol). The reaction mixture was degassed by bubbling argon through and heated at 120° C. under a CO atmosphere for 18 hours. The reaction mixture was concentrated in vacuo and purified by prep HPLC, Method B, to give the desired product (7.4 mg, 47%). $^1H$ NMR (500 MHz, DMSO-$d_6$) δ 9.30 (s, 1H), 8.85 (br d, J=5.2 Hz, 1H), 8.70 (s, 1H), 7.94 (br dd, J=8.2, 5.2 Hz, 1H), 7.64 (br d, J=5.5 Hz, 1H), 7.27 (s, 1H), 7.22 (s, 1H), 5.47 (s, 2H), 4.93 (q, J=8.5 Hz, 2H); MS (ESI+) m/z=422.0 $(M+H)^+$.

Example 357

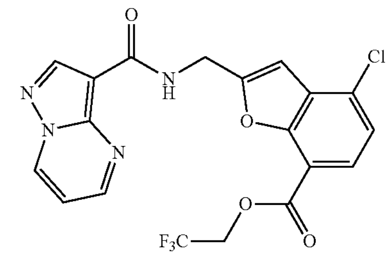 [SMILES: O=C(OCC(F)(F)F)c1ccc(Cl)c2cc(CNC(=O)c3cnn4cccnc34)oc12]

2,2,2-Trifluoroethyl 4-chloro-2-((pyrazolo[1,5-a]pyrimidine-3-carboxamido)methyl)benzofuran-7-carboxylate

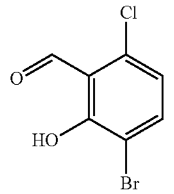

A) 3-Bromo-6-chloro-2-hydroxybenzaldehyde

To the mixture of magnesium chloride (0.64 g, 6.75 mmol), paraformaldehyde (0.30 g, 10.1 mmol) and triethylamine (0.94 mL, 6.75 mmol) in THF (15 mL) was added 2-bromo-5-chlorophenol (0.7 g, 3.37 mmol). The reaction mixture was heated in a microwave at 160° C. for 20 min. The residue was dissolved in ethyl acetate (40 mL) and washed with 1 N aqueous HCl solution and brine. The organic layer was dried over sodium sulfate, filtered, and concentrated in vacuo and purified through ISCO, 120 column, eluting with 0-20% EtOAc in hexane over 30 min to give the desired product as a light yellow solid. (0.29 g, 37% yield). $^1H$ NMR (400 MHz, CHLOROFORM-d) δ 12.59 (s, 1H), 10.40 (s, 1H), 7.71 (d, J=8.5 Hz, 1H), 6.93 (d, J=8.5 Hz, 1H).

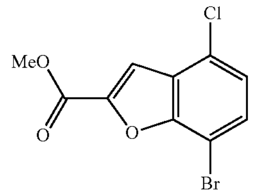 [SMILES: COC(=O)c1cc2c(Cl)ccc(Br)c2o1]

B) Methyl 7-bromo-4-chlorobenzofuran-2-carboxylate

The solution of 3-bromo-6-chloro-2-hydroxybenzaldehyde (0.59 g, 2.51 mmol) in DMF (10 mL) was added ethyl 2-bromoacetate (0.628 g, 3.76 mmol) and potassium carbonate (0.866 g, 6.26 mmol). The reaction mixture was stirred at 120° C. for 6 h. After cooled to rt, the reaction mixture was acidified to pH 3-4 with 1 N aqueous HCl solution, and extracted with EtOAc, 3×. The combined organic extracts were dried over sodium sulfate, filtered, and concentrated in vacuo and then purified by ISCO, 80 g column, eluting with 2-5% MeOH in DCM to give the product as a brown solid (530 mg, 70%). $^1H$ NMR (400 MHz, CHLOROFORM-d) δ 7.62 (s, 1H), 7.50 (d, J=8.3 Hz, 1H), 7.17 (d, J=8.3 Hz, 1H).

To a solution of the above acid (1.02 g, 3.70 mmol) in DCM (30 mL) and MeOH (6 mL) at room temperature was added (diazomethyl)trimethylsilane, 2 M in diethyl ether (3.70 mL, 7.41 mmol) dropwise. The reaction mixture was stirred for 1 h. The reaction mixture was concentrated in vacuo and purified with an ISCO, 80 g column, eluting with DCM to give the product as a light yellow solid (0.74 g, 69%). $^1H$ NMR (400 MHz, Chloroform-d) δ 7.68 (s, 1H), 7.56 (d, J=8.3 Hz, 1H), 7.22 (d, J=8.3 Hz, 1H), 4.02 (s, 3H); MS (ESI+) m/z=290.8 $(M+H)^+$.

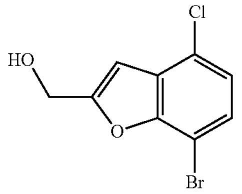 [SMILES: OCc1cc2c(Cl)ccc(Br)c2o1]

C) (7-Bromo-4-chlorobenzofuran-2-yl)methanol

To a stirred solution of methyl 7-bromo-4-chlorobenzofuran-2-carboxylate (0.74 g, 2.56 mmol) in THF (30 mL) at −20° C. under N2 was added lithium aluminum hydride, 1.0 M in THE (2.56 mL, 2.56 mmol) dropwise via syringe over 5 min. After stirring at this temperature for 30 min, the reaction was quenched with Fieser Method (at −20° C. add 0.1 ml of water, add 0.1 ml of 15% NaOH, add 0.3 ml of water, and stirred at rt for 30 min). Some anhydrous magnesium sulfate was added and the mixture was stirred at rt for 15 min and then filtered over celite. The filtrate was concentrated in vacuo and purified by ISCO, 80 g column, eluting with 0-30% EtOAc in DCM, to give the product as a light yellow solid (212 mg, 31.7% yield). $^1$H NMR (400 MHz, Chloroform-d) δ 7.37 (d, J=8.4 Hz, 1H), 7.12 (d, J=8.3 Hz, 1H), 6.85 (s, 1H), 4.84 (br d, J=3.1 Hz, 2H), 2.32 (br s, 1H); MS (ESI+) m/z=244.9 (M−OH)$^+$.

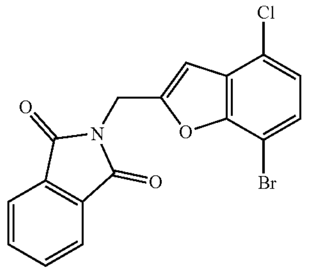 [SMILES: O=C1c2ccccc2C(=O)N1Cc1cc2c(Cl)ccc(Br)c2o1]

D) 2-((7-Bromo-4-chlorobenzofuran-2-yl)methyl) isoindoline-1,3-dione

To a stirred solution of (7-bromo-4-chlorobenzofuran-2-yl)methanol (0.21 g, 0.803 mmol) and phthalimide (0.118 g, 0.803 mmol) in THF (10 mL) under N2 was added triphenylphosphine (0.253 g, 0.964 mmol) and DIAD (0.187 mL, 0.964 mmol). The reaction mixture was stirred at room temperature for 2 hours. The reaction was concentrated and the residue was purified by flash chromatography (0% to 50% EtOAc in hexanes, 40 g column) to give the desired product (305 mg, 97% yield). $^1$H NMR (400 MHz, CHLOROFORM-d) δ 7.93 (dd, J=5.5, 3.0 Hz, 2H), 7.78 (dd, J=5.5, 3.1 Hz, 2H), 7.35 (d, J=8.3 Hz, 1H), 7.10 (d, J=8.4 Hz, 1H), 6.85 (s, 1H), 5.08 (d, J=0.9 Hz, 2H).

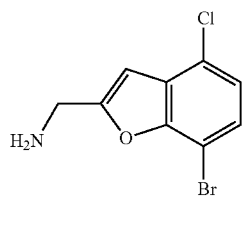 [SMILES: NCc1cc2c(Cl)ccc(Br)c2o1]

E) (7-Bromo-4-chlorobenzofuran-2-yl)methanamine

To a stirred suspension of 2-((7-bromo-4-chlorobenzofuran-2-yl)methyl)isoindoline-1,3-dione (0.305 g, 0.781 mmol) in ethanol (20 mL) was added hydrazine (0.560 mL, 6.25 mmol) and the reaction was heated at 50° C. with stirring for 1 hour. After the reaction mixture was cooled to rt $Et_2O$ (50 mL) was added and the mixture was stirred for 10 min. The solid formed was removed by filtration and washed with $Et_2O$. The filtrate was concentrated to give an oil. To the oil was added 50 ml of ether. Some more solid formed. The solid was removed by filtration and washed with ether. The filtrate was concentrated to give the product as a white solid (175 mg, 86%). $^1$H NMR (400 MHz, Chloroform-d) δ 7.33 (d, J=8.4 Hz, 1H), 7.09 (d, J=8.4 Hz, 1H), 6.71 (t, J=0.9 Hz, 1H), 4.03 (d, J=0.9 Hz, 2H), 2.43-2.13 (br, 2H). MS (ESI+) m/z=261.0 (M+H)$^+$.

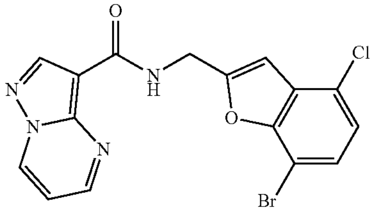

F) N-((7-Bromo-4-chlorobenzofuran-2-yl)methyl) pyrazolo[1,5-a]pyrimidine-3-carboxamide To a suspension of pyrazolo[1,5-a]pyrimidine-3-carboxylic acid (98 mg, 0.599 mmol) and BOP (306 mg, 0.691 mmol) in DMF (2 mL) was added (7-bromo-4-chlorobenzofuran-2-yl)methanamine (120 mg, 0.461 mmol) and DIPEA (0.322 mL, 1.84 mmol). The reaction mixture turned into a clear solution and was stirred at room temperature for 1 hour. The reaction mixture was diluted with cold water and the solid that formed was collected by filtration, washed with water and dried under vacuum to give the desired product as an off-white solid (170 mg, 91% yield). $^1$H NMR (500 MHz, DMSO-$d_6$) δ 9.26 (dd, J=7.0, 1.2 Hz, 1H), 8.85-8.77 (m, 1H), 8.61 (s, 1H), 8.58 (br t, J=6.0 Hz, 1H), 7.92 (dd, J=8.5, 5.2 Hz, 1H), 7.32-7.21 (m, 2H), 6.99 (s, 1H), 4.81 (d, J=5.8 Hz, 2H); MS (ESI+) m/z=406. (M+H)$^+$.

G) 2,2,2-Trifluoroethyl 4-chloro-2-((pyrazolo[1,5-a] pyrimidine-3-carboxamido)methyl)benzofuran-7-carboxylate To a solution of N-((7-bromo-4-chlorobenzofuran-2-yl) methyl)pyrazolo[1,5-a]pyrimidine-3-carboxamide (21 mg, 0.052 mmol) in DMSO (5 mL) was added 2,2,2-trifluoroethan-1-ol (104 mg, 1.035 mmol), palladium(II) acetate (1.162 mg, 5.18 μmol), 1,3-bis(diphenylphosphanyl)propane, dppp (2.135 mg, 5.18 μmol), and triethylamine (0.072 mL, 0.518 mmol). The reaction mixture was degassed by bubbling Ar through and heated at 80° C. under a CO atmosphere for 2 hours. The reaction mixture was concentrated in vacuo. The residue was diluted with 10% aqueous LiCl solution and then extracted with EtOAc, 3×. The combined organic extracts were dried over sodium sulfate, filtered and concentrated in vacuo. The residue was purified with prep HPLC, Method B, to give the desired product (4.2 mg, 18%). $^1$H NMR (500 MHz, DMSO-$d_6$) δ 9.32 (dd, J=7.0, 1.2 Hz, 1H), 8.83 (dd, J=4.0, 1.5 Hz, 1H), 8.63 (s, 1H), 8.56 (br t, J=5.6 Hz, 1H), 7.87 (d, J=8.2 Hz, 1H), 7.51 (d, J=8.2 Hz, 1H), 7.30 (dd, J=6.9, 4.1 Hz, 1H), 6.93 (s, 1H), 5.03 (q, J=9.0 Hz, 2H), 4.84 (br d, J=5.8 Hz, 2H); MS (ESI+) m/z=453.0 (M+H)$^+$.

Example 358

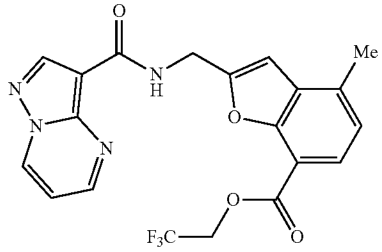

2,2,2-Trifluoroethyl 4-methyl-2-((pyrazolo[1,5-a]pyrimidine-3-carboxamido)methyl)benzofuran-7-carboxylate

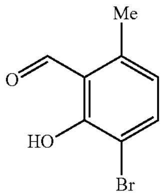 [SMILES: Cc1ccc(Br)c(O)c1C=O]

A) 3-Bromo-2-hydroxy-6-methylbenzaldehyde

To the solution of 2-bromo-5-methylphenol (2.0 g, 10.69 mmol) in $CH_3CN$ (40 mL) was added triethylamine (6.0 mL, 42.8 mmol) and manganese(II) chloride (2.02 g, 16.0 mmol). The reaction mixture was stirred at rt for 15 min. Then, paraformaldehyde (2.25 g, 74.9 mmol) was added. The reaction mixture was stirred at 80° C. for 16 h and then concentrated in vacuo. The residue was dissolved in hydrochloric acid (10% aqueous solution, 40 mL) and stirred at room temperature for 30 minutes. Ethyl acetate (40 mL) was added. The organic layer was separated, dried over sodium sulfate, filtered, and concentrated in vacuo. The residue was purified through flash chromatography with 120 g ISCO column, eluting with 0-20% EtOAc in hexane over 30 min to give the desired product as a light yellow solid (1.11 g, 48%). $^1$H NMR (400 MHz, Chloroform-d) δ 12.56 (s, 1H), 10.29 (s, 1H), 7.66 (d, J=8.1 Hz, 1H), 6.74-6.65 (m, 1H), 2.62 (s, 3H); MS (ESI+) m/z=215.1 (M+H)$^+$.

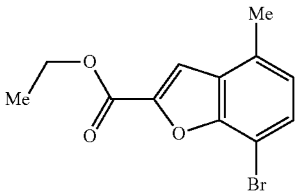 [SMILES: CCOC(=O)c1cc2c(C)ccc(Br)c2o1]

B) Ethyl 7-bromo-4-methylbenzofuran-2-carboxylate

To a solution of 3-bromo-2-hydroxy-6-methylbenzaldehyde (1.1 g, 5.12 mmol) in DMF (10 mL) was added ethyl 2-bromoacetate (1.28 g, 7.67 mmol) and potassium carbonate (1.77 g, 12.8 mmol). The reaction mixture was stirred at 120° C. under a CO atmosphere for 5 h. After cooling to room temperature, cold water (30 ml) was added. The solid formed was collected by filtration and purified by flash chromatography with an 80 g ISCO column, eluting with 0-30% EtOAc in hexanes to give the product as a white solid (0.71 g, 49% yield). $^1$H NMR (400 MHz, Chloroform-d) δ 7.63 (s, 1H), 7.51 (d, J=7.8 Hz, 1H), 7.00 (dd, J=7.9, 0.8 Hz, 1H), 4.48 (q, J=7.1 Hz, 2H), 2.54 (s, 3H), 1.46 (t, J=7.1 Hz, 3H); MS (ESI+) m/z=284.9 (M+H)$^+$.

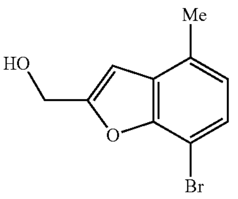 [SMILES: Cc1ccc(Br)c2oc(CO)cc12]

C) (7-Bromo-4-methylbenzofuran-2-yl)methanol

To a stirred solution of ethyl 7-bromo-4-methylbenzofuran-2-carboxylate (0.71 g, 2.49 mmol) in tetrahydrofuran (30 mL) at −20° C. under N2 was added lithium aluminum hydride, 1.0 M in THE (2.49 mL, 2.49 mmol) dropwise via syringe over 5 min. After stirring at −20° C. for 30 min, the reaction was quenched with Fieser Method (at −20° C. add 0.1 ml of water, add 0.2 ml of 15% NaOH, add 0.3 ml of water, and stirred at rt for 30 min). Some anhydrous magnesium sulfate was added and stirred at rt for 15 min and filtered over celite. The filtrate was concentrated to give the desired product as a white solid (0.6 g, 100%)$^1$H NMR (400 MHz, Chloroform-d) δ 7.35 (d, J=7.9 Hz, 1H), 6.93 (dd, J=7.9, 0.8 Hz, 1H), 6.78 (t, J=0.7 Hz, 1H), 4.84 (s, 2H), 2.48 (d, J=0.7 Hz, 3H); MS (ESI+) m/z=224.9 (M−OH)$^+$.

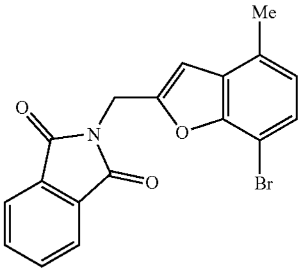 [SMILES: Cc1ccc(Br)c2oc(CN3C(=O)c4ccccc4C3=O)cc12]

D) 2-((7-Bromo-4-methylbenzofuran-2-yl)methyl)isoindoline-1,3-dione

To a stirred solution of (7-bromo-4-methylbenzofuran-2-yl)methanol (0.60 g, 2.489 mmol) and phthalimide (0.366 g, 2.489 mmol) in tetrahydrofuran (20 mL) under N2 was added triphenylphosphine (0.783 g, 2.99 mmol) and DIAD (0.581 mL, 2.99 mmol). The reaction mixture was stirred at room temperature for 1 h and was concentrated in vacuo. The residue was purified by flash chromatography with an 80 g ISCO column, eluting with 0% to 50% ethyl acetate in hexanes to give the product as a white solid (0.78 g, 84% yield). $^1$H NMR (400 MHz, Chloroform-d) δ 7.97 (dd, J=5.4, 3.1 Hz, 2H), 7.82 (dd, J=5.5, 3.1 Hz, 2H), 7.43-7.27 (m, 1H), 6.93 (d, J=7.9 Hz, 1H), 6.82 (s, 1H), 5.12 (s, 2H), 2.48 (s, 3H).

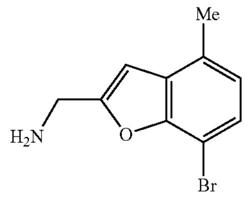 [SMILES: Cc1ccc(Br)c2oc(CN)cc12]

E) (7-Bromo-4-methylbenzofuran-2-yl)methanamine

To a stirred suspension of 2-((7-bromo-4-methylbenzofuran-2-yl)methyl)isoindoline-1,3-dione (0.77 g, 2.08 mmol) in ethanol (20 mL) was added hydrazine (1.49 mL, 16.6 mmol), and the reaction mixture was heated at 50° C. with stirring for 45 min. After cooling to room temperature, $Et_2O$ (50 mL) was added, and stirred for 10 min. The solid formed was removed by filtration. The filtrate was concentrated to give an oil. To the oil was added 50 ml of ether. Some more solid was formed. The solid was removed by filtration, and washed with ether. The filtrate was concentrated to give the product as an oil (0.41 g, 82% yield). $^1$H NMR (400 MHz, Chloroform-d) δ 7.31 (d, J=7.9 Hz, 1H), 6.91 (dd, J=7.9, 0.7 Hz, 1H), 6.64 (s, 1H), 4.04 (s, 2H), 2.46 (s, 3H); MS (ESI+) m/z=223.0 $(M-NH_2)^+$.

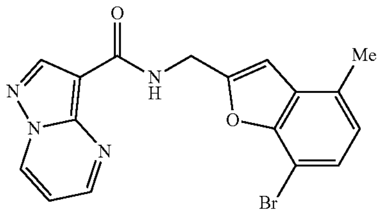

F) N-((7-Bromo-4-methylbenzofuran-2-yl)methyl) pyrazolo[1,5-a]pyrimidine-3-carboxamide To a suspension of pyrazolo[1,5-a]pyrimidine-3-carboxylic acid (71.9 mg, 0.441 mmol) and BOP (225 mg, 0.508 mmol) in DMF (2 mL) was added (7-bromo-4-methylbenzofuran-2-yl)methanamine (120 mg, 0.339 mmol) and DIPEA (0.237 mL, 1.36 mmol). The reaction was stirred at room temperature for 1 hour. The reaction mixture was diluted with cold water, and the solid that formed was collected by filtration, washed with water and dried under vacuum to give the product as a brown solid (0.122 g, 93% yield). $^1$H NMR (400 MHz, Chloroform-d) δ 8.81 (dd, J=7.0, 1.7 Hz, 1H), 8.74 (s, 1H), 8.68 (dd, J=4.2, 1.8 Hz, 1H), 8.46 (br s, 1H), 7.32 (d, J=7.8 Hz, 1H), 7.03 (dd, J=7.0, 4.2 Hz, 1H), 6.90 (dd, J=7.9, 0.7 Hz, 1H), 6.81 (s, 1H), 4.91 (d, J=6.0 Hz, 2H), 2.45 (s, 3H); MS (ESI+) m/z=387.0 $(M+H)^+$.

G) 2,2,2-Trifluoroethyl 4-methyl-2-((pyrazolo[1,5-a] pyrimidine-3-carboxamido)methyl)benzofuran-7-carboxylate To the solution of N-((7-bromo-4-methylbenzofuran-2-yl) methyl)pyrazolo[1,5-a]pyrimidine-3-carboxamide (120 mg, 0.312 mmol) in DMF (1 mL) was added triethylamine (0.868 mL, 6.23 mmol), 2,2,2-trifluoroethan-1-ol (623 mg, 6.23 mmol) and bis(triphenylphosphine)palladium (II) dichloride (21.9 mg, 0.031 mmol). The reaction mixture was degassed and heated at 130° C. under a CO atmosphere for 18 hours. After cooling to room temperature, the reaction mixture was filtered and purified with preparative HPLC, (Method A), to give the desired product (17.3 mg, 13% yield). $^1$H NMR (400 MHz, Chloroform-d) δ 8.81 (dd, J=7.0, 1.8 Hz, 1H), 8.73 (s, 1H), 8.68 (dd, J=4.2, 1.7 Hz, 1H), 8.50 (br t, J=5.6 Hz, 1H), 7.87 (d, J=7.8 Hz, 1H), 7.11 (dd, J=7.8, 0.7 Hz, 1H), 7.03 (dd, J=7.0, 4.2 Hz, 1H), 6.82 (s, 1H), 4.94 (dd, J=6.0, 0.6 Hz, 2H), 4.78 (q, J=8.4 Hz, 2H), 2.56 (s, 3H); MS (ESI+) m/z=433.0 $(M+H)^+$.

Example 359

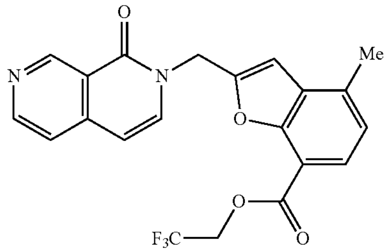 [SMILES: Cc1ccc(C(=O)OCC(F)(F)F)c2oc(Cn3ccc4ccncc4c3=O)cc12]

2,2,2-Trifluoroethyl 4-methyl-2-((1-oxo-1,2-dihydro-2,7-naphthyridine-2-carboxamido)methyl) benzofuran-7-carboxylate

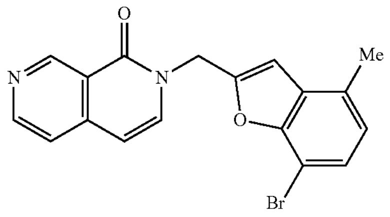 [SMILES: Cc1ccc(Br)c2oc(Cn3ccc4ccncc4c3=O)cc12]

A) N-((7-Bromo-4-methylbenzofuran-2-yl)methyl)-1-oxo-2,7-naphthyridine-2(1H)-carboxamide A mixture of methyl 4-methylnicotinate (283 mg, 1.87 mmol), and DMF-DMA (1.34 mL, 10.0 mmol) in DMF (1 mL) in a microwave vial was heated in the microwave at 130° C. for 30 min. The reaction mixture was concentrated in vacuo. To the residue was added acetic acid (1 mL) and (7-bromo-4-methylbenzofuran-2-yl)methanamine (150 mg, 0.625 mmol, Step E of Example 358) and the mixture was heated at 130° C. in a microwave for 45 min to give the title compound (170 mg, 63% yield). $^1$H NMR (400 MHz, Chloroform-d) δ 9.65 (s, 1H), 8.76 (d, J=5.5 Hz, 1H), 7.57 (d, J=7.5 Hz, 1H), 7.40-7.32 (m, 3H), 6.96-6.88 (m, 2H), 6.58-6.51 (m, 1H), 5.38 (s, 2H), 2.46 (s, 3H); MS (ESI+) m/z=370.9 $(M+H)^+$.

B) 2,2,2-Trifluoroethyl 4-methyl-2-((1-oxo-1,2-dihydro-2,7-naphthyridine-2-carboxamido)methyl) benzofuran-7-carboxylate To a solution of 2-((7-bromo-4-methylbenzofuran-2-yl) methyl)-2,7-naphthyridin-1(2H)-one (170 mg, 0.46 mmol)

in DMF (1 mL) was added triethylamine (1.28 mL, 9.21 mmol), 2,2,2-trifluoroethan-1-ol (921 mg, 9.21 mmol) and bis(triphenylphosphine)palladium (II) dichloride (32.3 mg, 0.046 mmol). The reaction mixture was degassed by bubbling argon through and heated at 130° C. under a CO atmosphere for 18 hours. The reaction mixture was purified by prep HPLC, Method C, to give the desired product compound (42 mg, 17% yield). $^1$H NMR (400 MHz, Methanol-$d_4$) δ 9.50 (s, 1H), 8.69 (d, J=6.0 Hz, 1H), 8.02 (d, J=7.5 Hz, 1H), 7.87 (d, J=7.8 Hz, 1H), 7.84-7.79 (m, 1H), 7.17 (dd, J=7.8, 0.6 Hz, 1H), 7.05 (s, 1H), 6.82 (d, J=7.5 Hz, 1H), 5.50 (s, 2H), 4.86 (m, 2H), 2.58 (s, 3H); MS (ESI+) m/z=417.0 $(M+H)^+$. Prep HPLC purification also gave 4-methyl-2-((pyrazolo[1,5-a]pyrimidine-3-carboxamido)methyl)benzofuran-7-carboxylic acid (30 mg, 27%) as a by-product. $^1$H NMR (500 MHz, DMSO-$d_6$) δ 9.31-9.21 (m, 1H), 8.82 (d, J=2.7 Hz, 1H), 8.62 (s, 1H), 8.55 (br t, J=5.6 Hz, 1H), 7.70 (d, J=7.6 Hz, 1H), 7.27 (dd, J=6.9, 4.1 Hz, 1H), 7.13 (d, J=7.9 Hz, 1H), 6.88 (s, 1H), 4.79 (br d, J=5.8 Hz, 2H); MS (ESI+) m/z=351.0 $(M+H)^+$.

Example 360

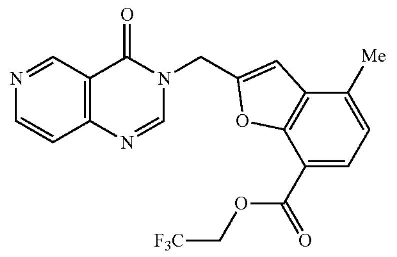 [SMILES: Cc1ccc(C(=O)OCC(F)(F)F)c2oc(Cn3cnc4ccncc4c3=O)cc12]

2,2,2-Trifluoroethyl 4-methyl-2-((4-oxo-3,4-dihydropyrido[4,3-d]pyrimidine-3-carboxamido)methyl)benzofuran-7-carboxylate

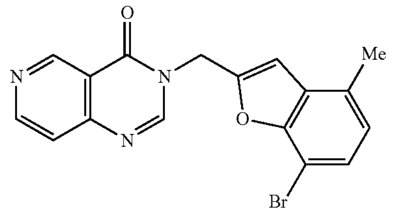 [SMILES: Cc1ccc(Br)c2oc(Cn3cnc4ccncc4c3=O)cc12]

A) N-((7-Bromo-4-methylbenzofuran-2-yl)methyl)-4-oxopyrido[4,3-d]pyrimidine-3(4H)-carboxamide A mixture of 4-aminonicotinic acid (86 mg, 0.625 mmol) and DMF-DMA (0.21 mL, 1.56 mmol) in DMF (1 mL) in a microwave vial was heated at 100° C. in the microwave for 20 min. The reaction mixture was concentrated in vacuo. To the residue was added acetic acid (1 mL) and (7-bromo-4-methylbenzofuran-2-yl)methanamine (100 mg, 0.416 mmol, Step E of Example 258) and the mixture was heated at 100° C. in the microwave for 20 min. The reaction mixture was concentrated and purified with ISCO, 24 g column, eluted with 0-50% acetone in DCM to give the desired product (110 mg, 71%). $^1$H NMR (400 MHz, Chloroform-d) δ 9.56 (s, 1H), 8.89 (br d, J=5.5 Hz, 1H), 8.50 (s, 1H), 7.58 (d, J=5.5 Hz, 1H), 7.35 (d, J=7.9 Hz, 1H), 6.96 (s, 1H), 6.92 (dd, J=7.9, 0.7 Hz, 1H), 5.38 (s, 2H), 2.46 (s, 3H); MS (ESI+) m/z=369.9 $(M+H)^+$.

B) 2,2,2-Trifluoroethyl 4-methyl-2-((4-oxo-3,4-dihydropyrido[4,3-d]pyrimidine-3-carboxamido)methyl)benzofuran-7-carboxylate To the solution of 3-((7-bromo-4-methylbenzofuran-2-yl)methyl)pyrido[4,3-d]pyrimidin-4(3H)-one (35 mg, 0.095 mmol) in DMSO (2 mL) was added 2,2,2-trifluoroethan-1-ol (189 mg, 1.89 mmol), palladium(II) acetate (2.1 mg, 9.45 μmol), 1,3-bis(diphenylphosphanyl)propane (dppp, 3.9 mg, 9.45 μmol)) and triethylamine (0.132 mL, 0.945 mmol). The reaction mixture was degassed and heated at 130° C. under a CO atmosphere for 18 h. The reaction mixture was purified with prep HPLC, Method B, to give the desired product (6.3 mg, 16%). $^1$H NMR (500 MHz, DMSO-$d_6$) δ 9.33 (s, 1H), 8.88 (br d, J=5.5 Hz, 1H), 8.94-8.84 (m, 1H), 8.74 (s, 1H), 7.80 (br d, J=7.9 Hz, 1H), 7.66 (br d, J=5.5 Hz, 1H), 7.24 (br d, J=7.9 Hz, 1H), 7.16 (s, 1H), 5.48 (s, 2H), 5.05-4.87 (m, 2H), 2.56 (s, 3H); MS (ESI+) m/z=418.0 $(M+H)^+$.

Example 361

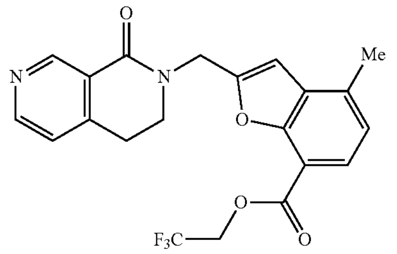 [SMILES: Cc1ccc(C(=O)OCC(F)(F)F)c2oc(CN3CCc4ccncc4C3=O)cc12]

2,2,2-Trifluoroethyl 4-methyl-2-((1-oxo-1,2,3,4-tetrahydro-2,7-naphthyridine-2-carboxamido)methyl)benzofuran-7-carboxylate

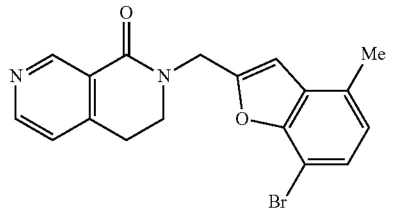 [SMILES: Cc1ccc(Br)c2oc(CN3CCc4ccncc4C3=O)cc12]

A) N-((7-Bromo-4-methylbenzofuran-2-yl)methyl)-1-oxo-3,4-dihydro-2,7-naphthyridine-2(1H)-carboxamide The suspension of 3,4-dihydro-1H-pyrano[3,4-c]pyridin-1-one, HCl (120 mg, 0.647 mmol) (WO 2005063768) and (7-bromo-4-methylbenzofuran-2-yl)methanamine (155 mg, 0.647 mmol, Step E of Example 258) in pyridine (0.5 mL) and NMP (0.5 mL) in a 2 dram vial was stirred at 130° C. for 3 h. The reaction mixture was concentrated and purified by prep HPLC, Method C, to give the title compound (107 mg, 41%). $^{1}$H NMR (400 MHz, Chloroform-d) δ 9.27 (s, 1H), 8.65 (d, J=5.0 Hz, 1H), 7.33 (d, J=7.9 Hz, 1H), 7.16 (dd, J=5.0, 0.7 Hz, 1H), 6.92 (dd, J=7.9, 0.8 Hz, 1H), 6.83 (s, 1H), 4.96 (s, 2H), 3.85 (t, J=6.6 Hz, 2H), 3.09 (t, J=6.6 Hz, 2H), 2.46 (s, 3H); MS (ESI+) m/z=370.9 (M+H)$^{+}$.

B) 2,2,2-Trifluoroethyl 4-methyl-2-((1-oxo-1,2,3,4-tetrahydro-2,7-naphthyridine-2-carboxamido) methyl)benzofuran-7-carboxylate To the solution of 2-((7-bromo-4-methylbenzofuran-2-yl) methyl)-3,4-dihydro-2,7-naphthyridin-1(2H)-one (40 mg, 0.108 mmol) in DMF (3 mL) was added triethylamine (0.300 mL, 2.16 mmol), 2,2,2-trifluoroethan-1-ol (216 mg, 2.16 mmol) and bis(triphenylphosphine)palladium (II) dichloride (7.6 mg, 10.8 μmol). The reaction mixture was degassed by bubbling Ar through and heated at 130° C. under a CO atmosphere for 5 h. The reaction mixture was purified with prep HPLC (Method A) to give the desired product (15.5 mg, 34%). $^{1}$H NMR (400 MHz, Chloroform-d) δ 9.17 (s, 1H), 8.64 (d, J=5.0 Hz, 1H), 7.31 (d, J=7.9 Hz, 1H), 7.11 (dd, J=5.0, 0.7 Hz, 1H), 6.92 (dd, J=7.9, 0.8 Hz, 1H), 6.83 (s, 1H), 5.18 (s, 2H), 5.01-4.77 (m, 2H), 3.81 (t, J=6.6 Hz, 2H), 3.12 (t, J=6.6 Hz, 2H), 2.46 (s, 3H); MS (ESI+) m/z 419.0=(M+H)$^{+}$.

Example 362

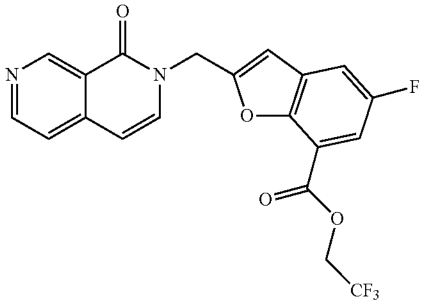 [SMILES: O=C(OCC(F)(F)F)c1cc(F)cc2cc(Cn3ccc4ccncc4c3=O)oc12]

2,2,2-Trifluoroethyl 5-fluoro-2-((1-oxo-2,7-naphthyridin-2(1H)-yl)methyl)benzofuran-7-carboxylate Methyl 4-methylnicotinate (57.1 mg, 0.378 mmol) and N,N-dimethylformamide dimethyl acetal (0.177 mL, 1.322 mmol) were taken up in DMF (0.5 mL) in a microwave vial. The vial was sealed and heated to 145° C. for 30 minutes in a microwave reactor. The reaction mixture was cooled and concentrated in vacuo. The residue was dissolved in DCM and concentrated in vacuo once again. The resulting residue was mixed with acetic acid (0.5 mL) and 2,2,2-trifluoroethyl 2-(aminomethyl)-5-fluorobenzofuran-7-carboxylate (55 mg, 0.094 mmol). The vial was sealed and heated to 110° C. for another 30 minutes in a microwave reactor. The reaction mixture was cooled and concentrated in vacuo. The residue was dissolved in MeOH, filtered, and purified via HPLC (method B) to give the title compound (8.8 mg, 17% yield). $^{1}$H NMR (500 MHz, DMSO-d6) δ9.38 (s, 1H), 8.74 (br d, J 5.3 Hz, 1H), 7.90 (d, J=7.3 Hz, 1H), 7.84 (dd, J=8.2, 2.5 Hz, 1H), 7.74 (d, J=5.6 Hz, 1H), 7.62 (dd, J=9.4, 2.5 Hz, 1H), 7.03 (s, 1H), 6.78 (d, J=7.3 Hz, 1H), 5.45 (s, 2H), 5.00 (q, J=8.8 Hz, 2H); MS (ESI+) m/z=420.9 (M+H)$^{+}$.

Examples 363-365

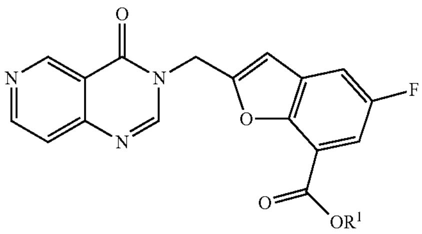

Examples 363-365 were prepared in the same manner as exemplified by Example 362 starting from Example 39.

| Ex. No. | $R^1$ | Name | $^{1}$H NMR | LC/MS [M + H]$^{+}$ |
|---|---|---|---|---|
| 363 | 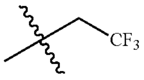 [SMILES: *CC(F)(F)F] | 2,2,2-Trifluoroethyl 5-fluoro-2-((4-oxopyrido-[4,3-d]pyrimidin-3(4H)-yl)methyl)benzo-furan-7-carboxylate | $^{1}$H NMR (500 MHz, DMSO-$d_6$) δ 9.32 (s, 1H), 8.88 (d, J = 5.5 Hz, 1H), 8.74 (s, 1H), 7.85 (dd, J = 8.2, 2.4 Hz, 1H), 7.71-7.52 (m, 2H), 7.11 (s, 1H), 5.49 (s, 2H), 5.00 (q, J = 9.1 Hz, 2H) | 422.2 |
| 364 | 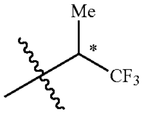 (Isomer-1) (Method F) | 1,1,1-Trifluoropropan-2-yl 5-fluoro-2-((4-oxo-pyrido[4,3-d]pyrimidin-3(4H)-yl)methyl)benzo-furan-7-carboxylate | $^{1}$H NMR (500 MHz, DMSO-$d_6$) δ 9.30 (s, 1H), 8.86 (d, J = 5.5 Hz, 1H), 8.72 (s, 1H), 7.83 (dd, J = 8.1, 2.6 Hz, 1H), 7.64 (d, J = 5.5 Hz, 1H), 7.60 (dd, J = 9.5, 2.4 Hz, 1H), 7.11 (s, 1H), 5.79-5.61 (m, 1H), 5.47 (s, 2H), 1.42 (d, J = 6.4 Hz, 3H) | 436.3 |

-continued

| Ex. No. | $R^1$ | Name | $^1$H NMR | LC/MS $[M + H]^+$ |
|---|---|---|---|---|
| 365 | 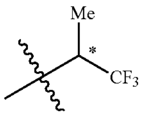 (Isomer-2) | 1,1,1-Trifluoropropan-2-yl 5-fluoro-2-((4-oxo-pyrido[4,3-d]pyrimidin-3(4H)-yl)methyl)benzo-furan-7-carboxylate | $^1$H NMR (500 MHz, DMSO-$d_6$) δ 9.30 (s, 1H), 8.86 (d, J = 5.5 Hz, 1H), 8.72 (s, 1H), 7.83 (dd, J = 8.1, 2.6 Hz, 1H), 7.64 (d, J = 5.5 Hz, 1H), 7.60 (dd, J = 9.5, 2.4 Hz, 1H), 7.11 (s, 1H), 5.79-5.61 (m, 1H), 5.47 (s, 2H), 1.42 (d, J = 6.4 Hz, 3H) | 436.3 |

Example 366

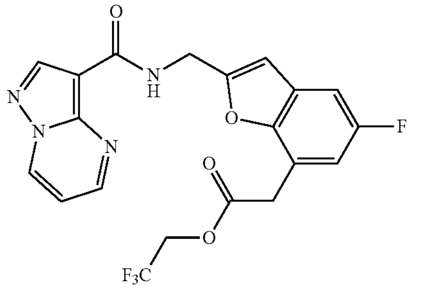 [SMILES: O=C(Cc1cc(F)cc2cc(CNC(=O)c3cnn4cccnc34)oc12)OCC(F)(F)F]

2,2,2-Trifluoroethyl 2-(5-fluoro-2-((pyrazolo[1,5-a]pyrimidine-3-carboxamido)methyl)benzofuran-7-yl)acetate

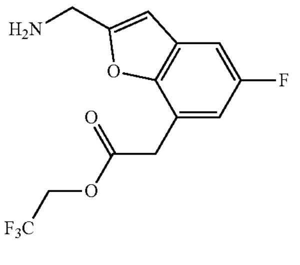 [SMILES: NCc1cc2cc(F)cc(CC(=O)OCC(F)(F)F)c2o1]

A) 2,2,2-Trifluoroethyl 2-(2-(aminomethyl)-5-fluorobenzofuran-7-yl)acetate

To a solution of 2-(2-(((tert-butoxycarbonyl)amino)methyl)-5-fluorobenzofuran-7-yl)acetic acid (100 mg, 0.309 mmol, Step C of Example 47) in DMF (1 mL) was added 2,2,2-trifluoroethan-1-ol (30.9 mg, 0.309 mmol), BOP (205 mg, 0.464 mmol) and DIPEA (0.162 mL, 0.928 mmol). The reaction mixture was stirred at room temperature for 72 hours. The reaction mixture was diluted with water and extracted with EtOAc. The combined organic extracts were dried over sodium sulfate, filtered, concentrated and purified by ISCO, 12 g column, eluting with 0-30% EtOAc in hexanes to give the desired product.

To a solution of above compound (33 mg, 0.081 mmol) in DCM (1 mL) was added TFA (0.3 mL). The reaction mixture was stirred at room temperature for 2 hours and concentrated to give the product as a light yellow solid (25 mg, 100% yield). $^1$H NMR (400 MHz, Chloroform-d) δ 7.14 (dd, J=8.3, 2.5 Hz, 1H), 6.95 (dd, J=9.6, 2.5 Hz, 1H), 6.60 (s, 1H), 4.54 (q, J=8.4 Hz, 2H), 4.45 (br d, J=5.7 Hz, 2H), 4.00 (s, 2H); MS (ESI+) m/z=306.1 $(M+H)^+$.

B) 2,2,2-Trifluoroethyl 2-(5-fluoro-2-((pyrazolo[1,5-a]pyrimidine-3-carboxamido)methyl)benzofuran-7-yl)acetate To a solution of 2,2,2-Trifluoroethyl 2-(2-(aminomethyl)-5-fluorobenzofuran-7-yl)acetate (25 mg, 0.081 mmol) in DMF (1 mL) were added pyrazolo[1,5-a]pyrimidine-3-carboxylic acid (12.3 mg, 0.075 mmol), BOP (50.0 mg, 0.113 mmol) and DIPEA (0.066 mL, 0.377 mmol). The reaction mixture was stirred at room temperature for 2 hours. The reaction mixture was concentrated and purified by preparative HPLC, Method B, to give the product (28 mg, 81% yield). $^1$H NMR (500 MHz, DMSO-$d_6$) δ 9.18 (br d, J=6.7 Hz, 1H), 8.78 (br d, J=3.0 Hz, 1H), 8.58 (s, 1H), 8.47 (br t, J=5.7 Hz, 1H), 7.34-7.28 (m, 1H), 7.25 (dd, J=6.9, 4.0 Hz, 1H), 7.03 (br d, J=9.8 Hz, 1H), 6.78 (s, 1H), 4.72 (br d, J=5.7 Hz, 2H), 4.69-4.60 (m, 2H), 4.04 (s, 2H); MS (ESI+) m/z=451.1 $(M+H)^+$.

Example 367

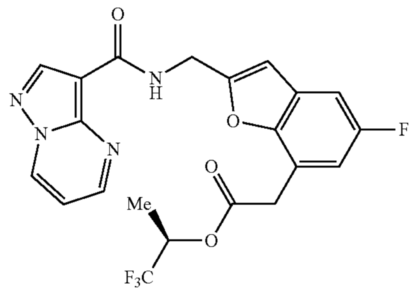 [SMILES: C[C@@H](OC(=O)Cc1cc(F)cc2cc(CNC(=O)c3cnn4cccnc34)oc12)C(F)(F)F]

(R)-1,1,1-Trifluoropropan-2-yl 2-(5-fluoro-2-((pyrazolo[1,5-a]pyrimidine-3-carboxamido)methyl)benzofuran-7-yl)acetate

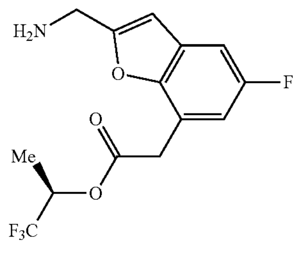 [SMILES: C[C@@H](OC(=O)Cc1cc(F)cc2cc(CN)oc12)C(F)(F)F]

A) (R)-1,1,1-Trifluoropropan-2-yl 2-(2-(aminomethyl)-5-fluorobenzofuran-7-yl)acetate To a solution of 2-(2-(((tert-butoxycarbonyl)amino)methyl)-5-fluorobenzofuran-7-yl)acetic acid (105 mg, 0.325 mmol, Step C of Example 47) in DMF (1 mL) was added (R)-1,1,1-trifluoropropan-2-ol (185 mg, 1.62 mmol), BOP (215 mg, 0.487 mmol) and DIPEA (0.284 mL, 1.624 mmol). The reaction mixture was stirred at room temperature for 72 hours. The reaction mixture was diluted with water and extracted with EtOAc three times. The combined organic extracts were dried over sodium sulfate, filtered, concentrated in vacuo, and purified by ISCO, 12 g column, eluting with 0-30% EtOAc in hexanes to give the desired product.

To a solution of the above compound (31 mg, 0.074 mmol) in DCM (1 mL) was added TFA (0.3 mL). The reaction mixture was stirred at room temperature for 2 hours and concentrated to give the product TFA salt as a light yellow solid (23 mg, 100% yield). $^1$H NMR (400 MHz, Chloroform-d) δ 7.14 (dd, J=8.3, 2.5 Hz, 1H), 6.95 (dd, J=9.6, 2.4 Hz, 1H), 6.60 (s, 1H), 5.36 (dt, J=13.1, 6.5 Hz, 1H), 4.45 (br d, J=5.6 Hz, 2H), 3.97 (s, 2H), 1.43 (d, J=6.7 Hz, 3H); MS (ESI+) m/z=306.1 (M+H)$^+$.

B) (R)-1,1,1-Trifluoropropan-2-yl 2-(5-fluoro-2-((pyrazolo[1,5-a]pyrimidine-3-carboxamido)methyl)benzofuran-7-yl)acetate To a solution of (R)-1,1,1-trifluoropropan-2-yl 2-(2-(aminomethyl)-5-fluorobenzofuran-7-yl)acetate (23 mg, 0.072 mmol) in DMF (1 mL) was added pyrazolo[1,5-a]pyrimidine-3-carboxylic acid (11.8 mg, 0.072 mmol), BOP (47.8 mg, 0.108 mmol) and DIPEA (0.063 mL, 0.36 mmol). The reaction mixture was stirred at rt for 2 h. The reaction mixture was concentrated in vacuo and purified by prep HPLC (Method B) to give the desired product (25.6 mg, 76% yield). $^1$H NMR (500 MHz, DMSO-$d_6$) δ 9.27-9.17 (m, 1H), 8.83-8.74 (m, 1H), 8.59 (s, 1H), 8.48-8.41 (m, 1H), 7.31 (br d, J=7.6 Hz, 1H), 7.26 (dd, J=5.7, 4.3 Hz, 1H), 7.04 (br d, J=9.8 Hz, 1H), 6.79 (s, 1H), 5.36 (td, J=6.7, 2.8 Hz, 1H), 4.73 (br d, J=5.7 Hz, 2H), 4.02 (d, J=1.3 Hz, 2H), 1.28 (br d, J=5.2 Hz, 3H); MS (ESI+) m/z=465.1 (M+H)$^+$.

Example 368

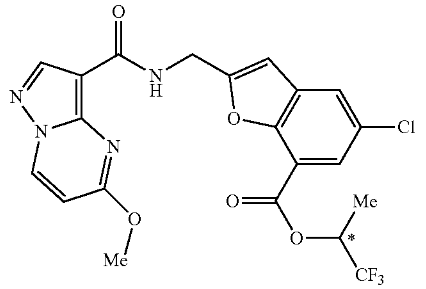 [SMILES: COc1ccn2ncc(C(=O)NCc3cc4cc(Cl)cc(C(=O)OC(C)C(F)(F)F)c4o3)c2n1]

1,1,1-Trifluoropropan-2-yl 5-chloro-2-((5-methoxypyrazolo[1,5-a]pyrimidine-3-carboxamido)methyl)benzofuran-7-carboxylate Enantiomer 1

5-Chloro-2-((5-methoxypyrazolo[1,5-a]pyrimidine-3-carboxamido)methyl)benzofuran-7-carboxylic acid (40 mg, 0.10 mmol, Example 139) was dissolved in DMF (0.4 mL) and then DIPEA (70 μl, 0.40 mmol) and 1,1,1-trifluoropropan-2-ol (34 mg, 0.30 mmol) were added. BOP (66 mg, 0.15 mmol) was added and the reaction was stirred at room temperature overnight. The reaction was diluted with DMSO, filtered, and purified via HPLC (Method B) to give racemic 1,1,1-trifluoropropan-2-yl 5-chloro-2-((5-methoxypyrazolo[1,5-a]pyrimidine-3-carboxamido)methyl)benzofuran-7-carboxylate. This material was further purified with chiral SFC (Method D) to give the enantiopure product as the first eluting enantiomer (7.2 mg, 0.014 mmol, 14.2% yield) (absolute stereochemistry was not determined). $^1$H NMR (500 MHz, DMSO-$d_6$) δ 9.02 (d, J=7.3 Hz, 1H), 8.40 (s, 1H), 8.21 (br t, J=5.6 Hz, 1H), 8.03 (d, J=2.1 Hz, 1H), 7.74 (d, J=2.1 Hz, 1H), 6.91 (s, 1H), 6.74 (d, J=7.6 Hz, 1H), 5.74 (dt, J=13.4, 6.6 Hz, 1H), 4.80 (br d, J=5.5 Hz, 2H), 4.02 (s, 3H), 1.48 (d, J=6.4 Hz, 3H); MS (ESI+) m/z=497.2 (M+H)$^+$.

Example 369

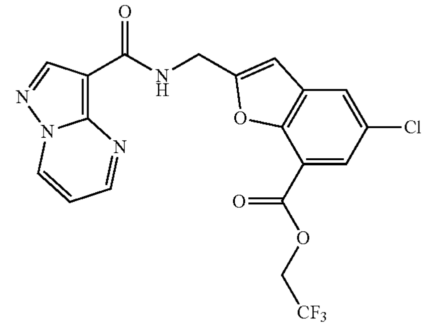 [SMILES: O=C(OCC(F)(F)F)c1cc(Cl)cc2cc(CNC(=O)c3cnn4cccnc34)oc12]

2,2,2-Trifluoroethyl 5-chloro-2-((imidazo[1,2-b]pyridazine-3-carboxamido)methyl)benzofuran-7-carboxylate

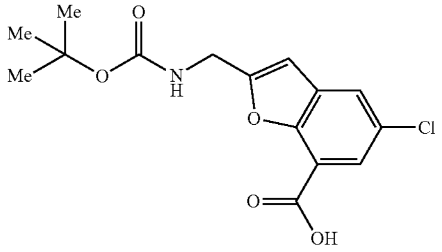 [SMILES: CC(C)(C)OC(=O)NCc1cc2cc(Cl)cc(C(=O)O)c2o1]

A) 2-(((tert-Butoxycarbonyl)amino)methyl)-5-chlorobenzofuran-7-carboxylic acid

To a solution of methyl 2-(((tert-butoxycarbonyl)amino)methyl)-5-chlorobenzofuran-7-carboxylate (1.1 g, 3.24 mmol, Step B of Example 48) in THF (6 mL) and MeOH (6 mL) was added LiOH (2 M aqueous solution, 9.7 mL, 19.4 mmol). The reaction mixture was stirred at room temperature for 3 h. To the reaction mixture was added 1 N aqueous HCl solution to adjust the pH to about 3. The resulting mixture was extracted with ethyl acetate. The organic layer was separated, washed with brine, dried over $MgSO_4$, and filtered. The filtrate was concentrated in vacuo to give the crude title compound as a light brown solid (1.0 g, 95%) which was used in the next step without further purification. MS (ESI+) m/z=270.1 (M−55+H)$^+$.

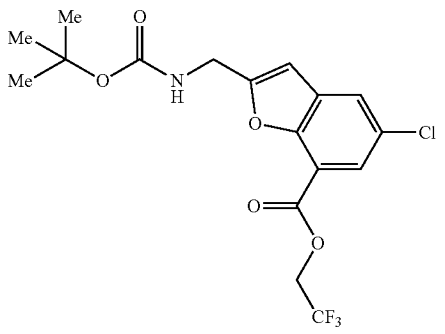 [SMILES: CC(C)(C)OC(=O)NCc1cc2cc(Cl)cc(C(=O)OCC(F)(F)F)c2o1]

B) 2,2,2-Trifluoroethyl 2-(((tert-butoxycarbonyl) amino)methyl)-5-chlorobenzofuran-7-carboxylate To a solution of 2-(((tert-butoxycarbonyl)amino)methyl)-5-chlorobenzofuran-7-carboxylic acid (1.0 g, 3.07 mmol) in DMF (8 mL) was added BOP (1.49 g, 3.38 mmol), 2,2,2-trifluoroethanol (0.36 mL, 4.91 mmol) and DIPEA (0.86 mL, 4.91 mmol). The reaction mixture was stirred at room temperature for 2 hours. The reaction was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO 40 g column, 0-30% ethyl acetate in hexanes) to give the title compound (1.15 g, 92%) as a white solid. $^1$H NMR (400 MHz, Chloroform-d) δ 7.91 (d, J=2.1 Hz, 1H), 7.75 (d, J=2.1 Hz, 1H), 6.66 (s, 1H), 5.09 (br s, 1H), 4.79 (q, J=8.3 Hz, 2H), 4.52 (br d, J=6.0 Hz, 2H), 1.48 (s, 9H); MS (ESI+) m/z=815.4 (2M+1) (M+H)$^+$.

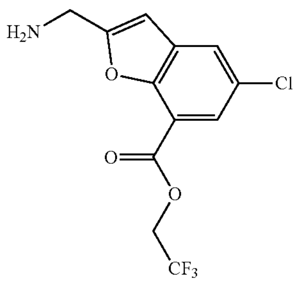 [SMILES: NCc1cc2cc(Cl)cc(C(=O)OCC(F)(F)F)c2o1]

C) 2,2,2-Trifluoroethyl 2-(aminomethyl)-5-chlorobenzofuran-7-carboxylate

To a solution of 2,2,2-trifluoroethyl 2-(((tert-butoxycarbonyl)amino)methyl)-5-chlorobenzofuran-7-carboxylate (0.7 g, 1.72 mmol) in DCM (8 mL) was added TFA (1.6 mL, 20.60 mmol). The reaction mixture was stirred at room temperature for 2 hours. The reaction was concentrated in vacuo to give the crude title compound (TFA salt) and as a white solid (0.7 g, 97%). $^1$H NMR (400 MHz, Methanol-d4) δ 8.03 (d, J=2.2 Hz, 1H), 7.98 (d, J=2.1 Hz, 1H), 7.12 (s, 1H), 4.98 (q, J=8.6 Hz, 2H), 4.43 (s, 2H); MS (ESI+) m/z=291.1 (M−17) (M+H)$^+$.

D) 2,2,2-Trifluoroethyl 5-chloro-2-((imidazo[1,2-b] pyridazine-3-carboxamido)methyl)benzofuran-7-carboxylate To a suspension of imidazo[1,2-b]pyridazine-3-carboxylic acid (15.1 mg, 0.092 mmol) and BOP (44 mg, 0.10 mmol) in DMF (1 mL) was added 2,2,2-trifluoroethyl 2-(aminomethyl)-5-chlorobenzofuran-7-carboxylate, TFA (30 mg, 0.071 mmol) and DIPEA (0.05 mL, 0.285 mmol). The reaction mixture became a clear solution and was stirred at rt for 4 h. The reaction mixture was concentrated in vacuo. The residue was dissolved in DMF, filtered and purified by preparative LC/MS (Method B). Fractions containing the desired product were combined and dried via centrifugal evaporation to give the title compound (32 mg, 99%). 1H NMR (500 MHz, DMSO-d6) δ 9.17 (br s, 1H), 8.75 (br d, J=4.4 Hz, 1H), 8.44-8.19 (m, 2H), 8.01 (s, 1H), 7.76 (s, 1H), 7.47 (dd, J=9.3, 4.5 Hz, 1H), 6.94 (s, 1H), 4.99 (q, J=8.8 Hz, 2H), 4.85 (br d, J=5.7 Hz, 2H); MS (ESI+) m/z=453.1 (M+H)$^+$.

Example 370

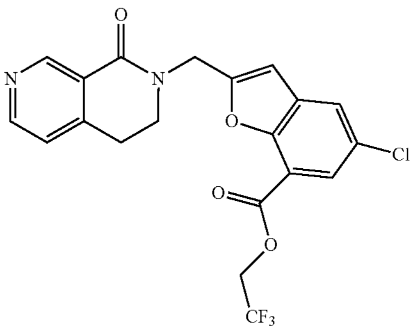 [SMILES: O=C(OCC(F)(F)F)c1cc(Cl)cc2cc(CN3CCc4ccncc4C3=O)oc12]

2,2,2-Trifluoroethyl 5-chloro-2-((1-oxo-3,4-dihydro-2,7-naphthyridin-2(1H)-yl)methyl)benzofuran-7-carboxylate 3,4-Dihydro-1H-pyrano[3,4-c]pyridin-1-one, HCl (18.40 mg, 0.099 mmol) and 2,2,2-trifluoroethyl 2-(aminomethyl)-5-chlorobenzofuran-7-carboxylate, TFA salt (38 mg, 0.090 mmol, Step C in Example 369) were taken up in Pyridine (0.8 mL) in a sealed tube. The reaction vessel was sealed and heated at 125° C. for 18 hours. The reaction mixture diluted with saturated $NaHCO_3$ solution and extracted with ethyl acetate. The combined organic extracts were concentrated in vacuo. The residue was dissolved in MeOH, filtered, and purified via HPLC (method B) to give the title compound (3.4 mg, 9% yield). $^1$H NMR (500 MHz, DMSO-$d_6$) δ 8.95 (br s, 1H), 8.61 (br d, J=3.4 Hz, 1H), 8.05 (d, J=2.1 Hz, 1H), 7.78 (d, J=2.1 Hz, 1H), 7.38 (d, J=4.9 Hz, 1H), 7.02 (s, 1H), 5.01 (q, J=9.1 Hz, 2H), 4.93 (s, 2H), 3.74 (t, J=6.6 Hz, 2H), 3.07 (t, J=6.6 Hz, 2H); MS (ESI+) m/z=439.1 (M+H)$^+$.

Example 371

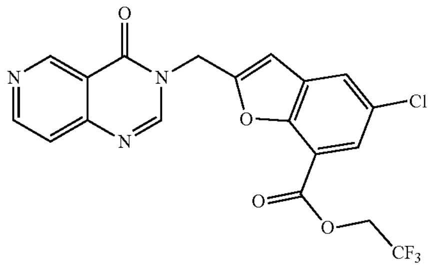 [SMILES: O=C(OCC(F)(F)F)c1cc(Cl)cc2cc(Cn3cnc4ccncc4c3=O)oc12]

2,2,2-Trifluoroethyl 5-chloro-2-((4-oxopyrido[4,3-d] pyrimidin-3(4H)-yl)methyl)benzofuran-7-carboxylate A mixture of 4-aminonicotinic acid (20.4 mg, 0.148 mmol), and 1,1-dimethoxy-N,N-dimethylmethanamine (0.12 mL, 0.91 mmol) in DMF (0.5 mL) in a microwave tube was heated in a microwave reactor at 100° C. for 15 min. The reaction mixture was concentrated in vacuo. To the residue was added 1 mL of acetic acid and 2,2,2-trifluoroethyl 2-(aminomethyl)-5-chlorobenzofuran-7-carboxylate, TFA (48 mg, 0.114 mmol, Step C in Example 369) in acetic acid (2 mL) and the mixture was again heated in a microwave at 110° C. for 15 min. The reaction mixture was concentrated in vacuo. The residue was dissolved in DMF, filtered and purified by preparative HPLC (Method B). Fractions containing the desired product were combined and dried via centrifugal evaporation to give the title compound (13.7 mg, 27%). $^1$H NMR (500 MHz, DMSO-$d_6$) δ 9.32 (s, 1H), 8.86 (d, J=5.6 Hz, 1H), 8.69 (s, 1H), 8.05 (d, J=2.1 Hz, 1H), 7.79 (d, J=2.1 Hz, 1H), 7.63 (d, J=5.6 Hz, 1H), 7.08 (s, 1H), 5.48 (s, 2H), 4.97 (q, J=8.9 Hz, 2H); MS (ESI+) m/z=437.9 $(M+H)^+$.

Example 372

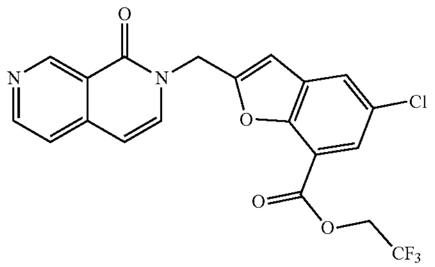 [SMILES: O=C(OCC(F)(F)F)c1cc(Cl)cc2cc(Cn3ccc4ccncc4c3=O)oc12]

2,2,2-Trifluoroethyl 5-chloro-2-((1-oxo-2,7-naphthyridin-2(1H)-yl)methyl)benzofuran-7-carboxylate A mixture of methyl 4-methylnicotinate (25.1 mg, 0.166 mmol), and 1,1-dimethoxy-N,N-dimethylmethanamine (0.18 mL, 1.33 mmol) in DMF (0.5 mL) in a microwave vial was heated in a microwave reactor at 140° C. for 30 min. The reaction mixture was concentrated in vacuo. The residue was mixed with acetic acid (0.5 mL) and 2,2,2-trifluoroethyl 2-(aminomethyl)-5-chlorobenzofuran-7-carboxylate, TFA (35 mg, 0.083 mmol, Step C in Example 369) and heated again in a microwave reactor at 110° C. for 18 min. The reaction mixture was concentrated in vacuo. The residue was dissolved in DMF, filtered and purified by preparative HPLC (Method B). Fractions containing the desired product were combined and dried via centrifugal evaporation to give the title compound (7.5 mg, 20.5%). 1H NMR (500 MHz, DMSO-d6) δ 9.33 (br s, 1H), 8.72 (br s, 1H), 8.05 (s, 1H), 7.86-7.74 (m, 2H), 7.62 (br d, J=5.2 Hz, 1H), 7.00 (s, 1H), 6.72 (d, J=7.3 Hz, 1H), 5.43 (s, 2H), 4.97 (q, J=8.9 Hz, 2H); MS (ESI+) m/z=437.1 $(M+H)^+$.

Example 373

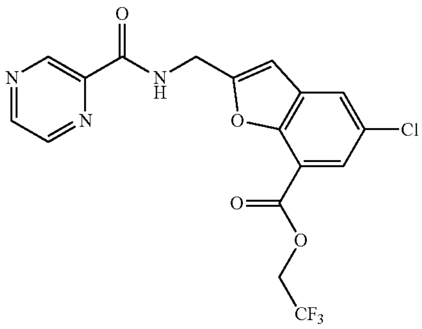 [SMILES: O=C(NCc1cc2cc(Cl)cc(C(=O)OCC(F)(F)F)c2o1)c1cnccn1]

2,2,2-Trifluoroethyl 5-chloro-2-((pyrazine-2-carboxamido)methyl)benzofuran-7-carboxylate To solution of pyrazine-2-carboxylic acid (10.59 mg, 0.085 mmol) and BOP (37.8 mg, 0.085 mmol) in DMF (1 mL) were added 2,2,2-trifluoroethyl 2-(aminomethyl)-5-chlorobenzofuran-7-carboxylate TFA salt (30 mg, 0.071 mmol, Step C of Example 369) and DIPEA (0.075 mL, 0.427 mmol). The reaction mixture was stirred at rt for 1 h. LC-MS showed new peak at tr=0.94 min, [M+H]+=414.2 as the desired product peak. The reaction mixture was concentrated in vacuo and the residue was dissolved in DMF, filtered and purified by preparative HPLC (Method B). Fractions containing the desired product were combined and dried via centrifugal evaporation to give the title compound (26 mg, 69%). $^1$H NMR (500 MHz, DMSO-$d_6$) δ 9.58 (br t, J=5.8 Hz, 1H), 9.23 (s, 1H), 8.91 (d, J=2.4 Hz, 1H), 8.77 (s, 1H), 8.04 (d, J=1.8 Hz, 1H), 7.77 (d, J=1.8 Hz, 1H), 6.89 (s, 1H), 5.04 (q, J=8.9 Hz, 2H), 4.74 (d, J=5.8 Hz, 2H); MS (ESI+) m/z=414.2 $(M+H)^+$.

Example 374

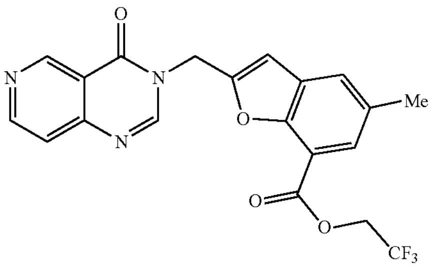 [SMILES: Cc1cc(C(=O)OCC(F)(F)F)c2oc(Cn3cnc4ccncc4c3=O)cc2c1]

2,2,2-Trifluoroethyl 5-methyl-2-((4-oxopyrido[4,3-d]pyrimidin-3(4H)-yl)methyl)benzofuran-7-carboxylate

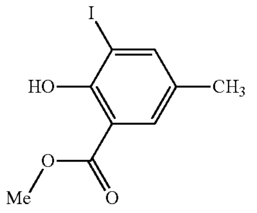

A) Methyl-2-hydroxy-3-iodo-5-methylbenzoate

To a solution of methyl 5-methylsalicylate (5 g, 30.1 mmol) in N,N-dimethylformamide (40 mL) was added sodium iodide (5.41 g, 36.1 mmol) followed by chloramine T trihydrate (10.17 g, 36.1 mmol) slowly in portions. The reaction was stirred at room temperature for 3 hours. The reaction mixture was quenched with ethyl acetate and 1N aqueous HCl solution. The organic layer was separated, washed with saturated aqueous sodium chloride solution followed by 10% aqueous $Na_2S_2O_3$ solution, and dried with anhydrous sodium sulfate. The dried organic extracts were filtered and concentrated in vacuo. The crude product mixture was purified by a silica gel ISCO 120 g column eluting with 0-20% ethyl acetate/hexane over a 15 minute gradient. The appropriate fractions were isolated and concentrated in vacuo to afford the product (8.2 g, 93% yield) as a solid. $^1H$ NMR (400 MHz, Chloroform-d) δ 11.52-11.27 (m, 1H), 7.86-7.72 (m, 1H), 7.72-7.52 (m, 1H), 4.09-3.89 (m, 3H), 2.39-2.08 (m, 3H); MS (ESI+) m/z=293.1 $(M+H)^+$.

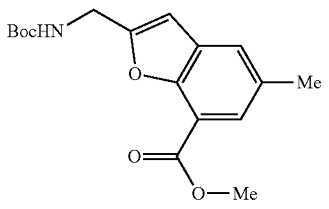 [SMILES: COC(=O)c1cc(C)cc2cc(CNC(=O)OC(C)(C)C)oc12]

B) Methyl 2-(((tert-butoxycarbonyl)amino)methyl)-5-methylbenzofuran-7-carboxylate A 100 ml flask was charged with methyl 2-hydroxy-3-iodo-5-methylbenzoate (8.2 g, 28.1 mmol), tert-butyl prop-2-yn-1-ylcarbamate (5.01 g, 32.3 mmol), and copper(I) iodide (0.428 g, 2.25 mmol) in DMF (20 mL) and TEA (30 mL). The reaction was purged with nitrogen, then bis(triphenylphosphine)palladium(II) chloride (0.985 g, 1.404 mmol) was added. The resulting mixture was heated at 80° C. for 4 hours. After cooling to room temperature, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 80 g column eluting with 0-35% ethyl acetate/hexane over a 15 minute gradient. The appropriate fractions were isolated and concentrated in vacuo to afford the title compound (6 g, 67% yield) as a light brown solid. $^1H$ NMR (400 MHz, Chloroform-d) δ 7.86-7.66 (m, 1H), 7.63-7.38 (m, 1H), 6.75-6.43 (m, 1H), 4.62-4.43 (m, 2H), 4.20-3.75 (m, 3H), 2.70-2.16 (m, 3H), 1.55-1.28 (m, 9H); MS (ESI+) m/z=264.1 $(M-55+H)^+$.

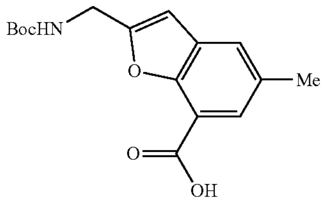 [SMILES: Cc1cc(C(=O)O)c2oc(CNC(=O)OC(C)(C)C)cc2c1]

C) 2-(((tert-Butoxycarbonyl)amino)methyl)-5-methylbenzofuran-7-carboxylic acid

A flask was charged with methyl 2-(((tert-butoxycarbonyl)amino)methyl)-5-methylbenzofuran-7-carboxylate (1.0 g, 3.13 mmol), THE (6 mL) and MeOH (6 mL). To the reaction was added aqueous LiOH (2 M, 9.39 mL, 18.8 mmol). The reaction mixture was stirred at room temperature for 3 hours. The solution was concentrated in vacuo, acidified with 1N aqueous HCl to pH 2, and extracted with ethyl acetate. The organic layer was washed with saturated aqueous sodium chloride solution, dried with anhydrous sodium sulfate, filtered and concentrated in vacuo to give a light brown solid (1.0. g, 100% yield). $^1H$ NMR (400 MHz, Methanol-$d_4$) δ 7.81-7.65 (m, 1H), 7.63-7.50 (m, 1H), 6.74-6.50 (m, 1H), 4.50-4.27 (m, 2H), 2.57-2.41 (m, 3H), 1.60-1.39 (m, 9H); MS (ESI+) m/z=270.1 $(M-55+H)^+$.

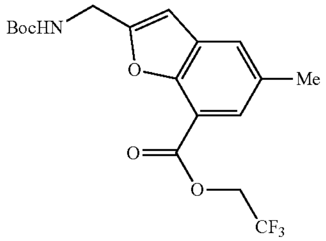 [SMILES: Cc1cc(C(=O)OCC(F)(F)F)c2oc(CNC(=O)OC(C)(C)C)cc2c1]

D) 2,2,2-Trifluoroethyl 2-(((tert-butoxycarbonyl)amino)methyl)-5-methylbenzofuran-7-carboxylate A 25 ml flask was charged with 2-(((tert-butoxycarbonyl)amino)methyl)-5-methylbenzofuran-7-carboxylic acid (0.6 g, 1.97 mmol) in DMF (8 mL). BOP (0.956 g, 2.16 mmol), 2,2,2-trifluroethanol (0.23 mL, 3.14 mmol) and DIPEA (0.55 mL, 3.14 mmol) were added. The reaction mixture was stirred at room temperature for 16 hours, then at 60° C. for 3 hours. After cooling to RT, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 40 g column eluting with 0-30% ethyl acetate in hexanes over a 15 minute gradient. The appropriate fractions were isolated and concentrated in vacuo to afford the product (0.7 g, 92% yield) as a solid. $^1H$ NMR (400 MHz, Chloroform-d) δ 7.81-7.70

(m, 1H), 7.63-7.54 (m, 1H), 6.83-6.48 (m, 1H), 4.91-4.69 (m, 2H), 4.64-4.39 (m, 2H), 2.57-2.43 (m, 3H), 1.56-1.48 (m, 9H); MS (ESI+) m/z=332.1 (M−55+H)$^+$.

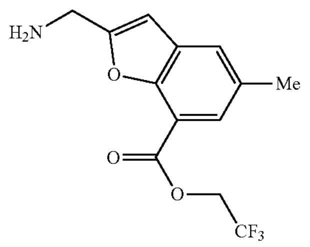 [SMILES: Cc1cc(C(=O)OCC(F)(F)F)c2oc(CN)cc2c1]

E) 2,2,2-Trifluoroethyl 2-(aminomethyl)-5-methylbenzofuran-7-carboxylate, TFA salt To a solution of 2,2,2-trifluoroethyl 2-(((tert-butoxycarbonyl) amino)methyl)-5-methylbenzofuran-7-carboxylate (0.7 g, 1.81 mmol) in $CH_2Cl_2$ (8 mL) was added TFA (1.67 mL, 21.7 mmol). The reaction mixture was stirred at RT for 2 hours. The reaction mixture was concentrated in vacuo to afford the product 2,2,2-trifluoroethyl 2-(aminomethyl)-5-methylbenzofuran-7-carboxylate (0.677 g, 93% yield) as a solid. $^1$H NMR (400 MHz, Methanol-d$_4$) δ 7.87 (d, J=1.7 Hz, 1H), 7.80 (dd, J=1.7, 0.8 Hz, 1H), 7.04 (s, 1H), 5.01-4.87 (m, 2H), 4.40 (s, 2H), 2.52 (s, 3H); MS (ESI+) m/z=271.0 (M−16)$^+$.

F) 2,2,2-Trifluoroethyl 5-methyl-2-((4-oxopyrido[4,3-d]pyrimidin-3(4H)-yl)methyl)benzofuran-7-carboxylate A mixture of 4-aminonicotinic acid (23.1 mg, 0.167 mmol), and N,N-dimethylformamide dimethyl acetal (0.128 mL, 0.957 mmol) in DMF (0.5 mL) in a microwave vial was heated at 100° C. in the microwave for 15 min. The reaction mixture was concentrated in vacuo. To the residue was added 0.5 mL of acetic acid and 2,2,2-trifluoroethyl 2-(aminomethyl)-5-methylbenzofuran-7-carboxylate, TFA salt (48 mg, 0.120 mmol) and the mixture was heated at 110° C. in the microwave for 15 min. The reaction mixture was concentrated in vacuo. The residue was dissolved in MeOH, and white precipitate formed. The solid was filtered to yield the title compound (10 mg, 19% yield). 1H NMR (400 MHz, Chloroform-d) δ 9.55 (s, 1H), 8.88 (d, J=5.6 Hz, 1H), 8.50 (s, 1H), 7.82 (d, J=1.2 Hz, 1H), 7.66-7.54 (m, 2H), 6.91 (s, 1H), 5.38 (m, 2H), 4.78 (q, J=8.4 Hz, 2H), 2.49 (s, 3H); MS (ESI+) m/z=418.0 (M+H)$^+$.

Example 375

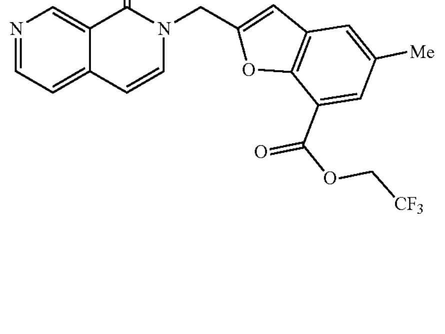

2,2,2-Trifluoroethyl 5-methyl-2-((1-oxo-2,7-naphthyridin-2(1H)-yl)methyl) benzofuran-7-carboxylate A mixture of methyl 4-methylnicotinate (56.5 mg, 0.374 mmol), N,N-dimethylformamide dimethyl acetal (0.267 mL, 1.99 mmol) in DMF (0.5 mL) was heated in the microwave at 150° C. for 60 minutes. The reaction mixture was concentrated in vacuo. The residue was mixed with acetic acid (0.5 mL) and 2,2,2-trifluoroethyl 2-(aminomethyl)-5-methylbenzofuran-7-carboxylate, TFA (50 mg, 0.125 mmol, Step E of Example 374) and heated in the microwave at 120° C. for 30 minutes. The reaction mixture was concentrated in vacuo. The crude material was purified via preparative HPLC (Method C), to afford the product (24 mg, 44% yield) as a solid. 1H NMR (400 MHz, Chloroform-d) δ 9.62 (s, 1H), 8.74 (d, J=5.5 Hz, 1H), 7.81 (d, J=1.2 Hz, 1H), 7.69-7.59 (m, 2H), 7.41-7.30 (m, 1H), 6.87 (s, 1H), 6.52 (d, J=7.5 Hz, 1H), 5.37 (s, 2H), 4.79 (q, J=8.5 Hz, 2H), 2.48 (s, 3H); MS (ESI+) m/z=417.0 (M+H)$^+$.

Example 376

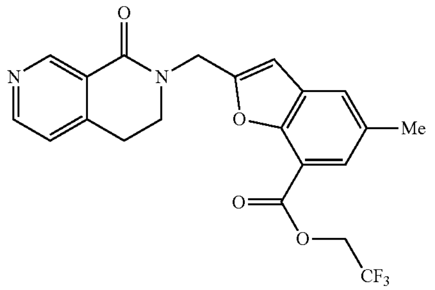 [SMILES: Cc1cc(C(=O)OCC(F)(F)F)c2oc(CN3CCc4ccncc4C3=O)cc2c1]

2,2,2-Trifluoroethyl 5-methyl-2-((1-oxo-3,4-dihydro-2,7-naphthyridin-2(1H)-yl)methyl)benzofuran-7-carboxylate 3,4-Dihydro-1H-pyrano[3,4-c]pyridin-1-one hydrochloride (24.1 mg, 0.13 mmol) (WO 2005063768) and 2,2,2-trifluoroethyl 2-(aminomethyl)-5-methylbenzofuran-7-carboxylate TFA salt (50 mg, 0.13 mmol, Step E of Example 374) were added to a pressure relief vial with pyridine (100 uL) and heated to 120° C. After 4 hours, the reaction was cooled, concentrated in vacuo to remove pyridine, taken up in DMF, filtered, and purified via HPLC (Method B) to give 2,2,2-trifluoroethyl 5-methyl-2-((1-oxo-3,4-dihydro-2,7-naphthyridin-2(1H)-yl)methyl)benzofuran-7-carboxylate (13.1 mg, 0.031 mmol, 23.6% yield). $^1$H NMR (500 MHz, DMSO-d$_6$) δ 8.94 (s, 1H), 8.60 (br d, J=4.5 Hz, 1H), 7.74 (s, 1H), 7.66 (s, 1H), 7.36 (d, J=4.9 Hz, 1H), 6.93 (s, 1H), 4.99 (q, J=8.7 Hz, 2H), 4.90 (s, 2H), 3.72 (br t, J=6.2 Hz, 2H), 3.05 (br t, J=6.3 Hz, 2H), 2.42 (s, 3H); MS (ESI+) m/z 419.2 (M+H)$^+$.

Example 377

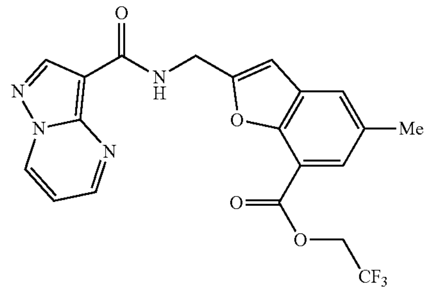 [SMILES: Cc1cc(C(=O)OCC(F)(F)F)c2oc(CNC(=O)c3cnn4cccnc34)cc2c1]

2,2,2-Trifluoroethyl 5-methyl-2-((pyrazolo[1,5-a]pyrimidine-3-carboxamido)methyl)benzofuran-7-carboxylate To a suspension of pyrazole[1,5-a]pyrimidine-3-carboxylic acid (15 mg, 0.092 mmol) and BOP (31.3 mg, 0.071 mmol) in DMF (2 mL) was added 2,2,2-trifluoroethyl 2-(aminomethyl)-5-methylbenzofuran-7-carboxylate, TFA salt (28.4 mg, 0.071 mmol, Step E of Example 374) and DIPEA (0.049 mL, 0.283 mmol). The reaction mixture turned into a clear solution and was stirred at room temperature for 2 hours. The reaction mixture was quenched with water, extracted with DCM, dried with anhydrous sodium sulfate, filtered and concentrated in vacuo. The crude material was purified via preparative HPLC (Method C) to give the title compound as a solid (23.5 mg, 73% yield). $^1$H NMR (400 MHz, Methanol-$d_4$) δ 9.10 (dd, J=7.0, 1.7 Hz, 1H), 8.79 (dd, J=4.2, 1.7 Hz, 1H), 8.62 (s, 1H), 7.75 (d, J=1.2 Hz, 1H), 7.67 (dd, J=1.6, 0.7 Hz, 1H), 7.23 (dd, J=7.0, 4.2 Hz, 1H), 6.78 (t, J=0.9 Hz, 1H), 4.91-4.87 (m, 4H), 2.48 (s, 3H); MS (ESI+) m/z=433.0 $(M+H)^+$.

Example 378

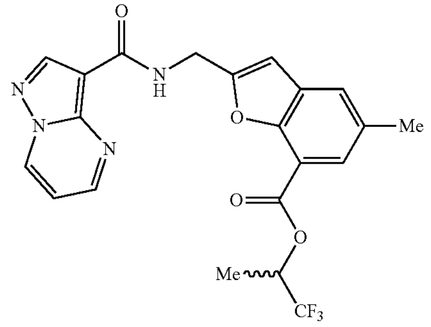 [SMILES: Cc1cc(C(=O)OC(C)C(F)(F)F)c2oc(CNC(=O)c3cnn4cccnc34)cc2c1]

1,1,1-Trifluoropropan-2-yl 5-methyl-2-((pyrazolo[1,5-a]pyrimidine-3-carboxamido)methyl)benzofuran-7-carboxylate

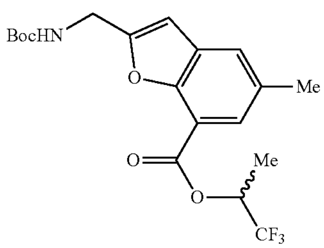 [SMILES: Cc1cc(C(=O)OC(C)C(F)(F)F)c2oc(CNC(=O)OC(C)(C)C)cc2c1]

A) 1,1,1-Trifluoropropan-2-yl 2-(((tert-butoxycarbonyl)amino)methyl)-5-methylbenzofuran-7-carboxylate To a scintillation vial was added 2-(((tert-butoxycarbonyl)amino)methyl)-5-methylbenzofuran-7-carboxylic acid (450 mg, 1.474 mmol, Step C of Example 374), 1,1,1-trifluoropropan-2-ol (0.534 mL, 5.90 mmol), and DIPEA (1.03 mL, 5.90 mmol) in DMF (10 mL). To the solution was added BOP (978 mg, 2.21 mmol) and the reaction stirred at room temperature for 16 hours. The reaction mixture was diluted with ethyl acetate, washed with saturated aqueous sodium bicarbonate solution, water and saturated aqueous sodium chloride solution, dried with anhydrous sodium sulfate, filtered and concentrated in vacuo. The crude product mixture was purified by a silica gel ISCO 80 g column eluting with 0-100% ethyl acetate in hexanes over a 15 minute gradient. The appropriate fractions were isolated and concentrated in vacuo to afford the product (0.233 g, 39% yield) as a solid. $^1$H NMR (400 MHz, Chloroform-d) δ 7.76-7.71 (m, 1H), 7.57 (s, 1H), 6.61 (s, 1H), 5.61 (dt, J=13.2, 6.6 Hz, 1H), 4.51 (br d, J=5.3 Hz, 2H), 2.49 (s, 3H), 1.59 (d, J=6.6 Hz, 3H), 1.48 (s, 9H); MS (ESI+) m/z=346.0 $(M-55+H)^+$.

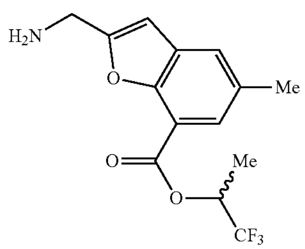 [SMILES: Cc1cc(C(=O)OC(C)C(F)(F)F)c2oc(CN)cc2c1]

B) 1,1,1-Trifluoropropan-2-yl 2-(aminomethyl)-5-methylbenzofuran-7-carboxylate, TFA salt To a solution of 1,1,1-trifluoropropan-2-yl 2-(((tert-butoxycarbonyl)amino)methyl)-5-methylbenzofuran-7-carboxylate (0.233 g, 0.58 mmol) in $CH_2Cl_2$ (5 mL) was added TFA (1.0 mL). The reaction mixture was stirred at room temperature for 2 hours. The reaction mixture was concentrated in vacuo to afford the crude product 2,2,2-trifluoroethyl 2-(aminomethyl)-5-methylbenzofuran-7-carboxylate (0.245 g, 40% yield) as a solid. $^1$H NMR (400 MHz, Chloroform-d) δ 7.73 (s, 1H), 7.56 (s, 1H), 6.78 (s, 1H), 5.51

(dt, J=12.6, 6.3 Hz, 1H), 4.40 (br s, 2H), 2.46 (s, 3H), 1.59-1.48 (m, 3H); MS (ESI+) m/z=302.0 $(M-16)^+$.

C) 1,1,1-Trifluoropropan-2-yl 5-methyl-2-((pyrazolo[1,5-a]pyrimidine-3-carboxamido)methyl)benzofuran-7-carboxylate To a solution of pyrazolo[1,5-a]pyrimidine-3-carboxylic acid (100 mg, 0.613 mmol) and 1,1,1-trifluoropropan-2-yl 2-(aminomethyl)-5-methylbenzofuran-7-carboxylate, TFA salt (255 mg, 0.613 mmol) in DMF (2 mL) was added BOP (407 mg, 0.919 mmol) and DIPEA (0.428 mL, 2.452 mmol). The reaction mixture was stirred at room temperature for 2 hours. The reaction was quenched with water, the precipitate that was resulted was filtered, then dissolved in 2 mL of DMF for purification. The crude material was purified via preparative HPLC (Method B) to afford the product (35.3 mg, 13% yield). $^1H$ NMR (500 MHz, DMSO-$d_6$) δ 9.24 (br d, J=5.9 Hz, 1H), 8.79 (br d, J=3.5 Hz, 1H), 8.60 (s, 1H), 8.45 (br s, 1H), 7.71 (s, 1H), 7.62 (s, 1H), 7.26 (dd, J=6.7, 4.4 Hz, 1H), 6.82 (s, 1H), 5.73-5.65 (m, 1H), 4.79 (br d, J=5.8 Hz, 2H), 2.43 (s, 3H), 1.48 (br d, J=6.6 Hz, 3H); MS (ESI+) m/z=447.1 $(M+H)^+$.

Example 379

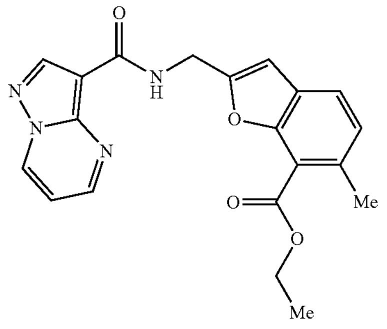 [SMILES: CCOC(=O)c1c(C)ccc2cc(CNC(=O)c3cnn4cccnc34)oc12]

Ethyl 6-methyl-2-((pyrazolo[1,5-a]pyrimidine-3-carboxamido)methyl)benzofuran-7-carboxylate

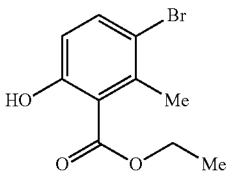 [SMILES: CCOC(=O)c1c(O)ccc(Br)c1C]

A) Ethyl 3-bromo-6-hydroxy-2-methylbenzoate

To a solution of ethyl 2-hydroxy-6-methylbenzoate (1.0 g, 5.55 mmol) in DCM (10 mL) was added $CaCO_3$ (0.66 g, 6.66 mmol) and bromine (0.3 mL, 5.83 mmol) in DCM (2 mL) at 0° C. very slowly over 40 min. The reaction mixture was stirred at rt for 1 h. The reaction mixture was diluted with water and ethyl acetate. The organic layer was separated, washed with brine and $Na_2S_2O_3$ solution successively, dried over $MgSO_4$, and filtered. The filtrate was concentrated in vacuo to give the title compound as a light yellow oil (1.4 g, 97%). The crude product was dried on high vacuum for 1 hour and during this time, the product solidified. $^1H$ NMR (400 MHz, Chloroform-d) δ 10.85 (s, 1H), 7.59 (d, J=8.8 Hz, 1H), 6.90-6.67 (m, 1H), 4.49 (q, J=7.2 Hz, 2H), 2.67 (s, 3H), 1.51-1.41 (m, 3H); MS (ESI+) m/z=261 $(M+H)^+$.

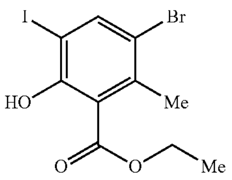 [SMILES: CCOC(=O)c1c(C)c(Br)cc(I)c1O]

B) Ethyl 3-bromo-6-hydroxy-5-iodo-2-methylbenzoate

To a solution of ethyl 3-bromo-6-hydroxy-2-methylbenzoate (1.8 g, 6.95 mmol) in N,N-dimethylformamide (10 mL) was added sodium iodide (1.25 g, 8.34 mmol) followed by chloramine T trihydrate (2.15 g, 7.64 mmol) slowly. The resulting mixture was stirred at rt for 2 h. The reaction mixture was diluted with ethyl acetate and 1 N aqueous HCl solution. The organic layer was separated and washed with brine followed by $Na_2S_2O_3$ solution, dried over $MgSO_4$, and filtered. The filtrate was concentrated in vacuo to give a light yellow solid. The solid was re-crystallized from MeOH and DCM to give the desired product as a white solid. The filtrate was concentrated in vacuo and the residue was dissolved in DCM and purified by flash chromatography (ISCO column 40 g, 0-20% ethyl acetate in hexanes). The purified product was combined with the crystallized solid to give the title compound (2.3 g, 86%) as a white solid. $^1H$ NMR (400 MHz, Chloroform-d) δ 11.53 (s, 1H), 8.10 (s, 1H), 4.50 (q, J=7.2 Hz, 2H), 2.64 (s, 3H), 1.46 (t, J=7.2 Hz, 3H); MS (ESI+) m/z=386.6 $(M+H)^+$.

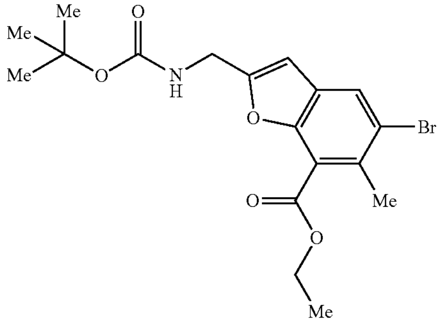 [SMILES: CCOC(=O)c1c(C)c(Br)cc2cc(CNC(=O)OC(C)(C)C)oc12]

C) Ethyl 5-bromo-2-(((tert-butoxycarbonyl)amino)methyl)-6-methylbenzofuran-7-carboxylate A mixture of ethyl 3-bromo-6-hydroxy-5-iodo-2-methylbenzoate (2.2 g, 5.71 mmol), tert-butyl prop-2-yn-1-ylcarbamate (1.02 g, 6.57 mmol), TEA (15.93 mL, 114 mmol), and copper(I) iodide (0.11 g, 0.57 mmol) in DMF (8 mL) was purged with a nitrogen stream for 6 mins. Bis(triphenylphosphine) palladium(II) chloride (0.40 g, 0.57 mmol) was then added. The resulting mixture was heated at 80° C. for 3 h. The reaction mixture was then cooled down and diluted with ethyl acetate and saturated aqueous $NaHCO_3$ solution. The organic layer was separated, washed with brine, dried over $MgSO_4$, and filtered. The filtrate was concentrated in vacuo and the residue was dissolved in DCM and purified by flash chromatography (ISCO column 120 g, 0-25% ethyl acetate in hexanes) to give the title compound (1.9 g, 81%) as a light brown oily solid. $^1$H NMR (500 MHz, Chloroform-d) δ 7.82 (s, 1H), 6.55 (s, 1H), 5.15-4.91 (m, 1H), 4.59-4.47 (m, 2H), 4.47-4.39 (m, 2H), 2.59 (s, 3H), 1.50-1.41 (m, 12H); MS (ESI+) m/z=358.0 $(M-55+H)^+$.

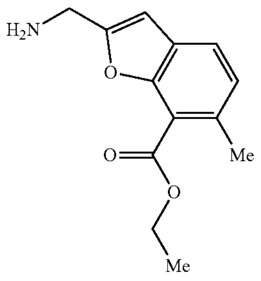 [SMILES: CCOC(=O)c1c(C)ccc2cc(CN)oc12]

D) Ethyl 2-(aminomethyl)-6-methylbenzofuran-7-carboxylate

To a mixture of ethyl 5-bromo-2-(((tert-butoxycarbonyl) amino) methyl)-6-methylbenzofuran-7-carboxylate (2.0 g, 4.85 mmol) in MeOH (20 mL) and ethyl acetate (6 mL) was added palladium hydroxide on carbon (20% on carbon, 0.34 g, 0.485 mmol). The mixture was evacuated and then flushed with hydrogen three times (balloon). The reaction mixture was stirred under a hydrogen atmosphere for 6 hours. The reaction mixture was filtered through a celite pad and the filtrate was concentrated in vacuo. The residue was resubjected to hydrogenation. To a mixture of ethyl 5-bromo-2-(((tert-butoxycarbonyl)amino)methyl)-6-methylbenzofuran-7-carboxylate (2.0 g, 4.85 mmol) in MeOH (20 mL) was added palladium hydroxide on carbon (20% on carbon, 0.341 g, 0.485 mmol). The reaction mixture was evacuated and then filled with hydrogen (balloon) and stirred under a hydrogen atmosphere for another 6 hours. The reaction mixture was filtered through a celite pad and the filtrate was concentrated in vacuo to give the desired des-bromo intermediate. To the crude intermediate in DCM (8 mL) was added TFA (3.0 mL, 38.8 mmol). The reaction mixture was stirred at room temperature for 3 hours. The reaction mixture was concentrated in vacuo and the residue was mixed with ethyl acetate and saturated aqueous $NaHCO_3$ solution. The organic layer was separated, washed with brine, dried over $MgSO_4$, and filtered. The filtrate was concentrated in vacuo to give the crude title compound as a brown oil (0.8 g, 71%). $^1$H NMR (500 MHz, Chloroform-d) δ 7.47 (d, J=7.9 Hz, 1H), 7.09 (d, J=7.9 Hz, 1H), 6.53 (s, 1H), 4.49 (q, J=7.2 Hz, 2H), 4.05 (s, 2H), 2.65-2.58 (s, 3H), 1.46 (t, J=7.2 Hz, 3H); MS (ESI+) m/z=467.2 $(2M+H)^+$.

E) Ethyl 6-methyl-2-((pyrazolo[1,5-a]pyrimidine-3-carboxamido) methyl)benzofuran-7-carboxylate To a suspension of pyrazolo[1,5-a]pyrimidine-3-carboxylic acid (109 mg, 0.67 mmol) and BOP (319 mg, 0.720 mmol) in DMF (3 mL) was added ethyl 2-(aminomethyl)-6-methylbenzofuran-7-carboxylate (120 mg, 0.514 mmol) and DIPEA (0.36 mL, 2.06 mmol). The reaction mixture turned into a clear solution after addition of the amine and was stirred at room temperature for 4 hours. The reaction mixture was diluted with water, ethyl acetate, and saturated aqueous $NaHCO_3$ solution. The organic layer was separated, washed with brine, dried over $MgSO_4$, and filtered. The filtrate was concentrated in vacuo. The residue was triturated with MeOH and filtered to give the title compound as a white solid (110 mg, 61%). $^1$H NMR (500 MHz, DMSO-$d_6$) δ 9.26 (br d, J=6.7 Hz, 1H), 8.80 (br d, J=3.5 Hz, 1H), 8.61 (s, 1H), 8.46-8.29 (m, 1H), 7.60 (d, J=7.9 Hz, 1H), 7.27 (dd, J=6.7, 4.3 Hz, 1H), 7.15 (d, J=7.9 Hz, 1H), 6.78 (s, 1H), 4.77 (br d, J=5.8 Hz, 2H), 4.36 (q, J=7.0 Hz, 2H), 2.48 (s, 3H), 1.29 (t, J=7.1 Hz, 3H); MS (ESI+) m/z=379.3 $(M+H)^+$.

Example 381

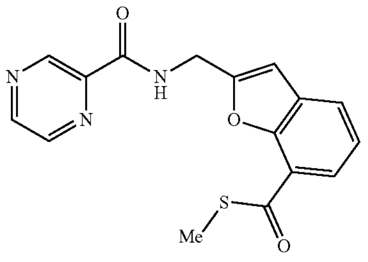 [SMILES: CSC(=O)c1cccc2cc(CNC(=O)c3cnccn3)oc12]

S-Methyl 2-((pyrazine-2-carboxamido)methyl)benzofuran-7-carbothioate

To a suspension of 2-((pyrazine-2-carboxamido)methyl) benzofuran-7-carboxylic acid (30 mg, 0.101 mmol, Example 130) in DCE (2 mL) was added oxalyl chloride (25.6 mg, 0.202 mmol) and 2 drops of DMF. The reaction mixture was stirred at room temperature for 5 hours. The reaction mixture was concentrated in vacuo and dried on high vacuum for 15 minutes. To the residue was added DCE (2 mL) followed by sodium thiomethoxide (14.15 mg, 0.202 mmol), and DIPEA (0.035 mL, 0.202 mmol). The reaction mixture was stirred at room temperature overnight. The reaction mixture was concentrated in vacuo. The residue was dissolved in DMF, filtered, and purified via HPLC (method B) to give the title compound (2.3 mg, 5%). $^1$H NMR (500 MHz, DMSO-$d_6$) δ 9.43 (br t, J=5.4 Hz, 1H), 9.20 (s, 1H), 8.86 (d, J=2.2 Hz, 1H), 8.73 (s, 1H), 7.87 (d, J=7.7 Hz, 1H), 7.78 (d, J=7.6 Hz, 1H), 7.36 (t, J=7.7 Hz, 1H), 6.88 (s, 1H), 4.74 (d, J=6.1 Hz, 2H), 2.46 (s, 3H); MS (ESI+) m/z=328.3 $(M+H)^+$.

Example 382

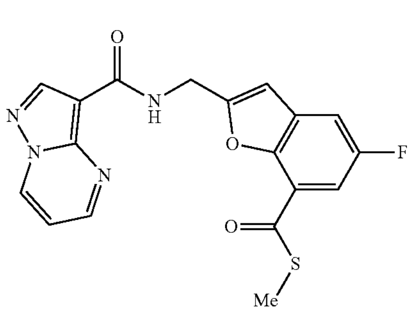 [SMILES: CSC(=O)c1cc(F)cc2cc(CNC(=O)c3cnn4cccnc34)oc12]

S-Methyl 5-fluoro-2-((pyrazolo[1,5-a]pyrimidine-3-carboxamido)methyl)benzofuran-7-carbothioate

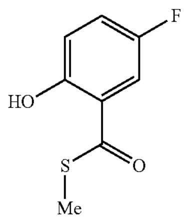 [SMILES: CSC(=O)c1cc(F)ccc1O]

A) S-Methyl 5-fluoro-2-hydroxybenzothioate

To 5-fluoro-2-hydroxybenzoic acid (1.6 g, 10.3 mmol) was added thionyl chloride (5.24 mL, 71.7 mmol) and a few drops of DMF. The reaction mixture was stirred at room temperature for 3 hours. The reaction mixture was concentrated in vacuo. Toluene was added to remove excess solvents to give a white solid. To the solid was added DCE (30 mL), sodium methanethiolate (0.79 g, 11.3 mmol), and then TEA (4.29 mL, 30.7 mmol). The reaction mixture was stirred at room temperature for 26 hours. The reaction mixture was diluted with brine and DCM. The organic layer was separated, washed with brine, and dried over $MgSO_4$. The filtrate was concentrated in vacuo. The residue was dissolved in DCM and purified by flash chromatography (ISCO 40 g column, 0-15% ethyl acetate in hexanes) to give the title compound (1.1 g, 58% yield) as a white solid. $^1$H NMR (400 MHz, CHLOROFORM-d) δ 10.83 (s, 1H), 7.57 (dd, J=8.9, 3.0 Hz, 1H), 7.22 (ddd, J=9.1, 7.7, 3.0 Hz, 1H), 6.97 (dd, J=9.1, 4.5 Hz, 1H), 2.52 (s, 3H).

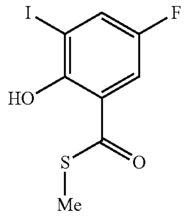 [SMILES: CSC(=O)c1cc(F)cc(I)c1O]

B) S-Methyl 5-fluoro-2-hydroxy-3-iodobenzothioate

To a solution of S-methyl 5-fluoro-2-hydroxybenzothioate (1.1 g, 5.9 mmol) in N,N-dimethylformamide (15 mL) was added sodium iodide (1.06 g, 7.1 mmol), followed by chloramine T trihydrate (1.83 g, 6.5 mmol) in several batches. The resulting mixture turned brown and was stirred at room temperature for 20 hours. The reaction mixture was diluted with ethyl acetate and saturated aqueous $NaHCO_3$ solution. The organic layer was separated, washed with brine followed by $Na_2S_2O_3$ solution, and dried over $MgSO_4$. The filtrate was concentrated in vacuo to give a light yellow solid. The residue was mixed with MeOH and the resulting mixture was filtered to give the title compound as a white solid (1.1 g, 60%). $^1$H NMR (400 MHz, CHLOROFORM-d) δ 11.72 (s, 1H), 7.74 (dd, J=7.2, 2.9 Hz, 1H), 7.63 (dd, J=8.5, 2.9 Hz, 1H), 2.54 (s, 3H).

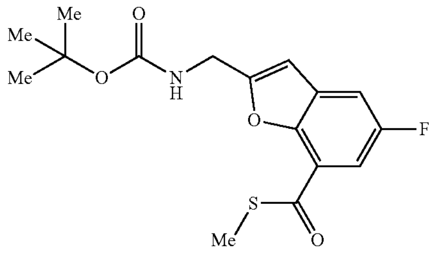 [SMILES: CSC(=O)c1cc(F)cc2cc(CNC(=O)OC(C)(C)C)oc12]

C) S-Methyl 2-(((tert-butoxycarbonyl)amino)methyl)-5-fluorobenzofuran-7-carbothioate A mixture of S-methyl 5-fluoro-2-hydroxy-3-iodobenzothioate (1.1 g, 3.52 mmol), tert-butyl prop-2-yn-1-ylcarbamate (0.63 g, 4.05 mmol), TEA (7.37 mL, 52.9 mmol), and copper(I) iodide (0.067 g, 0.352 mmol) in DMF (8 mL) was purged with a stream of nitrogen for 5 mins. Bis(triphenylphosphine)palladium(II) chloride (0.124 g, 0.176 mmol) was then added. The resulting mixture was heated at 80° C. for 2 hours. The reaction was cooled down and stirred at room temperature overnight. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DCM and purified by flash chromatography (ISCO 40 g column, 0-20% ethyl acetate in hexanes) to give the title compound (0.86 g, 72% yield) as a light brown oily solid. $^1$H NMR (400 MHz, Chloroform-d) δ 7.60 (dd, J=9.5, 2.6 Hz, 1H), 7.41 (dd, J=7.8, 2.6 Hz, 1H), 6.68 (s, 1H), 5.21-4.98 (m, 1H), 4.53 (br d, J=5.9 Hz, 2H), 2.56 (s, 3H), 1.49 (s, 9H); MS (ESI+) m/z=284.0 $(M-55+H)^+$.

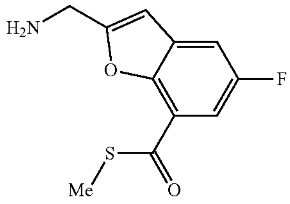 [SMILES: CSC(=O)c1cc(F)cc2cc(CN)oc12]

D) S-Methyl 2-(aminomethyl)-5-fluorobenzofuran-7-carbothioate

To a solution of S-methyl 2-(((tert-butoxycarbonyl)amino)methyl)-5-fluorobenzofuran-7-carbothioate (0.85 g, 2.51 mmol) in dichloromethane (6 mL) was added TFA (1.93 mL, 25.1 mmol). The reaction mixture was stirred at room temperature for 1 hour. The reaction was concentrated in vacuo to give the title compound (TFA salt, 0.85 g, 96%) as a light brown solid. $^1$H NMR (400 MHz, Chloroform-d) δ 7.63 (dd, J=9.2, 2.5 Hz, 1H), 7.45 (dd, J=7.5, 2.6 Hz, 1H), 6.89 (s, 1H), 4.43 (s, 2H), 2.48 (s, 3H); MS (ESI+) m/z=223.1 $(M-17+H)^+$.

E) S-Methyl 5-fluoro-2-((pyrazolo[1,5-a]pyrimidine-3-carboxamido)methyl)benzofuran-7-carbothioate A mixture of pyrazolo[1,5-a]pyrimidine-3-carboxylic acid (19.8 mg, 0.121 mmol) and BOP (53.7 mg, 0.121 mmol) in DMF (1 mL) was stirred at room temperature for 10 min. A solution of S-methyl 2-(aminomethyl)-5-fluorobenzofuran-7-carbothioate, TFA salt (33 mg, 0.093 mmol) in THE (1 mL) and DIPEA (0.049 mL, 0.28 mmol) was added. The reaction was stirred at room temperature for 1 hour. The reaction mixture was concentrated in vacuo. The residue was dissolved in DMF, filtered and purified by preparative HPLC (Method B). Fractions containing the desired product were combined and dried via centrifugal evaporation to give the title compound (10.7 mg, 29% yield). $^1$H NMR (500 MHz, DMSO-$d_6$) δ 9.29 (dd, J=7.0, 1.2 Hz, 1H), 8.93-8.78 (m, 1H), 8.63 (s, 1H), 8.58 (br t, J=5.8 Hz, 1H), 7.74 (dd, J=8.2, 2.4 Hz, 1H), 7.53 (dd, J=9.5, 2.4 Hz, 1H), 7.28 (dd, J=7.0, 4.3 Hz, 1H), 6.91 (s, 1H), 4.82 (d, J=5.8 Hz, 2H), 2.48 (s, 3H); MS (ESI) m/z=385.1 $(M+H)^+$.

Examples 383-384

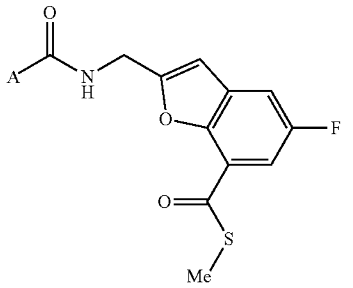

Examples 383 and 384 were prepared in the same general way as Example 382 using the corresponding benzofuran amine (Step D in Example 382) and the required acid.

Example 385

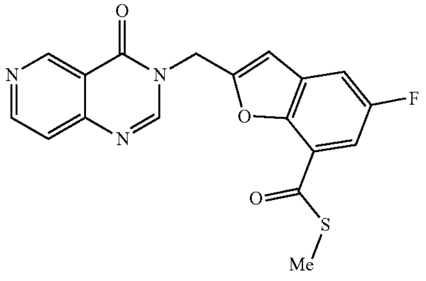

S-Methyl 5-fluoro-2-((4-oxopyrido[4,3-d]pyrimidin-3(4H)-yl)methyl)benzofuran-7-carbothioate A mixture of 4-aminonicotinic acid (29.9 mg, 0.217 mmol) and 1,1-dimethoxy-N,N-dimethylmethanamine (0.171 mL, 1.27 mmol) in DMF (1 mL) in a microwave tube was heated in a microwave reactor at 120° C. for 25 min. The reaction mixture was concentrated in vacuo. To the residue was added 1 mL of acetic acid and S-methyl 2-(aminomethyl)-5-fluorobenzofuran-7-carbothioate, TFA (45 mg, 0.127 mmol, Step D of Example 382) in acetic acid (2 mL). The mixture was heated in a microwave reactor at 110° C. for 20 min. The reaction mixture was then concentrated in vacuo. The residue was dissolved in DMF, filtered and purified by preparative HPLC (Method B). Fractions containing the desired product were combined and dried via centrifugal evaporation to give the title compound (18.1 mg, 38%). $^1$H NMR (500 MHz, DMSO-$d_6$) δ 9.32 (s, 1H), 8.86 (d, J=5.5 Hz, 1H), 8.78 (s, 1H), 7.76 (dd, J=8.2, 2.4 Hz, 1H), 7.65 (d, J=5.5 Hz, 1H), 7.55 (dd, J=9.5, 2.4 Hz, 1H), 7.08 (s, 1H), 5.48 (s, 2H), 2.44 (s, 3H); MS (ESI+) m/z=370.0 $(M+H)^+$.

| Ex. No. | A-CO— | Name | $^1$H NMR | LC/MS $(M + H)^+$ |
|---|---|---|---|---|
| 383 | 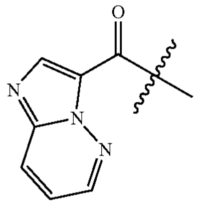 [SMILES: *C(=O)c1cnc2cccnn12] | S-Methyl 5-fluoro-2-((imidazo[1,2-b]pyridazine-3-carboxamido)methyl)benzofuran-7-carbothioate | $^1$H NMR (500 MHz,DMSO-$d_6$) δ 9.25 (br t, J = 5.6 Hz, 1H), 8.78 (br d, J = 4.3 Hz, 1H), 8.46-8.21 (m, 2H), 7.74 (dd, J = 8.1, 2.3 Hz, 1H), 7.53 (dd, J = 9.5, 2.4 Hz, 1H), 7.48 (dd, J = 9.2, 4.6 Hz, 1H), 6.95 (s, 1H), 4.86 (br d, J = 5.8 Hz, 2H), 2.47 (s, 3H) | 385.3 |
| 384 | 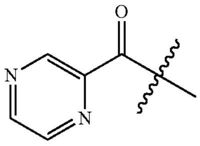 [SMILES: *C(=O)c1cnccn1] | S-Methyl 5-fluoro-2-((pyrazine-2-carboxamido)methyl)benzofuran-7-carbothioate | $^1$H NMR (500 MHz, DMSO-$d_6$) δ 9.61 (br t, J = 6.0 Hz, 1H), 9.22 (s, 1H), 8.89 (d, J = 2.1 Hz, 1H), 8.76 (s, 1H), 7.74 (dd, J = 8.2, 2.7 Hz, 1H), 7.53 (dd, J = 9.5, 2.4 Hz, 1H), 6.89 (s, 1H), 4.73 (d, J = 5.8 Hz, 2H), 2.47 (s, 3H) | 346.3 |

Example 386

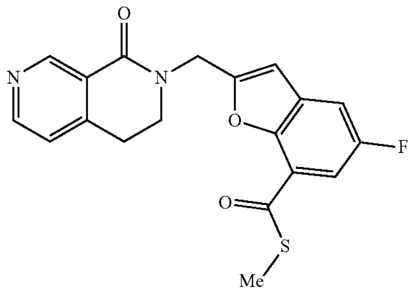 [SMILES: CSC(=O)c1cc(F)cc2cc(CN3CCc4ccncc4C3=O)oc12]

S-Methyl 5-fluoro-2-((1-oxo-3,4-dihydro-2,7-naphthyridin-2(1H)-yl)methyl)benzofuran-7-carbothioate A mixture of 3,4-dihydro-1H-pyrano[3,4-c]pyridin-1-one, HCl salt (23.1 mg, 0.125 mmol) (WO 2005063768) and crude S-methyl 2-(aminomethyl)-5-fluorobenzofuran-7-carbothioate, TFA salt (40 mg, 0.113 mmol, Step D in Example 382) in pyridine (1 mL) was heated in a vial with pressure relief septum at 125° C. for 18 hours. The reaction mixture was diluted with saturated aqueous $NaHCO_3$ solution and extracted with ethyl acetate. The organic layer was separated and concentrated in vacuo. The residue was dissolved in MeOH, filtered and purified by preparative HPLC (Method B). Fractions containing the desired product were combined and dried via centrifugal evaporation to give the title compound (2 mg, 5%). $^1$H NMR (500 MHz, DMSO-$d_6$) δ 8.95 (s, 1H), 8.61 (br d, J=4.6 Hz, 1H), 7.76 (dd, J=8.1, 2.3 Hz, 1H), 7.54 (dd, J=9.6, 2.3 Hz, 1H), 7.38 (br d, J=4.6 Hz, 1H), 7.02 (s, 1H), 4.94 (s, 2H), 3.76 (br t, J=6.6 Hz, 2H), 3.09 (br t, J=6.6 Hz, 2H), 2.45 (s, 3H); MS (ESI+) m/z=370.9 $(M+H)^+$.

Examples 387 and 388

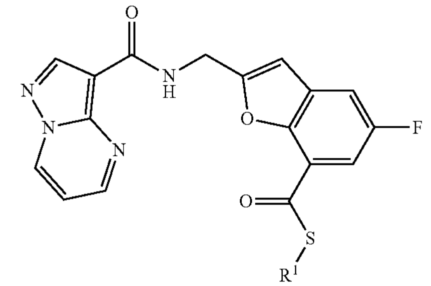

Examples 387 and 388 were prepared from Example 136 and the required thiol according to the procedure in Example 380.

| Ex. No. | $R^1$ | Name | $^1$H NMR | LC/MS $[M + H]^+$ |
|---|---|---|---|---|
| 387 | 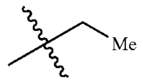 [SMILES: *CC] | S-Ethyl 5-fluoro-2-((pyrazolo[1,5-a]-pyrimidine-3-carbox-amido)methyl)benzo-furan-7-carbothioate | $^1$H NMR (500 MHz, DMSO-$d_6$) δ 9.32 (dd, J = 7.0, 1.5 Hz, 1H), 8.83 (dd, J = 4.0, 1.5 Hz, 1H), 8.63 (s, 1H), 8.57 (br t, J = 5.8 Hz, 1H), 7.74 (dd, J = 8.2, 2.4 Hz, 1H), 7.52 (dd, J = 9.8, 2.4 Hz, 1H), 7.29 (dd, J = 6.9, 4.1 Hz, 1H), 6.90 (s, 1H), 4.83 (br d, J = 5.8 Hz, 2H), 3.07 (q, J = 7.3 Hz, 2H), 1.26 (t, J = 7.3 Hz, 3H) | 399.3 |
| 388 | 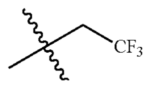 | S-(2,2,2-Trifluoro-ethyl)5-fluoro-2-((pyrazolo[1,5-a]-pyrimidine-3-carbox-amido)methyl)benzo-furan-7-carbothioate | $^1$H NMR (500 MHz, DMSO-$d_6$) δ 9.34 (br d, J = 6.7 Hz, 1H), 8.85 (br d, J = 3.1 Hz, 1H), 8.71-8.53 (m, 2H), 7.86 (dd, J = 8.1, 2.3 Hz, 1H), 7.66 (dd, J = 9.5, 2.1 Hz, 1H), 7.32 (dd, J =6.9, 4.1 Hz, 1H), 6.97 (s, 1H), 4.87 (br d, J = 5.8 Hz,2H), 4.17 (q, J = 10.4 Hz, 2H) | 453.3 |

Examples 389-390

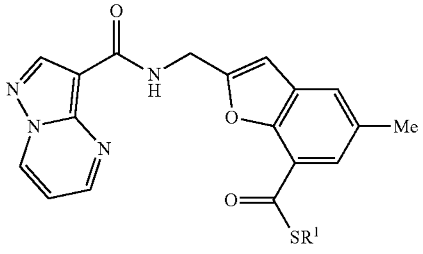

Examples 389 and 390 were prepared for corresponding acid Example 158 and the required thiol according to the procedure in Example 380.

| Ex. No. | $R^1$ | Name | $^1H$ NMR | LC/MS (M + H)+ |
|---|---|---|---|---|
| 389 | 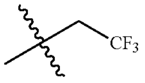 | S-(2,2,2-Trifluoroethyl) 5-methyl-2-((pyrazolo-[1,5-a]pyrimidine-3-carboxamido)methyl)-benzofuran-7-carbothioate | $^1H$ NMR (500 MHz, DMSO-$d_6$) δ 9.27 (d, J = 5.8 Hz, 1H), 8.81 (br d, J = 2.7 Hz, 1H), 8.62 (s, 1H), 8.57 (br t, J = 5.8 Hz, 1H), 7.75 (s, 1H), 7.66 (s, 1H), 7.27 (dd, J = 6.9, 4.1 Hz, 1H), 6.86 (s, 1H), 4.81 (br d, J = 5.8 Hz, 2H), 4.08 (q, J = 10.5 Hz, 2H), 2.43 (s, 3H) | 449.1 |
| 390 | 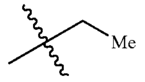 | S-Ethyl 5-methyl-2-((pyr-azolo[1,5-a]pyrimidine-3-carbox-amido)methyl)-benzofuran-7-carbothioate | $^1H$ NMR (500 MHz, DMSO-$d_6$) δ 9.30 (d, J = 5.8 Hz, 1H), 8.82 (br d, J = 2.7 Hz, 1H), 8.63 (s, 1H), 8.54 (br t, J = 6.0 Hz, 1H), 7.67 (s, 1H), 7.58 (s, 1H), 7.28 (dd, J = 7.0, 4.3 Hz, 1H), 6.81 (s, 1H), 4.80 (d, J = 5.8 Hz, 2H), 3.04 (q, J = 7.4 Hz, 2H), 2.42 (s, 3H), 1.26 (t, J = 7.3 Hz, 3H) | 395.1 |

Example 391

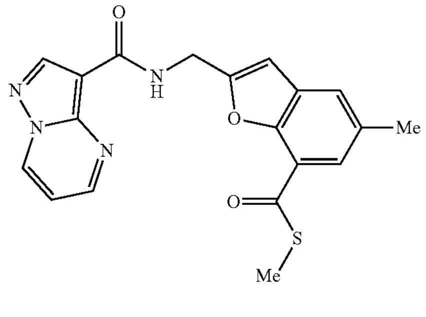 [SMILES: CSC(=O)c1cc(C)cc2cc(CNC(=O)c3cnn4cccnc34)oc12]

S-Methyl 5-methyl-2-((pyrazolo[1,5-a]pyrimidine-3-carboxamido)methyl)benzofuran-7-carbothioate

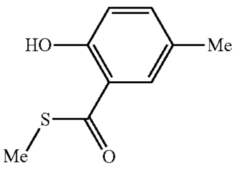 [SMILES: CSC(=O)c1cc(C)ccc1O]

A) S-Methyl 2-hydroxy-5-methylbenzothioate

To 2-hydroxy-5-methylbenzoic acid (1.5 g, 9.86 mmol) was added thionyl chloride (5.04 mL, 69.0 mmol) and a few drops of DMF. The reaction mixture was stirred at RT for 10 minutes during which time it turned into a clear solution. The reaction mixture was concentrated in vacuo to give white solid. To the solid was added dichloroethane (30 mL), sodium methanethiolate (0.760 g, 10.84 mmol) and TEA (4.12 mL, 29.6 mmol). The reaction mixture was stirred at room temperature for 16 hours. The reaction mixture was diluted with saturated sodium chloride and DCM. The organic layer was separated and washed with saturated sodium chloride, dried over sodium sulfate and was concentrated in vacuo. The residue was purified by a silica gel ISCO 40 g column eluting with 0-15% ethyl acetate in hexanes over a 15 minute gradient. The appropriate fractions were isolated and concentrated in vacuo to afford the product (1.46 g, 81% yield) as a solid. $^1H$ NMR (400 MHz, CHLOROFORM-d) δ 10.83 (s, 1H), 7.70-7.65 (m, 1H), 7.31-7.27 (m, 1H), 6.91 (d, J=8.5 Hz, 1H), 2.49 (s, 3H), 2.34 (s, 3H).

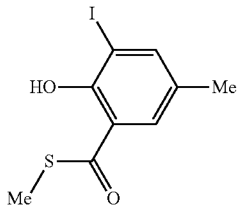 [SMILES: CSC(=O)c1cc(C)cc(I)c1O]

B) S-Methyl 2-hydroxy-3-iodo-5-methylbenzothioate

To a solution of S-methyl 2-hydroxy-5-methylbenzothioate (1.46 g, 8.01 mmol) in N,N-dimethylformamide (20 mL) was added sodium iodide (1.441 g, 9.61 mmol), followed by chloramine T trihydrate (2.482 g, 8.81 mmol) slowly in portions. The reaction was stirred at room temperature for 3 hours. The reaction mixture was quenched with ethyl acetate and 1N aqueous HCl solution. The organic layer was separated, washed with saturated aqueous sodium chloride solution followed by 10% $Na_2S_2O_3$ solution, dried with anhydrous sodium sulfate, filtered and concentrated in vacuo. The crude product mixture was purified by a silica gel ISCO 80 g column eluting with 0-20% ethyl acetate in hexanes over a 15 minute gradient. The appropriate fractions were isolated and concentrated in vacuo to afford the product (1.6 g, 70% yield) as a solid. 1H NMR (400 MHz, CHLOROFORM-d) δ 11.73 (s, 1H), 7.86-7.78 (m, 1H), 7.73-7.59 (m, 1H), 2.59-2.47 (m, 3H), 2.35-2.27 (m, 3H).

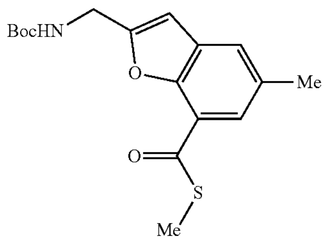 [SMILES: CSC(=O)c1cc(C)cc2cc(CNC(=O)OC(C)(C)C)oc12]

C) S-Methyl 2-(((tert-butoxycarbonyl)amino) methyl)-5-methylbenzofuran-7-carbothioate A 100 ml flask was charged with a mixture of S-methyl 2-hydroxy-3-iodo-5-methylbenzothioate (1.6 g, 3.63 mmol), tert-butyl prop-2-yn-1-ylcarbamate (0.649 g, 4.18 mmol), TEA (7.60 mL, 54.5 mmol), and copper(I) iodide (0.069 g, 0.363 mmol) in DMF (8 mL). The reaction solution was purged with a nitrogen stream for 5 mins, then bis(triphenylphosphine)palladium(II) chloride (0.128 g, 0.182 mmol) was added. The resulting mixture was heated at 85° C. for 2 hours. After cooling to room temperature, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 80 g column eluting with 0-30% ethyl acetate in hexanes over a 15 minute gradient. The appropriate fractions were isolated and concentrated in vacuo to afford the title compound (0.73 g, 60% yield) as a light brown solid. 1H NMR (400 MHz, Chloroform-d) δ 7.70 (d, J=1.7 Hz, 1H), 7.61-7.44 (m, 1H), 6.61 (s, 1H), 4.51 (br d, J=5.9 Hz, 2H), 2.54 (s, 3H), 2.52-2.44 (m, 3H), 1.51-1.43 (m, 9H); MS (ESI+) m/z=280 $(M-55+H)^+$.

D) S-Methyl 5-methyl-2-((pyrazolo[1,5-a]pyrimidine-3-carboxamido)methyl)benzofuran-7-carbothioate The above product was dissolved in DCM (10 mL) and TFA (1 mL). The reaction solution was stirred at RT for 2 hours. The reaction was concentrated in vacuo and used as is subsequently. To a suspension of pyrazolo[1,5-a]pyrimidine-3-carboxylic acid (20 mg, 0.123 mmol) and BOP (67.8 mg, 0.153 mmol) in DMF (2 mL) was added crude S-methyl 2-(aminomethyl)-5-methylbenzofuran-7-carbothioate, TFA salt (42.8 mg, 0.123 mmol) and DIPEA (0.086 mL, 0.490 mmol). The reaction mixture was stirred at room temperature for 16 hours. The reaction was quenched with water, and a precipitate resulted, which was filtered, then dissolved in 2 mL of DMF for purification. The crude material was purified via preparative HPLC (Method B) to afford the product (18.8 mg, 48.4% yield). $^1H$ NMR (500 MHz, DMSO-$d_6$) δ 9.27 (br d, J=5.8 Hz, 1H), 8.82 (br d, J=2.7 Hz, 1H), 8.62 (s, 1H), 8.55 (br t, J=5.8 Hz, 1H), 7.67 (s, 1H), 7.58 (s, 1H), 7.27 (dd, J=6.9, 4.1 Hz, 1H), 6.82 (s, 1H), 4.79 (br d, J=5.8 Hz, 2H), 2.45 (s, 3H), 2.43-2.40 (m, 3H); MS (ESI+) m/z=381.1 $(M+H)^+$.

Example 392

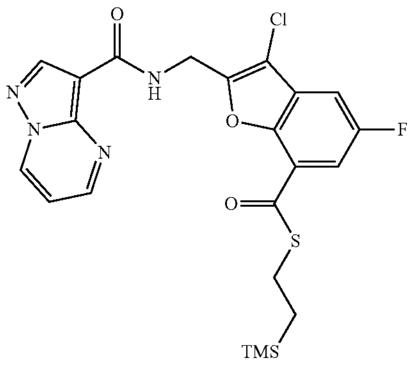 [SMILES: C[Si](C)(C)CCSC(=O)c1cc(F)cc2c(Cl)c(CNC(=O)c3cnn4cccnc34)oc12]

S-(2-(Trimethylsilyl)ethyl) 3-chloro-5-fluoro-2-((pyrazolo[1,5-a]pyrimidine-3-carboxamido)methyl) benzofuran-7-carbothioate A mixture of 3-chloro-5-fluoro-2-((pyrazolo[1,5-a]pyrimidine-3-carboxamido)methyl)benzofuran-7-carboxylic acid (45 mg, 0.116 mmol, Example 172) and BOP (71.7 mg, 0.162 mmol) in DMF (2 mL) was stirred at room temperature for 10 minutes. 2-(Trimethylsilyl)ethane-1-thiol (47 mg, 0.35 mmol) and DIPEA (0.04 mL, 0.23 mmol) were then added. The reaction mixture was stirred at room temperature for 2 hours. The reaction mixture was diluted with ethyl acetate and saturated aqueous $NaHCO_3$ solution. The organic layer was separated, washed with brine, dried over $MgSO_4$, and filtered. The filtrate was concentrated in vacuo. The residue was dissolved in DMF and purified by preparative HPLC (Method B). Fractions containing the desired product were combined and dried via centrifugal evaporation to give the title compound (40 mg, 70%). $^1H$ NMR (500 MHz, DMSO-$d_6$) δ 9.24 (br d, J=7.0 Hz, 1H), 8.78 (br d, J=3.9 Hz, 1H), 8.56 (s, 1H), 8.48 (br s, 1H), 7.66 (br d, J=7.5 Hz, 1H), 7.60-7.52 (m, 1H), 7.24 (dd, J=6.8, 4.3 Hz, 1H), 4.85 (d, J=5.8 Hz, 2H), 3.09-2.96 (m, 2H), 0.88-0.66 (m, 2H), 0.00 (s, 9H); MS (ESI+) m/z=505.3 $(M+H)^+$.

Example 393

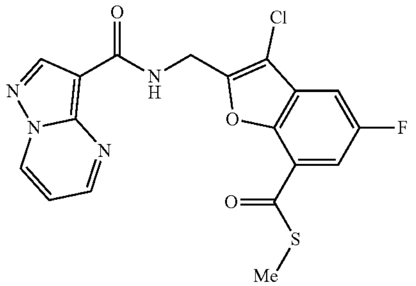 [SMILES: CSC(=O)c1cc(F)cc2c(Cl)c(CNC(=O)c3cnn4cccnc34)oc12]

S-Methyl 3-chloro-5-fluoro-2-((pyrazolo[1,5-a]pyrimidine-3-carboxamido)methyl)benzofuran-7-carbothioate To a solution of S-(2-(trimethylsilyl)ethyl) 3-chloro-5-fluoro-2-((pyrazolo[1,5-a]pyrimidine-3-carboxamido)

methyl)benzofuran-7-carbothioate (40 mg, 0.079 mmol, Example 392) in THF (2 mL) was added TBAF (1M solution in THF, 1.2 mL, 1.2 mmol) and methyl iodide (0.03 mL, 0.475 mmol). The reaction mixture was stirred at room temperature for 4 hours. The reaction mixture was concentrated in vacuo. The residue was diluted with water and extracted with ethyl acetate. The combined organics were dried with sodium sulfate and filtered. The filtrate was concentrated in vacuo. The residue was dissolved in DMF and purified by preparative HPLC (Method B). Fractions containing the desired product were combined and dried via centrifugal evaporation to give the title compound (8.4 mg, 25%). $^1$H NMR (500 MHz, DMSO-$d_6$) δ 9.25 (br d, J=6.4 Hz, 1H), 8.82 (br s, 1H), 8.60 (br s, 2H), 7.74 (br d, J=7.6 Hz, 1H), 7.65 (br d, J=7.3 Hz, 1H), 7.27 (br s, 1H), 4.85 (br d, J=4.3 Hz, 2H), 2.46-2.40 (m, 3H); MS (ESI+) m/z=419.1 $(M+H)^+$.

Examples 394-397

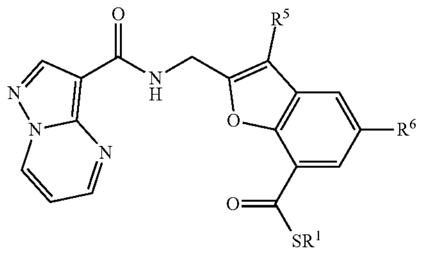

Examples 394 to 397 were prepared from corresponding intermediates (Examples 133, 138, 174, and 176) and the required thiol using the procedures outlined in Examples 392 and 393.

| Ex. No. | $R^1$, $R^5$, $R^6$ | Name | NMR | LC/MS $[M + H]^+$ |
|---|---|---|---|---|
| 394 | $R^1$ = $(CH_2)_2$-TMS<br>$R^5$ = H<br>$R^6$ = Cl | S-(2-(Trimethylsilyl) ethyl) 5-chloro-2-((pyrazolo[1,5-a]pyrimidine-3-carboxamido) methyl)benzofuran-7-carbothioate | $^1$H NMR (500 MHz, DMSO-d6) δ 9.20 (br dd, J = 5.2, 1.8 Hz, 1H), 8.76 (br d, J = 4.0 Hz, 1H), 8.55 (s, 1H), 8.47 (br s, 1H), 7.88 (s, 1H), 7.61 (s, 1H), 7.21 (dd, J = 6.5, 4.5 Hz, 1H), 6.84 (s, 1H), 4.77 (br d, J = 5.8 Hz, 2H), 3.09-3.01 (m, 2H), 0.83 (td, J = 8.6, 2.2 Hz, 2H), 0.00 (d, J = 1.8 Hz, 9H) | 487.4 |
| 395 | $R^1$ = Me<br>$R^5$ = H<br>$R^6$ = Cl | S-Methyl 5-chloro-2-((pyrazolo[1,5-a]pyrimidine-3-carboxamido) methyl)benzofuran-7-carbothioate | $^1$H NMR (500 MHz, DMSO-d6) δ 9.29 (br d, J = 7.0 Hz, 1H), 8.82 (br d, J = 2.7 Hz, 1H), 8.63 (s, 1H), 8.58 (s, 1H), 7.97 (d, J = 1.8 Hz, 1H), 7.69 (d, J = 1.8 Hz, 1H), 7.28 (dd, J = 6.7, 4.3 Hz, 1H), 6.89 (s, 1H), 4.82 (br d, J = 5.8 Hz, 2H), 2.49-2.44 (m, 3H) | 401.2 |
| 396 | $R^1$ = Me<br>$R^5$ = Cl<br>$R^6$ = Cl | S-Methyl 3,5-dichloro-2-((pyrazolo[1,5-a]pyrimidine-3-carboxamido) methyl)benzofuran-7-carbothioate | $^1$H NMR (400 MHz, CHLOROFORM-d) δ 8.81 (dd, J = 7.0, 1.8 Hz, 1H), 8.73 (s, 1H), 8.68 (dd, J = 4.1, 1.7 Hz, 1H), 8.45 (br s, 1H), 7.90 (d, J = 2.1 Hz, 1H), 7.74 (d, J = 2.1 Hz, 1H), 7.03 (dd, J = 7.0, 4.1 Hz, 1H), 5.00 (d, J = 5.9 Hz, 2H), 2.54 (s, 3H) | 435.2 |
| 397 | $R^1$ = Me<br>$R^5$ = Cl<br>$R^6$ = Me | S-Methyl 3-chloro-5-methyl-2-((pyrazolo[1,5-a]pyrimidine-3-carboxamido) methyl)benzofuran-7-carbothioate | $^1$H NMR (400 MHz, CHLOROFORM-d) δ 8.80 (dd, J = 7.0, 1.7 Hz, 1H), 8.73 (s, 1H), 8.67 (dd, J = 4.1, 1.7 Hz, 1H), 8.45 (br s, 1H), 7.76 (d, J = 1.2 Hz, 1H), 7.56 (d, J = 0.9 Hz, 1H), 7.02 (dd, J = 7.0, 4.2 Hz, 1H), 5.02-4.96 (m, 2H), 2.53 (s, 6H) | 415.1 |

Example 398-399

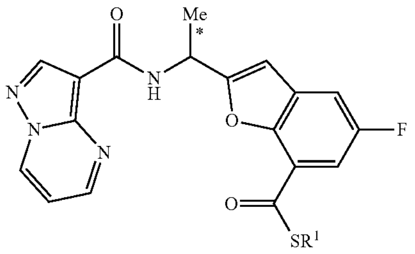

Examples 398 and 399 were prepared from corresponding intermediate Example 185 and the required thiol using the methods outlined in Examples 392 and 393.

| Ex. No. | $R^1$ | Name | NMR | LC/MS $[M + H]^+$ |
|---|---|---|---|---|
| 398 | 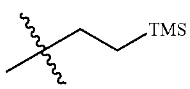 [SMILES: *CC[Si](C)(C)C] | S-(2-(Trimethylsilyl)ethyl) (S)-5-fluoro-2-(1-(pyrazolo[1,5-a]pyrimidine-3-carboxamido)ethyl)benzofuran-7-carbothioate | $^1$H NMR (500 MHZ, DMSO-$d_6$) δ 9.27 (br d, J = 6.4 Hz, 1H), 8.79 (br d, J = 3.1 Hz, 1H), 8.60 (s, 1H), 8.38 (br d, J = 8.2 Hz, 1H), 7.71 (dd, J = 8.2, 2.4 Hz, 1H), 7.48 (dd, J = 9.5, 2.1 Hz, 1H), 7.25 (dd, J = 6.7, 4.3 Hz, 1H), 6.92 (s, 1H), 5.47 (br t, J = 7.3 Hz, 1H), 3.08-2.97 (m, 2H), 1.64 (d, J = 7.0 Hz, 3H), 0.97-0.70 (m, 2H), 0.00 (s, 9H) | 485.4 |
| 399 | 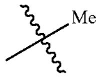 | S-Methyl (S)-5-fluoro-2-(1-(pyrazolo[1,5-a]pyrimidine-3-carboxamido)-ethyl)benzofuran-7-carbothioate | $^1$H NMR (500 MHz, DMSO-$d_6$) δ 9.17 (br d, J = 6.9 Hz, 1H), 8.78 (br d, J = 4.1 Hz, 1H), 8.59 (s, 1H), 8.43 (br d, J = 8.1 Hz, 1H), 7.79-7.62 (m, 1H), 7.50 (dd, J = 9.6, 2.3 Hz, 1H), 7.24 (dd, J = 6.9, 4.2 Hz, 1H), 6.93 (s, 1H), 5.49 (br t, J = 7.4 Hz, 1H), 2.44 (s, 3H), 1.66 (d, J = 7.0 Hz, 3H) | 399.2 |

Examples 400-402

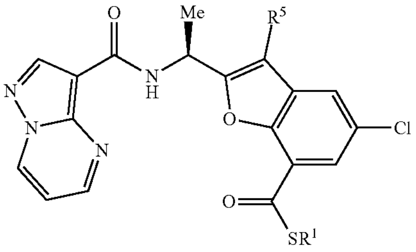

Examples 400 to 402 were prepared from corresponding intermediates (Examples 156 and 175) and required thiol using the methods outlined in Examples 392 and 393.

| Ex. No. | $R^1$, $R^5$ | Name | NMR | LC/MS $[M + H]^+$ |
|---|---|---|---|---|
| 400 | $R^1$ = $-(CH_2)_2$-TMS $R^5$ = H | S-(2-(Trimethylsilyl) ethyl) (S)-5-chloro-2-(1-(pyrazolo[1,5- | $^1$H NMR (500 MHz, DMSO-$d_6$) δ 9.27 (br d, J = 7.0 Hz, 1H), 8.79 (br d, J = 3.1 Hz, 1H), 8.60 (s, 1H), 8.39 (br d, J = 7.9 Hz, 1H), 7.95 (s, 1H), | 501.2 |

-continued

| Ex. No. | $R^1$, $R^5$ | Name | NMR | LC/MS [M + H]$^+$ |
|---|---|---|---|---|
| | | a]pyrimidine-3-carboxamido) ethyl)benzofuran-7-carbothioate | 7.65 (d, J = 1.5 Hz, 1H), 7.25 (dd, J = 6.9, 4.4 Hz, 1H), 6.92 (s, 1H), 5.47 (br t, J = 7.5 Hz, 1H), 3.08-2.98 (m, 2H), 1.64 (br d, J = 7.0 Hz, 3H), 0.91-0.64 (m, 2H), 0.00 (s, 9H) | |
| 401 | $R^1$ = —$CH_3$ $R^5$ = H | S-Methyl (S)-5-chloro-2-(1-(pyrazolo[1,5-a]pyrimidine-3-carboxamido) ethyl)benzofuran-7-carbothioate | $^1$H NMR (500 MHz, DMSO-$d_6$) δ 9.23 (br d, J = 6.9 Hz, 1H), 8.80 (br d, J = 4.0 Hz, 1H), 8.60 (s, 1H), 8.41 (br d, J = 8.2 Hz, 1H), 7.95 (s, 1H), 7.69 (s, 1H), 7.26 (dd, J = 6.8, 4.2 Hz, 1H), 6.94 (s, 1H), 5.51 (br t, J = 7.2 Hz, 1H), 2.48-2.43 (m, 3H), 1.68 (br d, J = 6.9 Hz, 3H) | 415.3 |
| 402 | $R^1$ = —$CH_3$ $R^5$ = Cl | S-Methyl (S)-3,5-dichloro-2-(1-(pyrazolo[1,5-a]pyrimidine-3-carboxamido) ethyl)benzofuran-7-carbothioate | $^1$H NMR (500 MHz, DMSO-$d_6$) δ 9.33-9.13 (m, 1H), 8.83 (br d, J = 4.0 Hz, 1H), 8.58 (s, 1H), 8.50 (br d, J = 7.7 Hz, 1H), 7.90 (s, 1H), 7.80 (s, 1H), 7.28 (dd, J = 6.8, 4.3 Hz, 1H), 5.60 (br t, J = 7.2 Hz, 1H), 3.43 (s, 3H), 1.70 (d, J = 7.0 Hz, 3H) | 449.1 |

Example 403

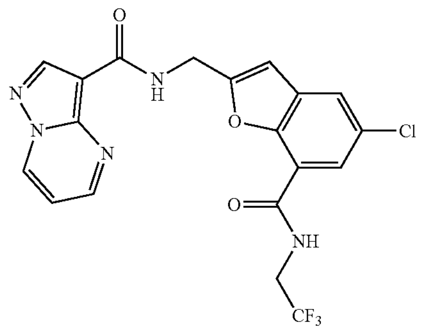 [SMILES: O=C(NCC(F)(F)F)c1cc(Cl)cc2cc(CNC(=O)c3cnn4cccnc34)oc12]

N-((5-Chloro-7-((2,2,2-trifluoroethyl)carbamoyl) benzofuran-2-yl)methyl)pyrazolo[1,5-a]pyrimidine-3-carboxamide To a solution of 5-chloro-2-((pyrazolo[1,5-a]pyrimidine-3-carboxamido)methyl)benzofuran-7-carboxylic acid (15 mg, 0.040 mmol) (Example 138) and BOP (26.8 mg, 0.061 mmol) in DMF (1 mL) were added 2,2,2-trifluoroethan-1-amine (20.04 mg, 0.202 mmol) and DIPEA (0.028 mL, 0.162 mmol). The reaction mixture was stirred at rt for 2 h. LC-MS showed new peak at tr=0.84 min, [M+H]+=452.2 as the desired product peak. The reaction mixture was concentrated in vacuo and the residue was dissolved in DMF, filtered and purified by preparative HPLC (Method B). Fractions containing the desired product were combined and dried via centrifugal evaporation to give the title compound (10.8 mg, 46%). $^1$H NMR (500 MHz, DMSO-$d_6$) δ 9.31 (br d, J=7.0 Hz, 1H), 9.00 (br t, J=6.1 Hz, 1H), 8.84 (br d, J=2.7 Hz, 1H), 8.64 (s, 1H), 8.60 (br t, J=5.8 Hz, 1H), 7.89 (d, J=1.5 Hz, 1H), 7.63 (d, J=1.8 Hz, 1H), 7.31 (dd, J=6.7, 4.3 Hz, 1H), 6.88 (s, 1H), 4.83 (br d, J=6.1 Hz, 2H), 4.28-4.11 (m, 2H); MS (ESI+) m/z=452.2 (M+H)$^+$.

Example 404

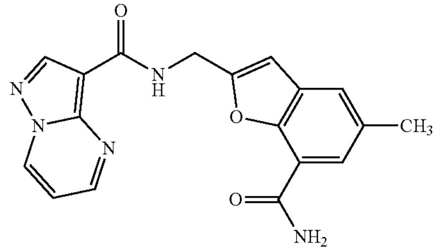 [SMILES: Cc1cc(C(N)=O)c2oc(CNC(=O)c3cnn4cccnc34)cc2c1]

N-((7-Carbamoyl-5-methylbenzofuran-2-yl)methyl) pyrazolo[1,5-a]pyrimidine-3-carboxamide To a solution of 5-methyl-2-((pyrazolo[1,5-a]pyrimidine-3-carboxamido)methyl)benzofuran-7-carboxylic acid (30 mg, 0.086 mmol, Example 158) in DMF (1 mL) was added HATU (42.3 mg, 0.111 mmol). The reaction mixture was stirred at room temperature for 15 min, followed by the addition of ammonium hydroxide (0.238 mL, 1.71 mmol) and DIPEA (0.045 mL, 0.257 mmol). The reaction mixture was stirred at room temperature for 2 hours. The reaction was quenched with water, and a precipitate formed, which was filtered. The crude material was purified via preparative HPLC (Method B) to afford the product (12 mg, 40% yield). $^1$H NMR (500 MHz, DMSO-$d_6$) δ 9.22 (d, J=6.7 Hz, 1H), 8.80 (br d, J=3.1 Hz, 1H), 8.61-8.57 (m, 2H), 7.71 (br s, 1H), 7.69-7.64 (m, 1H), 7.53 (br d, J=5.8 Hz, 2H), 7.26 (dd, J=7.0, 4.3 Hz, 1H), 6.78 (s, 1H), 4.77 (br d, J=5.8 Hz, 2H), 2.38 (s, 3H); MS (ESI+) m/z=350.1 (M+H)$^+$.

Examples 405-406

Examples 405 and 406 were prepared in the same general way as Example 403 starting from Example 138 and the corresponding amine.

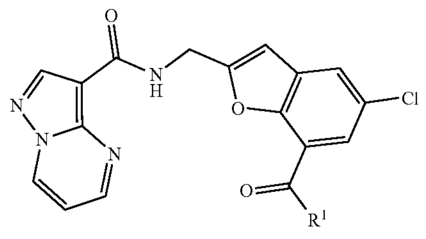

carboxylic acid (25 mg, 0.065 mmol, Example 176), hydroxylamine hydrochloride (6.77 mg, 0.097 mmol) and DIPEA (45.4 μl, 0.260 mmol) in DMF (325 μl). To the solution was added BOP (43.1 mg, 0.097 mmol) and the reaction stirred at room temperature for 1 hour. The solution was quenched with water and a precipitate formed. This precipitate was isolated via filtration and dissolved in 2 mL of DMF. The crude material was purified via preparative HPLC (Method B) to yield the title compound (8.8 mg, 33.9% yield). $^1$H NMR (500 MHz, DMSO-$d_6$) δ 9.24 (d, J=5.9 Hz, 1H), 8.84-8.80 (m, 1H), 8.60-8.58 (m, 1H), 8.47 (br t, J=5.4 Hz, 1H), 7.49 (br s, 2H), 7.29-7.24 (m, 1H), 4.84 (d, J=5.8 Hz, 2H), 2.46-2.44 (m, 3H); MS (ESI+) m/z=400.1 $(M+H)^+$.

| Ex. No. | $R^1$ | Name | NMR | LC/MS $[M + H]^+$ |
|---|---|---|---|---|
| 405 | 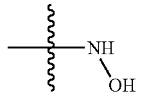 [SMILES: *NO] | N-((5-Chloro-7-(hydroxycarbamoyl)-benzofuran-2-yl)-methyl)pyrazolo-[1,5-a]pyrimidine-3-carboxamide | $^1$H NMR (500 MHz, DMSO-$d_6$) δ 9.24 (br t, J = 5.4 Hz, 1H), 8.88 - 8.79 (m, 1H), 8.59 (s, 1H), 8.49 (br s, 1H), 7.78 (s, 1H), 7.50 (br s, 1H), 7.26 (br dd, J = 6.9, 4.2 Hz, 1H), 6.83 (s, 1H), 4.79 (br d, J = 5.6 Hz, 2H) | 386.1 |
| 406 | 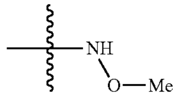 | N-((5-Chloro-7-(methoxycarbamoyl)-benzofuran-2-yl)-methyl)pyrazolo-[1,5-a]pyrimidine-3-carboxamide | $^1$H NMR (500 MHz, DMSO-$d_6$) δ 9.24 (br d, J = 6.4 Hz, 1H), 8.81 (br d, J = 3.1 Hz, 1H), 8.70 - 8.55 (m, 2H), 7.81 (s, 1H), 7.51 (s, 1H), 7.26 (dd, J = 6.9, 4.1 Hz, 1H), 6.83 (s, 1H), 4.78 (br d, J = 5.8 Hz, 2H), 3.64 (br s, 3H) | 400.2 |

Example 407

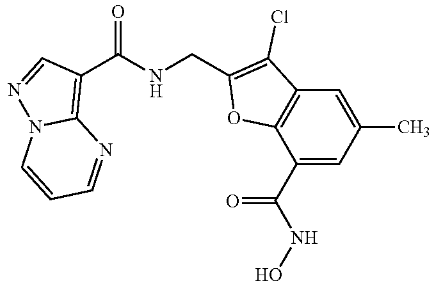 [SMILES: Cc1cc(C(=O)NO)c2oc(CNC(=O)c3cnn4cccnc34)c(Cl)c2c1]

N-((3-chloro-7-(hydroxycarbamoyl)-5-methylbenzofuran-2-yl)methyl)pyrazolo[1,5-a]pyrimidine-3-carboxamide A flask was charged with 3-chloro-5-methyl-2-((pyrazolo[1,5-a]pyrimidine-3-carboxamido)methyl)benzofuran-7-

Example 408

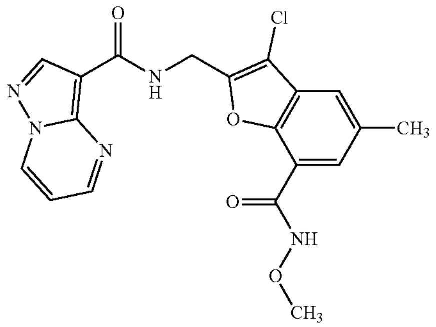 [SMILES: CONC(=O)c1cc(C)cc2c(Cl)c(CNC(=O)c3cnn4cccnc34)oc12]

N-((3-chloro-7-(methoxycarbamoyl)-5-methylbenzofuran-2-yl)methyl)pyrazolo[1,5-a]pyrimidine-3-carboxamide A flask was charged with 3-chloro-5-methyl-2-((pyrazolo[1,5-a]pyrimidine-3-carboxamido)methyl)benzofuran-7-carboxylic acid (25 mg, 0.065 mmol, Example 176), O-methylhydroxylamine hydrochloride (8.14 mg, 0.097 mmol) and DIPEA (45.4 μl, 0.260 mmol) in DMF (325 μl). To the solution was added BOP (43.1 mg, 0.097 mmol) and the reaction stirred at room temperature for 1 hour. The solution was quenched with water and a precipitate formed. This precipitate was isolated via filtration and dissolved in 2 mL of DMF. The crude material was purified via preparative HPLC (Method B) to yield the title compound (20.3 mg, 72.4% yield). $^{1}$H NMR (500 MHz, DMSO-$d_6$) δ 9.27-9.23 (m, 1H), 8.84-8.79 (m, 1H), 8.62-8.56 (m, 1H), 8.51-8.45 (m, 1H), 7.56-7.47 (m, 2H), 7.30-7.23 (m, 1H), 4.86 (d, J=5.9 Hz, 2H), 3.72 (s, 3H), 2.48-2.41 (m, 3H); MS (ESI+) m/z=414.0 $(M+H)^+$.

Example 409

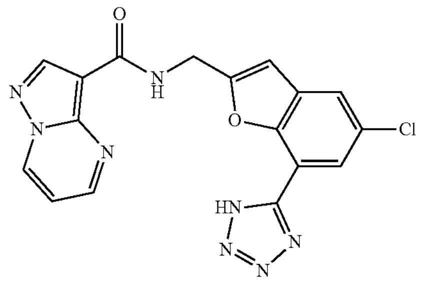 [SMILES: O=C(NCc1cc2cc(Cl)cc(-c3nnn[nH]3)c2o1)c1cnn2cccnc12]

N-((5-Chloro-7-(1H-tetrazol-5-yl)benzofuran-2-yl)methyl)pyrazolo[1,5-a]pyrimidine-3-carboxamide

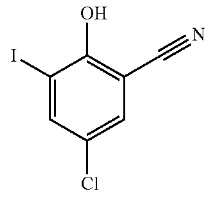 [SMILES: N#Cc1cc(Cl)cc(I)c1O]

A) 5-Chloro-2-hydroxy-3-iodobenzonitrile

To a solution of 5-chloro-2-hydroxybenzonitrile (2.0 g, 13.02 mmol) in DMF (30 mL) were added sodium iodide (2.440 g, 16.28 mmol) and chloramine T trihydrate (4.40 g, 15.63 mmol) slowly. The reaction mixture was stirred at rt over night. The reaction mixture was diluted with ethyl acetate and brine solution. The organic layer was separated, washed with 1 N HCl solution, and $Na_2S_2O_3$ solution successively. The organic layer was dried over $MgSO_4$, filtered, and the filtrate was concentrated in vacuo. The residue was dissolved in DCM and purified by ISCO (80 g column, 0-30% ethyl acetate in DCM) to give 5-chloro-2-hydroxy-3-iodobenzonitrile as a light yellow solid (2.2 g, 60.4% yield). $^{1}$H NMR (400 MHz, Chloroform-d) δ 7.89 (d, J=2.4 Hz, 1H), 7.53 (d, J=2.4 Hz, 1H), 6.13 (br s, 1H); MS (ESI+) m/z=280.0 $(M+H)^+$.

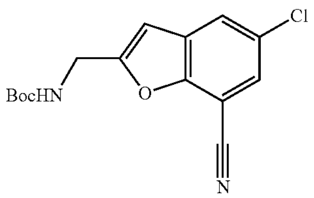 [SMILES: CC(C)(C)OC(=O)NCc1cc2cc(Cl)cc(C#N)c2o1]

B) tert-Butyl ((5-chloro-7-cyanobenzofuran-2-yl)methyl)carbamate

To a reaction mixture of 5-chloro-2-hydroxy-3-iodobenzonitrile (2.2 g, 7.87 mmol) and tert-butyl prop-2-yn-1-ylcarbamate (1.344 g, 8.66 mmol) in DMF (20 mL) were added TEA (8.78 mL, 63.0 mmol) and copper(I) iodide (0.150 g, 0.787 mmol). The reaction mixture was purged with nitrogen stream for 5 min, then bis(triphenylphosphine) palladium(II) chloride (0.553 g, 0.787 mmol) was added. The resulting mixture was heated at 80° C. under nitrogen stream for 2 hours. The reaction mixture was diluted with brine and ethyl acetate. The organic layer was separated, washed with saturated $NH_4Cl$ solution and brine successively, dried over $MgSO_4$, and filtered. The filtrate was concentrated in vacuo to give a light yellow oil. The crude residue was dissolved in DCM and purified by silica gel column chromatography (80 g column, 0-40% ethyl acetate in hexanes) to give tert-butyl ((5-chloro-7-cyanobenzofuran-2-yl)methyl)carbamate (2.1 g, 87% yield) as a light yellow solid. $^{1}$H NMR (400 MHz, CHLOROFORM-d) δ 7.75 (d, J=2.0 Hz, 1H), 7.54 (d, J=2.0 Hz, 1H), 6.68 (s, 1H), 5.21-5.01 (m, 1H), 4.51 (br d, J=6.0 Hz, 2H), 1.49 (s, 9H).

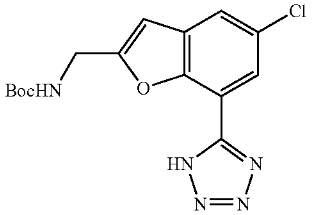 [SMILES: CC(C)(C)OC(=O)NCc1cc2cc(Cl)cc(-c3nnn[nH]3)c2o1]

C) tert-Butyl ((5-chloro-7-(1H-tetrazol-5-yl)benzofuran-2-yl)methyl)carbamate

A reaction mixture of tert-butyl ((5-chloro-7-cyanobenzofuran-2-yl)methyl)carbamate (1.1 g, 3.59 mmol), sodium azide (0.280 g, 4.30 mmol) and ceric ammonium nitrate (0.197 g, 0.359 mmol) in N,N-dimethylformamide (12 mL) was heated at 100° C. under nitrogen atmosphere over night. The reaction mixture was cooled, and diluted with brine and ethyl acetate. The organic layer was separated, washed with saturated $NH_4Cl$ solution and brine successively, dried over $MgSO_4$, and filtered. The filtrate was concentrated in vacuo. The crude residue was dissolved in DCM and purified by silica gel column chromatography (40 g column, 0-10% MeOH in DCM) to give tert-butyl ((5-chloro-7-(1H-tetrazol-5-yl)benzofuran-2-yl)methyl)carbamate (0.8 g, 64% yield) as light yellow oil. $^{1}$H NMR (400 MHz, Chloroform-d) δ 8.26 (d, J=2.0 Hz, 1H), 8.08 (s, 1H), 7.69 (d, J=2.0 Hz, 1H), 6.67 (s, 1H), 5.89-5.73 (m, 1H), 4.52 (d, J=6.2 Hz, 2H), 1.49 (s, 9H); MS (ESI+) m/z=350.2 $(M+H)^+$.

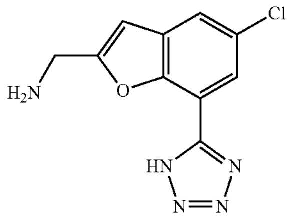 [SMILES: NCc1cc2cc(Cl)cc(-c3nnn[nH]3)c2o1]

D) (5-Chloro-7-(1H-tetrazol-5-yl)benzofuran-2-yl)methanamine

To a solution of tert-butyl ((5-chloro-7-(1H-tetrazol-5-yl)benzofuran-2-yl)methyl)carbamate (0.8 g, 2.287 mmol) in DCM (8 mL) was added TFA (1.41 mL, 18.30 mmol). The reaction mixture was stirred at room temperature for 3 hours. The reaction mixture was concentrated in vacuo. To the residue was added DCM (precipitate forms) and the resulting mixture was filtered to give (5-chloro-7-(1H-tetrazol-5-yl)benzofuran-2-yl)methanamine, TFA salt (0.5 g, 60%) as a white solid. $^1$H NMR (400 MHz, Methanol-$d_4$) δ 8.09 (d, J=2.0 Hz, 1H), 7.89 (d, J=2.1 Hz, 1H), 7.12 (s, 1H), 4.46 (s, 2H); MS (ESI+) m/z=233.1 (M−17+H)$^+$.

E) N-((5-chloro-7-(1H-tetrazol-5-yl)benzofuran-2-yl)methyl)pyrazolo[1,5-a]pyrimidine-3-carboxamide To a suspension of pyrazolo[1,5-a]pyrimidine-3-carboxylic acid (30 mg, 0.184 mmol) in DMF (1 mL) was added BOP (114 mg, 0.257 mmol). The reaction mixture was stirred at room temperature for 20 min, then (5-chloro-7-(1H-tetrazol-5-yl)benzofuran-2-yl)methanamine, TFA salt (66.9 mg, 0.184 mmol) and DIPEA (0.128 mL, 0.736 mmol) were added. The resulting mixture was stirred at room temperature for 1 hour. The reaction mixture was concentrated in vacuo. The residue was dissolved in DMF, filtered, and purified via HPLC (method B) to give N-((5-chloro-7-(1H-tetrazol-5-yl)benzofuran-2-yl)methyl)pyrazolo[1,5-a]pyrimidine-3-carboxamide (35.5 mg, 49% yield). $^1$H NMR (500 MHz, DMSO-$d_6$) δ 9.29 (d, J=7.0 Hz, 1H), 8.85-8.75 (m, 1H), 8.62 (s, 1H), 8.54 (br t, J=5.6 Hz, 1H), 7.96-7.81 (m, 2H), 7.28 (dd, J=6.9, 4.2 Hz, 1H), 6.92 (s, 1H), 4.86 (br d, J=5.9 Hz, 2H); MS (ESI+) m/z=395.2 (M+H)$^+$.

Example 410

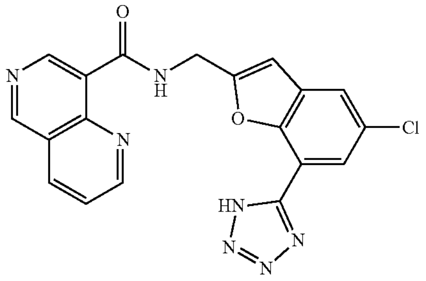 [SMILES: O=C(NCc1cc2cc(Cl)cc(-c3nnn[nH]3)c2o1)c1cncc2cccnc12]

N-((5-Chloro-7-(1H-tetrazol-5-yl)benzofuran-2-yl)methyl)-1,6-naphthyridine-8-carboxamide To a suspension of 1,6-naphthyridine-8-carboxylic acid HCl salt (15.06 mg, 0.071 mmol) in DMF (1 mL) was added BOP (34.1 mg, 0.077 mmol). The reaction mixture was stirred at room temperature for 20 min, then (5-chloro-7-(1H-tetrazol-5-yl)benzofuran-2-yl)methanamine TFA salt (58.6 mg, 0.161 mmol) (Step D of Example 409) and DIPEA (0.113 mL, 0.645 mmol) were added. The resulting mixture was stirred at rt for 1 hour. The reaction mixture was concentrated in vacuo. The residue was dissolved in DMF, filtered, and purified via HPLC (Method B) to give N-((5-Chloro-7-(1H-tetrazol-5-yl)benzofuran-2-yl)methyl)-1,6-naphthyridine-8-carboxamid (1.2 mg, 5.4% yield). $^1$H NMR (500 MHz, DMSO-$d_6$) δ 10.97 (br s, 1H), 9.58 (s, 1H), 9.34 (s, 1H), 9.30 (br d, J=2.7 Hz, 1H), 8.76 (br d, J=7.9 Hz, 1H), 7.89-7.82 (m, 2H), 7.75 (s, 1H), 6.94 (s, 1H), 4.91 (br d, J=5.5 Hz, 2H); MS (ESI+) m/z=405.9 (M+H)$^+$.

Example 411

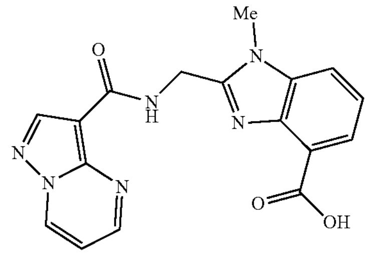 [SMILES: Cn1c(CNC(=O)c2cnn3cccnc23)nc2c(C(=O)O)cccc21]

1-methyl-2-((pyrazolo[1,5-a]pyrimidine-3-carboxamido)methyl)-1H-benzo[d]imidazole-4-carboxylic acid

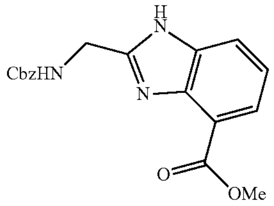 [SMILES: COC(=O)c1cccc2[nH]c(CNC(=O)OCc3ccccc3)nc12]

A) Methyl 2-((((benzyloxy)carbonyl)amino)methyl)-1H-benzo[d]imidazole-7-carboxylate Methyl 2,3-diaminobenzoate (1.15 g, 6.92 mmol) was taken up in acetonitrile (27.7 ml). ((benzyloxy)carbonyl)glycine (1.737 g, 8.30 mmol) was added followed by DIPEA (1.813 ml, 10.38 mmol) and BOP-$C_1$ (2.290 g, 9.00 mmol). Reaction stirred at room temperature overnight. The reaction was then diluted with sat. aq. bicarb and extracted with EtOAc. Organics were dried over sodium sulfate, filtered, and concentrated in vacuo. The crude mixture was purified via silica gel column chromatography to give an amide intermediate (ca. 1.1 g). This intermediate was taken up in 30 mL of acetic acid and heated for 1 hour at 65° C. The reaction was then concentrated in vacuo, diluted with water, and extracted with EtOAc. The organic extracts were combined, dried over sodium sulfate, filtered, and concentrated in vacuo to give the title compound (0.96 g, 2.83 mmol, 40.9% yield). $^1$H NMR (400 MHz, DMSO-$d_6$) δ 12.21 (br s, 1H), 7.88 (br d, J=7.9 Hz, 1H), 7.80 (d, J=6.9 Hz, 1H), 7.40-7.31 (m, 5H), 7.30-7.26 (m, 1H), 5.07 (s, 2H), 4.52 (d, J=5.9 Hz, 2H), 3.95 (s, 3H); MS (ESI+) m/z=340.5 (M+H)$^+$.

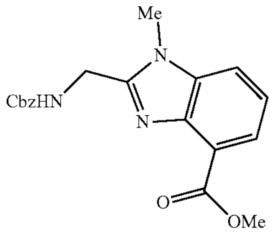 [SMILES: COC(=O)c1cccc2c1nc(CNC(=O)OCc1ccccc1)n2C]

B) Methyl 2-((((benzyloxy)carbonyl)amino)methyl)-1-methyl-1H-benzo[d]imidazole-4-carboxylate Methyl 2-((((benzyloxy)carbonyl)amino)methyl)-1H-benzo[d]imidazole-7-carboxylate (800 mg, 2.357 mmol) was taken up in DMF (9430 μl) and cesium carbonate (1152 mg, 3.54 mmol) was added followed by methyl iodide (177 μl, 2.83 mmol). The reaction was stirred at room temperature for 4 hours. The reaction was diluted with water, extracted with EtOAc, and the combined organics were back-extracted with ½ saturated brine to remove DMF. Organics were then dried over sodium sulfate, filtered, and concentrated in vacuo. The crude residue was purified via silica gel column chromatography to give the title compound (498 mg, 1.409 mmol, 59.8% yield). $^1$H NMR (500 MHz, DMSO-$d_6$) δ 7.82 (d, J=7.9 Hz, 1H), 7.76 (dd, J=7.6, 1.0 Hz, 1H), 7.39-7.28 (m, 6H), 5.08 (s, 2H), 4.57 (d, J=5.9 Hz, 2H), 3.88 (s, 3H), 3.83 (s, 3H); MS (ESI+) m/z=354.5 $(M+H)^+$.

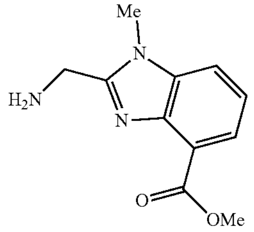 [SMILES: COC(=O)c1cccc2c1nc(CN)n2C]

C) Methyl 2-(aminomethyl)-1-methyl-1H-benzo[d]imidazole-4-carboxylate

Methyl 2-((((benzyloxy)carbonyl)amino)methyl)-1-methyl-1H-benzo[d]imidazole-4-carboxylate (498 mg, 1.409 mmol) was taken up in ethanol (14 mL) and placed under a nitrogen atmosphere. Palladium on carbon (10% by wt) (150 mg, 0.141 mmol) was added and the reaction was then vacated and flushed three times with hydrogen gas (balloon). The reaction stirred overnight at room temperature under a hydrogen balloon. The reaction was filtered over celite and the filtrate was concentrated in vacuo to the title compound (276 mg, 0.944 mmol, 67.0% yield). $^1$H NMR (400 MHz, DMSO-$d_6$) δ 7.10 (br d, J=7.3 Hz, 1H), 6.95 (br d, J=7.8 Hz, 1H), 6.62-6.52 (m, 1H), 4.04 (s, 3H), 3.17 (s, 3H), 3.07 (s, 2H); MS (ESI+) m/z=220.2 $(M+H)^+$.

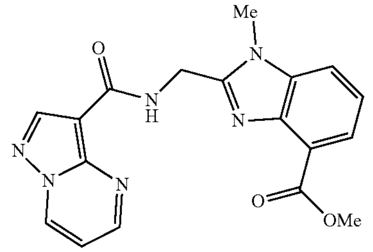 [SMILES: COC(=O)c1cccc2c1nc(CNC(=O)c1cnn3cccnc13)n2C]

D) Methyl 1-methyl-2-((pyrazolo[1,5-a]pyrimidine-3-carboxamido)methyl)-1H-benzo[d]imidazole-4-carboxylate Pyrazolo[1,5-a]pyrimidine-3-carboxylic acid (15 mg, 0.092 mmol) was dissolved in DMF (368 μl) and DIPEA (64.2 μl, 0.368 mmol) and methyl 2-(aminomethyl)-1-methyl-1H-benzo[d]imidazole-4-carboxylate (20.16 mg, 0.092 mmol) were added. BOP (61.0 mg, 0.138 mmol) was added and the reaction was stirred at room temperature for 2 hours. The reaction was diluted with DMF, filtered, and purified directly via preparative HPLC (method B) to give the title compound (13.4 mg, 0.035 mmol, 38.6% yield) as a white solid. $^1$H NMR (500 MHz, DMSO-$d_6$) δ 9.24 (dd, J=7.0, 1.2 Hz, 1H), 8.83-8.79 (m, 1H), 8.71 (br t, J=5.2 Hz, 1H), 8.61 (s, 1H), 7.81 (d, J=8.2 Hz, 1H), 7.76 (d, J=7.3 Hz, 1H), 7.34 (t, J=7.9 Hz, 1H), 7.26 (dd, J=7.0, 4.3 Hz, 1H), 4.92 (d, J=5.5 Hz, 2H), 3.87 (s, 3H), 3.64 (br s, 3H); MS (ESI+) m/z=365.1 $(M+H)^+$.

E) 1-Methyl-2-((pyrazolo[1,5-a]pyrimidine-3-carboxamido)methyl)-1H-benzo[d]imidazole-4-carboxylic acid Methyl 1-methyl-2-((pyrazolo[1,5-a]pyrimidine-3-carboxamido)methyl)-1H-benzo[d]imidazole-4-carboxylate (35 mg, 0.096 mmol) was taken up in THE (384 μl), water (384 μl), and MeOH (192 μl). LiOH (23.00 mg, 0.961 mmol) was added and reaction stirred at room temperature for 2 hours. The reaction was concentrated in vacuo, taken up in DMF, filtered, and purified directly by preparative HPLC (method B) to the title compound (5.7 mg, 0.016 mmol, 16.80% yield) as a white solid. $^1$H NMR (500 MHz, DMSO-$d_6$) δ 9.31 (br d, J=6.7 Hz, 1H), 8.89 (br s, 1H), 8.84 (br s, 1H), 8.64 (s, 1H), 7.88 (br d, J=7.6 Hz, 1H), 7.81 (br d, J=7.3 Hz, 1H), 7.41 (br t, J=7.8 Hz, 1H), 7.30 (br dd, J=6.7, 4.3 Hz, 1H), 4.97 (br d, J=4.9 Hz, 2H), 3.92 (s, 3H); MS (ESI+) m/z=351.3 $(M+H)^+$.

Example 412

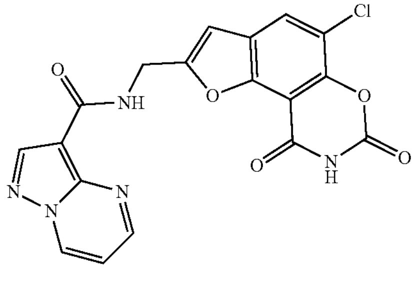 [SMILES: O=C(NCc1cc2cc(Cl)c3oc(=O)[nH]c(=O)c3c2o1)c1cnn2cccnc12]

N-((5-chloro-7,9-dioxo-8,9-dihydro-7H-benzofuro[7,6-e][1,3]oxazin-2-yl)methyl)pyrazolo[1,5-a]pyrimidine-3-carboxamide

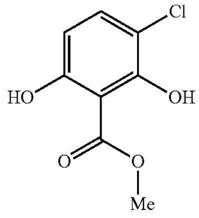 [SMILES: COC(=O)c1c(O)ccc(Cl)c1O]

A) Methyl 3-chloro-2,6-dihydroxybenzoate

To a flask charged with methyl 2,6-dihydroxybenzoate (1.5 g, 8.92 mmol) was added sulfuryl chloride, 1 M in DCM (13.38 mL, 13.38 mmol) under N2. The mixture was cooled to 0° C. and $Et_2O$ (1.391 mL, 13.38 mmol) was added. The reaction mixture was warmed to room temperature and stirred for 70 min. An additional portion of sulfuryl chloride, 1 M in DCM (4.5 mL, 4.5 mmol) and $Et_2O$ (0.47 mL, 4.5 mmol) was added and the reaction mixture was stirred for 30 min. An additional portion of sulfuryl chloride, 1 M in DCM (2.3 mL, 2.3 mmol) and $Et_2O$ (0.24 mL, 2.3 mmol) was added and the reaction mixture was stirred for 15 min. The reaction mixture was concentrated in vacuo to give the title compound (1.79 g, 99%). $^1H$ NMR (400 MHz, Chloroform-d) δ 10.31 (br s, 1H), 9.51 (br s, 1H), 7.44 (d, J=9.0 Hz, 1H), 6.51 (d, J=8.9 Hz, 1H), 4.14 (s, 3H); MS (ESI+) m/z=203.0 $(M+H)^+$.

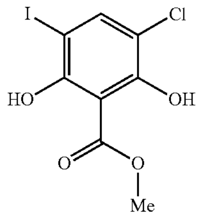 [SMILES: COC(=O)c1c(O)c(Cl)cc(I)c1O]

B) Methyl 3-chloro-2,6-dihydroxy-5-iodobenzoate

To a suspension of methyl 3-chloro-2,6-dihydroxybenzoate (1.79 g, 8.81 mmol) in AcOH (5.04 mL) was added NIS (2.97 g, 13.22 mmol). The headspace was flushed with N2 and the vessel was sealed and heated to 65° C. for 30 min. The reaction mixture was cooled to room temperature, quenched with a saturated aqueous solutions of $NaHCO_3$ and $Na_2S_2O_3$, and extracted with EtOAc. The organic layers were combined, washed with brine, dried over $MgSO_4$, filtered, and concentrated in vacuo. The residue was dissolved in DCM and purified by silica gel flash chromatography to give the title compound (1.63 g, 56%). $^1H$ NMR (400 MHz, Chloroform-d) δ 10.47 (s, 1H), 10.20 (br s, 1H), 7.91 (s, 1H), 4.17 (s, 3H); MS (ESI+) m/z=not observed; product does not ionize well on MS.

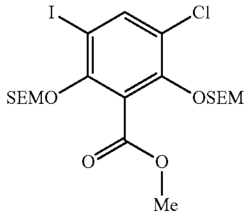

C) Methyl 3-chloro-5-iodo-2,6-bis((2-(trimethylsilyl)ethoxy) methoxy)benzoate

To a solution of methyl 3-chloro-2,6-dihydroxy-5-iodobenzoate (1.74 g, 5.29 mmol) in DCM (26.4 mL) was added Hunig's Base (5.54 mL, 31.7 mmol) at 0° C. SEMCl (2.34 mL, 13.22 mmol) was added and the reaction vessel was flushed with N2, sealed, and warmed to room temperature and stirred for 5 hours. An additional portion of SEMCl (0.47 mL, 2.65 mmoL) was added and the reaction mixture was stirred for 1.5 hours. The reaction mixture was quenched with water and extracted with EtOAc. The organic layers were combined, washed with brine, dried over $MgSO_4$, filtered, and concentrated in vacuo. The residue was dissolved in DCM and purified by flash chromatography to give the title compound (3.02 g, 97%). $^1H$ NMR (400 MHz, Chloroform-d) δ 7.88 (s, 1H), 5.19 (s, 2H), 5.15 (s, 2H), 3.93 (s, 3H), 3.91-3.81 (m, 4H), 1.05-0.99 (m, 4H), 0.06 (s, 9H), 0.05 (s, 9H). MS (ESI+) m/z=not observed; product does not ionize well on MS.

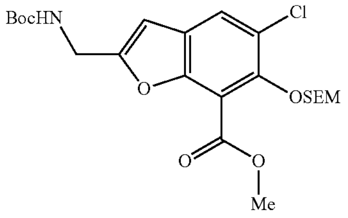

D) Methyl 2-(((tert-butoxycarbonyl)amino)methyl)-5-chloro-6-((2-(trimethylsilyl)ethoxy)methoxy)benzofuran-7-carboxylate To a solution of tert-butyl prop-2-yn-1-ylcarbamate (916 mg, 5.90 mmol) and methyl 3-chloro-5-iodo-2,6-bis((2-(trimethylsilyl)ethoxy)methoxy)benzoate (3.02 g, 5.13 mmol) in DMF (477 µl) was added $Et_3N$ (638 µl, 4.57 mmol). The mixture was sparged with N2 for 13 min and then copper(I) iodide (98 mg, 0.513 mmol) and bis(triphenylphosphine)palladium(II) chloride (180 mg, 0.257 mmol) was added. The reaction mixture was sparged with N2 for an additional 3 min, sealed, and heated to 80° C. for 2.5 h. The reaction mixture was cooled to room temperature and concentrated in vacuo. The residue was dissolved in DCM and purified by flash chromatography to give the title compound (1.35 g, 54%). $^1H$ NMR (400 MHz, Chloroform-d) δ 7.66 (s, 1H), 6.57 (s, 1H), 5.22 (s, 2H), 5.00 (br d, J=2.9 Hz, 1H), 4.45 (br d, J=5.9 Hz, 2H), 4.03 (s, 3H), 3.94-3.87 (m, 2H), 1.48 (s, 9H), 1.02 (d, J=17.2 Hz, 2H), 0.06 (s, 9H). MS (ESI+) m/z=524.0 $(M+K)^+$.

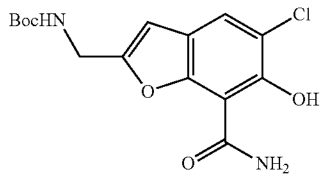 [SMILES: CC(C)(C)OC(=O)NCc1cc2cc(Cl)c(O)c(C(N)=O)c2o1]

E) Tert-butyl ((7-carbamoyl-5-chloro-6-hydroxybenzofuran-2-yl)methyl)carbamate

Methyl 2-(((tert-butoxycarbonyl)amino)methyl)-5-chloro-6-((2-(trimethylsilyl)ethoxy)methoxy)benzofuran-7-carboxylate (139.7 mg, 0.287 mmol) and ammonia, 7 M in MeOH (411 μl, 2.87 mmol) were added to a 2 dram pressure relief vial. The suspension was sonicated to give a homogenous tan solution. The reaction was sealed with a red safety pressure relief cap, placed behind a blast shield, and stirred at room temperature under ambient atmosphere. After 1.5 hours, reaction was heated to 65° C. After 1 hour, a second portion of ammonia, 7 M in MeOH (411 μl, 2.87 mmol), was added. The reaction was flushed with nitrogen gas, sealed with a red safety pressure relief cap, and heated to 65° C. After 5 hours, another 0.82 mL of ammonia, 7 M in MeOH was added and the reaction stirred at 65° C. overnight. After 20 hours, another 0.82 mL of ammonia, 7 M in MeOH was added and the reaction stirred at 65° C. overnight. The reaction was then cooled and concentrated under reduced pressure to give the title compound (105 mg, ca. quant) as a tan solid. 1H NMR (400 MHz, Chloroform-d) δ 13.49 (br s, 1H), 7.68 (s, 1H), 6.55 (s, 1H), 6.02 (br s, 1H), 4.76 (br s, 1H), 4.45 (br d, J=6.1 Hz, 2H), 1.49 (s, 9H); MS (ESI+) m/z=284.9 $(M-tBu+H)^+$.

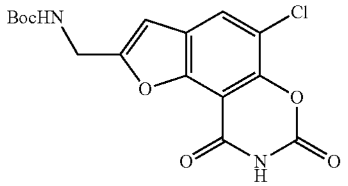 [SMILES: CC(C)(C)OC(=O)NCc1cc2cc(Cl)c3oc(=O)[nH]c(=O)c3c2o1]

F) Tert-butyl ((5-chloro-7,9-dioxo-8,9-dihydro-7H-benzofuro[7,6-e][1,3]oxazin-2-yl)methyl)carbamate Tert-butyl ((7-carbamoyl-5-chloro-6-hydroxybenzofuran-2-yl)methyl)carbamate (49.7 mg, 0.146 mmol) was suspended in MeCN (729 μl) in a 2 dram pressure relief vial and flushed with nitrogen gas. Pyridine (73.1 μl, 0.904 mmol) was added and the reaction was cooled to O ° C. A solution of ethyl chloroformate (15.41 μl, 0.160 mmol) in MeCN (729 μl) was added dropwise. The reaction was then sealed with a red safety pressure relief cap, placed behind a blast shield and heated to 100° C. for 24 hours. After 24 hours, the reaction was cooled and an additional portion of ethyl chloroformate (15.41 μl, 0.160 mmol) in MeCN (729 μl) was added. The reaction was again heated to 100° C. for an additional 15 hours. The reaction was purified directly via silica gel column chromatography to give the title compound (21.1 mg, 33% yield) as a colorless film. 1H NMR (400 MHz, Chloroform-d) δ 9.05-8.64 (m, 1H), 7.92 (s, 1H), 6.71 (s, 1H), 5.24 (br s, 1H), 4.55 (br d, J=6.0 Hz, 2H), 1.49 (s, 9H); MS (ESI+) m/z=310.9 $(M-tBu+H)^+$.

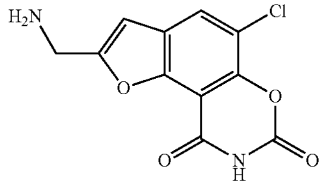 [SMILES: NCc1cc2cc(Cl)c3oc(=O)[nH]c(=O)c3c2o1]

G) 2-(Aminomethyl)-5-chloro-7H-benzofuro[7,6-e][1,3]oxazine-7,9(8H)-dione

Tert-butyl ((5-chloro-7,9-dioxo-8,9-dihydro-7H-benzofuro[7,6-e][1,3]oxazin-2-yl)methyl)carbamate (21.2 mg, 0.058 mmol) was taken up in DCM (434 μl). TFA (145 μl) was added and the reaction mixture turned from golden tan to red. The reaction was sealed with a septa and stirred at room temperature under ambient atmosphere for 1.5 hours. The reaction was then concentrated in vacuo and azeotroped with toluene before placing on high vacuum to give the title compound (25.4 mg, 96% yield) as a colorless film. $^1H$ NMR (400 MHz, MeOH-$d_4$) δ 8.18 (s, 1H), 7.12 (s, 1H), 5.19 (s, 1H), 4.45 (s, 2H); MS (ESI+) m/z=267.0 $(M+H)^+$.

H) N-((5-chloro-7,9-dioxo-8,9-dihydro-7H-benzofuro[7,6-e][1,3]oxazin-2-yl)methyl)pyrazolo[1,5-a]pyrimidine-3-carboxamide 2-(Aminomethyl)-5-chloro-7H-benzofuro[7,6-e][1,3]oxazine-7,9(8H)-dione, TFA (25.4 mg, 0.067 mmol) was suspended in (667 μl) in a 25 mL round bottom flask. Pyrazolo[1,5-a]pyrimidine-3-carboxylic acid (14.15 mg, 0.087 mmol) and ((1H-benzo[d][1,2,3]triazol-1-yl)oxy)tris(dimethylamino)phosphonium hexafluorophosphate(V) (38.4 mg, 0.087 mmol) were added followed by, followed by N-ethyl-N-isopropylpropan-2-amine (41.8 μl, 0.240 mmol). The reaction was sealed with a septa, sonicated, and stirred the suspension at room temperature under ambient atmosphere for 1 hour. The reaction was then diluted with 1.33 mL DMF, filtered and purified directly via preparative HPLC (method B) to give compound 19 (9.2 mg, 34% yield) as an off-white solid. $^1H$ NMR (500 MHz, DMSO-$d_6$) δ 12.26 (br s, 1H), 9.33 (dd, J=7.0, 1.7 Hz, 1H), 8.83 (dd, J=4.2, 1.7 Hz, 1H), 8.63 (s, 1H), 8.52 (t, J=5.9 Hz, 1H), 8.16 (s, 1H), 7.29 (dd, J=7.0, 4.2 Hz, 1H), 6.86 (s, 1H), 4.82 (d, J=5.7 Hz, 2H); MS (ESI+) m/z=412.0 $(M+H)^+$.

Evaluation of Biological Activity

Examplified compounds were evaluated for direct binding to STING as well as STING agonist functional activity on both the IRF and NF-κB pathways in a cellular reporter assay (protocols described subsequently). It was generally observed that some examplified compounds containing carboxylic acids bound to STING but did not possess agonist activity in the cellular reporter assay. Conversely, it was generally observed that some examplified compounds containing esters did not bind to STING but did possess agonist activity in the cellular reporter assay. One possible hypothesis consistent with these observations is that acids are the active species that bind to STING, but they are not cell membrane permeable (PAMPA data supports this statement), and therefore do not show agonist activity in the reporter assay. Furthermore, esters could be acting as prodrugs of the above acids that do not, themselves, bind to STING, but can pass through a cellular membrane (also supported by PAMPA data) where they are subsequently cleaved to unmask the analogous acid, which could then act as a STING agonist. Further evidence for this hypothesis includes: 1) co-crystals with either human or murine STING could only be obtained for acids and acid isosteres and not for esters, 2) cell-permeable acids and acid isosteres generally showed measurable agonist activity in the cellular reporter assay, and 3) metabolism studies showed that esters displaying agonist activity were readily cleaved to acids in cellular settings.

STING Reporter Assay Protocol

THP1-Dual™ cells were derived from the human THP-1 monocyte cell line by stable integration of two inducible reporter constructs. To this end, THP1-Dual™ cells allow the simultaneous study of the NF-κB pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.

THP1-Dual™ cells induce the activation of NF-κB in response to STING agonists. They also trigger the IRF pathway upon stimulation with STING agonists, such as cGAMP. Here, the THP-1-Dual cells were used to assess STING specific binders for function on the cellular level.

Serial dilutions of compounds in DMSO were added to low volume 384 well plates at 100 nl/well using an ECHO acoustic dispenser (Labcyte, model 550) to achieve final starting concentration of 100 μM in cell suspension. THP-1 Dual™ STING reporter cells (Invivogen, Dual cells cat #THPD-nfis) were added to the plates with compounds at 15,000 cells in 10 μL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 μM for 100% activation calculation and one column for no treatment (DMSO only) for baseline activation. Plates were then incubated in 37° C. incubator at 5% $CO_2$ for 20 hours.

In the SEAP assay, 5 μl of 2× QuantiBlue (Invivogen, cat #Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 μl of Quantiluc (Invivogen, Rep-qlc2) is added to white 384 well plates seeded with THP1 cells and read at 5 minutes on the Envision (Perkin Elmer) using a luminescence protocol (RLU). 100% activation was determined by value (RLU) of THP-1 Dual STING cells stimulated with 100 μM cGAMP (Invivogen, cat #TLRL-NACGA23-5).

| EXAMPLE # | IRF ($EC_{50}$ μM) | NFkB ($EC_{50}$ μM) |
|---|---|---|
| EXAMPLE 1 | 96 | 98 |
| EXAMPLE 2 | 12 | 13 |
| EXAMPLE 3 | 51 | 92 |
| EXAMPLE 4 | 13 | 14 |
| EXAMPLE 5 | 5.7 | 6.3 |

-continued

| EXAMPLE # | IRF ($EC_{50}$ μM) | NFkB ($EC_{50}$ μM) |
|---|---|---|
| EXAMPLE 6 | 5.1 | 3.1 |
| EXAMPLE 7 | 4.3 | 4.1 |
| EXAMPLE 8 | 21 | 18 |
| EXAMPLE 9 | 2.1 | 1.8 |
| EXAMPLE 10 | 7.5 | 7.6 |
| EXAMPLE 11 | 6.1 | 6.7 |
| EXAMPLE 12 | 33 | 39 |
| EXAMPLE 13 | 8.7 | 11 |
| EXAMPLE 14 | 3.8 | 6.0 |
| EXAMPLE 15 | 44 | 39 |
| EXAMPLE 16 | 6.8 | 9.3 |
| EXAMPLE 17 | 48 | 73 |
| EXAMPLE 18 | 79 | 97 |
| EXAMPLE 19 | 47 | 95 |
| EXAMPLE 20 | 48 | 49 |
| EXAMPLE 21 | 2.9 | 3.1 |
| EXAMPLE 22 | 0.60 | 0.67 |
| EXAMPLE 23 | 2.0 | 1.8 |
| EXAMPLE 25 | 10 | 15 |
| EXAMPLE 26 | 0.63 | 0.67 |
| EXAMPLE 28 | 3.1 | 3.6 |
| EXAMPLE 29 | 3.0 | 2.9 |
| EXAMPLE 30 | 27 | 31 |
| EXAMPLE 31 | 1.1 | 1.6 |
| EXAMPLE 32 | 3.5 | 3.4 |
| EXAMPLE 33 | 11 | 16 |
| EXAMPLE 34 | 79 | >100 |
| EXAMPLE 35 | 0.53 | 0.77 |
| EXAMPLE 36 | 3.6 | 4.1 |
| EXAMPLE 37 | 11 | 12 |
| EXAMPLE 38 | 2.3 | 2.5 |
| EXAMPLE 39 | 4.0 | 3.6 |
| EXAMPLE 40 | 2.1 | 3.2 |
| EXAMPLE 41 | >33 | 1.3 |
| EXAMPLE 42 | 4.1 | 3.6 |
| EXAMPLE 43 | 19 | 24 |
| EXAMPLE 44 | 12 | 13 |
| EXAMPLE 45 | 0.98 | 0.99 |
| EXAMPLE 46 | 1.5 | 1.5 |
| EXAMPLE 47 | 6.7 | 8.5 |
| EXAMPLE 48 | 0.64 | 0.68 |
| EXAMPLE 49 | 71 | 93 |
| EXAMPLE 50 | 0.93 | 1.1 |
| EXAMPLE 51 | 4.0 | 3.1 |
| EXAMPLE 52 | 8.0 | 9.8 |
| EXAMPLE 53 | 22 | 27 |
| EXAMPLE 54 | 2.6 | 2.6 |
| EXAMPLE 55 | 1.1 | 1.1 |
| EXAMPLE 56 | 30 | >33 |
| EXAMPLE 57 | 9.5 | 8.1 |
| EXAMPLE 58 | 2.7 | 2.9 |
| EXAMPLE 59 | 2.4 | 2.6 |
| EXAMPLE 60 | 7.7 | 8.9 |
| EXAMPLE 61 | 21 | 21 |
| EXAMPLE 62 | 42 | 46 |
| EXAMPLE 63 | 10 | 16 |
| EXAMPLE 64 | 68 | >100 |
| EXAMPLE 65 | 3.0 | 3.1 |
| EXAMPLE 66 | 28 | 33 |
| EXAMPLE 67 | 20 | 32 |
| EXAMPLE 68 | 1.7 | 2.1 |
| EXAMPLE 69 | 1.3 | 2.3 |
| EXAMPLE 70 | 24 | >100 |
| EXAMPLE 71 | 24 | 33 |
| EXAMPLE 72 | 1.2 | 17 |
| EXAMPLE 73 | 2.1 | 2.6 |
| EXAMPLE 74 | 3.3 | 3.5 |
| EXAMPLE 75 | 22 | 37 |
| EXAMPLE 76 | 3.0 | 4.1 |
| EXAMPLE 77 | 5.5 | 6.3 |
| EXAMPLE 78 | 3.4 | 3.7 |
| EXAMPLE 79 | 1.5 | 1.7 |
| EXAMPLE 80 | 0.80 | 1.1 |
| EXAMPLE 81 | 16 | 22 |
| EXAMPLE 82 | 27 | 20 |
| EXAMPLE 83 | 37 | 48 |

-continued

| EXAMPLE # | IRF (EC$_{50}$ μM) | NFkB (EC$_{50}$ μM) |
|---|---|---|
| EXAMPLE 84 | 30 | 27 |
| EXAMPLE 85 | 3.5 | 3.6 |
| EXAMPLE 86 | 1.7 | 1.8 |
| EXAMPLE 87 | 5.5 | 5.8 |
| EXAMPLE 88 | 21 | 20 |
| EXAMPLE 89 | 0.21 | 0.19 |
| EXAMPLE 90 | 2.2 | 3.0 |
| EXAMPLE 91 | 1.2 | 1.5 |
| EXAMPLE 92 | 0.80 | 0.81 |
| EXAMPLE 93 | 3.7 | 6.0 |
| EXAMPLE 94 | 1.8 | 2.1 |
| EXAMPLE 95 | 13 | 16 |
| EXAMPLE 96 | 1.7 | 2.0 |
| EXAMPLE 97 | 2.1 | 1.5 |
| EXAMPLE 98 | 11 | 10 |
| EXAMPLE 99 | 17 | 12 |
| EXAMPLE 100 | 2.5 | 2.2 |
| EXAMPLE 101 | 12 | 10 |
| EXAMPLE 102 | 2.5 | 3.0 |
| EXAMPLE 103 | 25 | 23 |
| EXAMPLE 104 | 63 | 37 |
| EXAMPLE 105 | 4.7 | 3.4 |
| EXAMPLE 106 | 0.75 | 1.1 |
| EXAMPLE 107 | 1.4 | 2.0 |
| EXAMPLE 108 | 21 | 31 |
| EXAMPLE 109 | 0.90 | 1.1 |
| EXAMPLE 110 | 0.22 | 0.27 |
| EXAMPLE 111 | 1.2 | 1.4 |
| EXAMPLE 112 | 0.20 | 0.26 |
| EXAMPLE 113 | 0.32 | 0.51 |
| EXAMPLE 114 | 0.97 | 0.89 |
| EXAMPLE 115 | 0.60 | 0.82 |
| EXAMPLE 116 | 2.9 | 3.1 |
| EXAMPLE 117 | 0.20 | 0.28 |
| EXAMPLE 118 | 0.30 | 0.37 |
| EXAMPLE 119 | 2.6 | 2.6 |
| EXAMPLE 120 | 2.7 | 3.2 |
| EXAMPLE 121 | 0.40 | 0.28 |
| EXAMPLE 122 | 0.53 | 0.54 |
| EXAMPLE 123 | 4.3 | 5.9 |
| EXAMPLE 124 | 5.7 | 6.7 |
| EXAMPLE 125 | 3.9 | 4.4 |
| EXAMPLE 126 | 1.4 | 1.6 |
| EXAMPLE 127 | 4.7 | 5.6 |
| EXAMPLE 139 | 90 | >100 |
| EXAMPLE 141 | 97 | 93 |
| EXAMPLE 158 | 63 | 52 |
| EXAMPLE 161 | 108 | 138 |
| EXAMPLE 172 | 62 | 74 |
| EXAMPLE 174 | 83 | 91 |
| EXAMPLE 176 | 51 | 56 |
| EXAMPLE 177 | 87 | >100 |
| EXAMPLE 178 | 42 | 50 |
| EXAMPLE 184 | 73 | 78 |
| EXAMPLE 186 | 84 | >100 |
| EXAMPLE 192 | 79 | 94 |
| EXAMPLE 203 | 44 | 65 |
| EXAMPLE 204 | 32 | 41 |
| EXAMPLE 205 | 9.8 | 9.9 |
| EXAMPLE 206 | 13 | 12 |
| EXAMPLE 207 | 9.2 | 17 |
| EXAMPLE 208 | 33 | 31 |
| EXAMPLE 209 | 18 | 19 |
| EXAMPLE 210 | 30 | 25 |
| EXAMPLE 211 | 23 | 31 |
| EXAMPLE 212 | 52 | 58 |
| EXAMPLE 213 | 79 | 86 |
| EXAMPLE 214 | 8.2 | 9.3 |
| EXAMPLE 215 | 12 | 14 |
| EXAMPLE 216 | 12 | 17 |
| EXAMPLE 217 | 1.3 | 1.6 |
| EXAMPLE 218 | 5.5 | 4.4 |
| EXAMPLE 219 | 7.7 | 10 |
| EXAMPLE 220 | 3.8 | 4.8 |
| EXAMPLE 221 | 42 | 83 |
| EXAMPLE 222 | 26 | 33 |

-continued

| EXAMPLE # | IRF (EC$_{50}$ μM) | NFkB (EC$_{50}$ μM) |
|---|---|---|
| EXAMPLE 223 | 0.67 | 0.62 |
| EXAMPLE 224 | 5.9 | 4.0 |
| EXAMPLE 225 | 7.5 | 7.5 |
| EXAMPLE 226 | 1.4 | 1.3 |
| EXAMPLE 227 | 3.8 | 4.2 |
| EXAMPLE 228 | 6.1 | 6.5 |
| EXAMPLE 229 | 4.2 | 4.2 |
| EXAMPLE 230 | 0.93 | 0.95 |
| EXAMPLE 231 | 0.50 | 0.65 |
| EXAMPLE 232 | 1.0 | 0.92 |
| EXAMPLE 233 | 1.7 | 2.0 |
| EXAMPLE 234 | 1.1 | 1.1 |
| EXAMPLE 235 | 0.69 | 0.68 |
| EXAMPLE 236 | 1.3 | 1.8 |
| EXAMPLE 237 | 1.2 | 1.2 |
| EXAMPLE 238 | 1.6 | 1.7 |
| EXAMPLE 239 | 0.53 | 0.39 |
| EXAMPLE 240 | 0.78 | 0.61 |
| EXAMPLE 241 | 2.3 | 2.3 |
| EXAMPLE 242 | 2.4 | 2.1 |
| EXAMPLE 243 | 1.6 | 1.9 |
| EXAMPLE 244 | 2.0 | 1.9 |
| EXAMPLE 245 | 1.8 | 1.0 |
| EXAMPLE 246 | 1.1 | 1.0 |
| EXAMPLE 247 | 9.0 | 13 |
| EXAMPLE 248 | 73 | 98 |
| EXAMPLE 249 | 2.4 | 2.5 |
| EXAMPLE 250 | 1.2 | 0.62 |
| EXAMPLE 251 | 0.93 | 1.0 |
| EXAMPLE 252 | 6.4 | 5.4 |
| EXAMPLE 253 | 0.96 | 0.93 |
| EXAMPLE 254 | 0.87 | 0.88 |
| EXAMPLE 255 | 13 | 19 |
| EXAMPLE 256 | 6.7 | 4.8 |
| EXAMPLE 257 | 28 | 11 |
| EXAMPLE 258 | 3.0 | 3.5 |
| EXAMPLE 259 | 2.3 | 2.2 |
| EXAMPLE 260 | 1.0 | 0.82 |
| EXAMPLE 261 | 0.95 | 0.82 |
| EXAMPLE 262 | 14 | 18 |
| EXAMPLE 263 | 4.8 | 5.2 |
| EXAMPLE 264 | 1.7 | 1.7 |
| EXAMPLE 265 | 0.84 | 0.82 |
| EXAMPLE 266 | 3.1 | 2.6 |
| EXAMPLE 267 | 5.8 | 6.6 |
| EXAMPLE 268 | 6.1 | 5.6 |
| EXAMPLE 269 | 1.1 | 1.1 |
| EXAMPLE 270 | 30 | 36 |
| EXAMPLE 271 | 0.80 | 0.91 |
| EXAMPLE 272 | 2.2 | 2.2 |
| EXAMPLE 273 | 0.70 | 0.75 |
| EXAMPLE 274 | 0.80 | 0.83 |
| EXAMPLE 275 | 0.94 | 0.72 |
| EXAMPLE 276 | 3.0 | 3.4 |
| EXAMPLE 277 | 13 | 16 |
| EXAMPLE 278 | 6.6 | 5.5 |
| EXAMPLE 279 | 35 | 25 |
| EXAMPLE 280 | 2.5 | 2.4 |
| EXAMPLE 281 | 11 | 14 |
| EXAMPLE 282 | 12 | 12 |
| EXAMPLE 283 | 0.40 | 0.52 |
| EXAMPLE 284 | 9.6 | 6.3 |
| EXAMPLE 285 | 1.4 | 1.9 |
| EXAMPLE 286 | 2.7 | 2.5 |
| EXAMPLE 287 | 12 | 18 |
| EXAMPLE 288 | 0.36 | 0.36 |
| EXAMPLE 289 | 0.62 | 0.71 |
| EXAMPLE 290 | 0.25 | 0.35 |
| EXAMPLE 291 | 0.34 | 0.31 |
| EXAMPLE 292 | 1.7 | 1.1 |
| EXAMPLE 293 | 4.4 | 3.8 |
| EXAMPLE 294 | 0.80 | 0.93 |
| EXAMPLE 295 | 1.1 | 0.56 |
| EXAMPLE 296 | 5.7 | 4.6 |
| EXAMPLE 297 | 3.1 | 3.2 |
| EXAMPLE 298 | 3.6 | 3.3 |

-continued

| EXAMPLE # | IRF ($EC_{50}$ μM) | NFkB ($EC_{50}$ μM) |
|---|---|---|
| EXAMPLE 299 | 0.28 | 0.33 |
| EXAMPLE 300 | 0.76 | 0.71 |
| EXAMPLE 301 | 2.1 | 2.7 |
| EXAMPLE 302 | 0.43 | 0.52 |
| EXAMPLE 303 | 0.53 | 0.58 |
| EXAMPLE 304 | 7.6 | 8.3 |
| EXAMPLE 305 | 5.0 | 3.9 |
| EXAMPLE 306 | 1.3 | 1.3 |
| EXAMPLE 307 | 7.7 | 8.9 |
| EXAMPLE 308 | 25 | 30 |
| EXAMPLE 309 | 6.1 | 7.2 |
| EXAMPLE 310 | 37 | 56 |
| EXAMPLE 311 | 2.0 | 2.3 |
| EXAMPLE 312 | 21 | 56 |
| EXAMPLE 313 | 3.1 | 3.0 |
| EXAMPLE 314 | 1.9 | 1.9 |
| EXAMPLE 315 | 2.1 | 1.9 |
| EXAMPLE 316 | 4.8 | 5.9 |
| EXAMPLE 317 | 1.4 | 1.3 |
| EXAMPLE 318 | 4.3 | 4.5 |
| EXAMPLE 319 | 2.4 | 2.5 |
| EXAMPLE 320 | 1.4 | 1.4 |
| EXAMPLE 321 | 0.30 | 0.38 |
| EXAMPLE 322 | 2.2 | 3.3 |
| EXAMPLE 323 | 0.75 | 0.70 |
| EXAMPLE 324 | 1.5 | 1.7 |
| EXAMPLE 325 | 1.7 | 1.4 |
| EXAMPLE 326 | 74 | >100 |
| EXAMPLE 327 | 73 | 79 |
| EXAMPLE 328 | 1.3 | 1.5 |
| EXAMPLE 329 | 0.88 | 0.89 |
| EXAMPLE 330 | 4.7 | 5.5 |
| EXAMPLE 331 | 1.7 | 1.8 |
| EXAMPLE 332 | 1.1 | 1.1 |
| EXAMPLE 333 | 11 | 12 |
| EXAMPLE 334 | 16 | 23 |
| EXAMPLE 335 | 3.5 | 3.5 |
| EXAMPLE 336 | 3.2 | 2.5 |
| EXAMPLE 337 | 9.8 | 13 |
| EXAMPLE 338 | 46 | 48 |
| EXAMPLE 339 | 1.8 | 1.4 |
| EXAMPLE 340 | 0.91 | 0.92 |
| EXAMPLE 341 | 1.6 | 2.5 |
| EXAMPLE 342 | 7.2 | 6.0 |
| EXAMPLE 343 | 0.73 | 0.76 |
| EXAMPLE 344 | 0.63 | 0.76 |
| EXAMPLE 345 | 5.7 | 3.6 |
| EXAMPLE 346 | 3.2 | 2.3 |
| EXAMPLE 347 | 3.3 | 2.3 |
| EXAMPLE 348 | 5.6 | 3.9 |
| EXAMPLE 349 | 3.8 | 3.5 |
| EXAMPLE 350 | 17 | 54 |
| EXAMPLE 351 | 1.9 | 2.4 |
| EXAMPLE 352 | 1.9 | 3.4 |
| EXAMPLE 353 | 10 | 18 |
| EXAMPLE 354 | 46 | 70 |
| EXAMPLE 355 | 0.96 | 1.3 |
| EXAMPLE 356 | 13 | 18 |
| EXAMPLE 357 | 0.90 | 1.0 |
| EXAMPLE 358 | 2.9 | 2.0 |
| EXAMPLE 359 | 3.8 | 4.0 |
| EXAMPLE 360 | 2.8 | 3.4 |
| EXAMPLE 361 | 5.5 | 7.2 |
| EXAMPLE 362 | 5.7 | 4.6 |
| EXAMPLE 363 | 3.5 | 3.2 |
| EXAMPLE 364 | 35 | 21 |
| EXAMPLE 365 | 7.5 | 4.4 |
| EXAMPLE 366 | 4.0 | 4.0 |
| EXAMPLE 367 | 7.5 | 9.5 |
| EXAMPLE 368 | 11 | 11 |
| EXAMPLE 369 | 0.91 | 1.1 |
| EXAMPLE 370 | 13 | 16 |
| EXAMPLE 371 | 2.5 | 2.8 |
| EXAMPLE 372 | 3.7 | 4.6 |
| EXAMPLE 373 | 3.9 | 3.9 |
| EXAMPLE 374 | 4.3 | 3.5 |

-continued

| EXAMPLE # | IRF ($EC_{50}$ μM) | NFkB ($EC_{50}$ μM) |
|---|---|---|
| EXAMPLE 375 | 2.6 | 2.3 |
| EXAMPLE 376 | 19 | 16 |
| EXAMPLE 377 | 0.40 | 0.30 |
| EXAMPLE 378 | 1.3 | 1.2 |
| EXAMPLE 379 | 13 | 19 |
| EXAMPLE 381 | 13 | 12 |
| EXAMPLE 382 | 1.3 | 1.1 |
| EXAMPLE 383 | 0.92 | 1.1 |
| EXAMPLE 384 | 3.2 | 3.0 |
| EXAMPLE 385 | 2.1 | 2.5 |
| EXAMPLE 386 | 3.4 | 3.7 |
| EXAMPLE 387 | 1.9 | 2.1 |
| EXAMPLE 388 | 1.5 | 1.4 |
| EXAMPLE 389 | 0.58 | 0.56 |
| EXAMPLE 390 | 0.53 | 0.29 |
| EXAMPLE 391 | 0.75 | 0.61 |
| EXAMPLE 392 | 3.4 | 2.7 |
| EXAMPLE 393 | 0.39 | 0.30 |
| EXAMPLE 394 | >100 | 11 |
| EXAMPLE 395 | 2.1 | 1.9 |
| EXAMPLE 396 | 0.36 | 0.37 |
| EXAMPLE 397 | 0.46 | 0.47 |
| EXAMPLE 398 | 9.4 | 5.7 |
| EXAMPLE 399 | 1.3 | 1.5 |
| EXAMPLE 400 | 25 | 22 |
| EXAMPLE 401 | 1.9 | 1.9 |
| EXAMPLE 402 | 2.4 | 2.4 |
| EXAMPLE 403 | >100 | 97 |
| EXAMPLE 404 | >100 | 83 |
| EXAMPLE 405 | 30 | 61 |
| EXAMPLE 406 | 9.4 | 7.1 |
| EXAMPLE 407 | 30 | 37 |
| EXAMPLE 408 | 0.91 | 1.2 |
| EXAMPLE 409 | 107 | 191 |
| EXAMPLE 410 | 79 | >100 |
| EXAMPLE 412 | 48 | 37 |

STING Displacement and Dimerization Protocols

Dimerization Protocol: A time resolved FRET-based assay was used to assess test article-induced dimerization of the cytoplasmic domain (amino acids 155-341) of WT (232R) STING, AQ (G230A-R293Q) STING, and mouse (M) STING. His-tagged STING and enzymatically biotinylated STING at a concentration of 10 nM each were incubated with 2.5 nM Tb-labeled anti-His antibody, 5 nM d2-labeled Streptavidin (Cisbio cat. no. 610SADLF), and test compound for one hour in PBS containing 0.005% Tween-20 and 0.1% BSA. Fluorescence at 660 nm and 610 nm was measured using an EnVision microplate reader to quantify FRET between Tb-labeled anti-His antibody and d2-labeled Streptavidin. Background was defined as the signal obtained in the absence of STING protein, and background subtracted FRET ratios were normalized to the maximum signal obtained with complete dimerization in the presence of 150 nM 2'3'-cGAMP (InvivoGen cat. no. tlrl-nacga23-02). These values were converted to percent dimerization. Percent dimerization was determined for test compounds at 11 concentrations. The EC50, defined as the concentration of test compound needed to induce 50% dimerization, was calculated using the 4 parameter logistic equation to fit the data.

Competition Binding (Displacement) Protocol: A time resolved FRET-based competition binding assay was used to assess test article binding to the cytoplasmic domain (amino acids 155-341) of WT (232R) STING, AQ (G230A-R293Q) STING, and mouse (M) STING. His-tagged STING cytoplasmic domain at a concentration of 20 nM was incubated with 2.5 nM Tb-labeled anti-His antibody, test compound, and fluorescein-labeled cGAMP analog probe (BioLog cat. no. C195) at a concentration of 200 nM (WT STING) or 40 nM (G230A-R293Q STING and mouse STING) for one hour in PBS containing 0.005% Tween-20 and 0.1% BSA. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The IC50, defined as the concentration of competing test compound needed to reduce specific binding of the probe by 5000, was calculated using the 4 parameter logistic equation to fit the data.

| | Dimerization $EC_{50}$ □M | | | Displacement $IC_{50}$ □M | | |
|---|---|---|---|---|---|---|
| EXAMPLE # | WT | AQ | M | WT | AQ | M |
| EXAMPLE 24 | >100 | 97 | 31 | >100 | 31 | 5.0 |
| EXAMPLE 27 | >100 | 45 | 35 | 90 | 15 | 7.7 |
| EXAMPLE 130 | >100 | >100 | >100 | >100 | >100 | 24 |
| EXAMPLE 131 | 71 | 50 | 14 | 40 | 15 | 1.1 |
| EXAMPLE 132 | >100 | 88 | 26 | 44 | 16 | 3.0 |
| EXAMPLE 133 | >100 | 83 | 65 | 58 | 24 | 19 |
| EXAMPLE 134 | >100 | 71 | 34 | >100 | 21 | 5.1 |
| EXAMPLE 135 | >100 | >100 | >100 | >100 | >100 | 45 |
| EXAMPLE 136 | 54 | 19 | 4.1 | 15 | 2.2 | 0.34 |
| EXAMPLE 137 | >100 | >100 | >100 | >100 | >100 | 8.1 |
| EXAMPLE 138 | 57 | 26 | 16 | 20 | 5.0 | 1.0 |
| EXAMPLE 140 | >100 | >100 | >100 | >100 | 58 | 45 |
| EXAMPLE 142 | >100 | 96 | 34 | >100 | 41 | 4.0 |
| EXAMPLE 143 | >100 | >100 | >100 | >100 | >100 | 98 |
| EXAMPLE 144 | 40 | 28 | 18 | 23 | 8.2 | 2.1 |
| EXAMPLE 147 | >100 | 36 | 15 | 21 | 4.9 | 1.5 |
| EXAMPLE 148 | >100 | >100 | 77 | 41 | 20 | 9.2 |
| EXAMPLE 149 | >100 | 97 | 50 | 99 | 39 | 16 |
| EXAMPLE 150 | >100 | >100 | >100 | >100 | 88 | 40 |
| EXAMPLE 151 | >100 | >100 | 35 | >100 | 44 | 8.6 |
| EXAMPLE 152 | >100 | >100 | 43 | >100 | 51 | 8.9 |
| EXAMPLE 153 | >100 | >100 | 51 | 99 | 35 | 6.7 |
| EXAMPLE 154 | >100 | >100 | >100 | >100 | >100 | 41 |
| EXAMPLE 155 | >100 | >100 | >100 | >100 | >100 | 42 |
| EXAMPLE 156 | >100 | 64 | 52 | 78 | 34 | 17 |
| EXAMPLE 157 | 56 | 31 | 15 | 29 | 8.5 | 2.4 |
| EXAMPLE 160 | >100 | 41 | 24 | 21 | 7.6 | 2.6 |
| EXAMPLE 162 | >100 | >100 | >100 | >100 | 73 | 20 |
| EXAMPLE 163 | >100 | >100 | >100 | >100 | >100 | 42 |
| EXAMPLE 164 | >100 | >100 | 66 | >100 | 94 | 25 |
| EXAMPLE 165 | >100 | >100 | >100 | >100 | 98 | 57 |
| EXAMPLE 166 | 94 | 35 | 10 | 90 | 14 | 2.7 |
| EXAMPLE 167 | >100 | 87 | 16 | >100 | 32 | 1.8 |
| EXAMPLE 168 | >100 | >100 | >100 | >100 | 57 | 2.9 |
| EXAMPLE 169 | 67 | 37 | 17 | 15 | 4.9 | 0.54 |
| EXAMPLE 170 | >100 | >100 | >100 | >100 | >100 | 16 |
| EXAMPLE 171 | 38 | 11 | 9.0 | 20 | 3.3 | 0.65 |
| EXAMPLE 173 | >100 | 69 | 60 | 80 | 19 | 16 |
| EXAMPLE 175 | >100 | 82 | 77 | 72 | 16 | 18 |
| EXAMPLE 179 | >100 | 76 | 39 | >100 | 35 | 28 |
| EXAMPLE 180 | >100 | >100 | >100 | >100 | 61 | 69 |
| EXAMPLE 182 | >100 | >100 | >100 | >100 | 49 | 48 |
| EXAMPLE 183 | >100 | 59 | 35 | 87 | 13 | 3.3 |
| EXAMPLE 185 | >100 | >100 | 61 | 28 | 4.5 | 2.6 |
| EXAMPLE 187 | >100 | >100 | 61 | >100 | 41 | 8.4 |
| EXAMPLE 188 | >100 | >100 | 22 | >100 | 72 | 2.2 |
| EXAMPLE 189 | >100 | 45 | 22 | 98 | 18 | 4.9 |
| EXAMPLE 190 | >100 | >100 | 71 | >100 | 64 | 40 |
| EXAMPLE 191 | >100 | >100 | 47 | 94 | 50 | 5.6 |
| EXAMPLE 194 | >100 | >100 | 20 | 69 | 30 | 2.1 |
| EXAMPLE 195 | >100 | 49 | 38 | 62 | 14 | 6.6 |
| EXAMPLE 196 | 59 | 46 | >100 | 85 | 38 | 37 |

-continued

| | Dimerization $EC_{50}$ □M | | | Displacement $IC_{50}$ □M | | |
|---|---|---|---|---|---|---|
| EXAMPLE # | WT | AQ | M | WT | AQ | M |
| EXAMPLE 197 | >100 | >100 | 38 | >100 | 40 | 23 |
| EXAMPLE 201 | 59 | 28 | 37 | 15 | 3.8 | 5.0 |
| EXAMPLE 202 | >100 | 42 | 65 | 60 | 8.8 | 19 |
| EXAMPLE 411 | 12 | 2.5 | 29 | 3.8 | 23 | 4.8 |

We claim:

1. A compound formula

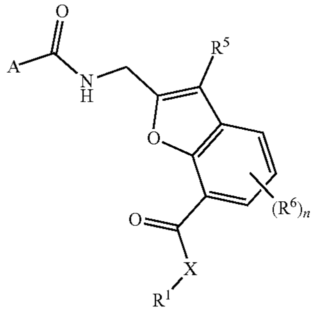

wherein

A is a pyrazinyl group, a pyrimidinyl group, a pyridinyl group, a pyrazole-pyrimidinyl group, an imidazo-pyridazinyl group, a thiazolo-pyrdinyl group, imidazo-pyridinyl group or a naphthyridinyl group, each of said groups substituted with 0-4 $R^2$ groups, X is O, $R^1$ is hydrogen, $CD_3$, $CF_3$, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$, $R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$, $R^{1b}$ is halogen or $C_{1-4}$ alkyl, R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

2. A compound of formula

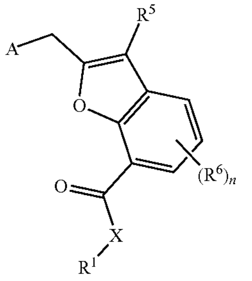

wherein A is

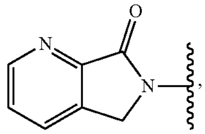,
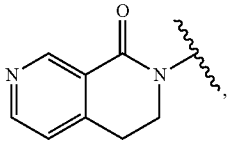,
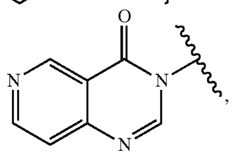,
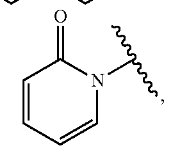,
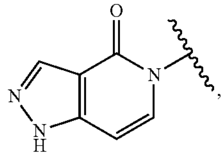,
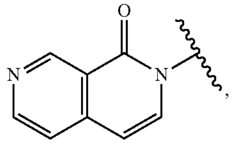,
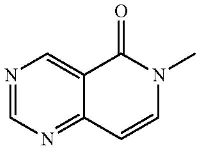,
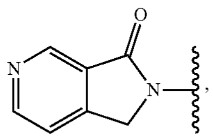, or
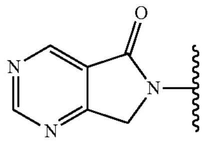

substituted with 0-4 $R^2$ groups,

X is O, S or NH, $R^1$ is hydrogen, $CD_3$, $CF_3$, OH, $C_{1-6}$ alkyl, $C_{1-6}$ alkoxy, $C_{3-6}$ cycloalkyl, halo $C_{1-3}$ alkyl, aryl $C_{1-3}$ alkyl, hydroxy $C_{1-4}$ alkyl, halo $C_{1-3}$ alkoxy, NHR', 4-10 membered heterocycle or aryl, all of said alkyl, cycloalkyl, heterocyclyl or aryl groups substituted with 0-4 $R^{1a}$, with the proviso that $R^1$ is OH only when X is NH;

$R^{1a}$ is halogen, CN, $C_{1-4}$ alkyl, halo $C_{1-3}$ alkyl, 4-10 membered heterocycle or aryl, all of said alkyl, heterocyclyl or aryl groups substituted with 0-2 $R^{1b}$, $R^{1b}$ is halogen or $C_{1-4}$ alkyl, R' is hydrogen, OH, $C_{1-3}$ alkoxy or $C_{1-3}$ alkyl;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen or $R^{1a}$ is halogen, $R^5$ is hydrogen, halogen, $CF_3$, $C_{1-6}$ alkyl, $C_{1-6}$ alkoxy or $C_{1-6}$ alkenyl, $R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

3. The compound according to claim 2 of the formula

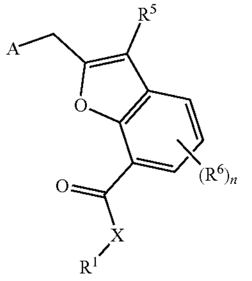

wherein A is

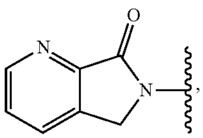,
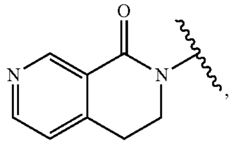,
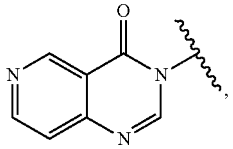,
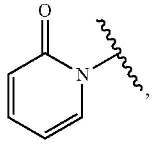,
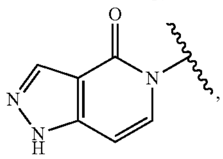,
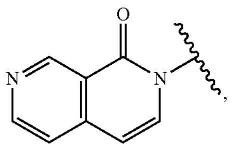,
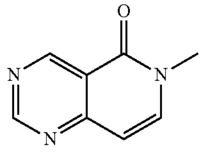,
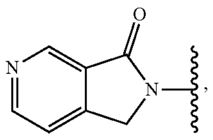, or
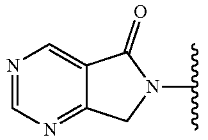

substituted with 0-4 $R^2$ groups,

X is O, $R^1$ is hydrogen, $CD_3$, $CF_3$, $C_{1-6}$ alkyl, $C_{1-6}$ alkoxy, $C_{3-6}$ cycloalkyl or halo $C_{1-3}$ alkyl, all of said alkyl groups substituted with 0-4 $R^{1a}$;

$R^{1a}$ is halogen;

$R^2$ is, independently at each occurrence, hydrogen, halogen, CN, OH, COOH, $C_{1-6}$ alkyl, $C_{1-6}$ alkoxy, $C_{3-6}$ cycloalkyl, halo $C_{1-3}$ alkyl, hydroxy $C_{1-4}$ alkyl, halo $C_{1-3}$ alkoxy, NHR', 4-10 membered heterocycle or aryl, all of said alkyl, heterocyclyl or aryl groups substituted with 0-2 $R^{2a}$, $R^{2a}$ is halogen or $R^{1a}$ is halogen, $R^5$ is hydrogen, halogen, $CF_3$, $C_{1-6}$ alkyl, $C_{1-6}$ alkoxy or $C_{1-6}$ alkenyl;

$R^6$ is hydrogen, halogen, OH, $CF_3$, $C_{1-6}$ alkyl, $C_{1-6}$ alkoxy, $C_{1-6}$ alkenyl, CN or $C_{3-6}$ cycloalkyl n is 0, 1, 2 or 3, or a pharmaceutically acceptable salt thereof.

4. A compound selected from

Tert-butyl 3-((5-chloro-2-((pyrazolo[1,5-a]pyrimidine-3-carboxamido)methyl)benzofuran-7-carbonyl)oxy)azetidine-1-carboxylate, (247)

Acetoxymethyl 5-chloro-2-((7yrazole[1,5-a]pyrimidine-3-carboxamido)methyl)benzofuran-7-carboxylate, (259)

((Ethoxycarbonyl)oxy)methyl 5-chloro-2-((pyrazolo[1,5-a]pyrimidine-3-carboxamido)methyl)benzofuran-7-carboxylate, (260), 1-((Ethoxycarbonyl)oxy)ethyl 5-chloro-2-((pyrazolo[1,5-a]pyrimidine-3-carboxamido)methyl)benzofuran-7-carboxylate, (261)

1-Ethoxy-2,2-difluoroethyl 5-fluoro-2-((pyrazolo[1,5-a]pyrimidine-3-carboxamido)methyl)benzofuran-7-carboxylate, (323,324)

S-(2-(Trimethylsilyl)ethyl) 3-chloro-5-fluoro-2-((pyrazolo[1,5-a]pyrimidine-3-carboxamido)methyl)benzofuran-7-carbothioate, (392)

S-(2-(Trimethylsilyl)ethyl) (S)-5-fluoro-2-(1-(pyrazolo[1,5-a]pyrimidine-3-carboxamido) ethyl)benzofuran-7-carbothioate (398)

S-(2-(Trimethylsilyl)ethyl) (S)-5-chloro-2-(1-(pyrazolo[1,5-a]pyrimidine-3-carboxamido) ethyl)benzofuran-7-carbothioate (400)

N-((5-Chloro-7-(1H-tetrazol-5-yl)benzofuran-2-yl)methyl) pyrazolo[1,5-a]pyrimidine-3-carboxamide (409), N-((5-Chloro-7-(1H-tetrazol-5-yl)benzofuran-2-yl)methyl)-1,6-naphthyridine-8-carboxamide (410), or a pharmaceutically acceptable salt thereof.

5. A pharmaceutical composition comprising a compound according to claim 4 or a pharmaceutically acceptable salt thereof and one or more pharmaceutically acceptable carriers, diluents or excipients.

6. A pharmaceutical composition comprising a compound according to claim 1 or a pharmaceutically acceptable salt thereof and one or more pharmaceutically acceptable carriers, diluents or excipients.

7. A method of treating diseases and conditions in which the modulation of STING is indicated in a subject in need thereof which comprises administering a therapeutically effective amount of compound according to claim 1 or a pharmaceutically acceptable salt thereof.

8. A method of treating cancer comprising administering a therapeutically effective amount of one or more compounds according to claim 2 or a pharmaceutically acceptable salt thereof.

9. The method of claim 8 wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers.

10. The method of claim 9 wherein the cancer is small cell lung cancer, non-small cell lung cancer, colorectal cancer, melanoma, renal cell carcinoma, head and neck cancer, Hodgkin's lymphoma or bladder cancer.

11. A method for treating cancer in a subject in need thereof, comprising administering an effective amount of a compound, according to claim 2, or a pharmaceutically acceptable salt thereof, in combination with the administration of a therapeutically effective amount of one or more immuno-oncology agents.

12. A compound selected from

N-((5-chloro-7,9-dioxo-8,9-dihydro-7H-benzofuro[7,6-e][1,3]oxazin-2-yl)methyl)pyrazolo[1,5-a]pyrimidine-3-carboxamide, N-((5-Chloro-7-(1H-tetrazol-5-yl)benzofuran-2-yl)methyl) pyrazolo[1,5-a]pyrimidine-3-carboxamide, N-((5-Chloro-7-(1H-tetrazol-5-yl)benzofuran-2-yl)methyl)-1,6-naphthyridine-8-carboxamide, 1-methyl-2-((pyrazolo[1,5-a]pyrimidine-3-carboxamido)methyl)-1H-benzo[d]imidazole-4-carboxylic acid, or a pharmaceutically acceptable salt thereof.

* * * * *